(12) United States Patent
Lescarbeau et al.

(10) Patent No.: US 12,152,034 B2
(45) Date of Patent: Nov. 26, 2024

(54) FGFR INHIBITORS AND METHODS OF MAKING AND USING THE SAME

(71) Applicant: Relay Therapeutics, Inc., Cambridge, MA (US)

(72) Inventors: André Lescarbeau, Cambridge, MA (US); Jethro Beamish-Cook, Cambridge (GB); Zoe Prentice, Cambridge (GB); Thomas Kendall, Cambridge (GB); Aaron Dumas, Hertfordshire (GB); Elisabeth Isaak, Hertfordshire (GB); Piera Trinchera, Hertfordshire (GB); Oleksandr Zhurakovskyi, Hertfordshire (GB); Osama Suleiman, Cambridge (GB)

(73) Assignee: Relay Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/455,507

(22) Filed: Nov. 18, 2021

(65) Prior Publication Data
US 2022/0194946 A1 Jun. 23, 2022

Related U.S. Application Data

(60) Provisional application No. 63/115,319, filed on Nov. 18, 2020.

(51) Int. Cl.
C07D 487/04 (2006.01)

(52) U.S. Cl.
CPC ........ *C07D 487/04* (2013.01); *C07B 2200/13* (2013.01)

(58) Field of Classification Search
CPC .................... C07D 487/04; C07B 2200/13
See application file for complete search history.

(56) References Cited

U.S. PATENT DOCUMENTS

| | | | |
|---|---|---|---|
| 5,721,359 A * | 2/1998 | Dunn | A61P 31/12 540/227 |
| 6,001,839 A | 12/1999 | Calderwood et al. | |
| 6,140,332 A | 10/2000 | Traxler et al. | |
| 6,180,636 B1 | 1/2001 | Traxler et al. | |
| 7,323,469 B2 | 1/2008 | Bold et al. | |
| 2006/0040965 A1 | 2/2006 | Farthing et al. | |
| 2022/0389029 A1 | 12/2022 | Guo et al. | |
| 2023/0104574 A1 | 4/2023 | Touréet al. | |
| 2023/0192709 A1 | 6/2023 | Touréet al. | |
| 2024/0114908 A1 | 4/2024 | Teranishi et al. | |

FOREIGN PATENT DOCUMENTS

| | | |
|---|---|---|
| CN | 102286048 A | 12/2011 |
| EP | 1661896 A1 | 5/2006 |
| EP | 2657233 A1 | 10/2013 |
| EP | 3269370 A1 | 1/2018 |
| WO | 1998041525 A1 | 9/1998 |
| WO | 200140230 A1 | 6/2001 |
| WO | 200250306 A1 | 6/2002 |
| WO | 2002100864 A1 | 12/2002 |
| WO | 2005121147 A1 | 12/2005 |
| WO | 2006004658 A2 | 1/2006 |
| WO | 2006004703 A2 | 1/2006 |
| WO | 2007079862 A1 | 7/2007 |
| WO | 2010126960 A1 | 11/2010 |
| WO | 2013078254 A1 | 5/2013 |
| WO | 2013085802 A1 | 6/2013 |
| WO | 2015107495 A1 | 7/2015 |
| WO | 2018049233 A1 | 3/2018 |
| WO | 2018057884 A1 | 3/2018 |
| WO | 2018136265 A1 | 7/2018 |
| WO | 2018172984 A1 | 9/2018 |
| WO | 2020231990 A1 | 11/2020 |
| WO | 2021091982 | 5/2021 |

(Continued)

OTHER PUBLICATIONS

Hickey et al. (Journal of Pharmaceutical Sciences, vol. 96, No. 5, May 2007, pp. 1090-1099).*
Azoury et al., "Fibroblast Growth Factor Receptor 2 (FGFR2) Mutation Related Syndromic Craniosynostosis," Int. J. Biol. Sci. 2017; 13(12):1479-88.
Babina and Turner, "Advances and challenges in targeting FGFR signalling in cancer," Nat. Rev. Cancer. 2017; 17(5):318-32.
Chae et al., "Inhibition of the fibroblast growth factor receptor (FGFR) pathway: the current landscape and barriers to clinical application," Oncotarget. 2017; 8(9):16052-74.
Dardaei et al., "SHP2 inhibition restores sensitivity in ALK-rearranged non-small-cell lung cancer resistant to ALK inhibitors," Nat Med. 2018; 24(4):512-17.
Fedele et al., "SHP2 Inhibition Abrogates MEK inhibitor Resistance in Multiple Cancer Models," BioRxiv. 2018; 307876.

(Continued)

*Primary Examiner* — Susanna Moore
(74) *Attorney, Agent, or Firm* — Dechert LLP; John P. Rearick; Gang Wang

(57) ABSTRACT

The disclosure is in part directed to crystalline forms of N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide represented by the following structure:

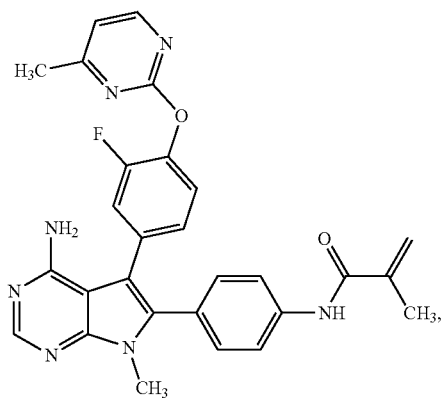

its salts, its cocrystals, and variants thereof.

19 Claims, 176 Drawing Sheets

(56) References Cited

FOREIGN PATENT DOCUMENTS

| WO | 2021209383 | 10/2021 |
|---|---|---|
| WO | 2022109577 A1 | 5/2022 |

OTHER PUBLICATIONS

Formisano et al., "Aberrant FGFR signaling mediates resistance to CDK4/6 inhibitors in ER+ breast cancer," Nat. Comm. 2019; 10(1):1373-86.

Gagné-Sansfaçon et al., "SHP-2 phosphatase contributes to KRAS-driven intestinal oncogenesis but prevents colitis-associated cancer development," Oncotarget. 2016; 7(40):65676-95.

Gattineni et al., "Regulation of renal phosphate transport by FGF23 is mediated by FGFR1 and FGFR4," Am. J. Physiol. Renal Physiol. 2014; 306(3):F351-8.

Han et al., "Conditional Deletion of Fgfr1 in the Proximal and Distal Tubule Identifies Distinct Roles in Phosphate and Calcium Transport," PLoS One. 2016; 11(2):e0147845.

International Search Report and Written Opinion from PCT/US2020/032474, dated Jul. 6, 2020 (10 pages).

International Search Report and Written Opinion from PCT/US2021/072480, dated Jan. 19, 2022 (11 pages).

Katoh, "Fibroblast growth factor receptors as treatment targets in clinical oncology," Nat. Rev. Clin. Oncol. 2019; 16:105-22.

Porta et al. "FGFR a promising druggable target in cancer: Molecular biology and new drugs," Crit. Rev. Oncol. Hematol. 2017; 113:256-67.

Prahallad et al., "PTPN11 Is a Central Node in Intrinsic and Acquired Resistance to Targeted Cancer Drugs," Cell Rep. 2015; 12(12):1978-85.

Torres-Ayuso et al., "Shipping Out MEK Inhibitor Resistance with SHP2 Inhibitors," Cancer Discov. 2018; 8(10):1210-12.

Turner and Grose, "Fibroblast growth factor signalling: from development to cancer," Nat. Rev. Cancer. 2010; 10(2):116-29.

Wu et al., "Identification of Targetable FGFR Gene Fusions in Diverse Cancers," Cancer Discov. 2013; 3(6):636-647.

U.S. Appl. No. 17/595,257, filed Nov. 12, 2021.

U.S. Appl. No. 18/162,127, filed Jan. 23, 2023.

Calvet et al., "Synthesis of Polysubstituted 5-Azaindoles via Palladium-Catalyzed Heteroannulation of Diarylalkynes," J. Org. Chem. 2011; 76(11):4734-40.

Katoh, "Fibroblast growth factor receptors as treatment targets in clinical oncology," Nature Reviews Clinical Oncology, 2019, 16:105-122.

\* cited by examiner

FIG. 34A

FGFR INHIBITORS AND METHODS OF MAKING AND USING THE SAME

CROSS-REFERENCE TO RELATED APPLICATIONS

This application claims the benefit of U.S. Provisional Application No. 63/115,319, filed on Nov. 18, 2020, the entirety of which is hereby incorporated by reference.

BACKGROUND

Fibroblast growth factor receptors (FGFR1, FGFR2, FGFR3, and FGFR4) are receptor tyrosine kinases consisting of an extracellular ligand binding domain and an intracellular tyrosine kinase domain. Binding of FGF ligands leads to receptor dimerization and a conformational change in the intracellular domain resulting in intermolecular transphosphorylation of the kinase domain and intracellular tail. Phosphorylated residues serve as docking sites for adaptor proteins that promote downstream signaling cascades leading to cellular behaviors including proliferation, survival, differentiation, migration, and angiogenesis. Deregulated FGFR signaling can occur via FGFR gene amplification or fusion, FGFR missense mutations, receptor overexpression resulting from dysregulation of epigenetic and/or transcriptional regulators, or upregulation of FGF ligands in the tumor microenvironment. FGFRs are expressed on many cell types; thus, aberrant FGFR signaling has been implicated in oncogenesis, tumor progression, and resistance to therapy across many tumor types. (For a review of FGFR signaling, see N. Turner and R. Grose, *Nat. Rev. Cancer* 2010, 10:116-129; and references cited therein).

Pan-FGFR1-3 inhibitors have generated clinical responses in numerous FGFR-altered cancers, however on-target toxicity limits dosing of these inhibitors. One of the most common adverse effects of pan-FGFR inhibition is hyperphosphatemia. Regulation of phosphate reabsorption is mediated by FGFR3 and FGFR1. Thus, there is a need for FGFR-selective inhibitors that spare FGFR1. (J. Gattineni et al., *Am. J. Physiol. Renal Physiol.* 2014, 306:F351-F358; X. Han et al., *PLoS One* 2016, 11:e0147845.) Cancers harboring FGFR2 gene fusions as well as those with FGFR2 amplification and/or FGFR2 activating mutations have demonstrated responses to pan-FGFR inhibition, however the low rates and duration of responses suggest they were limited by toxicities. Thus, there is a need for FGFR2-selective inhibitor compounds and methods for treating cancers and other disorders with these compounds. (For reviews of pan-FGFR1-3 inhibitors and clinical responses, see I. S. Babina and N. C. Turner, *Nat. Rev. Cancer* 2017, 17:318-332; M. Katoh, *Nat. Rev. Clin. Oncol.* 2019, 16:105-122; and references cited therein).

Polymorphism is the ability of a substance to crystallize in more than one crystal lattice arrangement. Crystallization, or polymorphism, can influence many aspects of solid state properties of a drug substance. A crystalline form may differ considerably from an amorphous form, and different crystal forms of a substance may differ considerably from one another in many respects including solubility, dissolution rate and/or bioavailability. Generally, it is difficult to predict whether or not a given compound will form various crystalline solid state forms. It is even more difficult to predict the physical properties of these crystalline solid state forms. Further, it can be advantageous to have a crystalline form of a therapeutic agent for certain formulations, e.g., formulations suitable for subcutaneous use.

SUMMARY OF THE INVENTION

This disclosure is generally directed to the compounds of formulas I-IV and solvates thereof, and crystalline forms thereof.

In one aspect, provided herein is a compound of Formula (I)

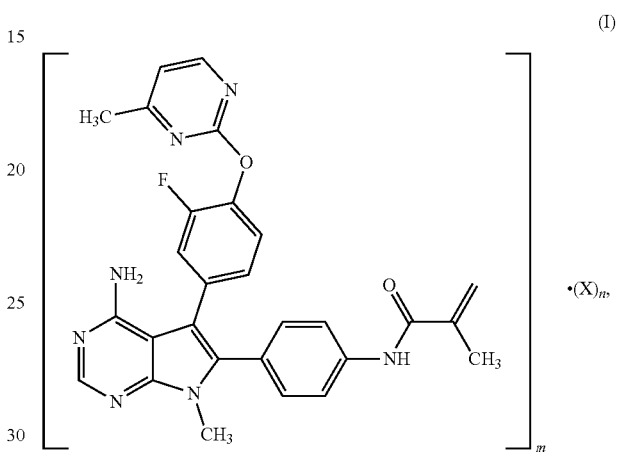

or a solvate thereof, wherein each of X, m, and n is independently as defined and described in embodiments herein. In some embodiments, a compound of Formula (I), or a solvate thereof, is a crystalline form as described herein.

In another aspect, provided herein is a compound of Formula (II)

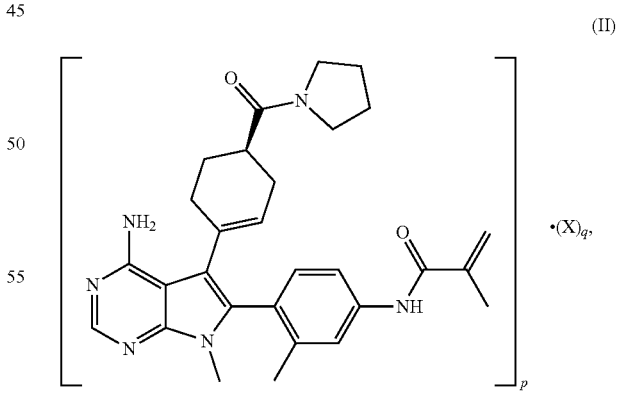

or a solvate thereof, wherein each of X, p, and q is independently as defined and described in embodiments herein. In some embodiments, a compound of Formula (II), or a solvate thereof, is a crystalline form as described herein.

In another aspect, provided herein is a compound of Formula (III)

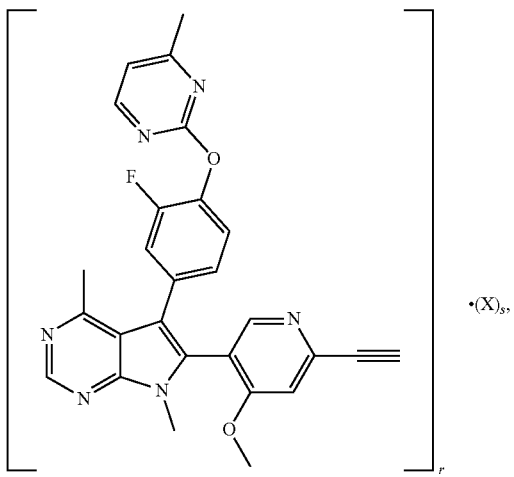

(III)

or a solvate thereof, wherein each of X, r, and s is independently as defined and described in embodiments herein. In some embodiments, a compound of Formula (III), or a solvate thereof, is a crystalline form as described herein.

In another aspect, provided herein is a compound of Formula (IV)

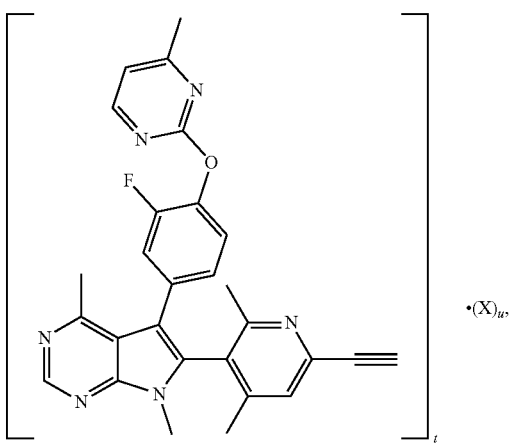

(IV)

or a solvate thereof, wherein each of X, t, and u is independently as defined and described in embodiments herein. In some embodiments, a compound of Formula (IV), or a solvate thereof, is a crystalline form as described herein.

In another aspect, provided herein is a pharmaceutical composition comprising a compound or a solvate thereof, or a crystalline form, as described herein, and a pharmaceutically acceptable excipient.

In another aspect, provided herein is a method of using a compound or a solvate thereof, or a crystalline form, or a pharmaceutical composition thereof, as described herein, for inhibiting FGFR2 activity and for treating a disorder, disease, and/or condition as described herein.

BRIEF DESCRIPTION OF THE DRAWINGS

FIG. 34A depicts an X-ray diffraction pattern of Form C of Compound III-1 (free form).

FIG. 35D depicts an XRPD diffractogram of Compound III-2 Form A (above) after storage at 40° C./75% RH for 7 days (below).

FIG. 36A depicts an X-ray diffraction pattern of Form B of Compound III-2 (hydrochloride salt).

FIG. 36B depicts the characterization of Form B of Compound III-2 by $^1$H nuclear magnetic resonance ($^1$H NMR) in D6-DMSO at 400 MHz.

FIG. 36C depicts the characterization of Form B of Compound III-2 by thermogravimetric analysis (above) and differential scanning calorimetry (below).

FIG. 36D depicts an XRPD diffractogram of Compound III-2 Form B (above) after storage at 40° C./75% RH for 7 days (below).

FIG. 37A depicts an X-ray diffraction pattern of Form C and Form E mixture (above) and Form C (below) of Compound III-2 (hydrochloride salt).

FIG. 37B depicts the characterization of Form C and Form E mixture of Compound III-2 by $^1$H nuclear magnetic resonance ($^1$H NMR) in D6-DMSO at 400 MHz.

FIG. 37C depicts the characterization of Form C and Form E mixture of Compound III-2 by thermogravimetric analysis (above) and differential scanning calorimetry (below).

FIG. 37D depicts an XRPD diffractogram of Compound III-2 Form C and Form E mixture (above) after storage at 40° C./75% RH for 7 days (below).

FIG. 38A depicts an X-ray diffraction pattern of Form D of Compound III-2 (hydrochloride salt).

FIG. 38B depicts the characterization of Form D of Compound III-2 by $^1$H nuclear magnetic resonance ($^1$H NMR) in D6-DMSO at 400 MHz.

FIG. 38C depicts the characterization of Form D of Compound III-2 by thermogravimetric analysis (above) and differential scanning calorimetry (below).

Figure 38A:
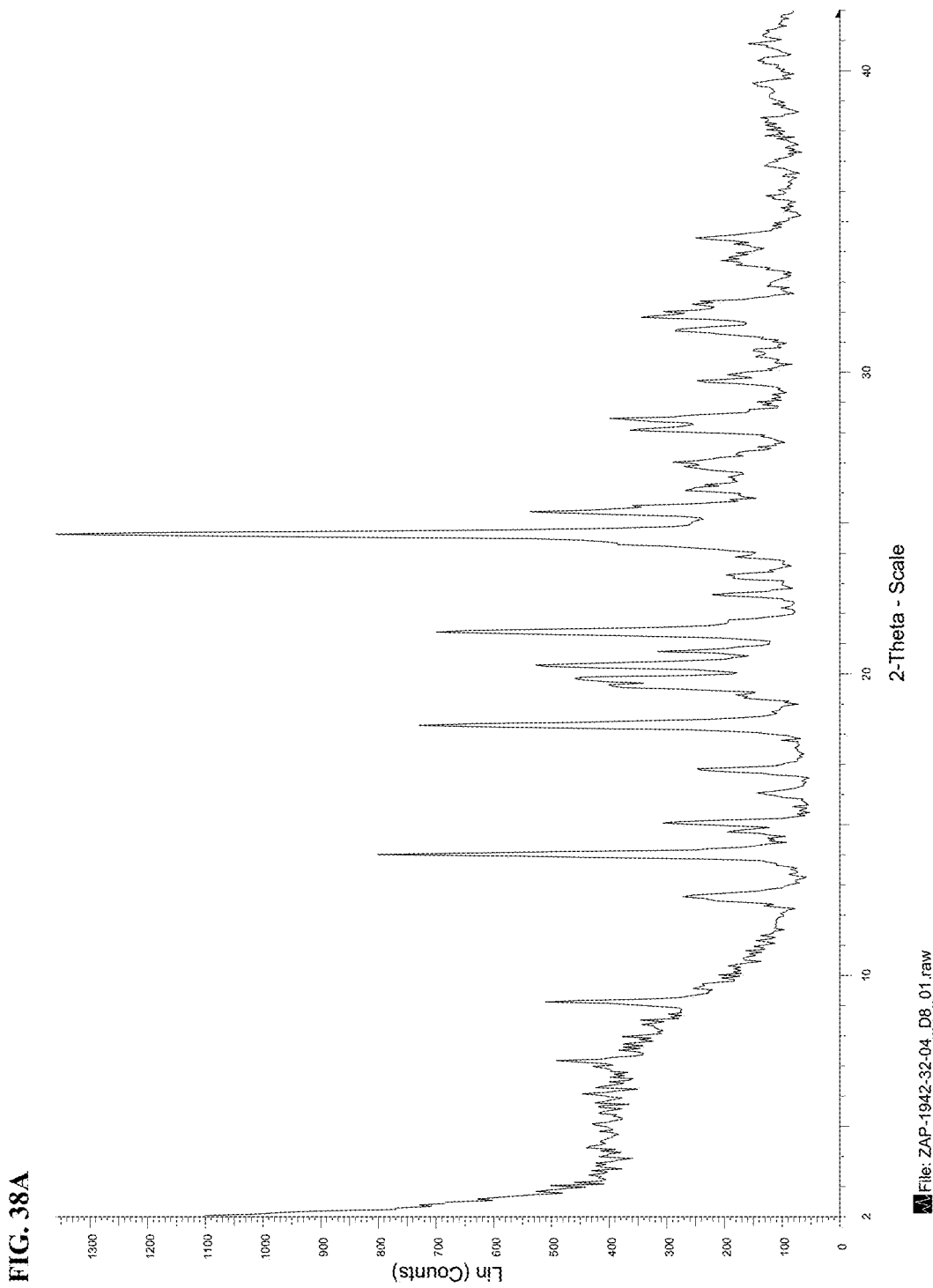
Figure 38B:
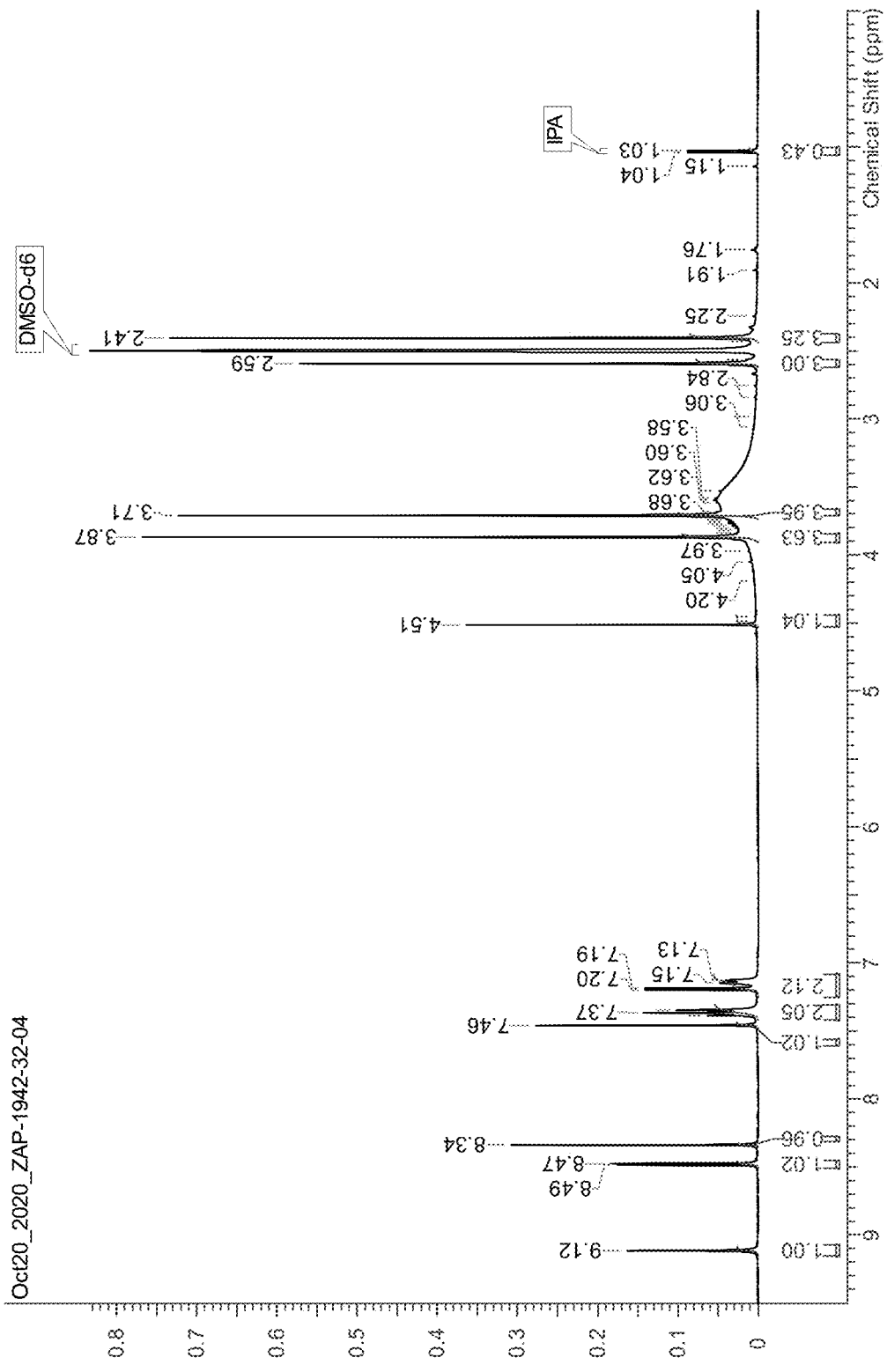
Figure 38C:
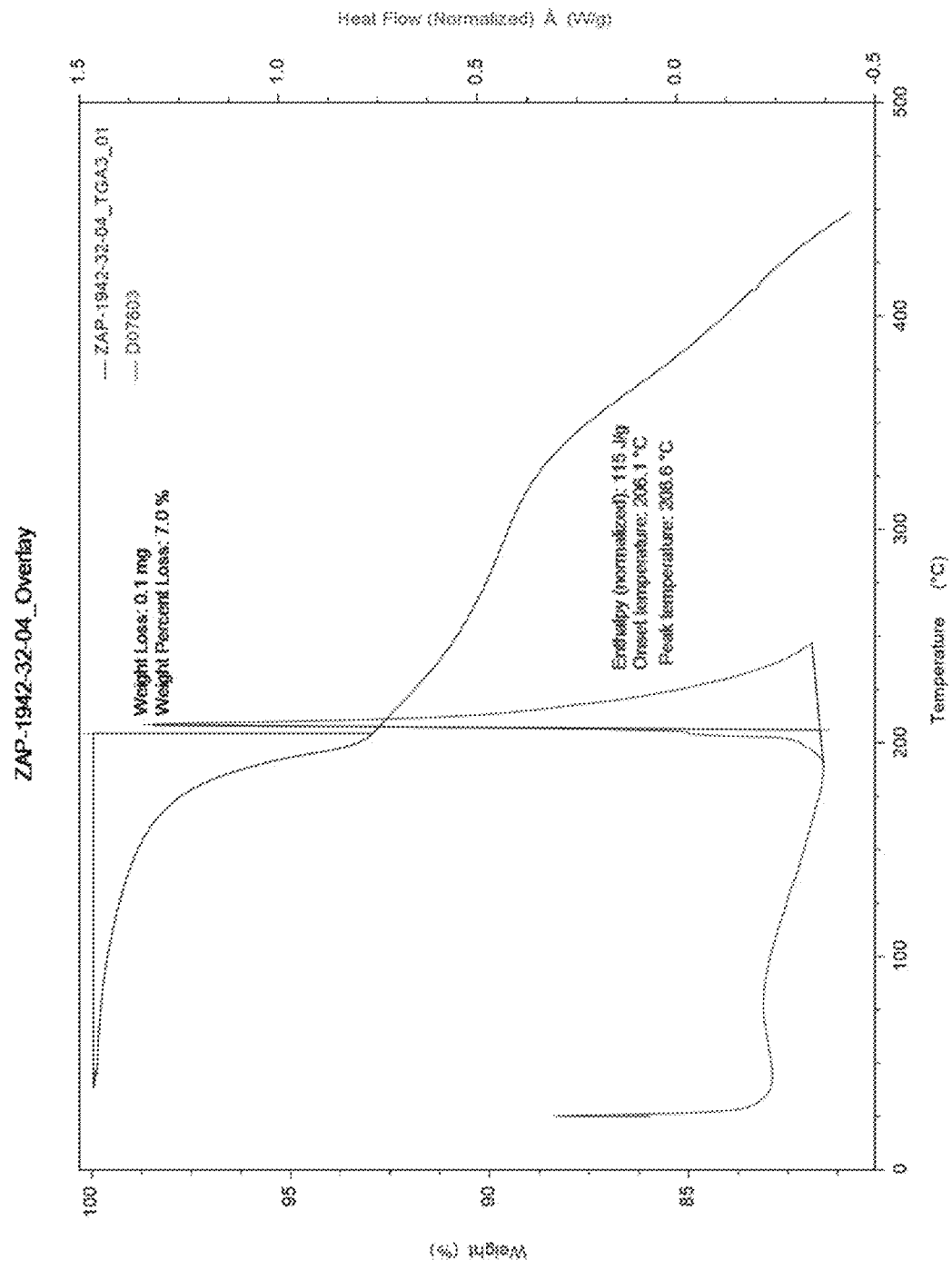
Figure 38D:
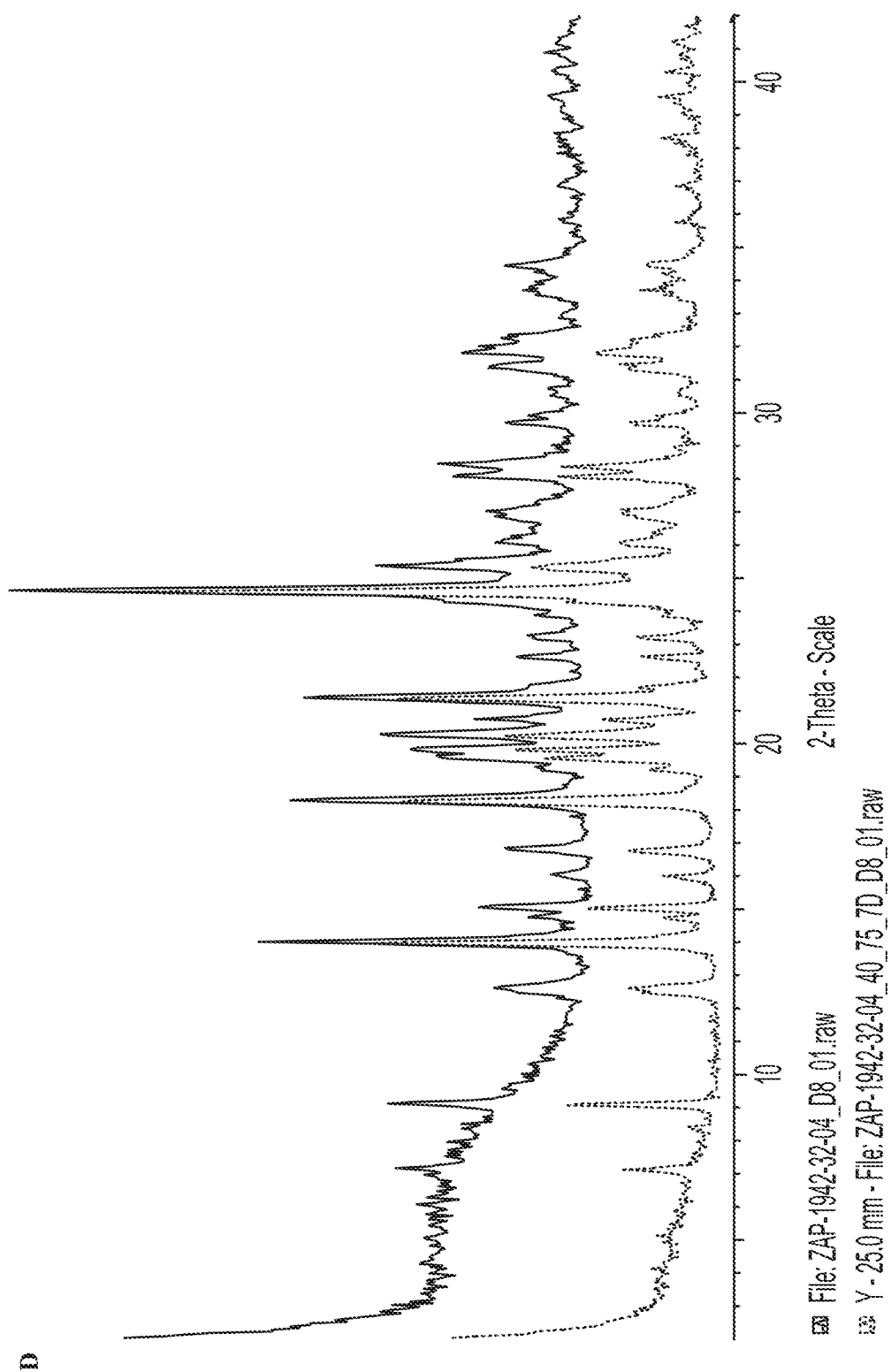

FIG. 38D depicts an XRPD diffractogram of Compound III-2 Form D (above) after storage at 40° C./75% RH for 7 days (below).

Figure 39A:
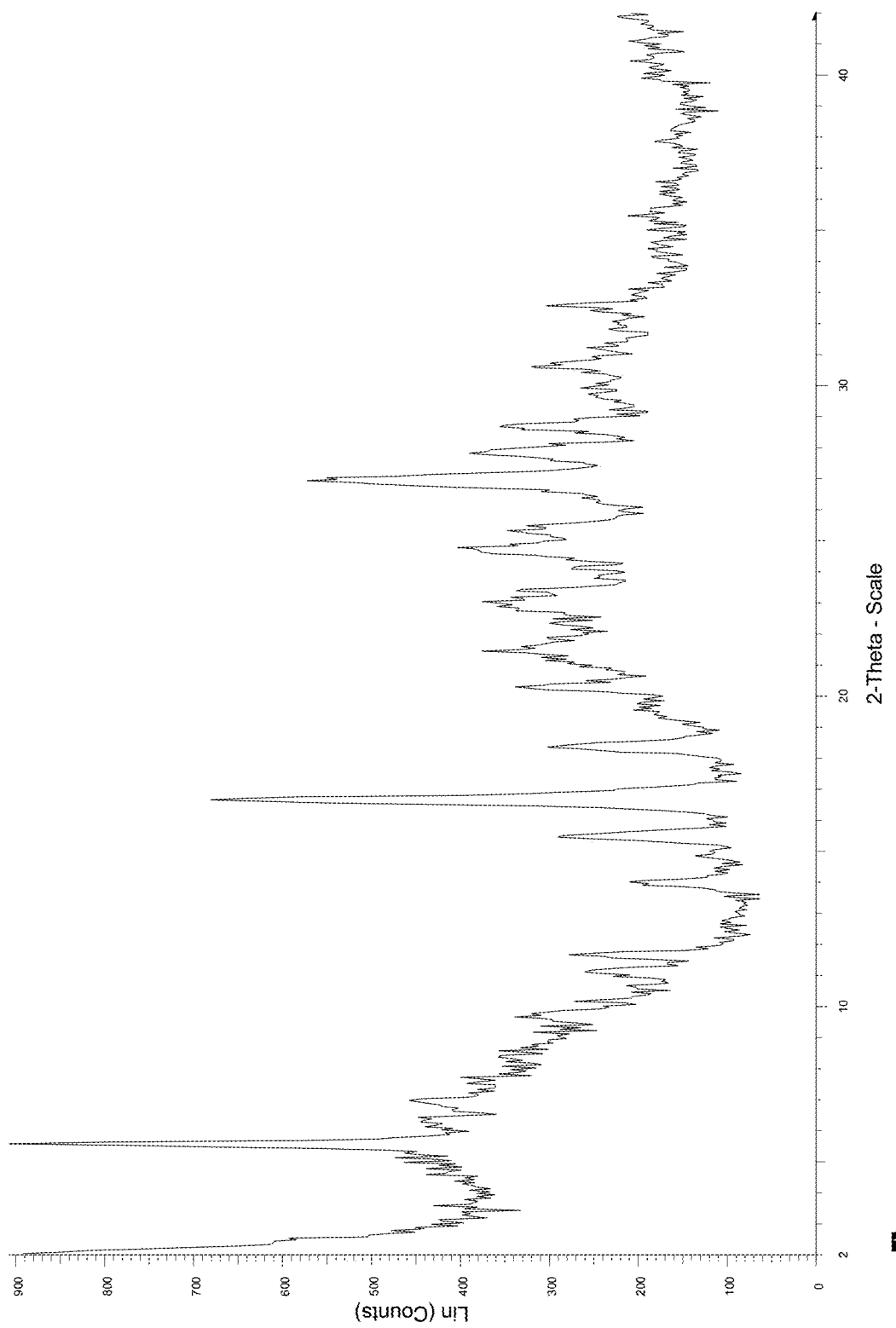

FIG. 39A depicts an X-ray diffraction pattern of Form A of Compound III-3 (hydrobromide salt).

Figure 39B:
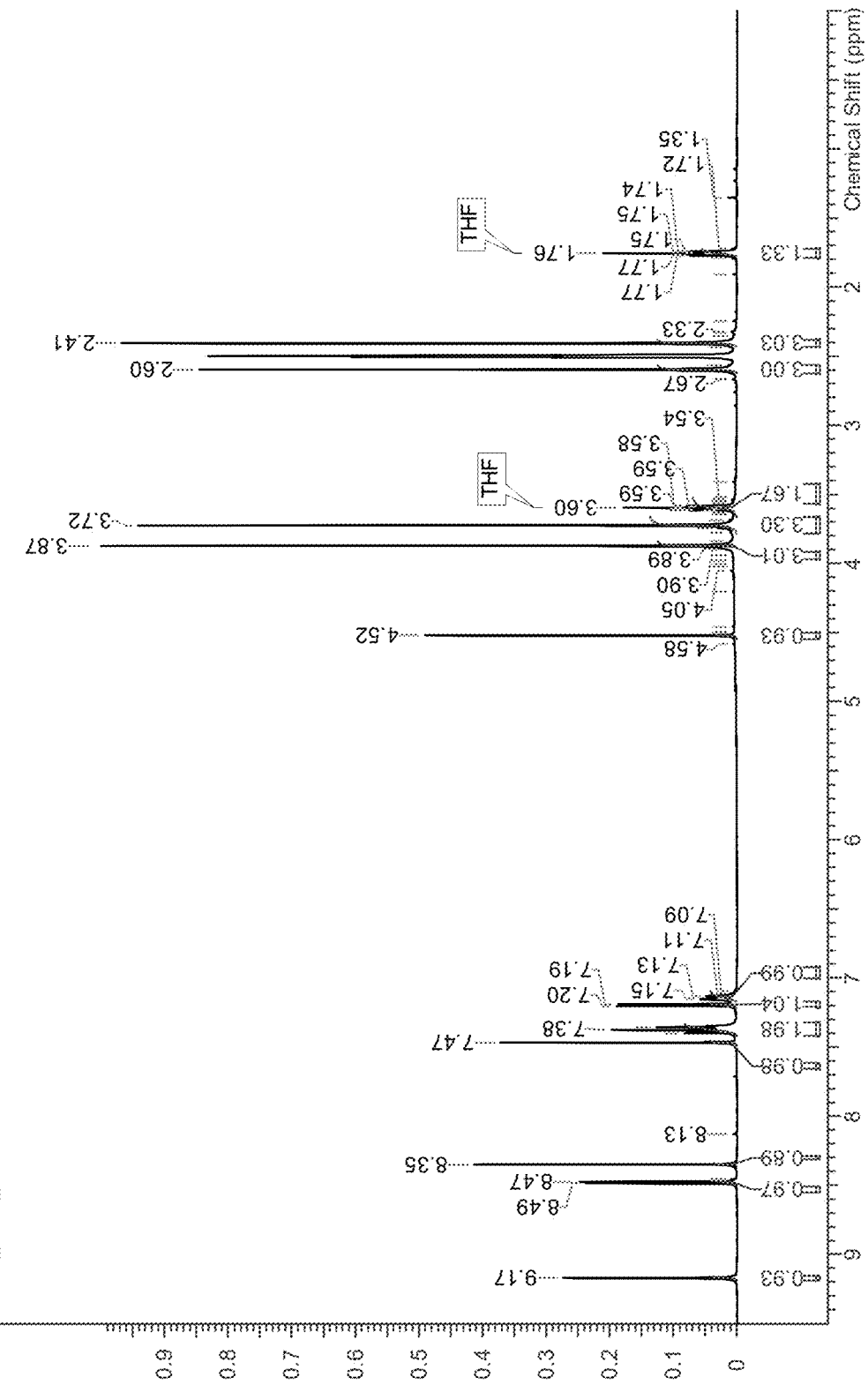

FIG. 39B depicts the characterization of Form A of Compound III-3 by $^1$H nuclear magnetic resonance ($^1$H NMR) in D6-DMSO at 400 MHz.

Figure 39C:
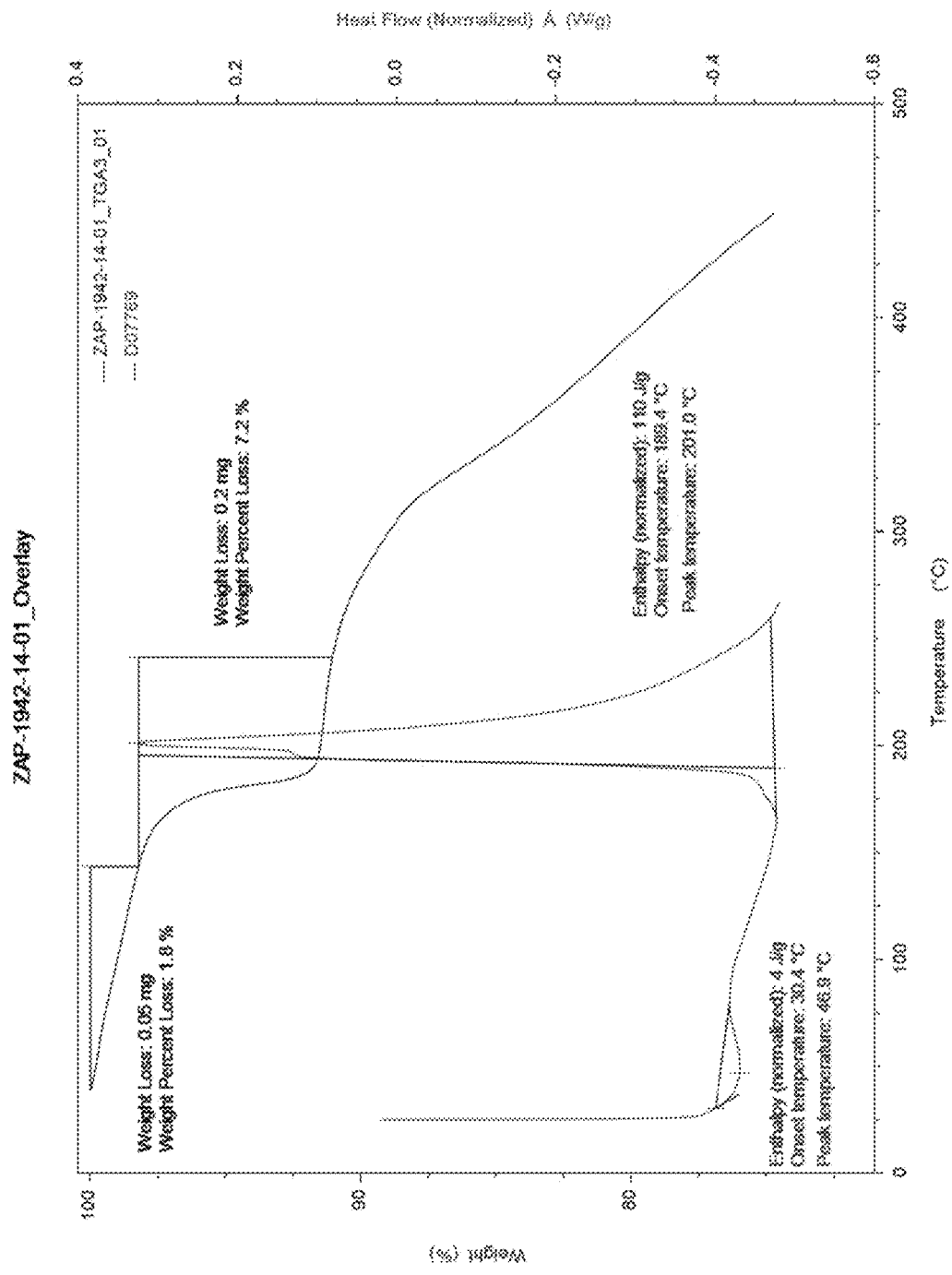

FIG. 39C depicts the characterization of Form A of Compound III-3 by thermogravimetric analysis (above) and differential scanning calorimetry (below).

Figure 39D:
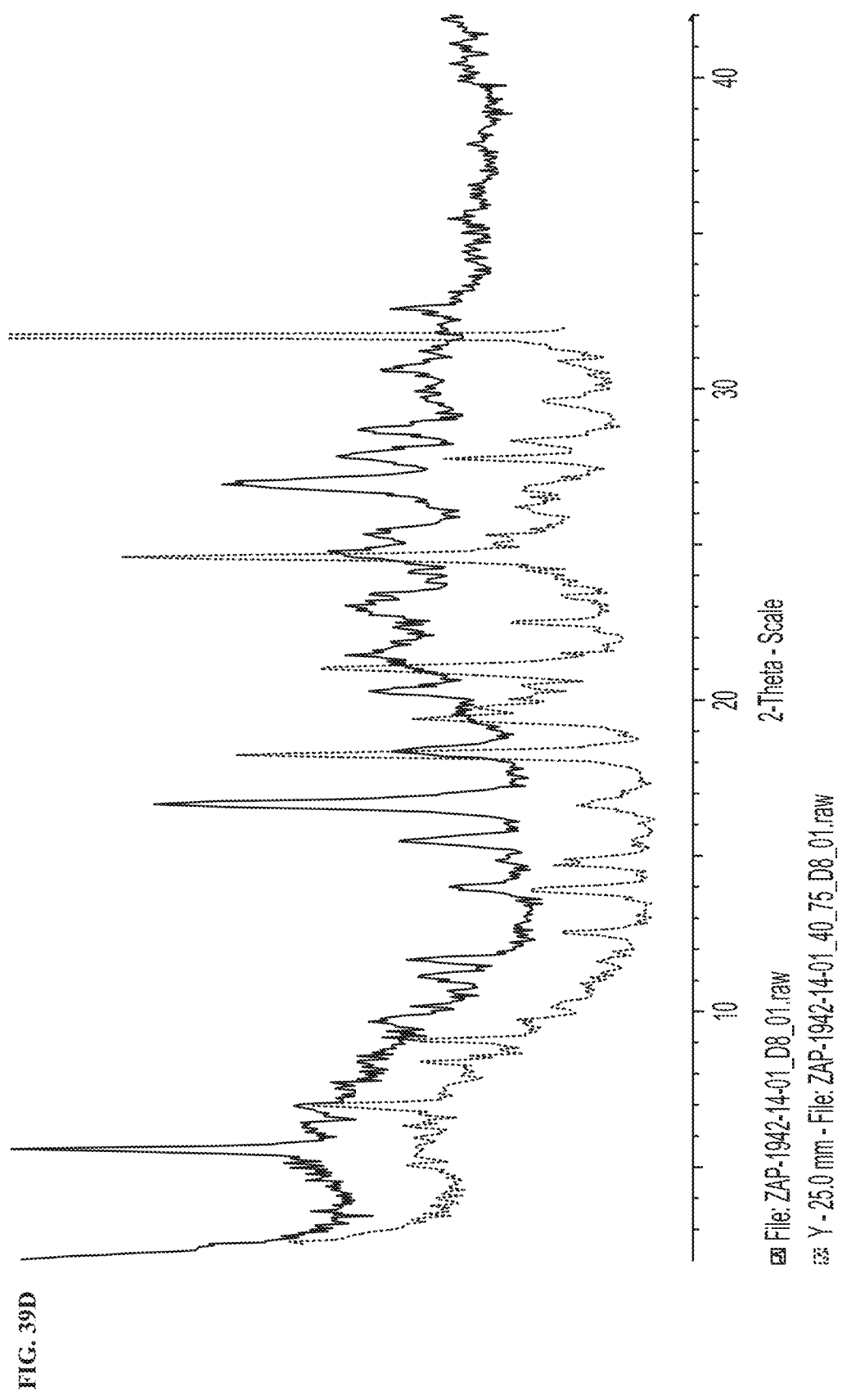

FIG. 39D depicts an XRPD diffractogram of Compound III-3 Form A (above) after storage at 40° C./75% RH for 7 days (below).

Figure 40A:
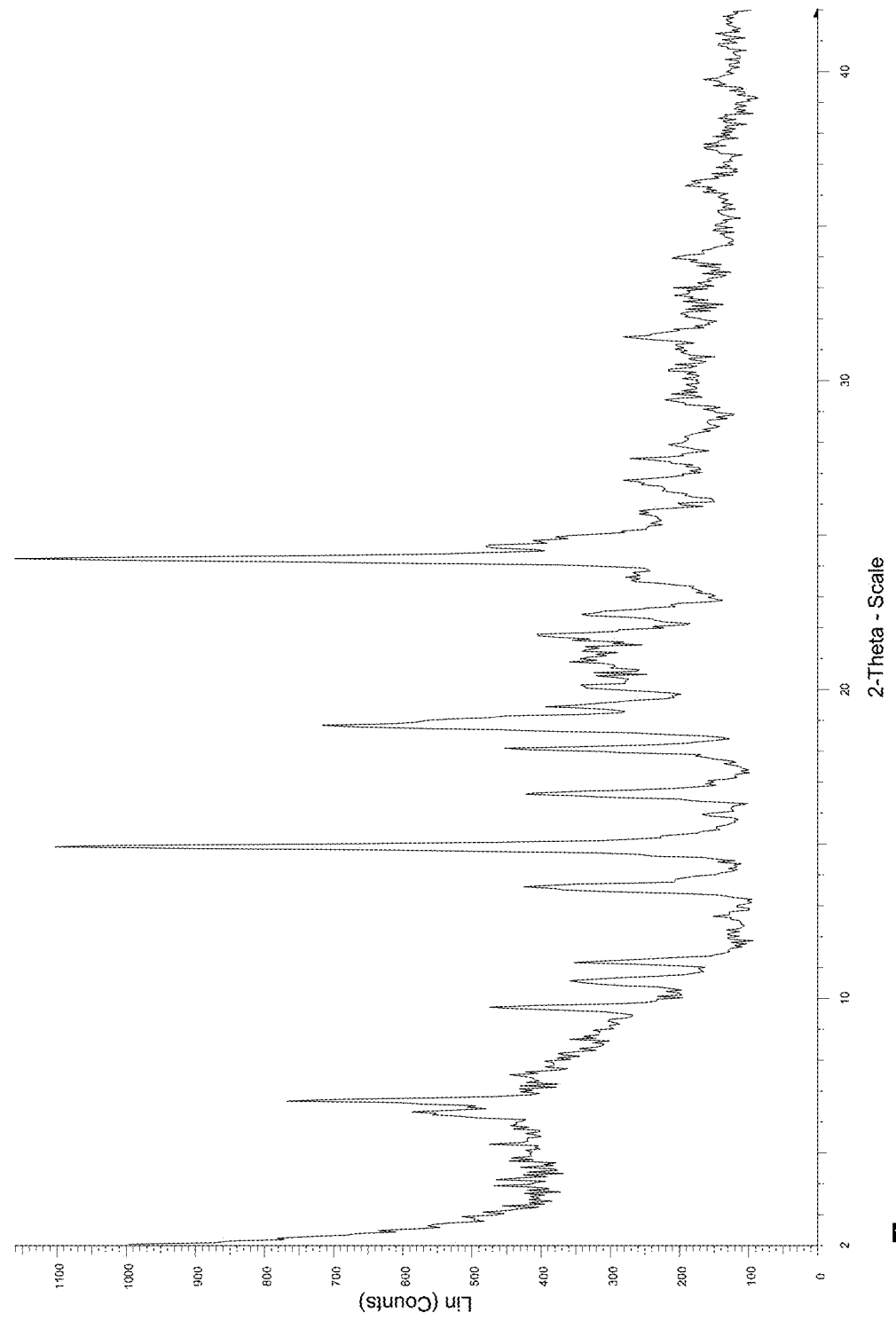

FIG. 40A depicts an X-ray diffraction pattern of Form A of Compound III-4 (sulfate salt).

Figure 40B:
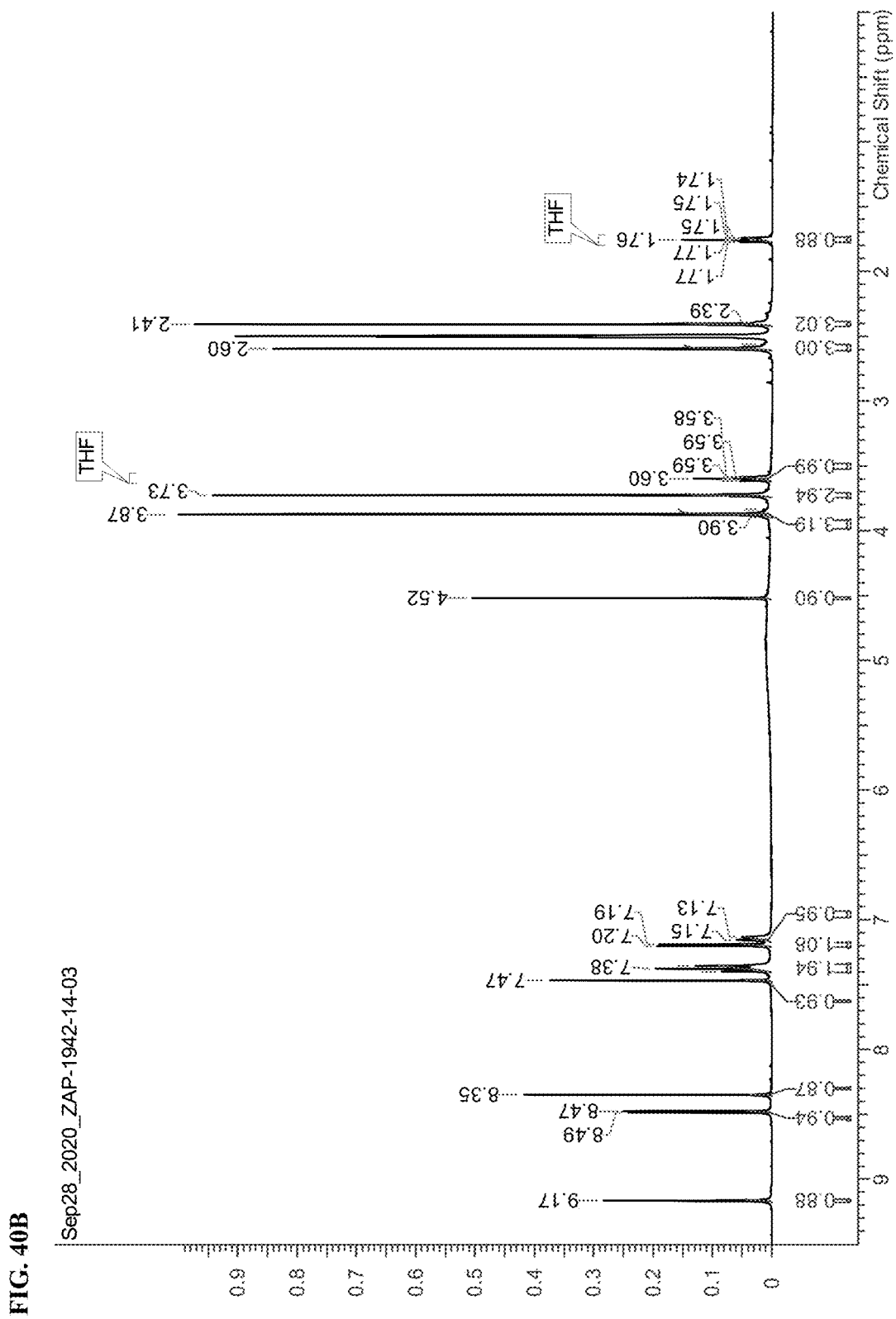

FIG. 40B depicts the characterization of Form A of Compound III-4 by $^1$H nuclear magnetic resonance ($^1$H NMR) in D6-DMSO at 400 MHz.

Figure 40C:
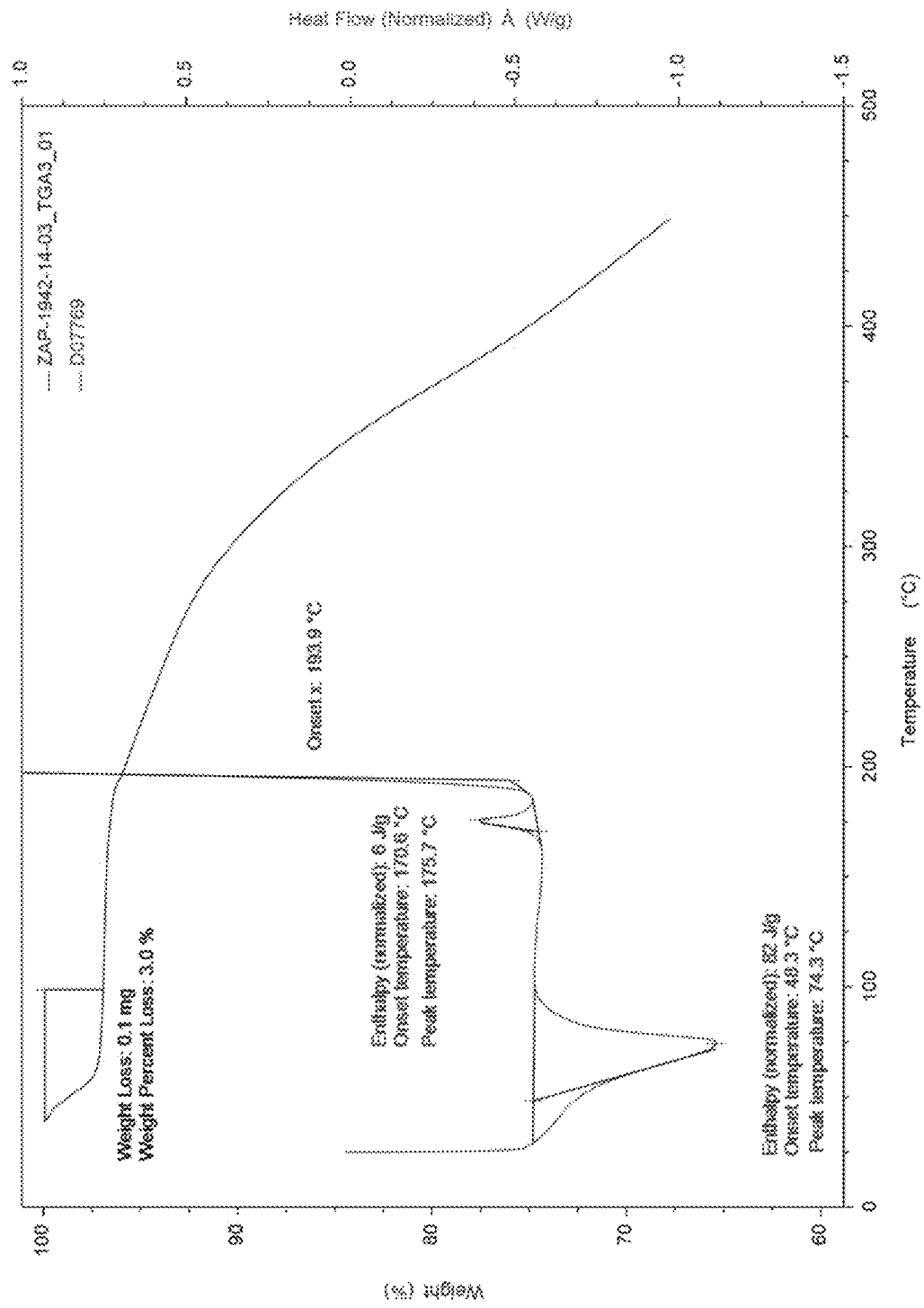

FIG. 40C depicts the characterization of Form A of Compound III-4 by thermogravimetric analysis (above) and differential scanning calorimetry (below).

Figure 40D:
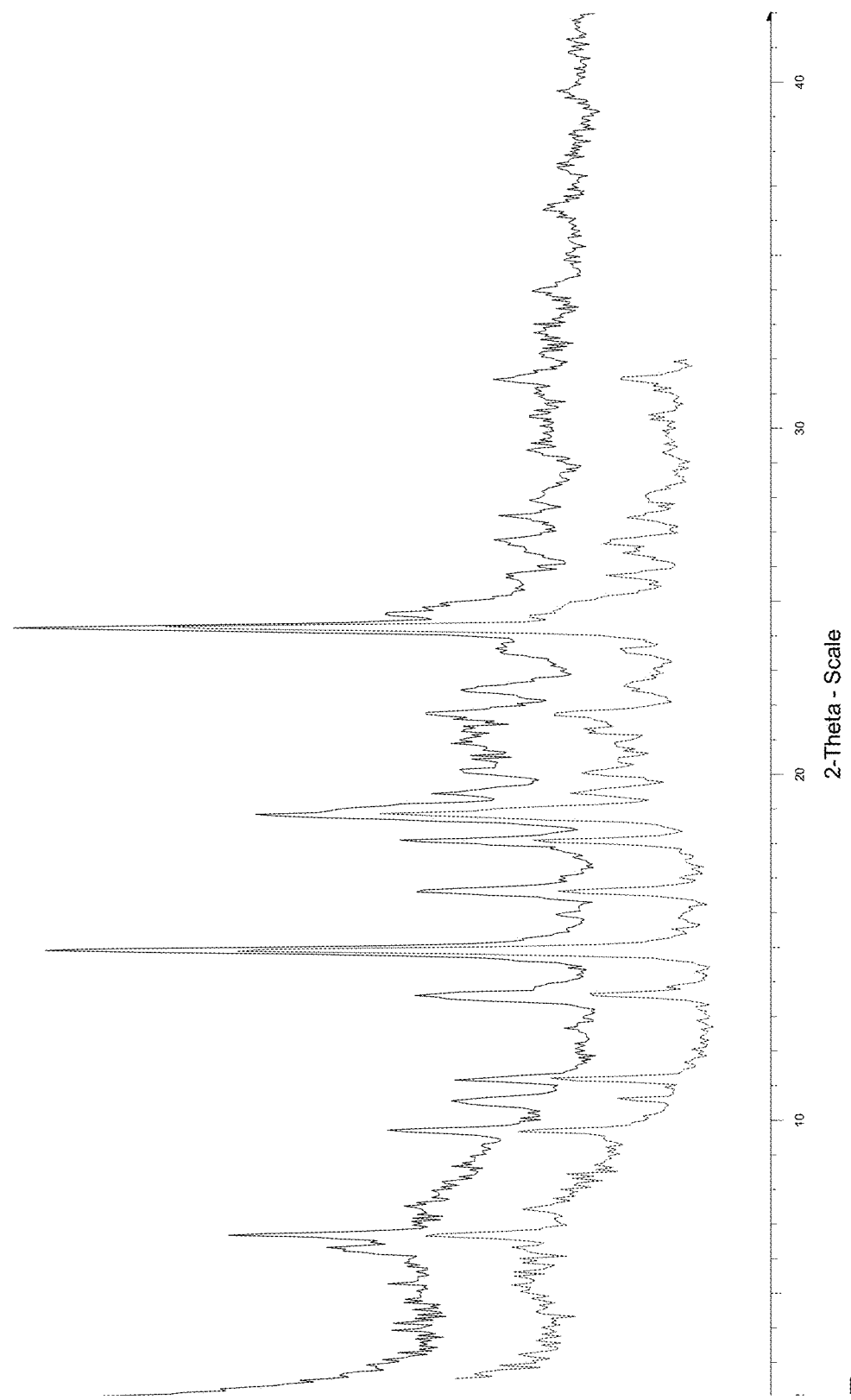

FIG. 40D depicts an XRPD diffractogram of Compound III-4 Form A (above) after storage at 40° C./75% RH for 7 days (below).

Figure 41A:
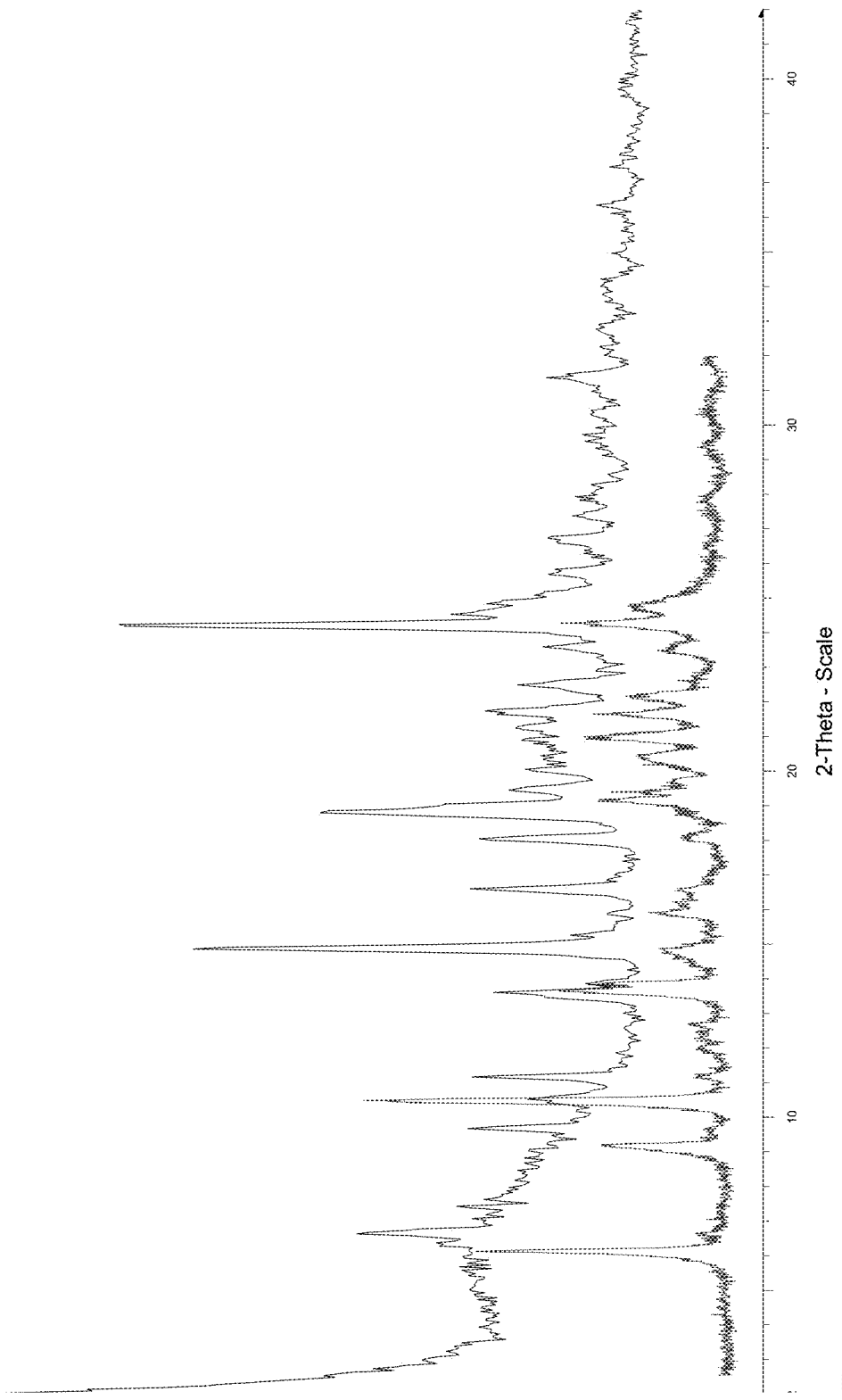

FIG. 41A depicts an X-ray diffraction pattern of Form B (below) and Form A (above) of Compound III-4 (sulfate salt).

Figure 41B:
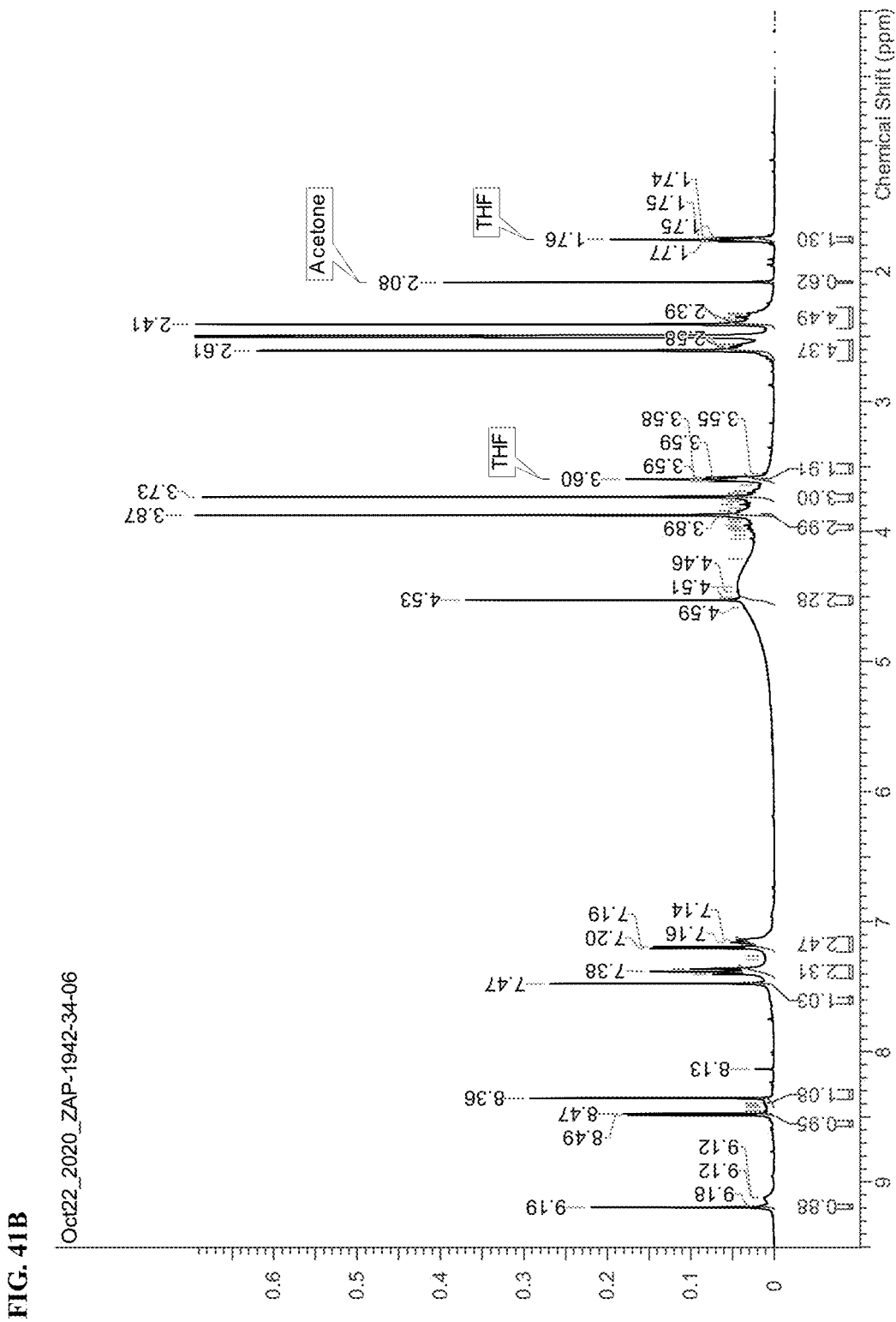

FIG. 41B depicts the characterization of Form A of Compound III-4 by $^1$H nuclear magnetic resonance ($^1$H NMR) in D6-DMSO at 400 MHz.

Figure 41C:
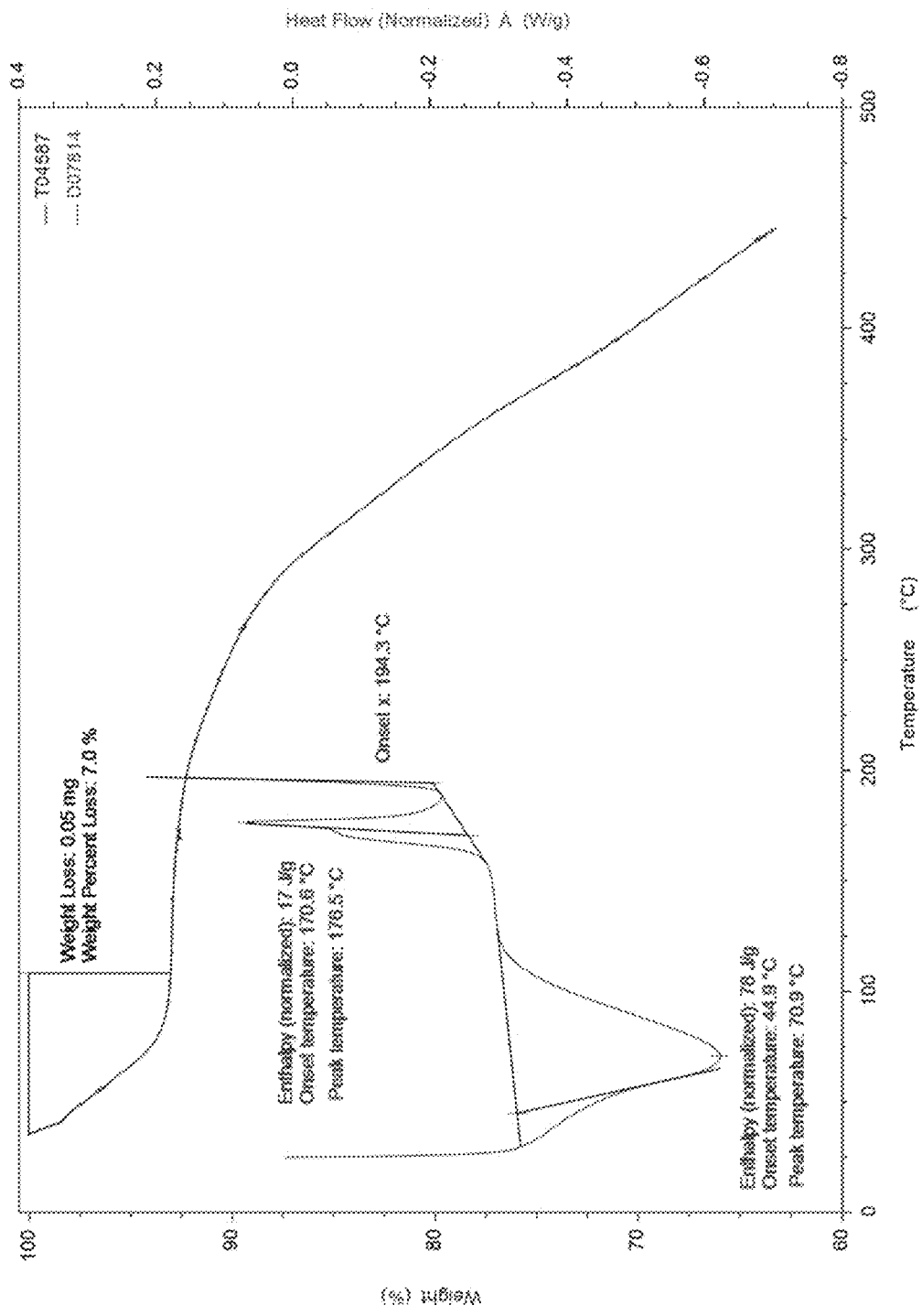

FIG. 41C depicts the characterization of Form A of Compound III-4 by thermogravimetric analysis (above) and differential scanning calorimetry (below).

Figure 41D:
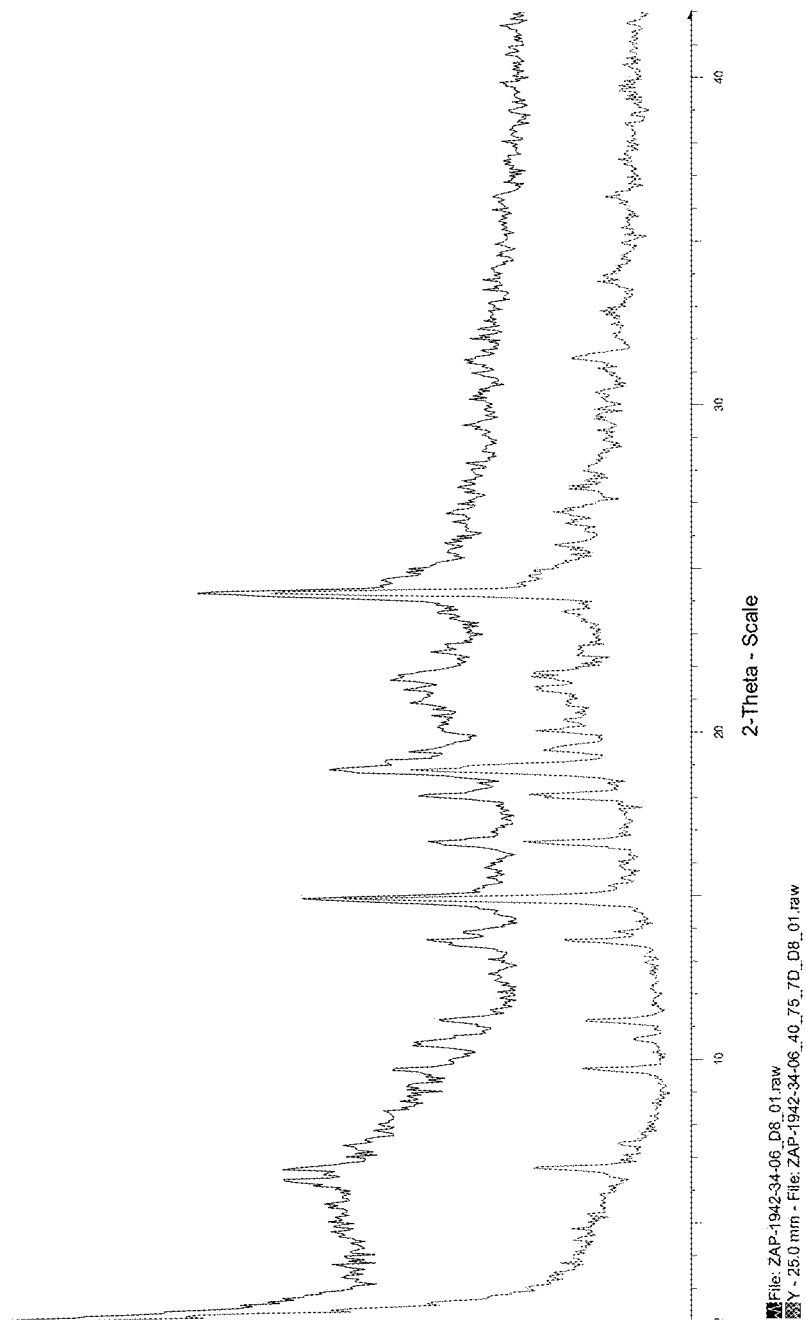

FIG. 41D depicts an XRPD diffractogram of Compound III-4 Form A (above) after storage at 40° C./75% RH for 7 days (below).

Figure 42A:
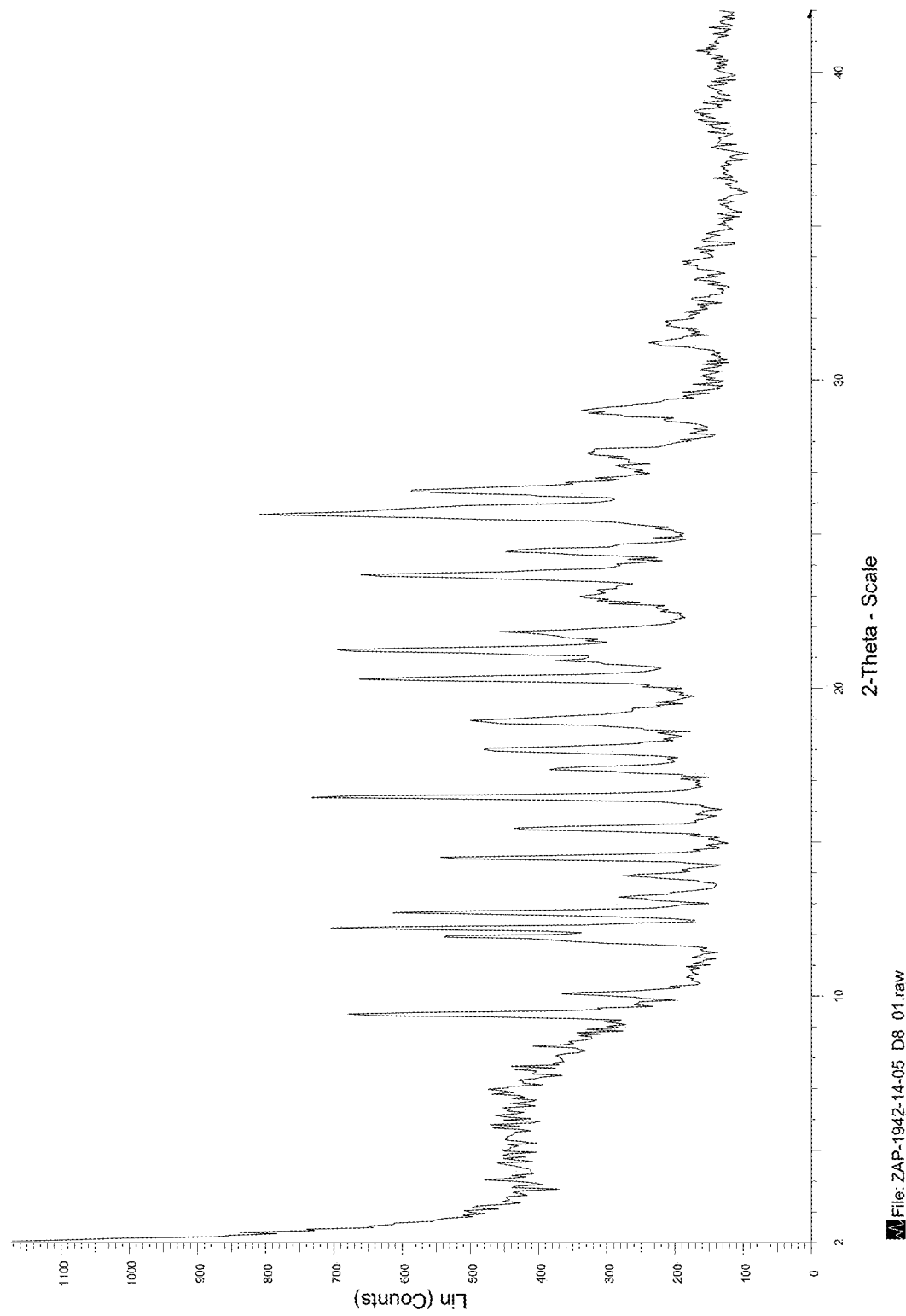

FIG. 42A depicts an X-ray diffraction pattern of Form A of Compound III-5 (mesylate salt).

Figure 42B:
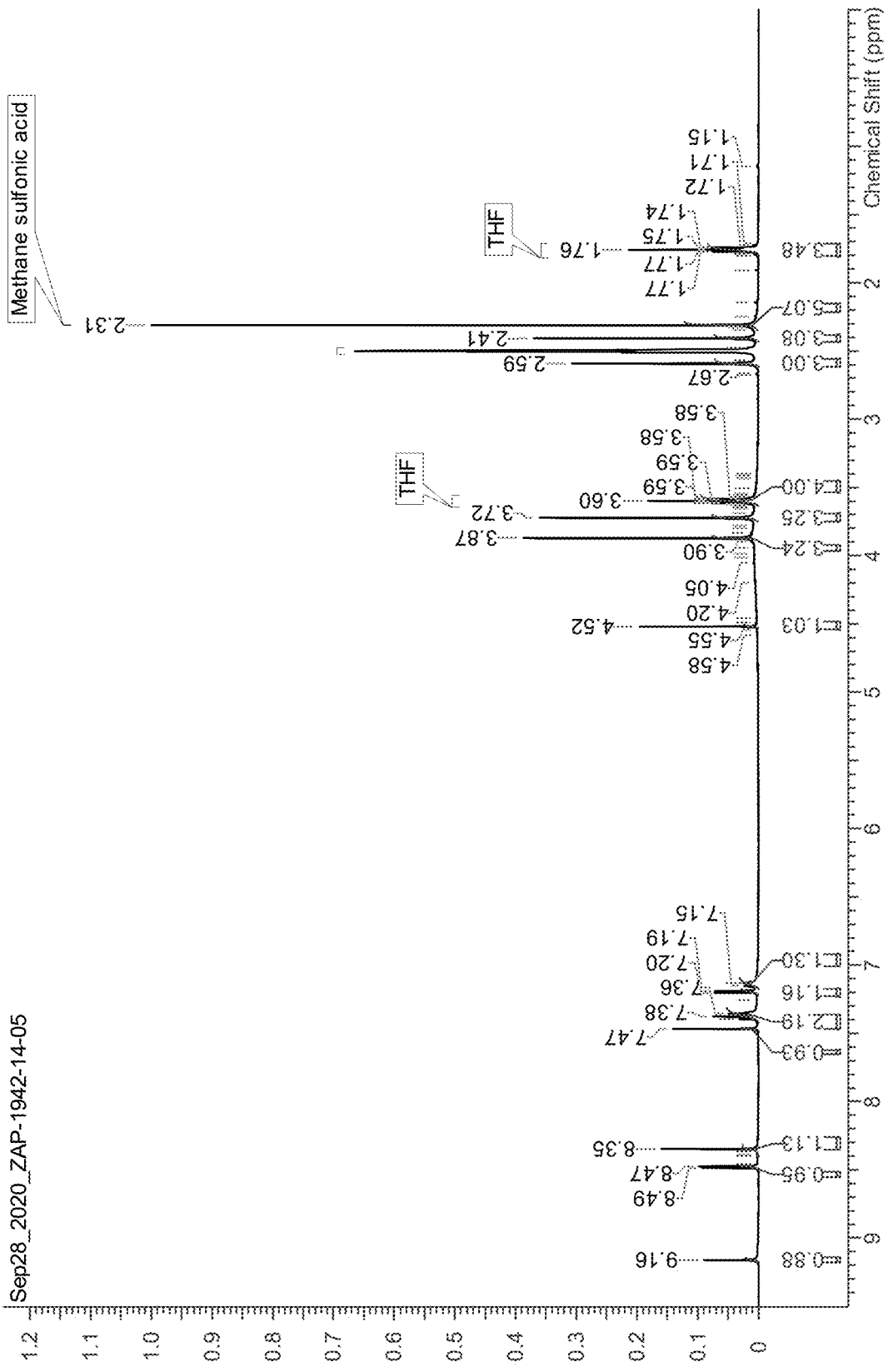

FIG. 42B depicts the characterization of Form A of Compound III-5 by $^1$H nuclear magnetic resonance ($^1$H NMR) in D6-DMSO at 400 MHz.

Figure 42C:
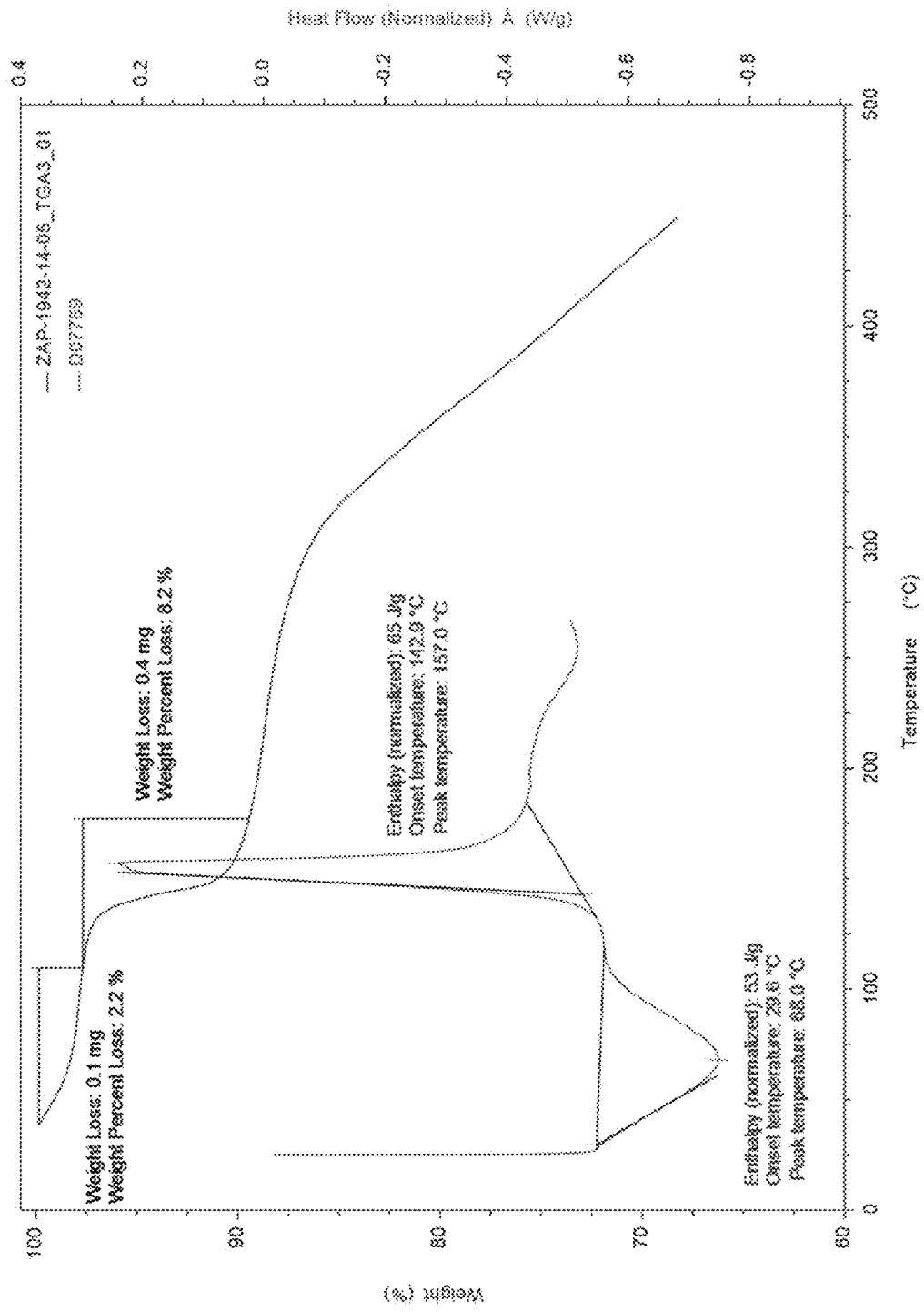

FIG. 42C depicts the characterization of Form A of Compound III-5 by thermogravimetric analysis (above) and differential scanning calorimetry (below).

Figure 42D:
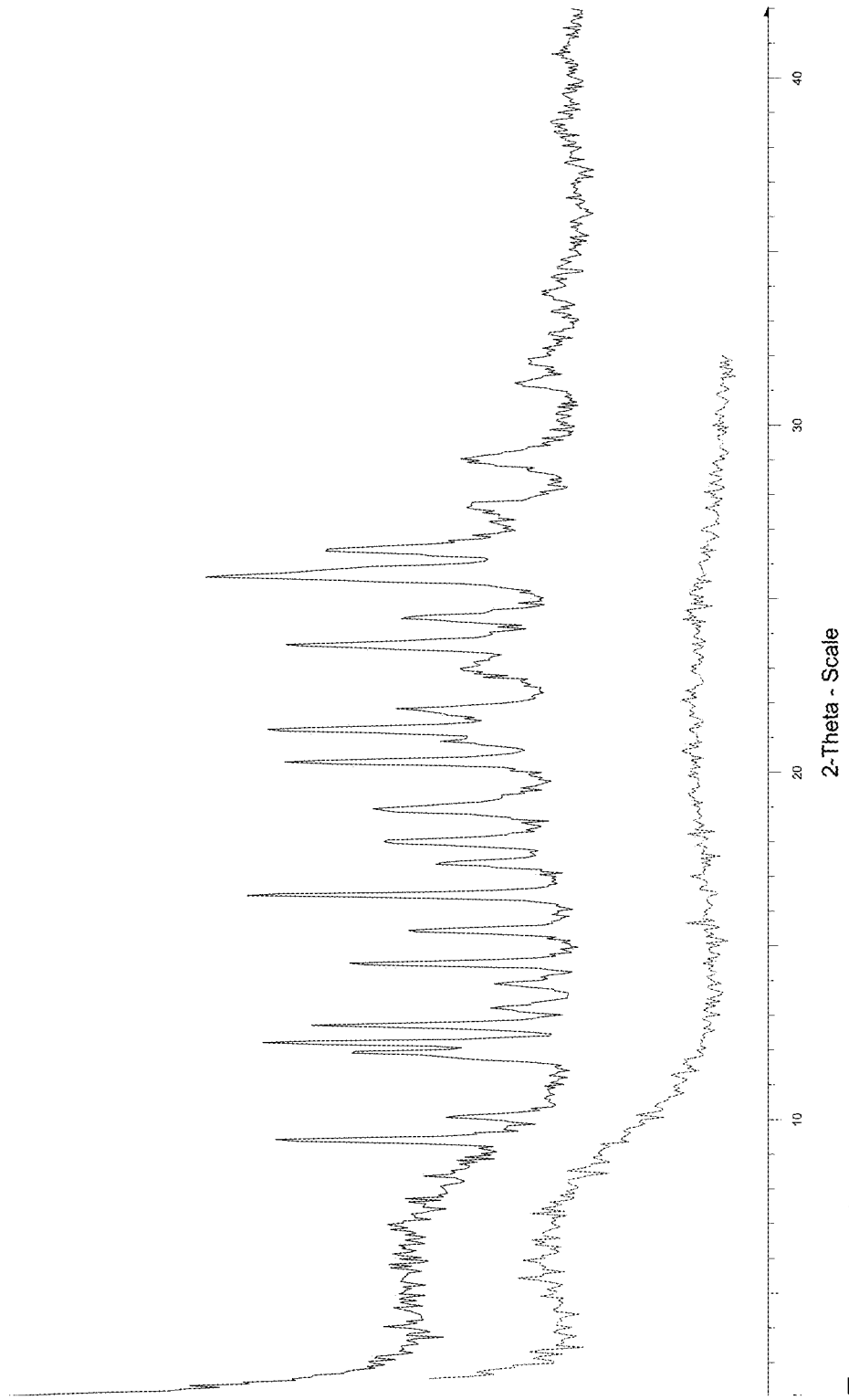

FIG. 42D depicts an XRPD diffractogram of Compound III-5 Form A (above) after storage at 40° C./75% RH for 7 days (below).

Figure 43A:
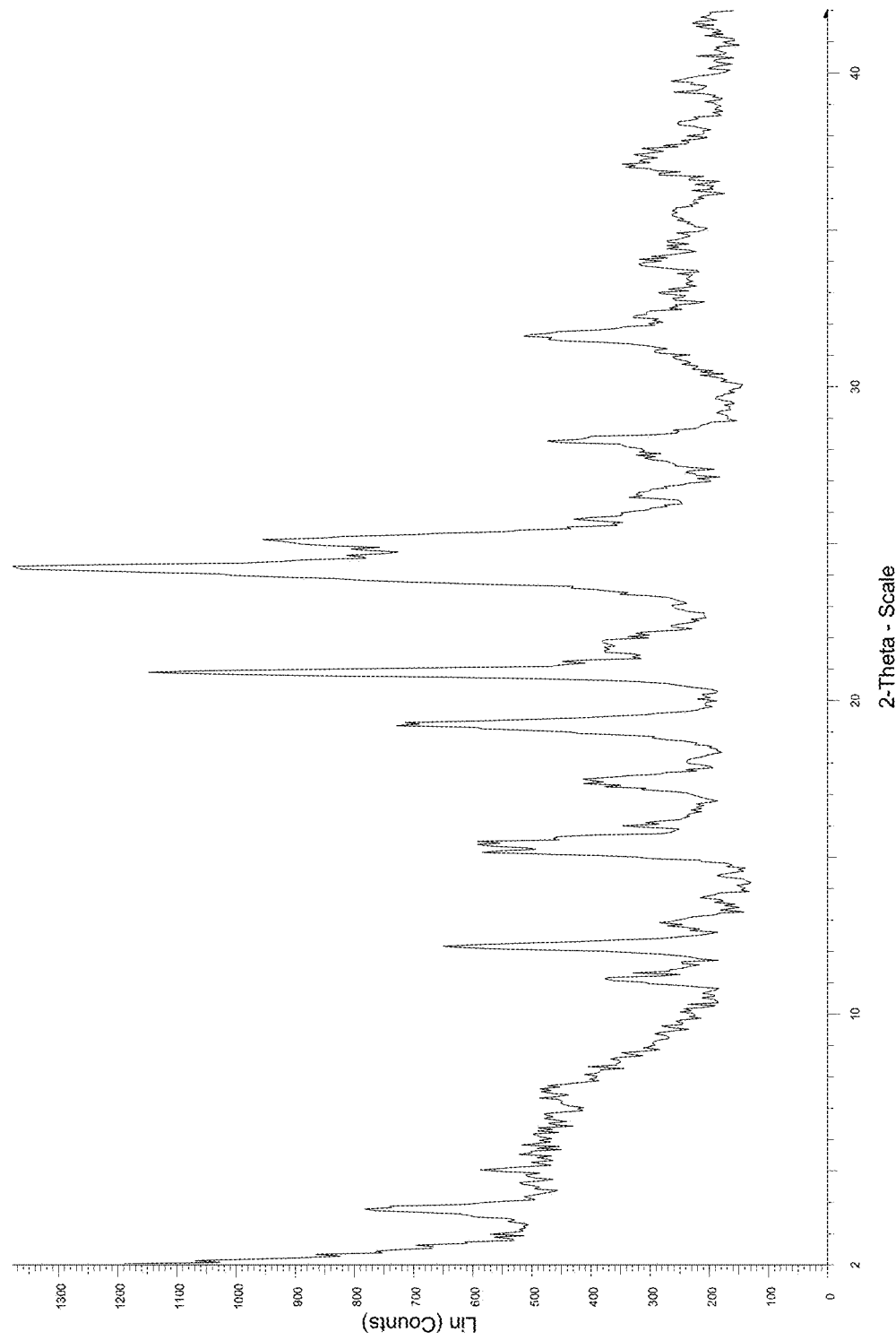

FIG. 43A depicts an X-ray diffraction pattern of Form A of Compound III-6 (tartrate salt).

Figure 43B:
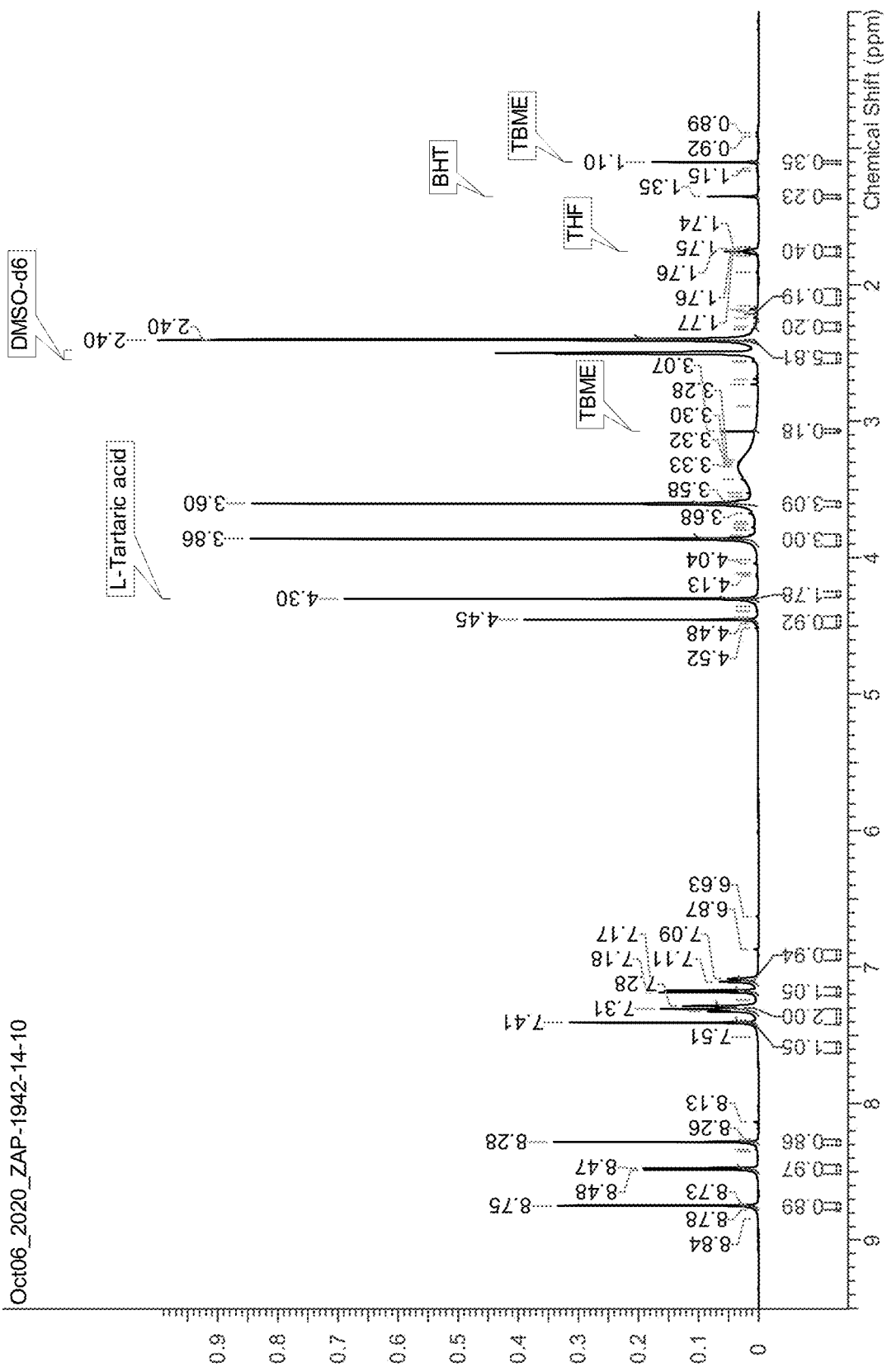

FIG. 43B depicts the characterization of Form A of Compound III-6 by $^1$H nuclear magnetic resonance ($^1$H NMR) in D6-DMSO at 400 MHz.

Figure 43C:
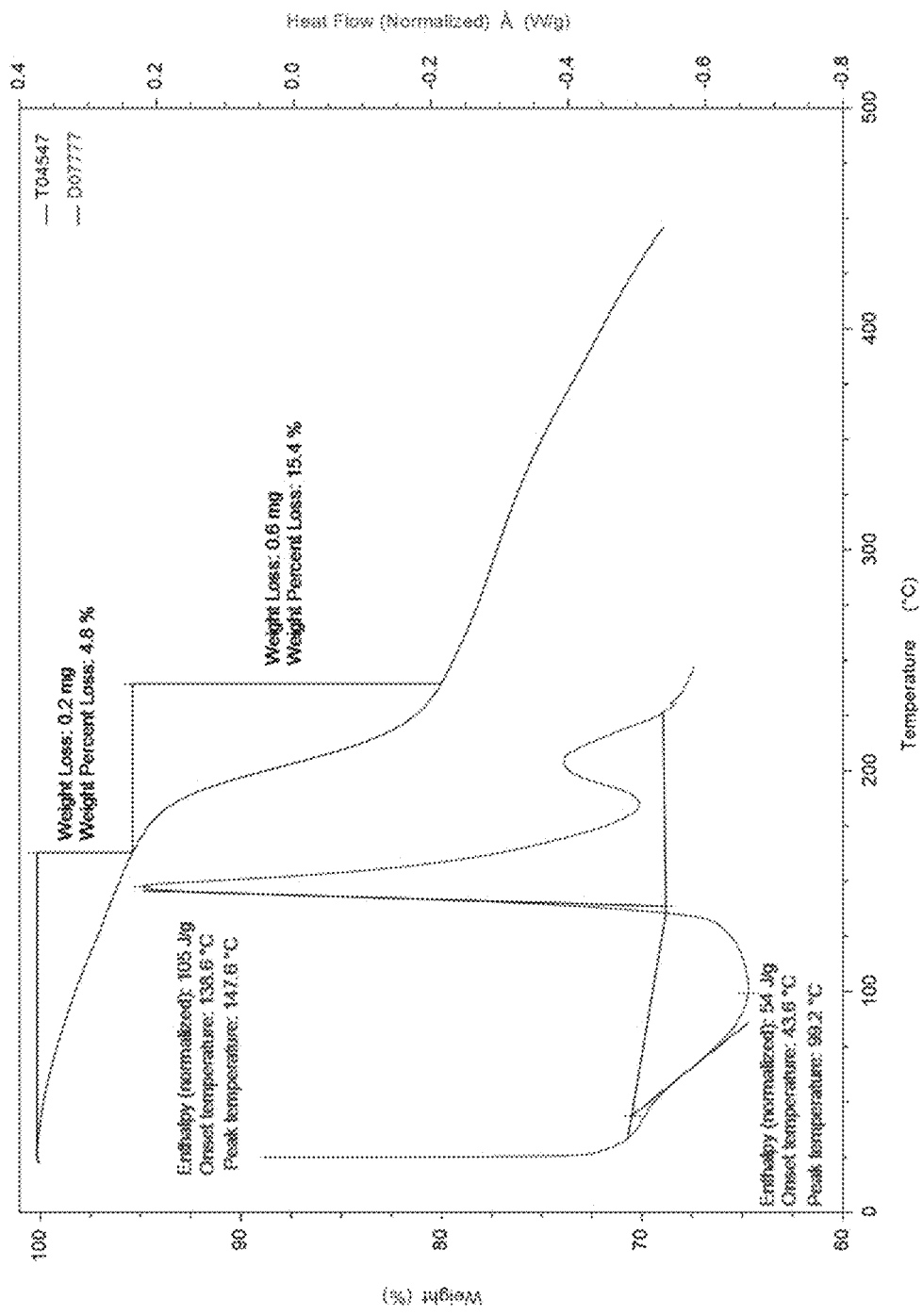

FIG. 43C depicts the characterization of Form A of Compound III-6 by thermogravimetric analysis (above) and differential scanning calorimetry (below).

Figure 43D:
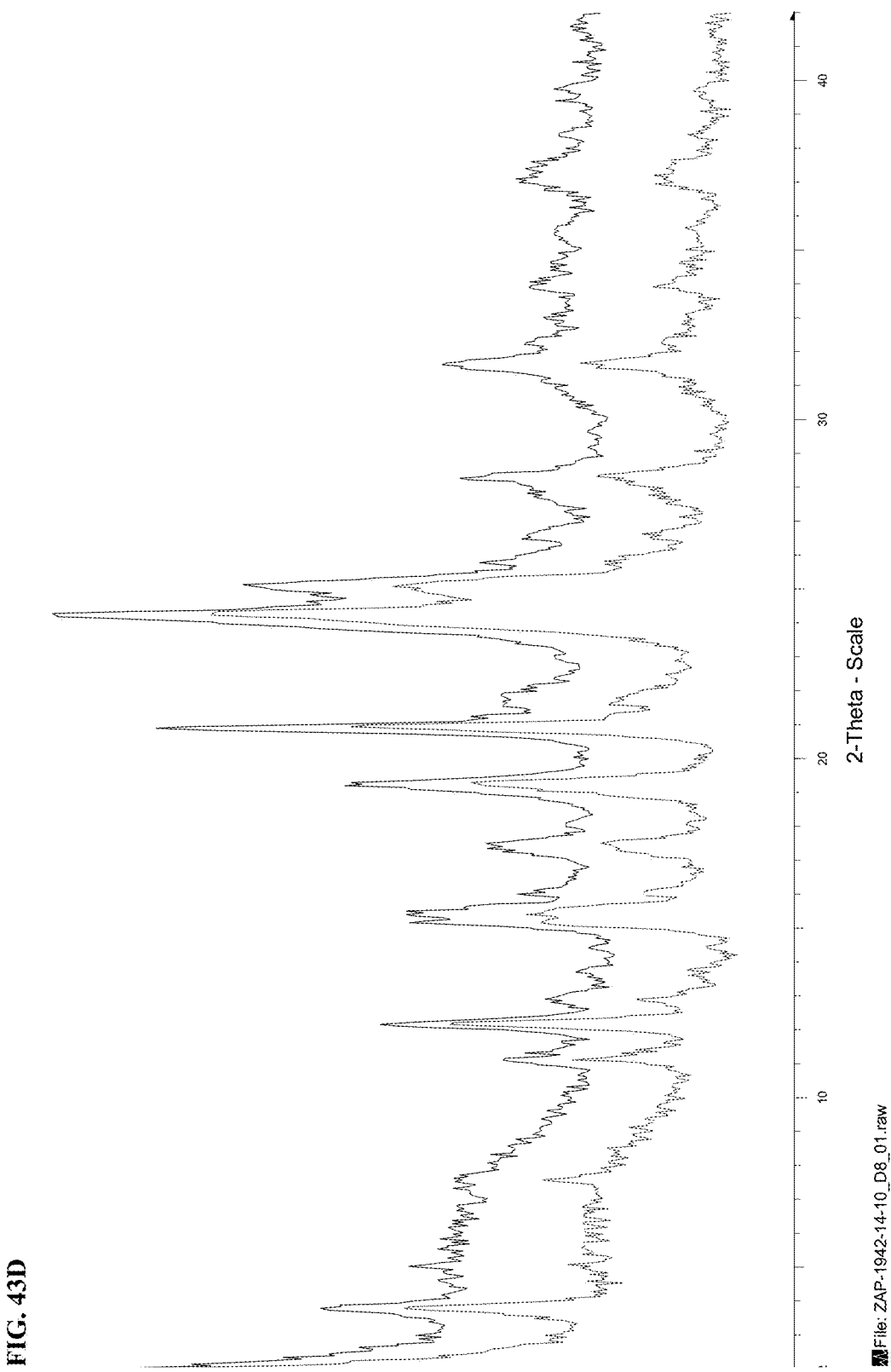

FIG. 43D depicts an XRPD diffractogram of Compound III-6 Form A (above) after storage at 40° C./75% RH for 7 days (below).

Figure 44A:
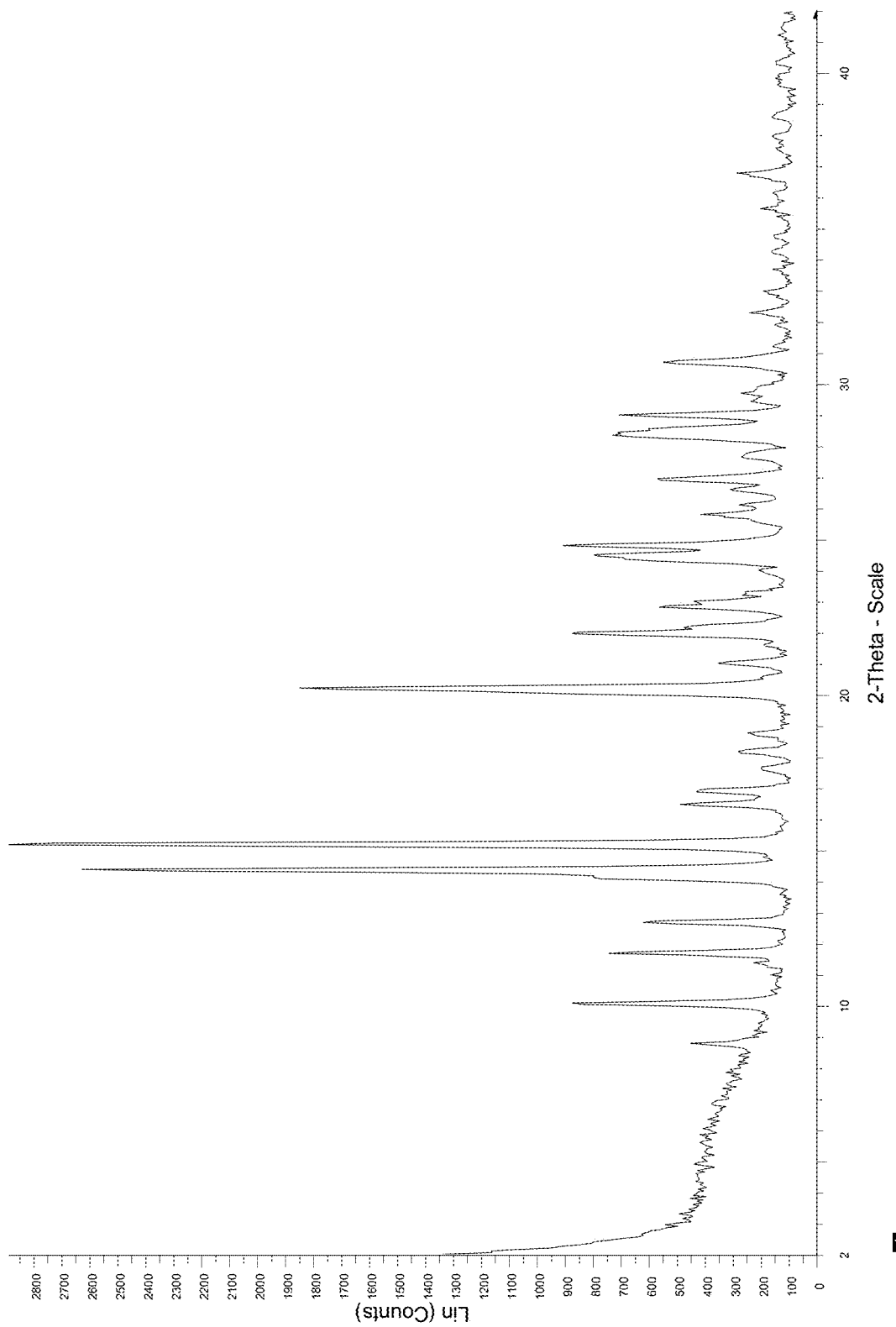

FIG. 44A depicts an X-ray diffraction pattern of Form A of Compound IV-1 (free form).

Figure 44B:
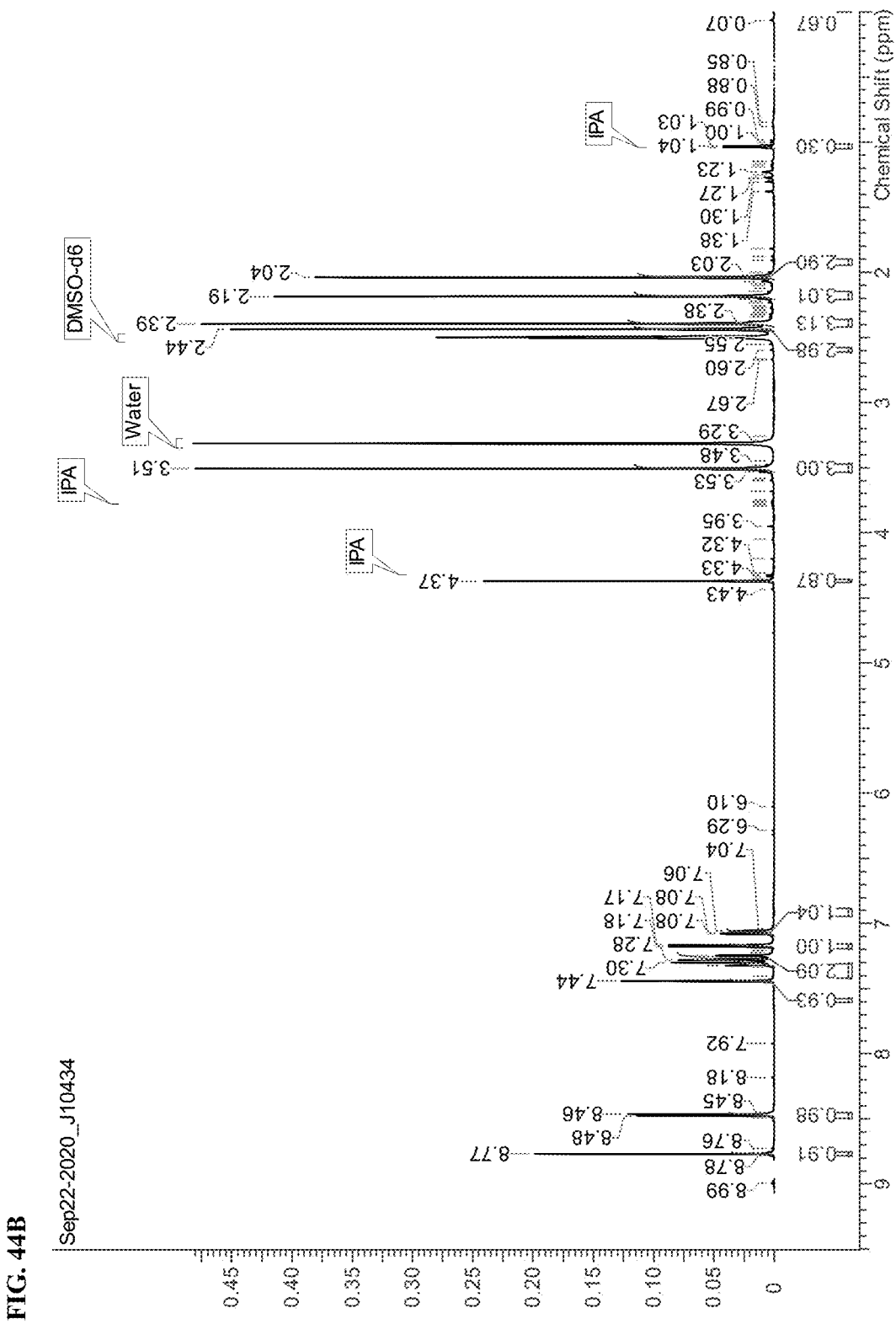

FIG. 44B depicts the characterization of Form A of Compound IV-1 by $^1$H nuclear magnetic resonance ($^1$H NMR) in D6-DMSO at 400 MHz.

Figure 44C:
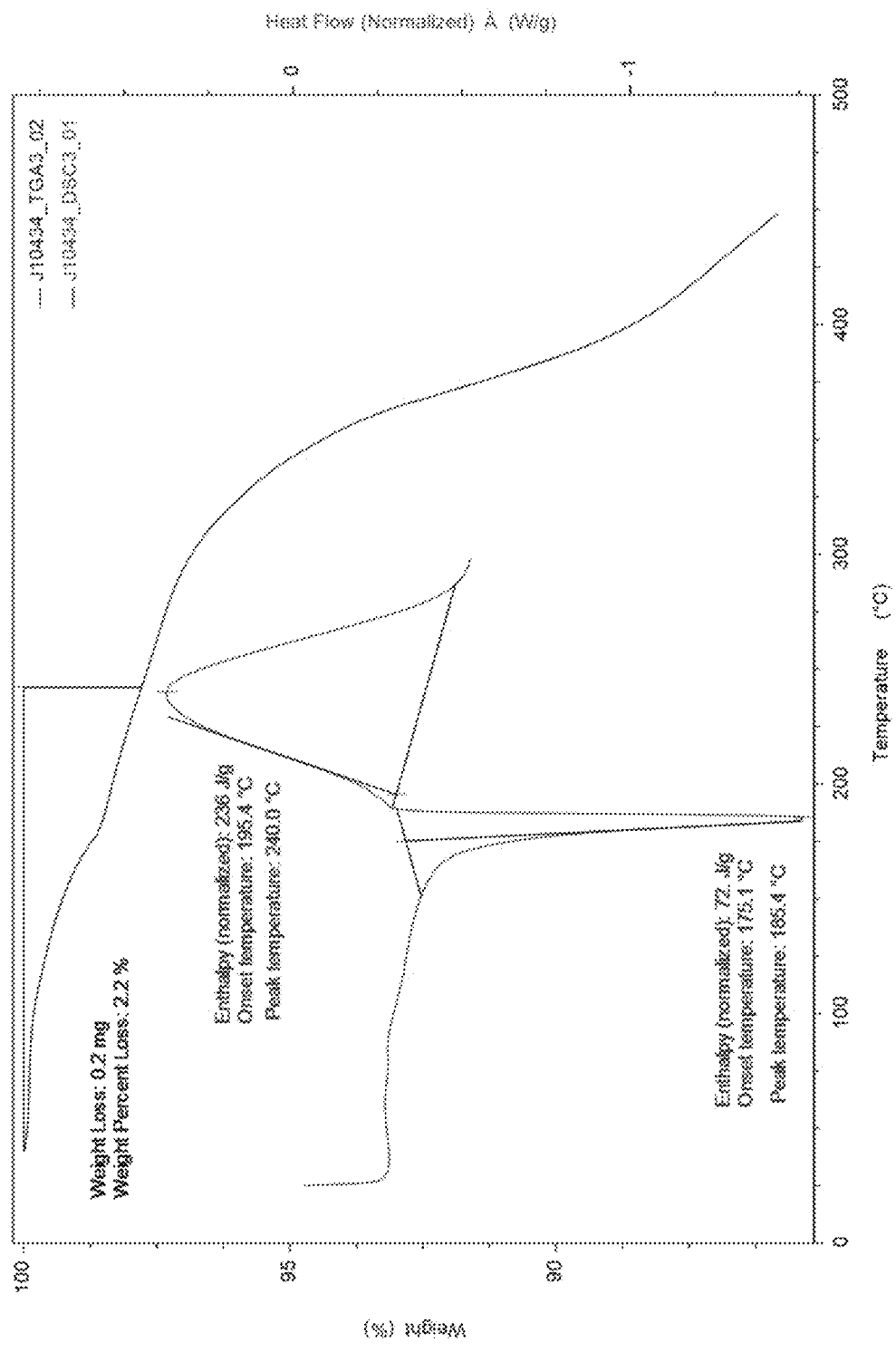

FIG. 44C depicts the characterization of Form A of Compound IV-1 by thermogravimetric analysis (above) and differential scanning calorimetry (below).

Figure 44D:
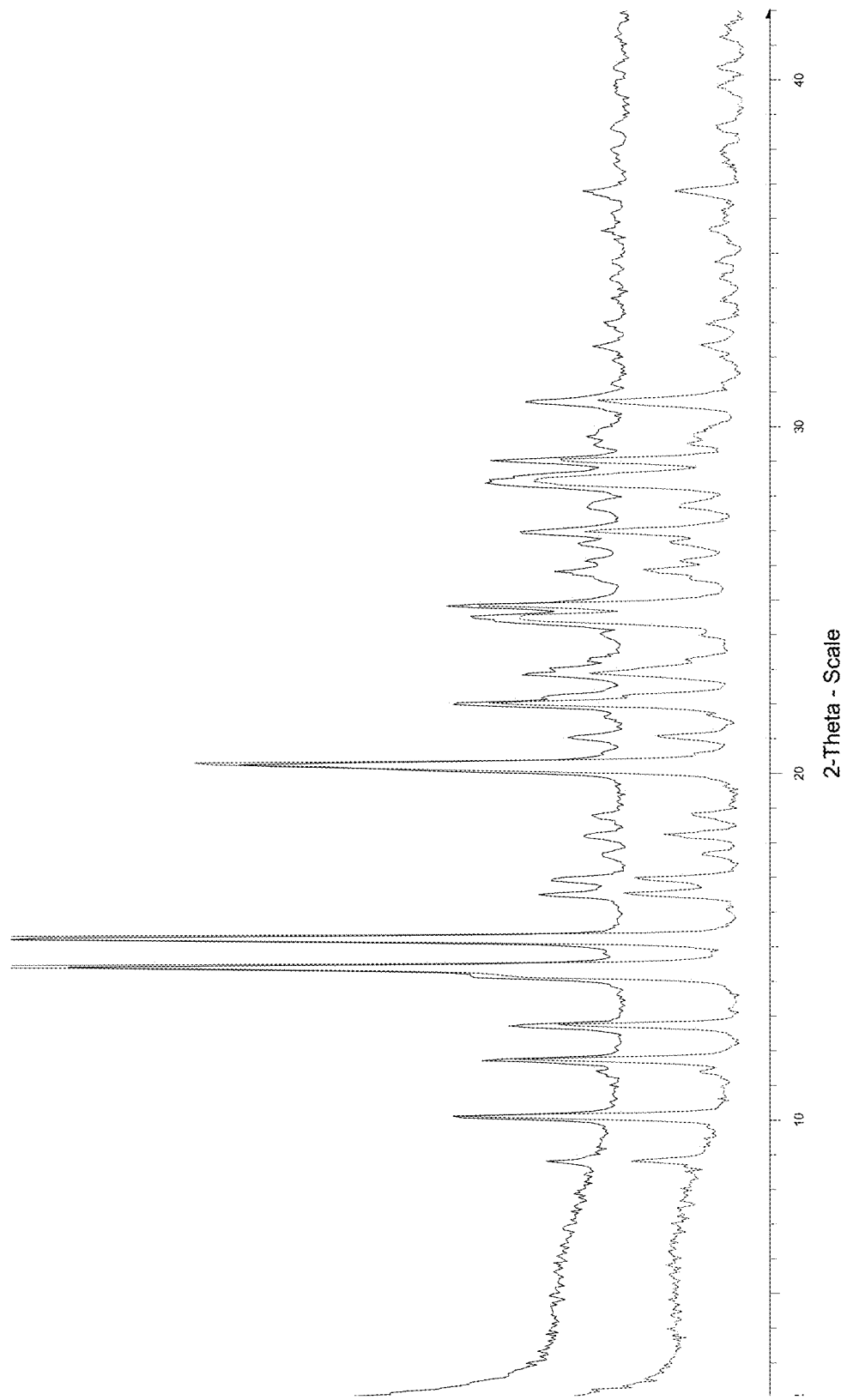

FIG. 44D depicts an XRPD diffractogram of Compound IV-1 Form A (above) after storage at 40° C./75% RH for 7 days (below).

Figure 45A:
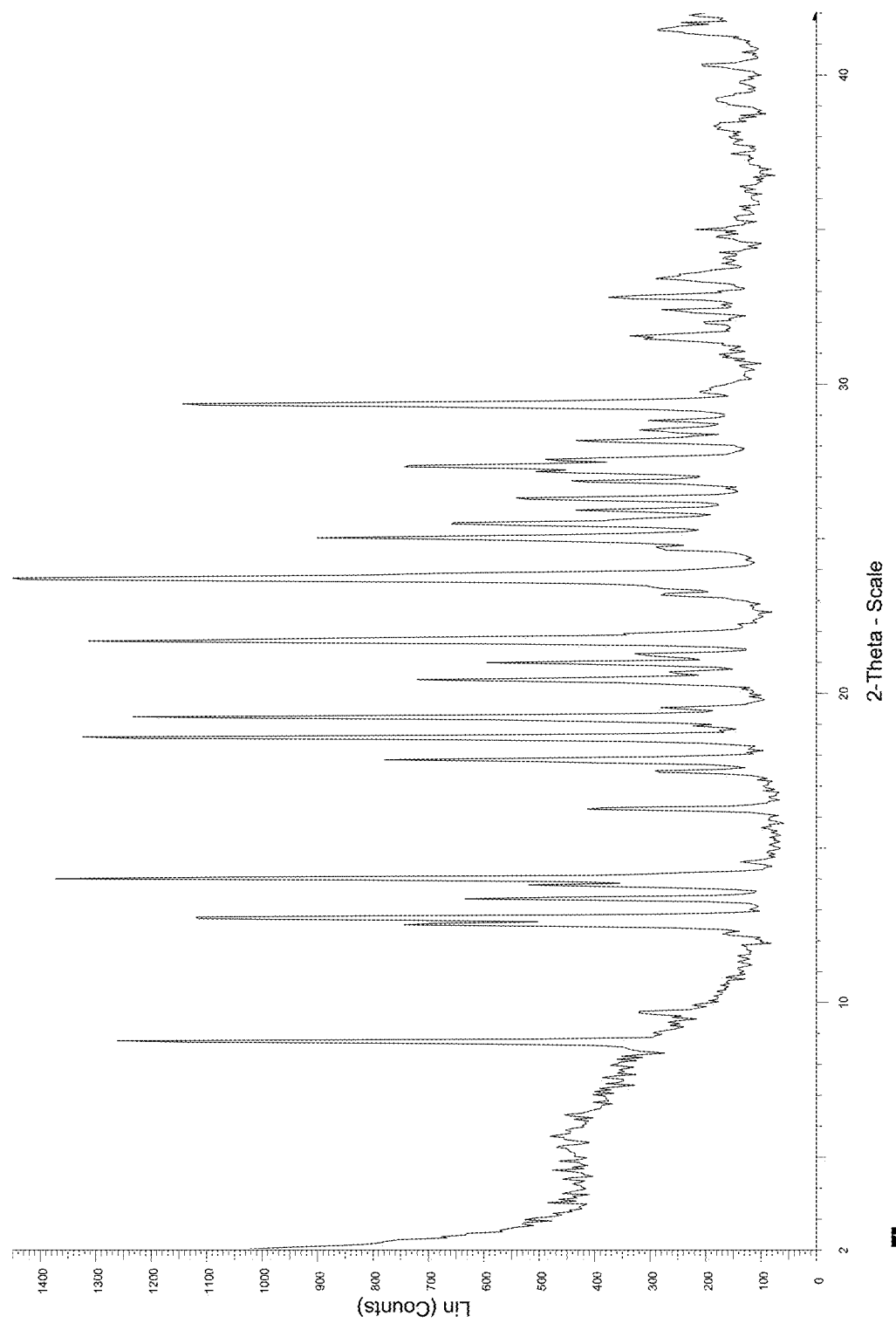

FIG. 45A depicts an X-ray diffraction pattern of Form A of Compound IV-2 (hydrochloride salt).

Figure 45B:
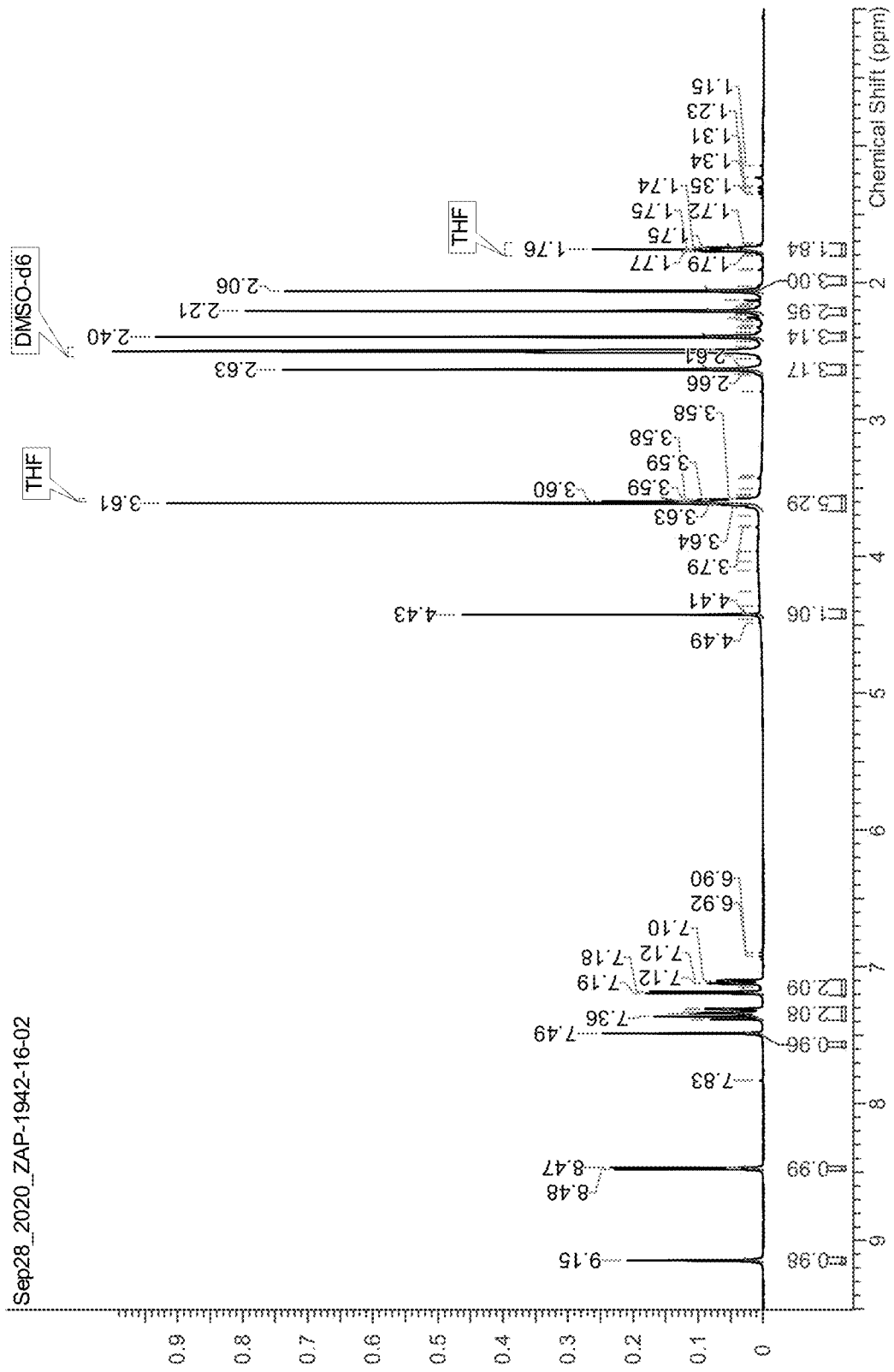

FIG. 45B depicts the characterization of Form A of Compound IV-2 by $^1$H nuclear magnetic resonance ($^1$H NMR) in D6-DMSO at 400 MHz.

Figure 45C:
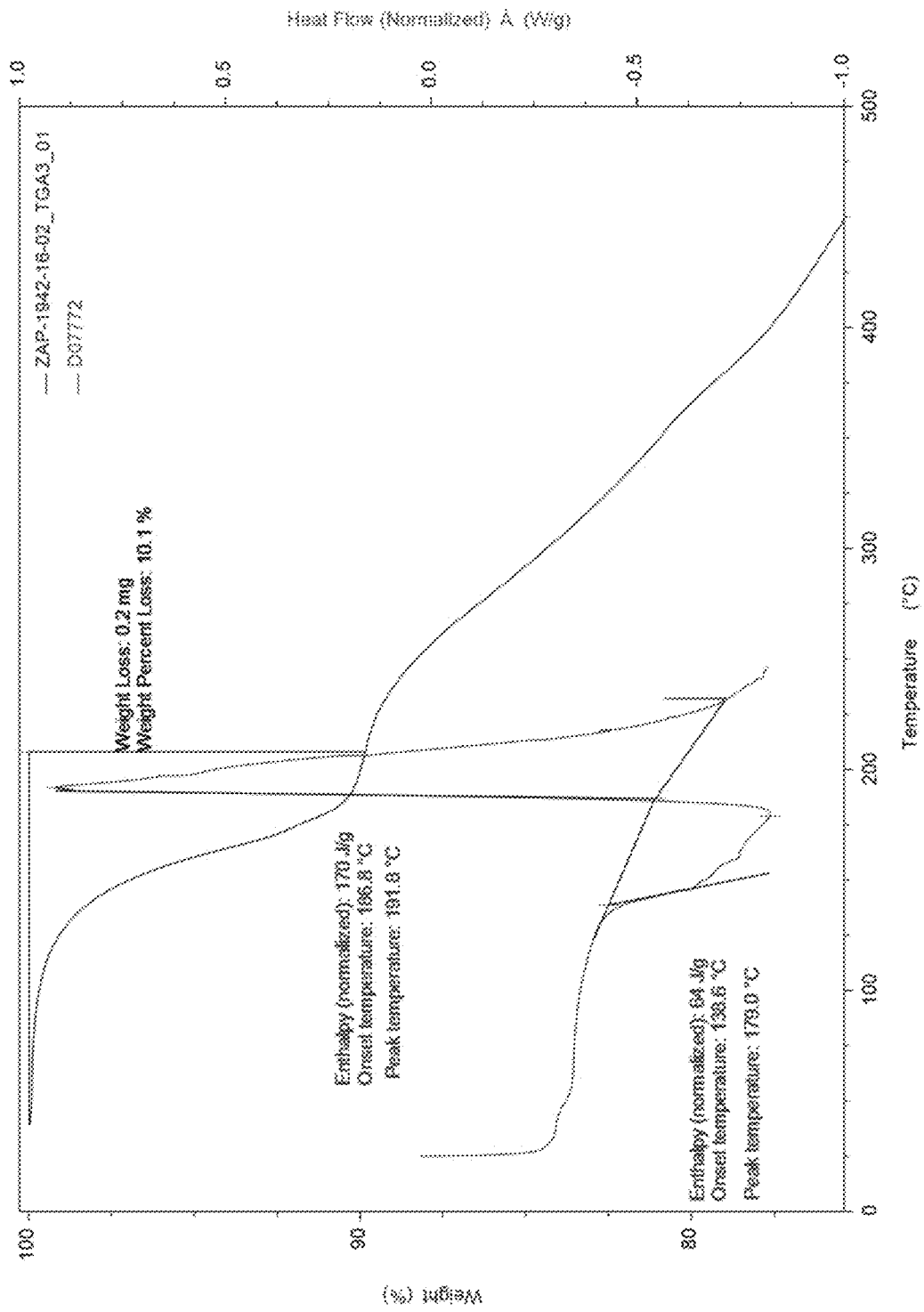

FIG. 45C depicts the characterization of Form A of Compound IV-2 by thermogravimetric analysis (above) and differential scanning calorimetry (below).

Figure 45D:
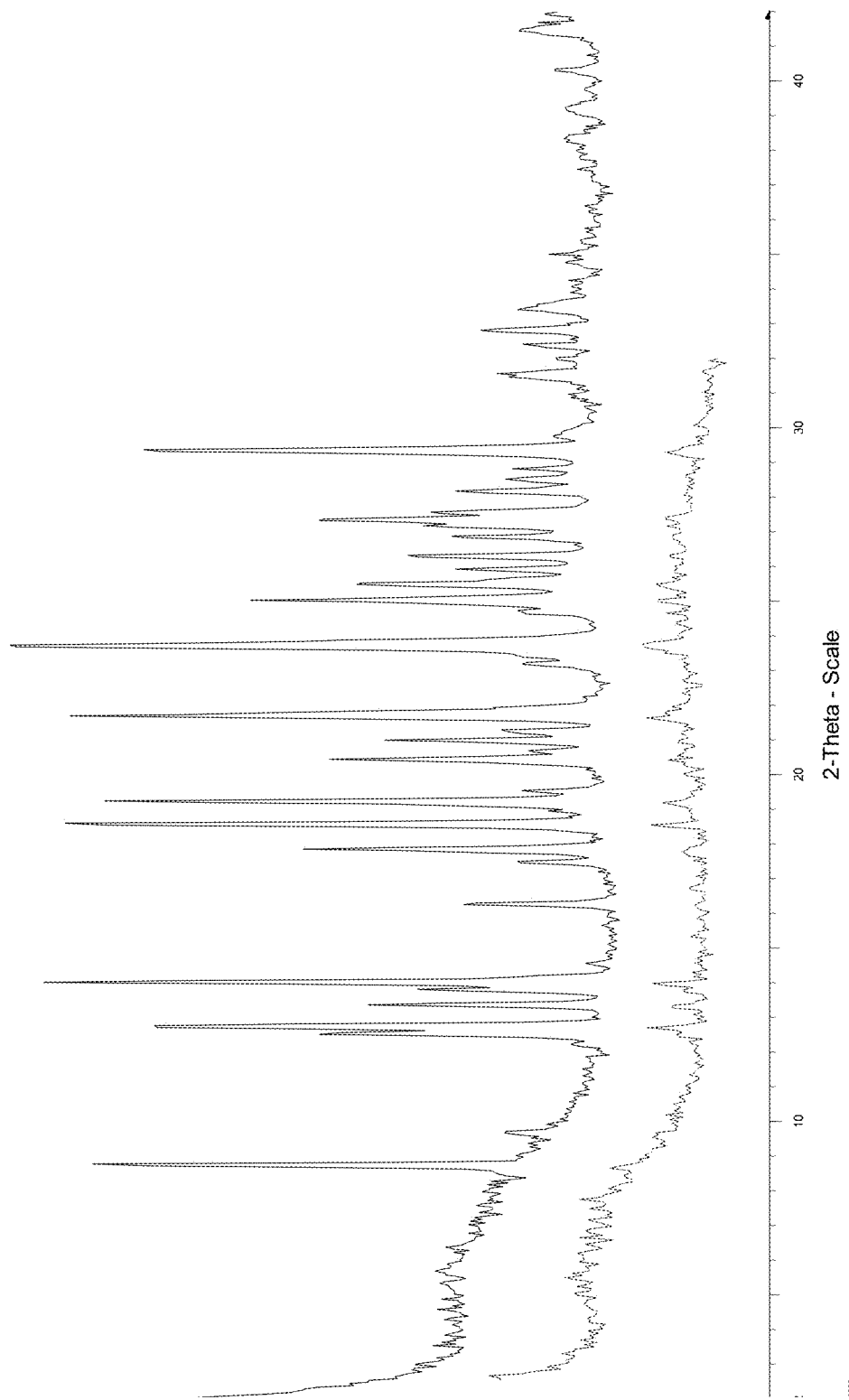

FIG. 45D depicts an XRPD diffractogram of Compound IV-2 Form A (above) after storage at 40° C./75% RH for 7 days (below).

Figure 46A:
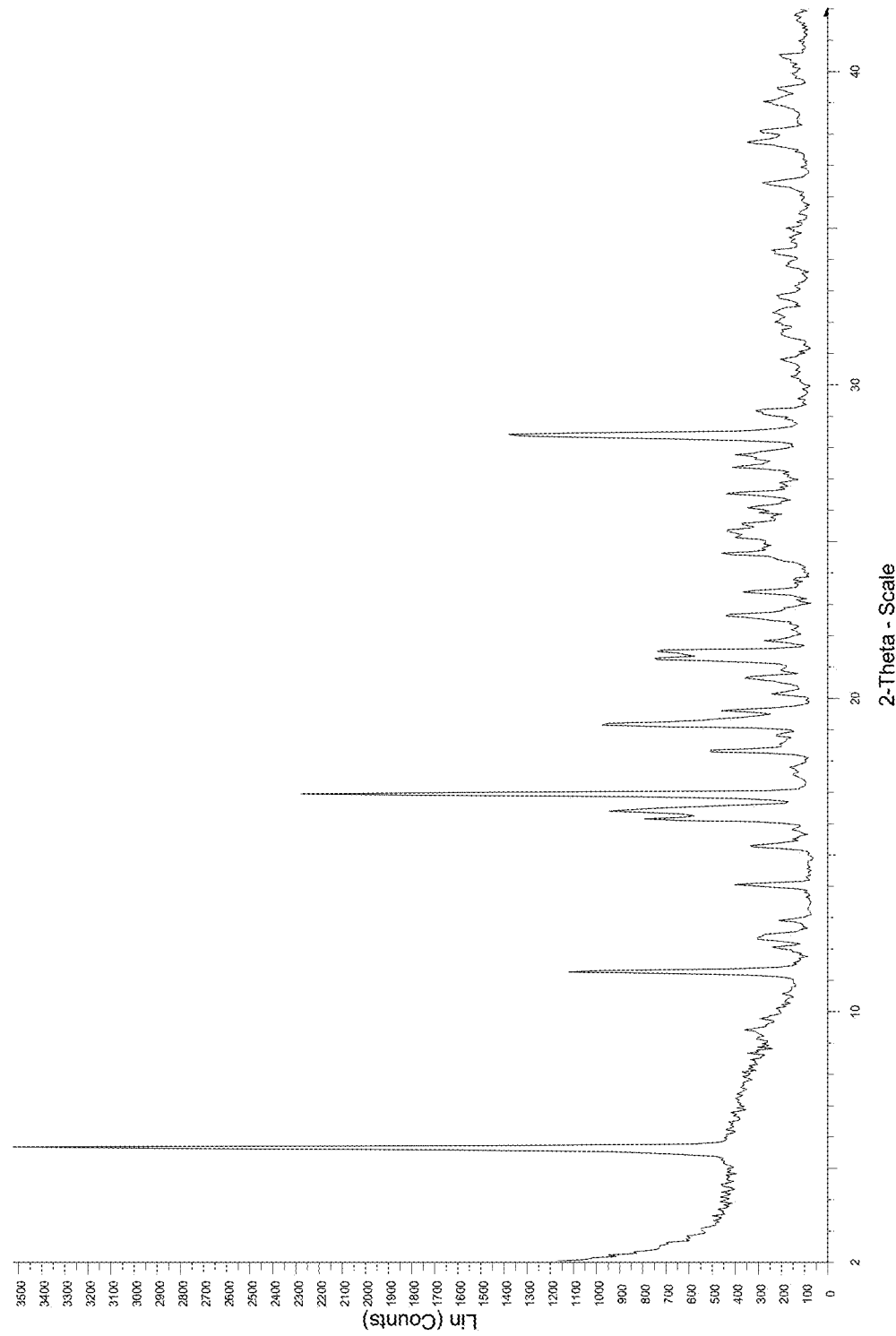

FIG. 46A depicts an X-ray diffraction pattern of Form A of Compound IV-3 (tosylate salt).

Figure 46B:
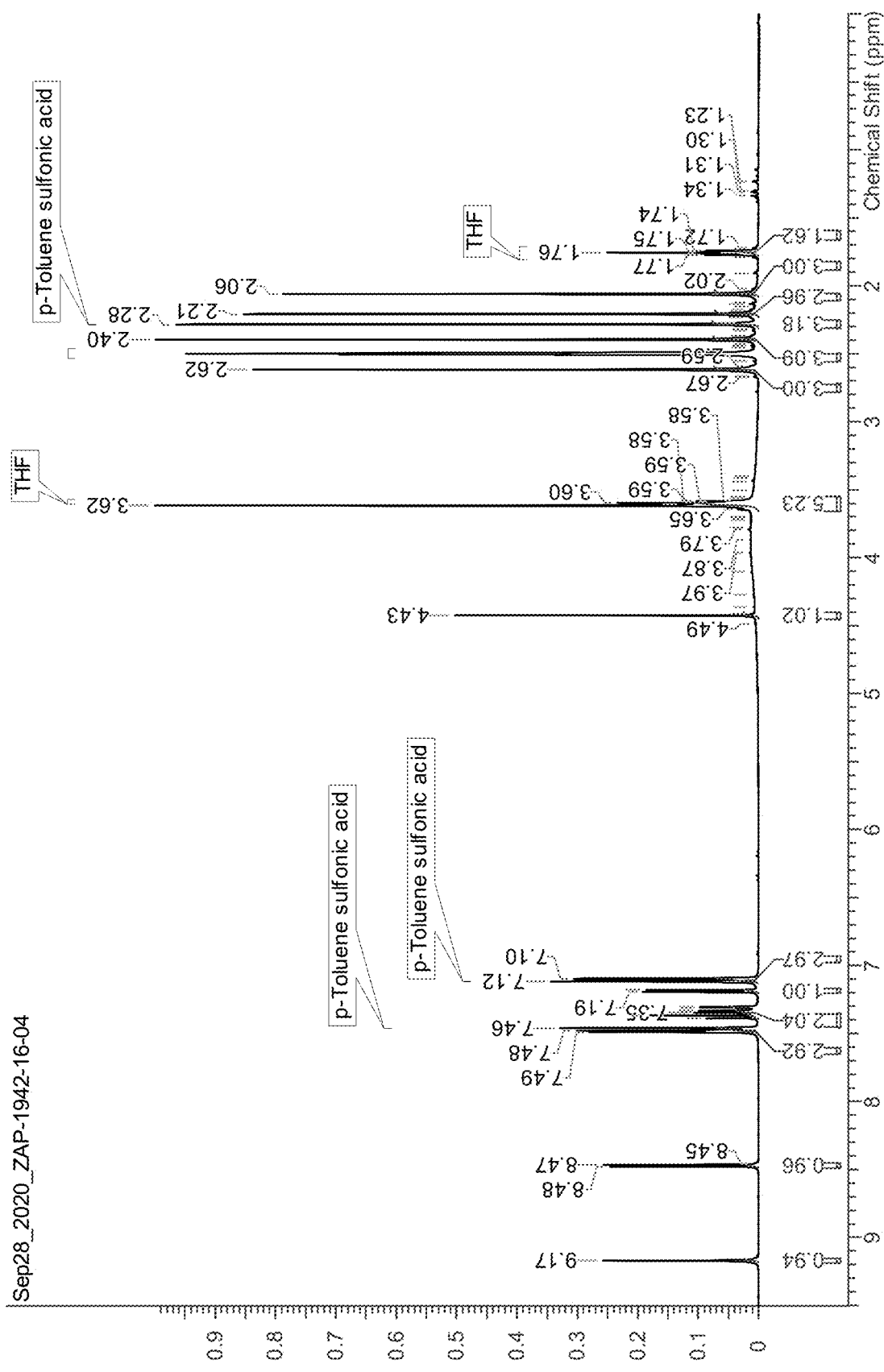

FIG. 46B depicts the characterization of Form A of Compound IV-3 by $^1$H nuclear magnetic resonance ($^1$HNMR) in D6-DMSO at 400 MHz.

Figure 46C:
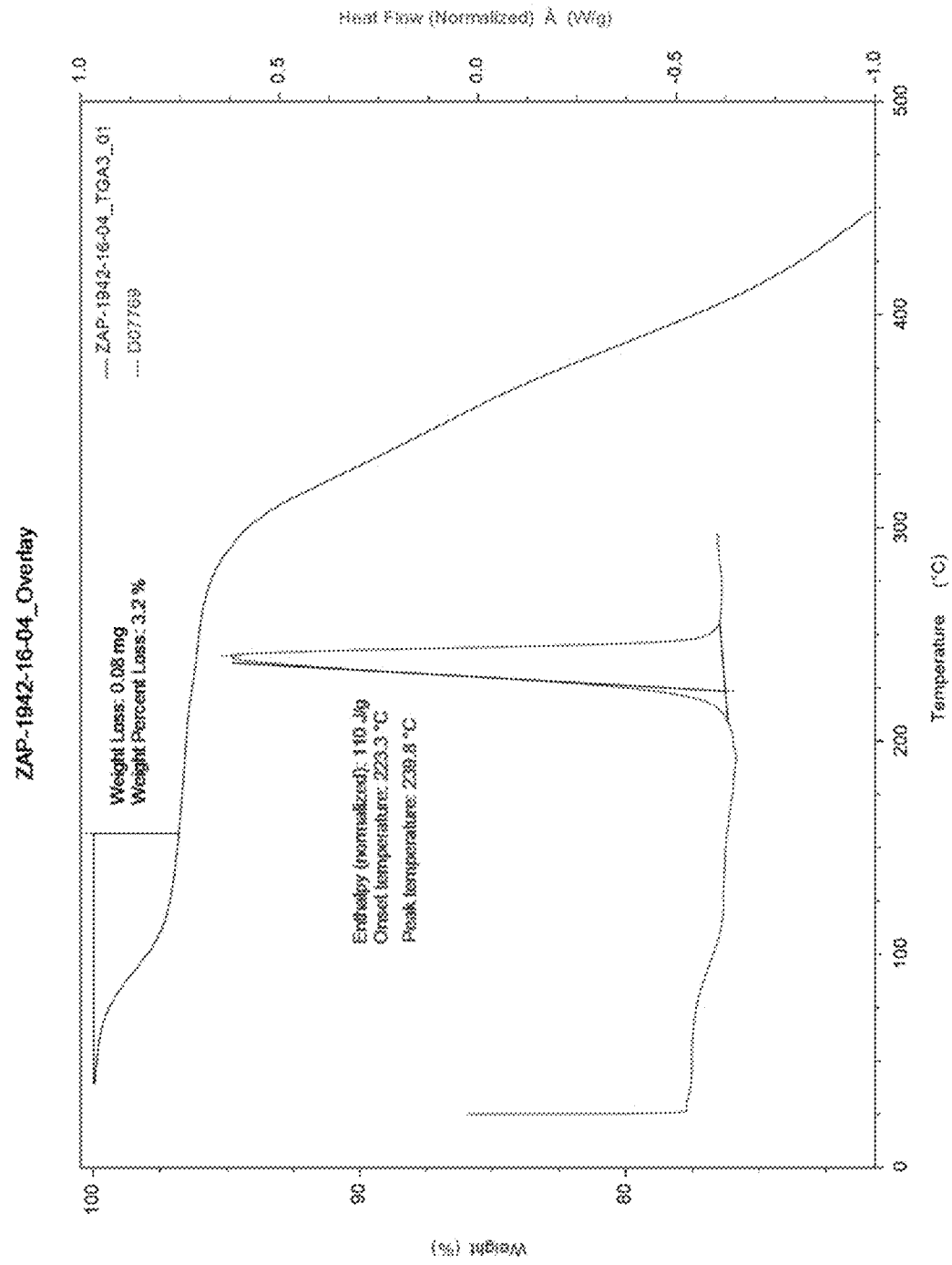

FIG. 46C depicts the characterization of Form A of Compound IV-3 by thermogravimetric analysis (above) and differential scanning calorimetry (below).

Figure 46D:
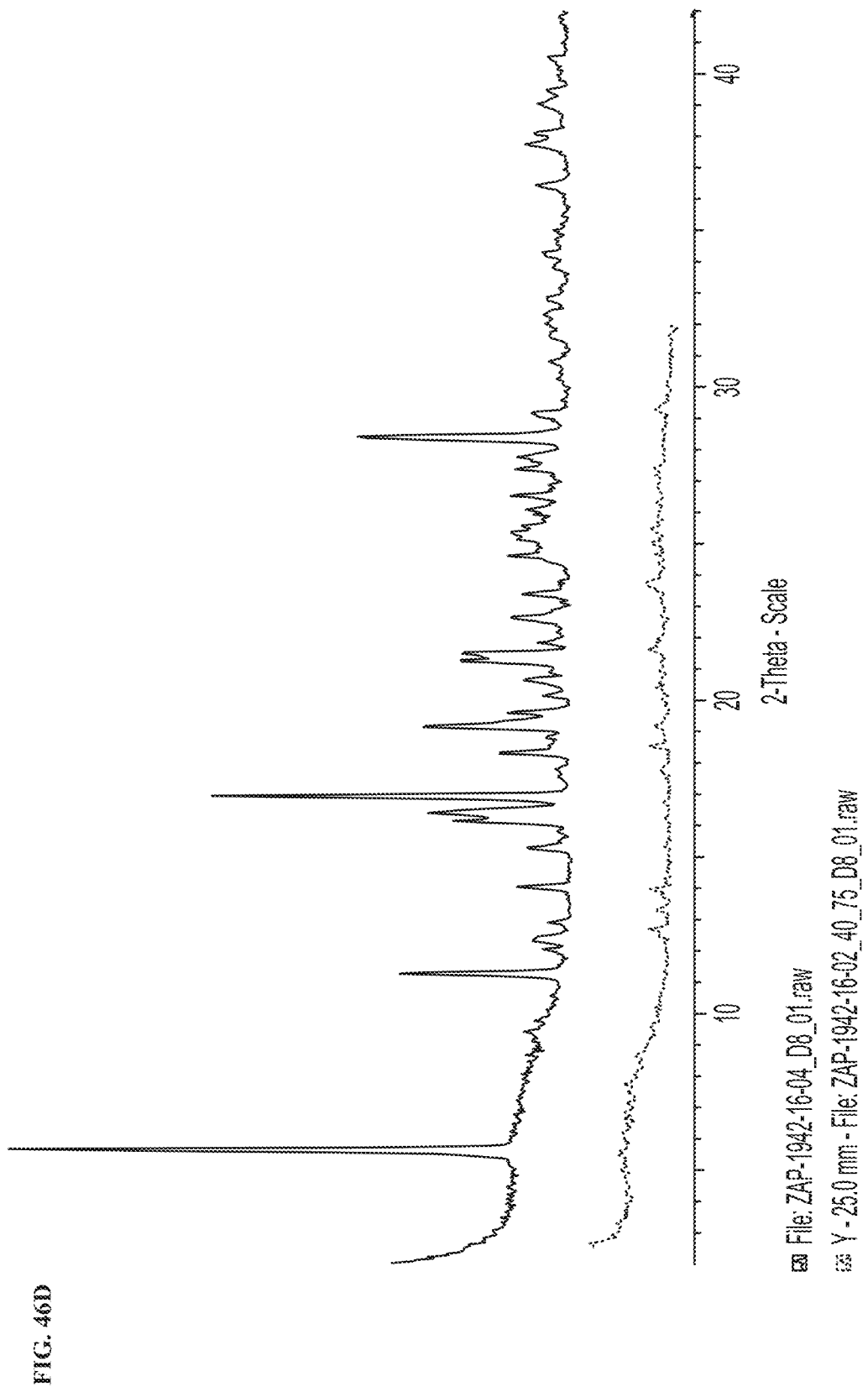

FIG. 46D depicts an XRPD diffractogram of Compound IV-3 Form A (above) after storage at 40° C./75% RH for 7 days (below).

Figure 47A:
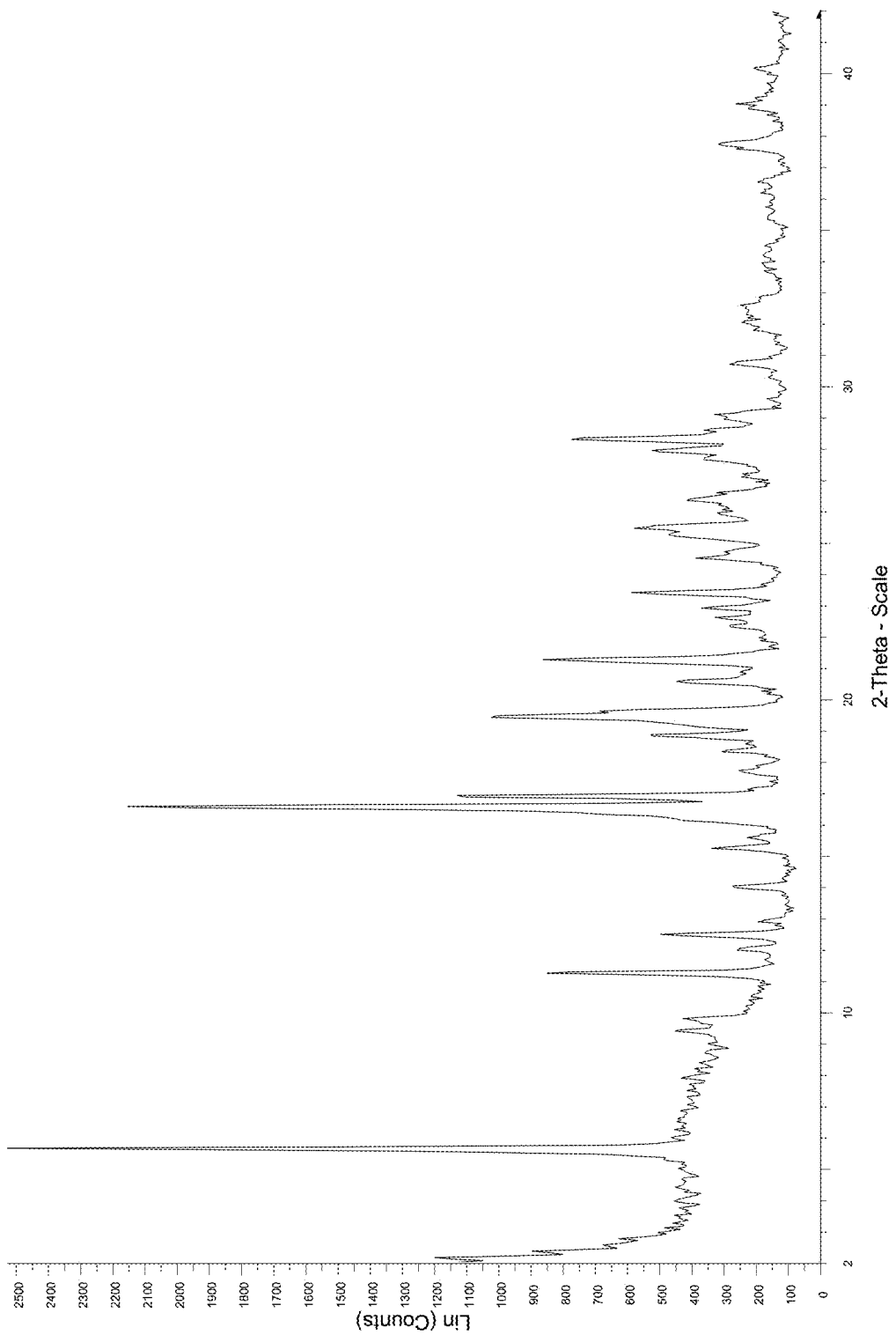

FIG. 47A depicts an X-ray diffraction pattern of Form B of Compound IV-3 (tosylate salt).

Figure 47B:
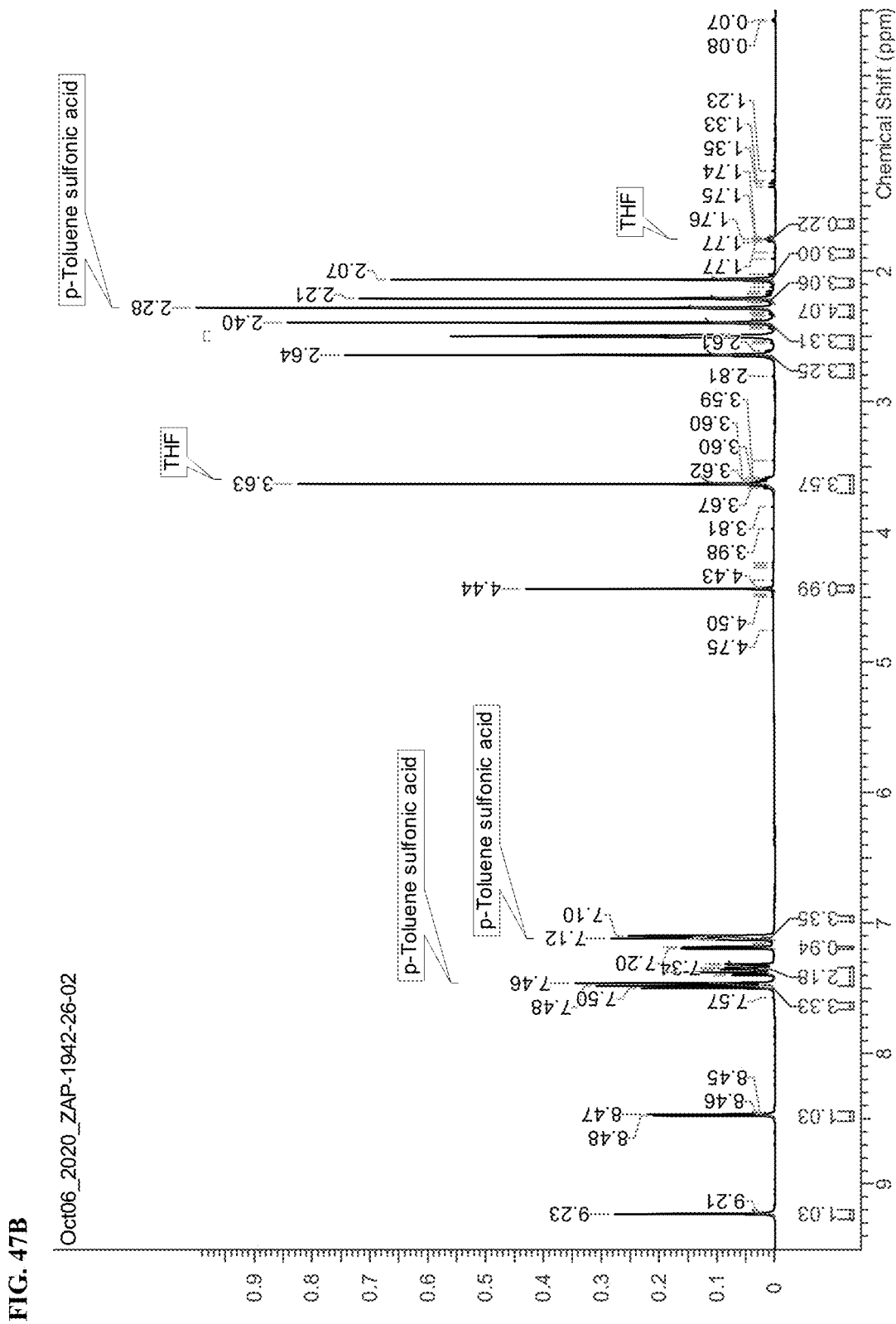

FIG. 47B depicts the characterization of Form B of Compound IV-3 by $^1$H nuclear magnetic resonance ($^1$HNMR) in D6-DMSO at 400 MHz.

Figure 48A:
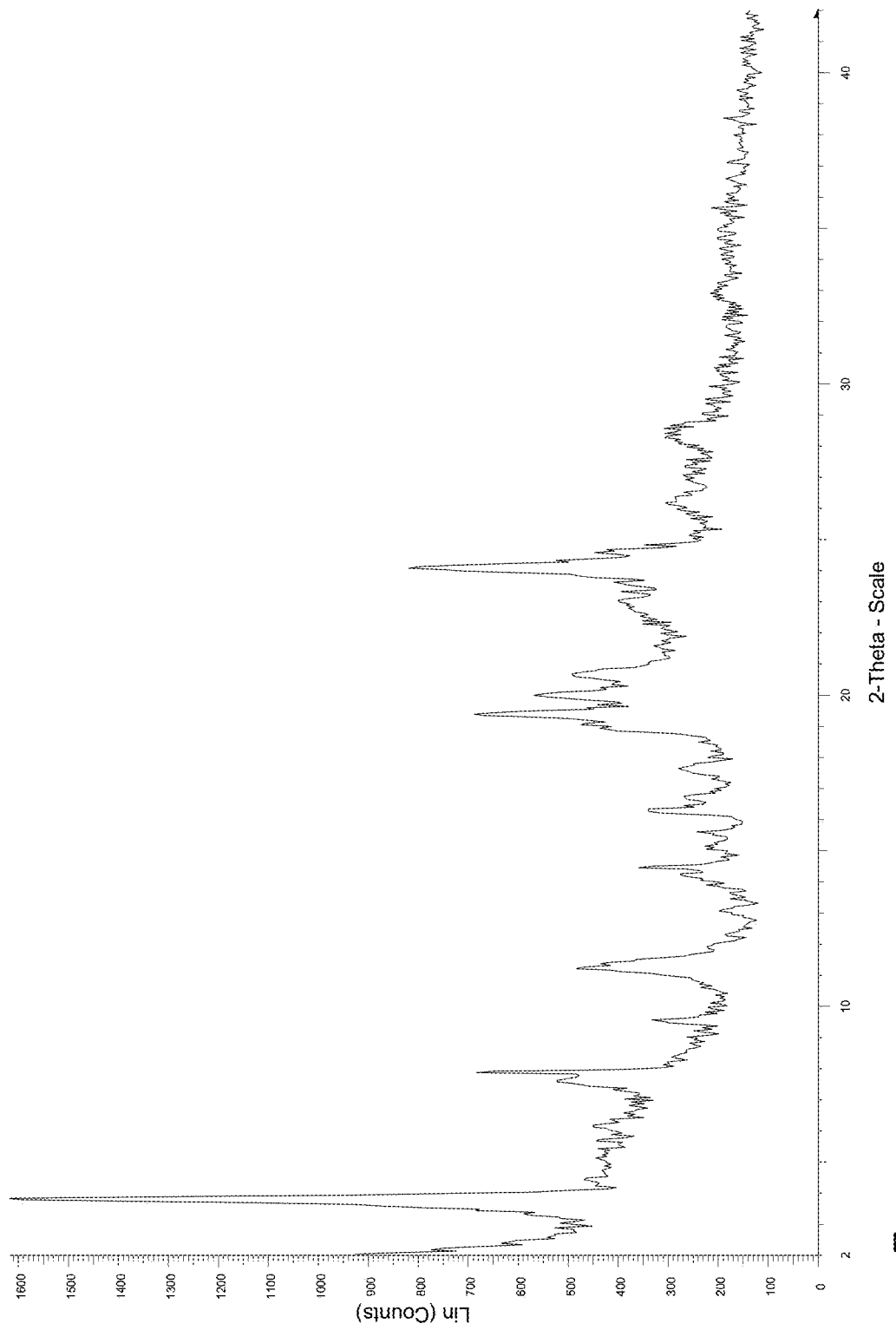

FIG. 48A depicts an X-ray diffraction pattern of Form A of Compound IV-4 (mesylate salt).

Figure 48B:
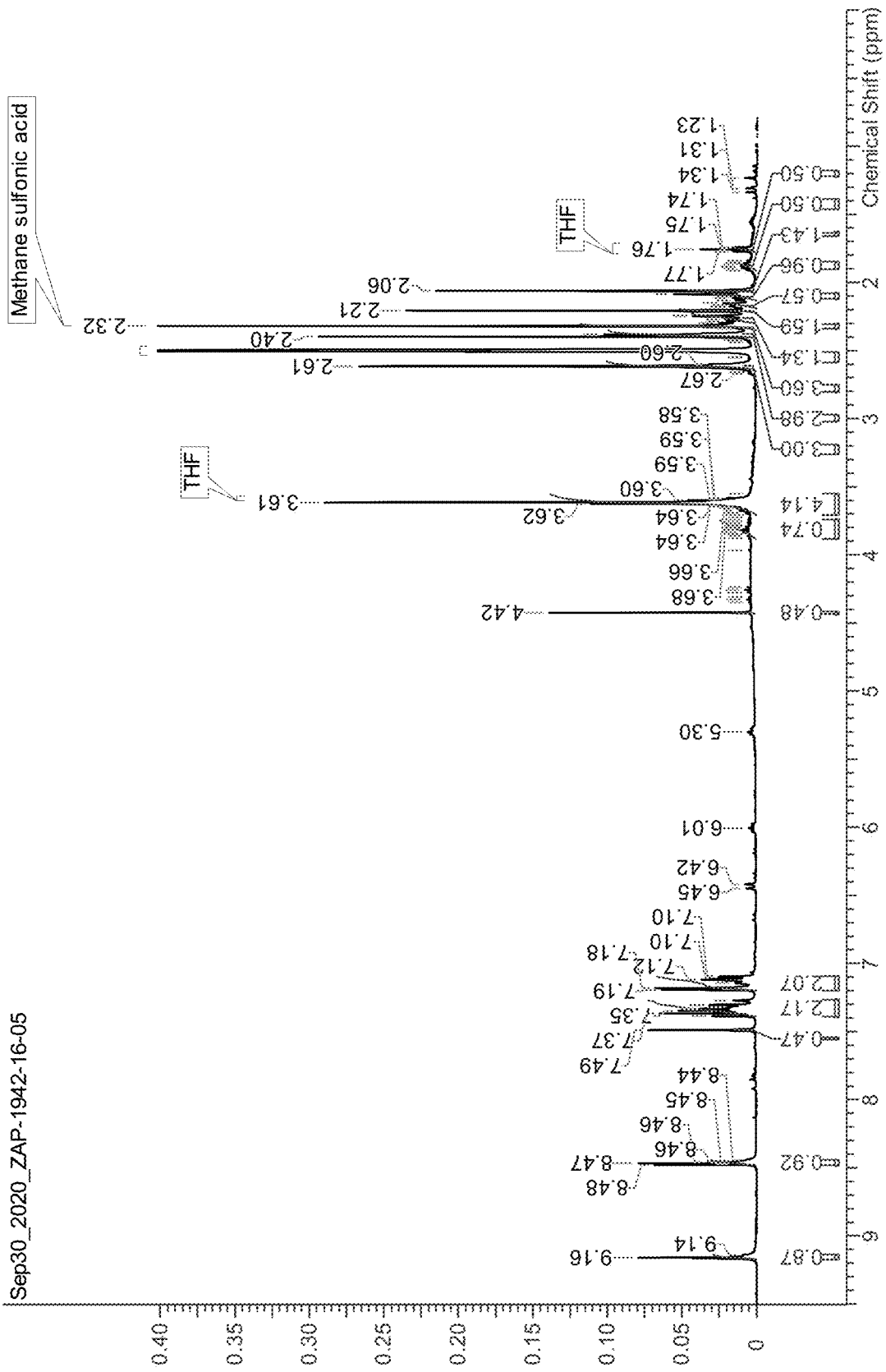

FIG. 48B depicts the characterization of Form A of Compound IV-4 by $^1$H nuclear magnetic resonance ($^1$HNMR) in D6-DMSO at 400 MHz.

Figure 48C:
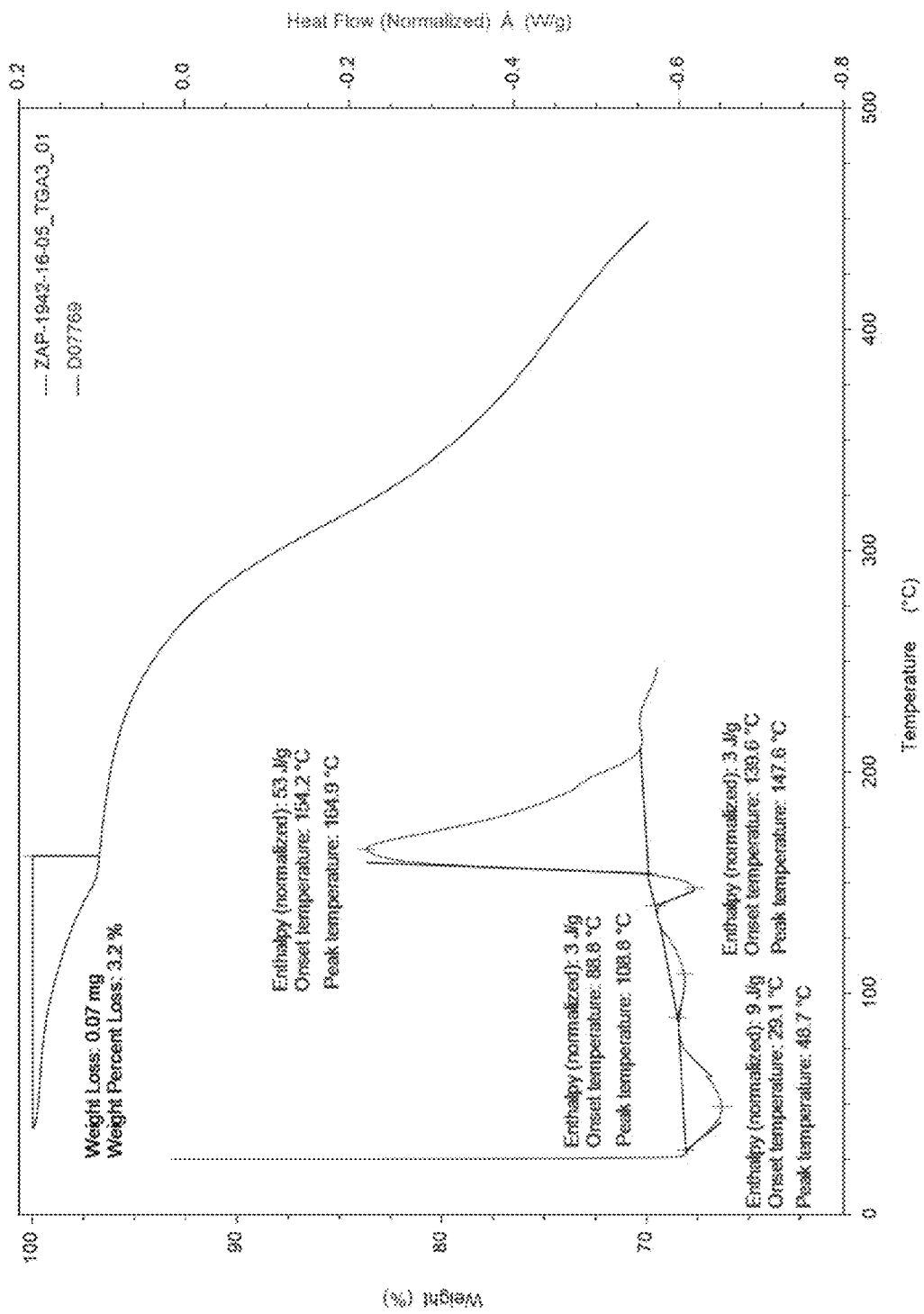

FIG. 48C depicts the characterization of Form A of Compound IV-4 by thermogravimetric analysis (above) and differential scanning calorimetry (below).

Figure 48D:
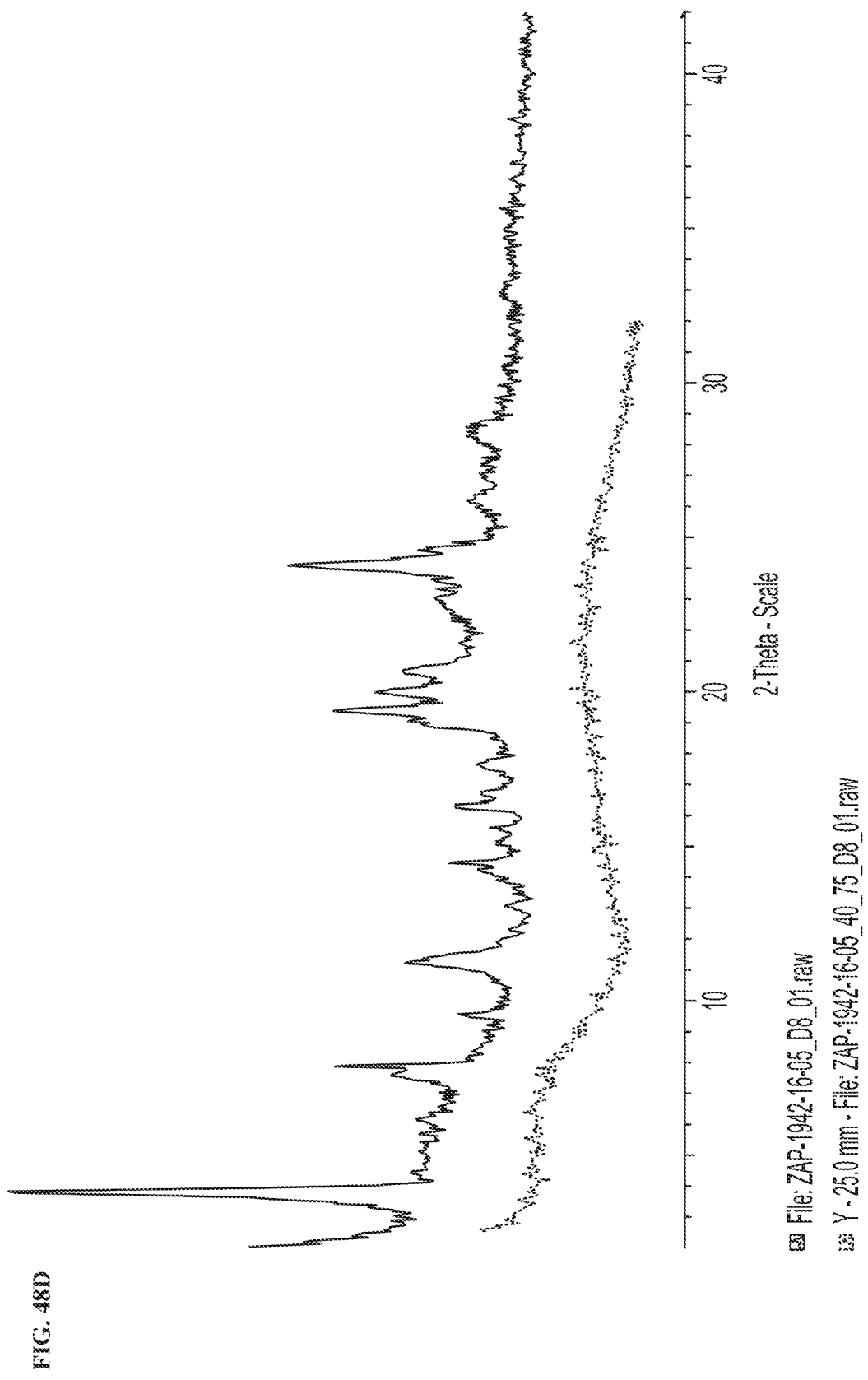

FIG. 48D depicts an XRPD diffractogram of Compound IV-4 Form A (above) after storage at 40° C./75% RH for 7 days (below).

Figure 49A:
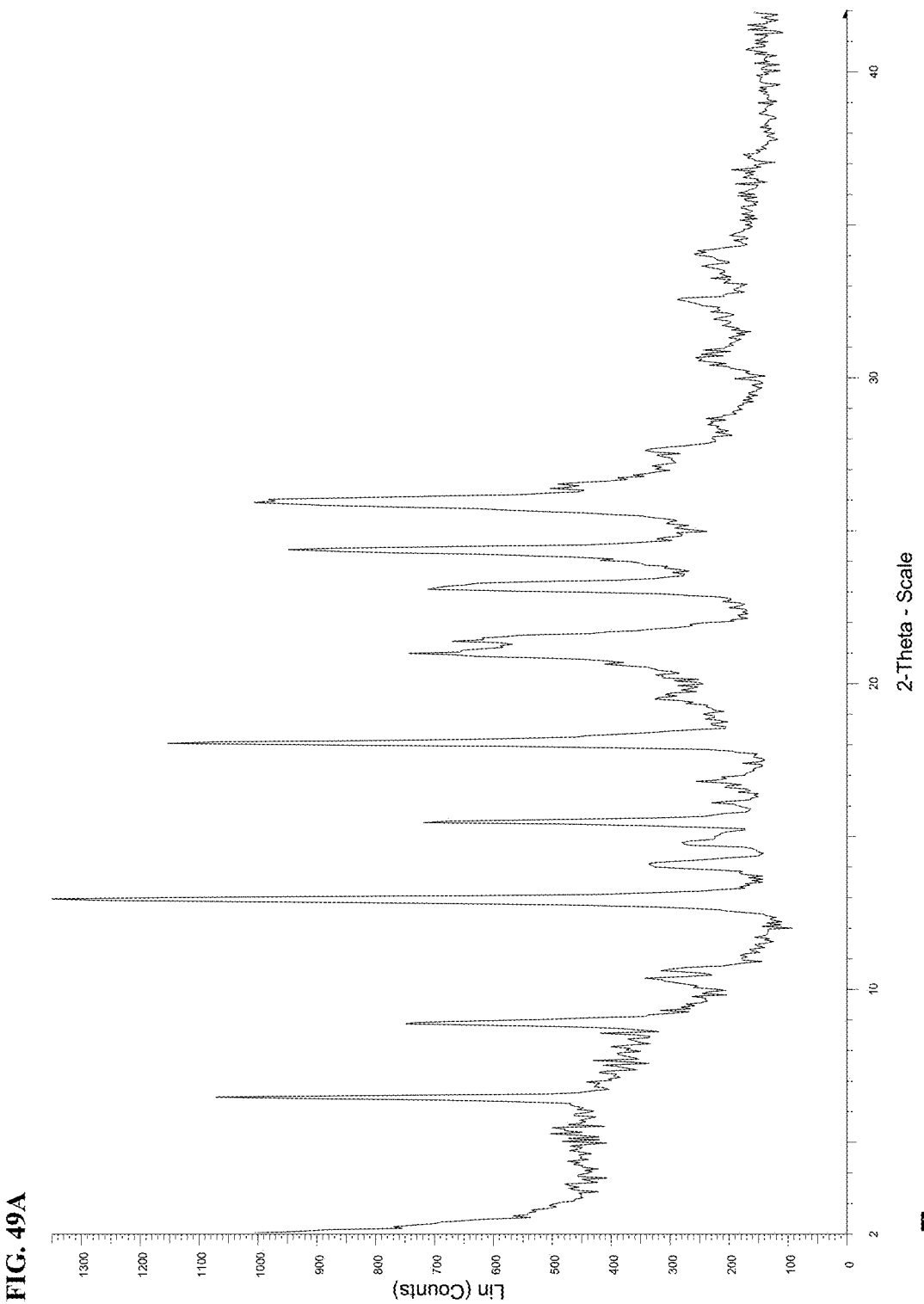

FIG. 49A depicts an X-ray diffraction pattern of Form A of Compound IV-5 (besylate salt).

Figure 49B:
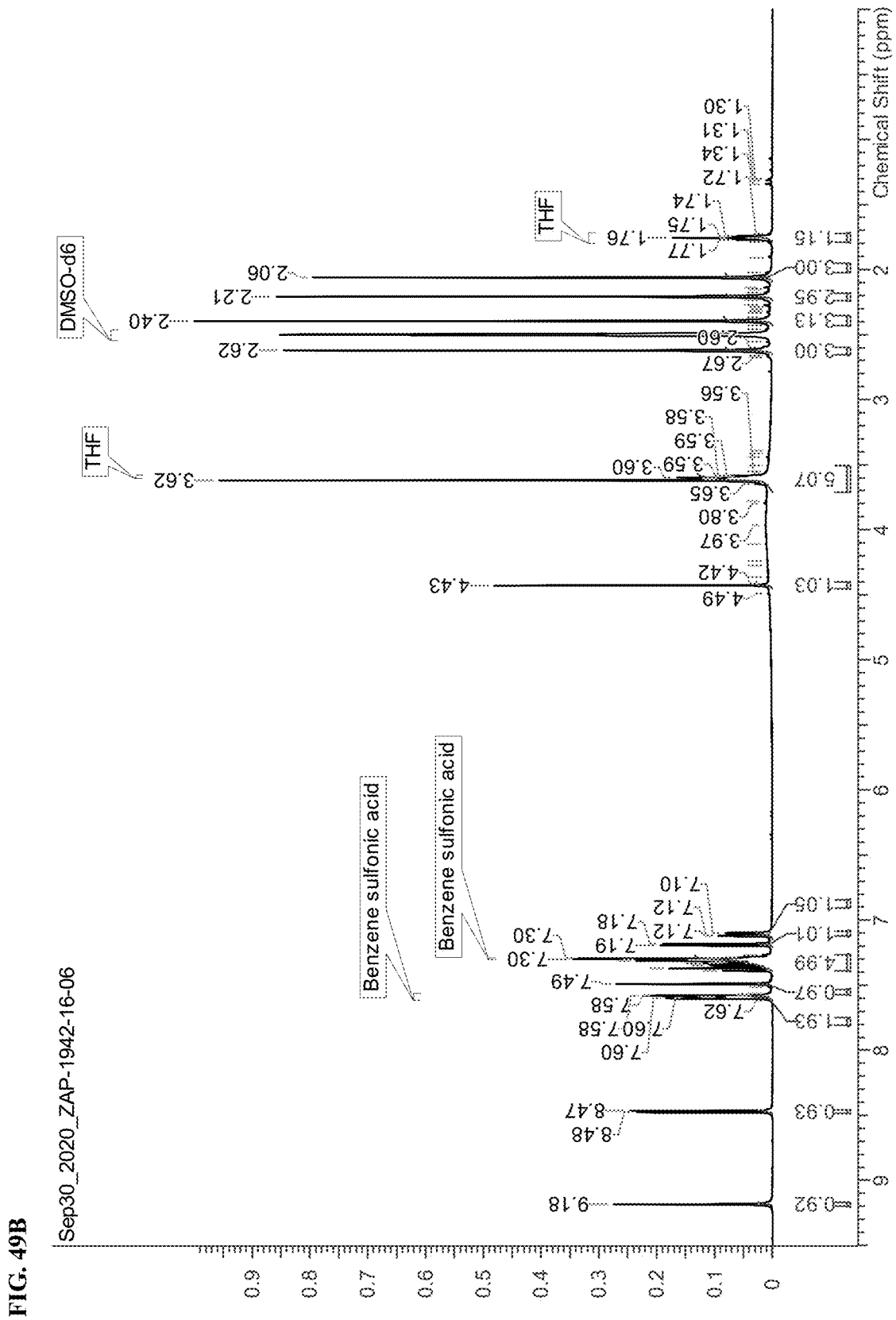

FIG. 49B depicts the characterization of Form A of Compound IV-5 by $^1$H nuclear magnetic resonance ($^1$HNMR) in D6-DMSO at 400 MHz.

Figure 49C:
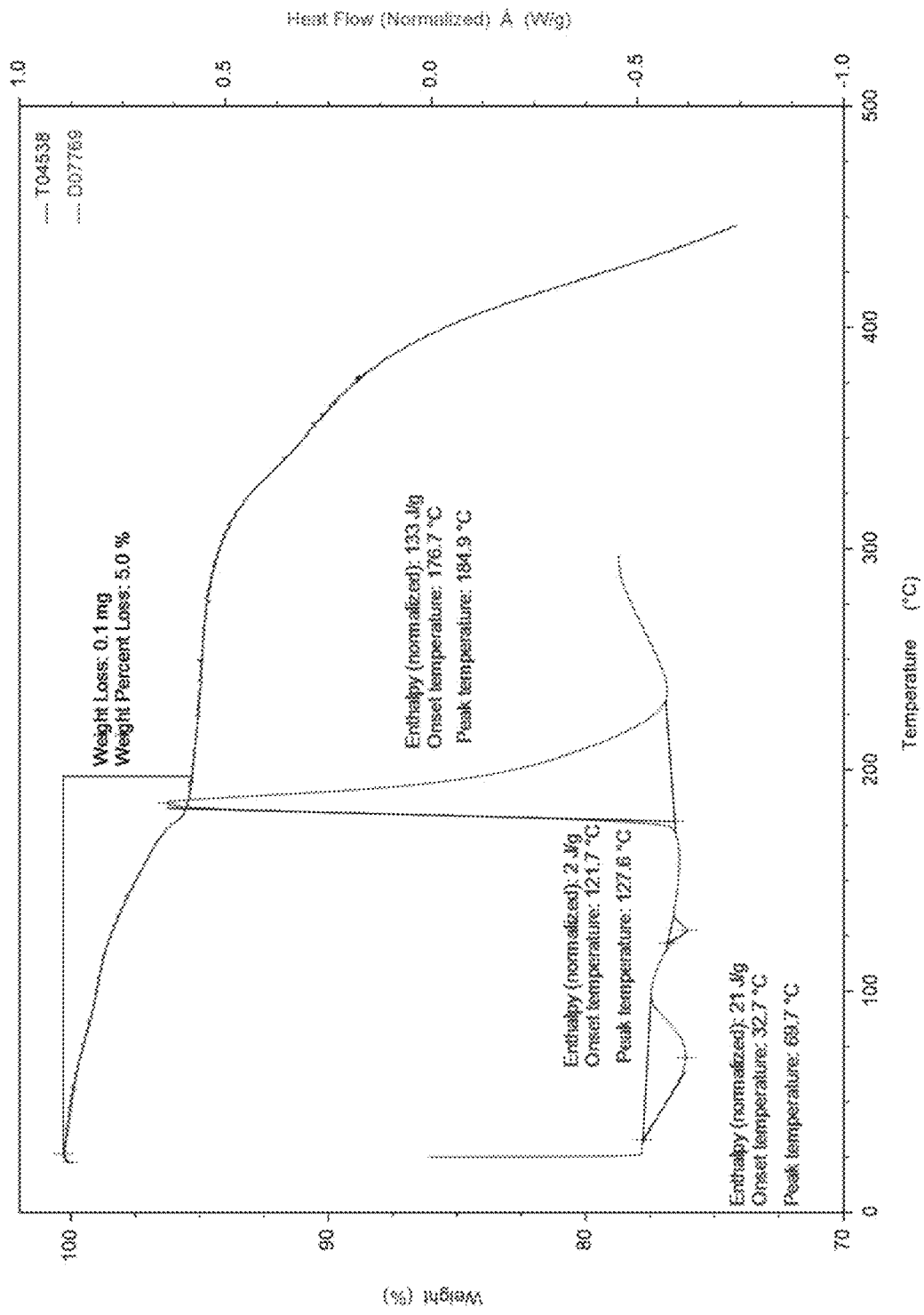

FIG. 49C depicts the characterization of Form A of Compound IV-5 by thermogravimetric analysis (above) and differential scanning calorimetry (below).

Figure 49D:
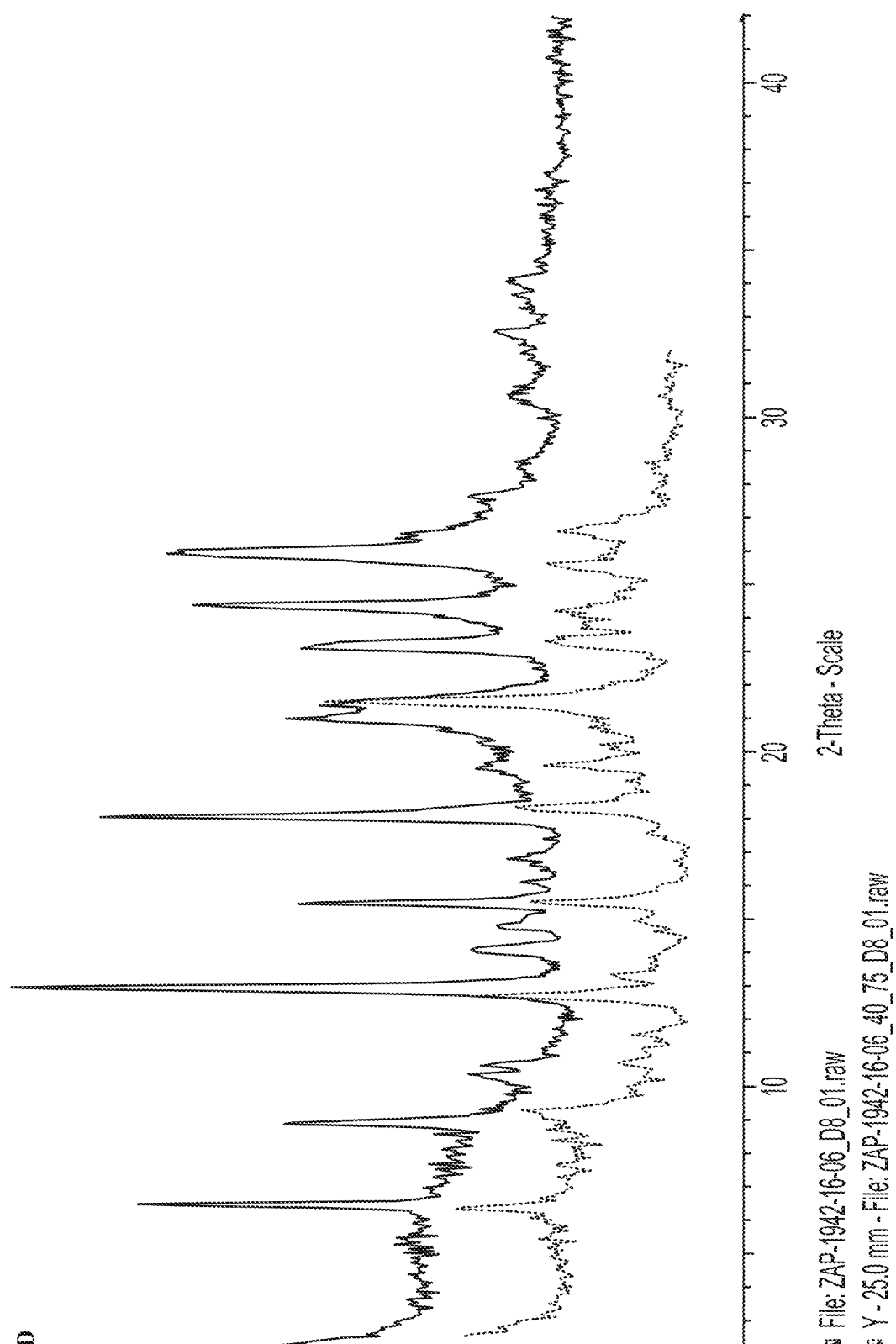

FIG. 49D depicts an XRPD diffractogram of Compound IV-5 Form A (above) after storage at 40° C./75% RH for 7 days (below).

DETAILED DESCRIPTION OF THE INVENTION

It has been found that compounds of formulas:

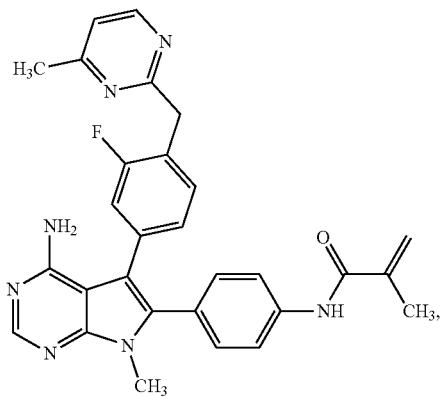 [SMILES: C=C(C)C(=O)Nc1ccc(-c2c(-c3ccc(Oc4nccc(C)n4)c(F)c3)c3c(N)ncnc3n2C)cc1]

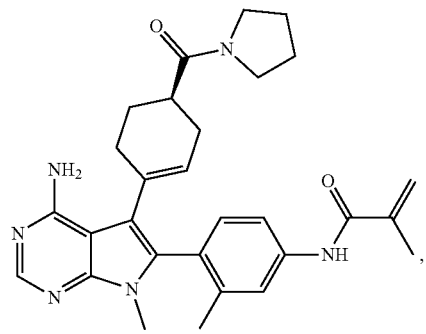

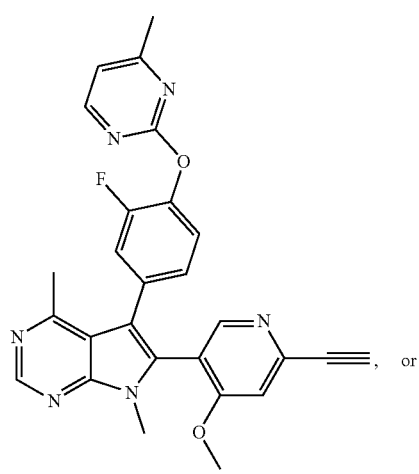

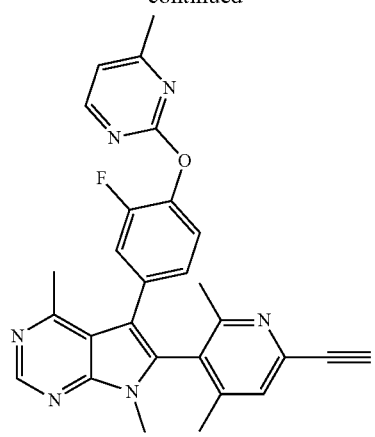

are FGFR inhibitors and useful for treating disorders, diseases, and/or conditions, for example, the "FGFR2-mediated" disorders, diseases, and/or conditions as described herein. It would be desirable to provide solid forms of the compounds (e.g., as a freebase, or a salt, or a solvate) that imparts characteristics such as improved aqueous solubility, stability, and ease of formulation.

It has also been found that an optimized process can significantly increase the purity of compound

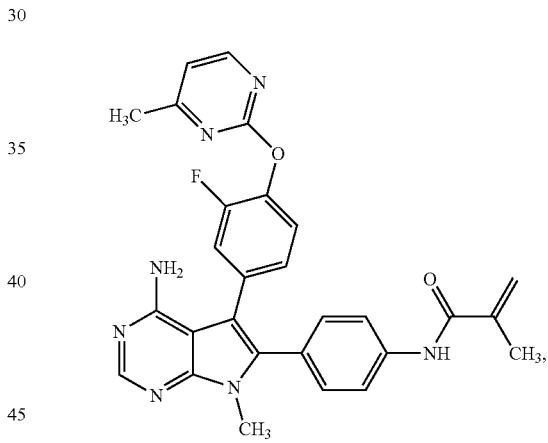

and can reduce an impurity compound 6:

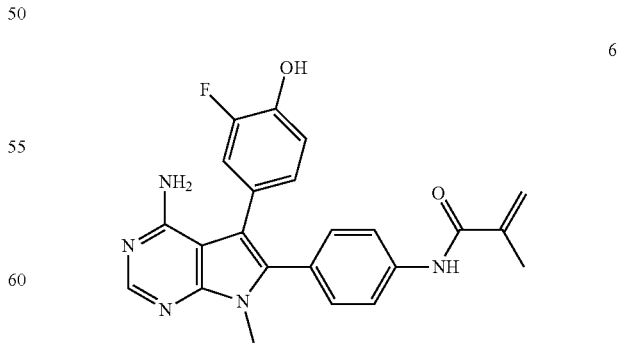

to less than a liquid chromatography area percentage (LCAP) of about 0.15, as shown in Examples 1 and 2. Accordingly, the compound

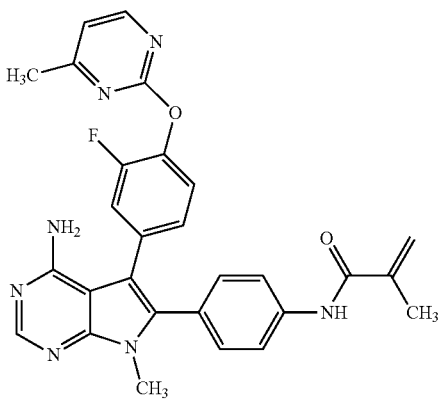 [SMILES: C=C(C)C(=O)Nc1ccc(-c2c(-c3ccc(Oc4nccc(C)n4)c(F)c3)c3c(N)ncnc3n2C)cc1]

as provided herein is substantially free of impurities, for example, compound 6.

Compound of Formula (I)

In some embodiments, provided herein is a compound of Formula (I)

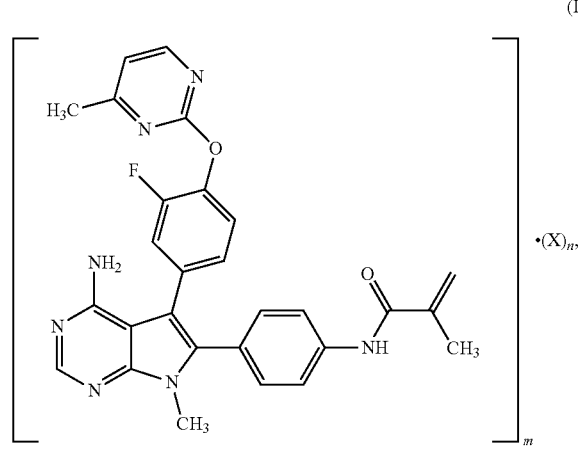

or a solvate thereof;
wherein,
m is 1, 2, 3, 4, 5, 6, 7, 8, or 9;
n is 0, 0.5, 1, 1.5, 2, 2.5, or 3; and
X is hydrochloric acid, hydrobromic acid, sulfuric acid, p-toluene sulfonic acid, methane sulfonic acid, benzene sulfonic acid, or maleic acid.

It will be appreciated by one of ordinary skill in the art that the acid moiety indicated as "X" and N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide are ionically bonded to form a compound of Formula (I). It will also be appreciated that when n is 0, X is absent, indicating that the compound of Formula (I) exists as a "free base," i.e., "free form."

It is contemplated that a compound of Formula (I) can exist in a variety of physical forms. For example, a compound of Formula (I) can be in solution, suspension, or in solid form. In certain embodiments, a compound of Formula (I) is in solid form. When a compound of Formula (I) is in solid form, said compound may be amorphous, crystalline, or a mixture thereof. Exemplary solid forms are described in more detail below.

In some embodiments, a compound of Formula (I), may be in a hydrate form. In some embodiments, a compound of Formula (I), may be in a hemi-hydrate form.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9.

In some embodiments, n is 0. In some embodiments, n is 1. In some embodiments, n is 2. In some embodiments, n is 3. In some embodiments, n is 0.5. In some embodiments, n is 1.5. In some embodiments, n is 2.5.

In some embodiments, X is hydrochloric acid. In some embodiments, X is hydrobromic acid. In some embodiments, X is sulfuric acid. In some embodiments, X is p-toluene sulfonic acid. In some embodiments, X is methane sulfonic acid. In some embodiments, X is benzene sulfonic acid. In some embodiments, X is maleic acid.

In some embodiments, the present invention provides a form of compound I substantially free of impurities. As used herein, the term "substantially free of impurities" means that the compound contains no significant amount of extraneous matter. Such extraneous matter may include different forms of compound I, residual solvents, or any other impurities that may result from the preparation of, and/or isolation of, compound I.

In some embodiments, a compound of Formula (I), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, a compound of Formula (I), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, a compound of Formula (I), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, a compound of Formula (I), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, a compound of Formula (I), or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, a compound of Formula (I), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound of Formula (I) is also meant to include all tautomeric forms. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In some embodiments, provided herein is a N-(4-(4-amino-5-(3-fluoro-4-((4-methylpyrimidin-2-yl)oxy)phenyl)-7-methyl-7H-pyrrolo[2,3-d]pyrimidin-6-yl)phenyl) methacrylamide hydrochloride salt. In some embodiments, a N-(4-(4-amino-5-(3-fluoro-4-((4-methylpyrimidin-2-yl) oxy)phenyl)-7-methyl-7H-pyrrolo[2,3-d]pyrimidin-6-yl) phenyl)methacrylamide hydrochloride salt is a mono-hydrochloride salt. In some embodiments, a N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide hydrochloride salt is a bis-hydrochloride salt. In some embodiments, a N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide hydrochloride salt is a tris-hydrochloride salt.

Compound I-1

In some embodiments, a compound of Formula (I) is Compound I-1:

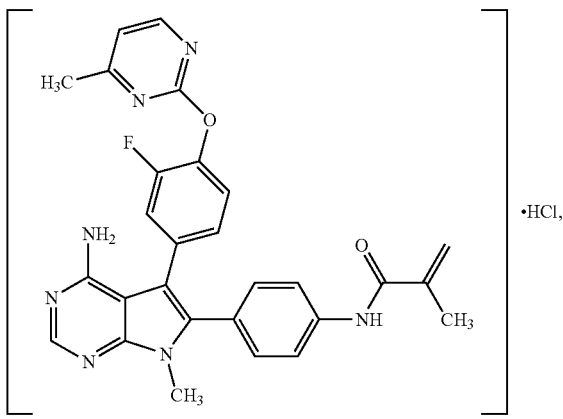

I-1 or a solvate thereof.

In some embodiments, Compound I-1 is an anhydrous solid.

In some embodiments, Compound I-1 is an amorphous solid. In other embodiments, Compound I-1 is a crystalline solid. In some embodiments, Compound I-1 is a mixture of amorphous solid form and crystalline solid form.

In some embodiments, the present invention provides a form of compound I-1 substantially free of impurities. As used herein, the term "substantially free of impurities" means that the compound contains no significant amount of extraneous matter. Such extraneous matter may include different forms of compound I-1, residual solvents, or any other impurities that may result from the preparation of, and/or isolation of, compound I-1.

In some embodiments, compound I-1, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-1, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-1, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-1, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-1, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-1, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-1 is also meant to include all tautomeric forms of compound I-1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In certain embodiments, compound I-1 is a crystalline solid. In other embodiments, compound I-1 is a crystalline solid substantially free of amorphous compound I-1. As used herein, the term "substantially free of amorphous compound I-1" means that the compound contains no significant amount of amorphous compound I-1. In certain embodiments, at least about 95% by weight of crystalline compound I-1 is present. In still other embodiments of the invention, at least about 99% by weight of crystalline compound I-1 is present.

It has been found that compound I-1 can exist in a variety of solid forms. Exemplary such forms include polymorphs such as those described herein.

In some embodiments, the solid crystalline form of Compound I-1 is Form A. In some embodiments, Form A of Compound I-1 may be characterized by a powder X-ray diffraction pattern with at least two characteristic peaks, in degrees 2θ, each selected from the group consisting of about 12.3 2θ, about 24.0 2θ and about 15.6 2θ. In some embodiments, Form A of Compound I-1 may be characterized by a powder X-ray diffraction pattern with at least two characteristic peaks, in degrees 2θ, each selected from the group consisting of about 12.3 2θ, about 24.0 2θ, about 15.6 2θ, about 12.7 2θ, about 10.4 2θ, about 11.1 2θ and about 15.2 2θ. In some embodiments, Form A of Compound I-1 may be characterized by a powder X-ray diffraction pattern with at least three characteristic peaks, in degrees 2θ, each selected from the group consisting of about 12.3 2θ, about 24.0 2θ, about 15.6 2θ, about 12.7 2θ, about 10.4 2θ, about 11.1 2θ and about 15.2 2θ. In some embodiments, Form A of Compound I-1 may be characterized by a powder X-ray diffraction pattern with at least four characteristic peaks, in degrees 2θ, each selected from the group consisting of about 12.3 2θ, about 24.0 2θ, about 15.6 2θ, about 12.7 2θ, about 10.4 2θ, about 11.1 2θ and about 15.2 2θ. In some embodiments, Form A of Compound I-1 may be characterized by a powder X-ray diffraction pattern with at least five characteristic peaks, in degrees 2θ, each selected from the group consisting of about 12.3 2θ, about 24.0 2θ, about 15.6 2θ, about 12.7 2θ, about 10.4 2θ, about 11.1 2θ and about 15.2 2θ. In some embodiments, Form A of Compound I-1 may be characterized by a powder X-ray diffraction pattern with at least six characteristic peaks, in degrees 2θ, each selected from the group consisting of about 12.3 2θ, about 24.0 2θ, about 15.6 2θ, about 12.7 2θ, about 10.4 2θ, about 11.1 2θ and about 15.2 2θ. In some embodiments, Form A of Compound I-1 has a X-Ray diffraction pattern substantially similar to that depicted in FIG. 1A. In some embodiments, Form A of Compound I-1 may be characterized by a powder X-ray diffraction pattern with at least two characteristic peaks, in degrees 2θ, each selected from the group consisting of the peaks listed in Table 2.1. In some embodiments, Form A of Compound I-1 may be characterized by a powder X-ray diffraction pattern with at least three characteristic peaks, in degrees 2θ, each selected from the group consisting of the peaks listed in Table 2.1. In some embodiments, Form A of Compound I-1 may be characterized by a powder X-ray diffraction pattern with at least four characteristic peaks, in degrees 2θ, each selected from the group consisting of the peaks listed in Table 2.1. In some embodiments, Form A of Compound I-1 may be characterized by a powder X-ray diffraction pattern with at least five characteristic peaks, in degrees 2θ, each selected from the group consisting of the peaks listed in Table 2.1. In some embodiments, Form A of Compound I-1 may be characterized by a powder X-ray diffraction pattern with at least six characteristic peaks, in degrees 2θ, each selected from the group consisting of the peaks listed in Table 2.1.

As used herein, the term "about" in the context of peaks at degrees 2θ means that a peak can be the given 2θ value±0.2, or the given 2θ value±0.1, or the given value. For example, a peak of "about 23.8 2θ" means a peak can be 23.6 2θ, 23.7 2θ, 23.8 2θ, 23.9 2θ, or 24.0 2θ.

Figure 1A:
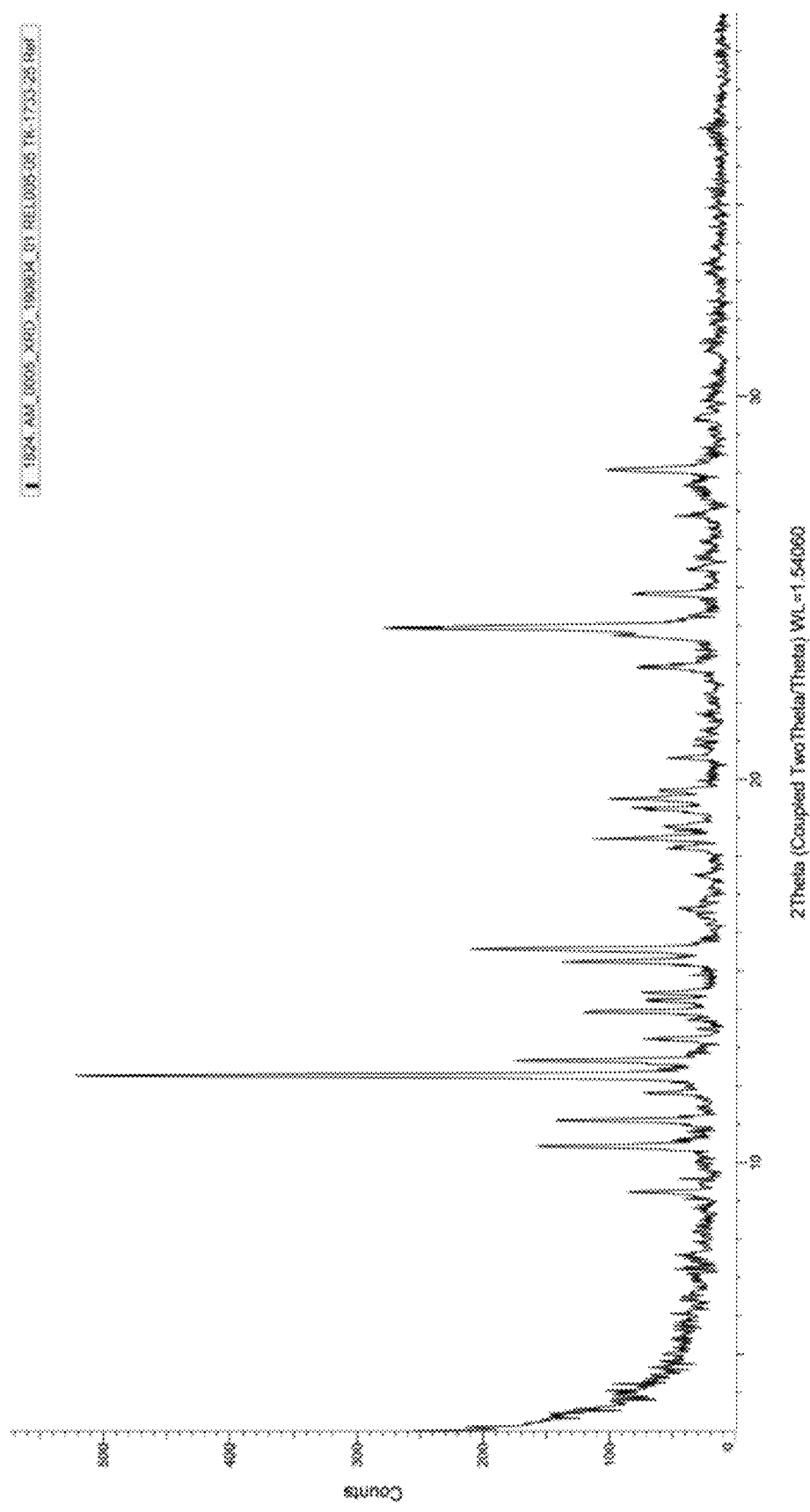
FIG. 1A depicts an X-ray diffraction pattern of Form A of Compound I-1.
Figure 1B:
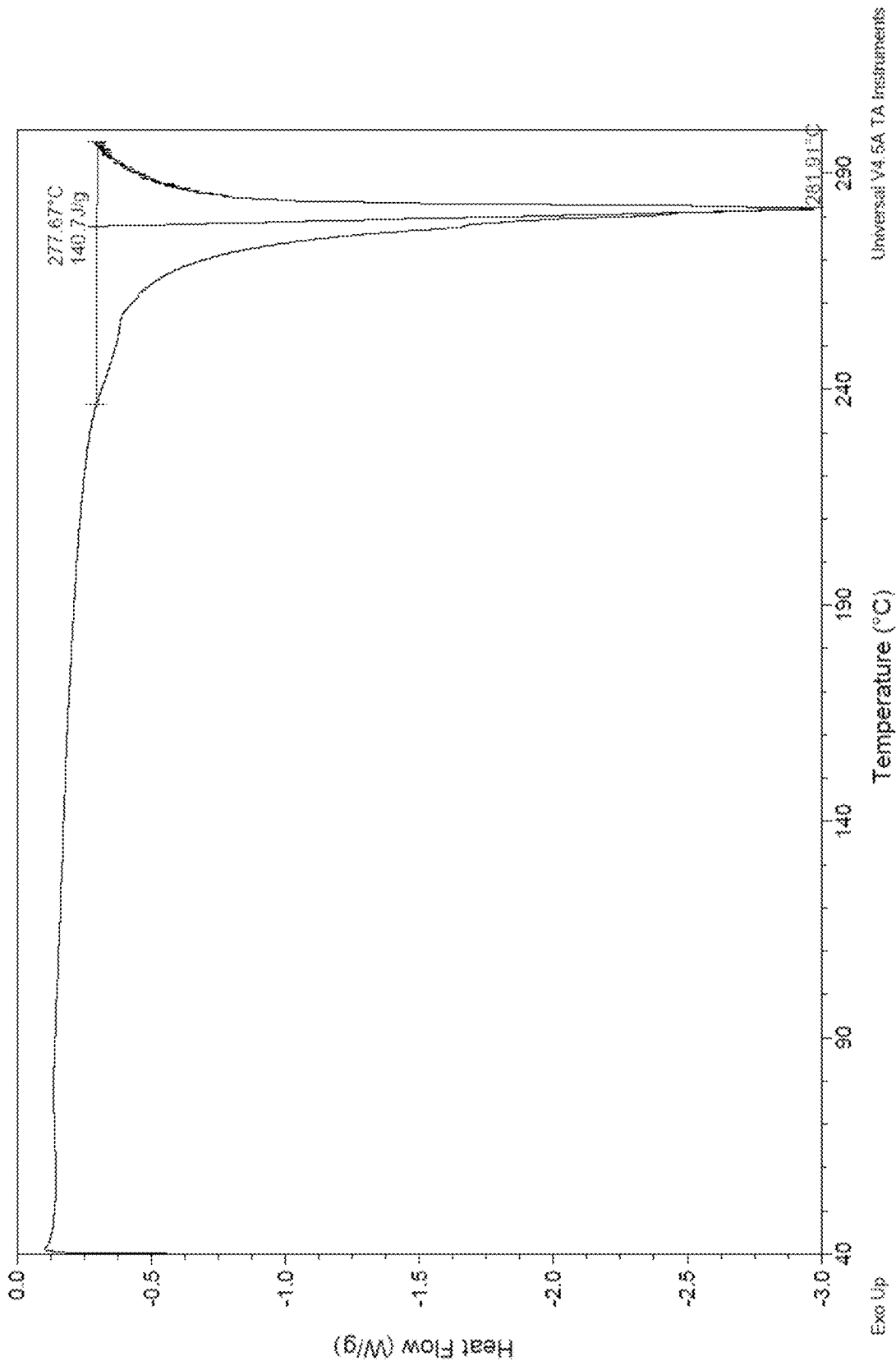
FIG. 1B depicts the characterization of Form A of Compound I-1 by differential scanning calorimetry (DSC).

In some embodiments, Form A of Compound I-1 has a differential scanning calorimetry (DSC) pattern substantially similar to that depicted in FIG. 1B. In some embodiments, Form A of Compound I-1 has a thermogravimetric analysis (TGA) pattern substantially similar to that depicted in FIG. 1C. In some embodiments, Form A of Compound I-1 can be characterized by substantial similarity to two or more of these figures simultaneously.

In some embodiments, the solid crystalline form of Compound I-1 is Form B. In some embodiments, Form B of compound I-I has a X-Ray diffraction pattern substantially similar to that depicted in FIG. 2A. In some embodiments, Form B of Compound I-1 may be characterized by a powder X-ray diffraction pattern with at least two characteristic peaks, in degrees 2θ, each selected from the group consisting of the peaks listed in Table 2.2. In some embodiments, Form B of Compound I-1 may be characterized by a powder X-ray diffraction pattern with at least three characteristic peaks, in degrees 2θ, each selected from the group consisting of the peaks listed in Table 2.2. In some embodiments, Form B of Compound I-1 may be characterized by a powder X-ray diffraction pattern with at least four characteristic peaks, in degrees 2θ, each selected from the group consisting of the peaks listed in Table 2.2. In some embodiments, Form B of Compound I-1 may be characterized by a powder X-ray diffraction pattern with at least five characteristic peaks, in degrees 2θ, each selected from the group consisting of the peaks listed in Table 2.2. In some embodiments, Form B of Compound I-1 may be characterized by a powder X-ray diffraction pattern with at least six characteristic peaks, in degrees 2θ, each selected from the group consisting of the peaks listed in Table 2.2.

Figure 2A:
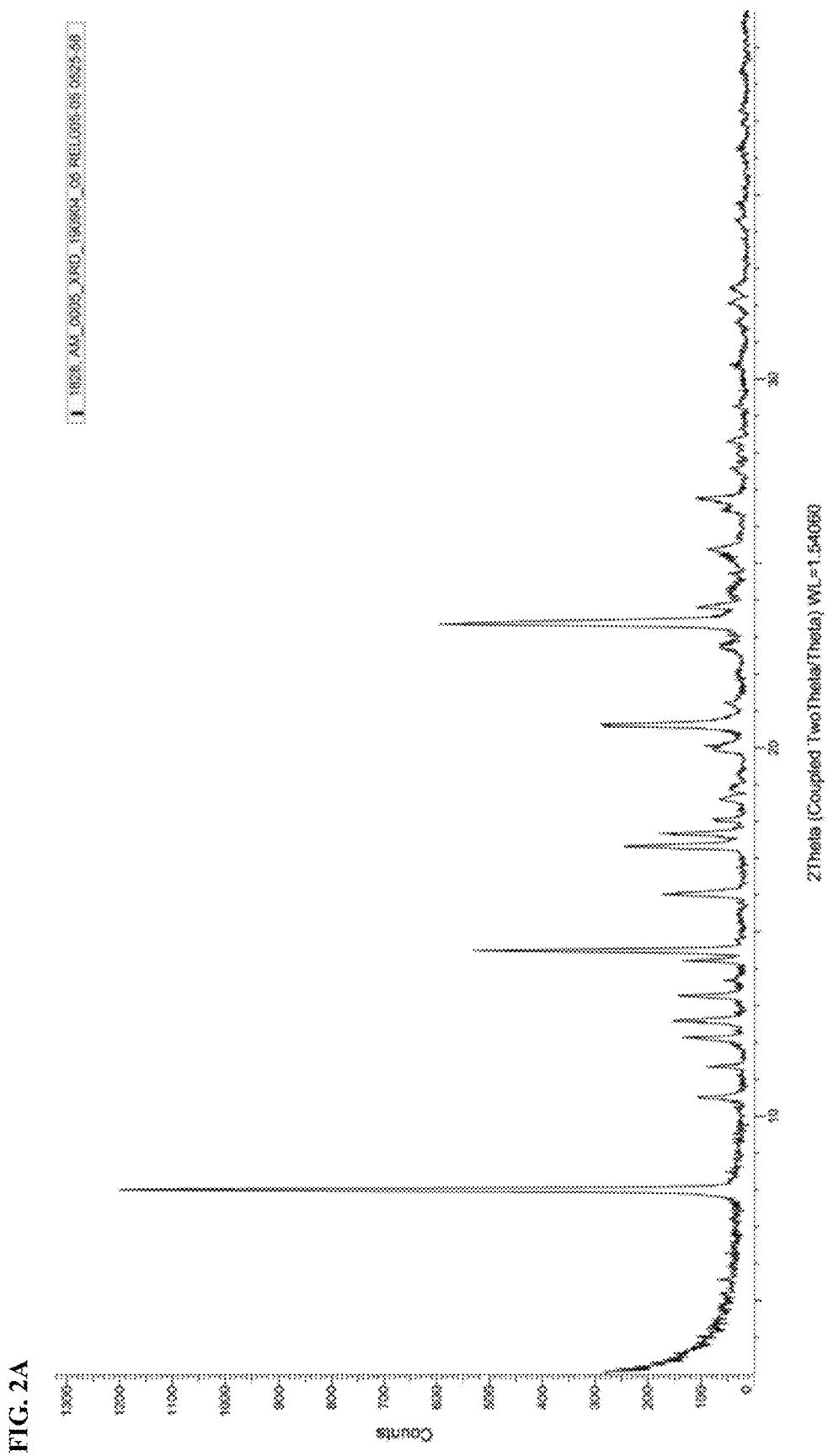
FIG. 2A depicts an X-ray diffraction pattern of Form B of Compound I-1.
Figure 2B:
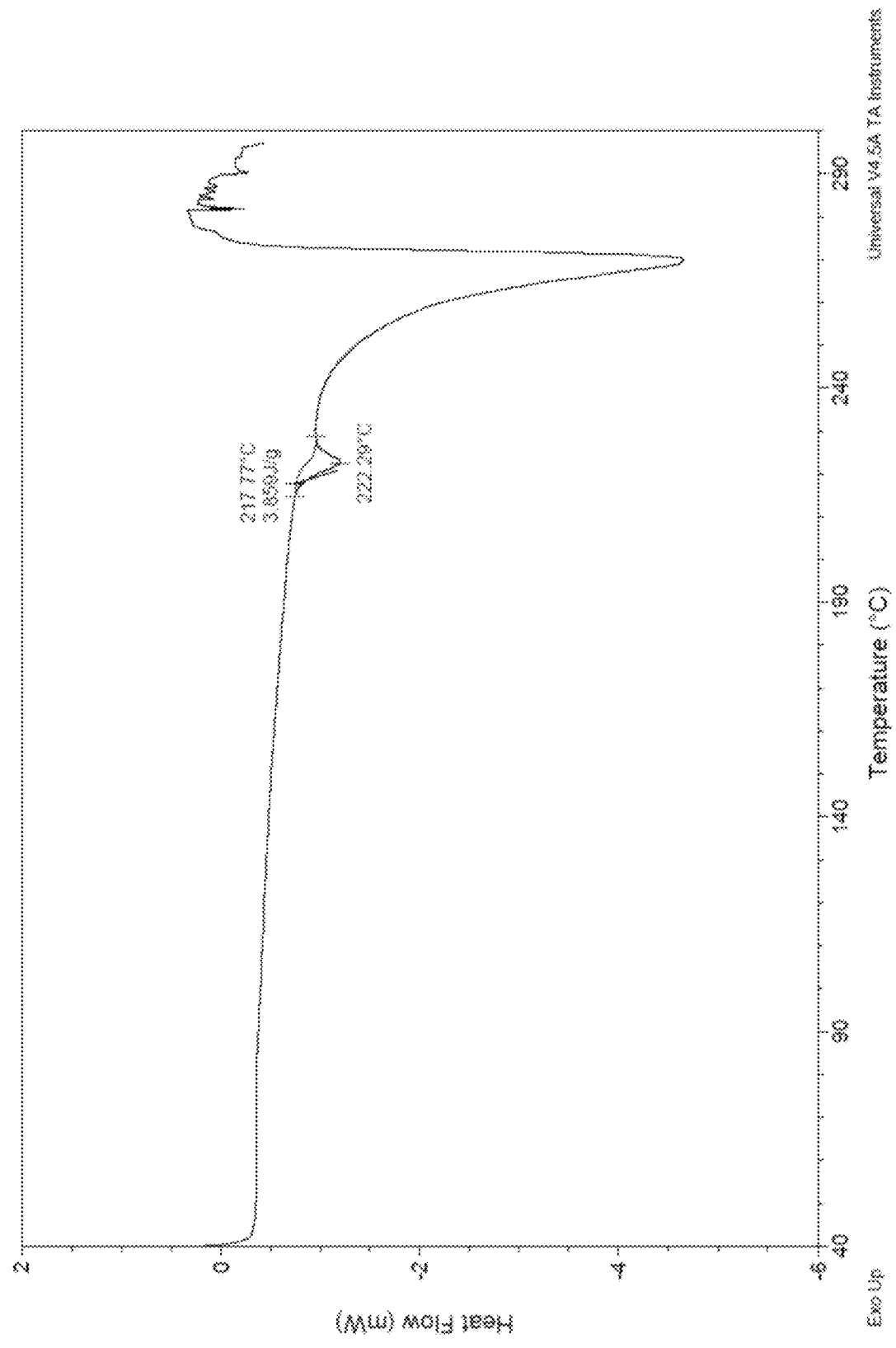
FIG. 2B depicts the characterization of Form B of Compound I-1 by differential scanning calorimetry (DSC).
Figure 2C:
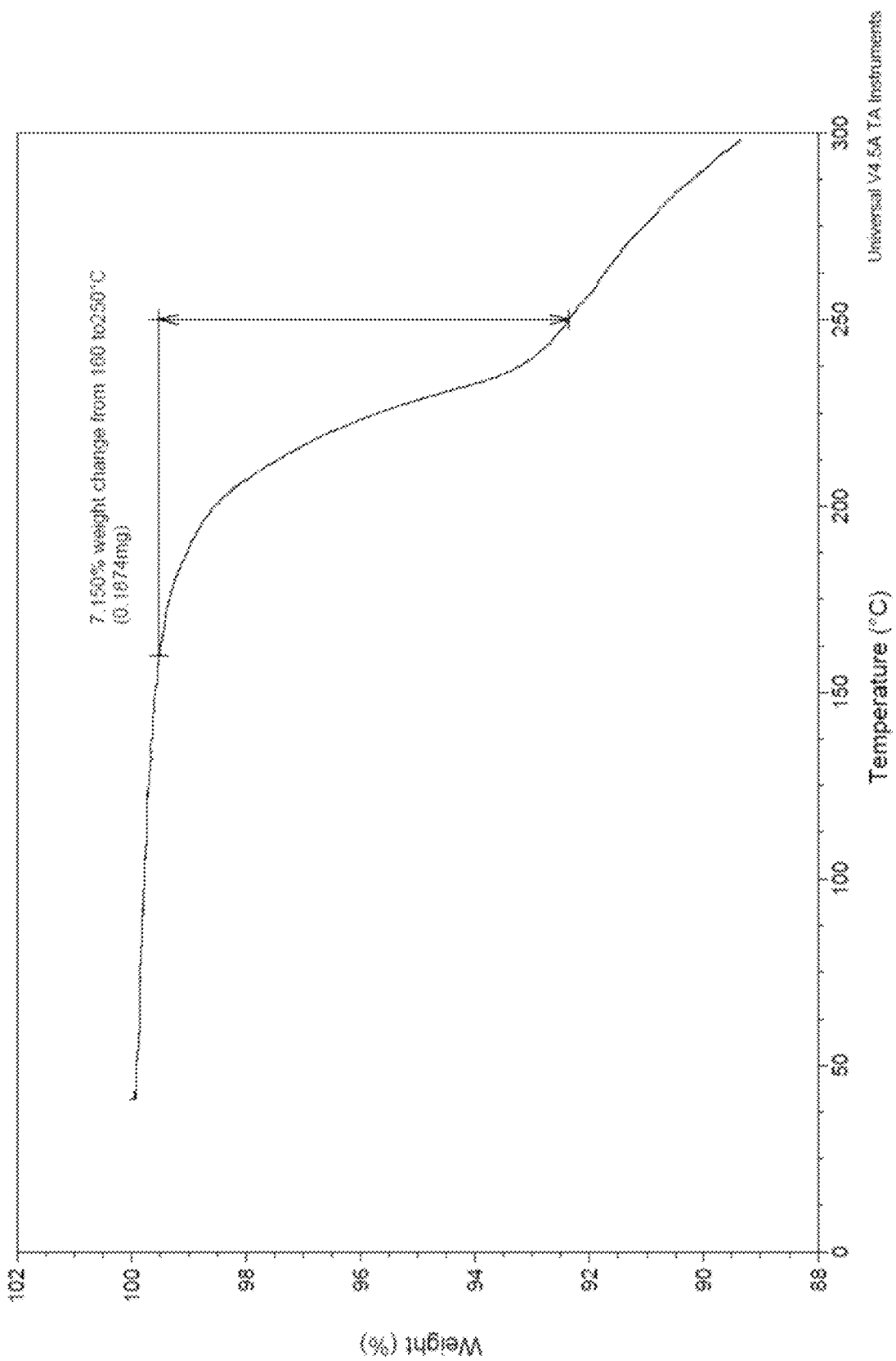
FIG. 2C depicts the characterization of Form B of Compound I-1 by thermogravimetric analysis (TGA).

In some embodiments, Form B of Compound I-1 has a differential scanning calorimetry (DSC) pattern substantially similar to that depicted in FIG. 2B. In some embodiments, Form B of Compound I-1 has a thermogravimetric analysis (TGA) pattern substantially similar to that depicted in FIG. 2C. In some embodiments, Form B of Compound I-1 can be characterized by substantial similarity to two or more of these figures simultaneously.

In some embodiments, the solid crystalline form of Compound I-1 is Form C. In some embodiments, Form C of compound I-I has a X-Ray diffraction pattern substantially similar to that depicted in FIG. 3A. In some embodiments, Form C of Compound I-1 may be characterized by a powder X-ray diffraction pattern with at least two characteristic peaks, in degrees 2θ, each selected from the group consisting of the peaks listed in Table 2.3. In some embodiments, Form C of Compound I-1 may be characterized by a powder X-ray diffraction pattern with at least three characteristic peaks, in degrees 2θ, each selected from the group consisting of the peaks listed in Table 2.3. In some embodiments, Form C of Compound I-1 may be characterized by a powder X-ray diffraction pattern with at least four characteristic peaks, in degrees 2θ, each selected from the group consisting of the peaks listed in Table 2.3. In some embodiments, Form C of Compound I-1 may be characterized by a powder X-ray diffraction pattern with at least five characteristic peaks, in degrees 2θ, each selected from the group consisting of the peaks listed in Table 2.3. In some embodiments, Form C of Compound I-1 may be characterized by a powder X-ray diffraction pattern with at least six characteristic peaks, in degrees 2θ, each selected from the group consisting of the peaks listed in Table 2.3.

Figure 3A:
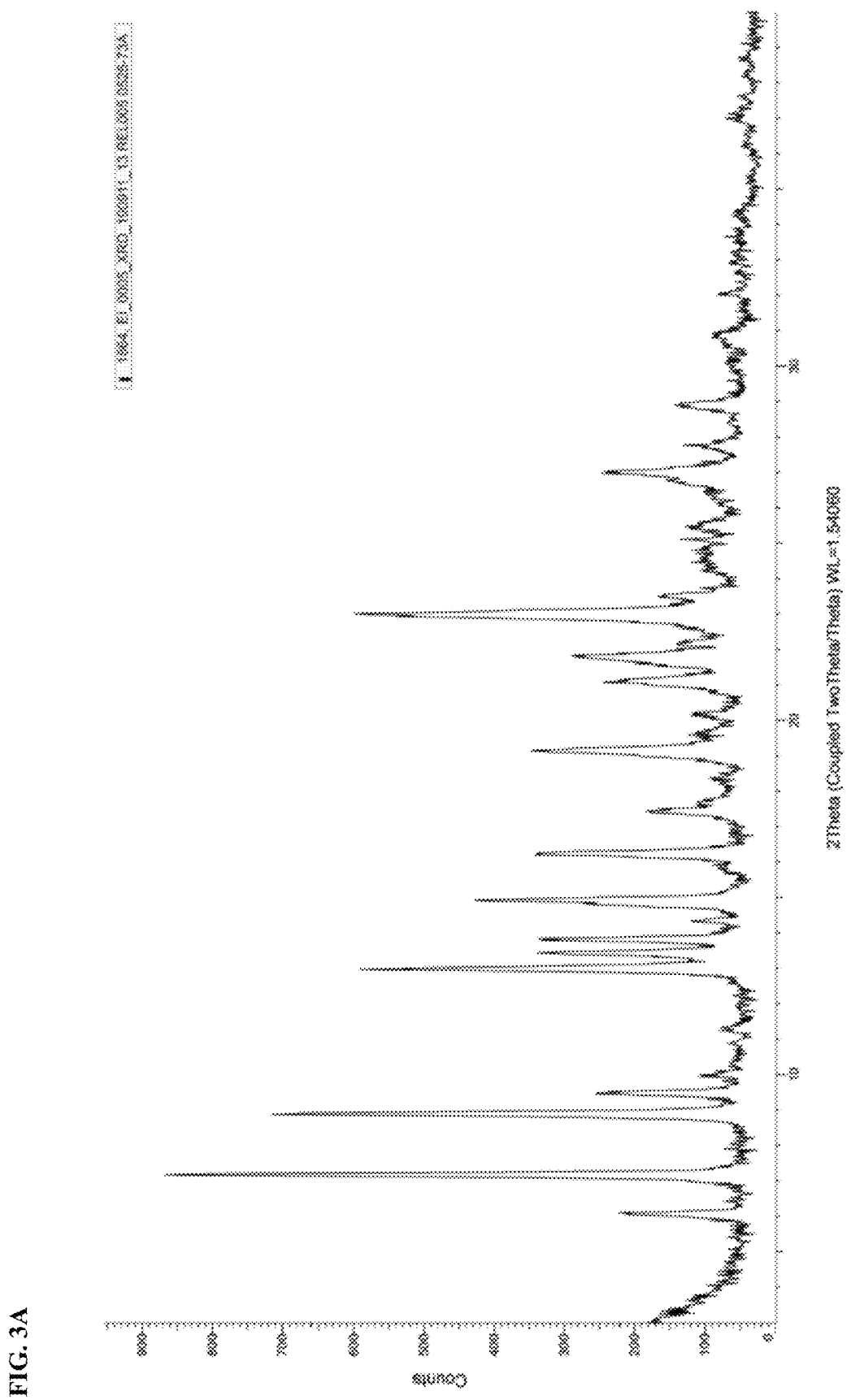
FIG. 3A depicts an X-ray diffraction pattern of Form C of Compound I-1.
Figure 3B:
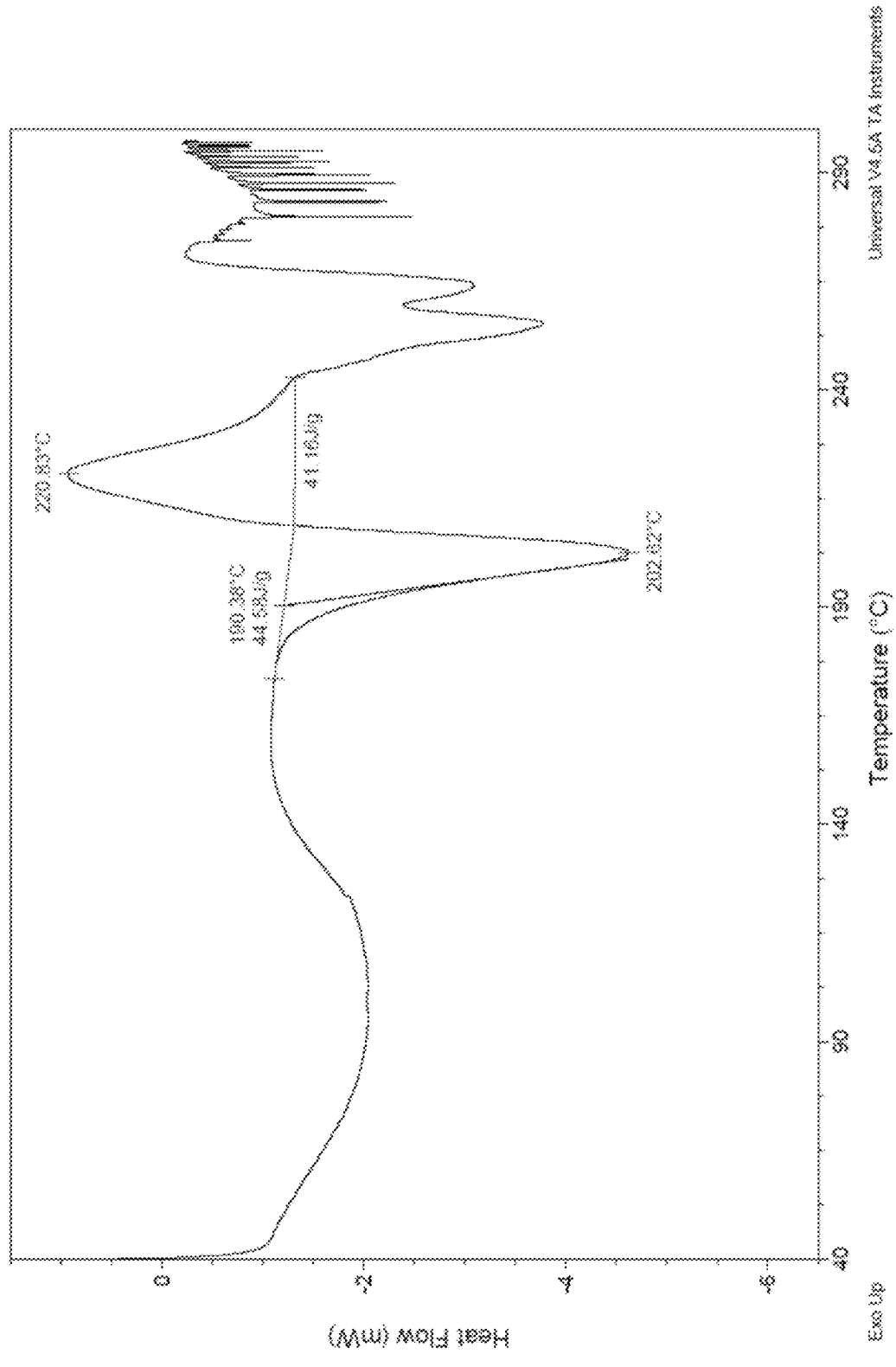
FIG. 3B depicts the characterization of Form C of Compound I-1 by differential scanning calorimetry (DSC).
Figure 3C:
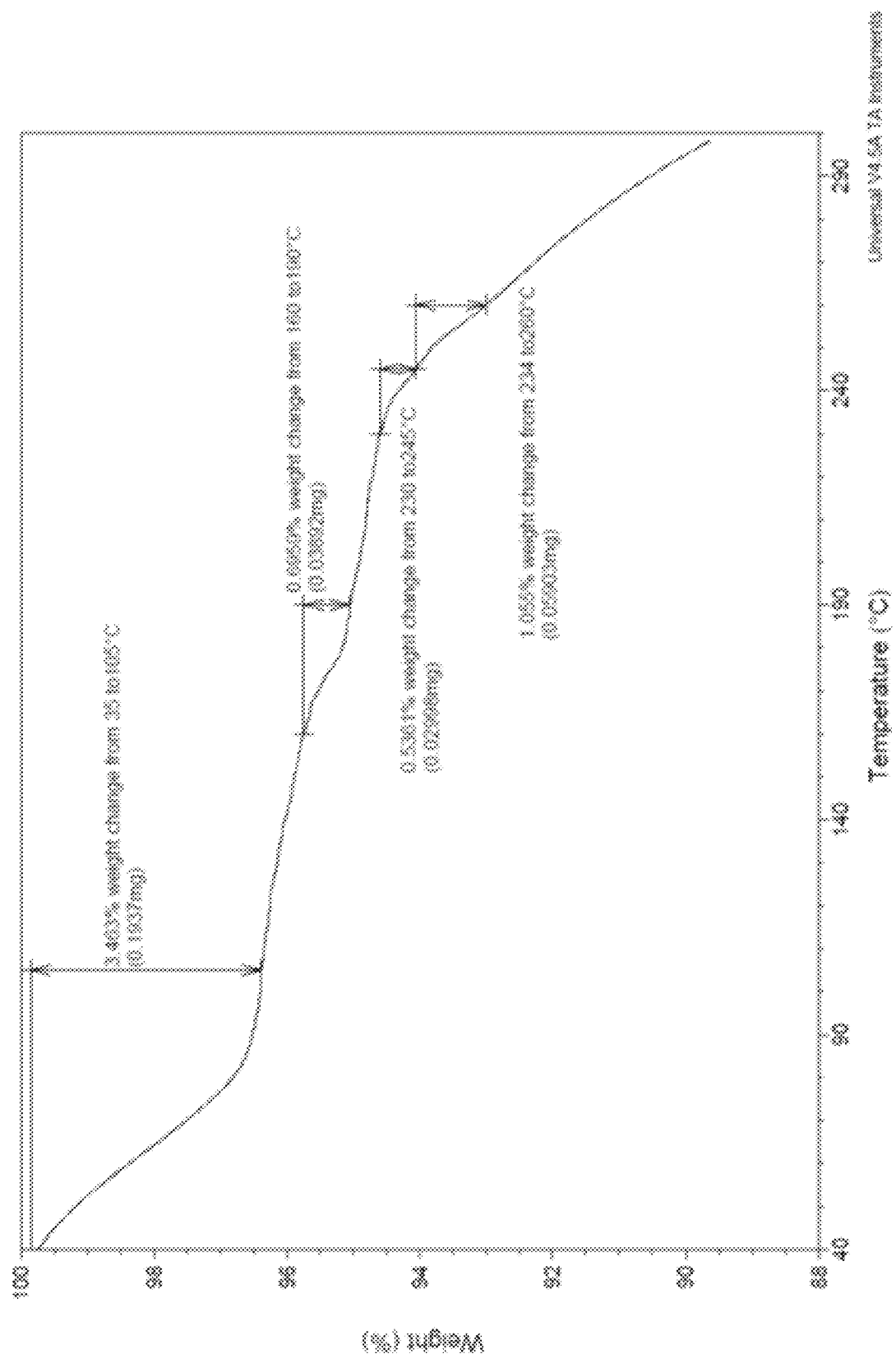
FIG. 3C depicts the characterization of Form C of Compound I-1 by thermogravimetric analysis (TGA).

In some embodiments, Form C of Compound I-1 has a differential scanning calorimetry (DSC) pattern substantially similar to that depicted in FIG. 3B. In some embodiments, Form C of Compound I-1 has a thermogravimetric analysis (TGA) pattern substantially similar to that depicted in FIG. 3C. In some embodiments, Form C of Compound I-1 can be characterized by substantial similarity to two or more of these figures simultaneously.

In some embodiments, the solid crystalline form of Compound I-1 is Form D. In some embodiments, Form D of compound I-I has a X-Ray diffraction pattern substantially similar to that depicted in FIG. 4A. In some embodiments, Form D of Compound I-1 may be characterized by a powder X-ray diffraction pattern with at least two characteristic peaks, in degrees 2θ, each selected from the group consisting of the peaks listed in Table 2.4. In some embodiments, Form D of Compound I-1 may be characterized by a powder X-ray diffraction pattern with at least three characteristic peaks, in degrees 2θ, each selected from the group consisting of the peaks listed in Table 2.4. In some embodiments, Form D of Compound I-1 may be characterized by a powder X-ray diffraction pattern with at least four characteristic peaks, in degrees 2θ, each selected from the group consisting of the peaks listed in Table 2.4. In some embodiments, Form D of Compound I-1 may be characterized by a powder X-ray diffraction pattern with at least five characteristic peaks, in degrees 2θ, each selected from the group consisting of the peaks listed in Table 2.4. In some embodiments, Form D of Compound I-1 may be characterized by a powder X-ray diffraction pattern with at least six characteristic peaks, in degrees 2θ, each selected from the group consisting of the peaks listed in Table 2.4.

Figure 4A:
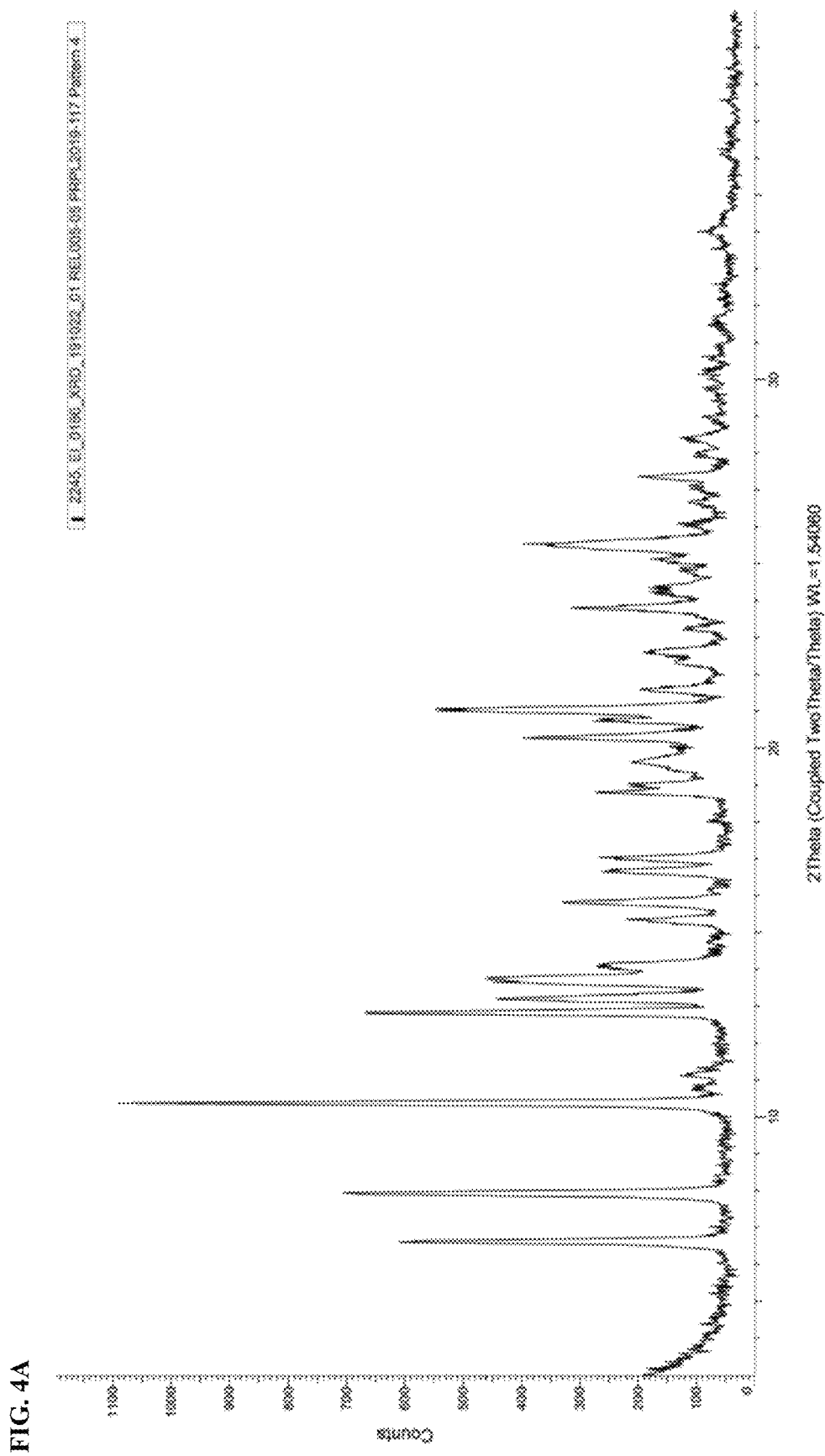
FIG. 4A depicts an X-ray diffraction pattern of Form D of Compound I-1.
Figure 4B:
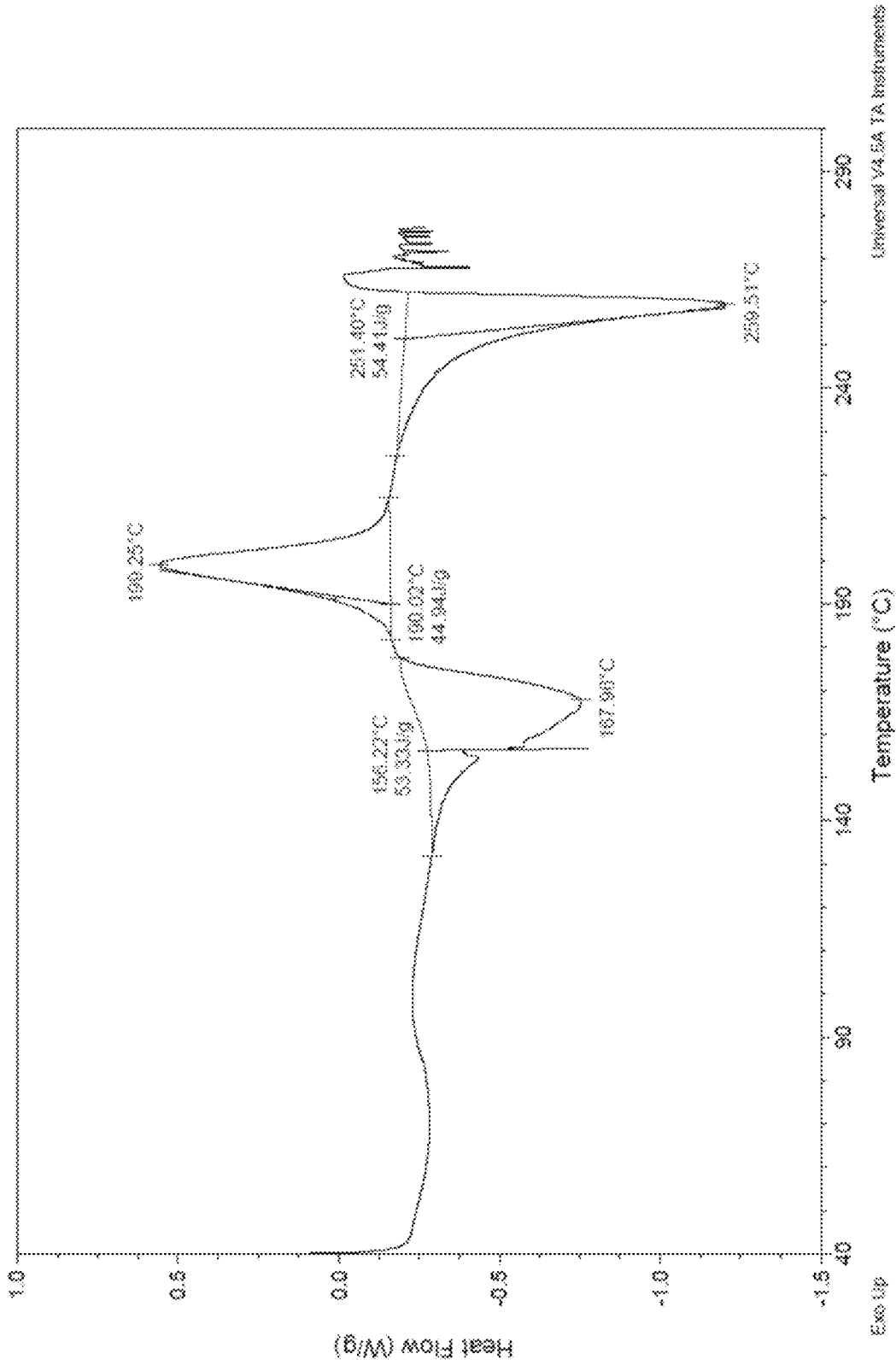
FIG. 4B depicts the characterization of Form D of Compound I-1 by differential scanning calorimetry (DSC).
Figure 4C:
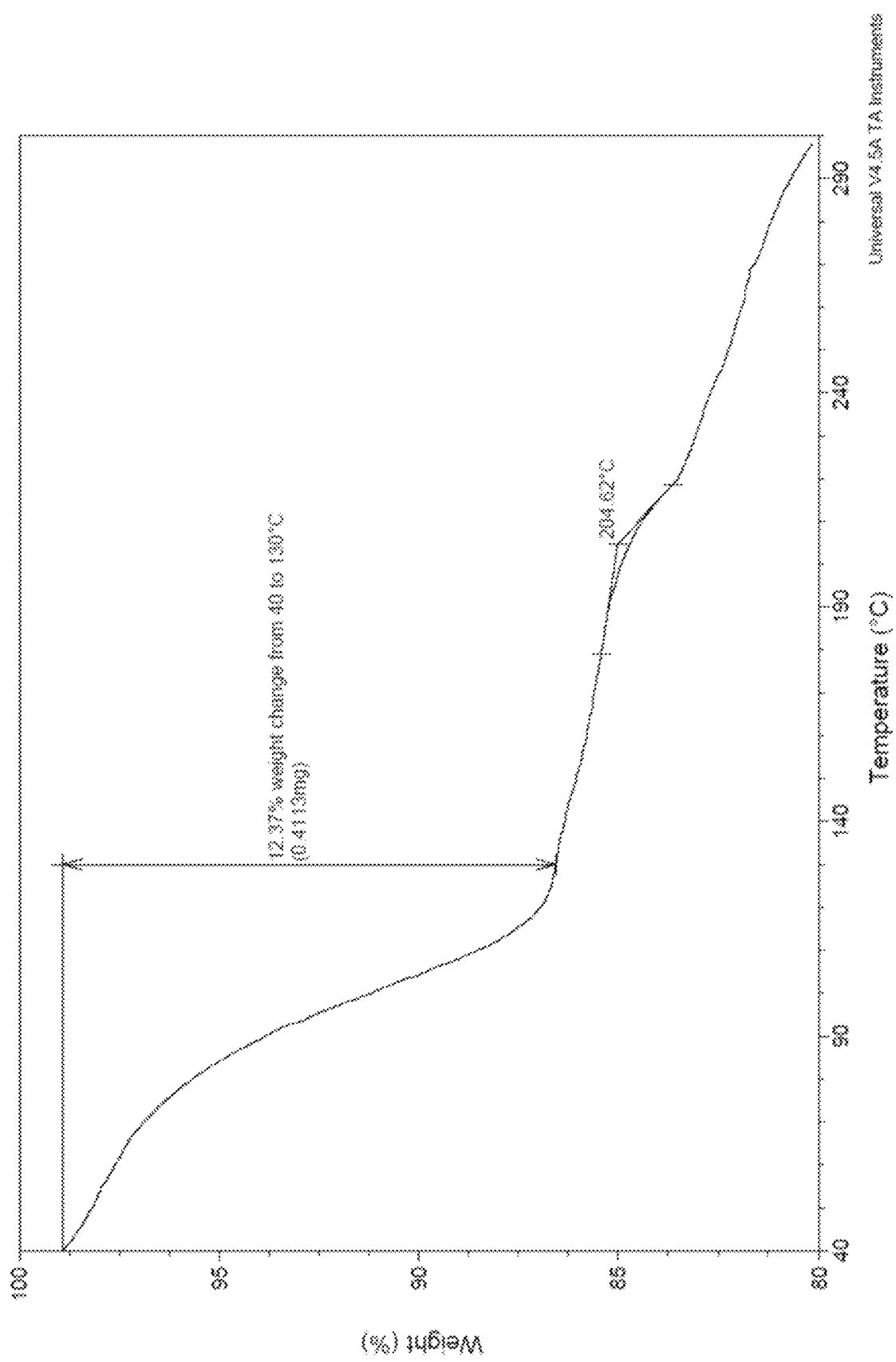
FIG. 4C depicts the characterization of Form D of Compound I-1 by thermogravimetric analysis (TGA).

In some embodiments, Form D of Compound I-1 has a differential scanning calorimetry (DSC) pattern substantially similar to that depicted in FIG. 4B. In some embodiments, Form D of Compound I-1 has a thermogravimetric analysis (TGA) pattern substantially similar to that depicted in FIG. 4C. In some embodiments, Form D of Compound I-1 can be characterized by substantial similarity to two or more of these figures simultaneously.

In some embodiments, the solid crystalline form of Compound I-1 is Form E. In some embodiments, Form E of compound I-I has a X-Ray diffraction pattern substantially similar to that depicted in FIG. 5A. In some embodiments, Form E of Compound I-1 may be characterized by a powder X-ray diffraction pattern with at least two characteristic peaks, in degrees 2θ, each selected from the group consisting of the peaks listed in Table 2.5. In some embodiments, Form E of Compound I-1 may be characterized by a powder X-ray diffraction pattern with at least three characteristic peaks, in degrees 2θ, each selected from the group consisting of the peaks listed in Table 2.5. In some embodiments, Form E of Compound I-1 may be characterized by a powder X-ray diffraction pattern with at least four characteristic peaks, in degrees 2θ, each selected from the group consisting of the peaks listed in Table 2.5. In some embodiments, Form E of Compound I-1 may be characterized by a powder X-ray diffraction pattern with at least five characteristic peaks, in degrees 2θ, each selected from the group consisting of the peaks listed in Table 2.5. In some embodiments, Form E of Compound I-1 may be characterized by a powder X-ray diffraction pattern with at least six characteristic peaks, in degrees 2θ, each selected from the group consisting of the peaks listed in Table 2.5.

Figure 5A:
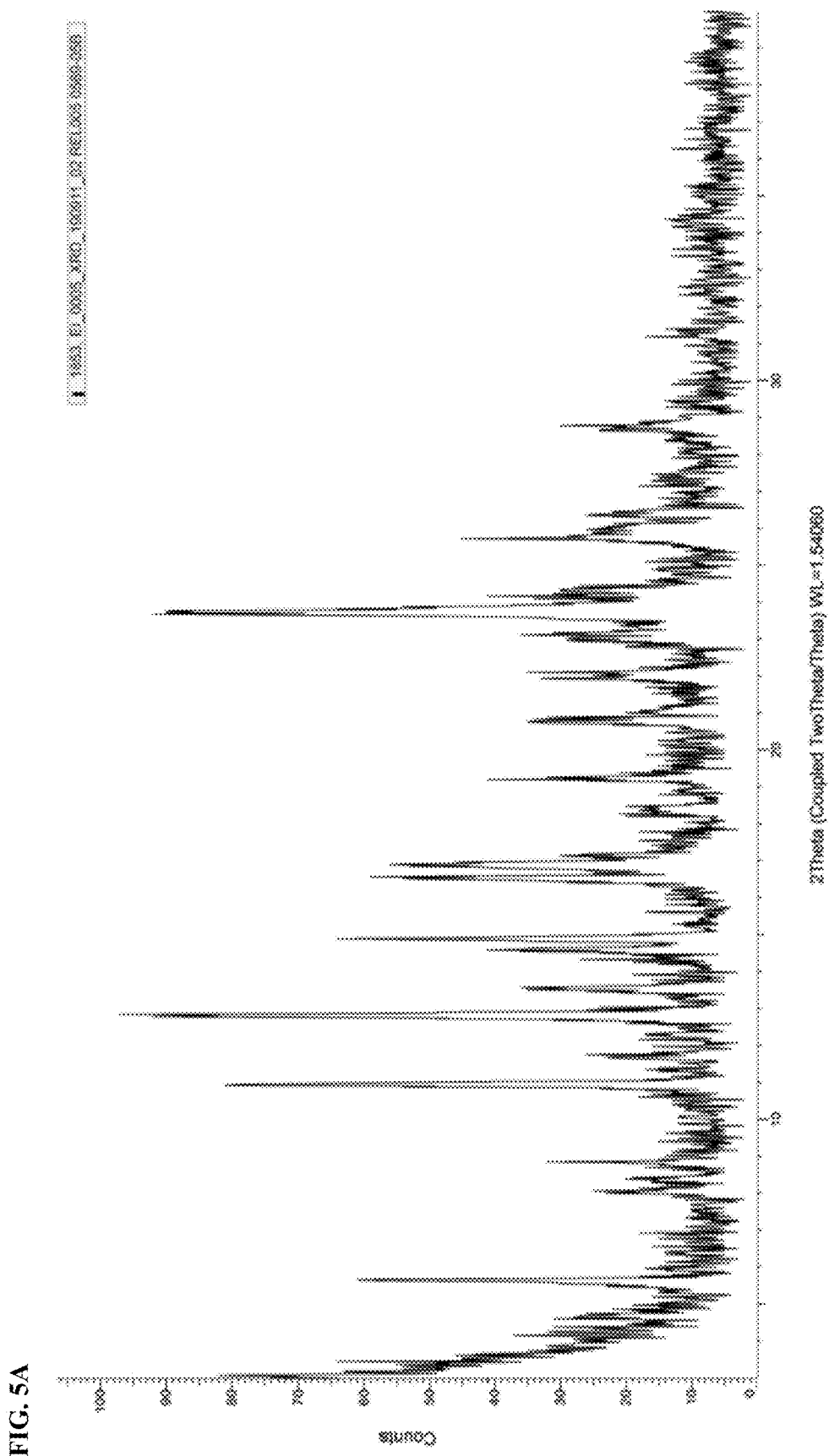
FIG. 5A depicts an X-ray diffraction pattern of Form E of Compound I-1.
Figure 5B:
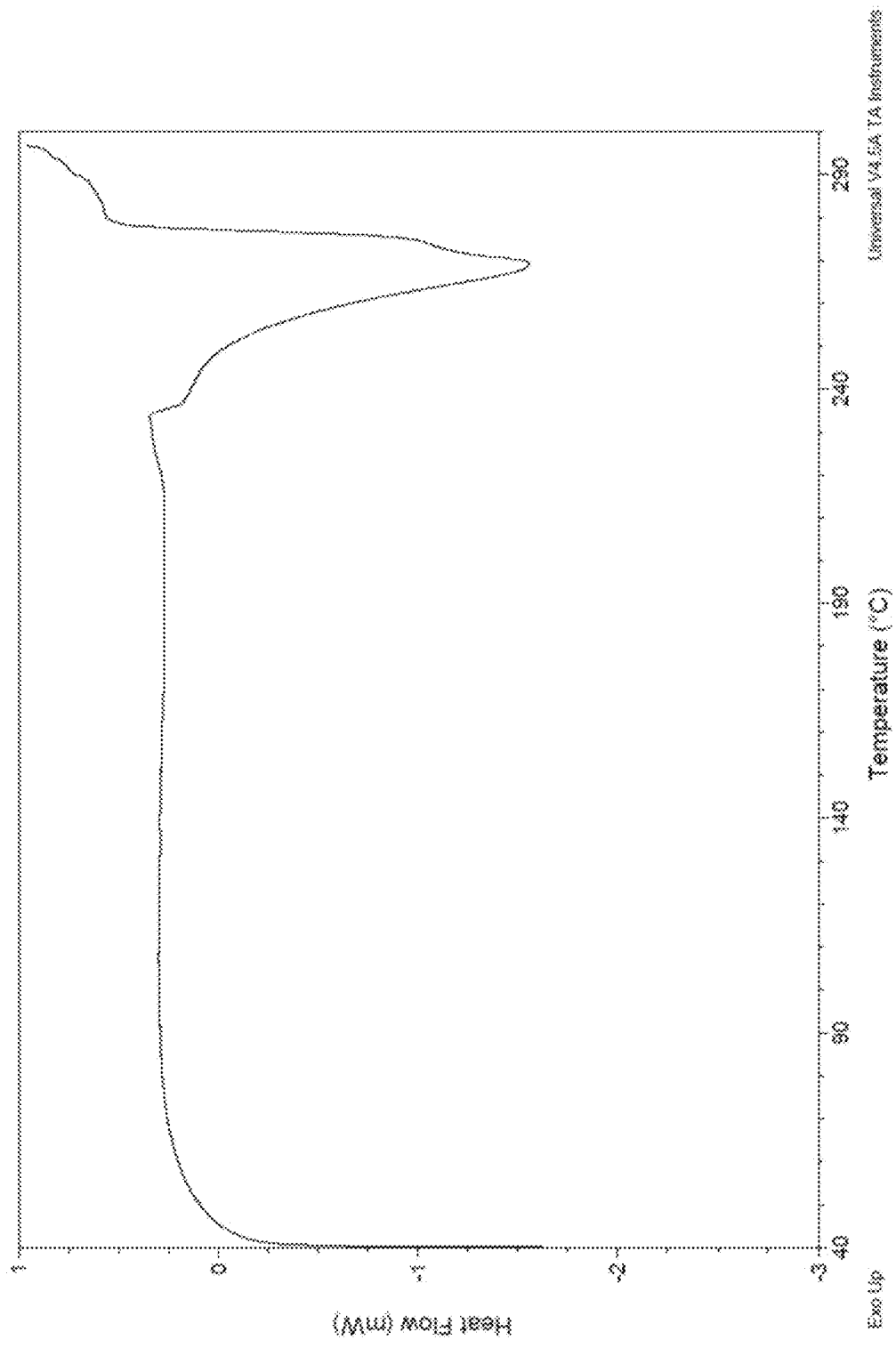
FIG. 5B depicts the characterization of Form E of Compound I-1 by differential scanning calorimetry (DSC).

In some embodiments, Form E of Compound I-1 has a differential scanning calorimetry (DSC) pattern substantially similar to that depicted in FIG. 5B. In some embodiments, Form E of Compound I-1 has a thermogravimetric analysis (TGA) pattern substantially similar to that depicted in FIG. 5C. In some embodiments, Form E of Compound I-1 can be characterized by substantial similarity to two or more of these figures simultaneously.

In some embodiments, the solid crystalline form of Compound I-1 is Form F. In some embodiments, Form F of compound I-I has a X-Ray diffraction pattern substantially similar to that depicted in FIG. 6A. In some embodiments, Form F of Compound I-1 may be characterized by a powder X-ray diffraction pattern with at least two characteristic peaks, in degrees 2θ, each selected from the group consisting of the peaks listed in Table 2.6. In some embodiments, Form F of Compound I-1 may be characterized by a powder X-ray diffraction pattern with at least three characteristic peaks, in degrees 2θ, each selected from the group consisting of the peaks listed in Table 2.6. In some embodiments, Form F of Compound I-1 may be characterized by a powder X-ray diffraction pattern with at least four characteristic peaks, in degrees 2θ, each selected from the group consisting of the peaks listed in Table 2.6. In some embodiments, Form F of Compound I-1 may be characterized by a powder X-ray diffraction pattern with at least five characteristic peaks, in degrees 2θ, each selected from the group consisting of the peaks listed in Table 2.6. In some embodiments, Form F of Compound I-1 may be characterized by a powder X-ray diffraction pattern with at least six characteristic peaks, in degrees 2θ, each selected from the group consisting of the peaks listed in Table 2.6.

Figure 6A:
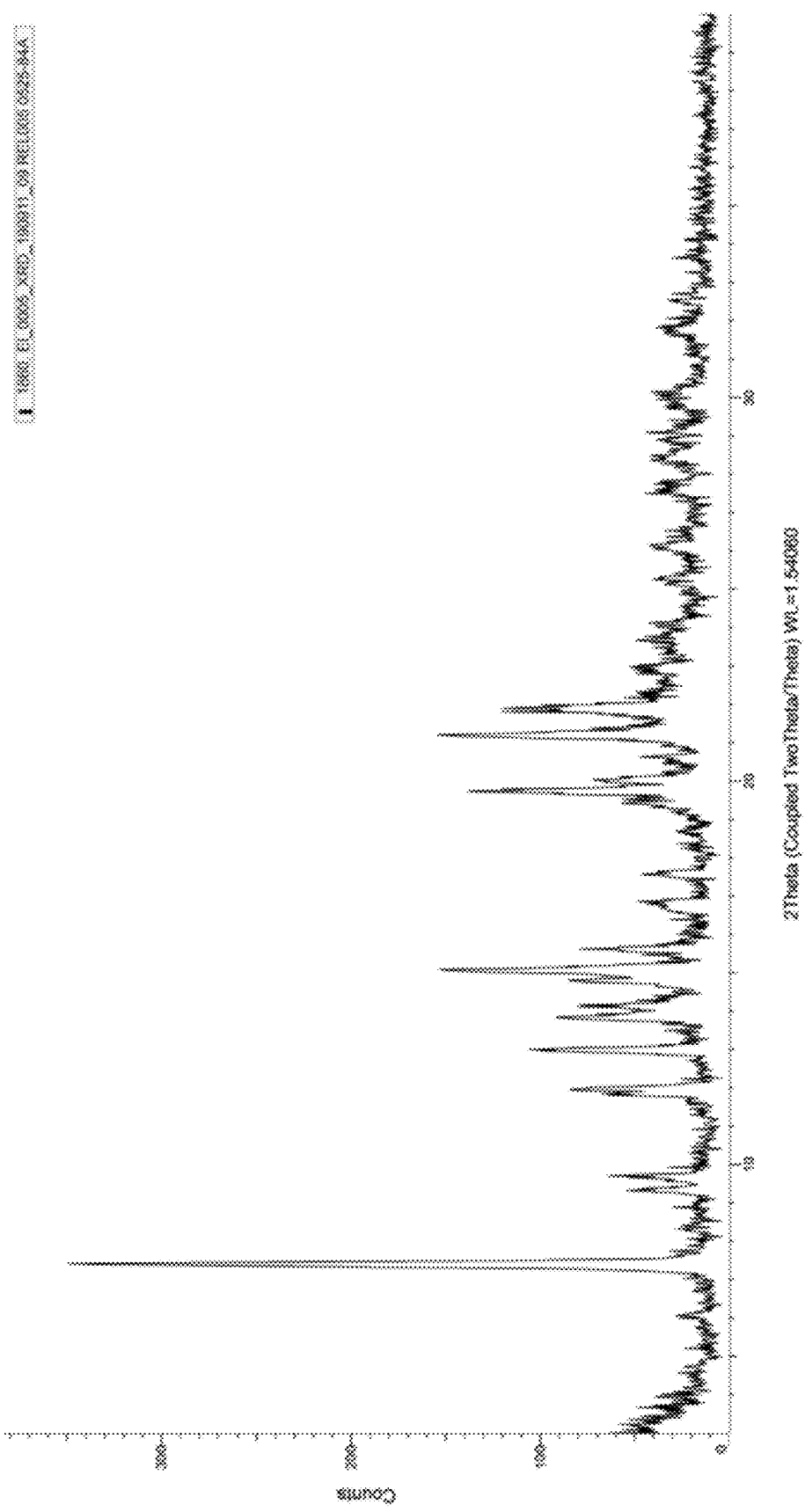
FIG. 6A depicts an X-ray diffraction pattern of Form F of Compound I-1.
Figure 6B:
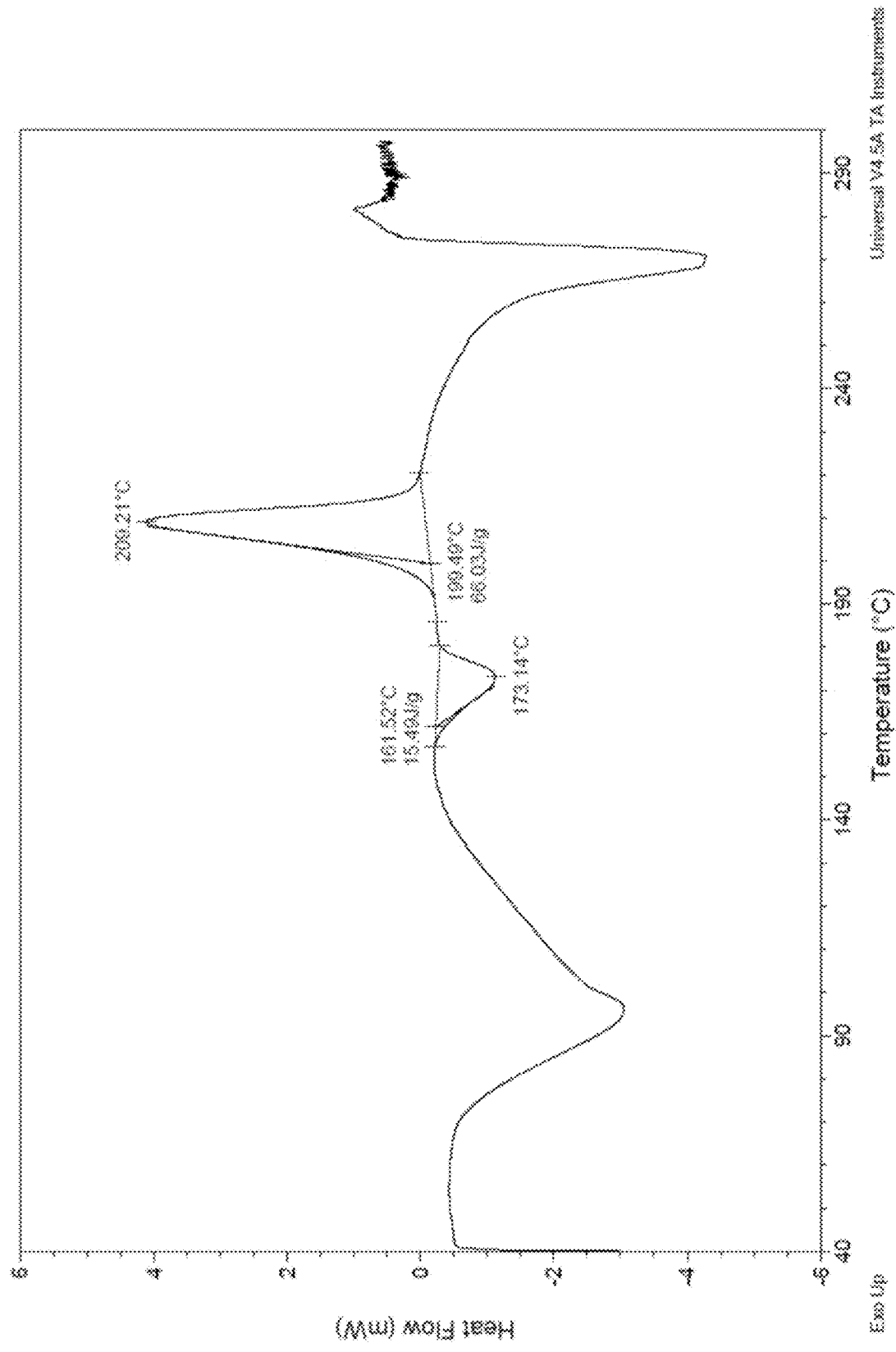
FIG. 6B depicts the characterization of Form F of Compound I-1 by differential scanning calorimetry (DSC).
Figure 6C:
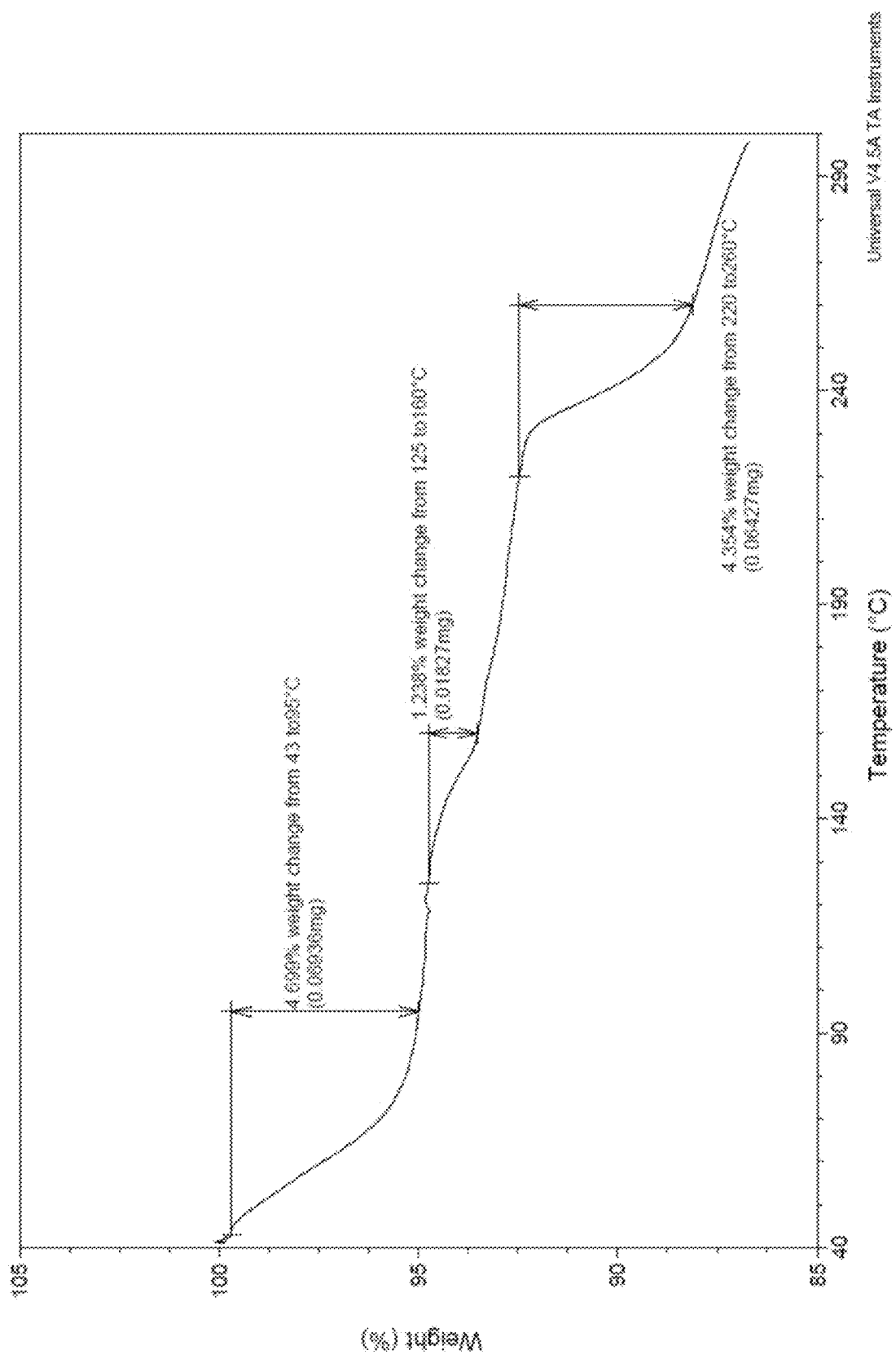
FIG. 6C depicts the characterization of Form F of Compound I-1 by thermogravimetric analysis (TGA).

In some embodiments, Form F of Compound I-1 has a differential scanning calorimetry (DSC) pattern substantially similar to that depicted in FIG. 6B. In some embodiments, Form F of Compound I-1 has a thermogravimetric analysis (TGA) pattern substantially similar to that depicted in FIG. 6C. In some embodiments, Form F of Compound I-1 can be characterized by substantial similarity to two or more of these figures simultaneously.

In some embodiments, the solid crystalline form of Compound I-1 is Form G. In some embodiments, Form G of compound I-I has a X-Ray diffraction pattern substantially similar to that depicted in FIG. 7A. In some embodiments, Form G of Compound I-1 may be characterized by a powder X-ray diffraction pattern with at least two characteristic peaks, in degrees 2θ, each selected from the group consisting of the peaks listed in Table 2.7. In some embodiments, Form G of Compound I-1 may be characterized by a powder X-ray diffraction pattern with at least three characteristic peaks, in degrees 2θ, each selected from the group consisting of the peaks listed in Table 2.7. In some embodiments, Form G of Compound I-1 may be characterized by a powder X-ray diffraction pattern with at least four characteristic peaks, in degrees 2θ, each selected from the group consisting of the peaks listed in Table 2.7. In some embodiments, Form G of Compound I-1 may be characterized by a powder X-ray diffraction pattern with at least five characteristic peaks, in degrees 2θ, each selected from the group consisting of the peaks listed in Table 2.7. In some embodiments, Form G of Compound I-1 may be characterized by a powder X-ray diffraction pattern with at least six characteristic peaks, in degrees 2θ, each selected from the group consisting of the peaks listed in Table 2.7.

Figure 7A:
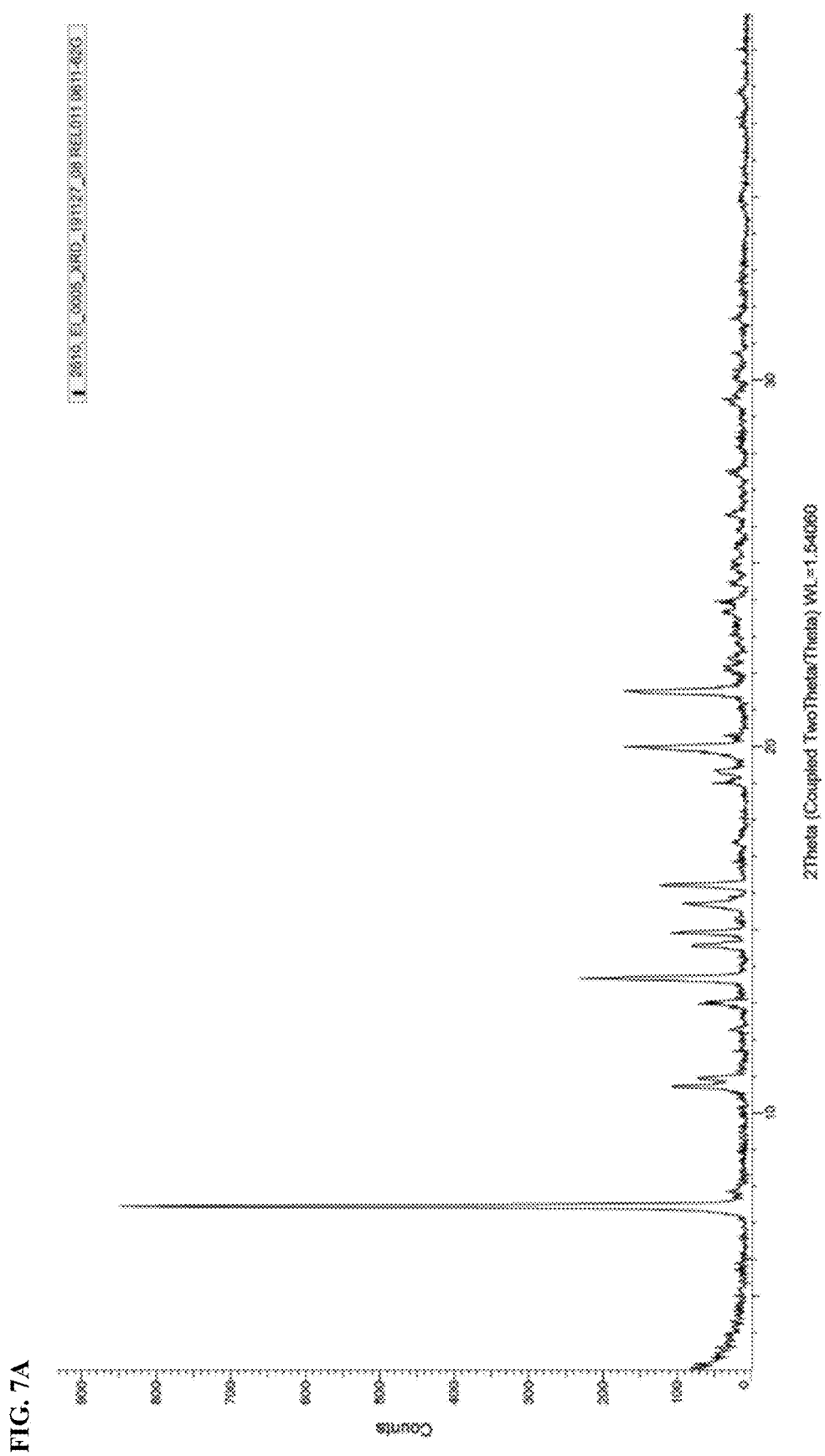
FIG. 7A depicts an X-ray diffraction pattern of Form G of Compound I-1.
Figure 7B:
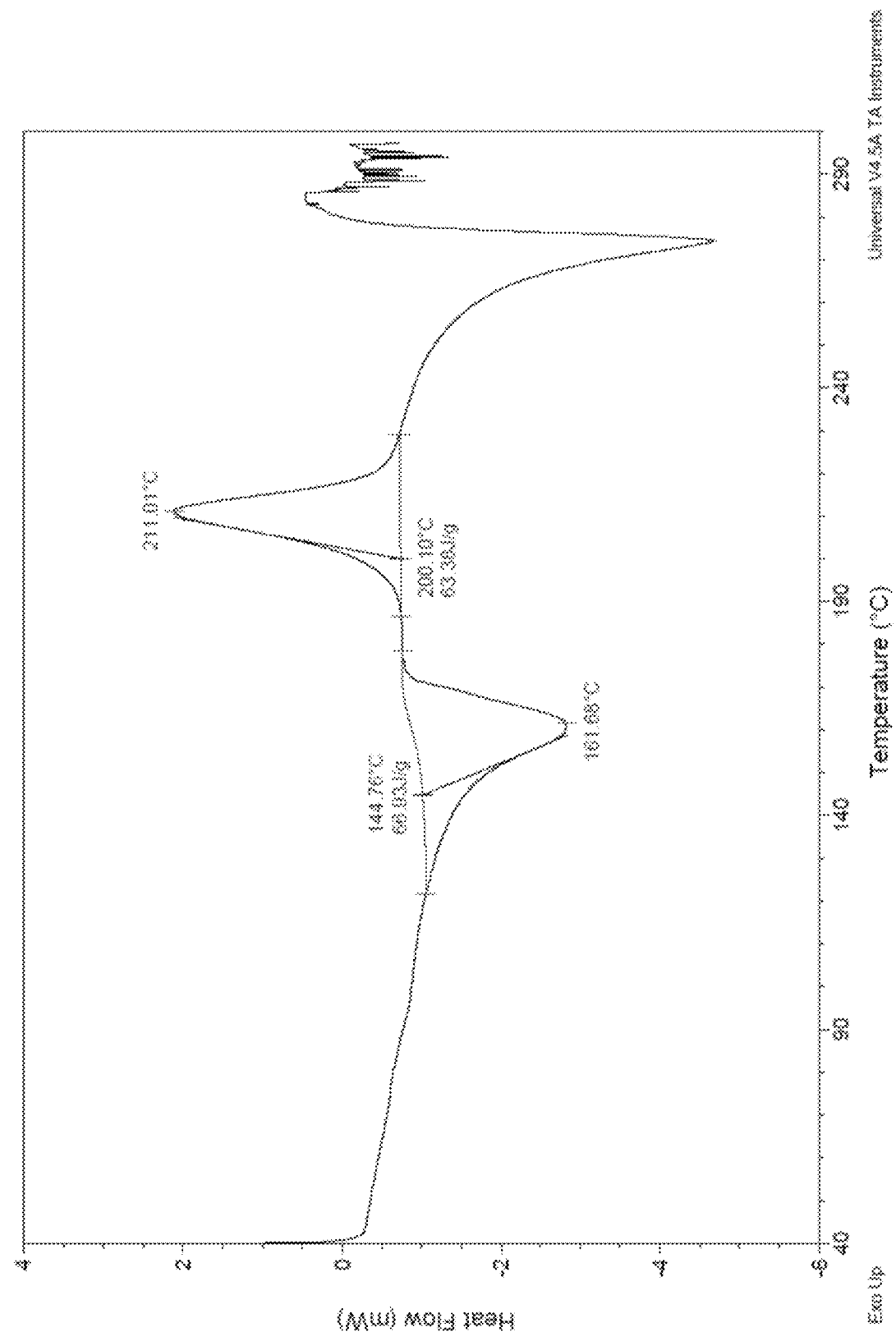
FIG. 7B depicts the characterization of Form G of Compound I-1 by differential scanning calorimetry (DSC).
Figure 7C:
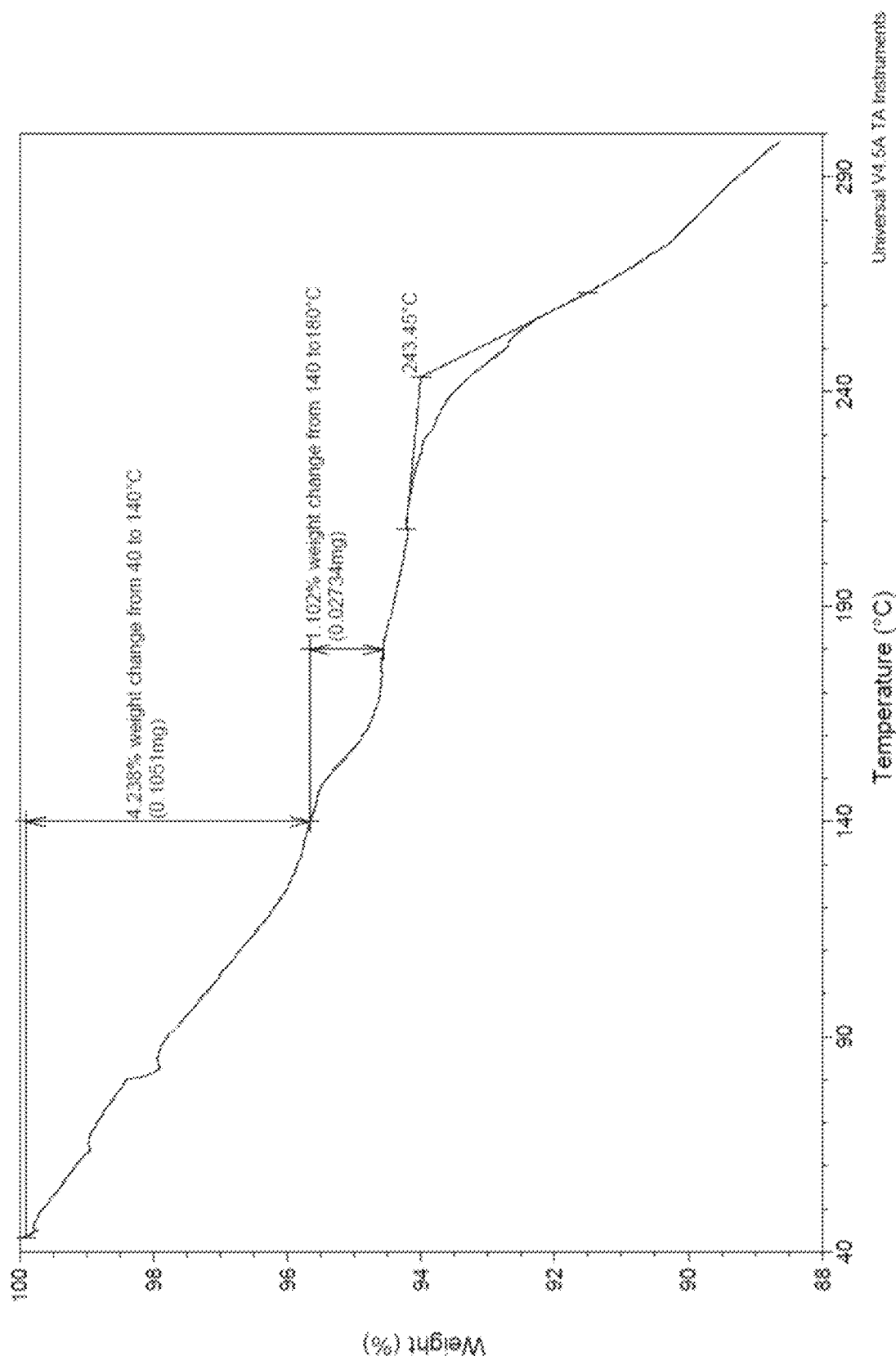
FIG. 7C depicts the characterization of Form G of Compound I-1 by thermogravimetric analysis (TGA).

In some embodiments, Form G of Compound I-1 has a differential scanning calorimetry (DSC) pattern substantially similar to that depicted in FIG. 7B. In some embodiments, Form G of Compound I-1 has a thermogravimetric analysis (TGA) pattern substantially similar to that depicted in FIG. 7C. In some embodiments, Form G of Compound I-1 can be characterized by substantial similarity to two or more of these figures simultaneously.

In some embodiments, the solid crystalline form of Compound I-1 is Form H. In some embodiments, Form H of compound I-I has a X-Ray diffraction pattern substantially similar to that depicted in FIG. 8A. In some embodiments, Form H of Compound I-1 may be characterized by a powder X-ray diffraction pattern with at least two characteristic peaks, in degrees 2θ, each selected from the group consisting of the peaks listed in Table 2.8. In some embodiments, Form H of Compound I-1 may be characterized by a powder X-ray diffraction pattern with at least three characteristic peaks, in degrees 2θ, each selected from the group consisting of the peaks listed in Table 2.8. In some embodiments, Form H of Compound I-1 may be characterized by a powder X-ray diffraction pattern with at least four characteristic peaks, in degrees 2θ, each selected from the group consisting of the peaks listed in Table 2.8. In some embodiments, Form H of Compound I-1 may be characterized by a powder X-ray diffraction pattern with at least five characteristic peaks, in degrees 2θ, each selected from the group consisting of the peaks listed in Table 2.8. In some embodiments, Form H of Compound I-1 may be characterized by a powder X-ray diffraction pattern with at least six characteristic peaks, in degrees 2θ, each selected from the group consisting of the peaks listed in Table 2.8.

Figure 8A:
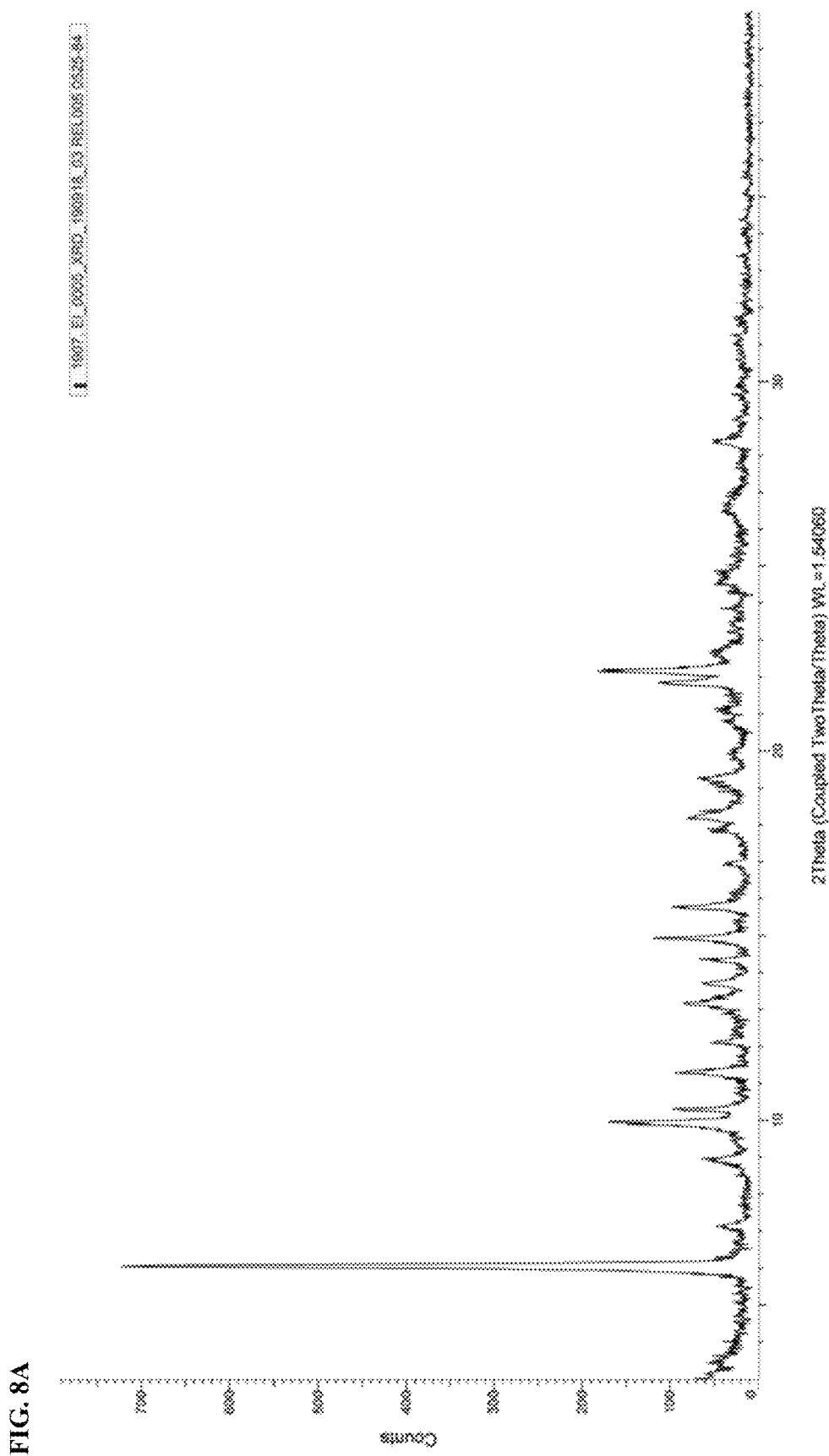
FIG. 8A depicts an X-ray diffraction pattern of Form H of Compound I-1.
Figure 8B:
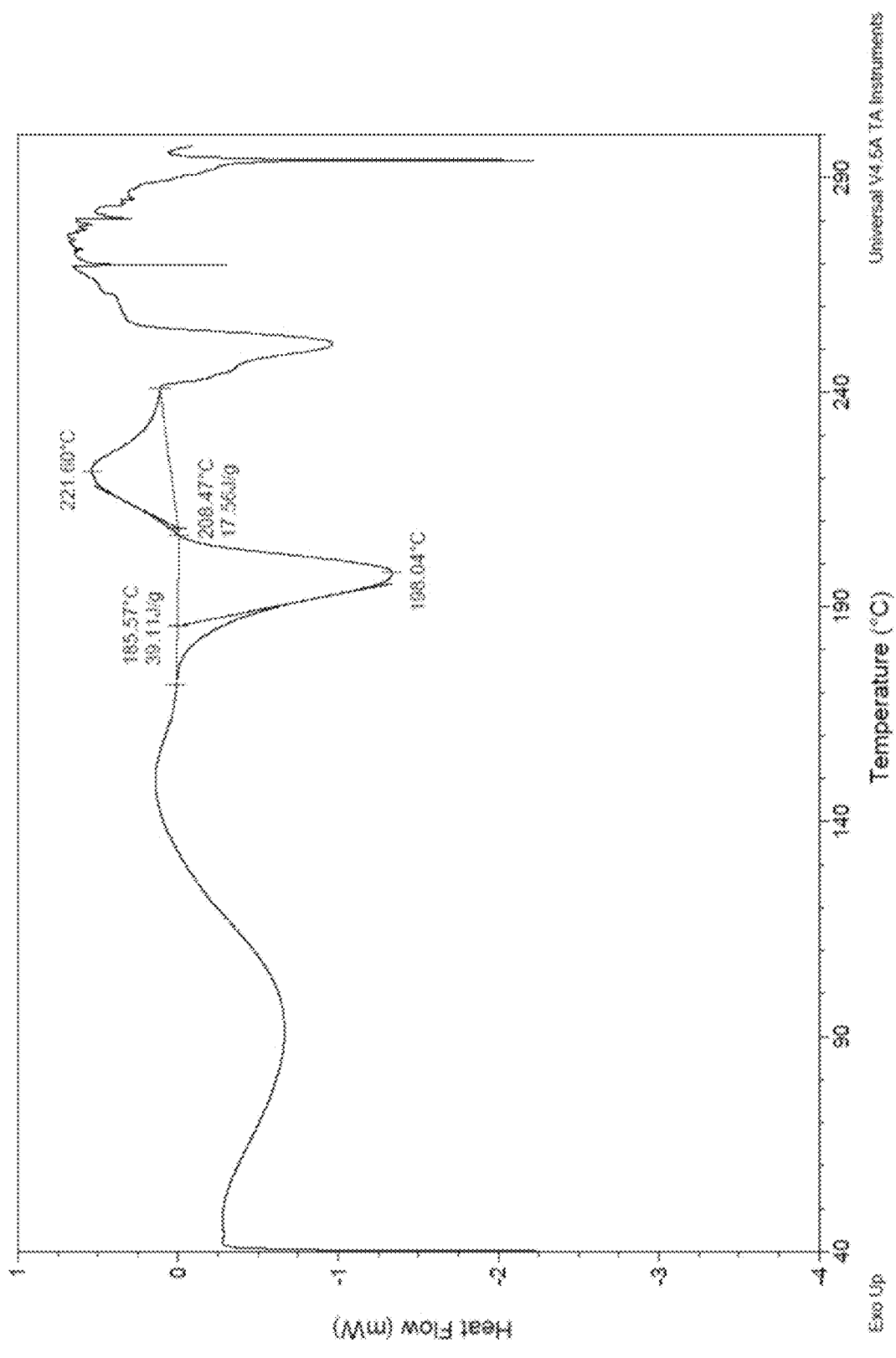
FIG. 8B depicts the characterization of Form H of Compound I-1 by differential scanning calorimetry (DSC).
Figure 8C:
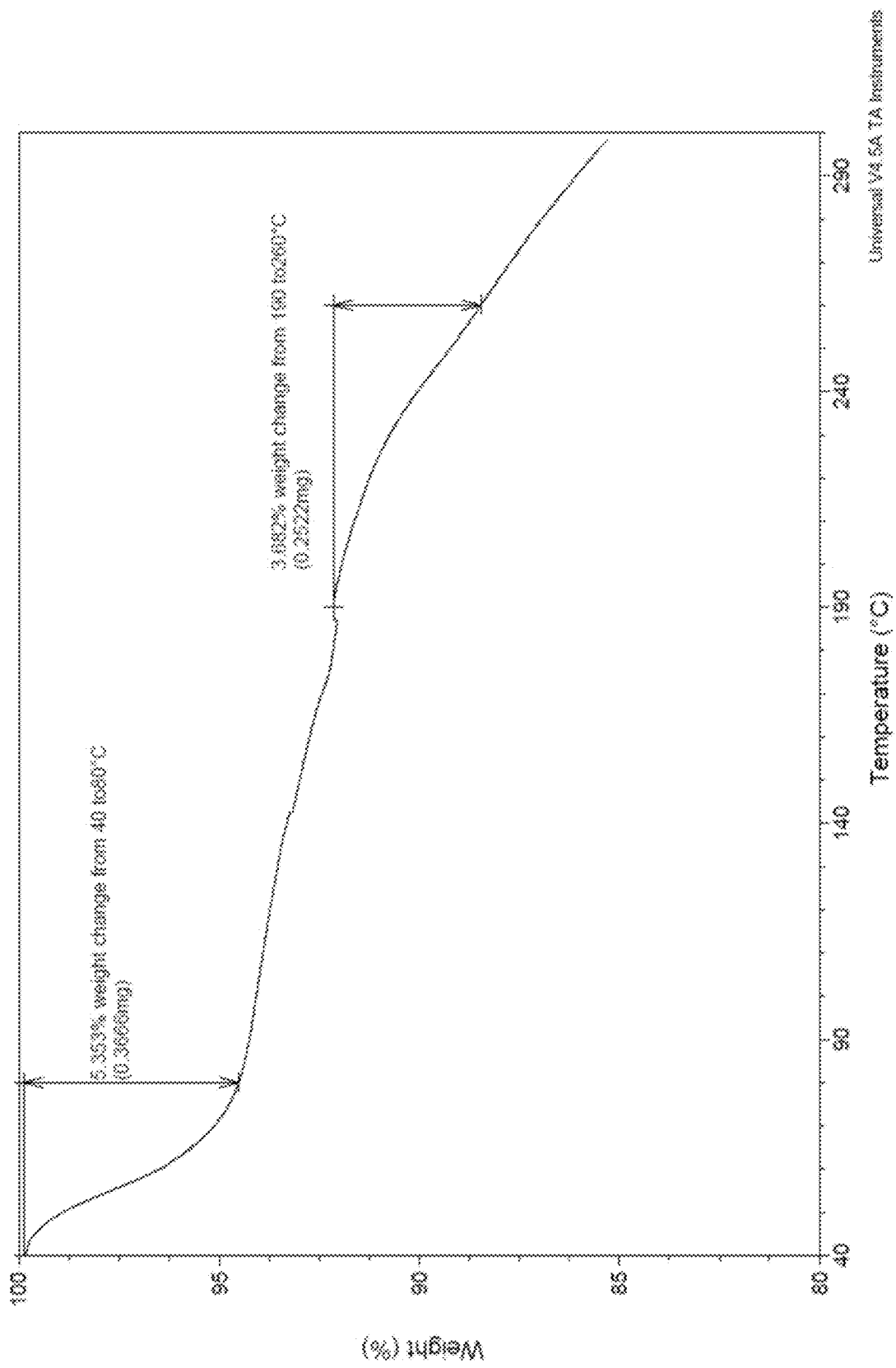
FIG. 8C depicts the characterization of Form H of Compound I-1 by thermogravimetric analysis (TGA).

In some embodiments, Form H of Compound I-1 has a differential scanning calorimetry (DSC) pattern substantially similar to that depicted in FIG. 8B. In some embodiments, Form H of Compound I-1 has a thermogravimetric analysis (TGA) pattern substantially similar to that depicted in FIG. 8C. In some embodiments, Form H of Compound I-1 can be characterized by substantial similarity to two or more of these figures simultaneously.

In some embodiments, the solid crystalline form of Compound I-1 is Form I. In some embodiments, Form I of compound I-I has a X-Ray diffraction pattern substantially similar to that depicted in FIG. 9A. In some embodiments, Form I of Compound I-1 may be characterized by a powder X-ray diffraction pattern with at least two characteristic peaks, in degrees 2θ, each selected from the group consisting of the peaks listed in Table 2.9. In some embodiments, Form I of Compound I-1 may be characterized by a powder X-ray diffraction pattern with at least three characteristic peaks, in degrees 2θ, each selected from the group consisting of the peaks listed in Table 2.9. In some embodiments, Form I of Compound I-1 may be characterized by a powder X-ray diffraction pattern with at least four characteristic peaks, in degrees 2θ, each selected from the group consisting of the peaks listed in Table 2.9. In some embodiments, Form I of Compound I-1 may be characterized by a powder X-ray diffraction pattern with at least five characteristic peaks, in degrees 2θ, each selected from the group consisting of the peaks listed in Table 2.9. In some embodiments, Form I of Compound I-1 may be characterized by a powder X-ray diffraction pattern with at least six characteristic peaks, in degrees 2θ, each selected from the group consisting of the peaks listed in Table 2.9. In some embodiments, Form I of Compound I-1 has a differential scanning calorimetry (DSC) pattern substantially similar to that depicted in FIG. 9B. In some embodiments, Form I of Compound I-1 has a thermogravimetric analysis (TGA) pattern substantially similar to that depicted in FIG. 9C. In some embodiments, Form I of Compound I-1 can be characterized by substantial similarity to two or more of these figures simultaneously.

In some embodiments, the solid crystalline form of Compound I-1 is Form J. In some embodiments, Form J of compound I-I has a X-Ray diffraction pattern substantially similar to that depicted in FIG. 10A. In some embodiments, Form J of Compound I-1 may be characterized by a powder X-ray diffraction pattern with at least two characteristic peaks, in degrees 2θ, each selected from the group consisting of the peaks listed in Table 2.10. In some embodiments, Form J of Compound I-1 may be characterized by a powder X-ray diffraction pattern with at least three characteristic peaks, in degrees 2θ, each selected from the group consisting of the peaks listed in Table 2.10. In some embodiments, Form J of Compound I-1 may be characterized by a powder X-ray diffraction pattern with at least four characteristic peaks, in degrees 2θ, each selected from the group consisting of the peaks listed in Table 2.10. In some embodiments, Form J of Compound I-1 may be characterized by a powder X-ray diffraction pattern with at least five characteristic peaks, in degrees 2θ, each selected from the group consisting of the peaks listed in Table 2.10. In some embodiments, Form J of Compound I-1 may be characterized by a powder X-ray diffraction pattern with at least six characteristic peaks, in degrees 2θ, each selected from the group consisting of the peaks listed in Table 2.10.

Figure 10A:
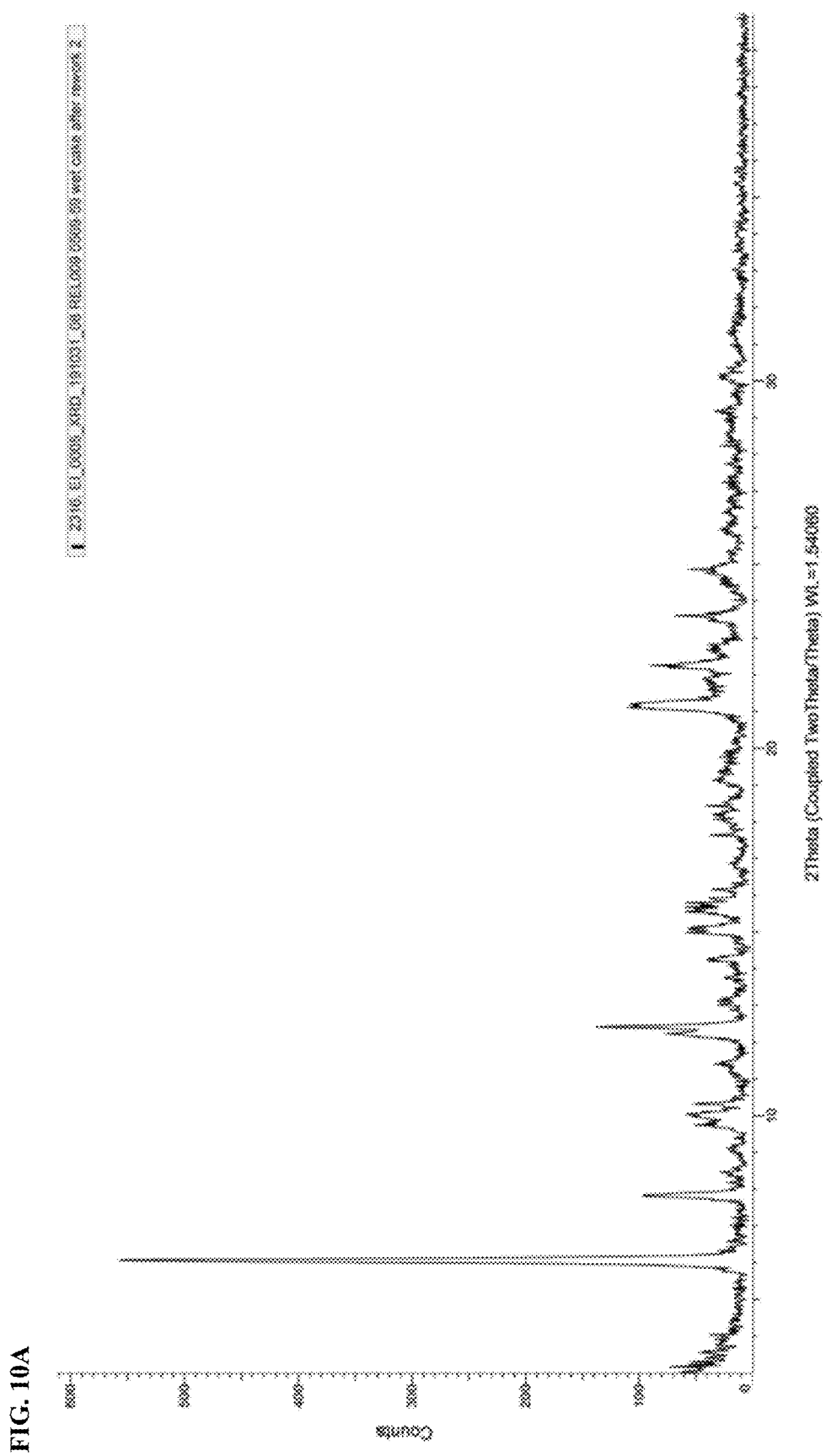
FIG. 10A depicts an X-ray diffraction pattern of Form J of Compound I-1.
Figure 10B:
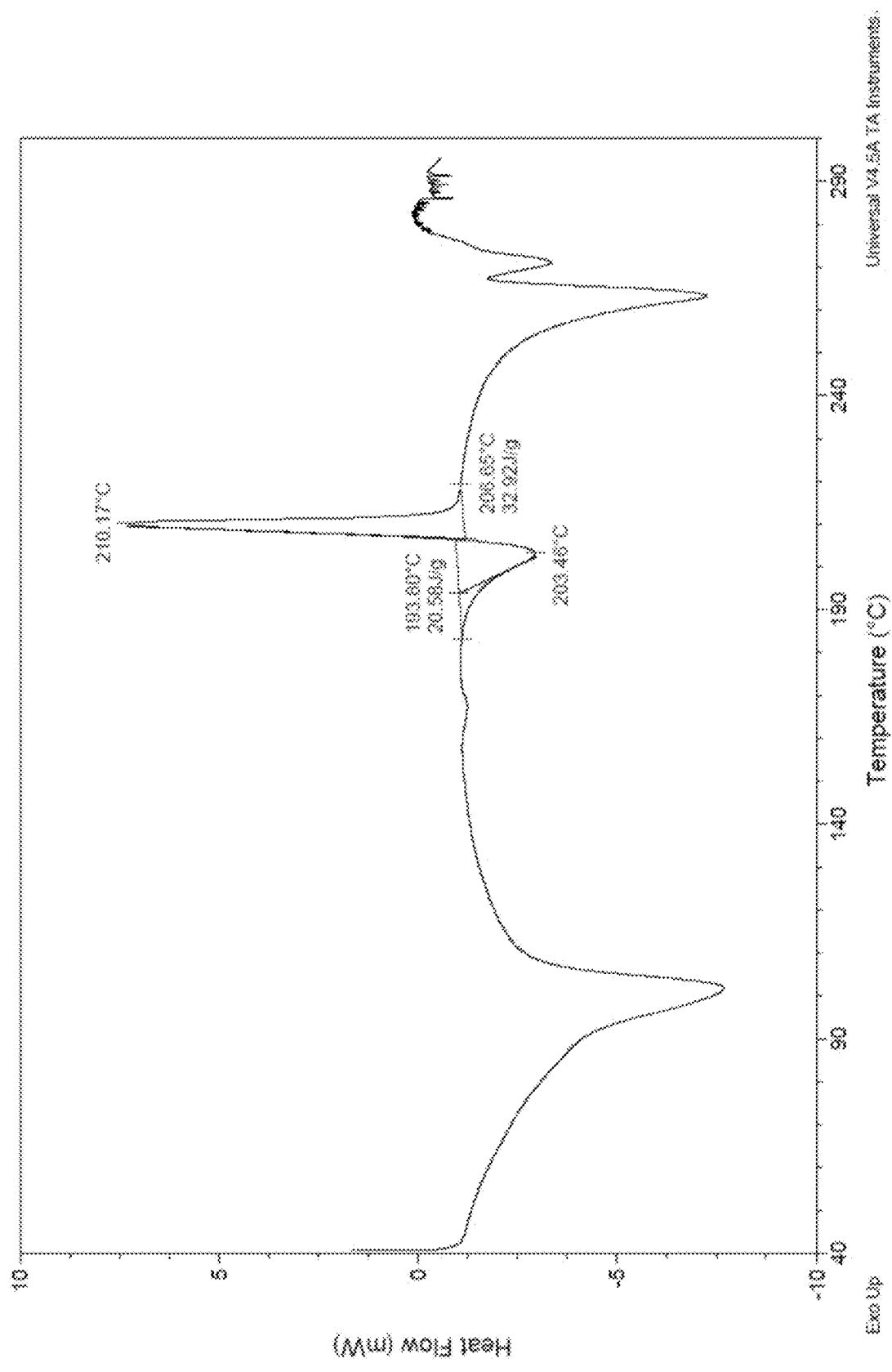
FIG. 10B depicts the characterization of Form J of Compound I-1 by differential scanning calorimetry (DSC).
Figure 10C:
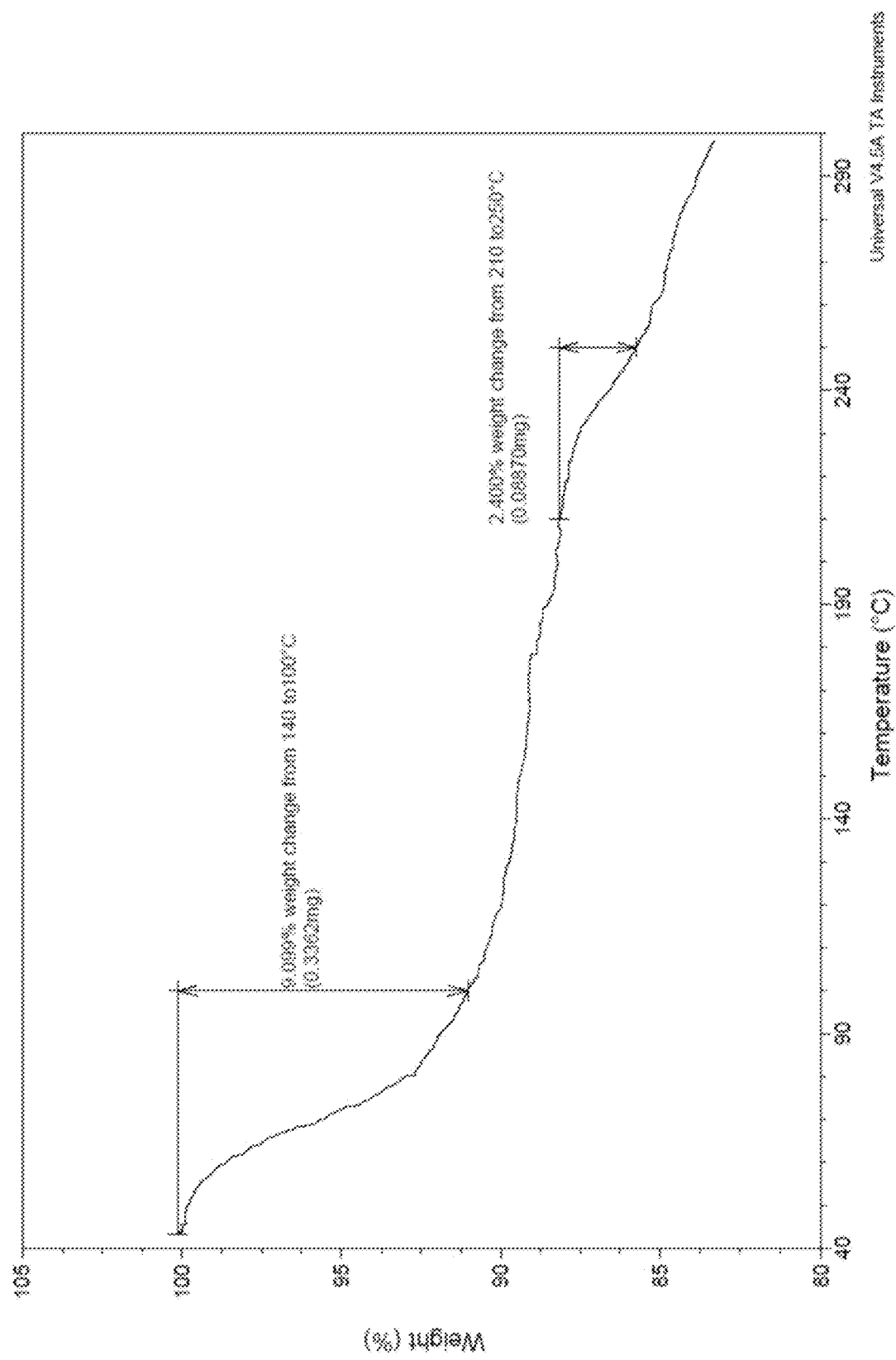
FIG. 10C depicts the characterization of Form J of Compound I-1 by thermogravimetric analysis (TGA).

In some embodiments, Form J of Compound I-1 has a differential scanning calorimetry (DSC) pattern substantially similar to that depicted in FIG. 10B. In some embodiments, Form J of Compound I-1 has a thermogravimetric analysis (TGA) pattern substantially similar to that depicted in FIG. 10C. In some embodiments, Form J of Compound I-1 can be characterized by substantial similarity to two or more of these figures simultaneously.

In some embodiments, the solid crystalline form of Compound I-1 is Form K. In some embodiments, Form K of compound I-I has a X-Ray diffraction pattern substantially similar to that depicted in FIG. 11A. In some embodiments, Form K of Compound I-1 may be characterized by a powder X-ray diffraction pattern with at least two characteristic peaks, in degrees 2θ, each selected from the group consisting of the peaks listed in Table 2.11. In some embodiments, Form K of Compound I-1 may be characterized by a powder X-ray diffraction pattern with at least three characteristic peaks, in degrees 2θ, each selected from the group consisting of the peaks listed in Table 2.11. In some embodiments, Form K of Compound I-1 may be characterized by a powder X-ray diffraction pattern with at least four characteristic peaks, in degrees 2θ, each selected from the group consisting of the peaks listed in Table 2.11. In some embodiments, Form K of Compound I-1 may be characterized by a powder X-ray diffraction pattern with at least five characteristic peaks, in degrees 2θ, each selected from the group consisting of the peaks listed in Table 2.11. In some embodiments, Form K of Compound I-1 may be characterized by a powder X-ray diffraction pattern with at least six characteristic peaks, in degrees 2θ, each selected from the group consisting of the peaks listed in Table 2.11.

Figure 11A:
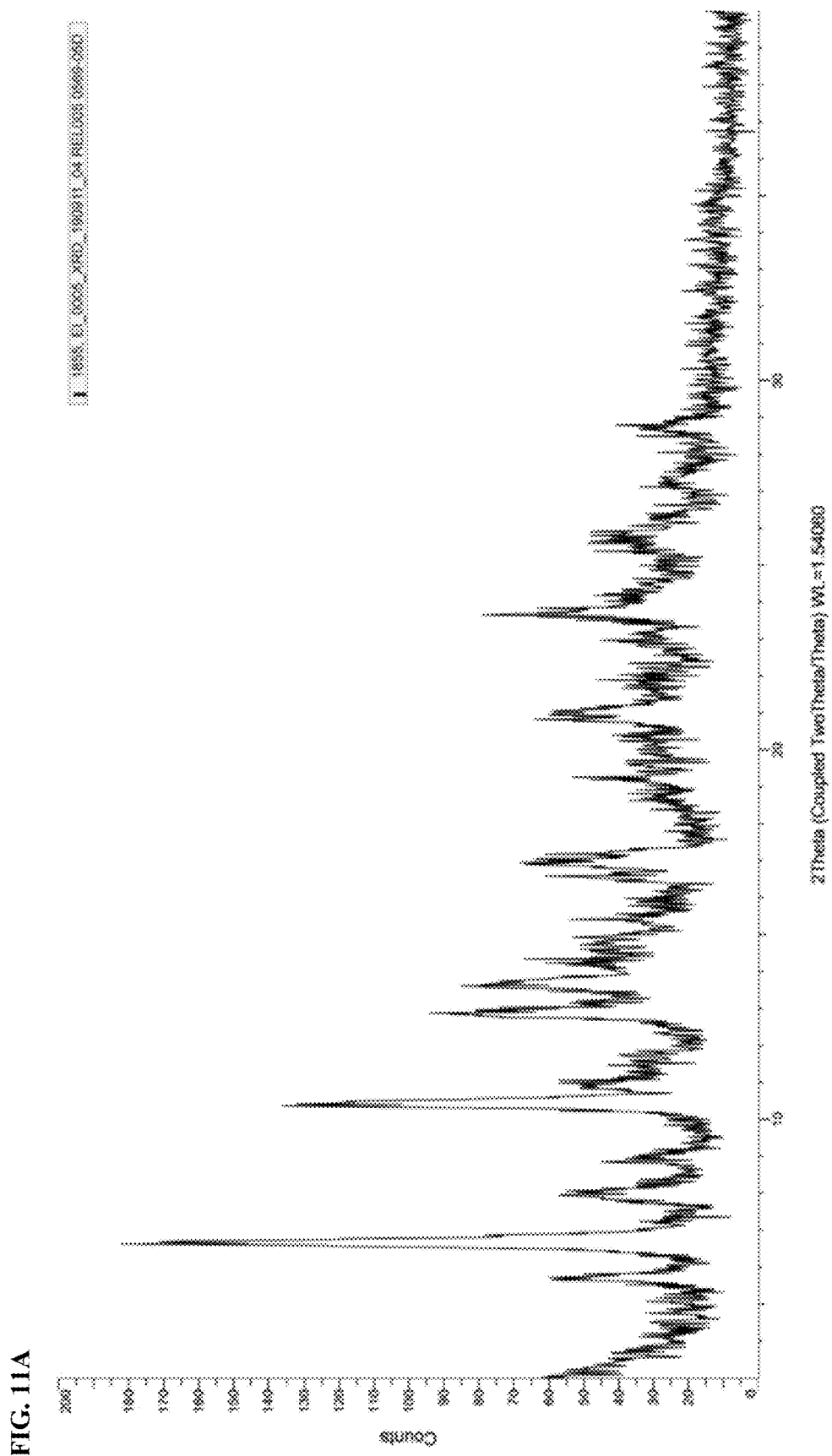
FIG. 11A depicts an X-ray diffraction pattern of Form K of Compound I-1.
Figure 11B:
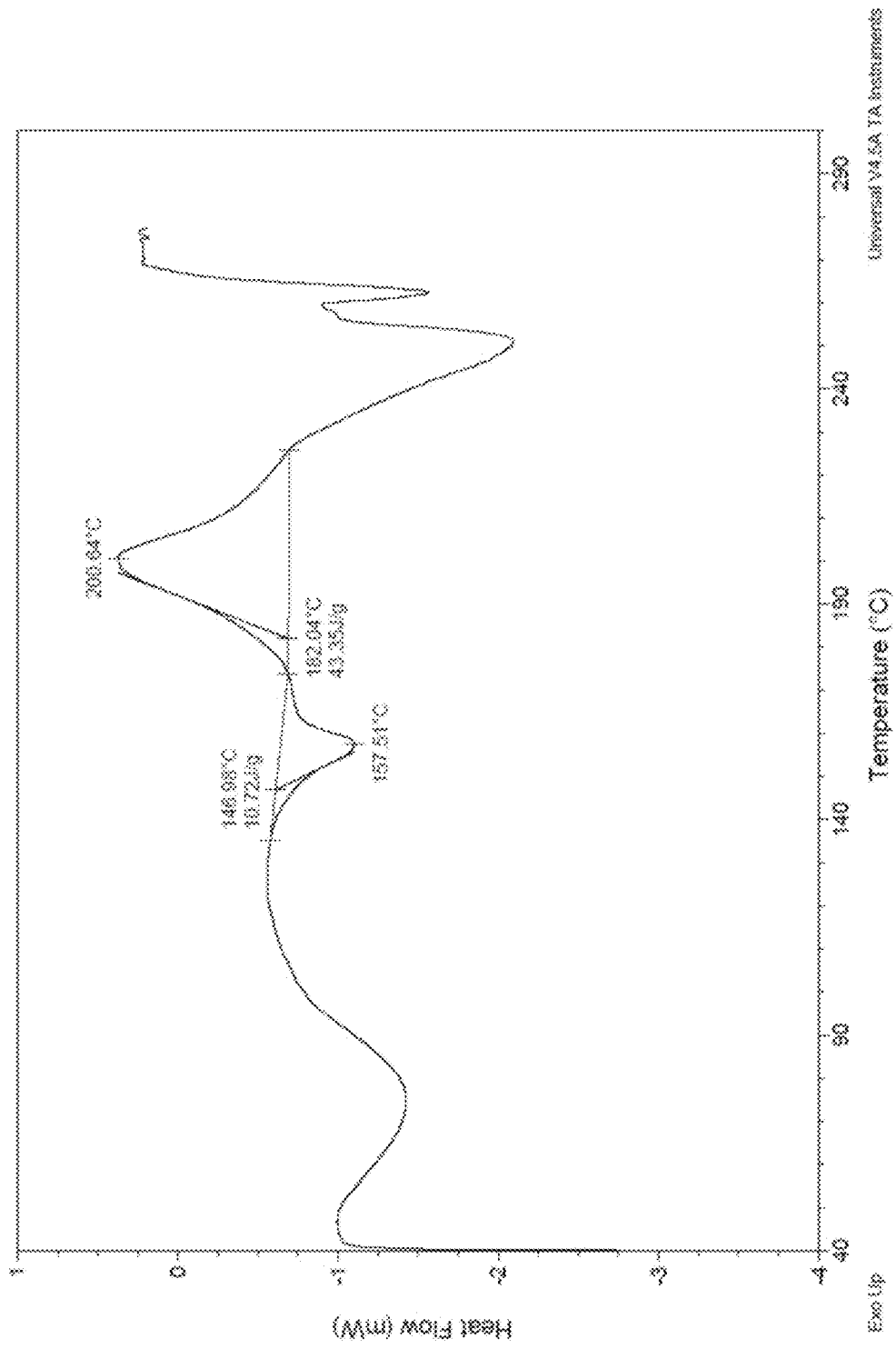
FIG. 11B depicts the characterization of Form K of Compound I-1 by differential scanning calorimetry (DSC).
Figure 11C:
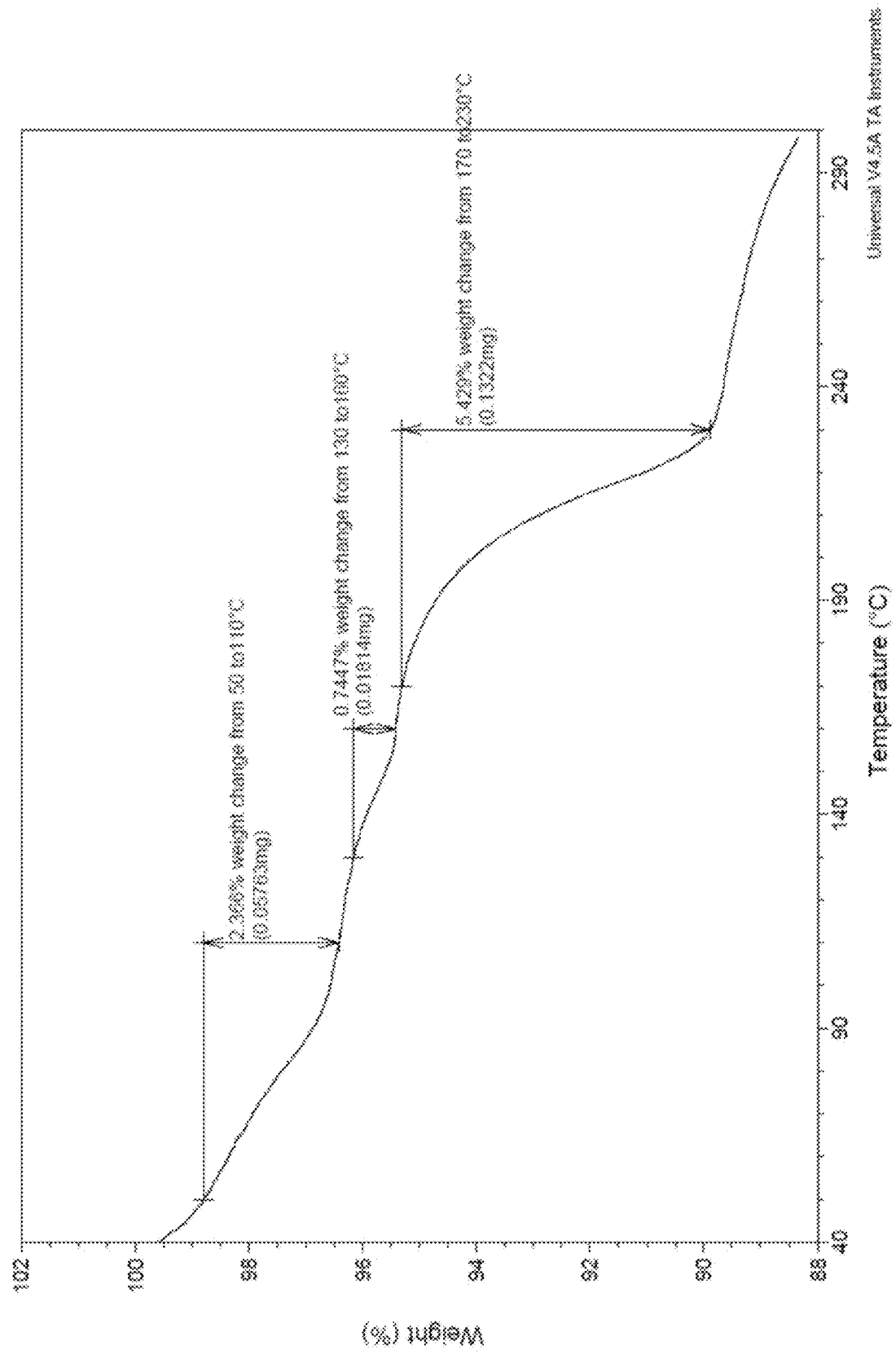
FIG. 11C depicts the characterization of Form K of Compound I-1 by thermogravimetric analysis (TGA).

In some embodiments, Form K of Compound I-1 has a differential scanning calorimetry (DSC) pattern substantially similar to that depicted in FIG. 11B. In some embodiments, Form K of Compound I-1 has a thermogravimetric analysis (TGA) pattern substantially similar to that depicted in FIG. 11C. In another embodiment, Form K of Compound I-1 can be characterized by substantial similarity to two or more of these figures simultaneously.

Compound I-2

In another embodiment, a compound of Formula (I) is compound I-2 wherein, compound I-2 is a free base (or "free form").

In some embodiments compound I-2 is an amorphous solid. In some embodiments, Compound I-2 is a crystalline solid. In some embodiments, Compound I-2 is a mixture of amorphous solid form and crystalline solid form.

In some embodiments, the present invention provides a form of compound I-2 substantially free of impurities. As used herein, the term "substantially free of impurities" means that the compound contains no significant amount of extraneous matter. Such extraneous matter may include different forms of compound I-2, residual solvents, or any other impurities that may result from the preparation of, and/or isolation of, compound I-2.

In some embodiments, compound I-2, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-2, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-2, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-2, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-2, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-2, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-2 is also meant to include all tautomeric forms of compound I-2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In other embodiments, compound I-2 is a crystalline solid substantially free of amorphous compound I-2. As used herein, the term "substantially free of amorphous compound I-2" means that the compound contains no significant amount of amorphous compound I-2. In certain embodiments, at least about 95% by weight of crystalline compound I-2 is present. In certain embodiments, at least about 99% by weight of crystalline compound I-2 is present.

It has been found that compound I-2 can exist in a variety of solid forms. Exemplary such forms include polymorphs such as those described herein.

In certain embodiments, the solid crystalline form of Compound I-2 is Form A. In some embodiments, Form A of Compound I-2 has a X-Ray diffraction pattern substantially similar to Pattern 1 depicted in FIG. 13A.

In certain embodiments, the solid crystalline form of Compound I-2 is Form B. In some embodiments, Form B of Compound I-2 has a X-Ray diffraction pattern substantially similar to Pattern 2 depicted in FIG. 13A. In certain embodiments, Form B of compound I-2 has a X-Ray diffraction pattern substantially similar to that depicted in FIG. 13B. In certain embodiments, Form B of compound I-2 has a thermogravimetric analysis (TGA) pattern substantially similar to that depicted in FIG. 13D. In certain embodiments, Form B of compound I-2 has an X-ray diffraction pattern before and after static storage at 40 C, 75% relative humidity, and 25 C, 97% relative humidity substantially similar to that depicted in FIG. 13E. In certain embodiments, Form B of Compound I-2 can be characterized by substantial similarity to two or more of these figures simultaneously.

In certain embodiments, the solid crystalline form of Compound I-2 is Form C. In some embodiments, Form C of Compound I-2 has a X-Ray diffraction pattern substantially similar to Pattern 3 depicted in FIG. 13A.

In certain embodiments, the solid crystalline form of Compound I-2 is Form D. In some embodiments, Form D of Compound I-2 has a X-Ray diffraction pattern substantially similar to Pattern 4 depicted in FIG. 13A.

In certain embodiments, the solid crystalline form of Compound I-2 is Form E. In some embodiments, Form E of Compound I-2 has a X-Ray diffraction pattern substantially similar to Pattern 5 depicted in FIG. 13A.

Compound I-3

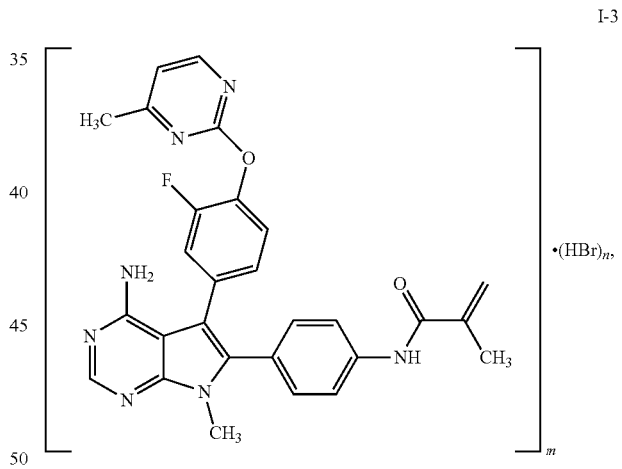

In another embodiment, a compound of Formula (I) is compound I-3, which is a hydrobromide salt. In some embodiments, compound I-3 is a mono-hydrobromide salt. In some embodiments, compound I-3 is a bis-hydrobromide salt. In some embodiments, compound I-3 is a tris-hydrobromide salt.

In some embodiments compound I-3 is an amorphous solid. In some embodiments compound I-3 is a crystalline solid. In some embodiments, Compound I-3 is a mixture of amorphous solid form and crystalline solid form.

In some embodiments, the present invention provides a form of compound I-3 substantially free of impurities. As used herein, the term "substantially free of impurities" means that the compound contains no significant amount of extraneous matter. Such extraneous matter may include different forms of compound I-3, residual solvents, or any other impurities that may result from the preparation of, and/or isolation of, compound I-3.

In some embodiments, compound I-3, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-3, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-3, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-3, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-3, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-3, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-3 is also meant to include all tautomeric forms of compound I-3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In other embodiments, compound I-3 is a crystalline solid substantially free of amorphous compound I-3. As used herein, the term "substantially free of amorphous compound I-3" means that the compound contains no significant amount of amorphous compound I-3. In certain embodiments, at least about 95% by weight of crystalline compound I-3 is present. In certain embodiments, at least about 99% by weight of crystalline compound I-3 is present.

Figure 14A:
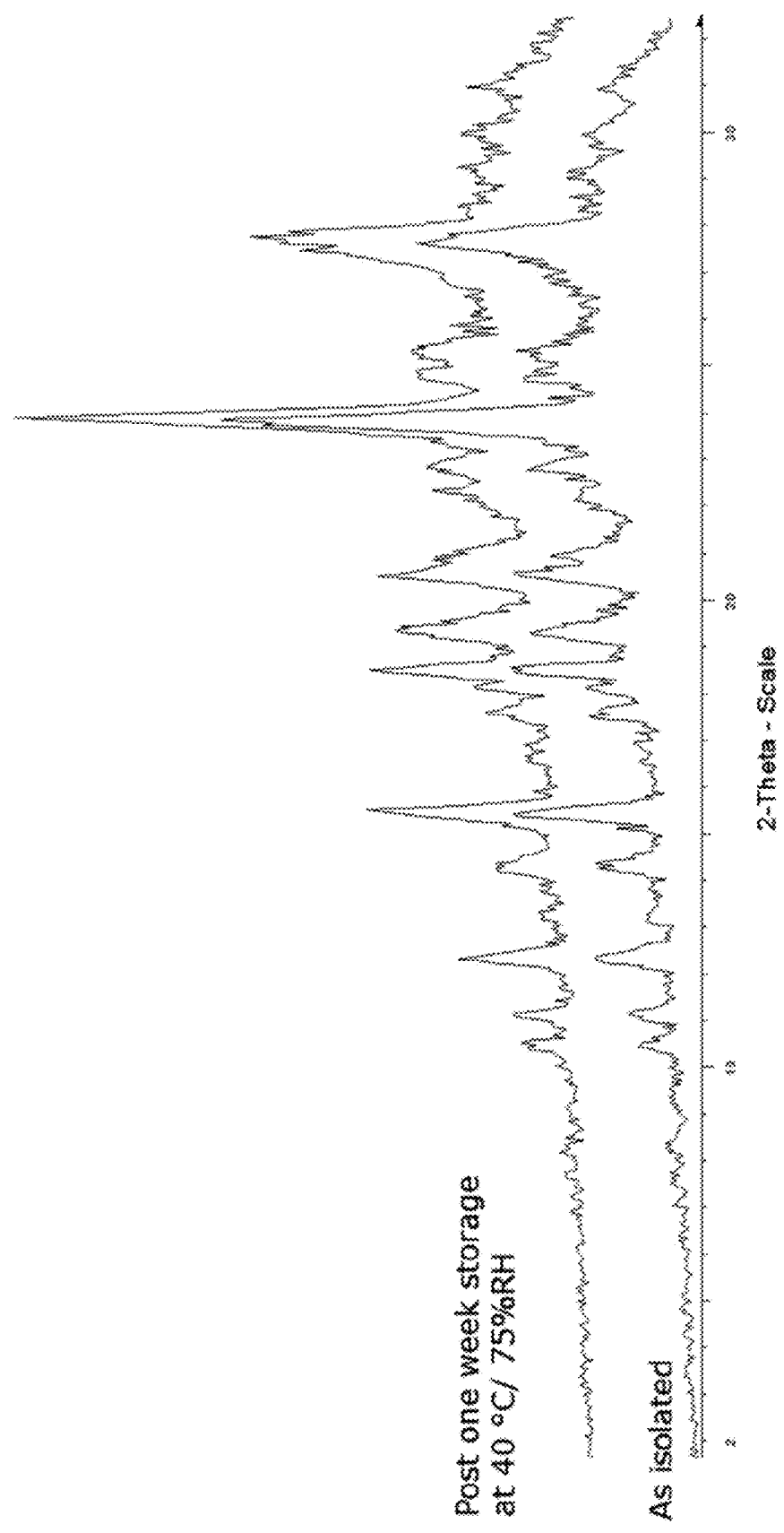
FIG. 14A depicts an X-ray diffraction pattern of Form A of Compound I-3 (HBr salt) before and after one week of storage at 40 C and 75% relative humidity.
Figure 14B:
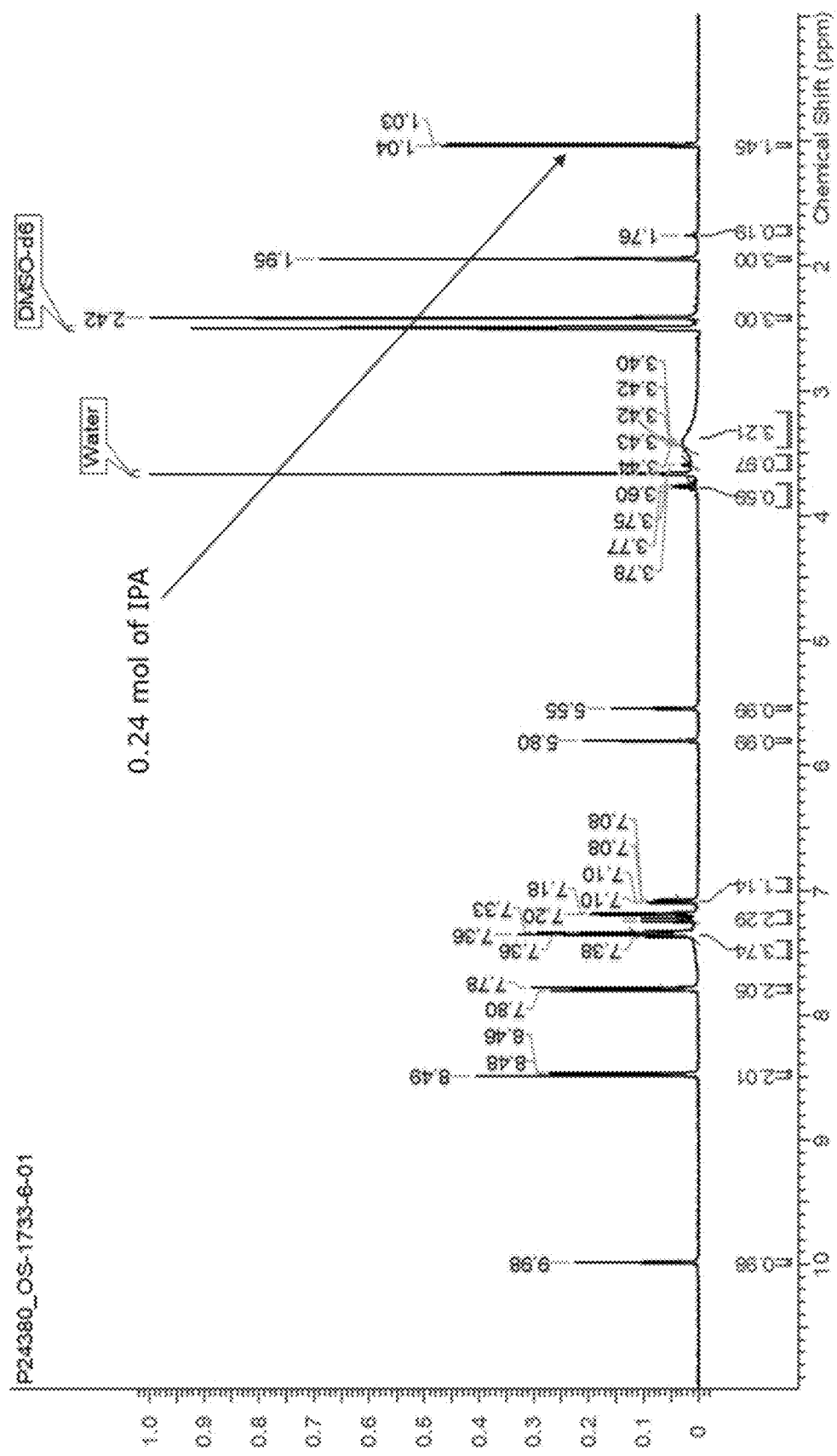
FIG. 14B depicts the characterization of Form A of Compound I-3 by $^1$H nuclear magnetic resonance ($^1$H NMR) in D6-DMSO at 400 MHz.
Figure 14C:
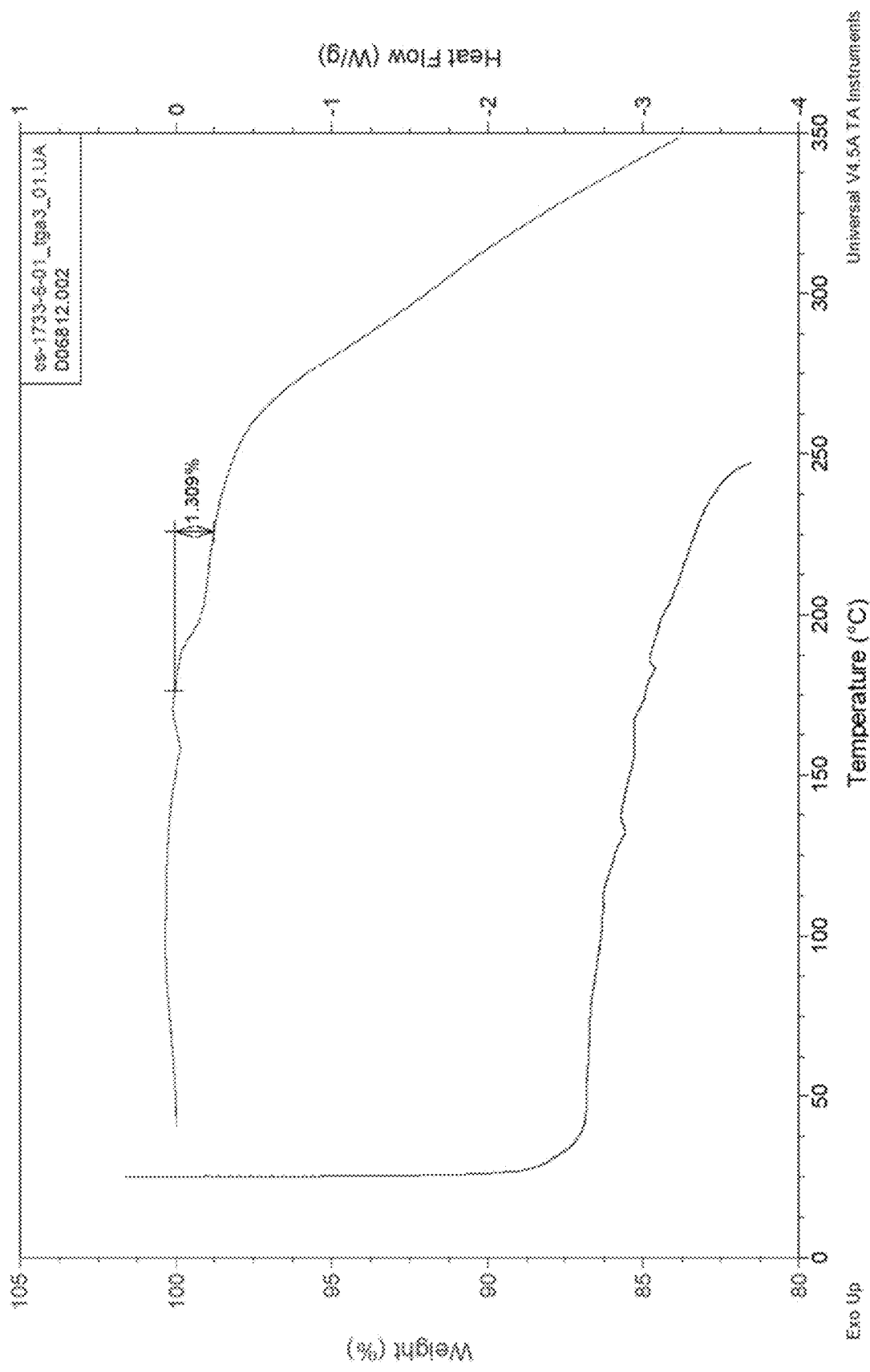
FIG. 14C depicts the characterization of Form A of Compound I-3 by thermogravimetric analysis (above) and differential scanning calorimetry (below).

In certain embodiments, a solid crystalline form of compound I-3 has a X-Ray diffraction pattern substantially similar to any one of the patterns depicted in FIG. 14A. In certain embodiments, a solid crystalline form of compound I-3 has a thermogravimetric analysis pattern substantially similar to that depicted in FIG. 14C. In certain embodiments, a solid crystalline form of Compound I-3 can be characterized by substantial similarity to two or more of these figures simultaneously.

Compound I-4

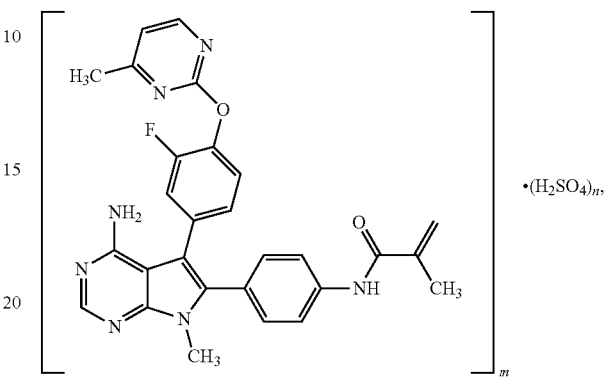

In another embodiment, a compound of Formula (I) is compound I-4, which is a sulfuric acid salt (or sulfate).

In some embodiments compound I-4 is an amorphous solid. In some embodiments compound I-4 is a crystalline solid. In some embodiments, Compound I-4 is a mixture of amorphous solid form and crystalline solid form.

In some embodiments, the present invention provides a form of compound I-4 substantially free of impurities. As used herein, the term "substantially free of impurities" means that the compound contains no significant amount of extraneous matter. Such extraneous matter may include different forms of compound I-4, residual solvents, or any other impurities that may result from the preparation of, and/or isolation of, compound I-4.

In some embodiments, compound I-4, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-4, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-4, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-4, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-4, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-4, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-4 is also meant to include all tautomeric forms of compound I-4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In other embodiments, compound I-4 is a crystalline solid substantially free of amorphous compound I-4. As used herein, the term "substantially free of amorphous compound I-4" means that the compound contains no significant amount of amorphous compound I-4. In certain embodiments, at least about 95% by weight of crystalline compound I-4 is present. In certain embodiments, at least about 99% by weight of crystalline compound I-4 is present.

Figure 15A:
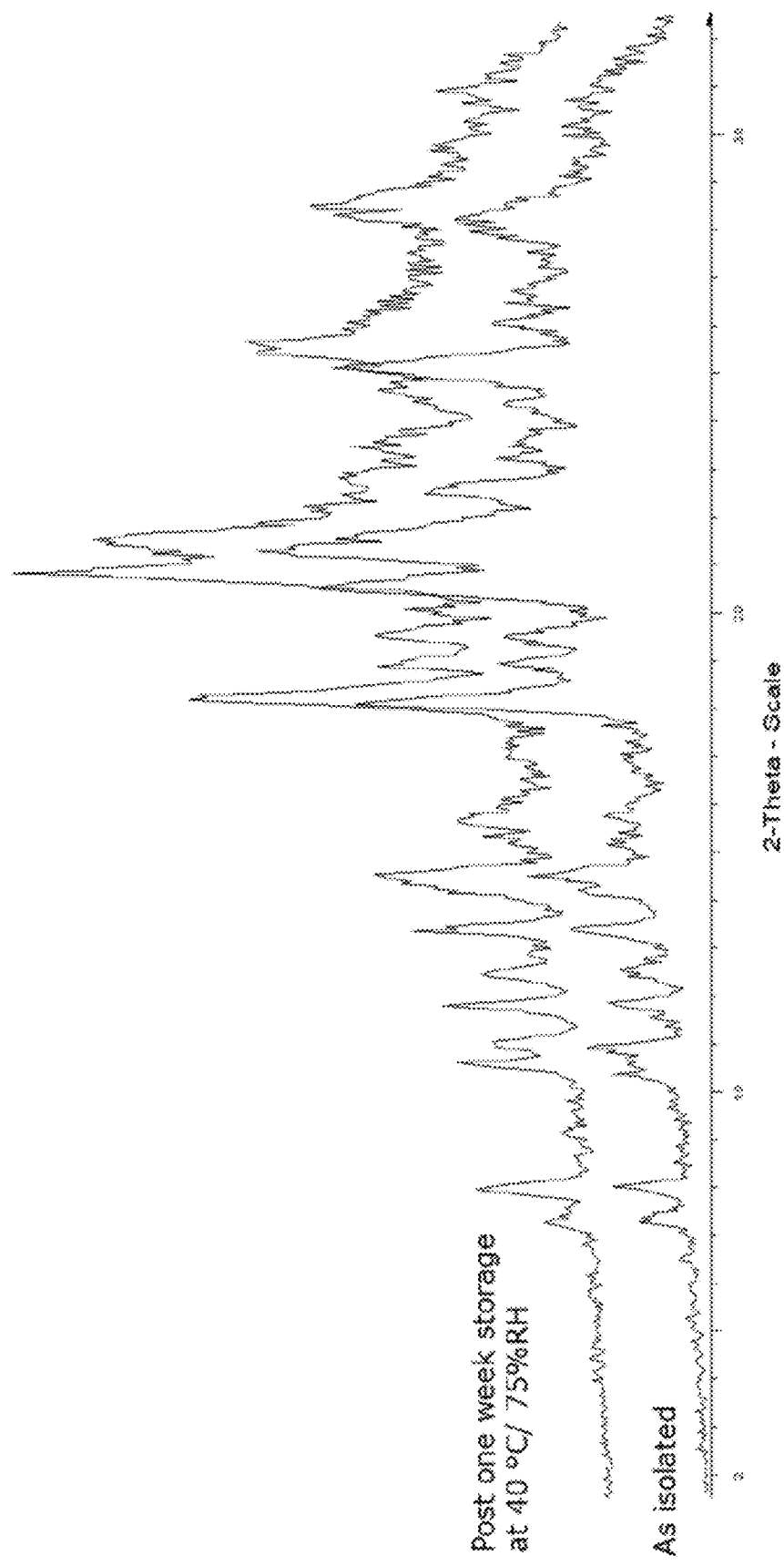
FIG. 15A depicts an X-ray diffraction pattern of Form B of Compound I-4 (sulfate salt) before and after one week of storage at 40 C and 75% relative humidity.
Figure 15B:
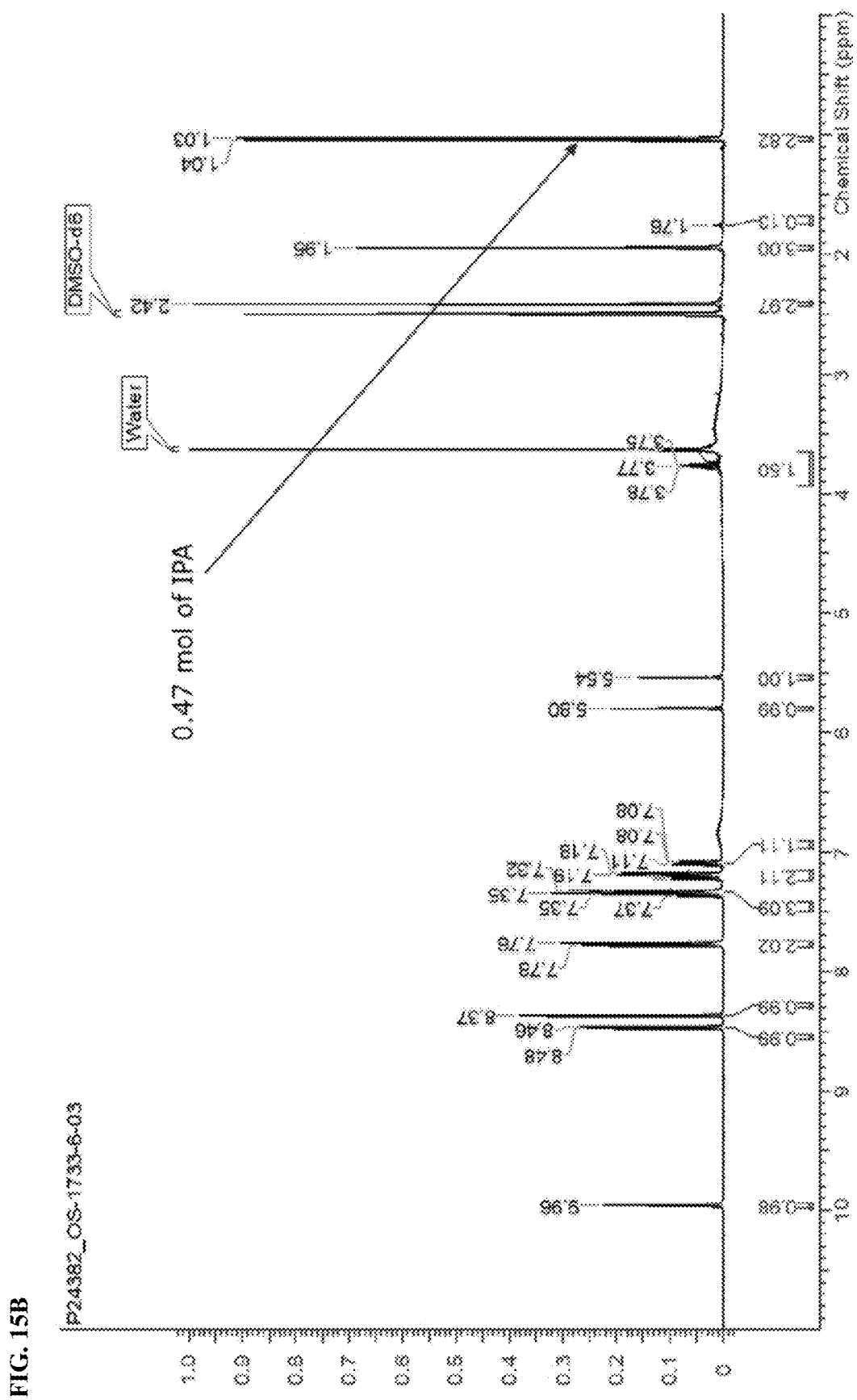
FIG. 15B depicts the characterization of Form B of Compound I-4 by $^1$H nuclear magnetic resonance ($^1$H NMR) in D6-DMSO at 400 MHz.
Figure 15C:
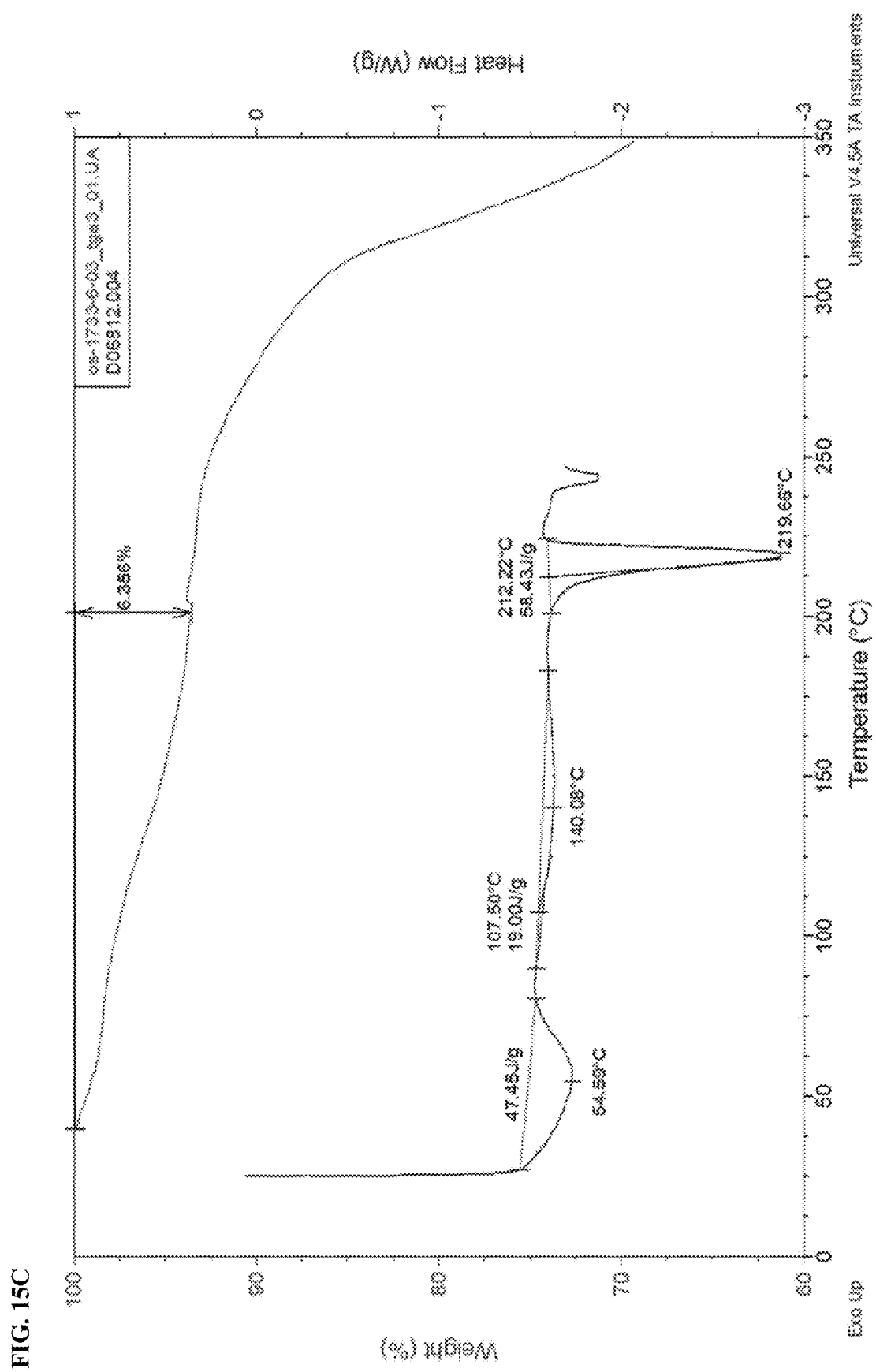
FIG. 15C depicts the characterization of Form B of Compound I-4 by thermogravimetric analysis (above) and differential scanning calorimetry (below).

In certain embodiments, a solid crystalline form of compound I-4 has a X-Ray diffraction pattern substantially similar to any one of the patterns depicted in FIG. 15A. In certain embodiments, a solid crystalline form of compound I-4 has a thermogravimetric analysis pattern substantially similar to that depicted in FIG. 15C. In certain embodiments, a solid crystalline form of Compound I-4 can be characterized by substantial similarity to two of these figures simultaneously.

Compound I-5

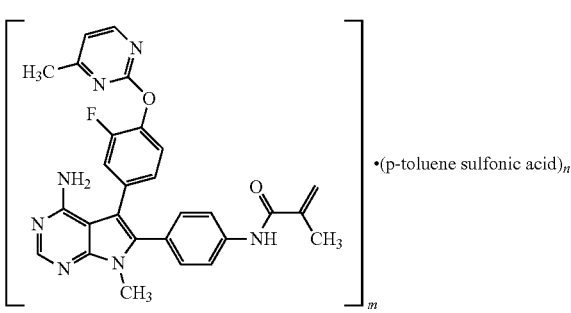

I-5

In another embodiment, a compound of Formula (I) is compound I-5, which is a p-toluene sulfonic acid salt.

In some embodiments compound I-5 is an amorphous solid. In some embodiments compound I-5 is a crystalline solid. In some embodiments, Compound I-5 is a mixture of amorphous solid form and crystalline solid form.

In some embodiments, the present invention provides a form of compound I-5 substantially free of impurities. As used herein, the term "substantially free of impurities" means that the compound contains no significant amount of extraneous matter. Such extraneous matter may include different forms of compound I-5, residual solvents, or any other impurities that may result from the preparation of, and/or isolation of, compound I-5.

In some embodiments, compound I-5, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-5, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-5, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-5, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-5, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-5, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-5 is also meant to include all tautomeric forms of compound I-5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In other embodiments, compound I-5 is a crystalline solid substantially free of amorphous compound I-5. As used herein, the term "substantially free of amorphous compound I-5" means that the compound contains no significant amount of amorphous compound I-5. In certain embodiments, at least about 95% by weight of crystalline compound I-5 is present. In certain embodiments, at least about 99% by weight of crystalline compound I-5 is present.

Figure 16A:
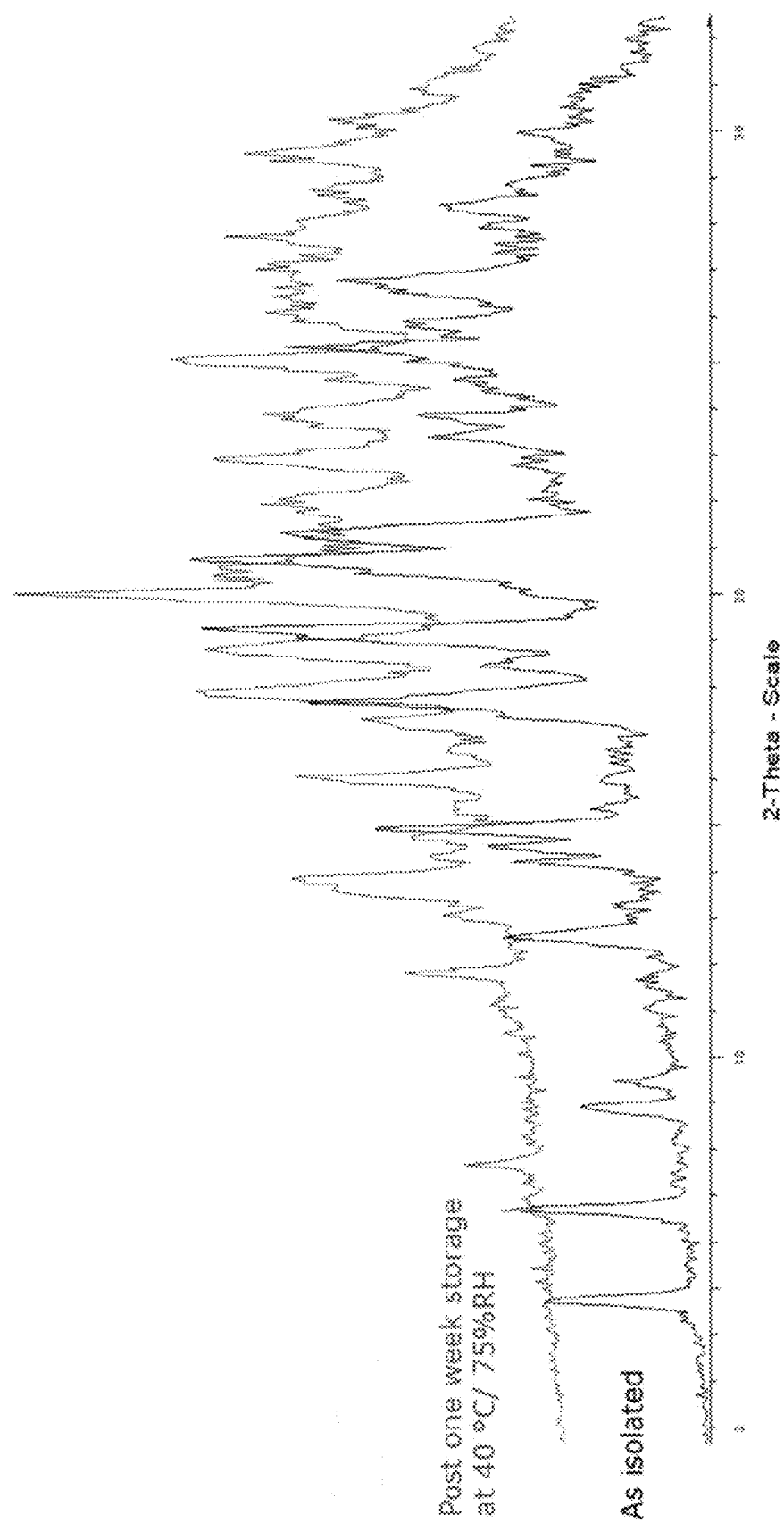
FIG. 16A depicts an X-ray diffraction pattern of Form A of Compound I-5 (p-tosylate salt) before and after one week of storage at 40 C and 75% relative humidity.
Figure 16B:
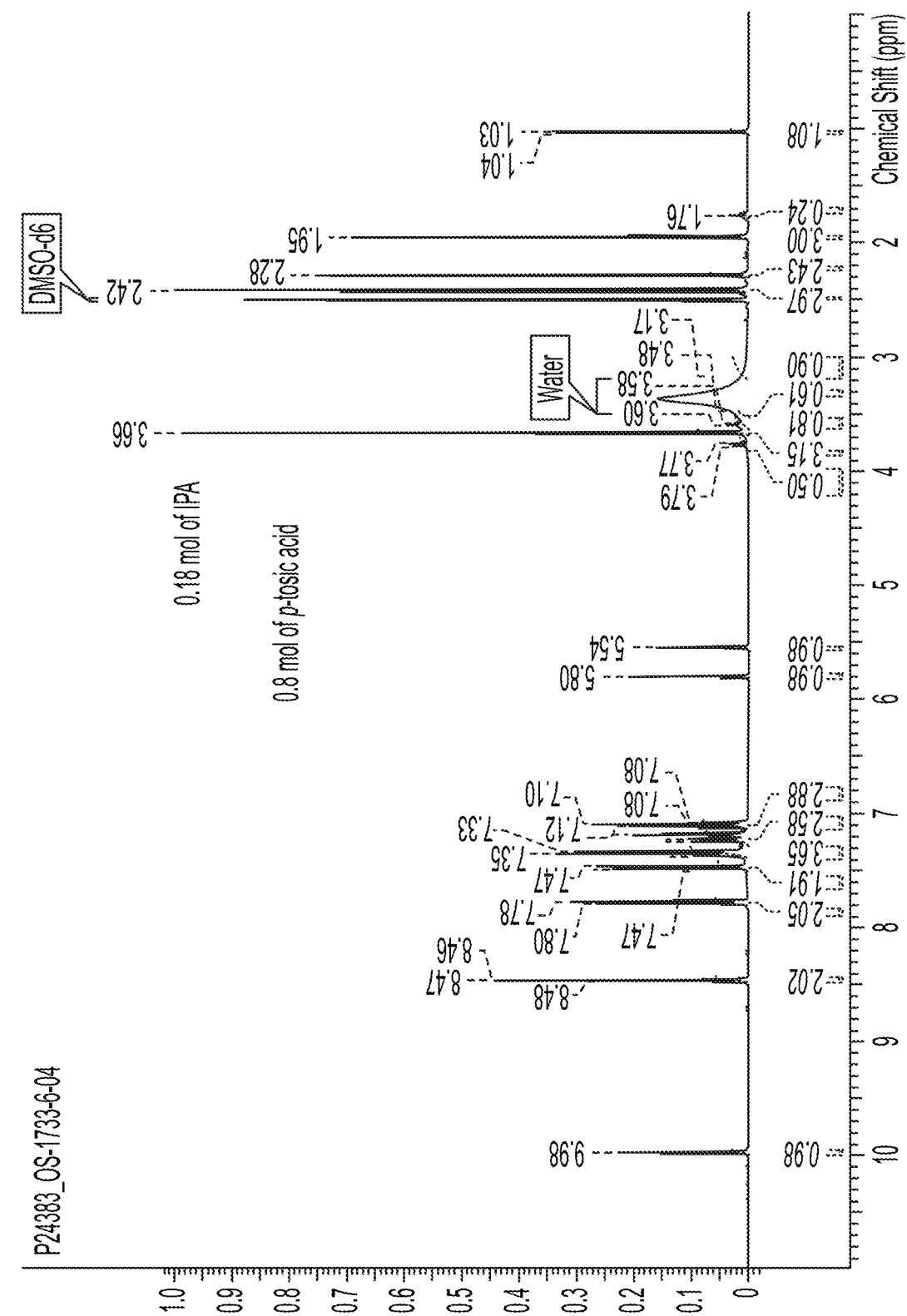
FIG. 16B depicts the characterization of Form A of Compound I-5 by $^1$H nuclear magnetic resonance ($^1$H NMR) in D6-DMSO at 400 MHz.
Figure 16C:
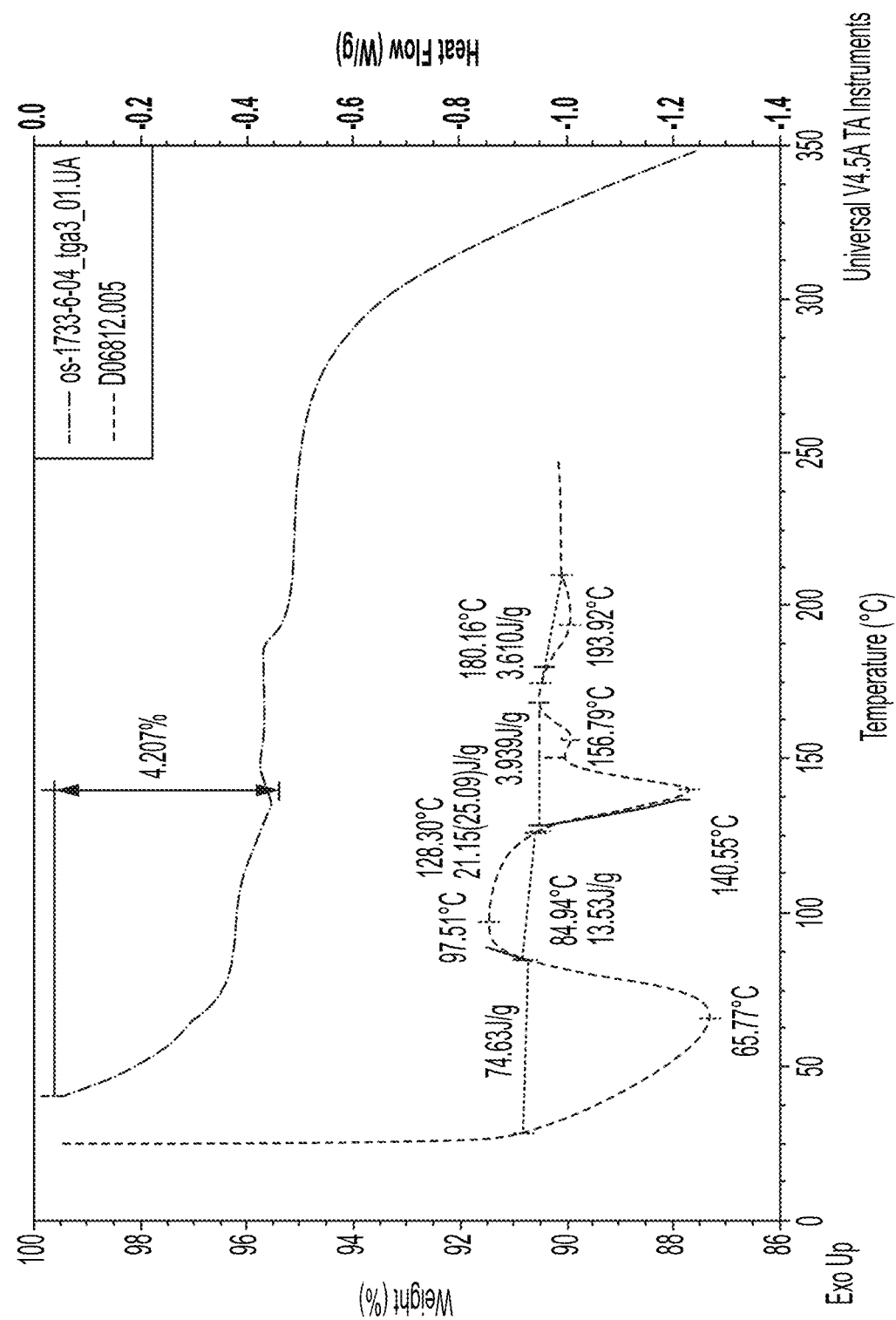
FIG. 16C depicts the characterization of Form A of Compound I-5 by thermogravimetric analysis (above) and differential scanning calorimetry (below).

In certain embodiments, a solid crystalline form of compound I-5 has a X-Ray diffraction pattern substantially similar to any one of the patterns depicted in FIG. 16A. In certain embodiments, a solid crystalline form of compound I-5 has a thermogravimetric analysis pattern substantially similar to that depicted in FIG. 16C. In certain embodiments, a solid crystalline form of Compound I-5 can be characterized by substantial similarity to two or more of these figures simultaneously.

Compound I-6

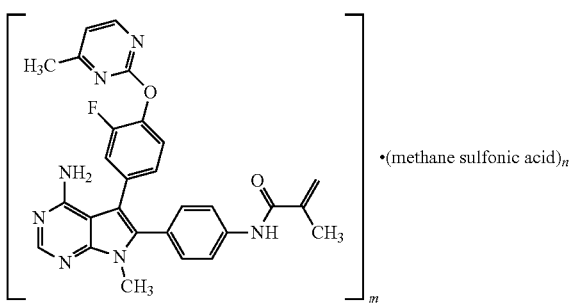

In another embodiment, a compound of Formula (I) is compound I-6, which is a methane sulfonic acid salt.

In some embodiments, compound I-6 is an amorphous solid. In some embodiments, compound I-6 is a crystalline solid. In some embodiments, Compound I-6 is a mixture of amorphous solid form and crystalline solid form.

In some embodiments, the present invention provides a form of compound I-6 substantially free of impurities. As used herein, the term "substantially free of impurities" means that the compound contains no significant amount of extraneous matter. Such extraneous matter may include different forms of compound I-6, residual solvents, or any other impurities that may result from the preparation of, and/or isolation of, compound I-6.

In some embodiments, compound I-6, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-6, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-6, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-6, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-6, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-6, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-6 is also meant to include all tautomeric forms of compound I-6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In other embodiments, compound I-6 is a crystalline solid substantially free of amorphous compound I-6. As used herein, the term "substantially free of amorphous compound I-6" means that the compound contains no significant amount of amorphous compound I-6. In certain embodiments, at least about 95% by weight of crystalline compound I-6 is present. In certain embodiments, at least about 99% by weight of crystalline compound I-6 is present.

Figure 17A:
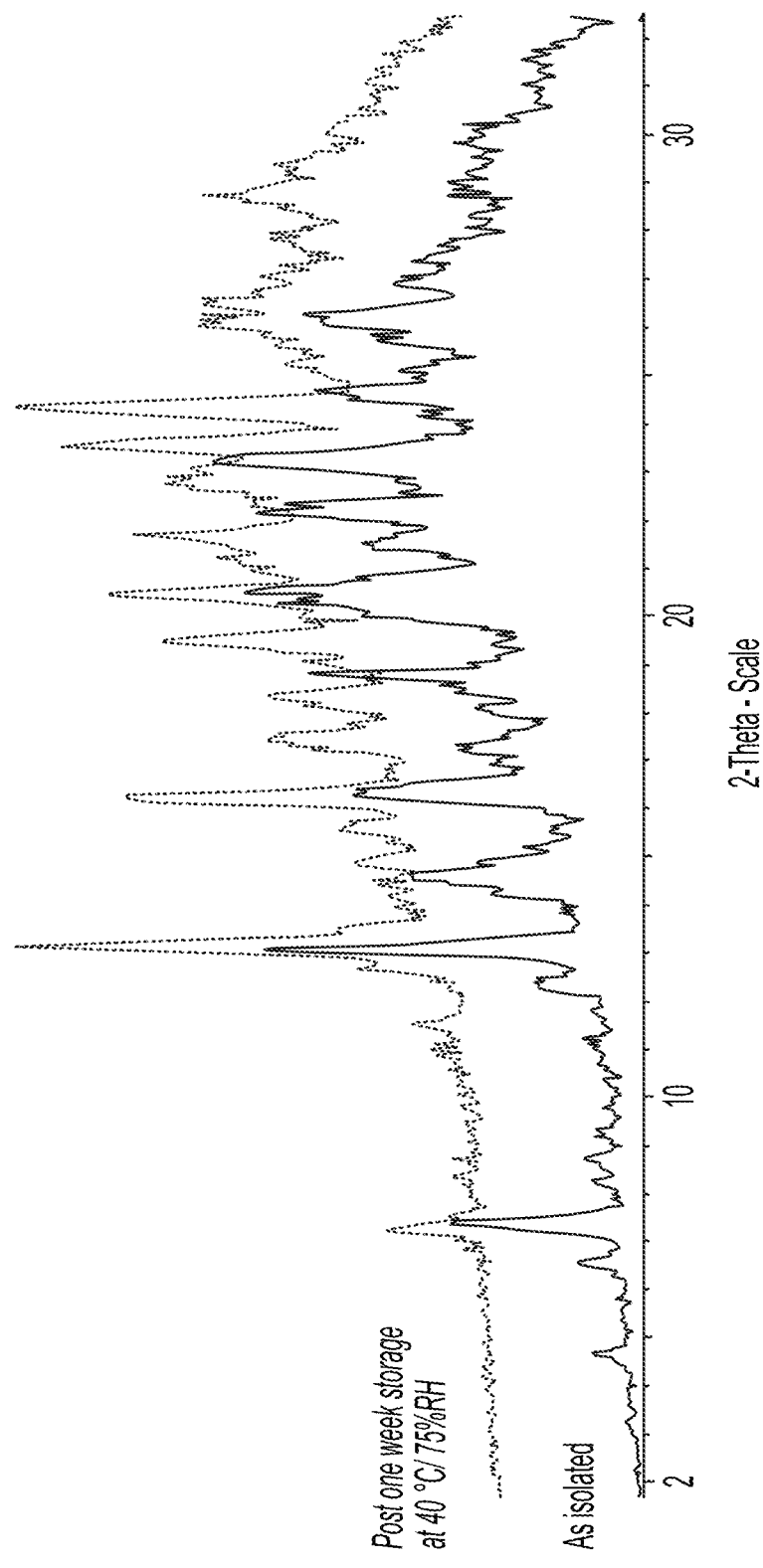
FIG. 17A depicts an X-ray diffraction pattern of Form A of Compound I-6 (mesylate salt) before and after one week of storage at 40 C and 75% relative humidity.
Figure 17B:
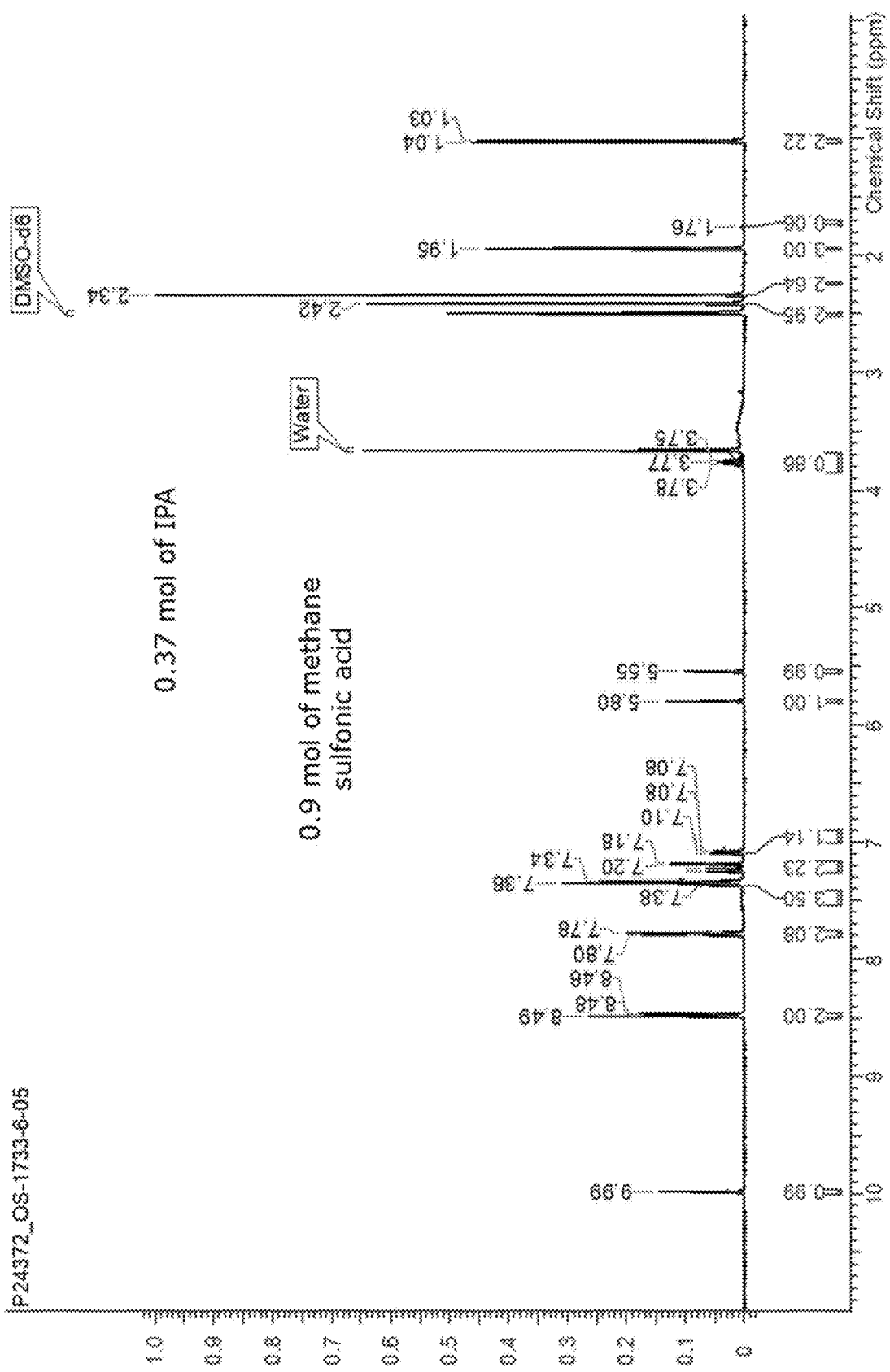
FIG. 17B depicts the characterization of Form A of Compound I-6 by $^1$H nuclear magnetic resonance ($^1$H NMR) in D6-DMSO at 400 MHz.
Figure 17C:
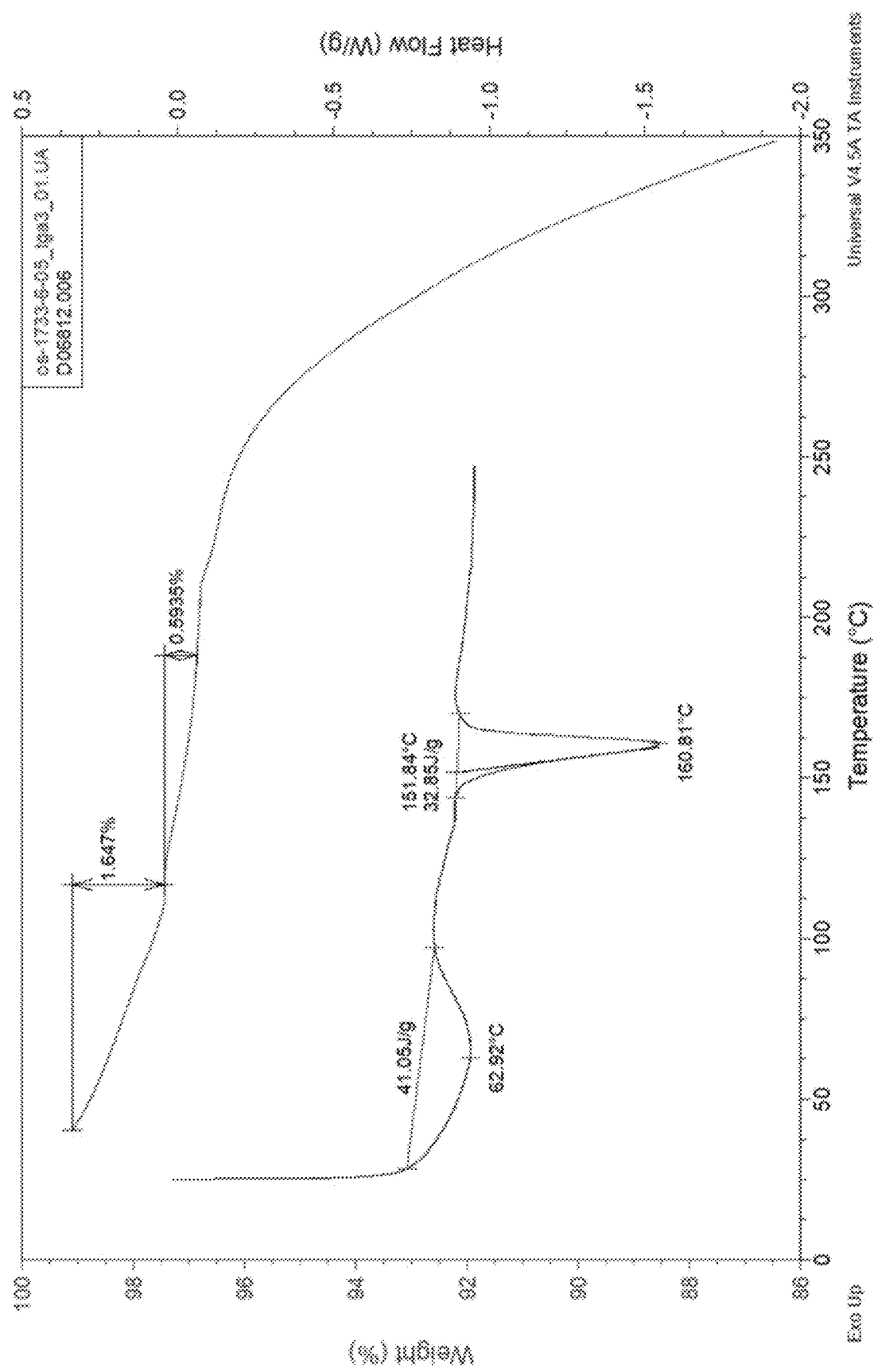
FIG. 17C depicts the characterization of Form A of Compound I-6 by thermogravimetric analysis (above) and differential scanning calorimetry (below).

In certain embodiments, a solid crystalline form of compound I-6 has a X-Ray diffraction pattern substantially similar to that depicted in FIG. 17A. In certain embodiments, a solid crystalline form of compound I-6 has a thermogravimetric analysis pattern substantially similar to that depicted in FIG. 17C. In certain embodiments, a solid crystalline form of Compound I-6 can be characterized by substantial similarity to two of these figures simultaneously.

Compound I-7

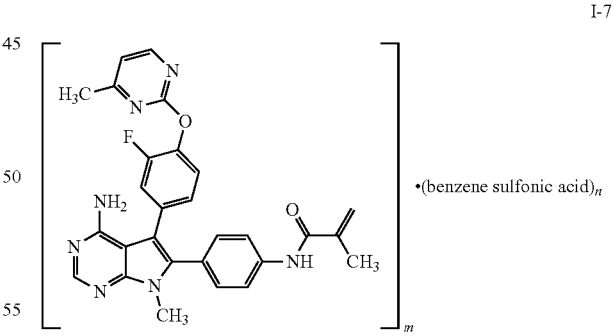

In another embodiment, a compound of Formula (I) is compound I-7, which is a benzene sulfonic acid salt.

In some embodiments, compound I-7 is an amorphous solid. In some embodiments compound I-7 is a crystalline solid. In some embodiments, Compound I-7 is a mixture of amorphous solid form and crystalline solid form.

In some embodiments, the present invention provides a form of compound I-7 substantially free of impurities. As used herein, the term "substantially free of impurities" means that the compound contains no significant amount of extraneous matter. Such extraneous matter may include different forms of compound I-7, residual solvents, or any other impurities that may result from the preparation of, and/or isolation of, compound I-7.

In some embodiments, compound I-7, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-7, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-7, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-7, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-7, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-7, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-7 is also meant to include all tautomeric forms of compound I-7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In other embodiments, compound I-7 is a crystalline solid substantially free of amorphous compound I-7. As used herein, the term "substantially free of amorphous compound I-7" means that the compound contains no significant amount of amorphous compound I-7. In certain embodiments, at least about 95% by weight of crystalline compound I-7 is present. In certain embodiments, at least about 99% by weight of crystalline compound I-7 is present.

Figure 18A:
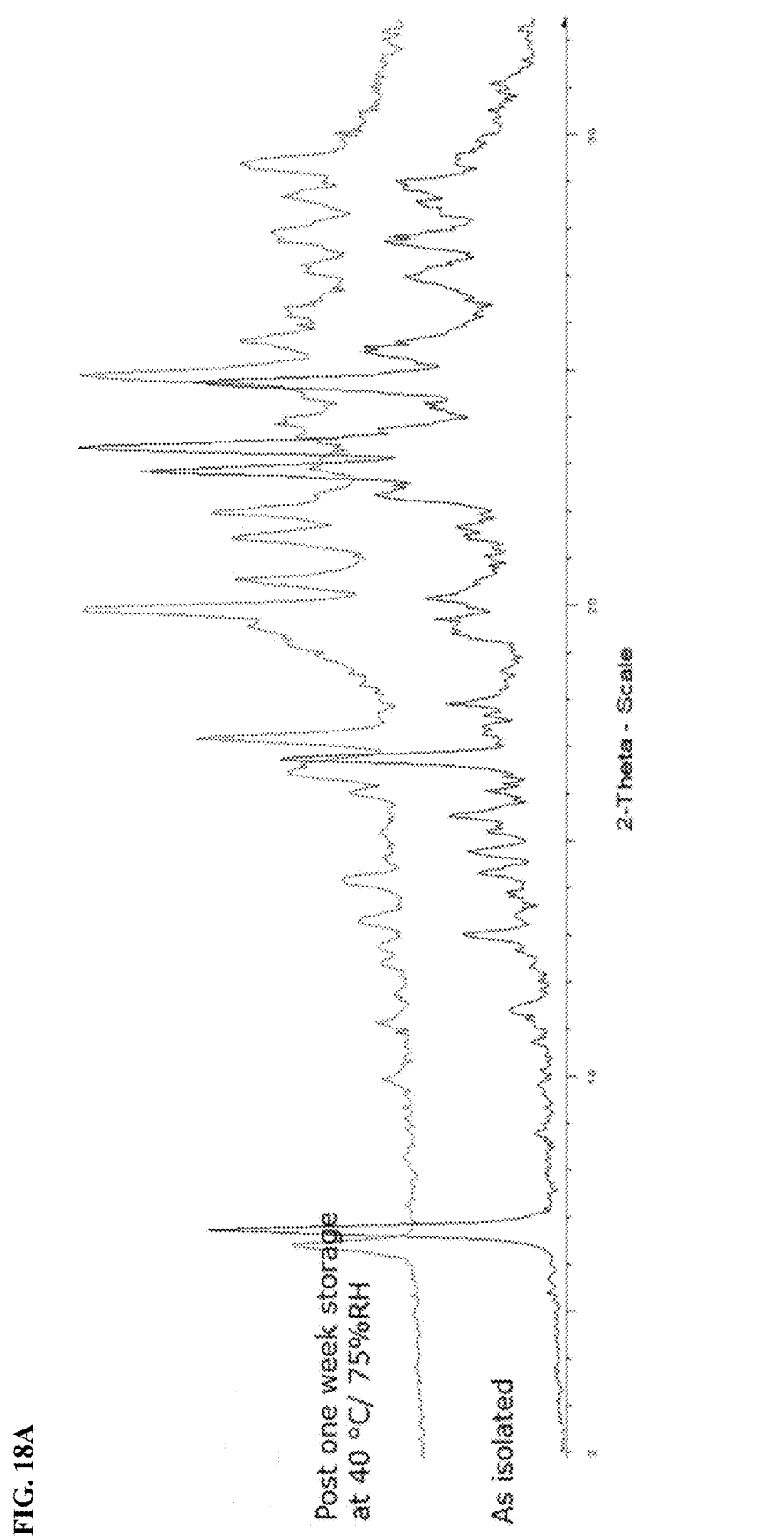
FIG. 18A depicts an X-ray diffraction pattern of Form A of Compound I-7 (besylate salt) before and after one week of storage at 40 C and 75% relative humidity.
Figure 18B:
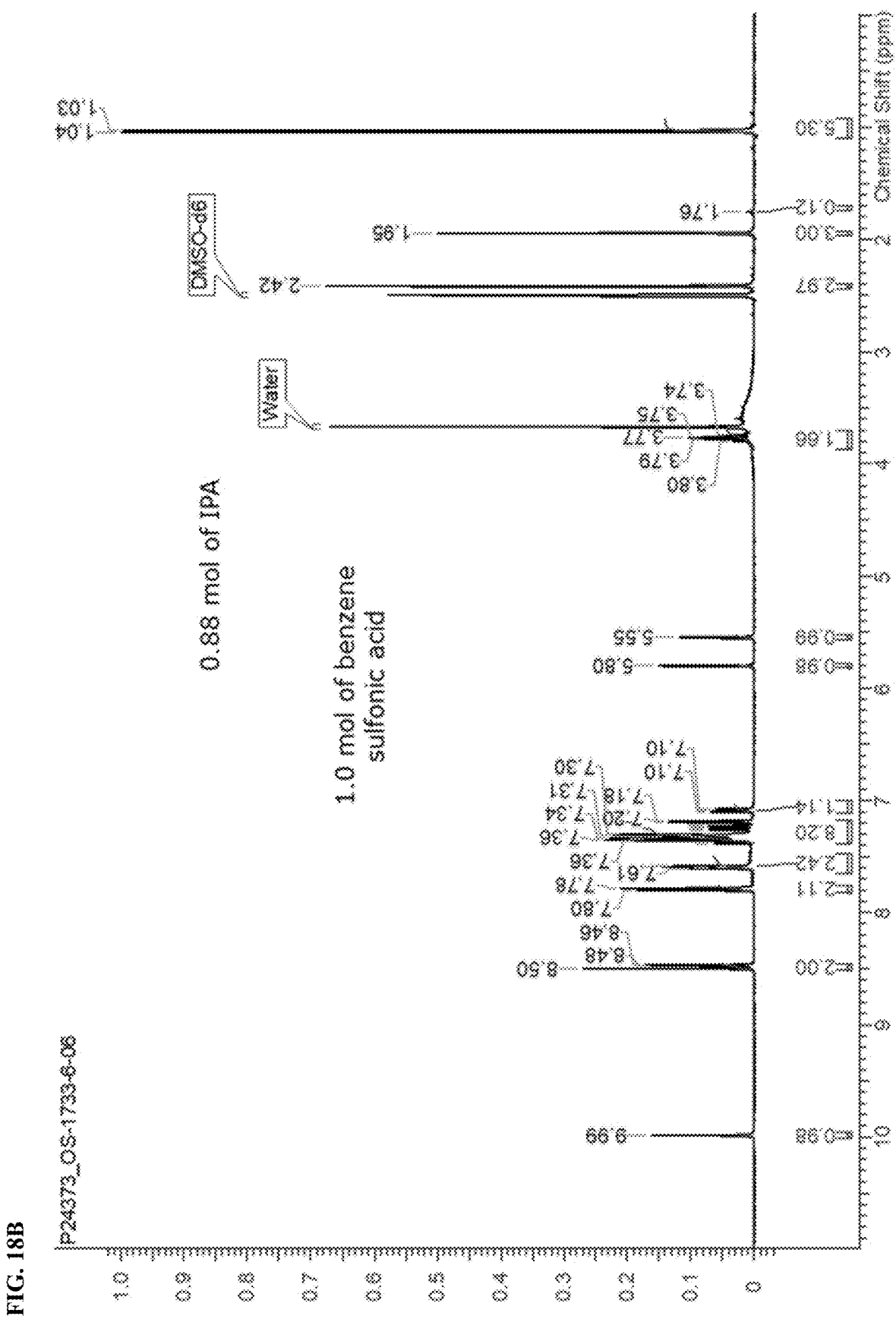
FIG. 18B depicts the characterization of Form A of Compound I-7 by $^1$H nuclear magnetic resonance ($^1$H NMR) in D6-DMSO at 400 MHz.
Figure 18C:
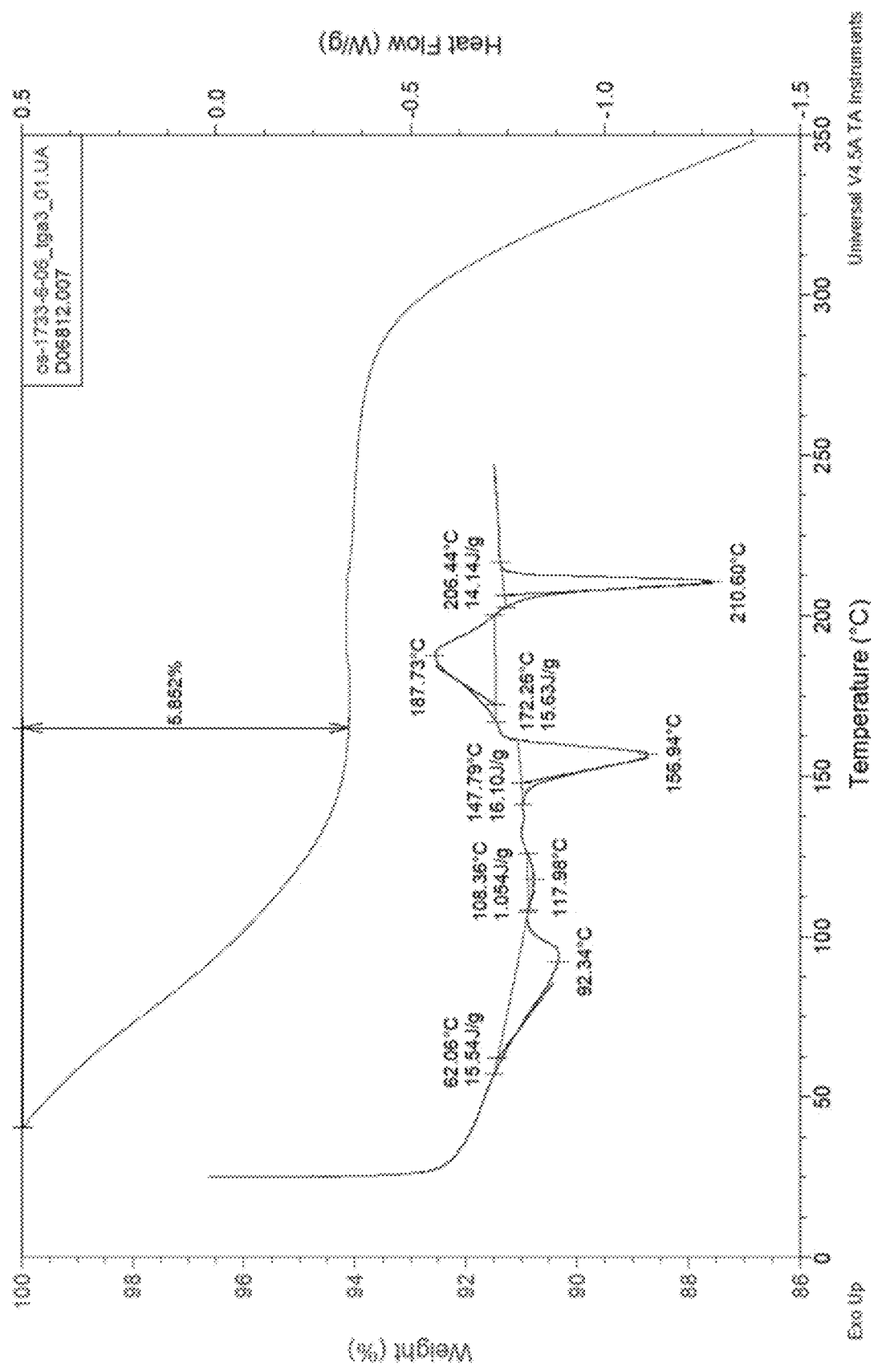
FIG. 18C depicts the characterization of Form A of Compound I-7 by thermogravimetric analysis (above) and differential scanning calorimetry (below).

In certain embodiments, a solid crystalline form of compound I-7 has a X-Ray diffraction pattern substantially similar any one of the patterns depicted in FIG. 18A. In certain embodiments, a solid crystalline form of compound I-7 has a thermogravimetric analysis pattern substantially similar to that depicted in FIG. 18C. In certain embodiments, a solid crystalline form of Compound I-7 can be characterized by substantial similarity to two of these figures simultaneously.

Compound I-8

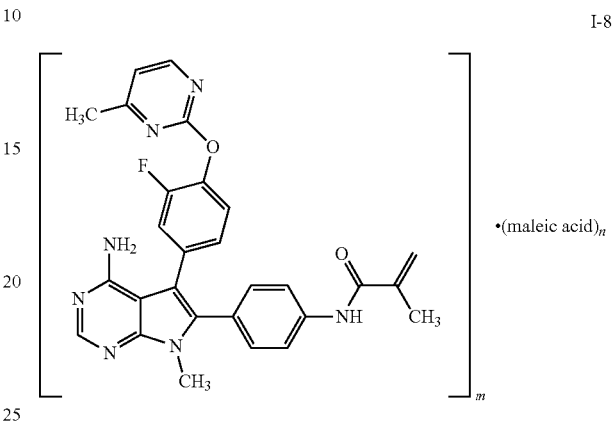

In another embodiment, a compound of Formula (I) is compound I-8, which is a maleic acid salt.

In some embodiments, compound I-8 is an amorphous solid. In some embodiments compound I-8 is a crystalline solid. In some embodiments, Compound I-8 is a mixture of amorphous solid form and crystalline solid form.

In some embodiments, the present invention provides a form of compound I-8 substantially free of impurities. As used herein, the term "substantially free of impurities" means that the compound contains no significant amount of extraneous matter. Such extraneous matter may include different forms of compound I-8, residual solvents, or any other impurities that may result from the preparation of, and/or isolation of, compound I-8.

In some embodiments, compound I-8, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, compound I-8, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition. In some embodiments, compound I-8, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of impurity compound 6 (including the free base and salts of compound 6, or solvates thereof, or solid forms thereof), wherein the percentages are based on the total weight of the composition.

In some embodiments, compound I-8, or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, compound I-8, or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, compound I-8, or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 area percent HPLC of impurity compound 6 (including the free base and salts of compound 6, or solvates thereof, or solid forms thereof) relative to the total area of the HPLC chromatogram. In some embodiments, a HPLC method is the HPLC method as described in Example 1.

The structure depicted for compound I-8 is also meant to include all tautomeric forms of compound I-8. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In other embodiments, compound I-8 is a crystalline solid substantially free of amorphous compound I-8. As used herein, the term "substantially free of amorphous compound I-8" means that the compound contains no significant amount of amorphous compound I-8. In certain embodiments, at least about 95% by weight of crystalline compound I-8 is present. In certain embodiments, at least about 99% by weight of crystalline compound I-8 is present.

Figure 19A:
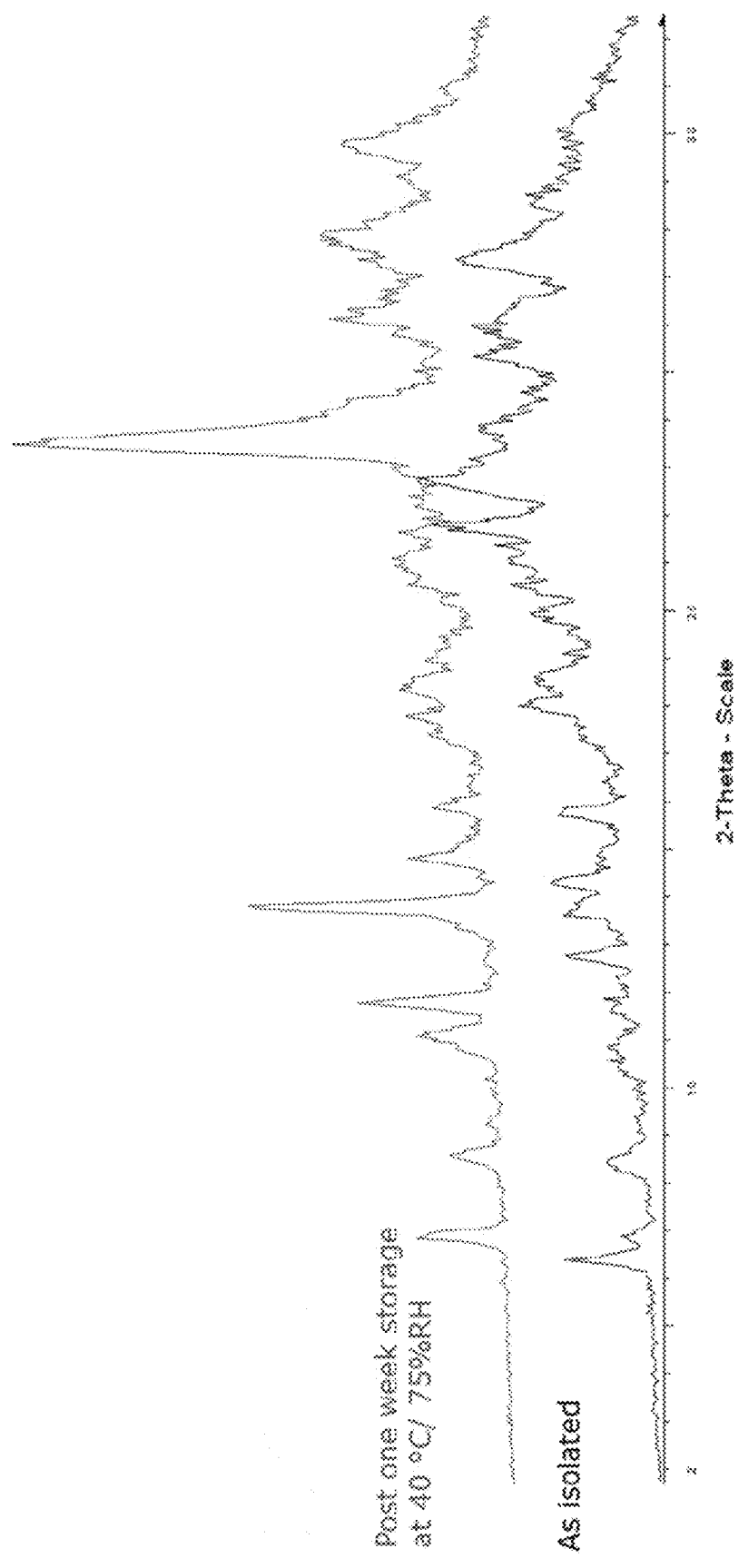
FIG. 19A depicts an X-ray diffraction pattern of Form A of Compound I-8 (maleate salt) before and after one week of storage at 40 C and 75% relative humidity.
Figure 19B:
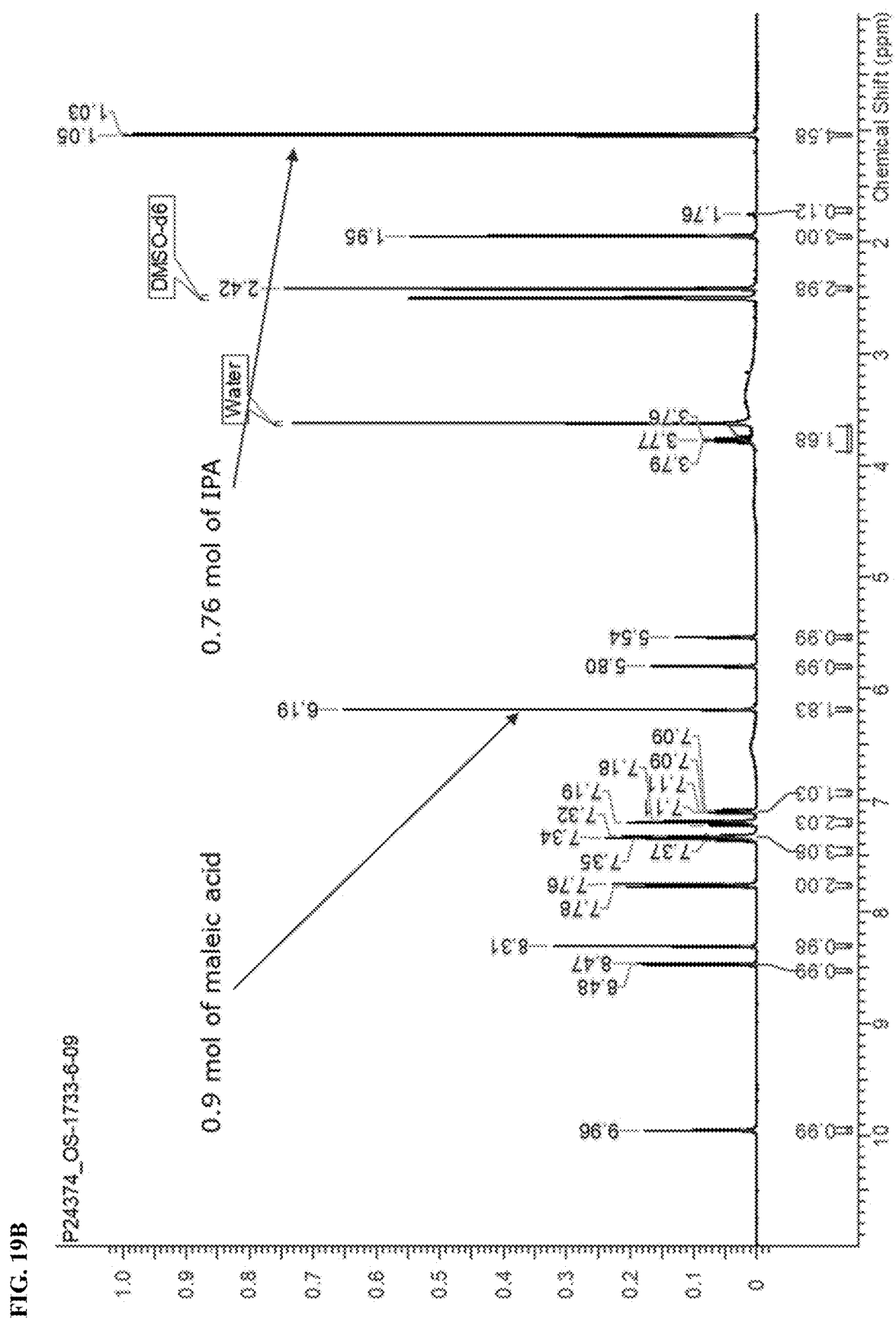
FIG. 19B depicts the characterization of Form A of Compound I-8 by $^1$H nuclear magnetic resonance ($^1$H NMR) in D6-DMSO at 400 MHz.
Figure 19C:
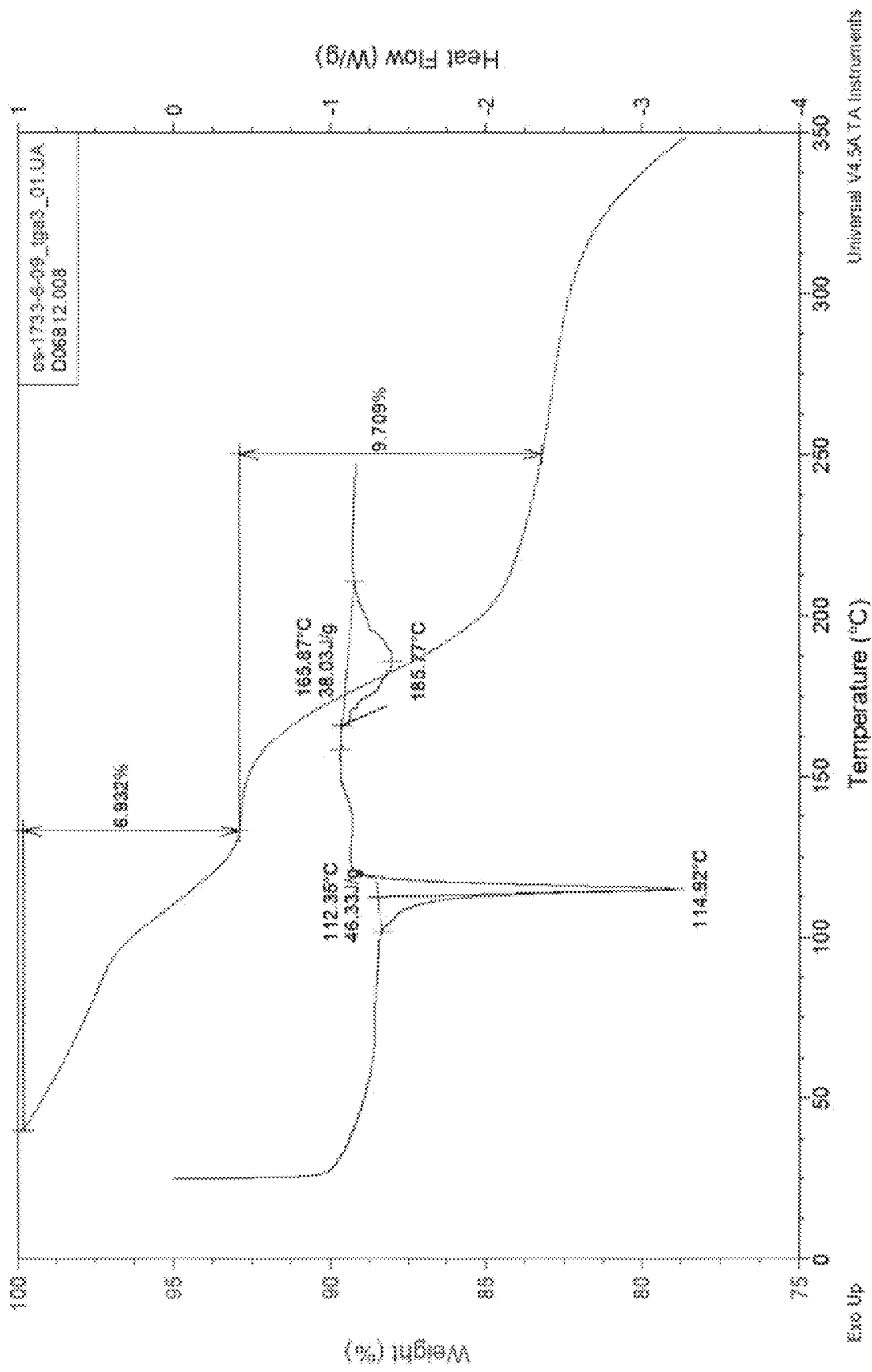
FIG. 19C depicts the characterization of Form A of Compound I-8 by thermogravimetric analysis (above) and differential scanning calorimetry (below).

In certain embodiments, a solid crystalline form of compound I-8 has a X-Ray diffraction pattern substantially similar to any one of the patterns depicted in FIG. 19A. In certain embodiments, a solid crystalline form of compound I-8 has a thermogravimetric analysis pattern substantially similar to that depicted in FIG. 19C. In certain embodiments, a solid crystalline form of Compound I-8 can be characterized by substantial similarity to two of these figures simultaneously.

Compound of Formula (II)

In one embodiment, provided herein is a compound of Formula (II)

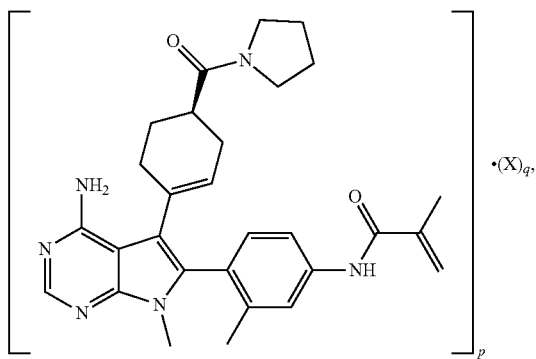

or a solvate thereof;

wherein,
p is 1, 2, 3, 4, 5, 6, 7, 8, or 9;
q is 0, 0.5, 1, 1.5, 2, 2.5, or 3; and
X is hydrochloric acid, hydrobromic acid, p-toluene sulfonic acid, methane sulfonic acid, benzene sulfonic acid, or fumaric acid.

It will be appreciated by one of ordinary skill in the art that the acid moiety indicated as "X" and (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide are ionically bonded to form a compound of Formula (II). It will also be appreciated that when q is 0, X is absent, indicating that the compound of Formula (II) exists as a "free base," i.e., "free form."

It is contemplated that a compound of Formula (II) can exist in a variety of physical forms. For example, a compound of Formula (II) can be in solution, suspension, or in solid form. In certain embodiments, a compound of Formula (II) is in solid form. When a compound of Formula (II) is in solid form, said compound may be amorphous, crystalline, or a mixture thereof. Exemplary solid forms are described in more detail below.

In some embodiments, a compound of Formula (II), may be in a hydrate form. In some embodiments, a compound of Formula (II), may be in a hemi-hydrate form.

In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9.

In some embodiments, q is 0. In some embodiments, q is 1. In some embodiments, q is 2. In some embodiments, q is 3. In some embodiments, q is 0.5. In some embodiments, q is 1.5. In some embodiments, q is 2.5.

In some embodiments, X is hydrochloric acid. In some embodiments, X is hydrobromic acid. In some embodiments, X is p-toluene sulfonic acid. In some embodiments, X is methane sulfonic acid. In some embodiments, X is benzene sulfonic acid. In some embodiments, X is fumaric acid.

In some embodiments, the present invention provides a form of a compound of Formula (II) substantially free of impurities. As used herein, the term "substantially free of impurities" means that the compound contains no significant amount of extraneous matter. Such extraneous matter may include different forms of a compound of Formula (II), residual solvents, or any other impurities that may result from the preparation of, and/or isolation of, a compound of Formula (II).

In some embodiments, a compound of Formula (II), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, a compound of Formula (II), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition.

In some embodiments, a compound of Formula (II), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, a compound of Formula (II), or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, a HPLC method is the HPLC method as described in Example 1.

The structure depicted for compound of Formula (II) is also meant to include all tautomeric forms. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In some embodiments, a compound of Formula (II) is compound II-1 wherein, compound II-1 is a free base (or "free form"). In some embodiments, compound II-1 is an amorphous solid. In some embodiments, compound II-1 is a crystalline solid. In some embodiments, Compound II-1 is a mixture of amorphous solid form and crystalline solid form.

In some embodiments, the present invention provides a form of compound II-1 substantially free of impurities. As used herein, the term "substantially free of impurities" means that the compound contains no significant amount of extraneous matter. Such extraneous matter may include different forms of compound II-1, residual solvents, or any other impurities that may result from the preparation of, and/or isolation of, compound II-1. In certain embodiments, at least about 95% by weight of compound II-1 is present. In certain embodiments, at least about 99% by weight of compound II-1 is present.

In other embodiments, compound II-1 is a crystalline solid substantially free of amorphous compound II-1. As used herein, the term "substantially free of amorphous compound II-1" means that the compound contains no significant amount of amorphous compound II-1. In certain embodiments, at least about 95% by weight of crystalline compound II-1 is present. In certain embodiments, at least about 99% by weight of crystalline compound II-1 is present.

It has been found that compound II-1 can exist in a variety of solid forms. Exemplary such forms include polymorphs such as those described herein.

Figure 24A:
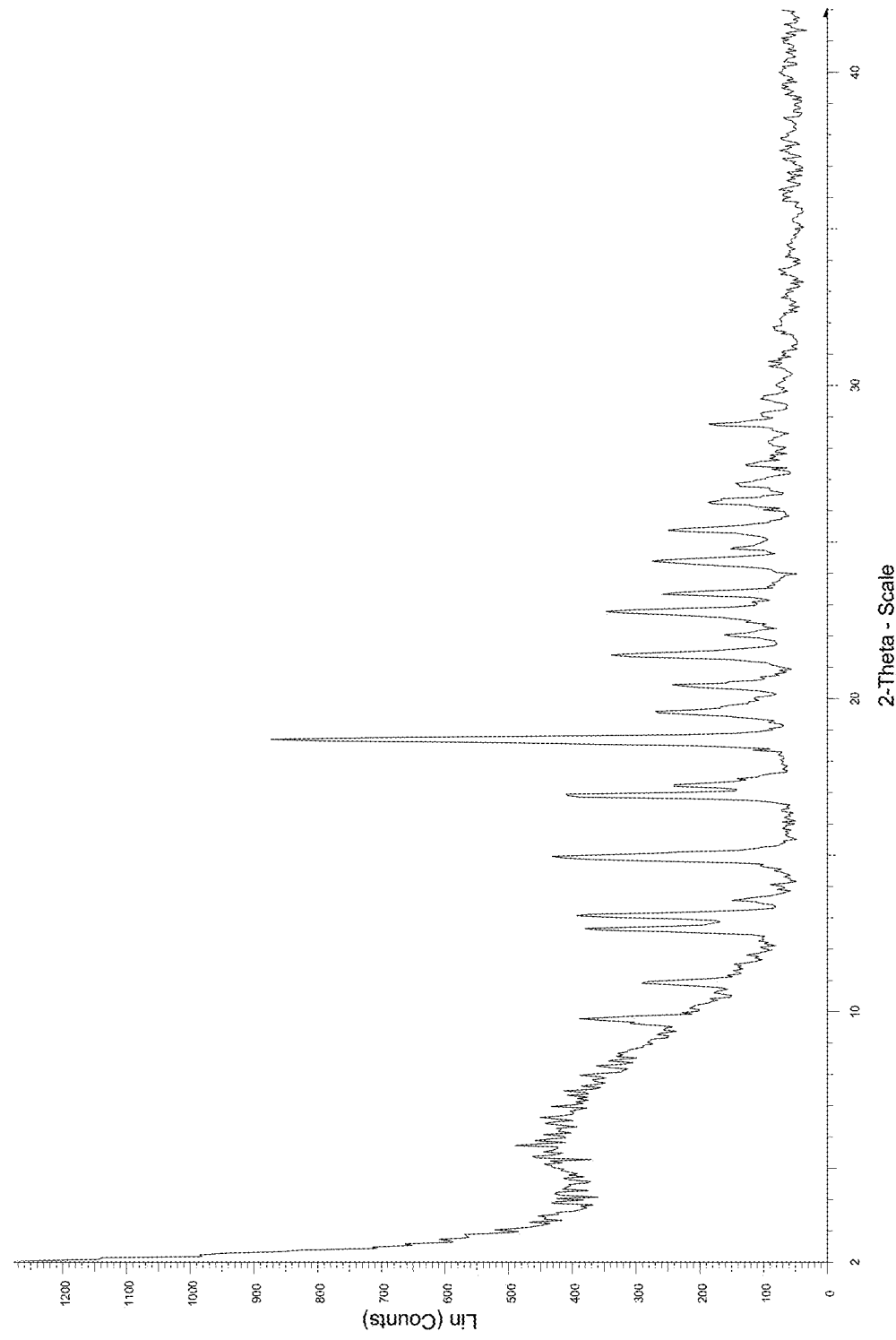
FIG. 24A depicts an X-ray diffraction pattern of Form A of Compound II-1 (free form).
Figure 24B:
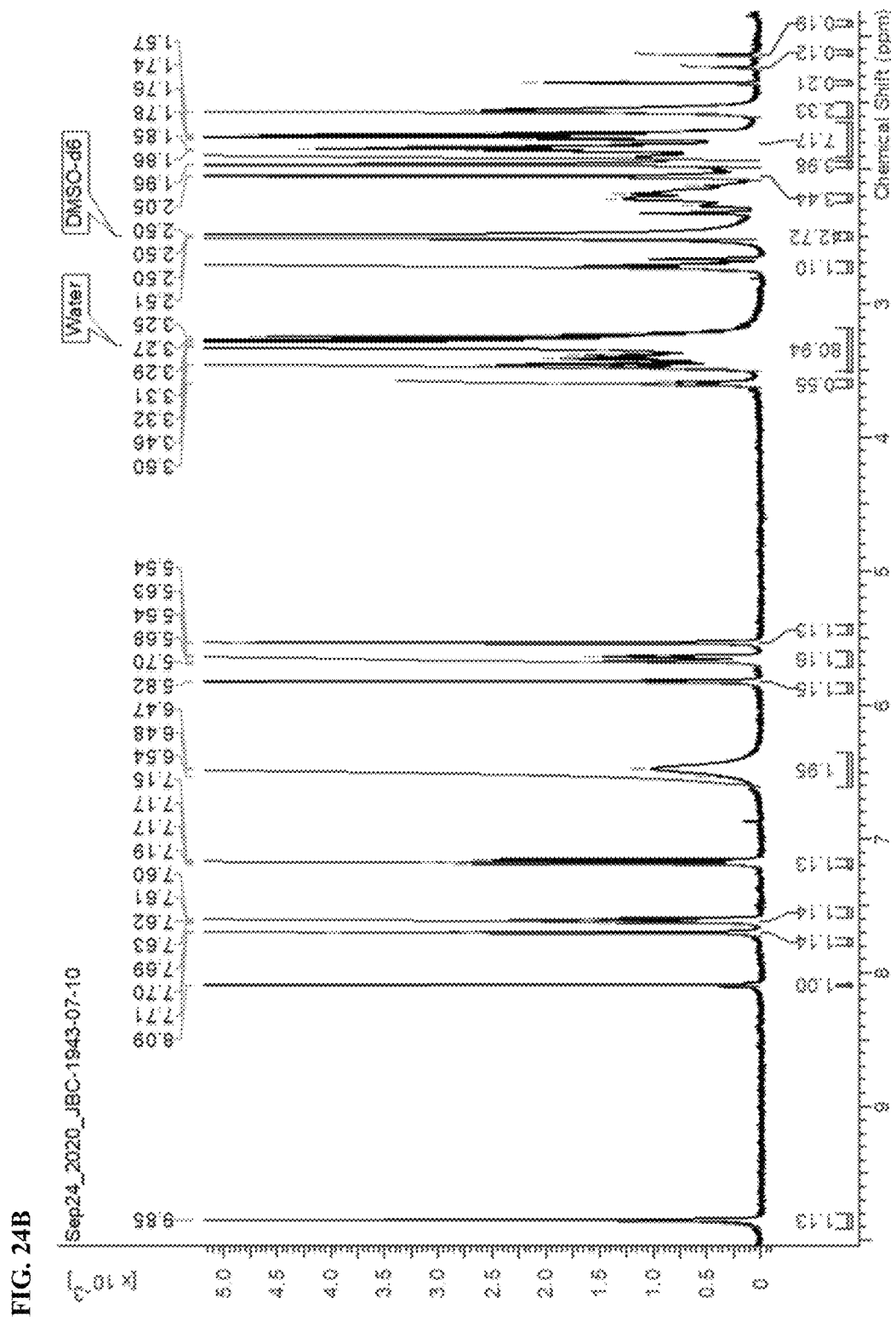
FIG. 24B depicts the characterization of Form A of Compound II-1 by $^1$H nuclear magnetic resonance ($^1$H NMR) in D6-DMSO at 400 MHz.

In some embodiments, the solid crystalline form of Compound II-1 is Form A. In certain embodiments, Form A of compound II-1 has a X-Ray diffraction pattern substantially similar to that depicted in FIG. 24A. In some embodiments, Form A of Compound II-1 may be characterized by a powder X-ray diffraction pattern with at least two characteristic peaks, in degrees 2θ, each selected from the group consisting of the peaks listed in Table 8. In some embodiments, Form A of Compound II-1 may be characterized by a powder X-ray diffraction pattern with at least three characteristic peaks, in degrees 2θ, each selected from the group consisting of the peaks listed in Table 8. In some embodiments, Form A of Compound II-1 may be characterized by a powder X-ray diffraction pattern with at least four characteristic peaks, in degrees 2θ, each selected from the group consisting of the peaks listed in Table 8. In some embodiments, Form A of Compound II-1 may be characterized by a powder X-ray diffraction pattern with at least five characteristic peaks, in degrees 2θ, each selected from the group consisting of the peaks listed in Table 8. In some embodiments, Form A of Compound II-1 may be characterized by a powder X-ray diffraction pattern with at least six characteristic peaks, in degrees 2θ, each selected from the group consisting of the peaks listed in Table 8.

Figure 24C:
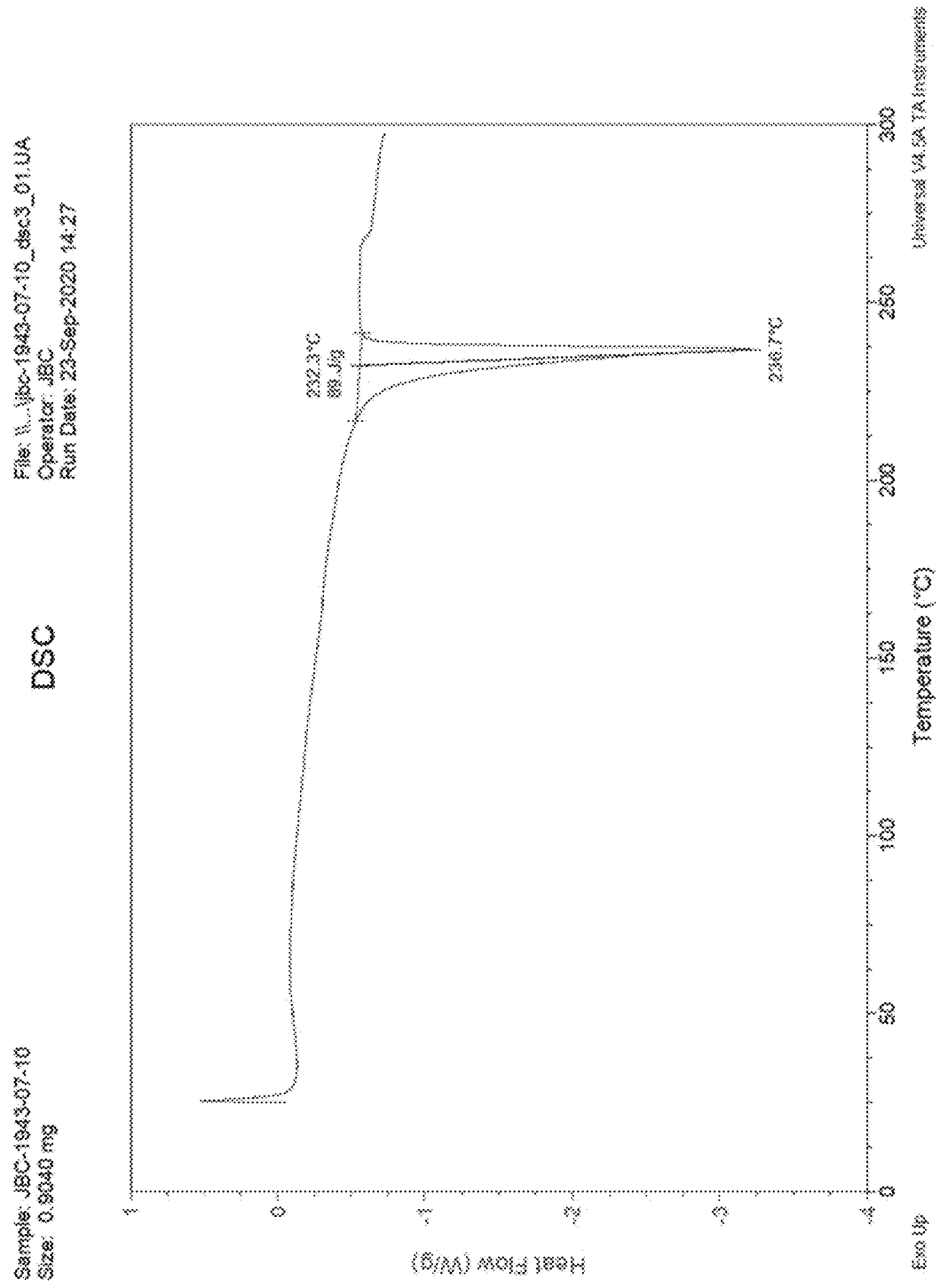
FIG. 24C depicts the characterization of Form A of Compound II-1 by differential scanning calorimetry (DSC).
Figure 24D:
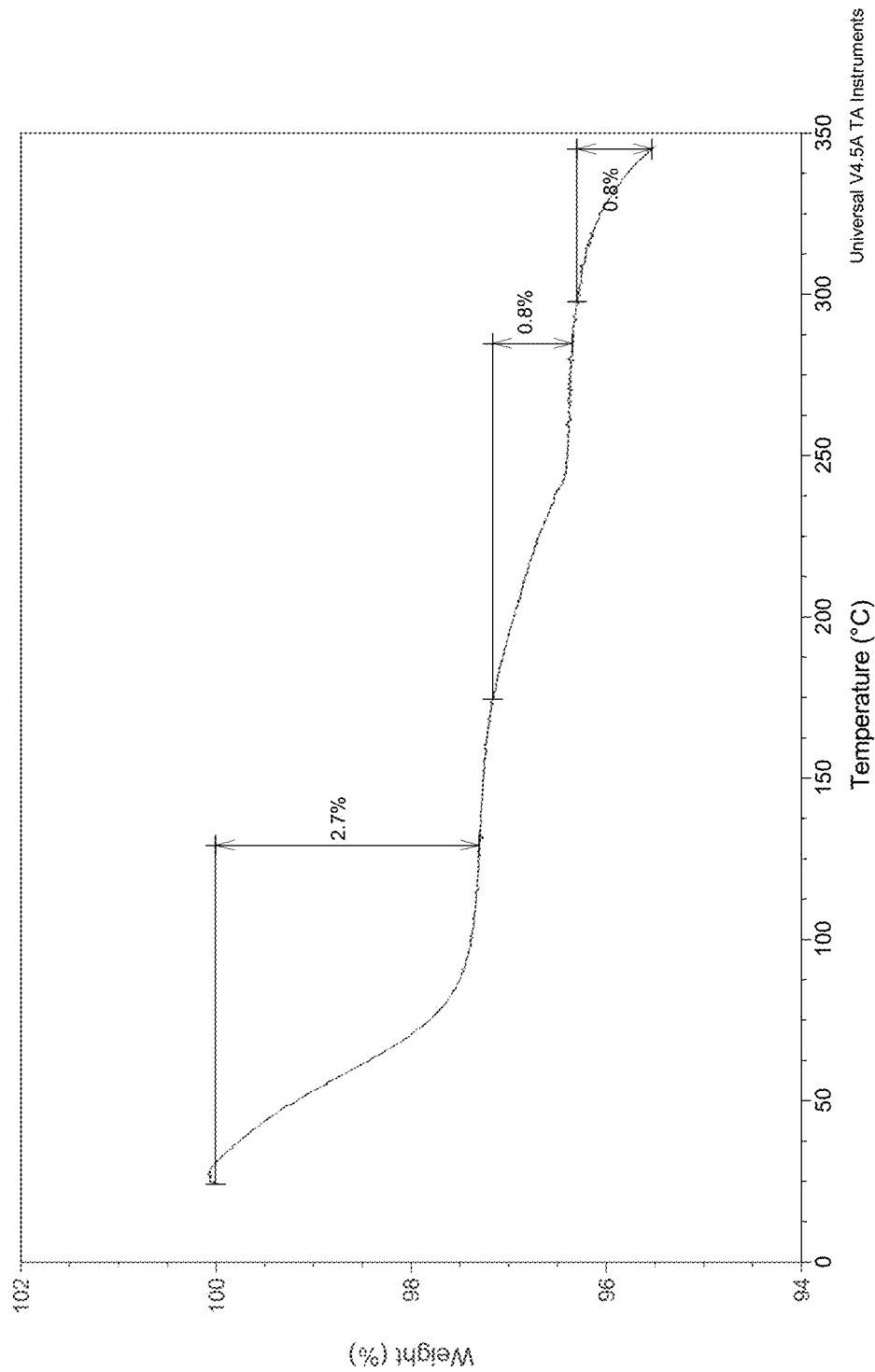
FIG. 24D depicts the characterization of Form A of Compound II-1 by thermogravimetric analysis (TGA).
Figure 24E:
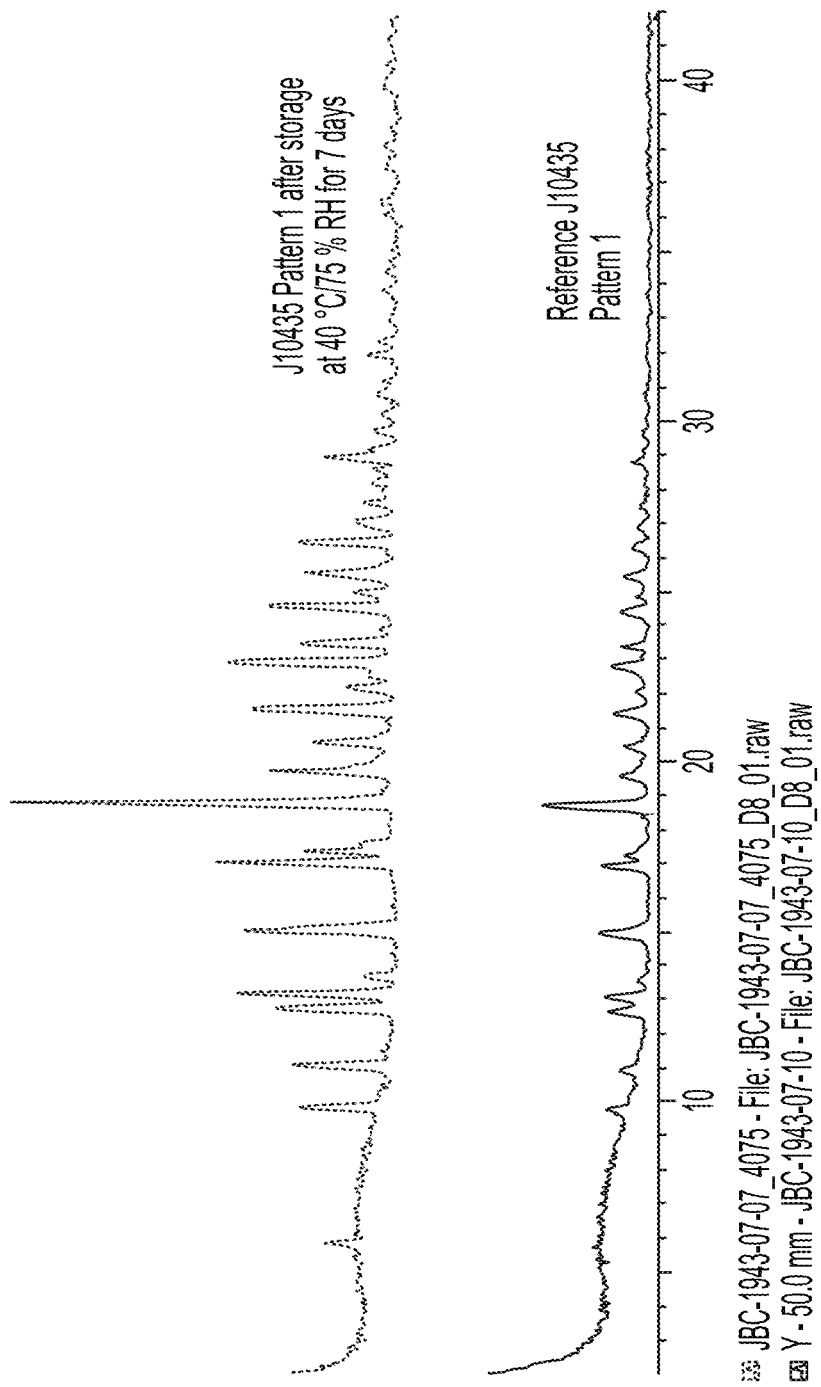
FIG. 24E depicts an XRPD diffractogram of Compound II-1 Form A (below) after storage at 40° C./75% RH for 7 days (above).

In certain embodiments, Form A of compound II-1 has a differential scanning calorimetry (DSC) pattern substantially similar to that depicted in FIG. 24C. In certain embodiments, Form A of compound II-1 has a thermogravimetric analysis (TGA) pattern substantially similar to that depicted in FIG. 24D. In certain embodiments, Compound II-1 Form A can be characterized by substantial similarity to two or more of these figures simultaneously.

Figure 25A:
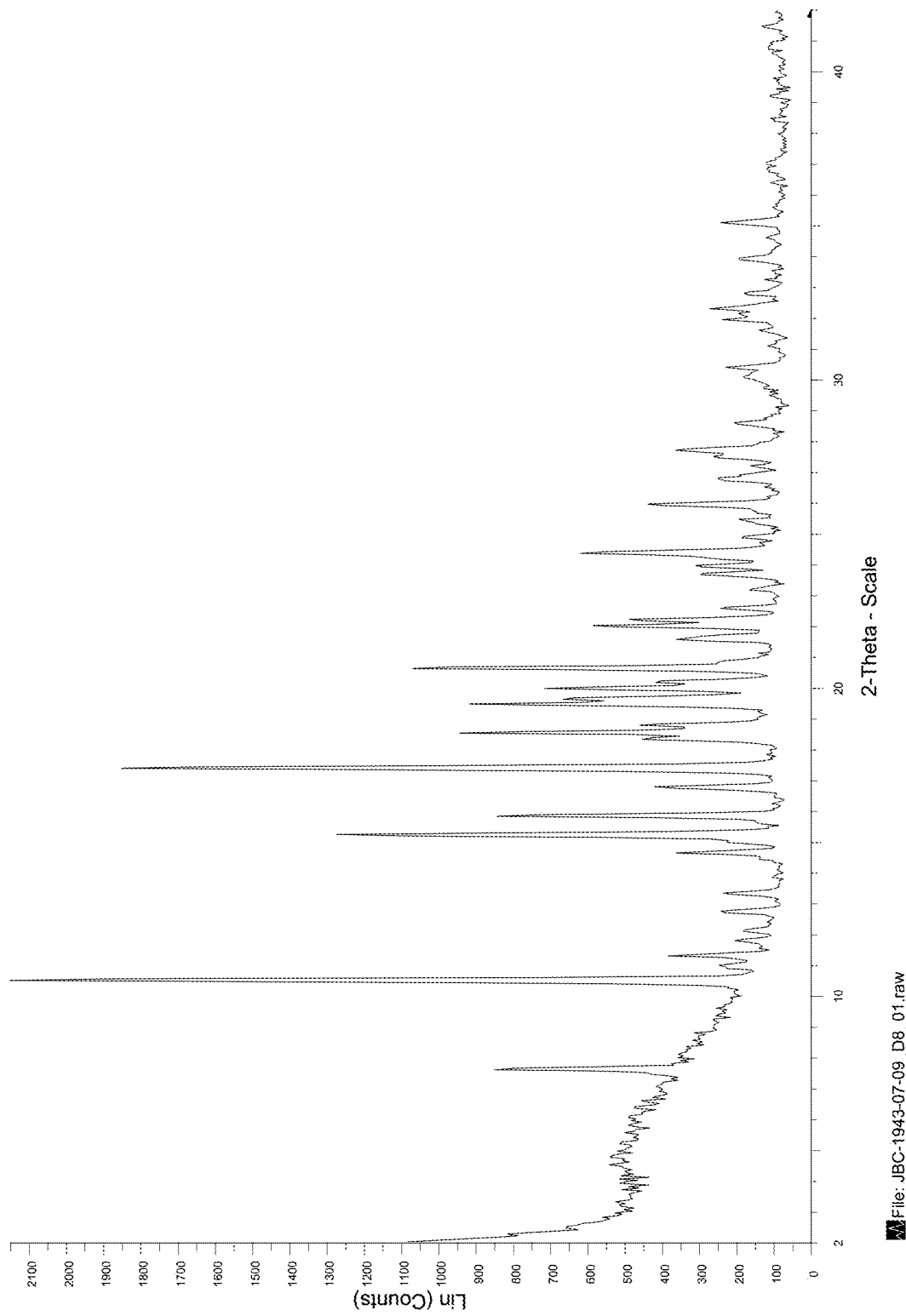
FIG. 25A depicts an X-ray diffraction pattern of Form B of Compound II-1 (free form).
Figure 25B:
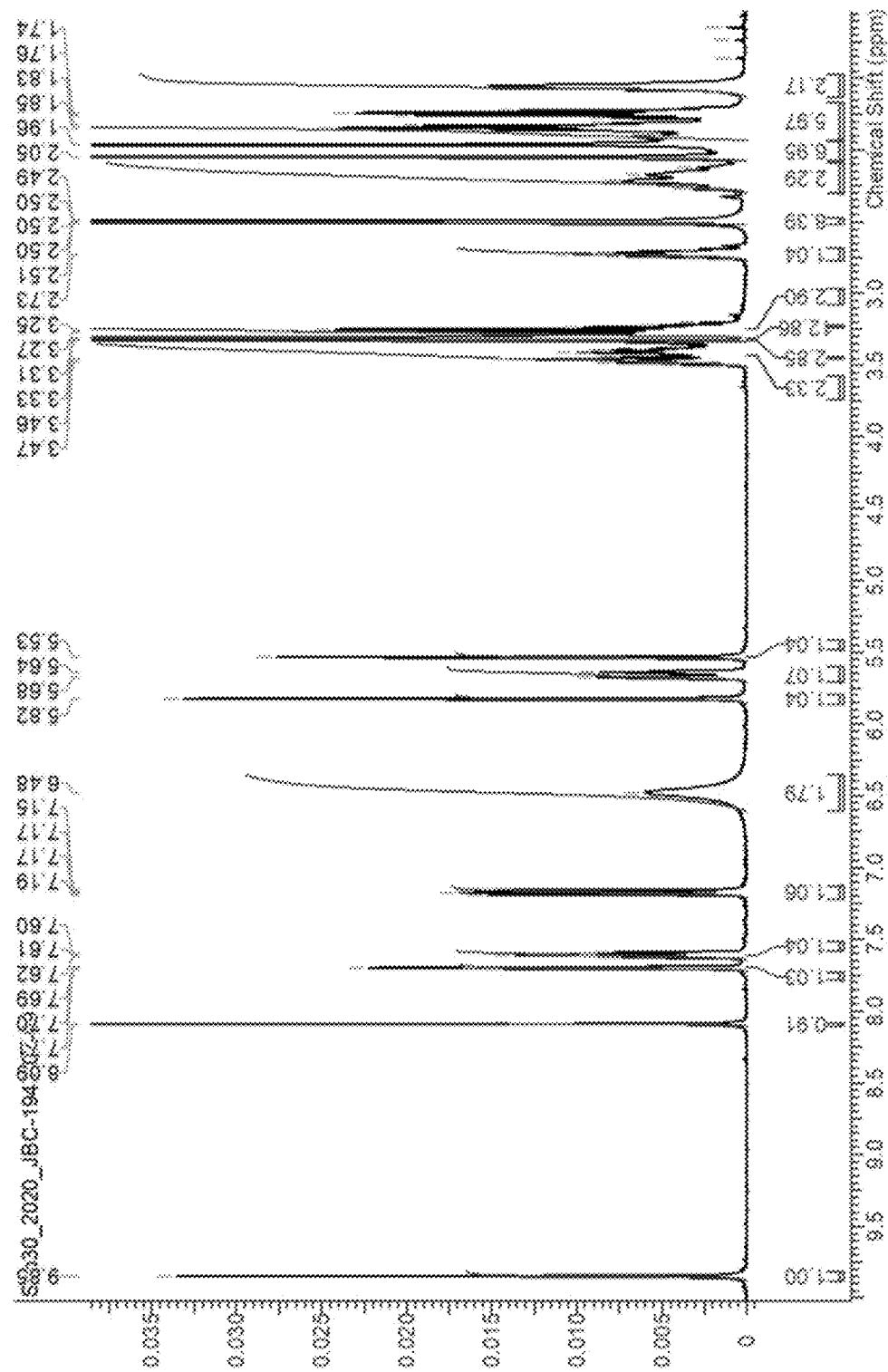
FIG. 25B depicts the characterization of Form B of Compound II-1 by $^1$H nuclear magnetic resonance ($^1$H NMR) in D6-DMSO at 400 MHz.

In some embodiments, the solid crystalline form of Compound II-1 is Form B. In certain embodiments, Form B of compound II-1 has a X-Ray diffraction pattern substantially similar to that depicted in FIG. 25A. In some embodiments, Form B of Compound II-1 may be characterized by a powder X-ray diffraction pattern with at least two characteristic peaks, in degrees 2θ, each selected from the group consisting of the peaks listed in Table 9. In some embodiments, Form B of Compound II-1 may be characterized by a powder X-ray diffraction pattern with at least three characteristic peaks, in degrees 2θ, each selected from the group consisting of the peaks listed in Table 9. In some embodiments, Form B of Compound II-1 may be characterized by a powder X-ray diffraction pattern with at least four characteristic peaks, in degrees 2θ, each selected from the group consisting of the peaks listed in Table 9. In some embodiments, Form B of Compound II-1 may be characterized by a powder X-ray diffraction pattern with at least five characteristic peaks, in degrees 2θ, each selected from the group consisting of the peaks listed in Table 9. In some embodiments, Form B of Compound II-1 may be characterized by a powder X-ray diffraction pattern with at least six characteristic peaks, in degrees 2θ, each selected from the group consisting of the peaks listed in Table 9.

Figure 25C:
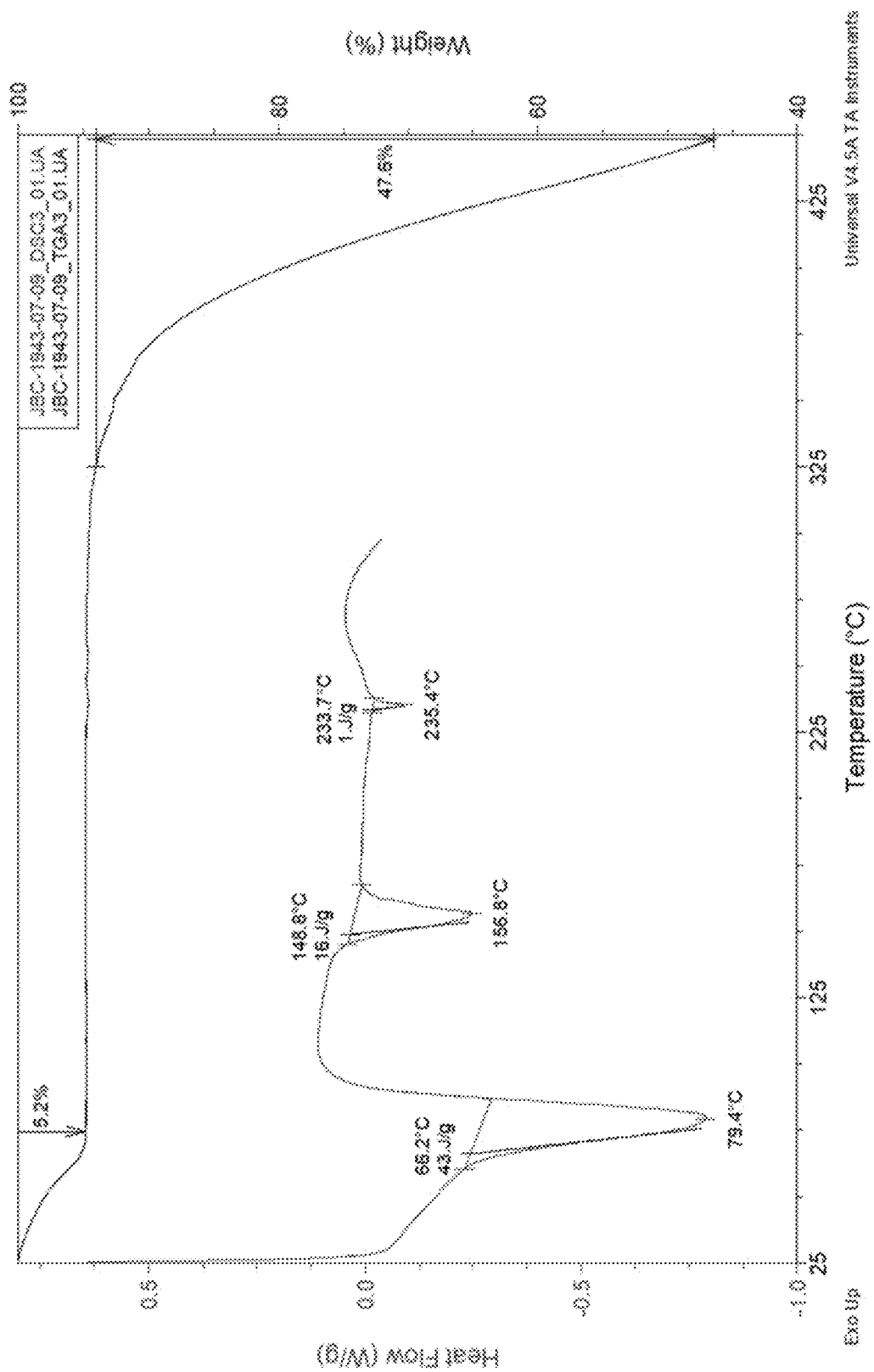
FIG. 25C depicts the characterization of Form B of Compound II-1 by thermogravimetric analysis (above) and differential scanning calorimetry (below).
Figure 25D:
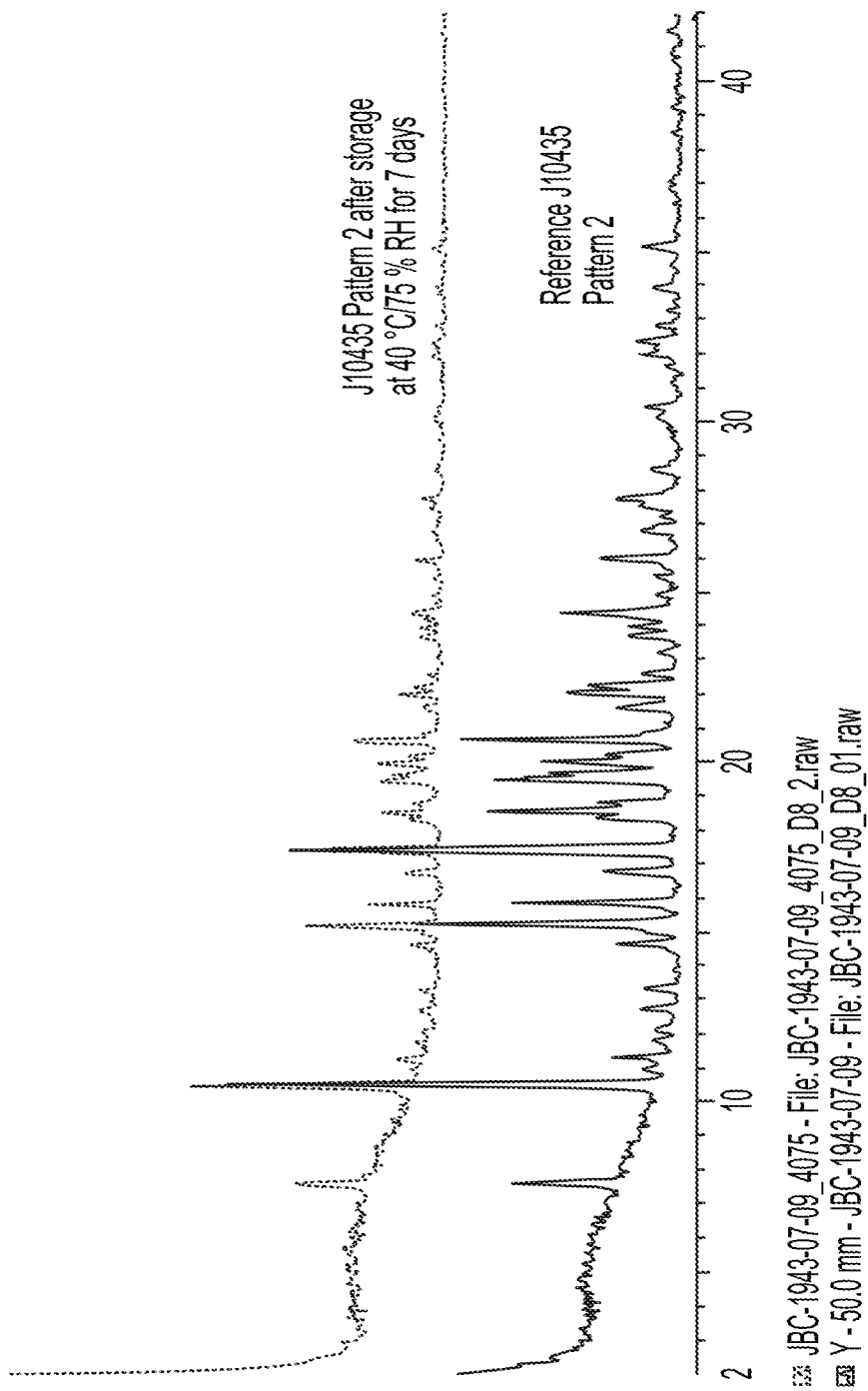
FIG. 25D depicts an XRPD diffractogram of Compound II-1 Form B (below) after storage at 40° C./75% RH for 7 days (above).

In certain embodiments, Form B of compound II-1 has a differential scanning calorimetry (DSC) pattern substantially similar to that depicted in FIG. 25C. In certain embodiments, Form B of compound II-1 has a thermogravimetric analysis (TGA) pattern substantially similar to that depicted in FIG. 25D. In certain embodiments, Compound II-1 Form B can be characterized by substantial similarity to two or more of these figures simultaneously.

In another embodiment, a compound of Formula (II) is compound II-2 wherein, compound II-2 is a hydrochloride salt. In some embodiments, compound II-2 is a mono-hydrochloride salt. In some embodiments, compound II-2 is a bis-hydrochloride salt. In some embodiments, compound II-2 is a tris-hydrochloride salt.

In some embodiments, Compound II-2 is an amorphous solid. In some embodiments, compound II-2 is a crystalline solid. In some embodiments, Compound II-2 is a mixture of amorphous solid form and crystalline solid form.

In some embodiments, the present invention provides a form of compound II-2 substantially free of impurities. As used herein, the term "substantially free of impurities" means that the compound contains no significant amount of extraneous matter. Such extraneous matter may include different forms of compound II-2, residual solvents, or any other impurities that may result from the preparation of, and/or isolation of, compound II-2. In certain embodiments, at least about 95% by weight of compound II-2 is present. In certain embodiments, at least about 99% by weight of compound II-2 is present.

In certain embodiments, compound II-2 is a crystalline solid. In other embodiments, compound II-2 is a crystalline solid substantially free of amorphous compound II-2. As used herein, the term "substantially free of amorphous compound II-2" means that the compound contains no significant amount of amorphous compound II-2. In certain embodiments, at least about 95% by weight of crystalline compound II-2 is present. In still other embodiments of the invention, at least about 99% by weight of crystalline compound II-2 is present.

Figure 26A:
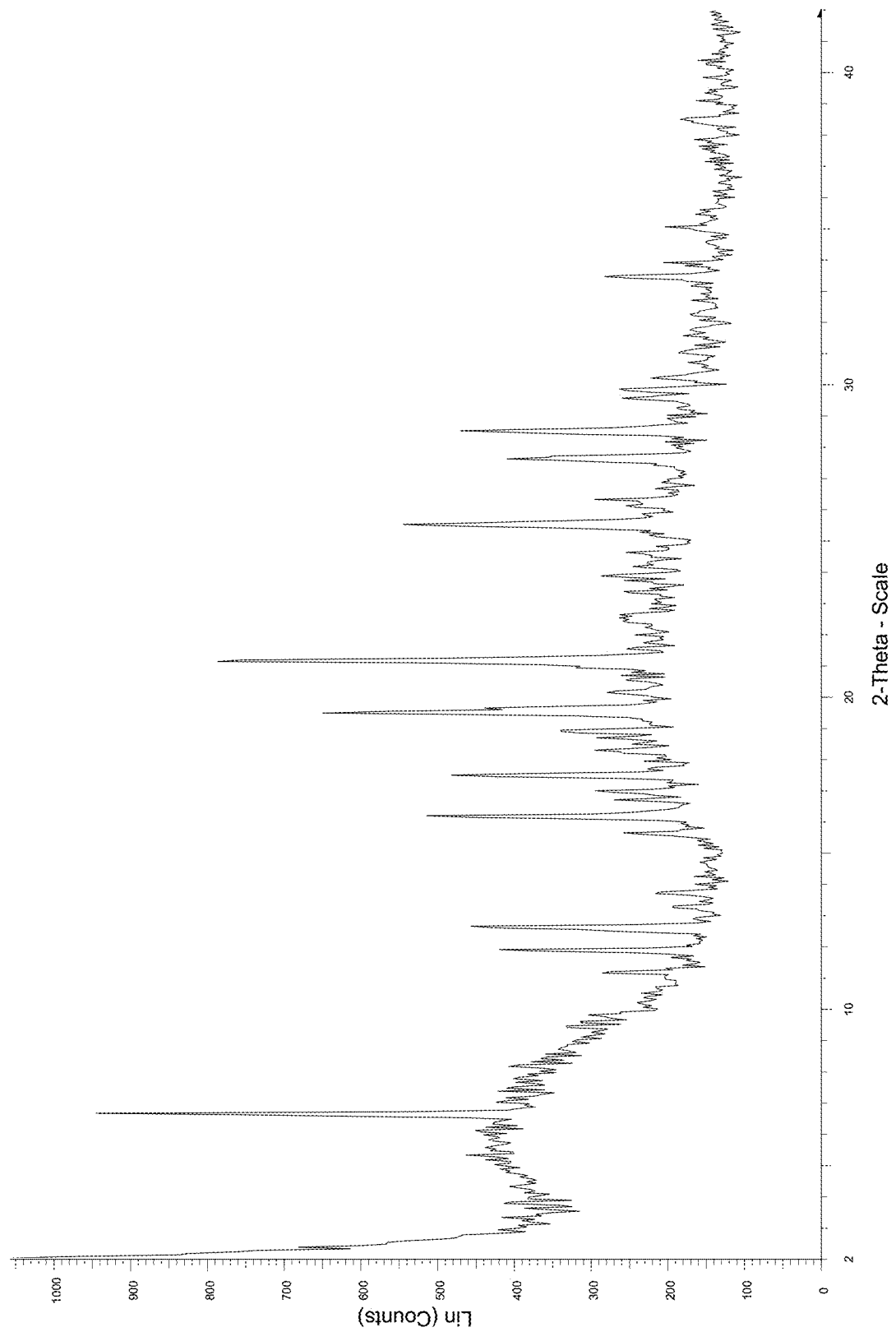
FIG. 26A depicts an X-ray diffraction pattern of Form A of Compound II-2 (hydrochloride salt).
Figure 26B:
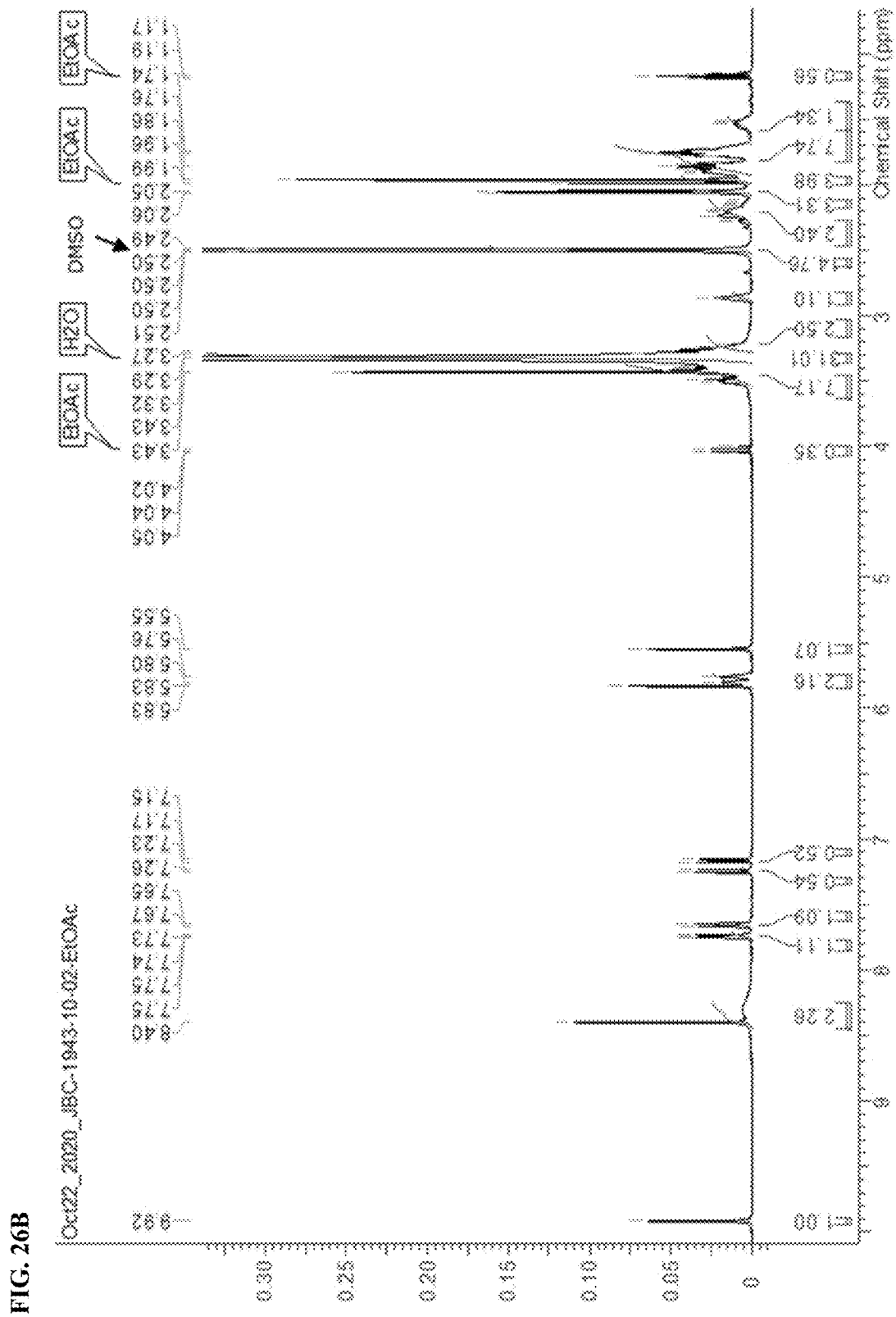
FIG. 26B depicts the characterization of Form A of Compound II-2 by $^1$H nuclear magnetic resonance ($^1$H NMR) in D6-DMSO at 400 MHz.

In some embodiments, the solid crystalline form of Compound II-2 is Form A. In some embodiments, Form A of compound II-2 has a X-Ray diffraction pattern substantially similar that depicted in FIG. 26A. In some embodiments, Form A of Compound II-2 may be characterized by a powder X-ray diffraction pattern with at least two characteristic peaks, in degrees 2θ, each selected from the group consisting of the peaks listed in Table 14. In some embodiments, Form A of Compound II-2 may be characterized by a powder X-ray diffraction pattern with at least three characteristic peaks, in degrees 2θ, each selected from the group consisting of the peaks listed in Table 14. In some embodiments, Form A of Compound II-2 may be characterized by a powder X-ray diffraction pattern with at least four characteristic peaks, in degrees 2θ, each selected from the group consisting of the peaks listed in Table 14. In some embodiments, Form A of Compound II-2 may be characterized by a powder X-ray diffraction pattern with at least five characteristic peaks, in degrees 2θ, each selected from the group consisting of the peaks listed in Table 14. In some embodiments, Form A of Compound II-2 may be characterized by a powder X-ray diffraction pattern with at least six characteristic peaks, in degrees 2θ, each selected from the group consisting of the peaks listed in Table 14.

Figure 26C:
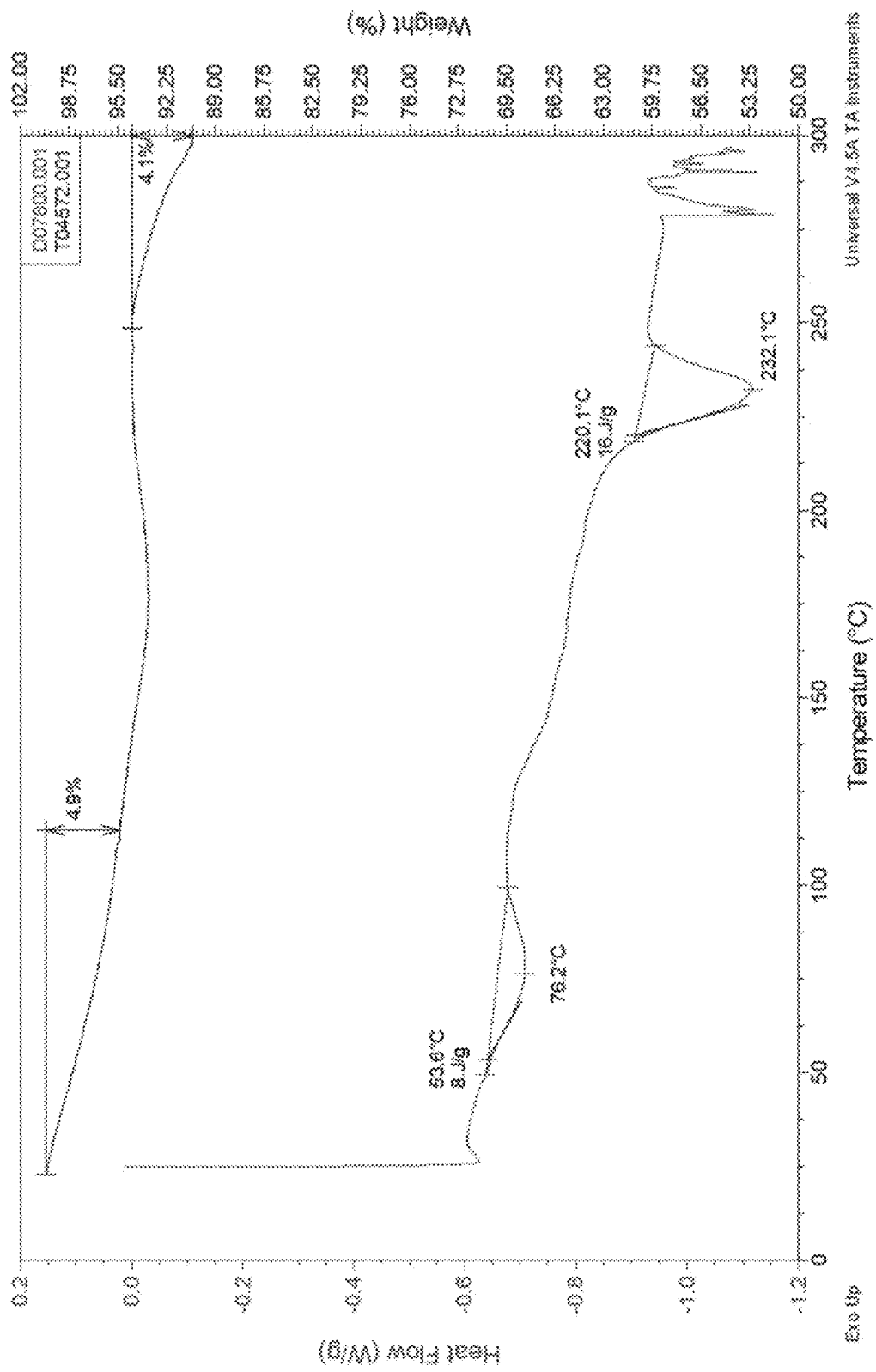
FIG. 26C depicts the characterization of Form A of Compound II-2 by thermogravimetric analysis (above) and differential scanning calorimetry (below).
Figure 26D:
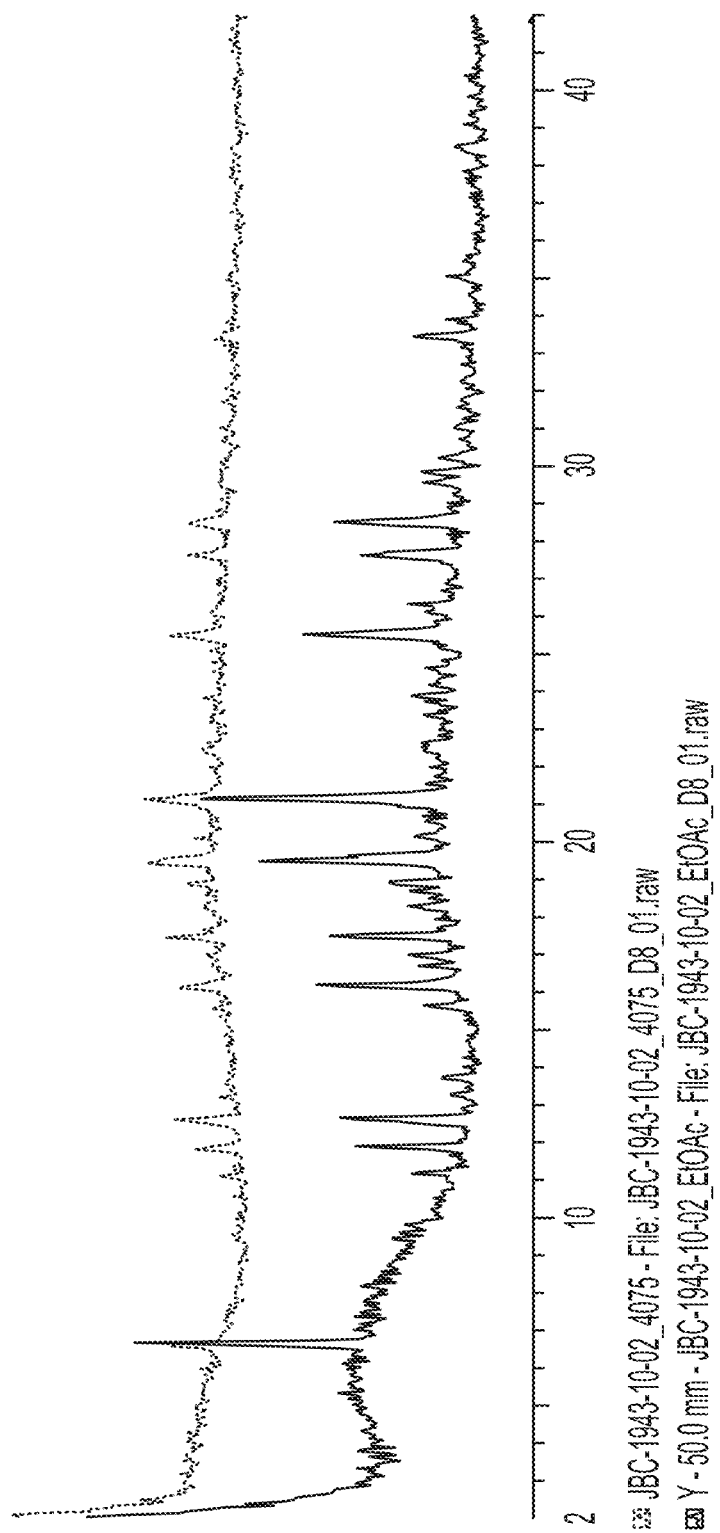
FIG. 26D depicts an XRPD diffractogram of Compound II-2 Form A (below) after storage at 40° C./75% RH for 7 days (above).

In some embodiments, Form A of compound II-2 has a differential scanning calorimetry (DSC) pattern substantially similar to that depicted in FIG. 26C. In some embodiments, Form A of compound II-2 has a thermogravimetric analysis pattern substantially similar to that depicted in FIG. 26C. In some embodiments, Form A of Compound II-2 can be characterized by substantial similarity to two or more of these figures simultaneously.

In another embodiment, a compound of Formula (II) is compound II-3 wherein, compound II-3 is a hydrobromide salt. In some embodiments, compound II-3 is a mono-hydrobromide salt. In some embodiments, compound II-3 is a bis-hydrobromide salt. In some embodiments, compound II-3 is a tris-hydrobromide salt.

In some embodiments, Compound II-3 is an amorphous solid. In some embodiments, compound II-3 is a crystalline solid. In some embodiments, Compound II-3 is a mixture of amorphous solid form and crystalline solid form.

In some embodiments, the present invention provides a form of compound II-3 substantially free of impurities. As used herein, the term "substantially free of impurities" means that the compound contains no significant amount of extraneous matter. Such extraneous matter may include different forms of compound II-3, residual solvents, or any other impurities that may result from the preparation of, and/or isolation of, compound II-3. In certain embodiments, at least about 95% by weight of compound II-3 is present. In certain embodiments, at least about 99% by weight of compound II-3 is present.

In certain embodiments, compound II-3 is a crystalline solid. In other embodiments, compound II-3 is a crystalline solid substantially free of amorphous compound II-3. As used herein, the term "substantially free of amorphous compound II-3" means that the compound contains no significant amount of amorphous compound II-3. In certain embodiments, at least about 95% by weight of crystalline compound II-3 is present. In still other embodiments of the invention, at least about 99% by weight of crystalline compound II-3 is present.

Figure 27A:
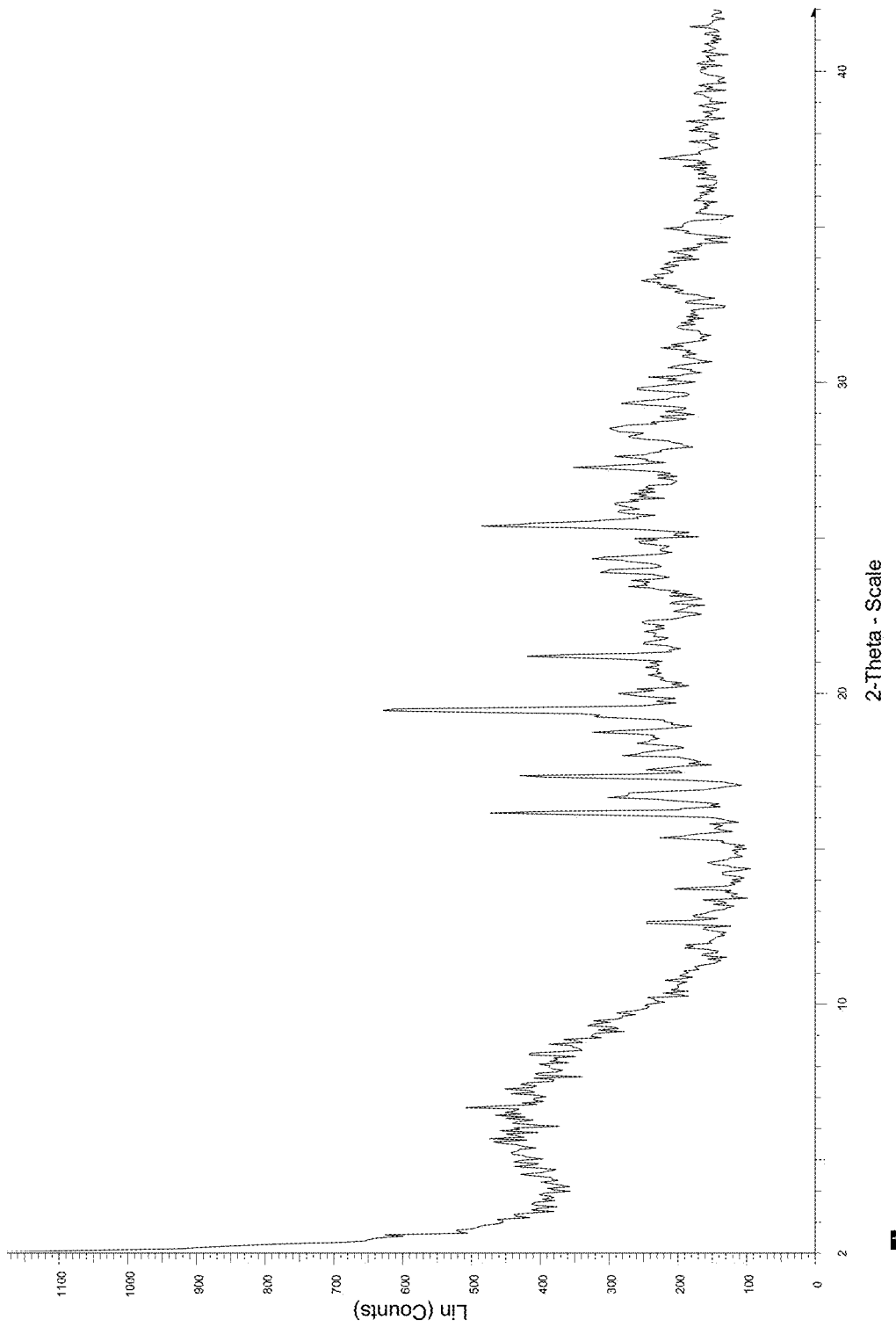
FIG. 27A depicts an X-ray diffraction pattern of Form A of Compound II-3 (hydrobromide salt).
Figure 27B:
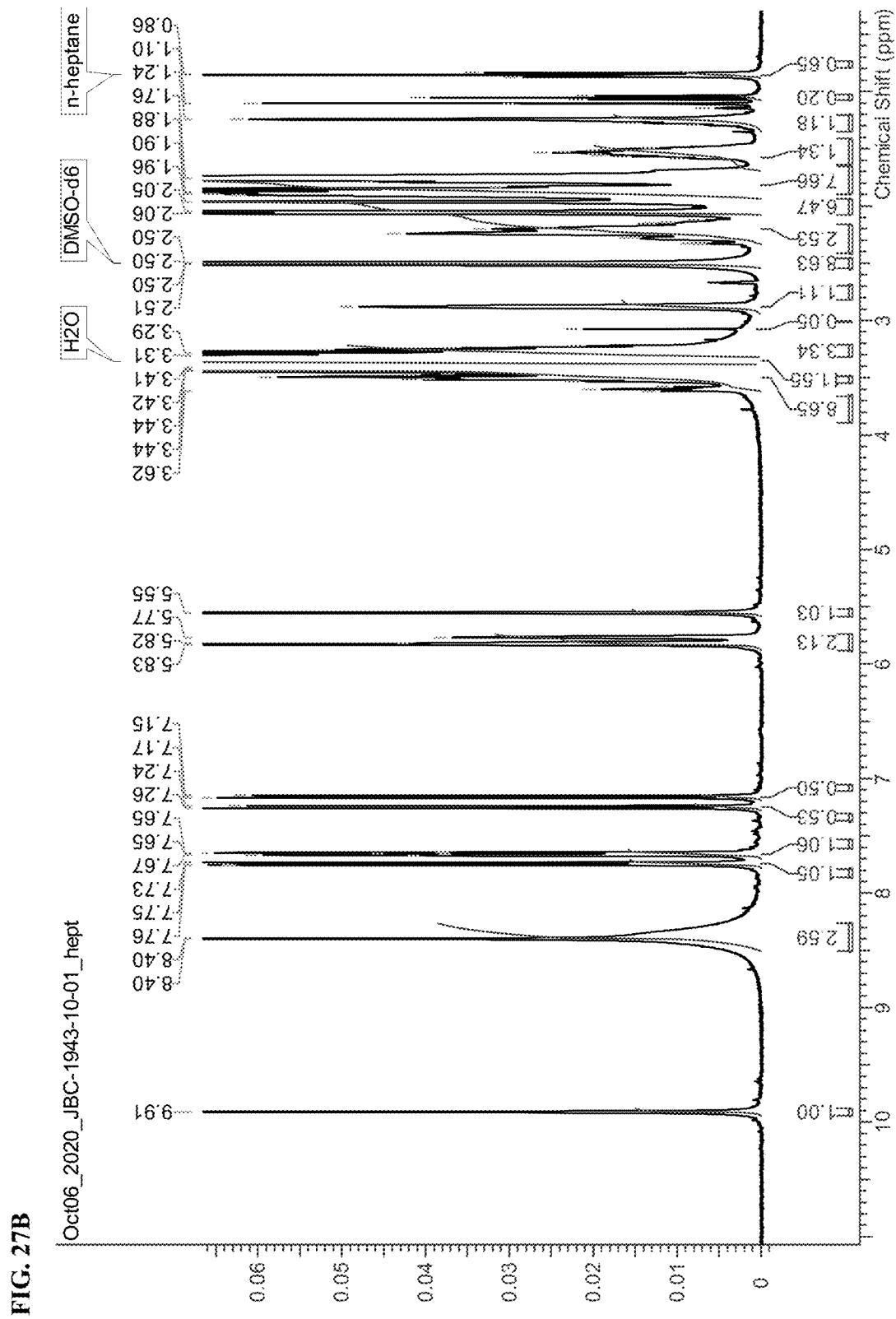
FIG. 27B depicts the characterization of Form A of Compound II-3 by $^1$H nuclear magnetic resonance ($^1$H NMR) in D6-DMSO at 400 MHz.

In some embodiments, the solid crystalline form of Compound II-3 is Form A. In some embodiments, Form A of compound II-3 has a X-Ray diffraction pattern substantially similar to that of FIG. 27A. In some embodiments, Form A of Compound II-3 may be characterized by a powder X-ray diffraction pattern with at least two characteristic peaks, in degrees 2θ, each selected from the group consisting of the peaks listed in Table 15. In some embodiments, Form A of Compound II-3 may be characterized by a powder X-ray diffraction pattern with at least three characteristic peaks, in degrees 2θ, each selected from the group consisting of the peaks listed in Table 15. In some embodiments, Form A of Compound II-3 may be characterized by a powder X-ray diffraction pattern with at least four characteristic peaks, in degrees 2θ, each selected from the group consisting of the peaks listed in Table 15. In some embodiments, Form A of Compound II-3 may be characterized by a powder X-ray diffraction pattern with at least five characteristic peaks, in degrees 2θ, each selected from the group consisting of the peaks listed in Table 15. In some embodiments, Form A of Compound II-3 may be characterized by a powder X-ray diffraction pattern with at least six characteristic peaks, in degrees 2θ, each selected from the group consisting of the peaks listed in Table 15.

Figure 27C:
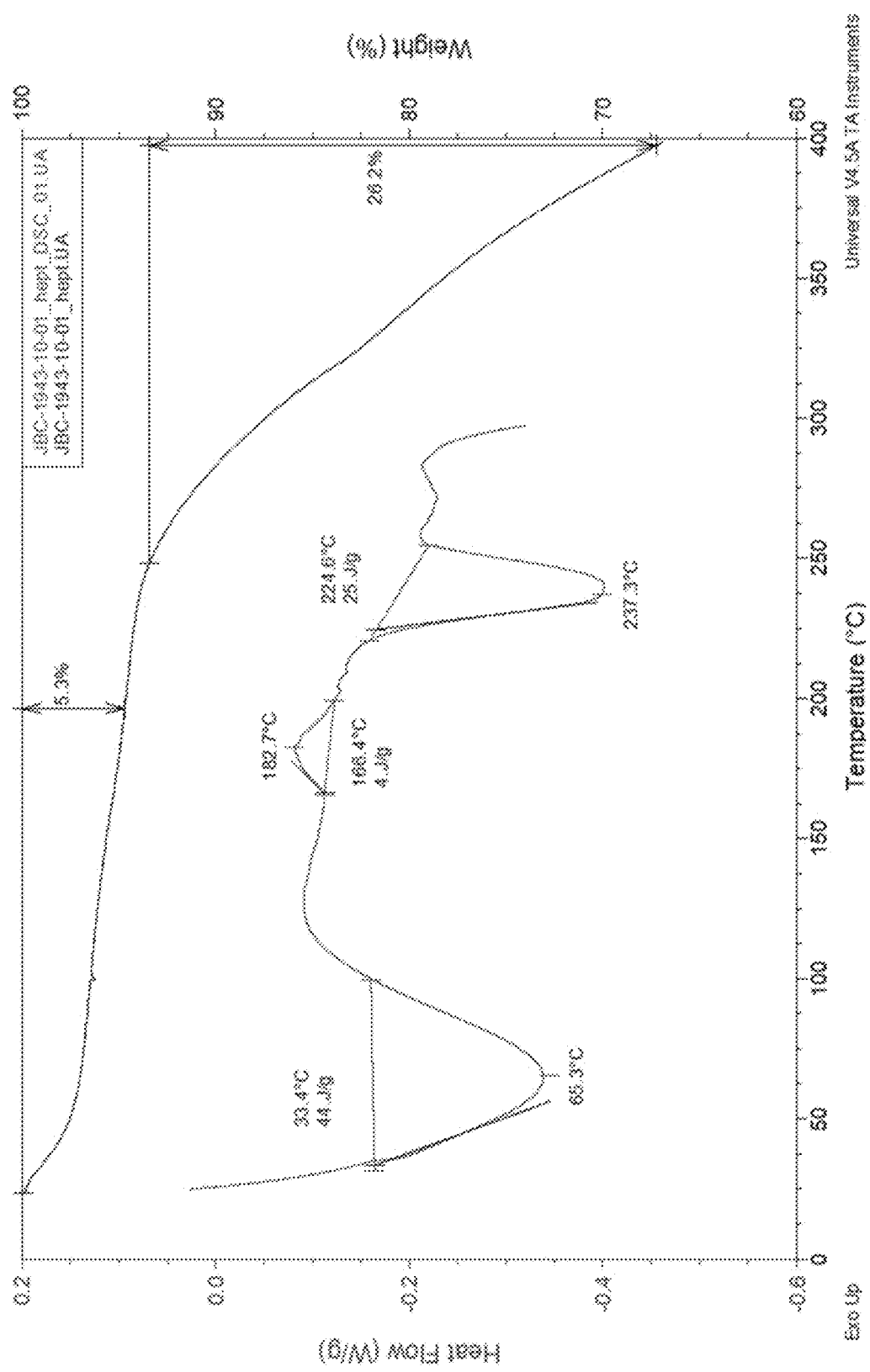
FIG. 27C depicts the characterization of Form A of Compound II-3 by thermogravimetric analysis (above) and differential scanning calorimetry (below).
Figure 27D:
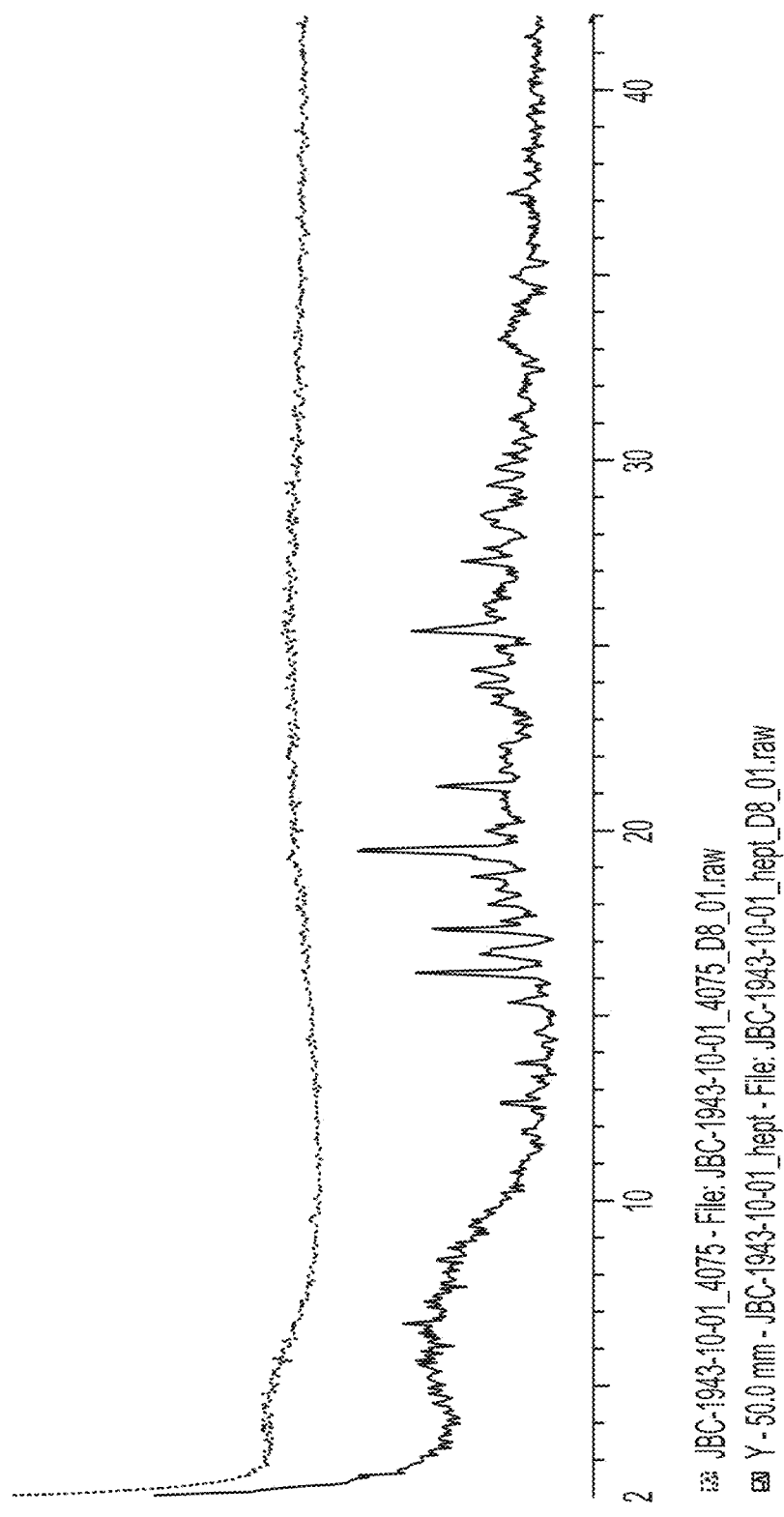
FIG. 27D depicts an XRPD diffractogram of Compound II-3 Form A (below) after storage at 40° C./75% RH for 7 days (above).

In some embodiments, Form A of compound II-3 has a differential scanning calorimetry (DSC) pattern substantially similar to that depicted in FIG. 27C. In some embodiments, Form A of compound II-3 has a thermogravimetric analysis pattern substantially similar to that depicted in FIG. 27C. In some embodiments, Form A of Compound II-3 can be characterized by substantial similarity to two or more of these figures simultaneously.

In another embodiment, a compound of Formula (II) is compound II-4 wherein, compound II-4 is a p-toluene sulfonic acid salt.

In some embodiments, Compound II-4 is an amorphous solid. In some embodiments, compound II-4 is a crystalline solid. In some embodiments, Compound II-4 is a mixture of amorphous solid form and crystalline solid form.

In some embodiments, the present invention provides a form of compound II-4 substantially free of impurities. As used herein, the term "substantially free of impurities" means that the compound contains no significant amount of extraneous matter. Such extraneous matter may include different forms of compound II-4, residual solvents, or any other impurities that may result from the preparation of, and/or isolation of, compound II-4. In certain embodiments, at least about 95% by weight of compound II-4 is present. In certain embodiments, at least about 99% by weight of compound II-4 is present.

In certain embodiments, compound II-4 is a crystalline solid. In other embodiments, compound II-4 is a crystalline solid substantially free of amorphous compound II-4. As used herein, the term "substantially free of amorphous compound II-4" means that the compound contains no significant amount of amorphous compound II-4. In certain embodiments, at least about 95% by weight of crystalline compound II-4 is present. In still other embodiments of the invention, at least about 99% by weight of crystalline compound II-4 is present.

Figure 28A:
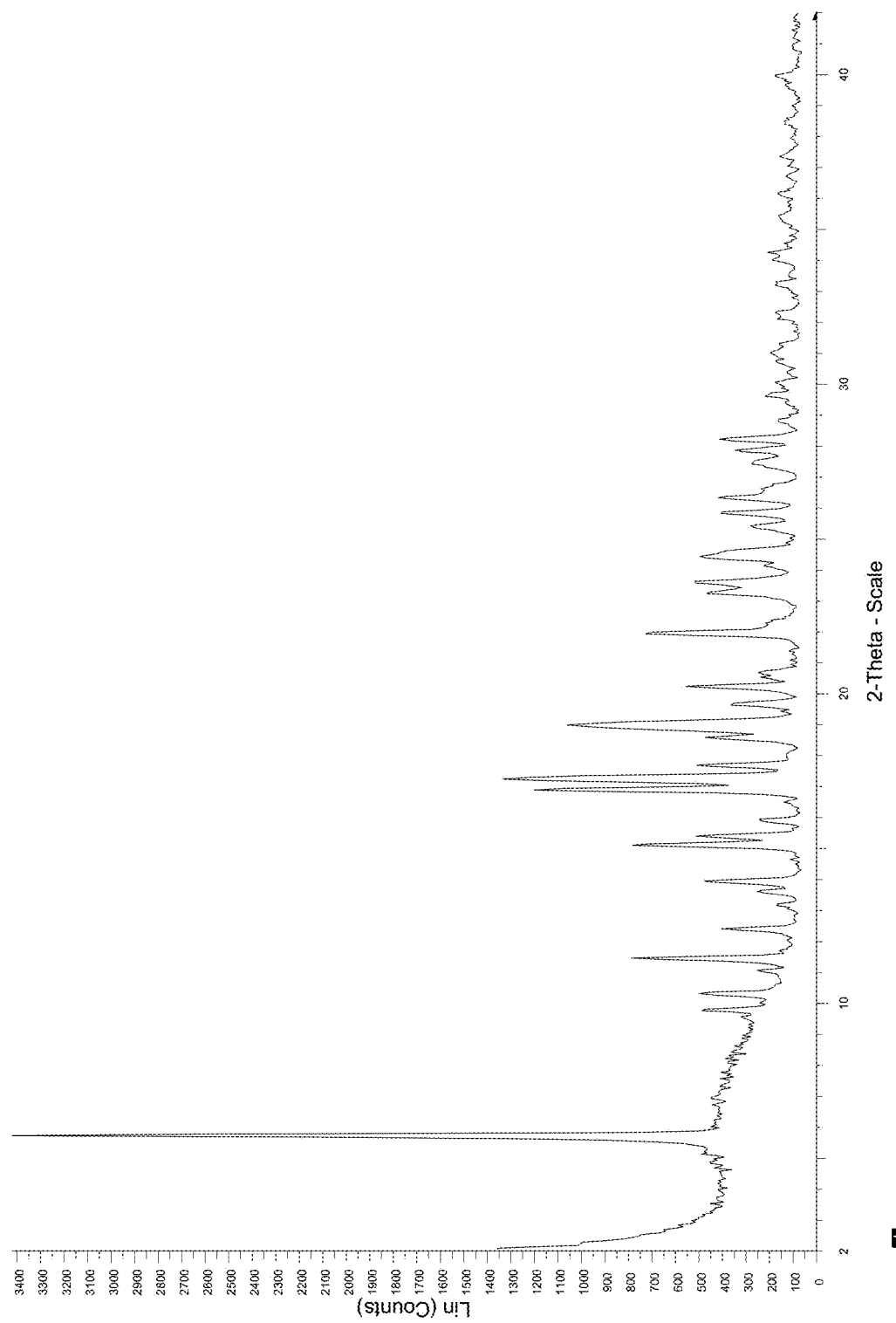
FIG. 28A depicts an X-ray diffraction pattern of Form A of Compound II-4 (tosylate salt).
Figure 28B:
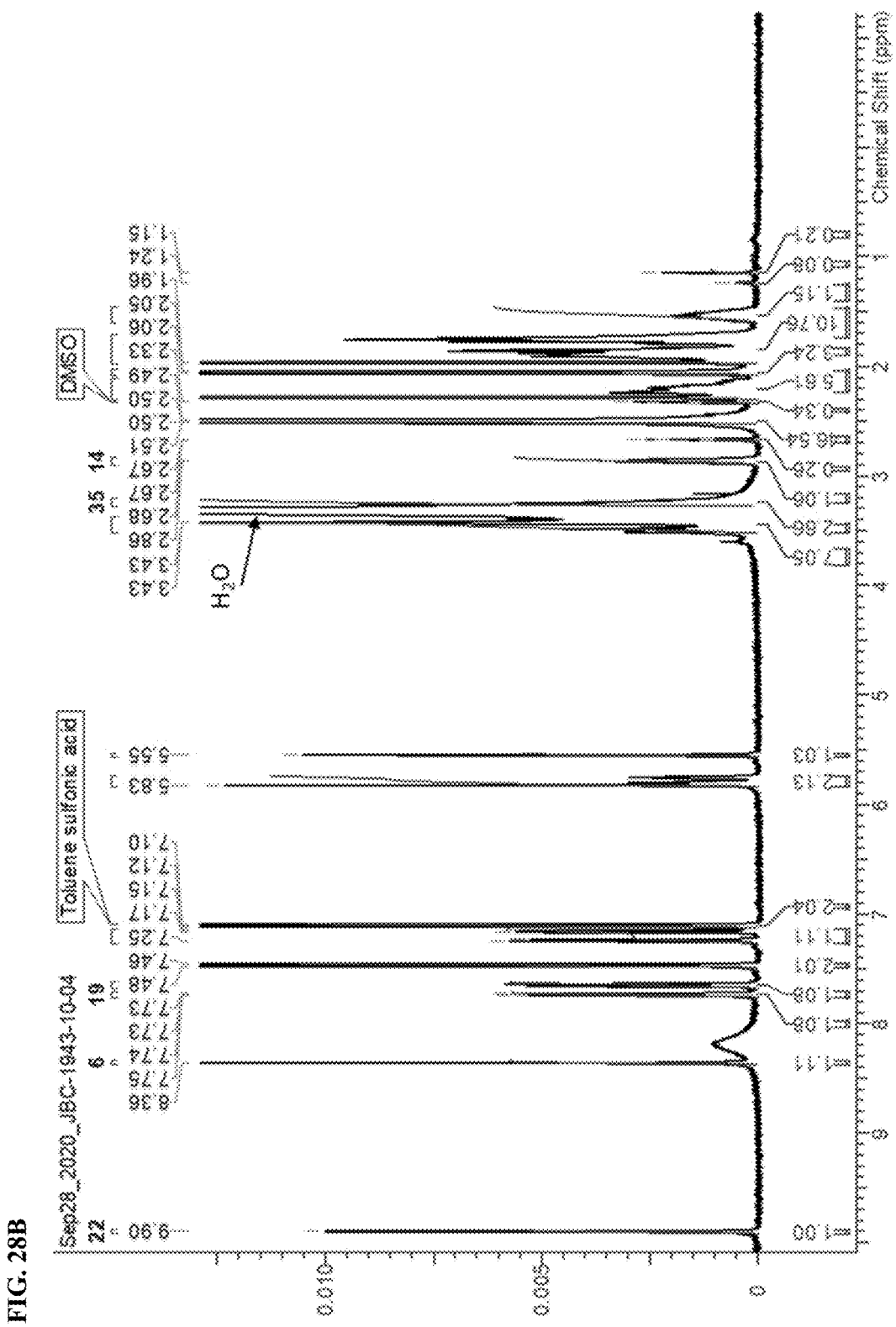
FIG. 28B depicts the characterization of Form A of Compound II-4 by $^1$H nuclear magnetic resonance ($^1$H NMR) in D6-DMSO at 400 MHz.

In some embodiments, the solid crystalline form of Compound II-4 is Form A. In some embodiments, Form A of compound II-4 has a X-Ray diffraction pattern substantially similar to that of FIG. 28A. In some embodiments, Form A of Compound II-4 may be characterized by a powder X-ray diffraction pattern with at least two characteristic peaks, in degrees 2θ, each selected from the group consisting of the peaks listed in Table 16. In some embodiments, Form A of Compound II-4 may be characterized by a powder X-ray diffraction pattern with at least three characteristic peaks, in degrees 2θ, each selected from the group consisting of the peaks listed in Table 16. In some embodiments, Form A of Compound II-4 may be characterized by a powder X-ray diffraction pattern with at least four characteristic peaks, in degrees 2θ, each selected from the group consisting of the peaks listed in Table 16. In some embodiments, Form A of Compound II-4 may be characterized by a powder X-ray diffraction pattern with at least five characteristic peaks, in degrees 2θ, each selected from the group consisting of the peaks listed in Table 16. In some embodiments, Form A of Compound II-4 may be characterized by a powder X-ray diffraction pattern with at least six characteristic peaks, in degrees 2θ, each selected from the group consisting of the peaks listed in Table 16.

Figure 28C:
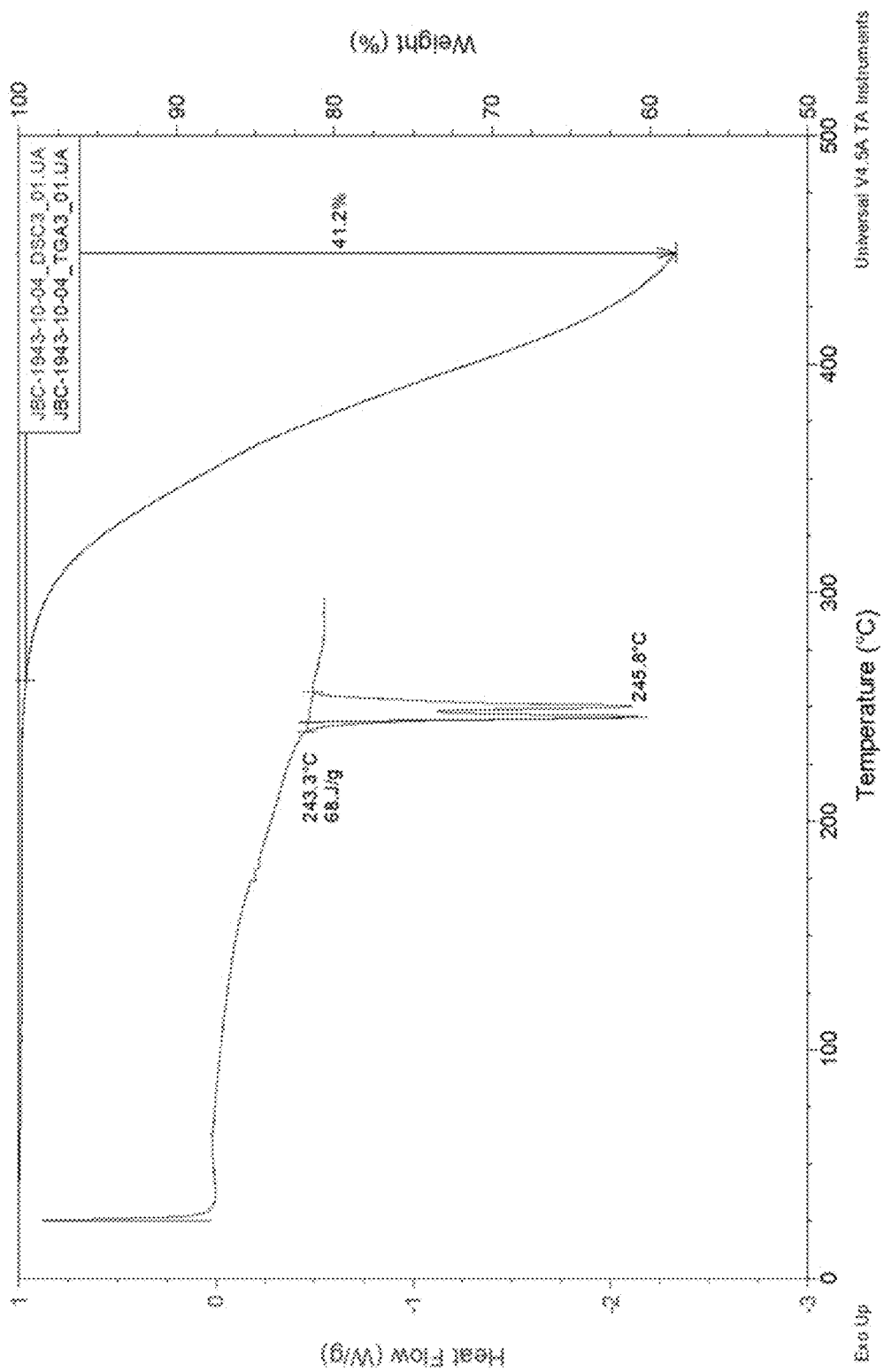
FIG. 28C depicts the characterization of Form A of Compound II-4 by thermogravimetric analysis (above) and differential scanning calorimetry (below).
Figure 28D:
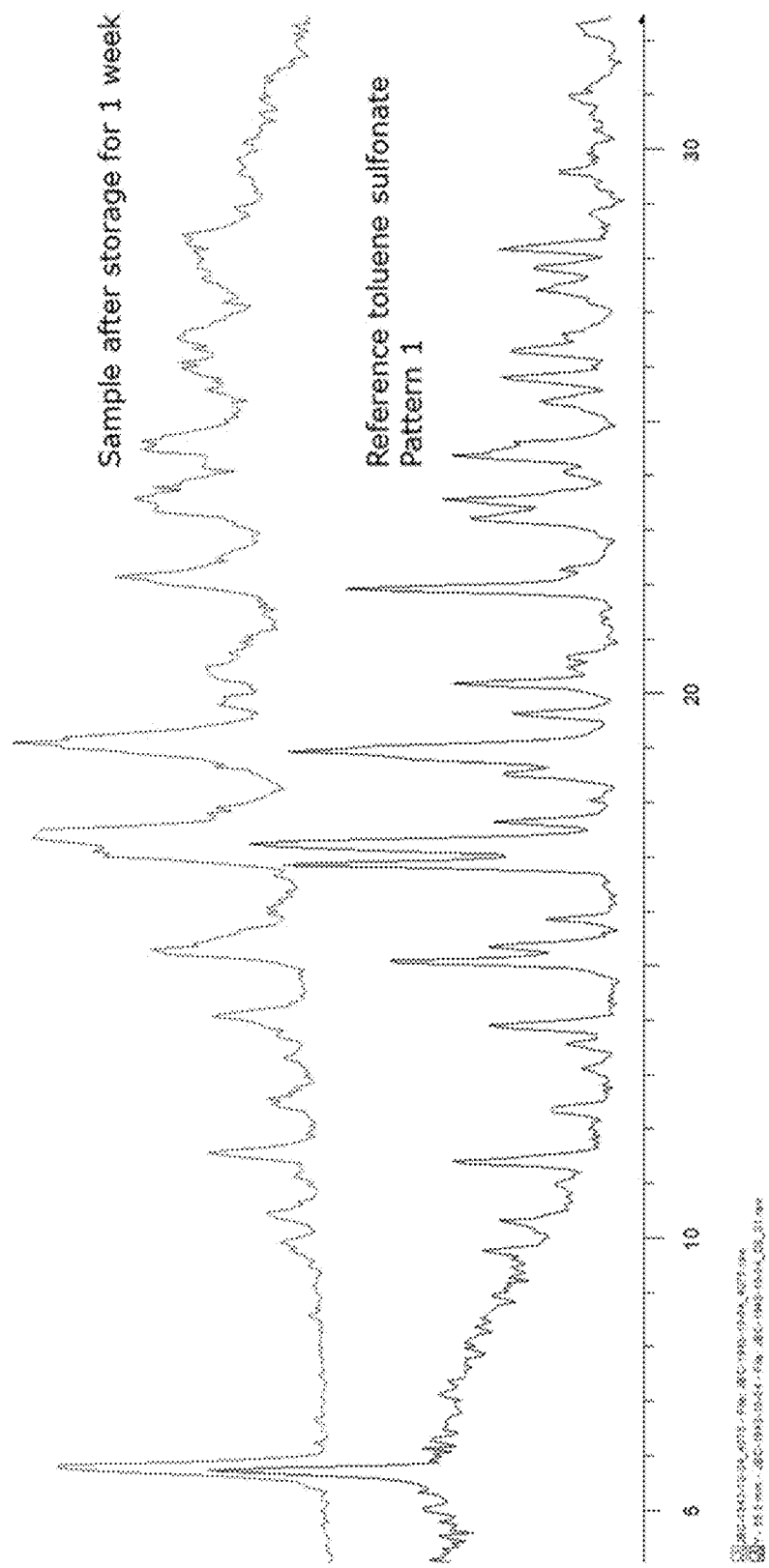
FIG. 28D depicts an XRPD diffractogram of Compound II-4 Form A (below) after storage at 40° C./75% RH for 7 days (above).

In some embodiments, Form A of compound II-4 has a differential scanning calorimetry (DSC) pattern substantially similar to that depicted in FIG. 28C. In some embodiments, Form A of compound II-4 has a thermogravimetric analysis pattern substantially similar to that depicted in FIG. 28C. In some embodiments, Form A of Compound II-4 can be characterized by substantial similarity to two or more of these figures simultaneously.

In another embodiment, a compound of Formula (II) is compound II-5 wherein, compound II-5 is a methane sulfonic acid salt.

In some embodiments, Compound II-5 is an amorphous solid. In some embodiments, compound II-5 is a crystalline solid. In some embodiments, Compound II-5 is a mixture of amorphous solid form and crystalline solid form.

In some embodiments, the present invention provides a form of compound II-5 substantially free of impurities. As used herein, the term "substantially free of impurities" means that the compound contains no significant amount of extraneous matter. Such extraneous matter may include different forms of compound II-5, residual solvents, or any other impurities that may result from the preparation of, and/or isolation of, compound II-5. In certain embodiments, at least about 95% by weight of compound II-5 is present. In certain embodiments, at least about 99% by weight of compound II-5 is present.

In certain embodiments, compound II-5 is a crystalline solid. In other embodiments, compound II-5 is a crystalline solid substantially free of amorphous compound II-5. As used herein, the term "substantially free of amorphous compound II-5" means that the compound contains no significant amount of amorphous compound II-5. In certain embodiments, at least about 95% by weight of crystalline compound II-5 is present. In still other embodiments of the invention, at least about 99% by weight of crystalline compound II-5 is present.

Figure 29A:
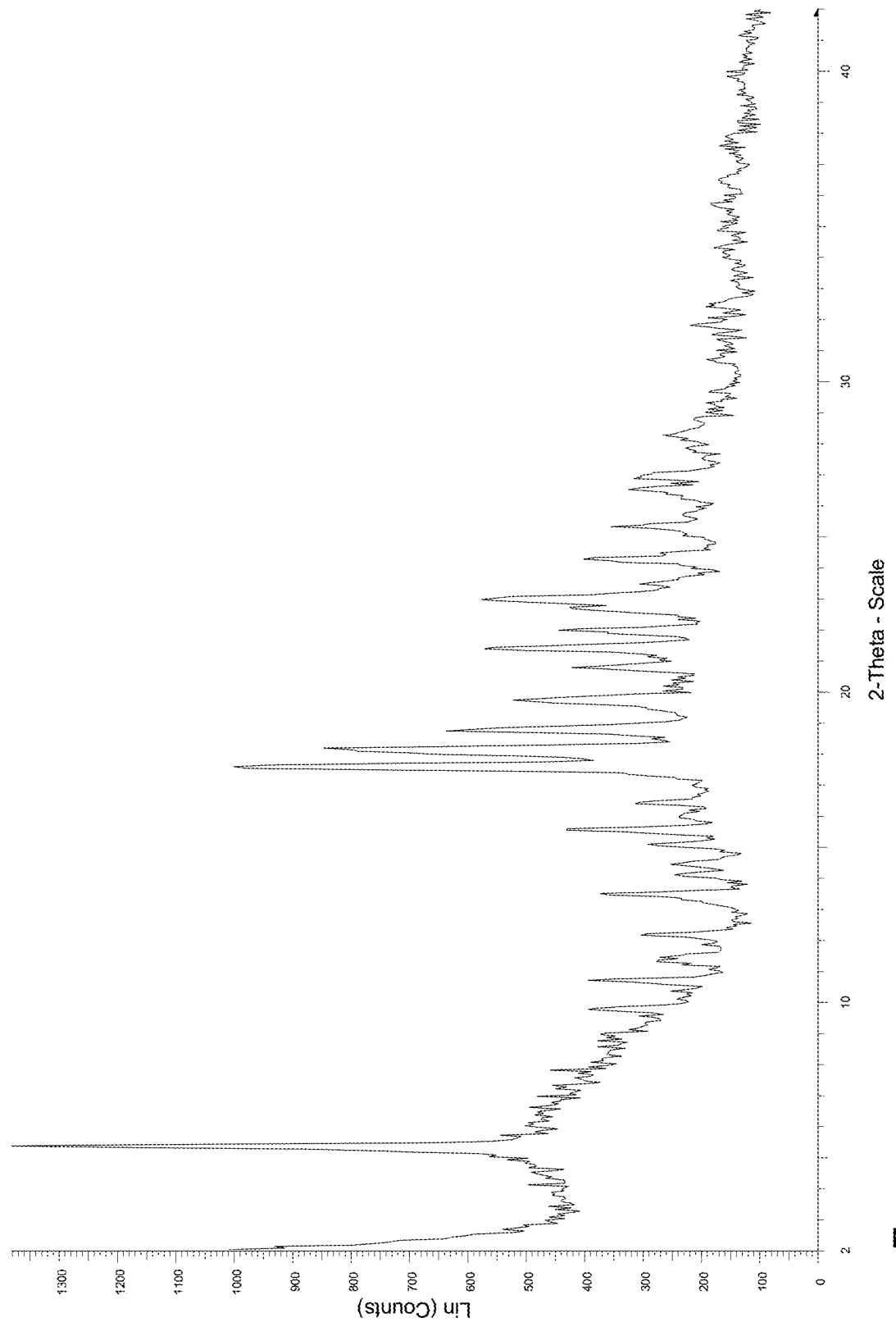
FIG. 29A depicts an X-ray diffraction pattern of Form A of Compound II-5 (mesylate salt).
Figure 29B:
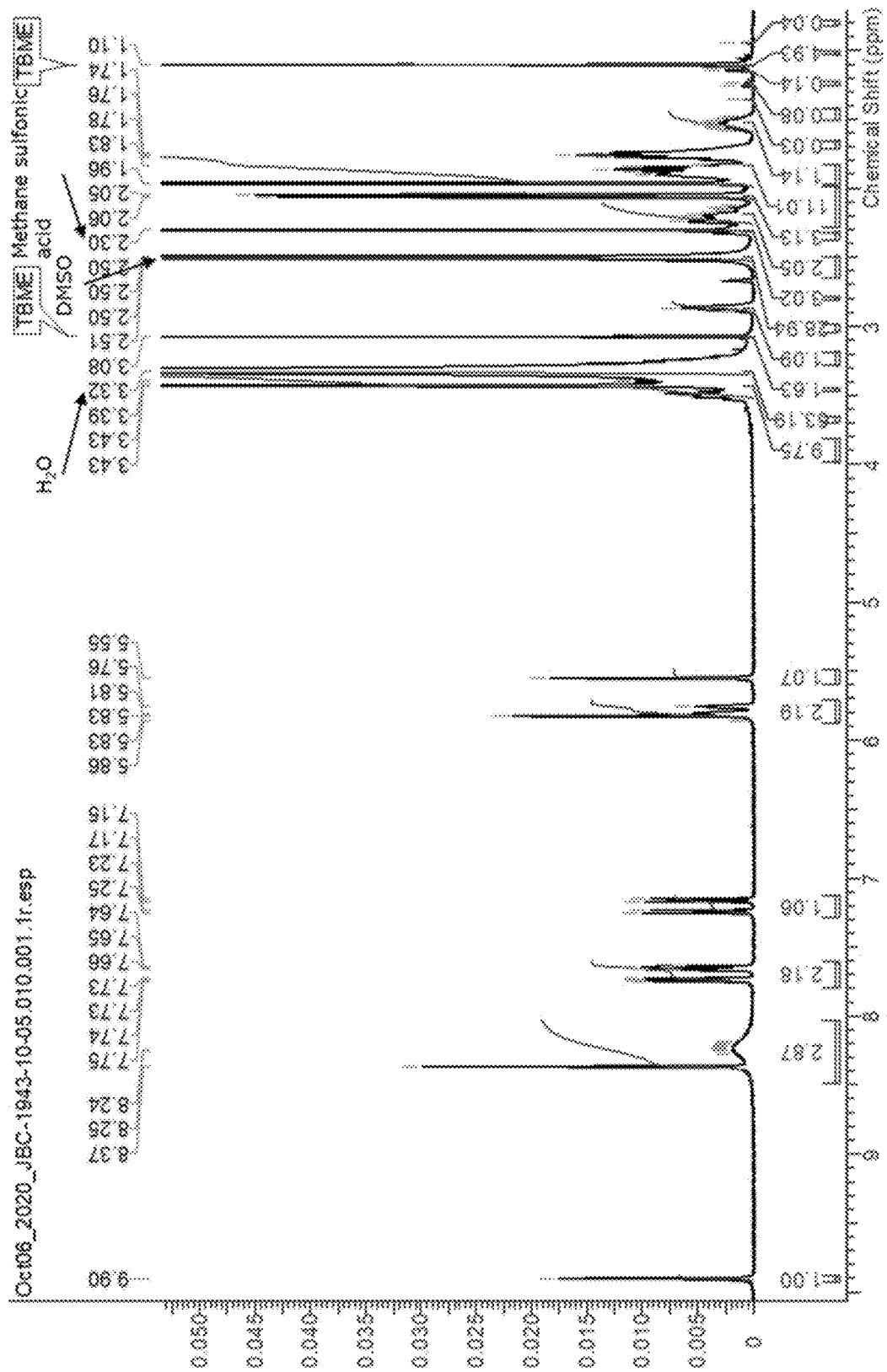
FIG. 29B depicts the characterization of Form A of Compound II-5 by $^1$H nuclear magnetic resonance ($^1$H NMR) in D6-DMSO at 400 MHz.

In some embodiments, the solid crystalline form of Compound II-5 is Form A. In certain embodiments, Form A of compound II-5 has a X-Ray diffraction pattern substantially similar to that depicted in FIG. 29A. In some embodiments, Form A of Compound II-5 may be characterized by a powder X-ray diffraction pattern with at least two characteristic peaks, in degrees 2θ, each selected from the group consisting of the peaks listed in Table 17. In some embodiments, Form A of Compound II-5 may be characterized by a powder X-ray diffraction pattern with at least three characteristic peaks, in degrees 2θ, each selected from the group consisting of the peaks listed in Table 17. In some embodiments, Form A of Compound II-5 may be characterized by a powder X-ray diffraction pattern with at least four characteristic peaks, in degrees 2θ, each selected from the group consisting of the peaks listed in Table 17. In some embodiments, Form A of Compound II-5 may be characterized by a powder X-ray diffraction pattern with at least five characteristic peaks, in degrees 2θ, each selected from the group consisting of the peaks listed in Table 17. In some embodiments, Form A of Compound II-5 may be characterized by a powder X-ray diffraction pattern with at least six characteristic peaks, in degrees 2θ, each selected from the group consisting of the peaks listed in Table 17.

Figure 29C:
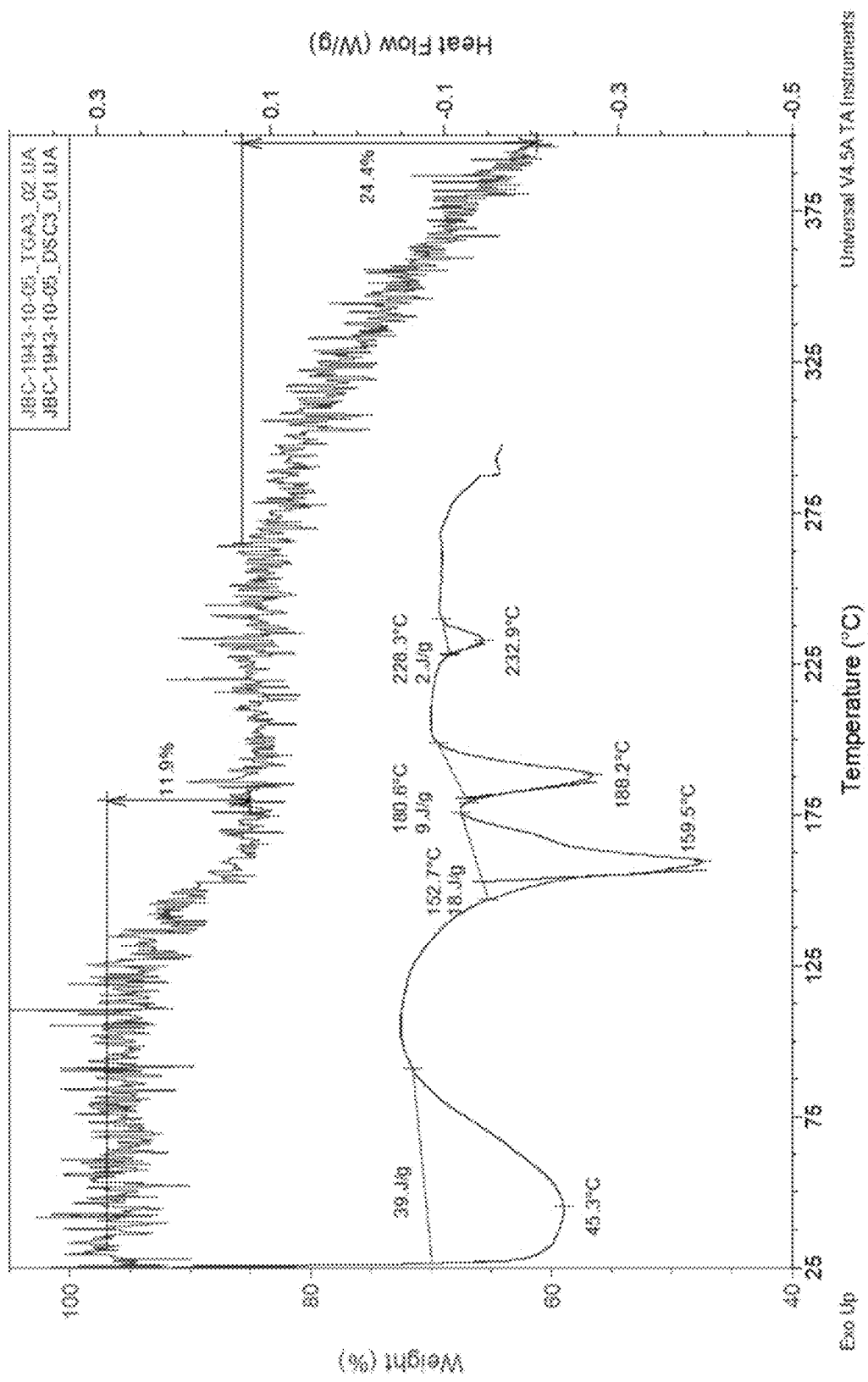
FIG. 29C depicts the characterization of Form A of Compound II-5 by thermogravimetric analysis (above) and differential scanning calorimetry (below).

In certain embodiments, Form A of compound II-5 has a differential scanning calorimetry (DSC) pattern substantially similar to that depicted in FIG. 29C. In certain embodiments, Form A of compound II-5 has a thermogravimetric analysis pattern substantially similar to that depicted in FIG. 29C. In certain embodiments, Form A of Compound II-5 can be characterized by substantial similarity to two or more of these figures simultaneously.

In another embodiment, a compound of Formula (II) is compound II-6 wherein, compound II-6 is a benzene sulfonic acid salt.

In some embodiments, Compound II-6 is an amorphous solid. In some embodiments, compound II-6 is a crystalline solid. In some embodiments, Compound II-6 is a mixture of amorphous solid form and crystalline solid form.

In some embodiments, the present invention provides a form of compound II-6 substantially free of impurities. As used herein, the term "substantially free of impurities" means that the compound contains no significant amount of extraneous matter. Such extraneous matter may include different forms of compound II-6, residual solvents, or any other impurities that may result from the preparation of, and/or isolation of, compound II-6. In certain embodiments, at least about 95% by weight of compound II-6 is present. In certain embodiments, at least about 99% by weight of compound II-6 is present.

In certain embodiments, compound II-6 is a crystalline solid. In other embodiments, compound II-6 is a crystalline solid substantially free of amorphous compound II-6. As used herein, the term "substantially free of amorphous compound II-6" means that the compound contains no significant amount of amorphous compound II-6. In certain embodiments, at least about 95% by weight of crystalline compound II-6 is present. In still other embodiments of the invention, at least about 99% by weight of crystalline compound II-6 is present.

Figure 30A:
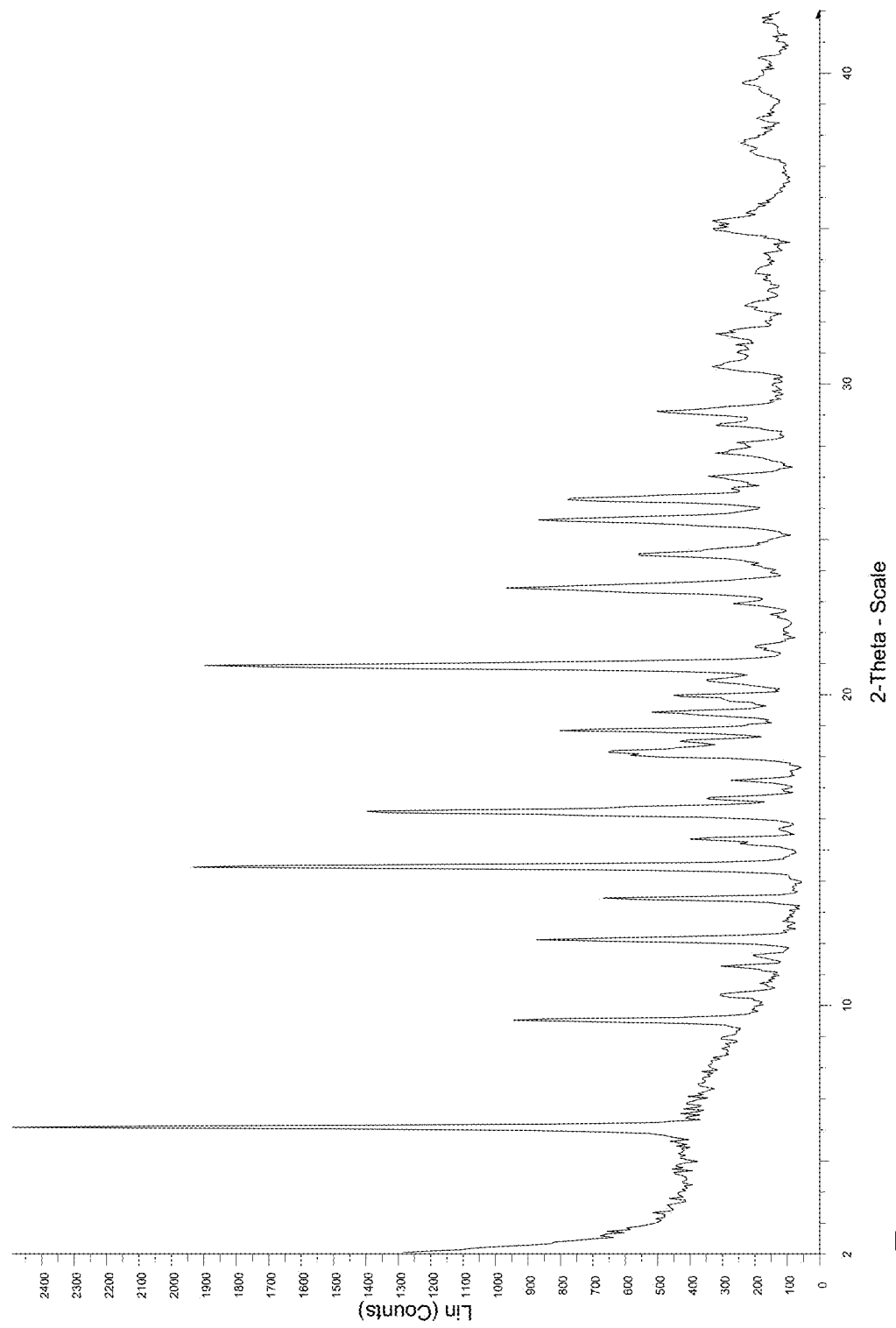
FIG. 30A depicts an X-ray diffraction pattern of Form A of Compound II-6 (besylate salt).
Figure 30B:
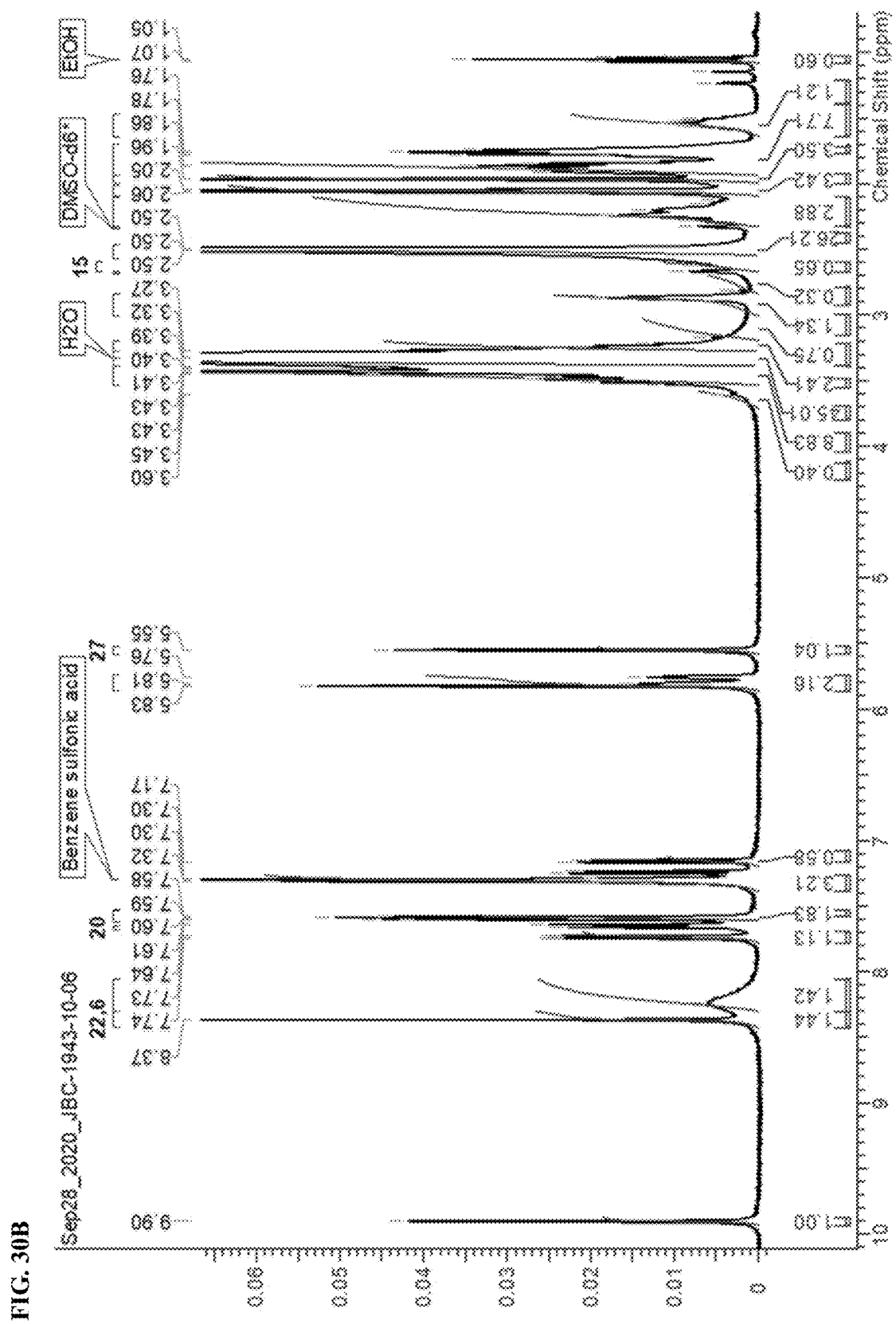
FIG. 30B depicts the characterization of Form A of Compound II-6 by $^1$H nuclear magnetic resonance ($^1$H NMR) in D6-DMSO at 400 MHz.

In some embodiments, the solid crystalline form of Compound II-6 is Form A. In certain embodiments, Form A of compound II-6 has a X-Ray diffraction pattern substantially similar any one of the patterns depicted in FIG. 30A. In some embodiments, Form A of Compound II-6 may be characterized by a powder X-ray diffraction pattern with at least two characteristic peaks, in degrees 2θ, each selected from the group consisting of the peaks listed in Table 18. In some embodiments, Form A of Compound II-6 may be characterized by a powder X-ray diffraction pattern with at least three characteristic peaks, in degrees 2θ, each selected from the group consisting of the peaks listed in Table 18. In some embodiments, Form A of Compound II-6 may be characterized by a powder X-ray diffraction pattern with at least four characteristic peaks, in degrees 2θ, each selected from the group consisting of the peaks listed in Table 18. In some embodiments, Form A of Compound II-6 may be characterized by a powder X-ray diffraction pattern with at least five characteristic peaks, in degrees 2θ, each selected from the group consisting of the peaks listed in Table 18. In some embodiments, Form A of Compound II-6 may be characterized by a powder X-ray diffraction pattern with at least six characteristic peaks, in degrees 2θ, each selected from the group consisting of the peaks listed in Table 18.

Figure 30C:
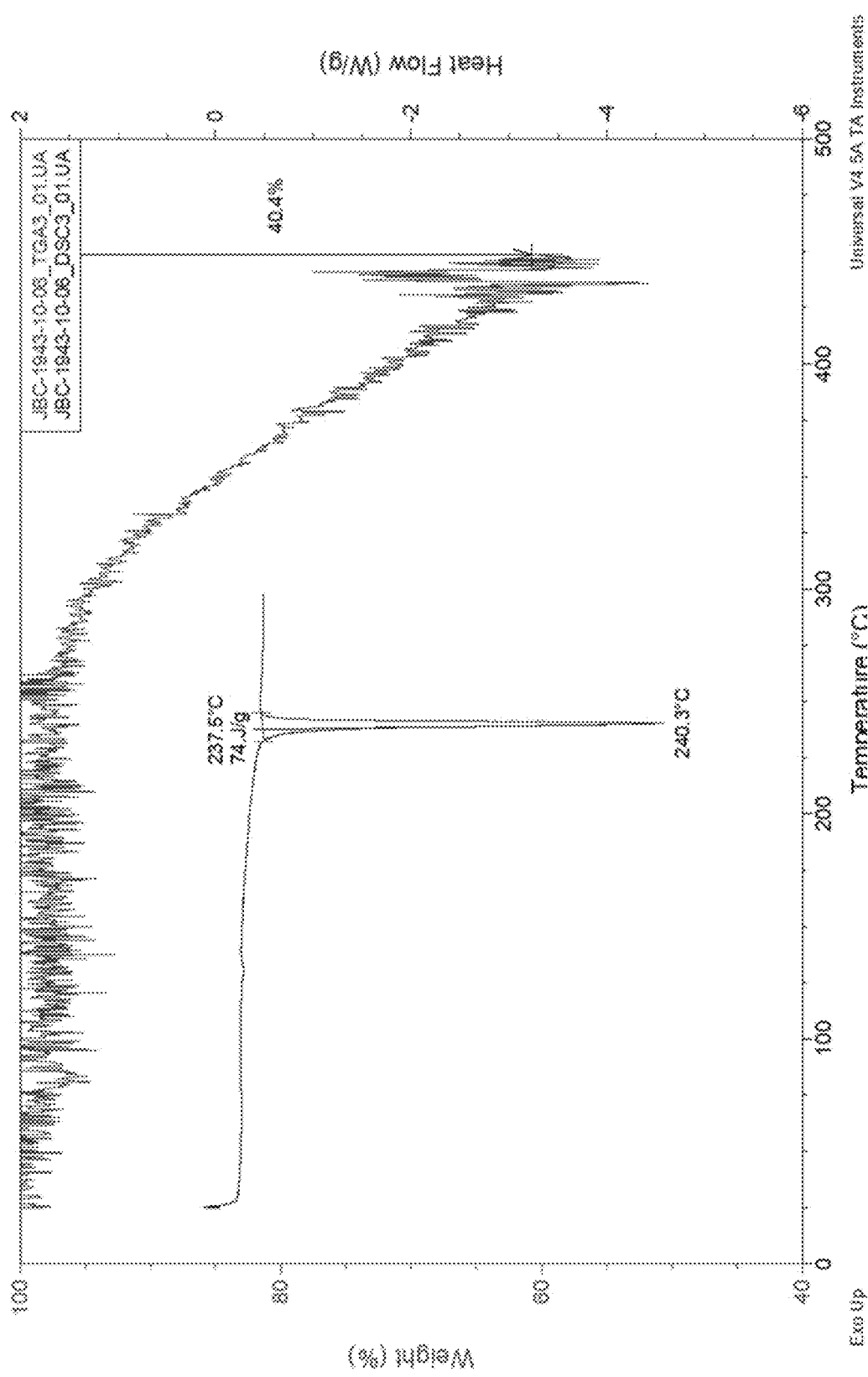
FIG. 30C depicts the characterization of Form A of Compound II-6 by thermogravimetric analysis (above) and differential scanning calorimetry (below).
Figure 30D:
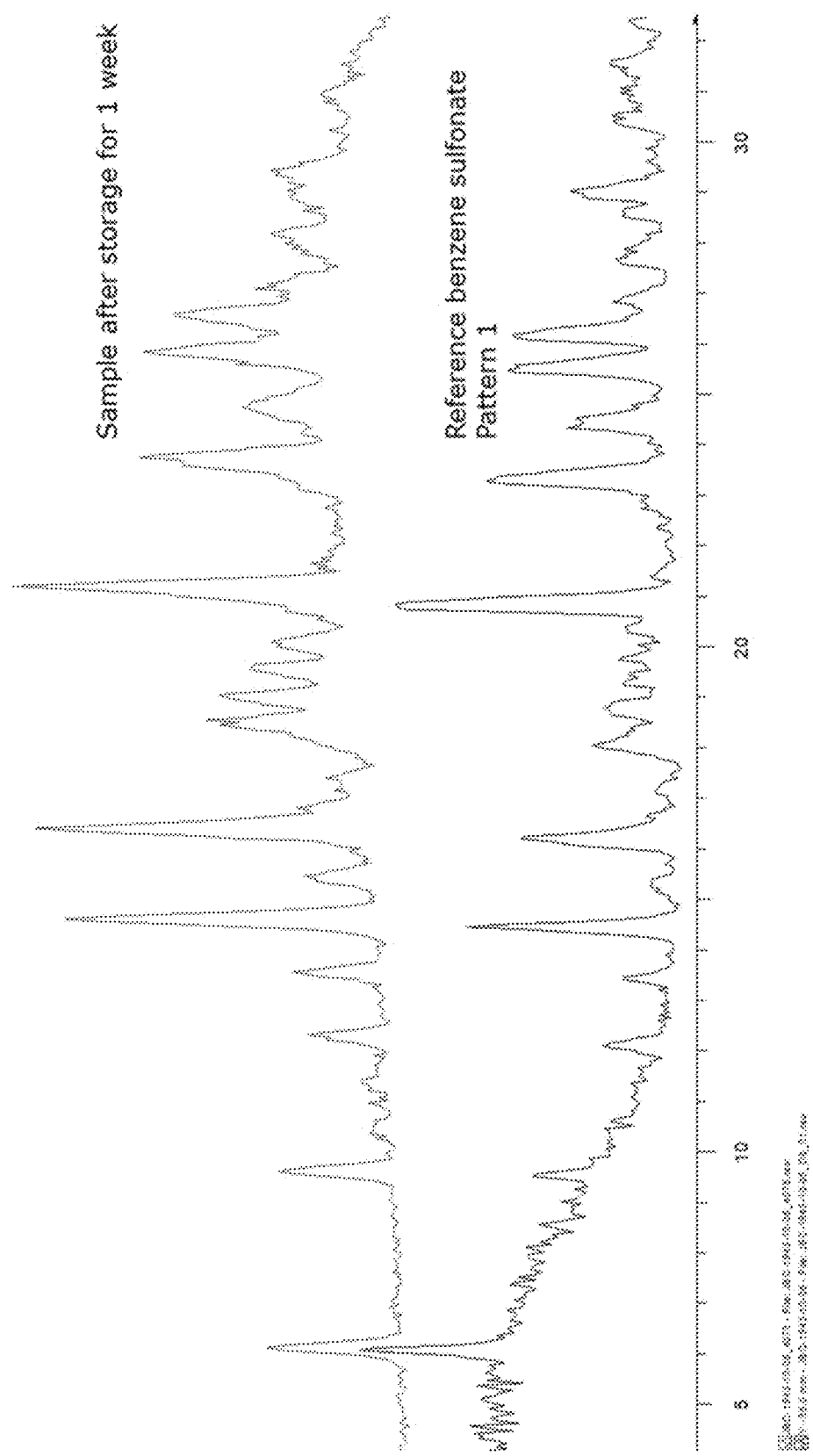
FIG. 30D depicts an XRPD diffractogram of Compound II-6 Form A (below) after storage at 40° C./75% RH for 7 days (above).

In certain embodiments, Form A of compound II-6 has a differential scanning calorimetry (DSC) pattern substantially similar to that depicted in FIG. 30C. In certain embodiments, Form A of compound II-6 has a thermogravimetric analysis pattern substantially similar to that depicted in FIG. 30C. In certain embodiments, Form A of Compound II-6 can be characterized by substantial similarity to two of these figures simultaneously.

In another embodiment, a compound of Formula (II) is compound II-7 wherein, compound II-7 is a fumaric acid salt.

In some embodiments, Compound II-7 is an amorphous solid. In some embodiments, compound II-7 is a crystalline solid. In some embodiments, Compound II-7 is a mixture of amorphous solid form and crystalline solid form.

In some embodiments, the present invention provides a form of compound II-7 substantially free of impurities. As used herein, the term "substantially free of impurities" means that the compound contains no significant amount of extraneous matter. Such extraneous matter may include different forms of compound II-7, residual solvents, or any other impurities that may result from the preparation of, and/or isolation of, compound II-7. In certain embodiments, at least about 95% by weight of compound II-7 is present. In certain embodiments, at least about 99% by weight of compound II-7 is present.

In certain embodiments, compound II-7 is a crystalline solid. In other embodiments, compound II-7 is a crystalline solid substantially free of amorphous compound II-7. As used herein, the term "substantially free of amorphous compound II-7" means that the compound contains no significant amount of amorphous compound II-7. In certain embodiments, at least about 95% by weight of crystalline compound II-7 is present. In still other embodiments of the invention, at least about 99% by weight of crystalline compound II-7 is present.

Figure 31A:
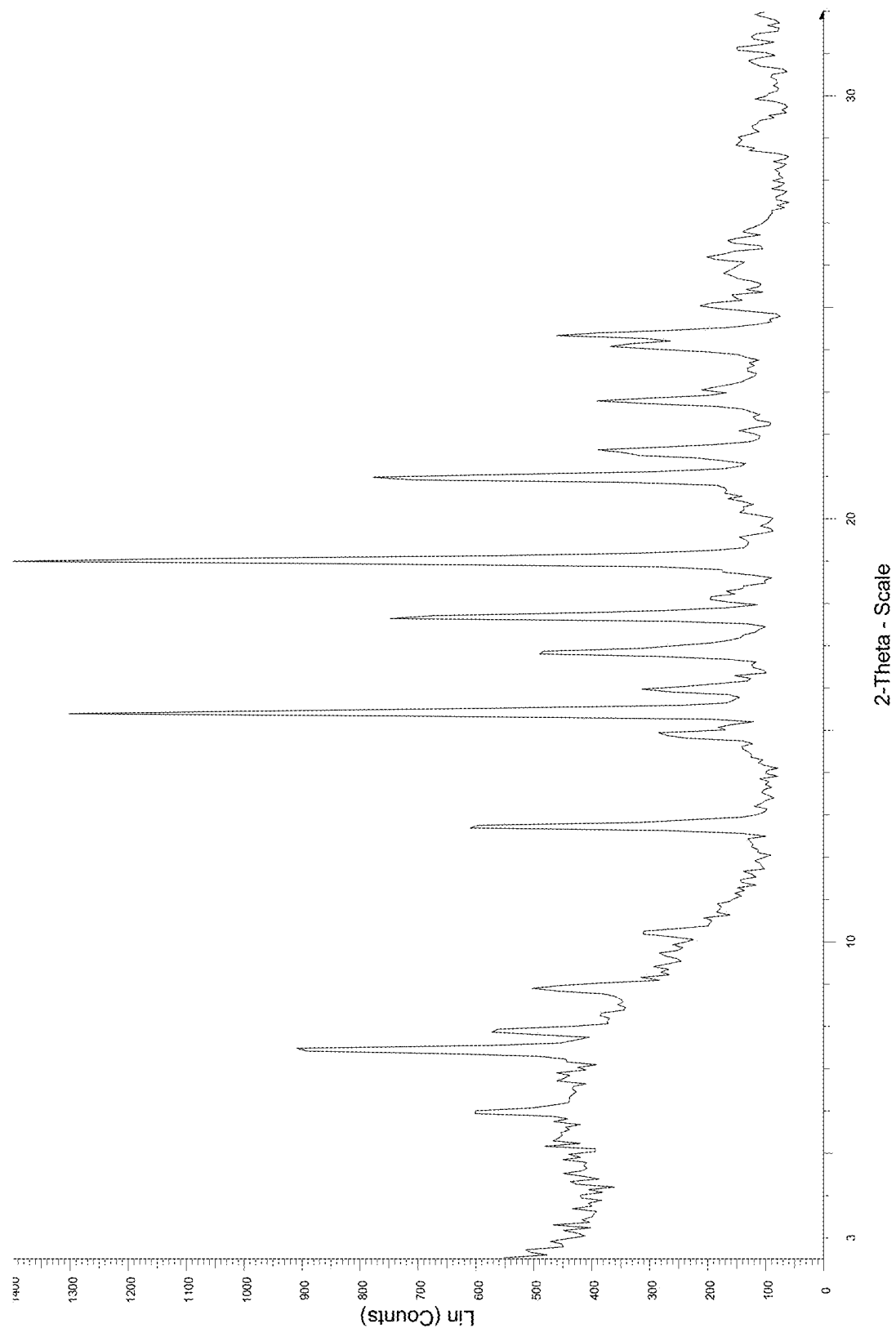
FIG. 31A depicts an X-ray diffraction pattern of Form A of Compound II-7 (fumarate salt).
Figure 31B:
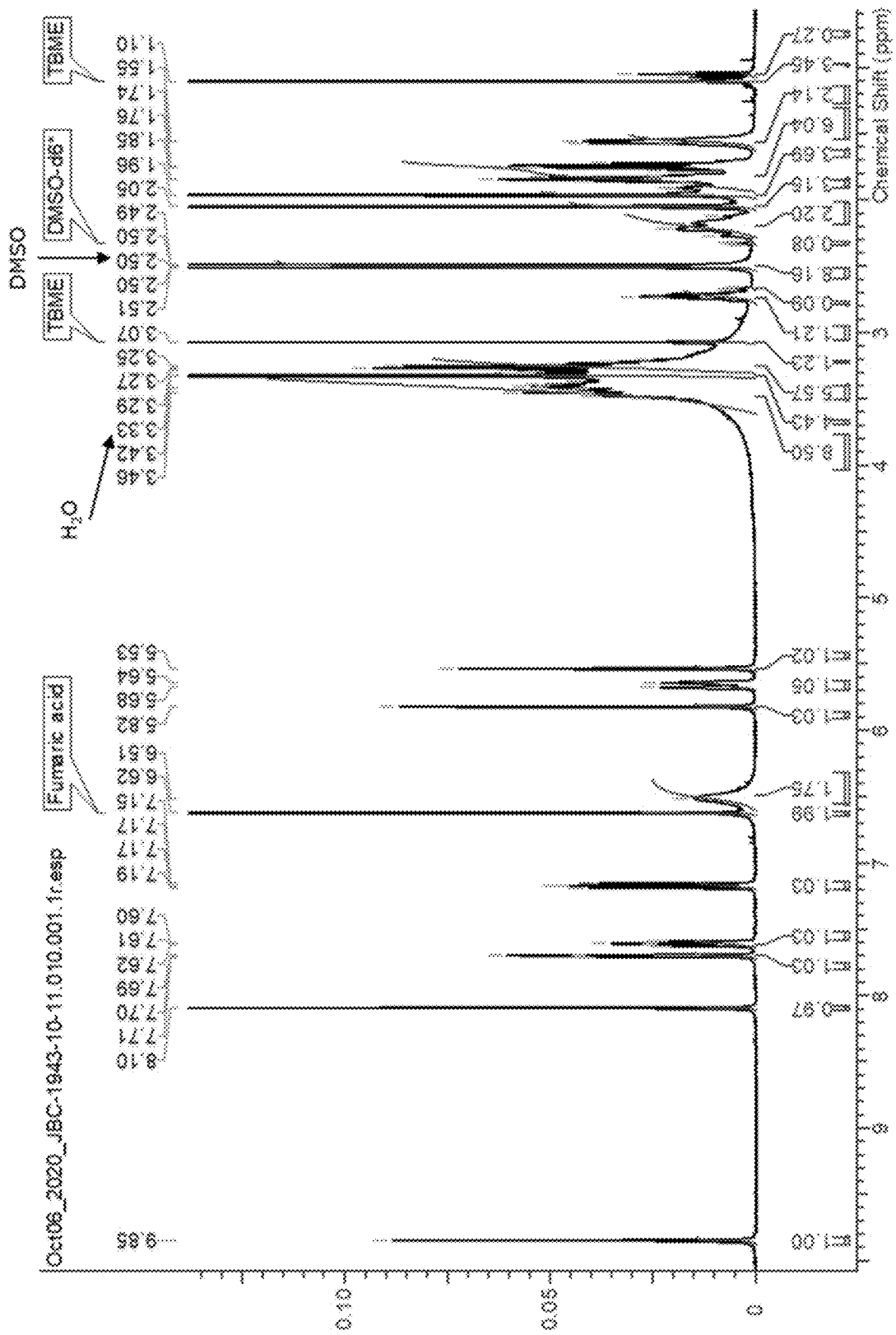
FIG. 31B depicts the characterization of Form A of Compound II-7 by $^1$H nuclear magnetic resonance ($^1$H NMR) in D6-DMSO at 400 MHz.

In some embodiments, the solid crystalline form of Compound II-7 is Form A. In certain embodiments, Form A of compound II-7 has a X-Ray diffraction pattern substantially similar any one of the patterns depicted in FIG. 31A. In some embodiments, Form A of Compound II-7 may be characterized by a powder X-ray diffraction pattern with at least two characteristic peaks, in degrees 2θ, each selected from the group consisting of the peaks listed in Table 19. In some embodiments, Form A of Compound II-7 may be characterized by a powder X-ray diffraction pattern with at least three characteristic peaks, in degrees 2θ, each selected from the group consisting of the peaks listed in Table 19. In some embodiments, Form A of Compound II-7 may be characterized by a powder X-ray diffraction pattern with at least four characteristic peaks, in degrees 2θ, each selected from the group consisting of the peaks listed in Table 19. In some embodiments, Form A of Compound II-7 may be characterized by a powder X-ray diffraction pattern with at least five characteristic peaks, in degrees 2θ, each selected from the group consisting of the peaks listed in Table 19. In some embodiments, Form A of Compound II-7 may be characterized by a powder X-ray diffraction pattern with at least six characteristic peaks, in degrees 2θ, each selected from the group consisting of the peaks listed in Table 19.

Figure 31C:
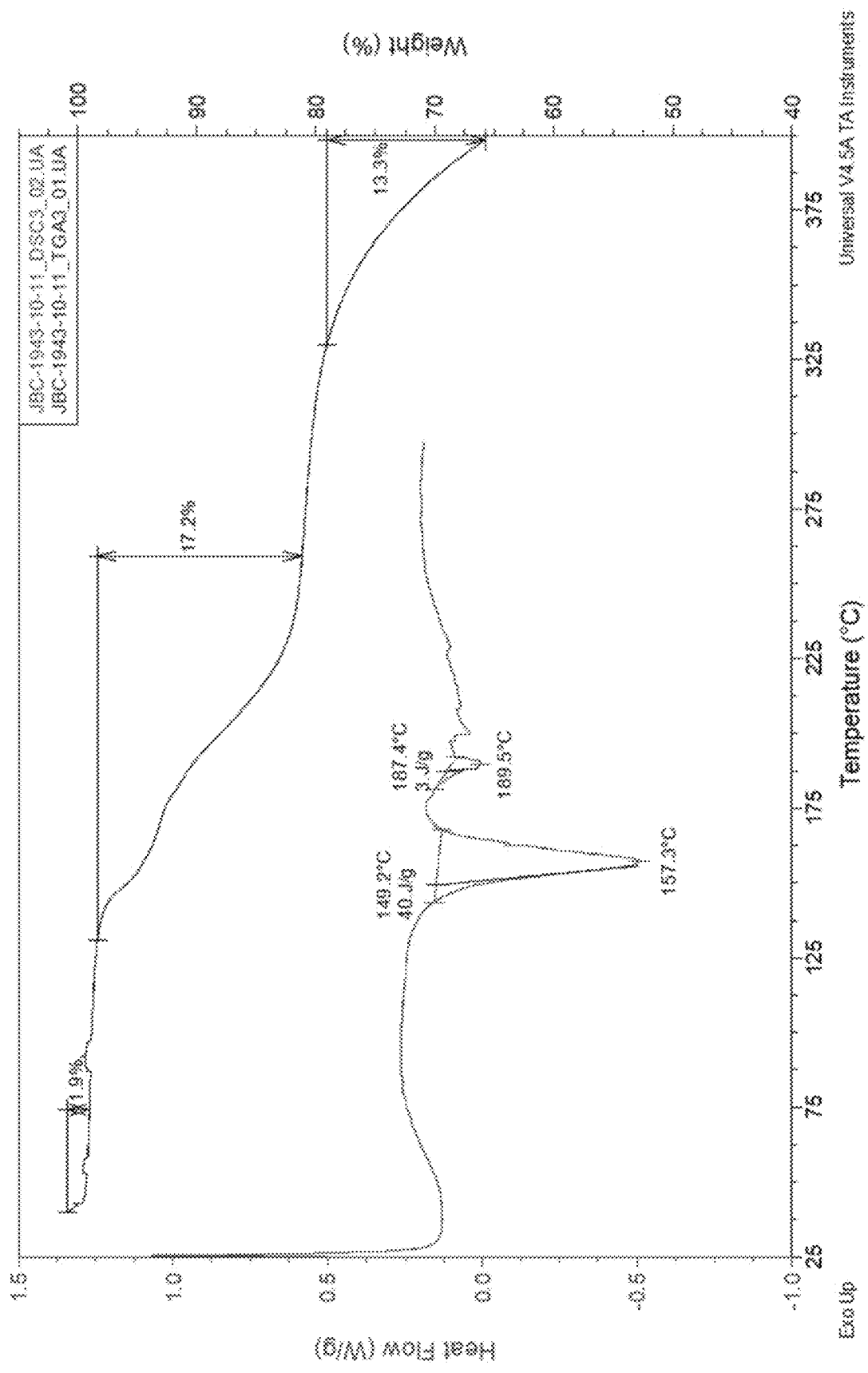
FIG. 31C depicts the characterization of Form A of Compound II-7 by thermogravimetric analysis (above) and differential scanning calorimetry (below).
Figure 31D:
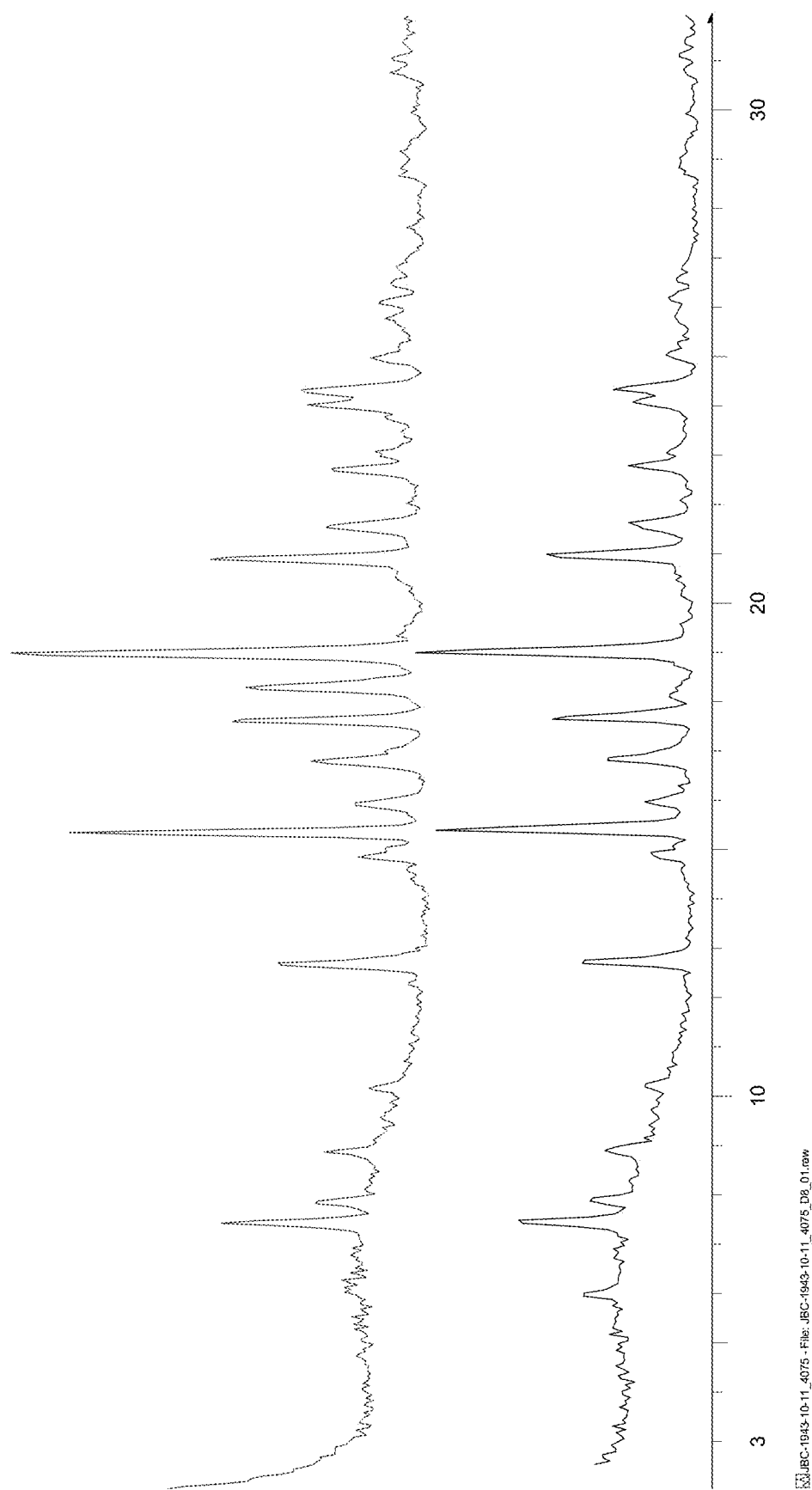
FIG. 31D depicts an XRPD diffractogram of Compound II-7 Form A (below) after storage at 40° C./75% RH for 7 days (above).

In certain embodiments, Form A of compound II-7 has a differential scanning calorimetry (DSC) pattern substantially similar to that depicted in FIG. 31C. In certain embodiments, Form A of compound II-7 has a thermogravimetric analysis pattern substantially similar to that depicted in FIG. 31C. In certain embodiments, Form A of Compound II-7 can be characterized by substantial similarity to two or more of these figures simultaneously.

Compound of Formula (III)

In one embodiment, provided herein is a compound of Formula (III)

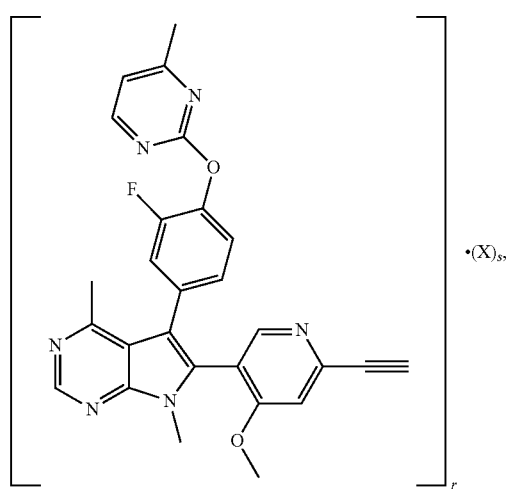

or a solvate thereof;
wherein,
r is 1, 2, 3, 4, 5, 6, 7, 8, or 9;
s is 0, 0.5, 1, 1.5, 2, 2.5, or 3; and
X is hydrochloric acid, hydrobromic acid, sulfuric acid, methane sulfonic acid, or tartaric acid.

It will be appreciated by one of ordinary skill in the art that the acid moiety indicated as "X" and 6-(6-ethynyl-4-methoxypyridin-3-yl)-5-(3-fluoro-4-((4-methylpyrimidin-2-yl)oxy)phenyl)-4,7-dimethyl-7H-pyrrolo[2,3-d]pyrimidine are ionically bonded to form a compound of Formula (III). It will also be appreciated that when s is 0, X is absent, indicating that the compound of Formula (III) exists as a "free base," i.e., "free form."

It is contemplated that a compound of Formula (III) can exist in a variety of physical forms. For example, a compound of Formula (III) can be in solution, suspension, or in solid form. In certain embodiments, a compound of Formula (III) is in solid form. When a compound of Formula (III) is in solid form, said compound may be amorphous, crystalline, or a mixture thereof. Exemplary solid forms are described in more detail below.

In some embodiments, a compound of Formula (III), may be in a hydrate form. In some embodiments, a compound of Formula (III), may be in a hemi-hydrate form.

In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9.

In some embodiments, s is 0. In some embodiments, s is 1. In some embodiments, s is 2. In some embodiments, s is 3. In some embodiments, s is 0.5. In some embodiments, s is 1.5. In some embodiments, s is 2.5.

In some embodiments, X is hydrochloric acid. In some embodiments, X is hydrobromic acid. In some embodiments, X is sulfuric acid. In some embodiments, X is methane sulfonic acid. In some embodiments, X is tartaric acid.

In some embodiments, the present invention provides a form of a compound of Formula (III) substantially free of impurities. As used herein, the term "substantially free of impurities" means that the compound contains no significant amount of extraneous matter. Such extraneous matter may include different forms of a compound of Formula (III), residual solvents, or any other impurities that may result from the preparation of, and/or isolation of, a compound of Formula (III).

In some embodiments, a compound of Formula (III), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, a compound of Formula (III), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition.

In some embodiments, a compound of Formula (III), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, a compound of Formula (III), or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, a HPLC method is the HPLC method as described in Example 1.

The structure depicted for compound of Formula (III) is also meant to include all tautomeric forms. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In some embodiments, a compound of Formula (III) is compound III-1 wherein, compound III-1 is a free base (or "free form"). In some embodiments, compound III-1 is an amorphous solid. In some embodiments, compound III-1 is a crystalline solid. In some embodiments, Compound III-1 is a mixture of amorphous solid form and crystalline solid form.

In some embodiments, the present invention provides a form of compound III-1 substantially free of impurities. As used herein, the term "substantially free of impurities" means that the compound contains no significant amount of extraneous matter. Such extraneous matter may include different forms of compound III-1, residual solvents, or any other impurities that may result from the preparation of, and/or isolation of, compound III-1. In certain embodiments, at least about 95% by weight of compound III-1 is present. In certain embodiments, at least about 99% by weight of compound III-1 is present.

In other embodiments, compound III-1 is a crystalline solid substantially free of amorphous compound III-1. As used herein, the term "substantially free of amorphous compound III-1" means that the compound contains no significant amount of amorphous compound III-1. In certain embodiments, at least about 95% by weight of crystalline compound III-1 is present. In certain embodiments, at least about 99% by weight of crystalline compound III-1 is present.

It has been found that compound III-1 can exist in a variety of solid forms. Exemplary such forms include polymorphs such as those described herein.

Figure 32A:
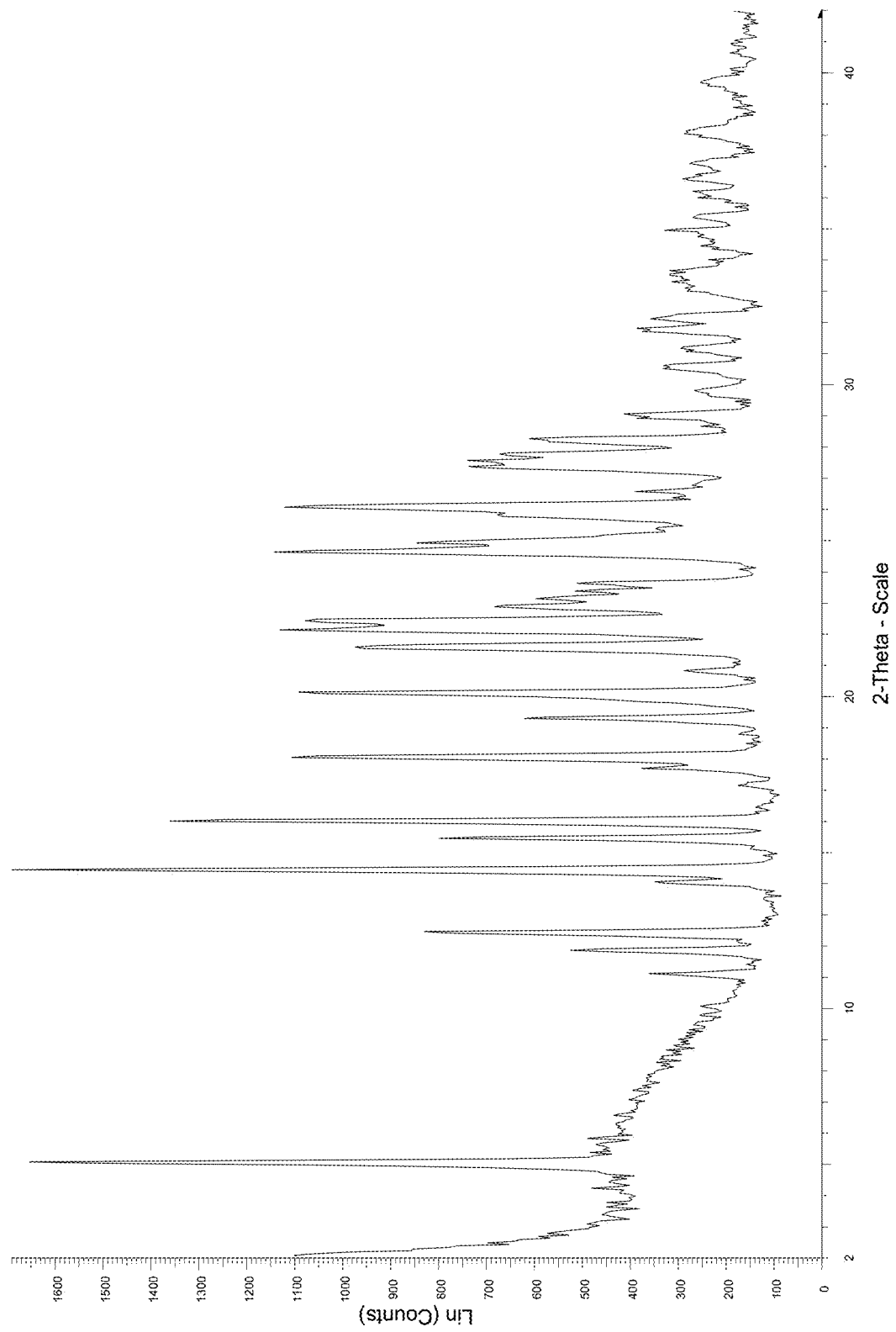
FIG. 32A depicts an X-ray diffraction pattern of Form A of Compound III-1 (free form).
Figure 32B:
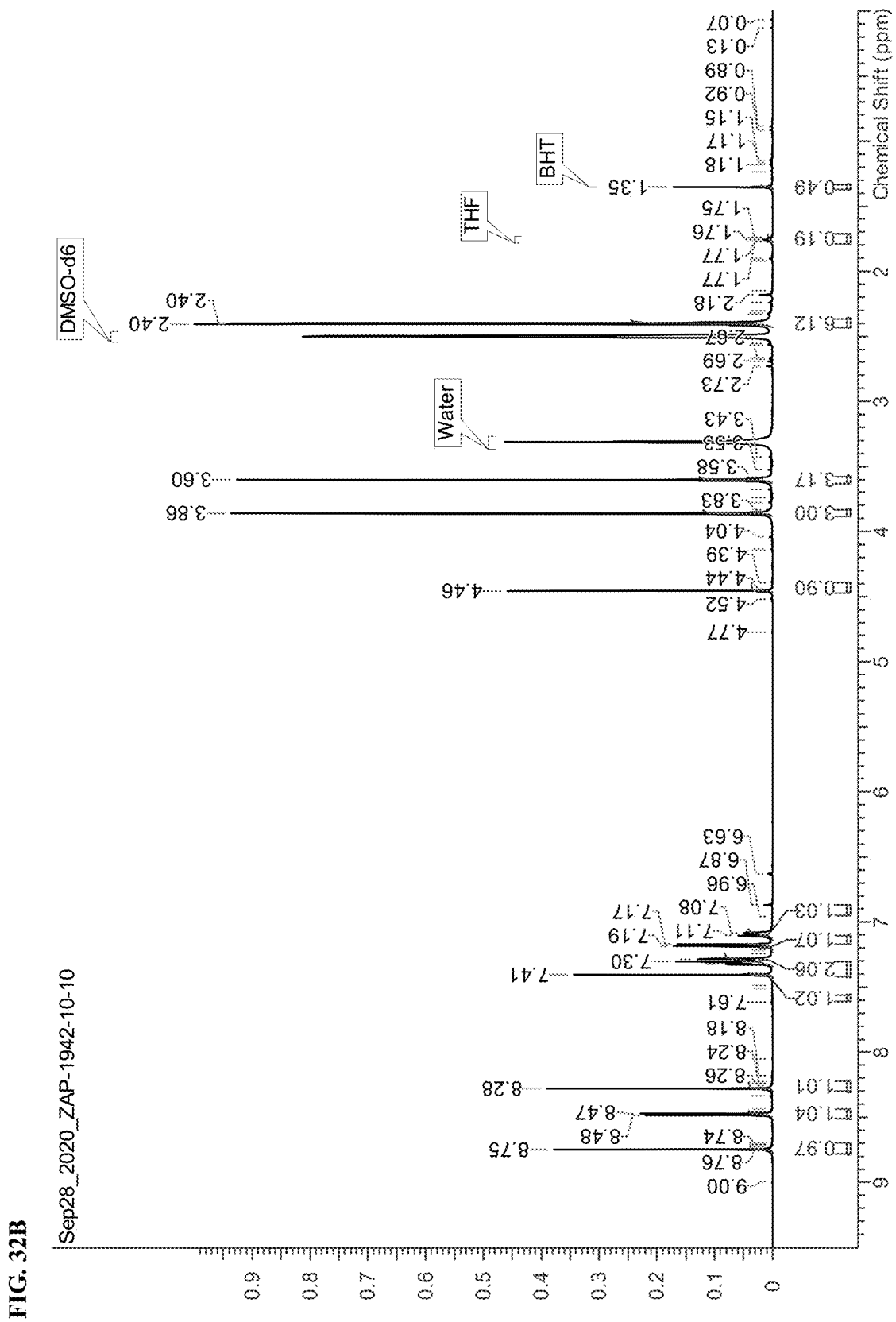
FIG. 32B depicts the characterization of Form A of Compound III-1 by $^1$H nuclear magnetic resonance ($^1$H NMR) in D6-DMSO at 400 MHz.

In some embodiments, the solid crystalline form of Compound III-1 is Form A. In some embodiments, Form A of compound III-1 has a X-Ray diffraction pattern substantially similar to that depicted in FIG. 32A. In some embodiments, Form A of Compound III-1 may be characterized by a powder X-ray diffraction pattern with at least two characteristic peaks, in degrees 2θ, each selected from the group consisting of the peaks listed in Table 23. In some embodiments, Form A of Compound III-1 may be characterized by a powder X-ray diffraction pattern with at least three characteristic peaks, in degrees 2θ, each selected from the group consisting of the peaks listed in Table 23. In some embodiments, Form A of Compound III-1 may be characterized by a powder X-ray diffraction pattern with at least four characteristic peaks, in degrees 2θ, each selected from the group consisting of the peaks listed in Table 23. In some embodiments, Form A of Compound III-1 may be characterized by a powder X-ray diffraction pattern with at least five characteristic peaks, in degrees 2θ, each selected from the group consisting of the peaks listed in Table 23. In some embodiments, Form A of Compound III-1 may be characterized by a powder X-ray diffraction pattern with at least six characteristic peaks, in degrees 2θ, each selected from the group consisting of the peaks listed in Table 23.

Figure 32C:
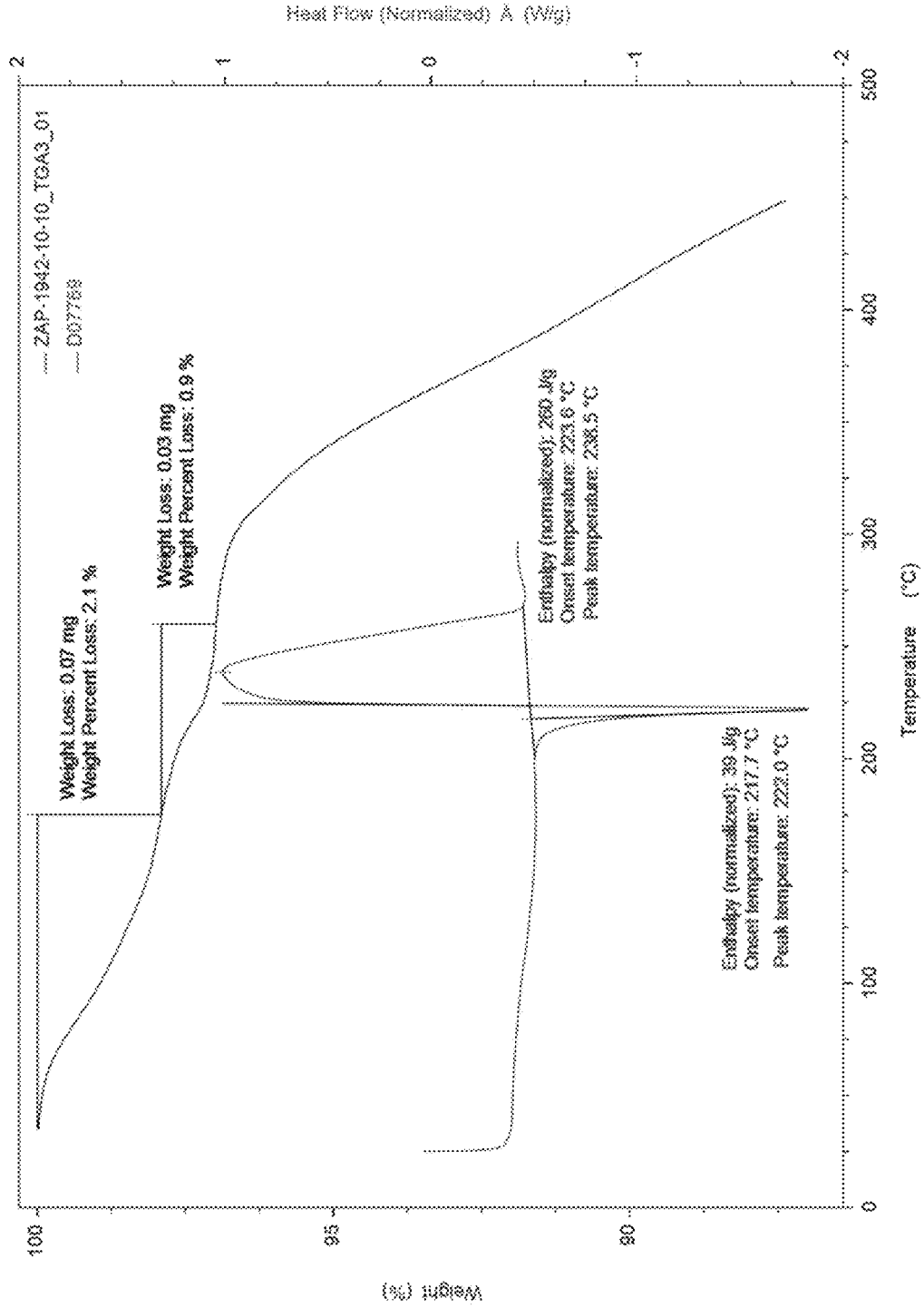
FIG. 32C depicts the characterization of Form A of Compound III-1 by thermogravimetric analysis (above) and differential scanning calorimetry (below).
Figure 32D:
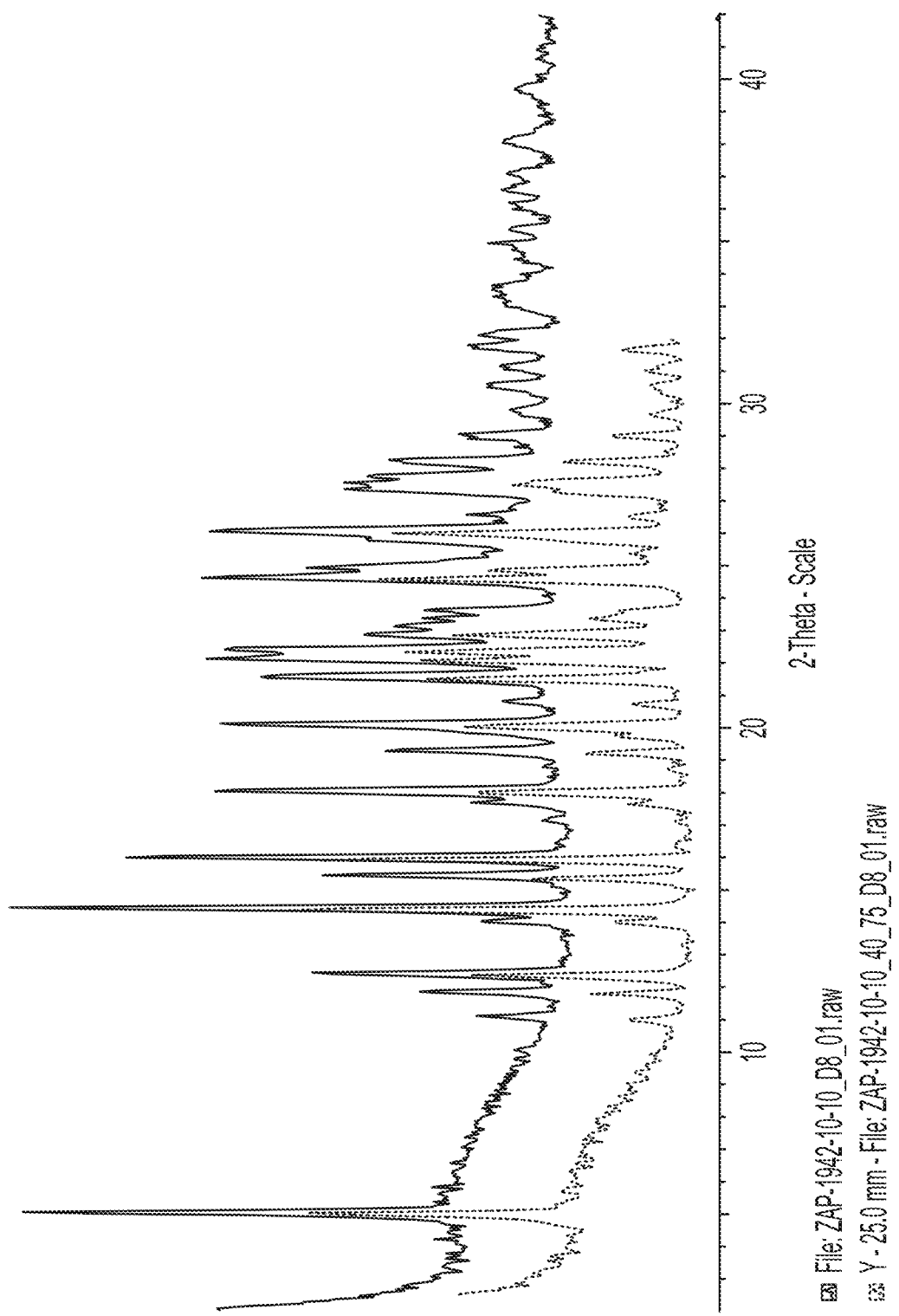
FIG. 32D depicts an XRPD diffractogram of Compound III-1 Form A (above) after storage at 40° C./75% RH for 7 days (below).

In some embodiments, Form A of compound III-1 has a differential scanning calorimetry (DSC) pattern substantially similar to that depicted in FIG. 32C. In some embodiments, Form A of compound III-1 has a thermogravimetric analysis pattern substantially similar to that depicted in FIG. 32C. In some embodiments, Form A of Compound III-1 can be characterized by substantial similarity to two or more of these figures simultaneously.

Figure 33A:
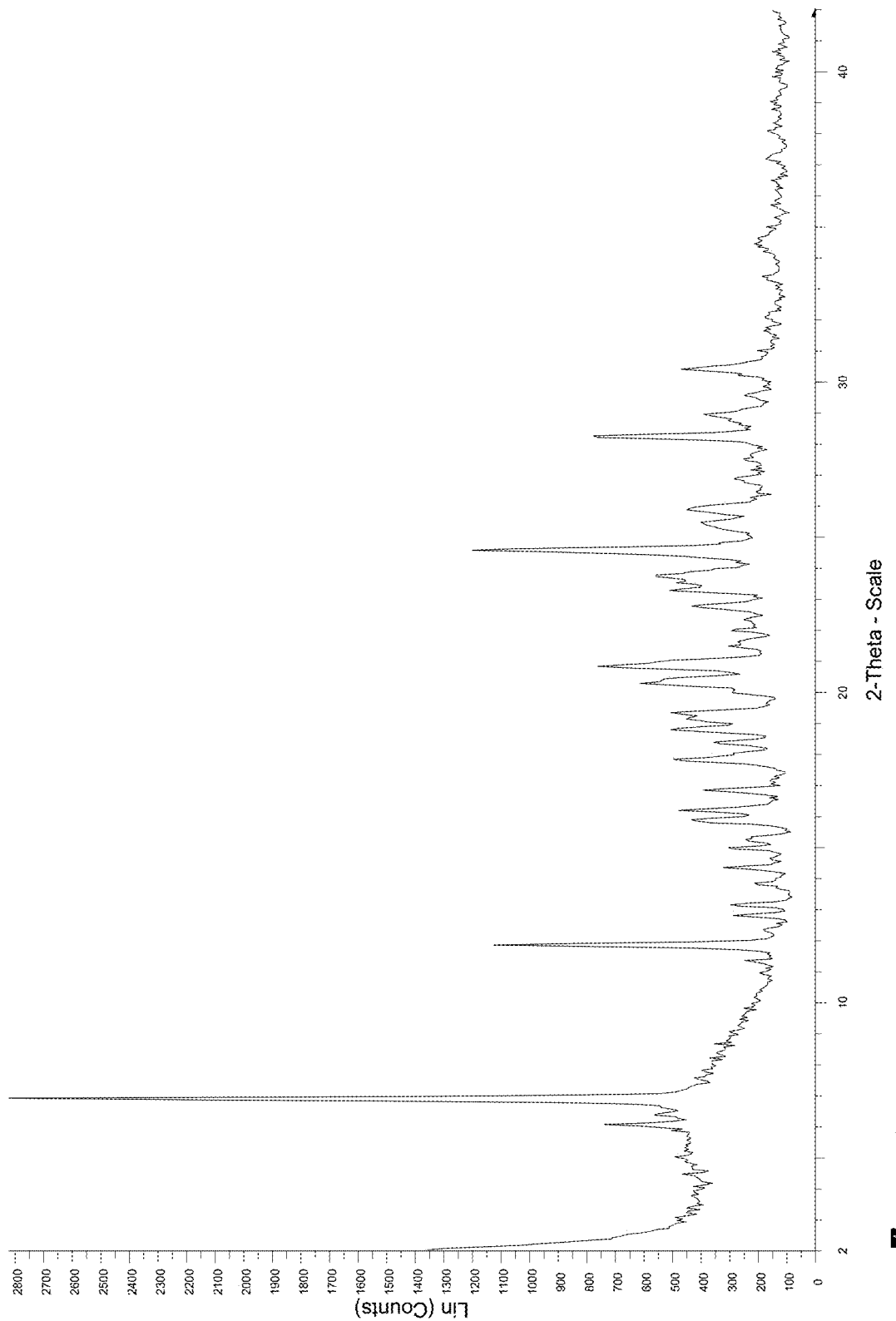
FIG. 33A depicts an X-ray diffraction pattern of Form B of Compound III-1 (free form).
Figure 33B:
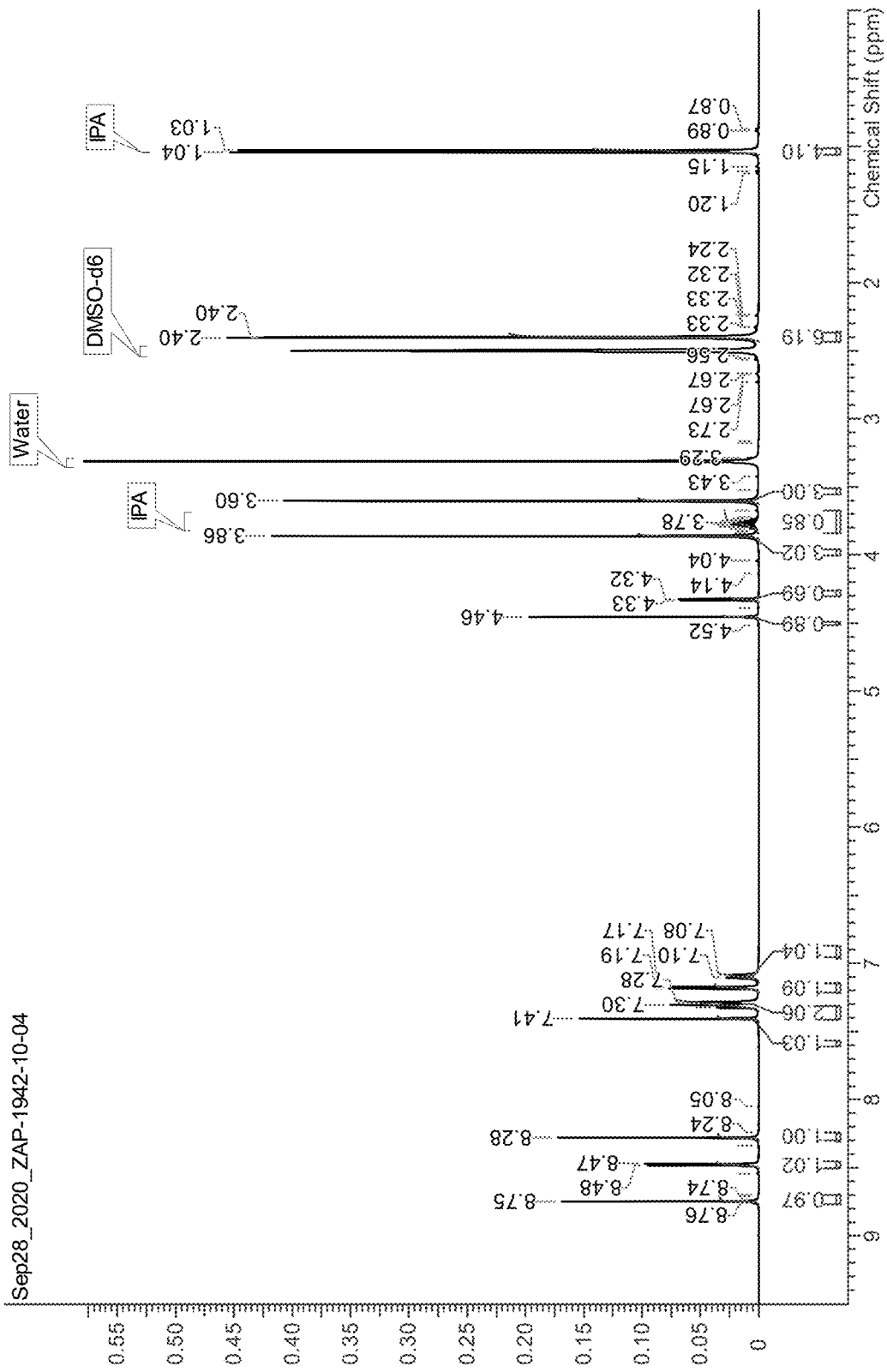
FIG. 33B depicts the characterization of Form B of Compound III-1 by $^1$H nuclear magnetic resonance ($^1$H NMR) in D6-DMSO at 400 MHz.
Figure 33C:
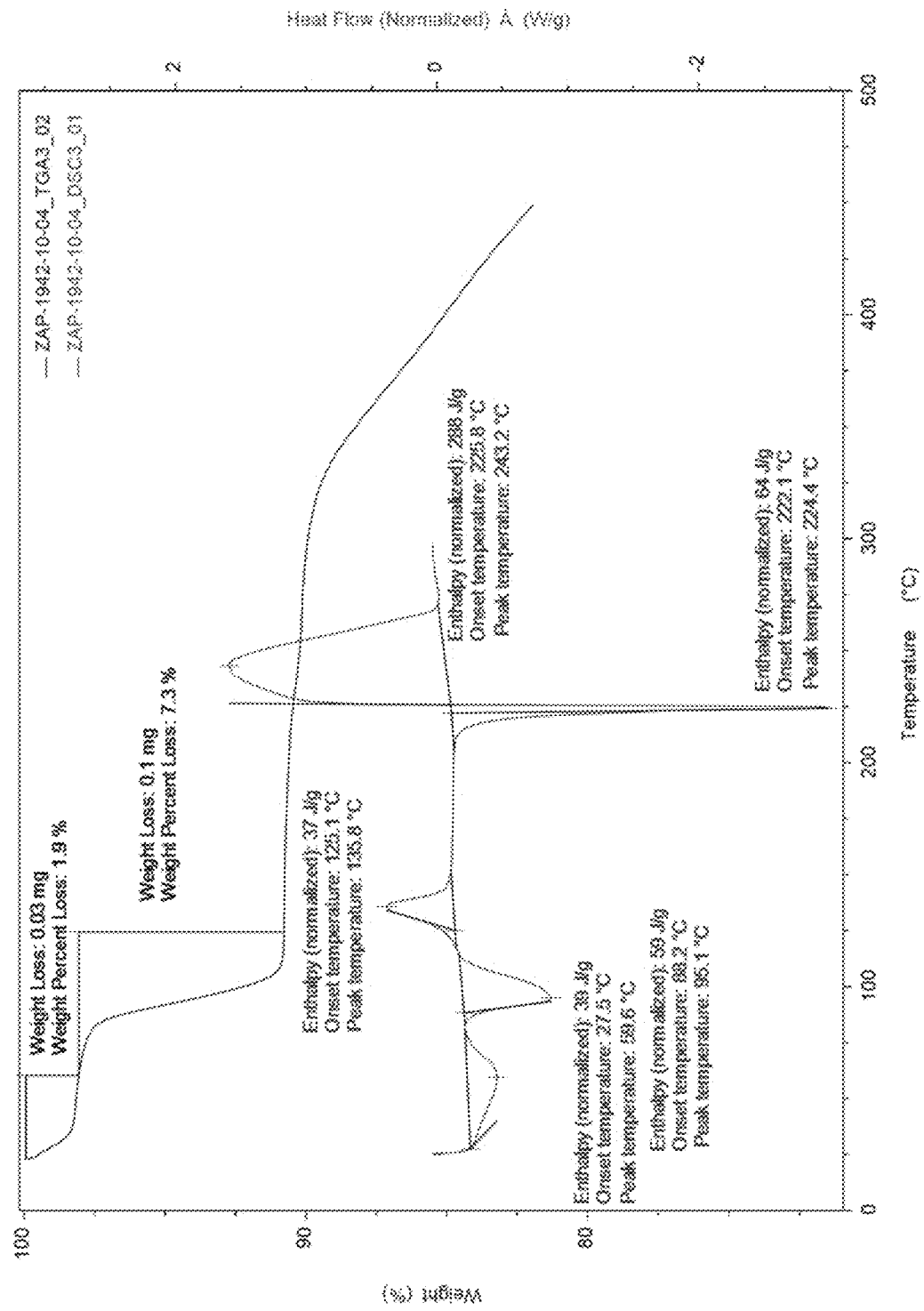
FIG. 33C depicts the characterization of Form B of Compound III-1 by thermogravimetric analysis (above) and differential scanning calorimetry (below).
Figure 33D:
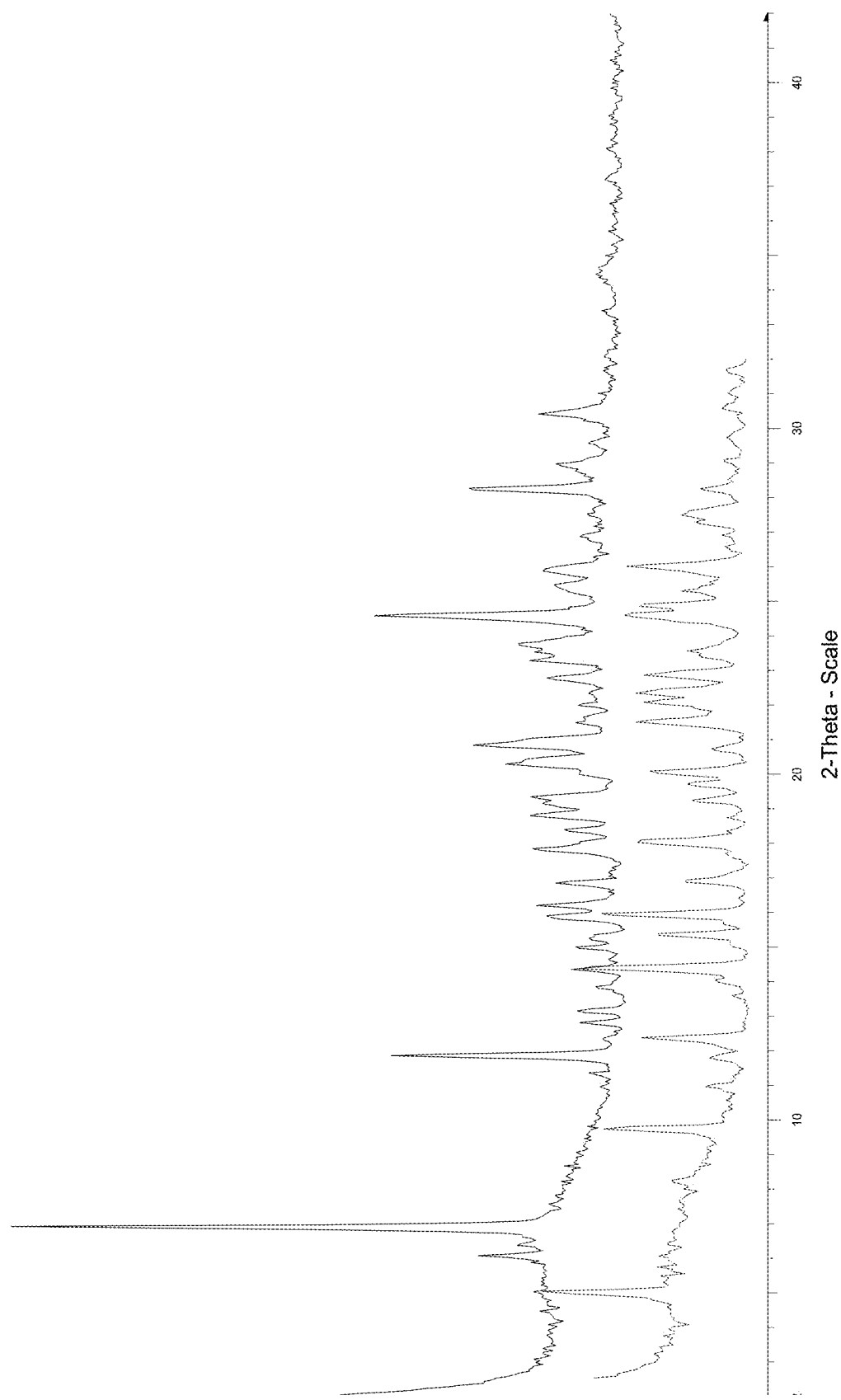
FIG. 33D depicts an XRPD diffractogram of Compound III-1 Form B (above) after storage at 40° C./75% RH for 7 days (below).

In some embodiments, the solid crystalline form of Compound III-1 is Form B. In some embodiments, Form B of compound III-1 has a X-Ray diffraction pattern substantially similar to that depicted in FIG. 33A. In some embodiments, Form B of compound III-1 has a differential scanning calorimetry (DSC) pattern substantially similar to that depicted in FIG. 33C. In some embodiments, Form A of compound III-1 has a thermogravimetric analysis pattern substantially similar to that depicted in FIG. 33C. In some embodiments, Form B of Compound III-1 can be characterized by substantial similarity to two or more of these figures simultaneously.

Figure 34A:
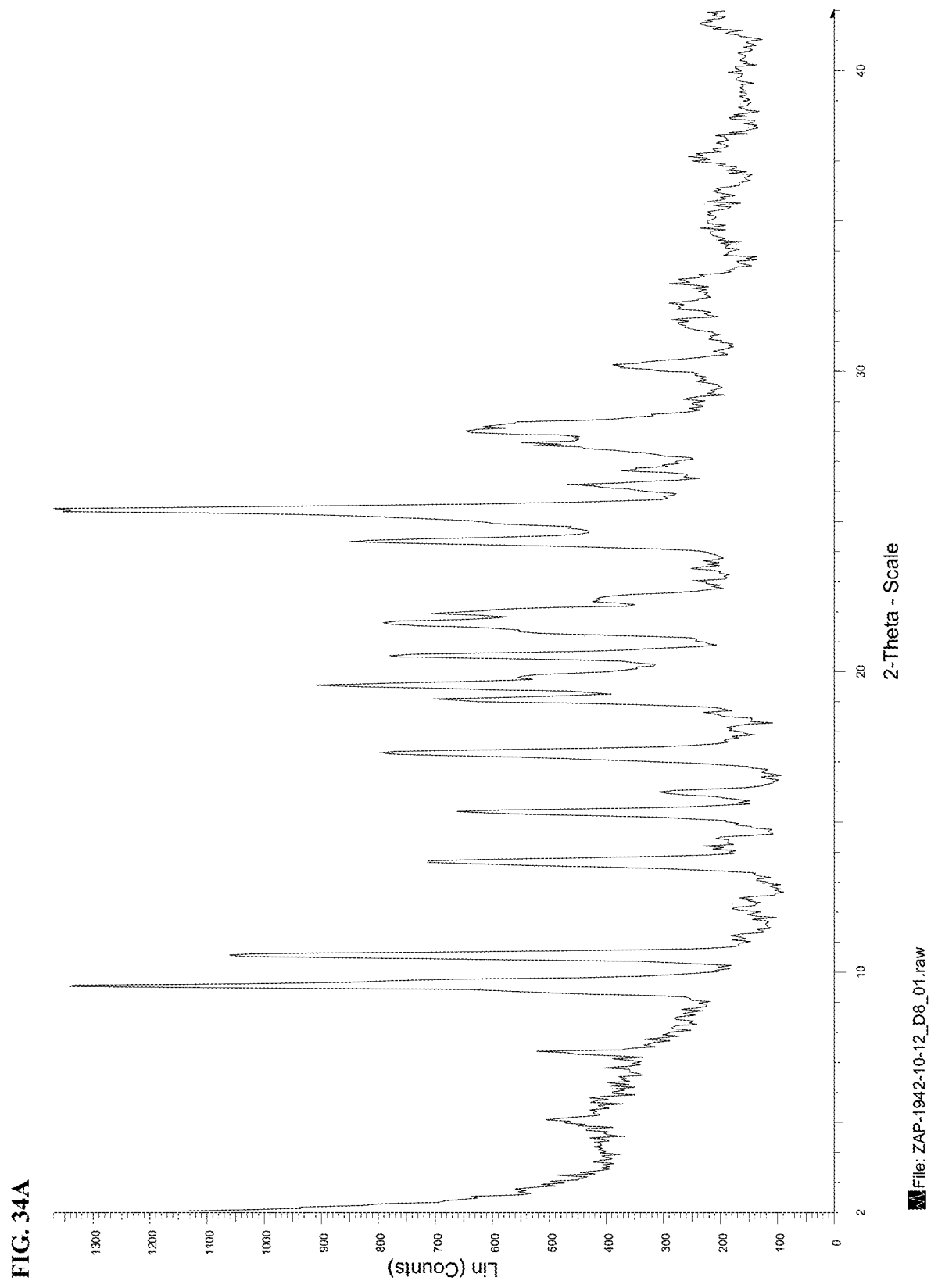
Figure 34B:
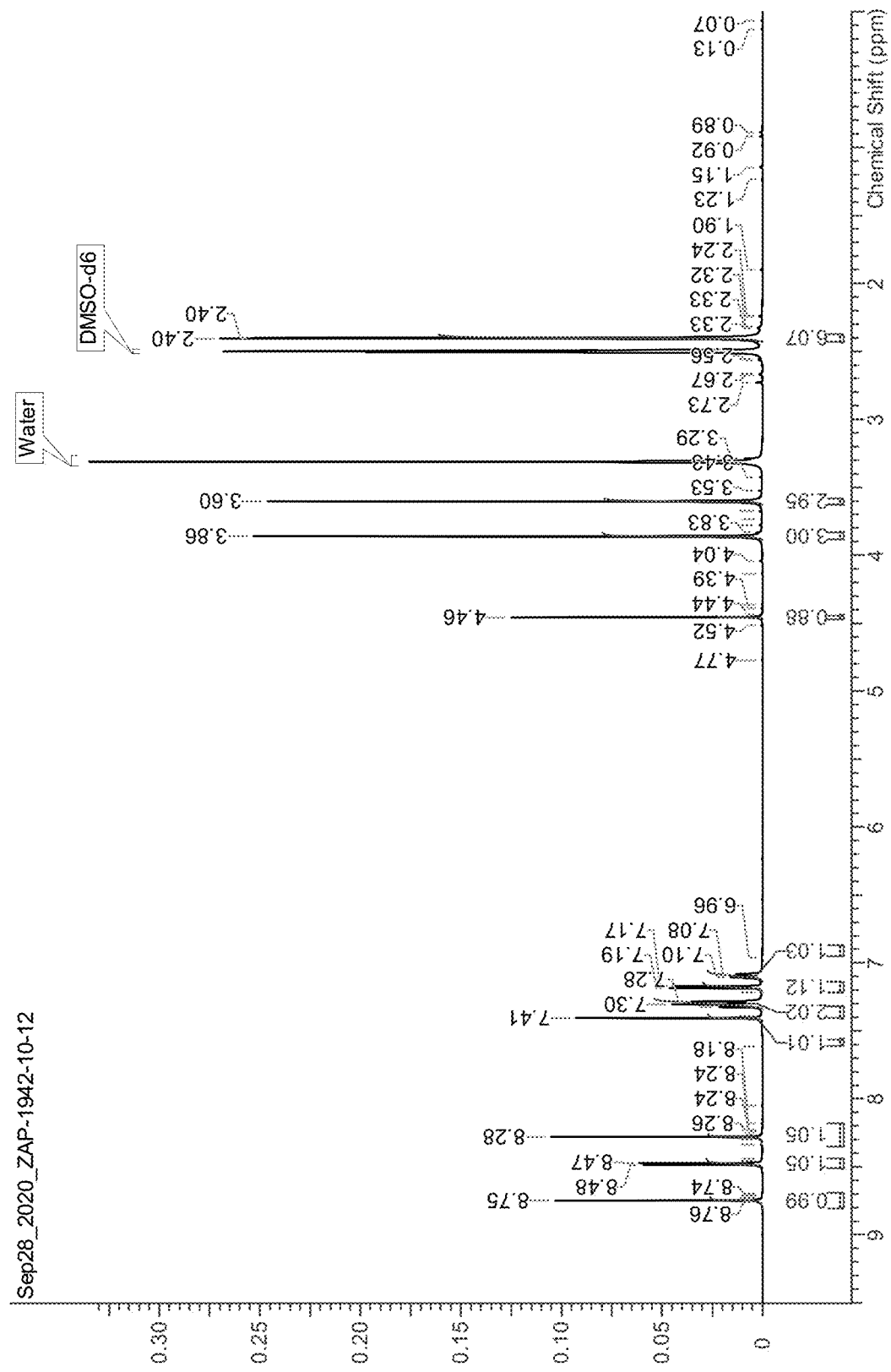
FIG. 34B depicts the characterization of Form C of Compound III-1 by $^1$H nuclear magnetic resonance ($^1$H NMR) in D6-DMSO at 400 MHz.
Figure 34C:
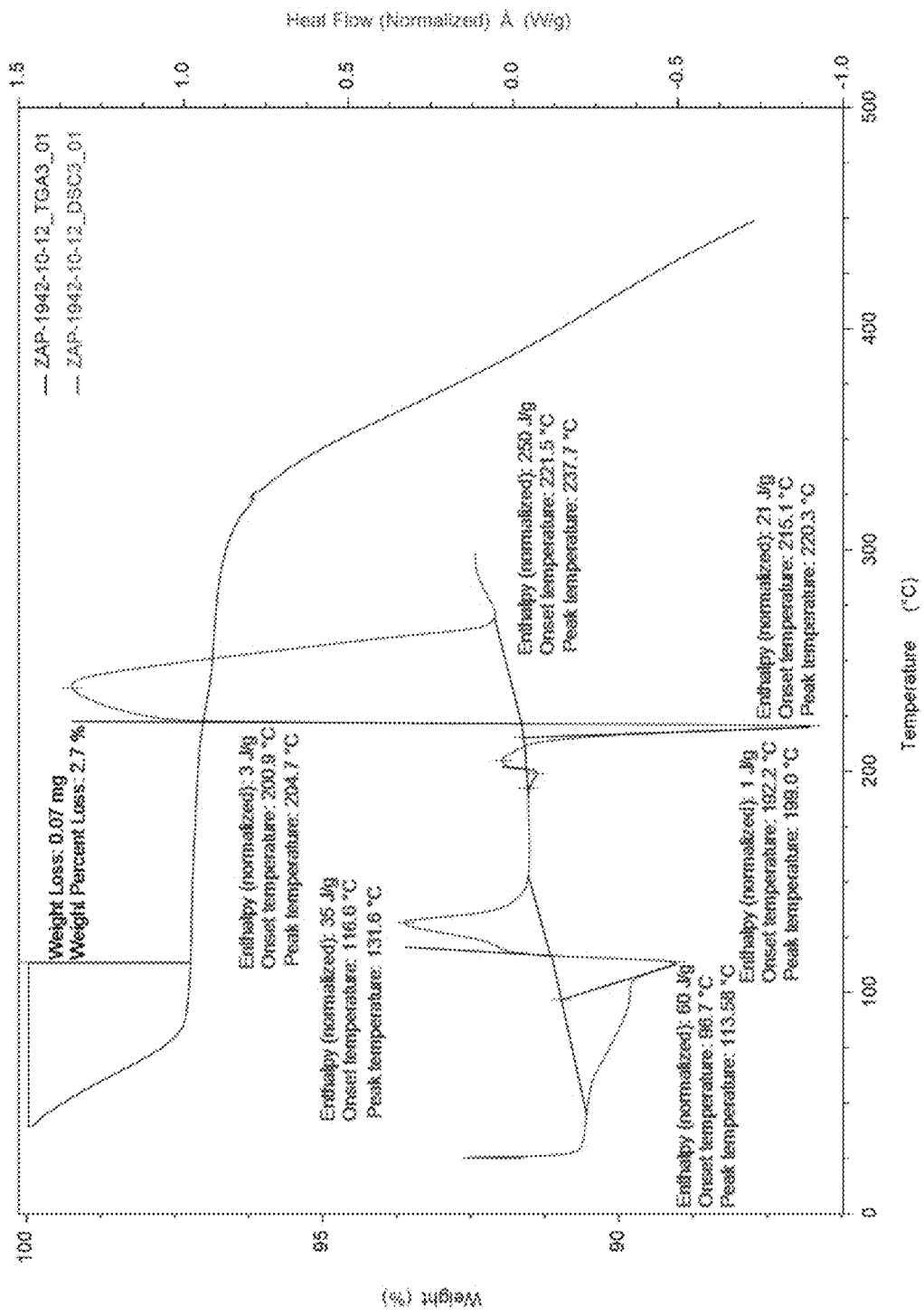
FIG. 34C depicts the characterization of Form C of Compound III-1 by thermogravimetric analysis (above) and differential scanning calorimetry (below).
Figure 34D:
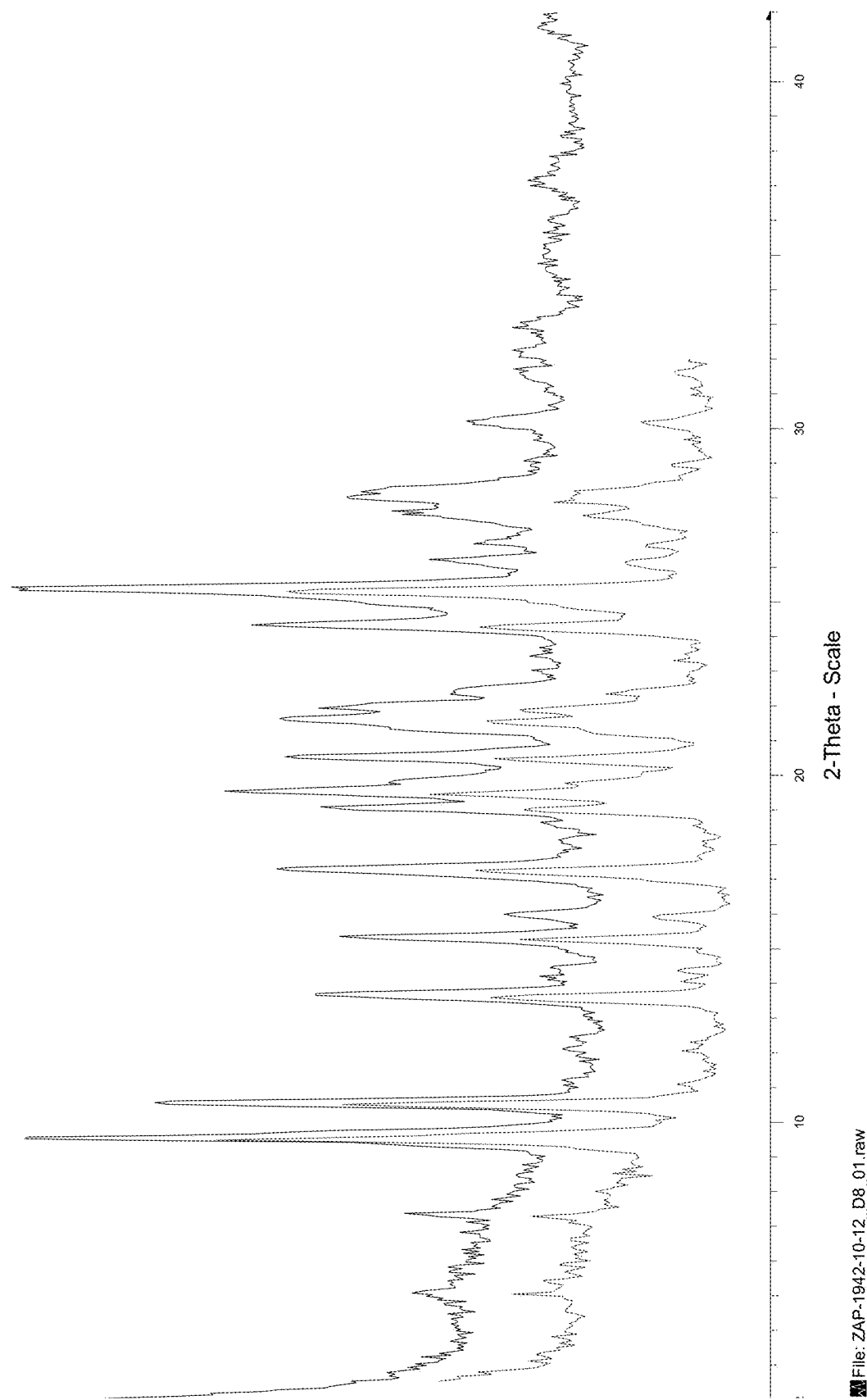
FIG. 34D depicts an XRPD diffractogram of Compound III-1 Form C (above) after storage at 40° C./75% RH for 7 days (below).

In some embodiments, the solid crystalline form of Compound III-1 is Form C. In some embodiments, Form C of compound III-1 has a X-Ray diffraction pattern substantially similar to that depicted in FIG. 34A. In some embodiments, Form C of compound III-1 has a differential scanning calorimetry (DSC) pattern substantially similar to that depicted in FIG. 34C. In some embodiments, Form C of compound III-1 has a thermogravimetric analysis pattern substantially similar to that depicted in FIG. 34C. In some embodiments, Form C of Compound III-1 can be characterized by substantial similarity to two or more of these figures simultaneously.

In another embodiment, a compound of Formula (III) is compound III-2 wherein, compound III-2 is a hydrochloride salt. In some embodiments, compound III-2 is a monohydrochloride salt. In some embodiments, compound III-2 is a bis-hydrochloride salt. In some embodiments, compound III-2 is a tris-hydrochloride salt.

In some embodiments, Compound III-2 is an amorphous solid. In some embodiments, compound III-2 is a crystalline solid. In some embodiments, Compound III-2 is a mixture of amorphous solid form and crystalline solid form.

In some embodiments, the present invention provides a form of compound III-2 substantially free of impurities. As used herein, the term "substantially free of impurities" means that the compound contains no significant amount of extraneous matter. Such extraneous matter may include different forms of compound III-2, residual solvents, or any other impurities that may result from the preparation of, and/or isolation of, compound III-2. In certain embodiments, at least about 95% by weight of compound III-2 is present. In certain embodiments, at least about 99% by weight of compound III-2 is present.

In other embodiments, compound III-2 is a crystalline solid substantially free of amorphous compound III-2. As used herein, the term "substantially free of amorphous compound III-2" means that the compound contains no significant amount of amorphous compound III-2. In certain embodiments, at least about 95% by weight of crystalline compound III-2 is present. In certain embodiments, at least about 99% by weight of crystalline compound III-2 is present.

It has been found that compound III-2 can exist in a variety of solid forms. Exemplary such forms include polymorphs such as those described herein.

Figure 35A:
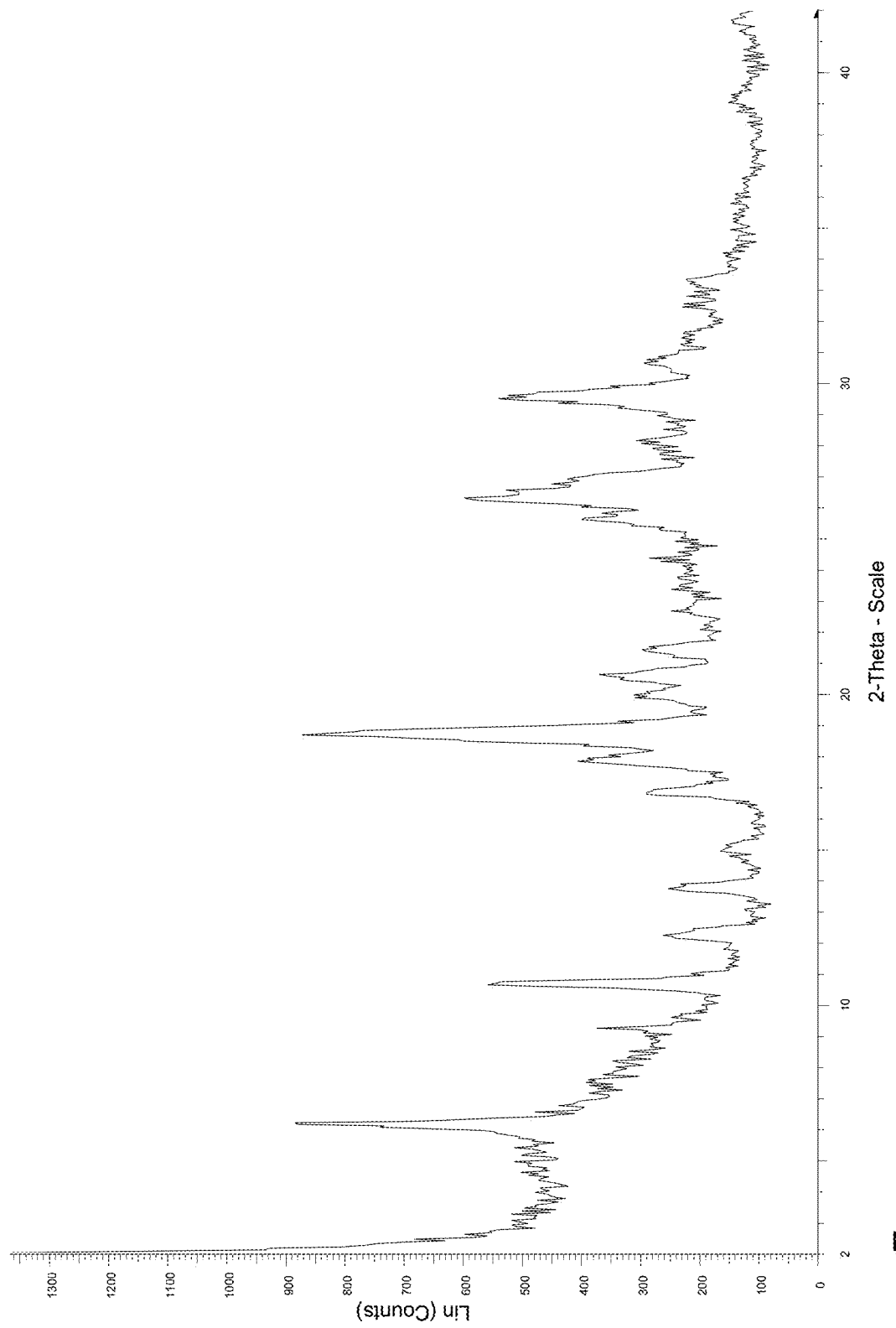
FIG. 35A depicts an X-ray diffraction pattern of Form A of Compound III-2 (hydrochloride salt).
Figure 35B:
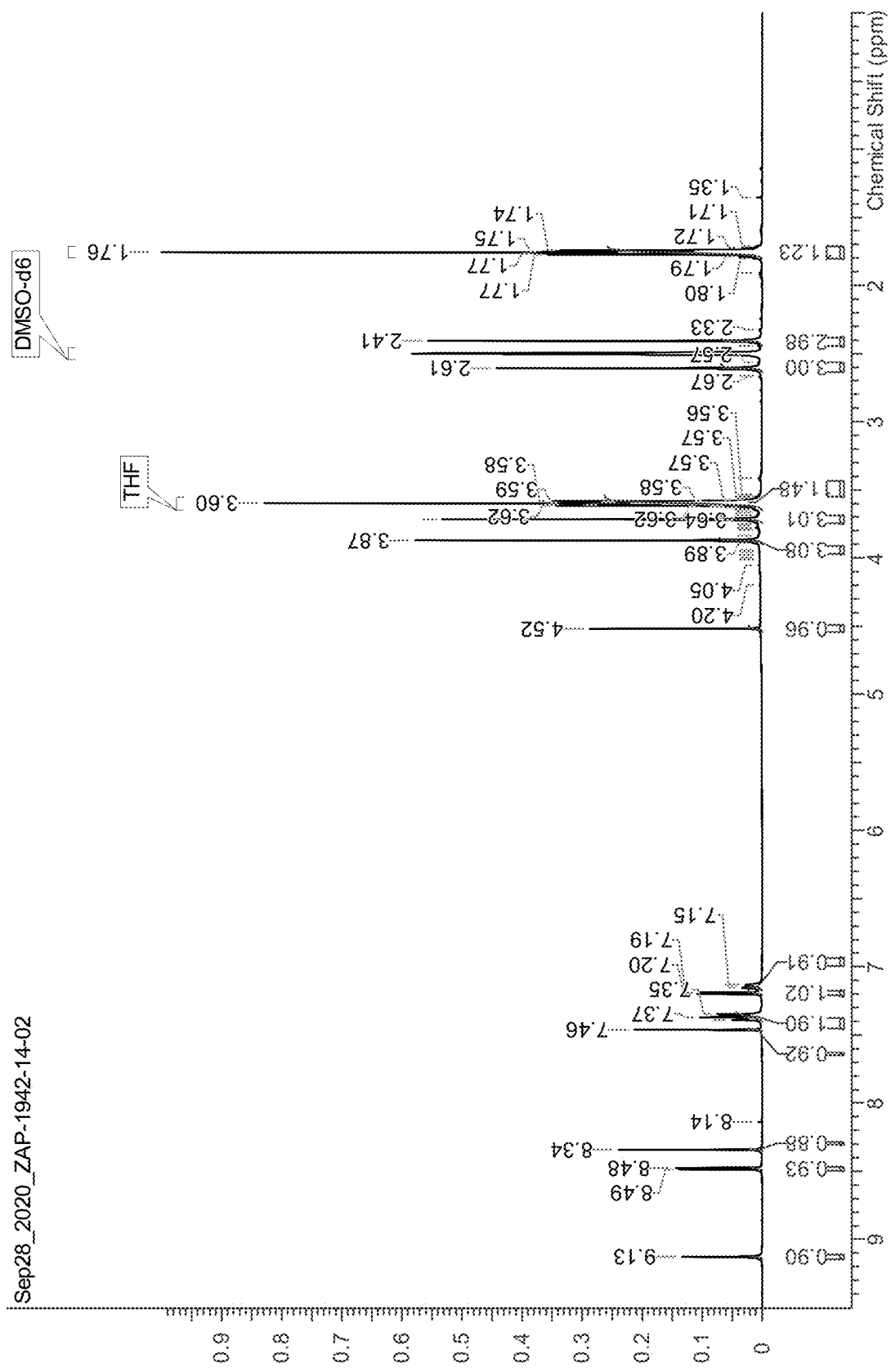
FIG. 35B depicts the characterization of Form A of Compound III-2 by $^1$H nuclear magnetic resonance ($^1$H NMR) in D6-DMSO at 400 MHz.

In some embodiments, the solid crystalline form of Compound III-2 is Form A. In certain embodiments, Form A of compound III-2 has a X-Ray diffraction pattern substantially similar to that depicted in FIG. 35A. In some embodiments, Form A of Compound III-2 may be characterized by a powder X-ray diffraction pattern with at least two characteristic peaks, in degrees 2θ, each selected from the group consisting of the peaks listed in Table 31. In some embodiments, Form A of Compound III-2 may be characterized by a powder X-ray diffraction pattern with at least three characteristic peaks, in degrees 2θ, each selected from the group consisting of the peaks listed in Table 31. In some embodiments, Form A of Compound III-2 may be characterized by a powder X-ray diffraction pattern with at least four characteristic peaks, in degrees 2θ, each selected from the group consisting of the peaks listed in Table 31. In some embodiments, Form A of Compound III-2 may be characterized by a powder X-ray diffraction pattern with at least five characteristic peaks, in degrees 2θ, each selected from the group consisting of the peaks listed in Table 31. In some embodiments, Form A of Compound III-2 may be characterized by a powder X-ray diffraction pattern with at least six characteristic peaks, in degrees 2θ, each selected from the group consisting of the peaks listed in Table 31.

Figure 35C:
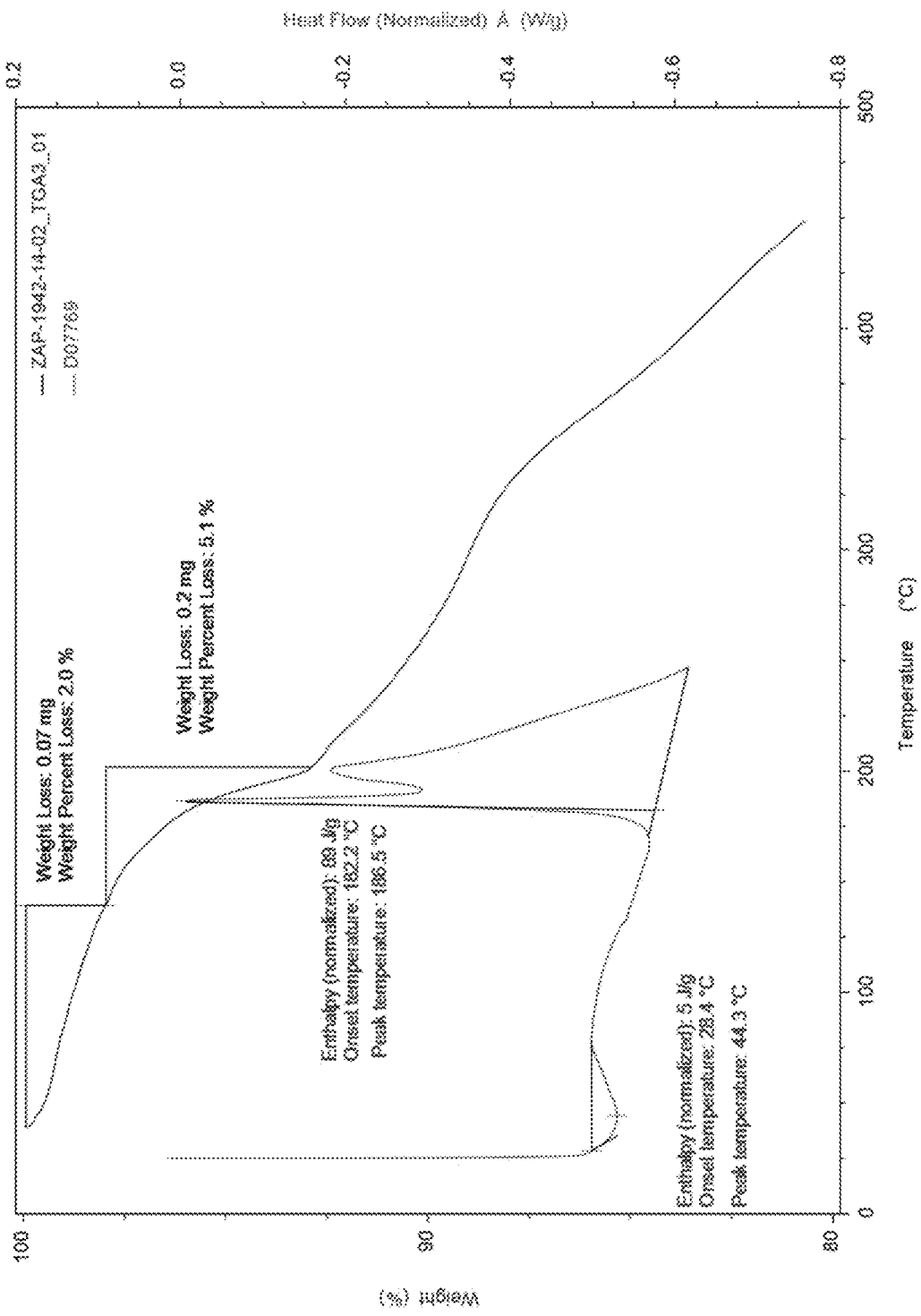
FIG. 35C depicts the characterization of Form A of Compound III-2 by thermogravimetric analysis (above) and differential scanning calorimetry (below).
Figure 35D:
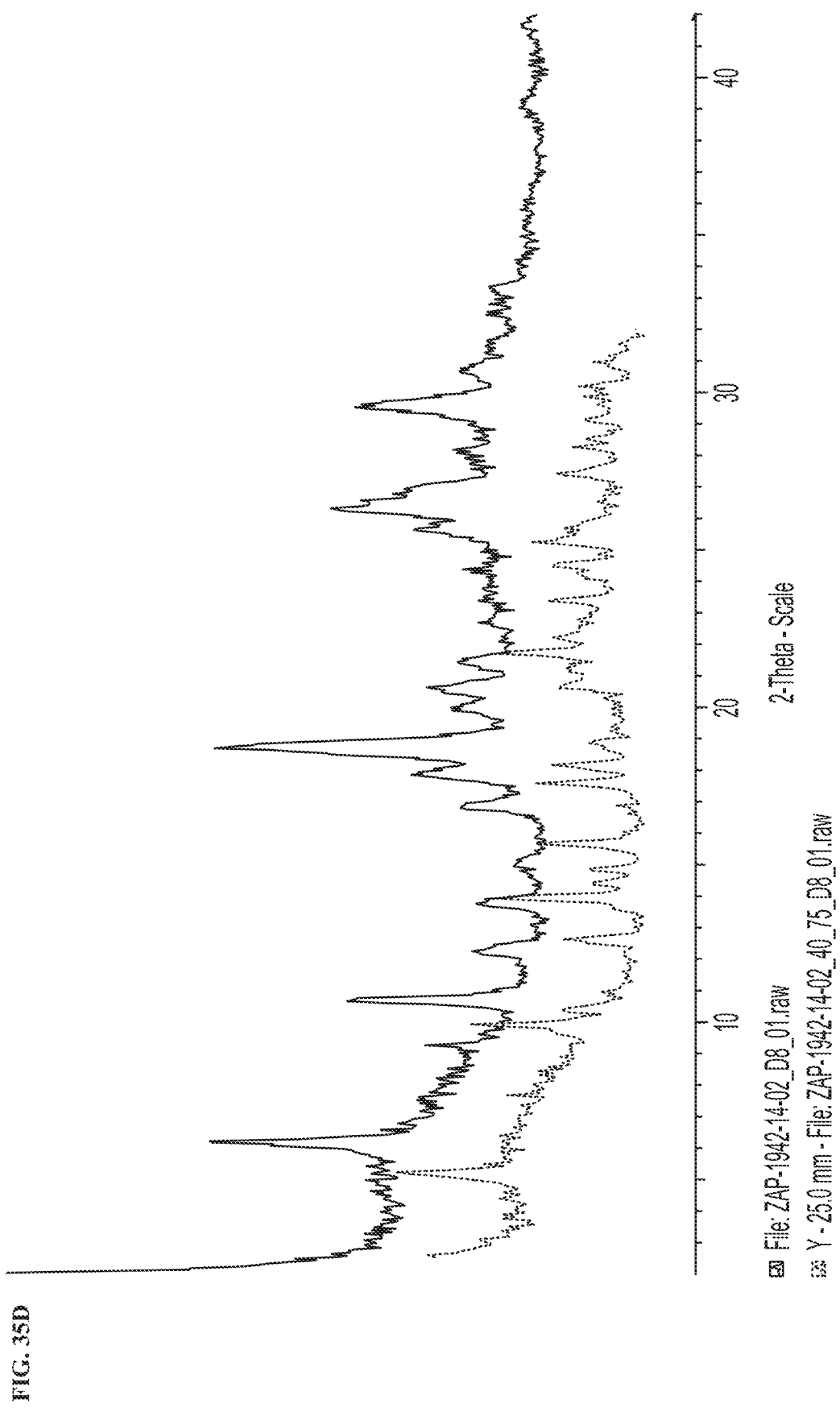

In some embodiments, Form A of compound III-2 has a differential scanning calorimetry (DSC) pattern substantially similar to that depicted in FIG. 35C. In some embodiments, Form A of compound III-2 has a thermogravimetric analysis pattern substantially similar to that depicted in FIG. 35C. In some embodiments, Form A of Compound III-2 can be characterized by substantial similarity to two or more of these figures simultaneously.

Figure 36A:
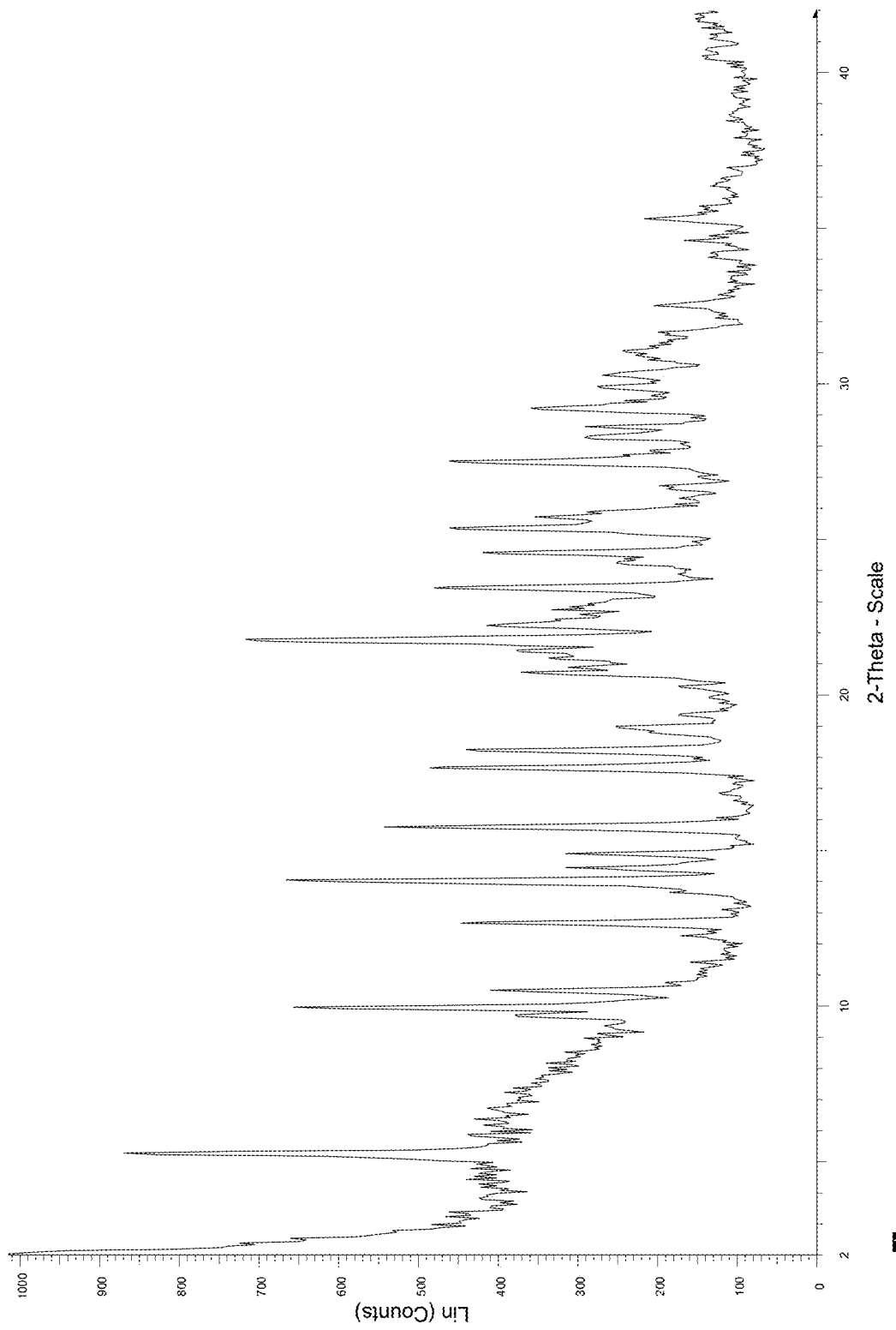
Figure 36B:
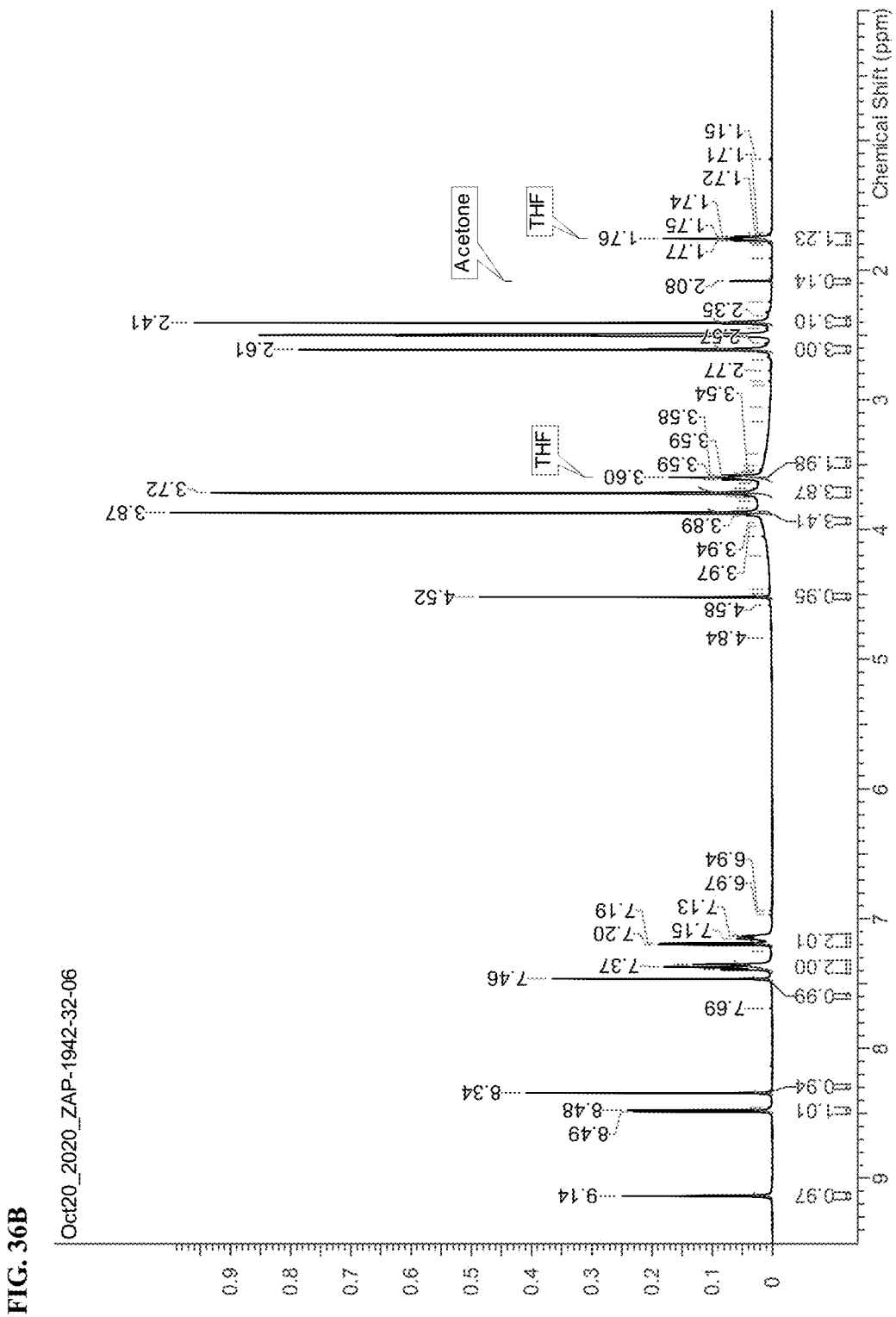

In some embodiments, the solid crystalline form of Compound III-2 is Form B. In some embodiments, Form B of compound III-2 has a X-Ray diffraction pattern substantially similar to that depicted in FIG. 36A. In some embodiments, Form B of Compound III-2 may be characterized by a powder X-ray diffraction pattern with at least two characteristic peaks, in degrees 2θ, each selected from the group consisting of the peaks listed in Table 32. In some embodiments, Form B of Compound III-2 may be characterized by a powder X-ray diffraction pattern with at least three characteristic peaks, in degrees 2θ, each selected from the group consisting of the peaks listed in Table 32. In some embodiments, Form B of Compound III-2 may be characterized by a powder X-ray diffraction pattern with at least four characteristic peaks, in degrees 2θ, each selected from the group consisting of the peaks listed in Table 32. In some embodiments, Form B of Compound III-2 may be characterized by a powder X-ray diffraction pattern with at least five characteristic peaks, in degrees 2θ, each selected from the group consisting of the peaks listed in Table 32. In some embodiments, Form B of Compound III-2 may be characterized by a powder X-ray diffraction pattern with at least six characteristic peaks, in degrees 2θ, each selected from the group consisting of the peaks listed in Table 32.

Figure 36C:
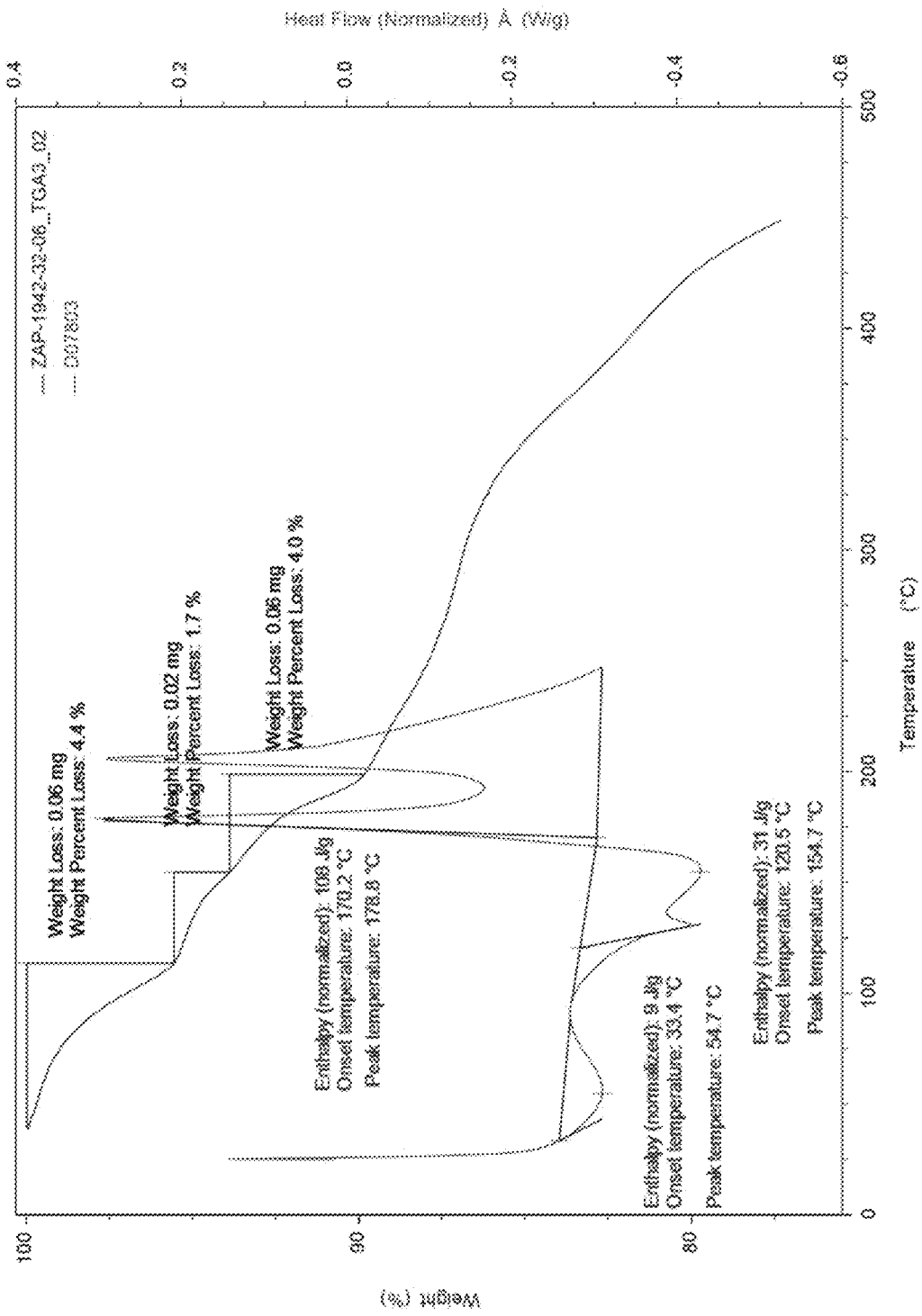
Figure 36D:
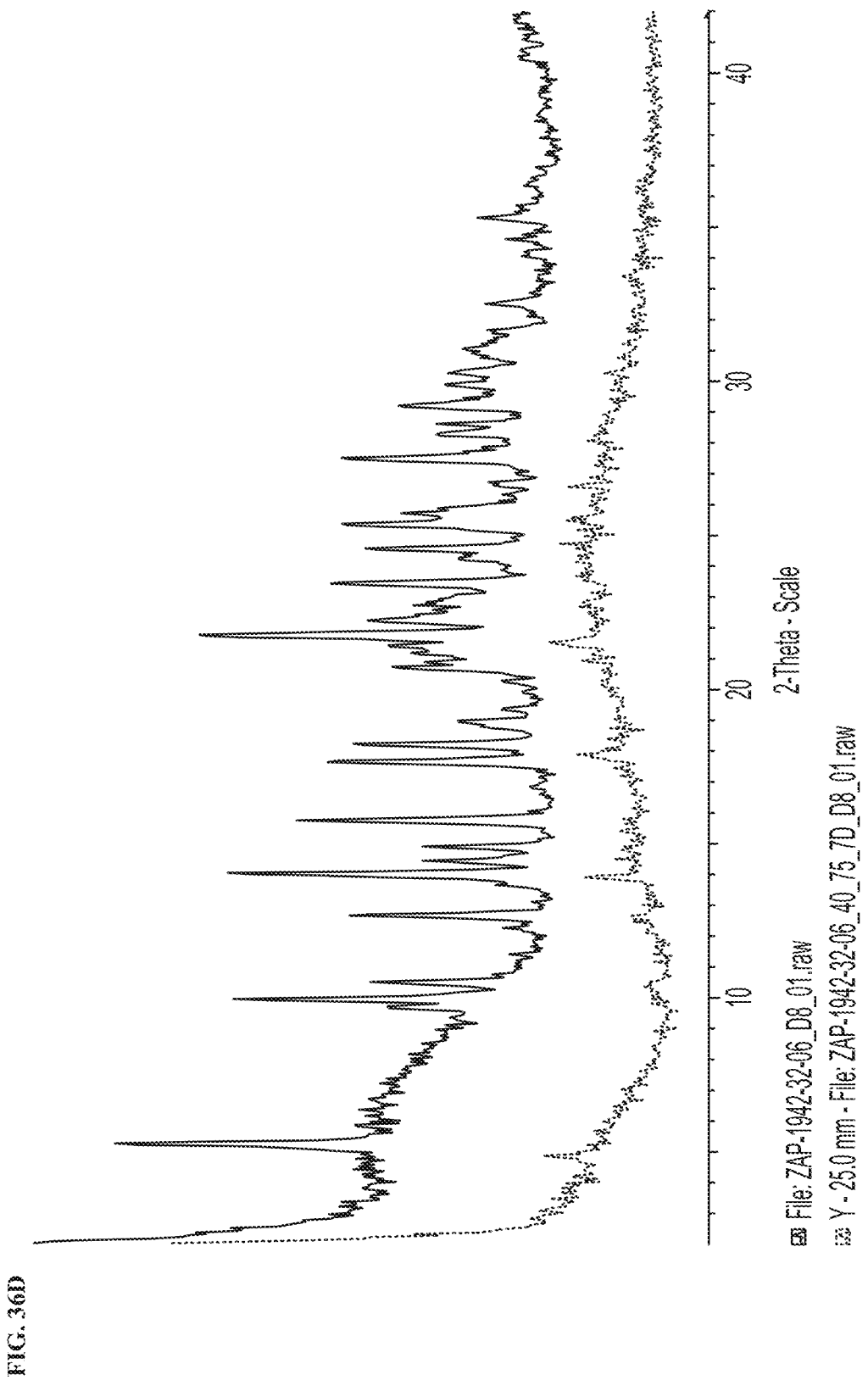

In some embodiments, Form B of compound III-2 has a differential scanning calorimetry (DSC) pattern substantially similar to that depicted in FIG. 36C. In some embodiments, Form B of compound III-2 has a thermogravimetric analysis pattern substantially similar to that depicted in FIG. 36C. In some embodiments, Form B of Compound III-2 can be characterized by substantial similarity to two or more of these figures simultaneously.

Figure 37A:
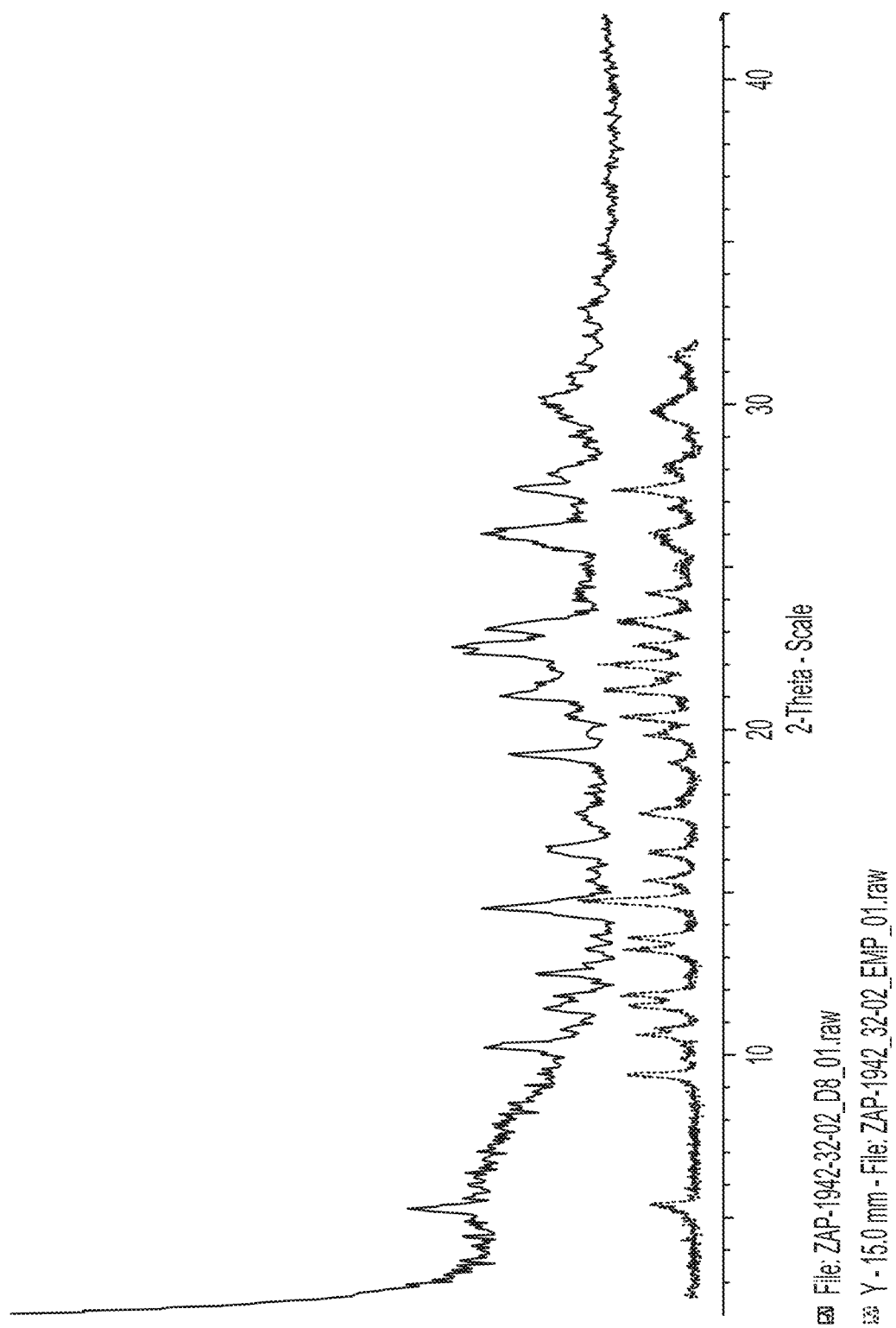
Figure 37B:
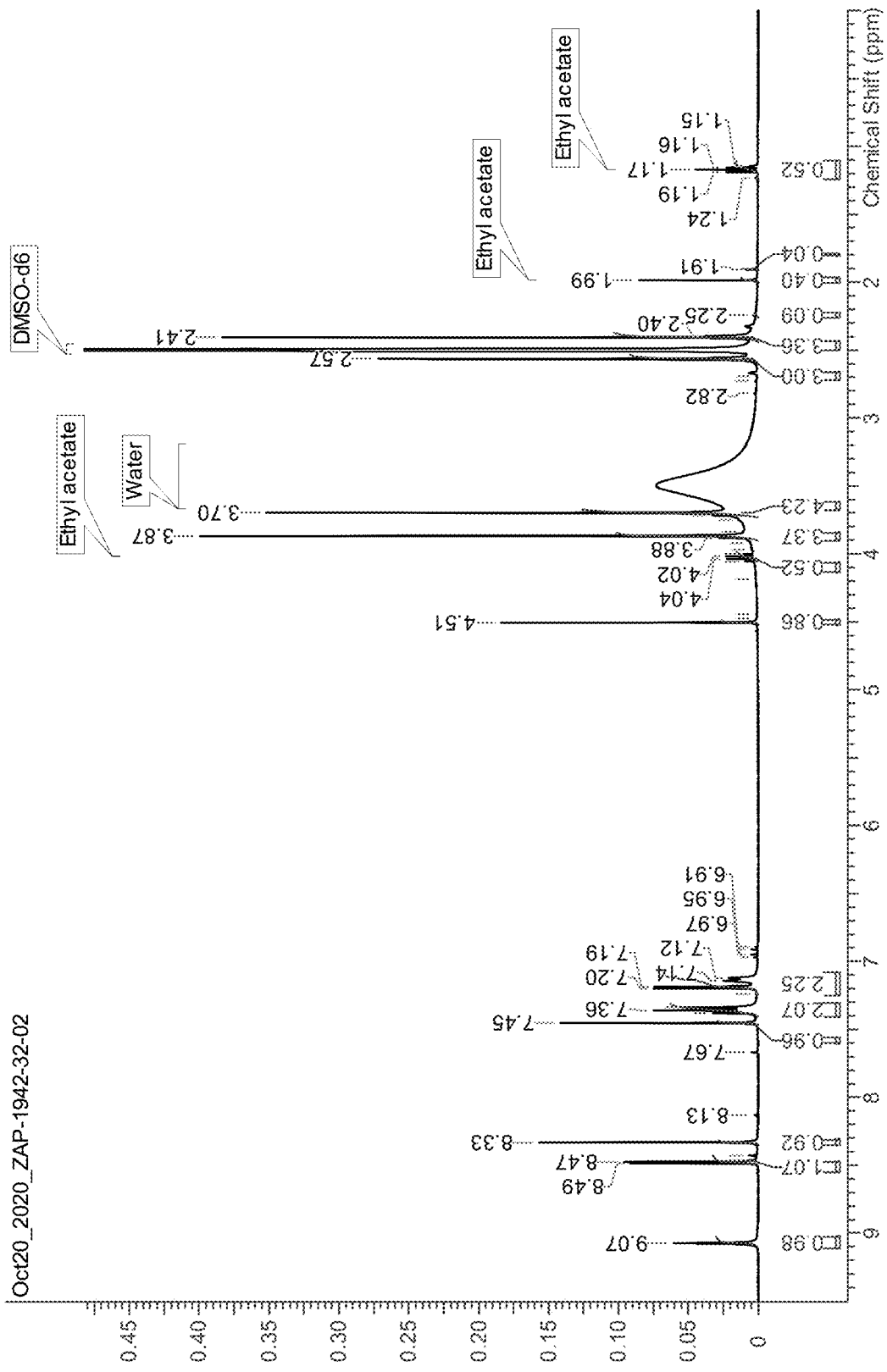
Figure 37C:
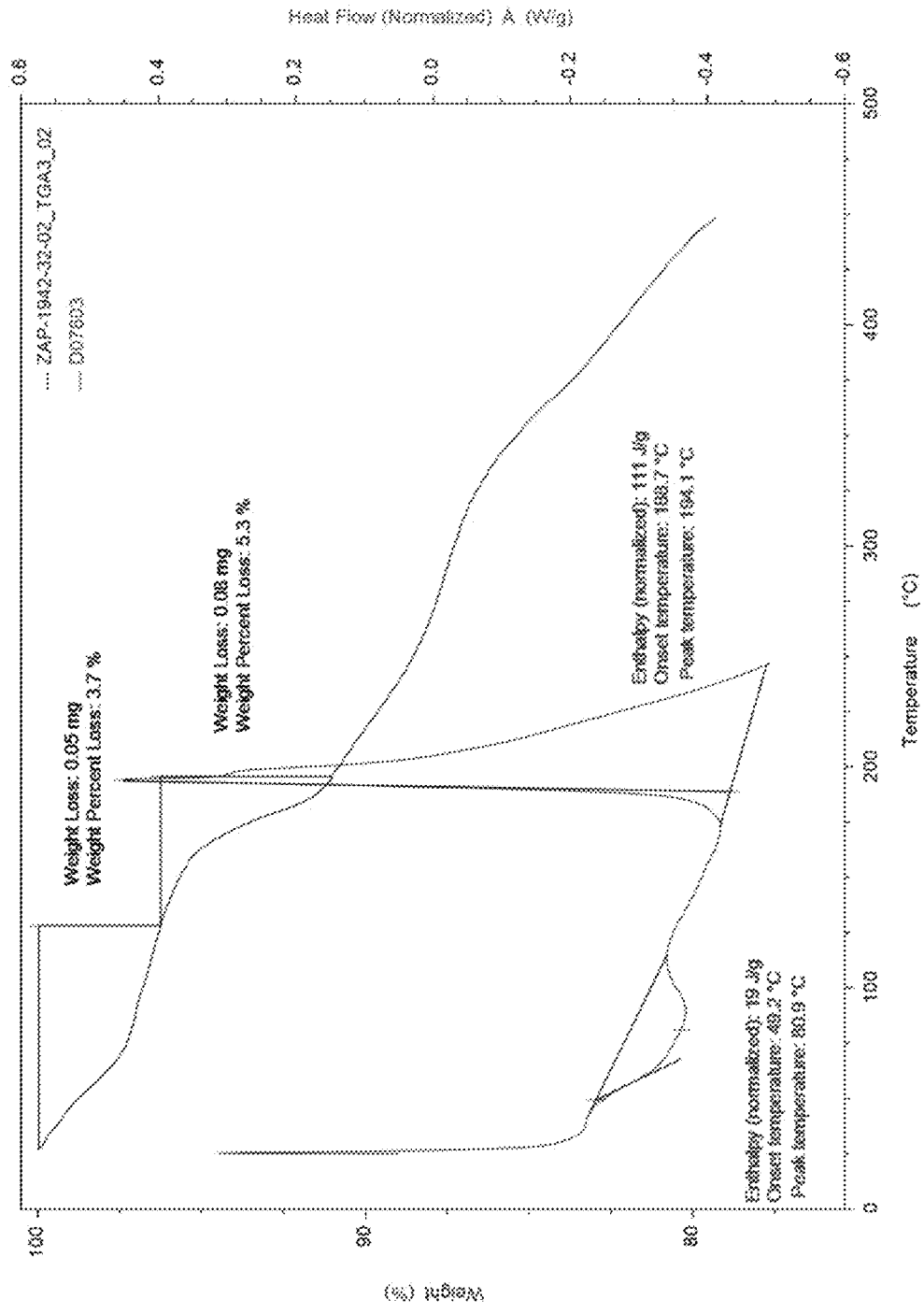
Figure 37D:
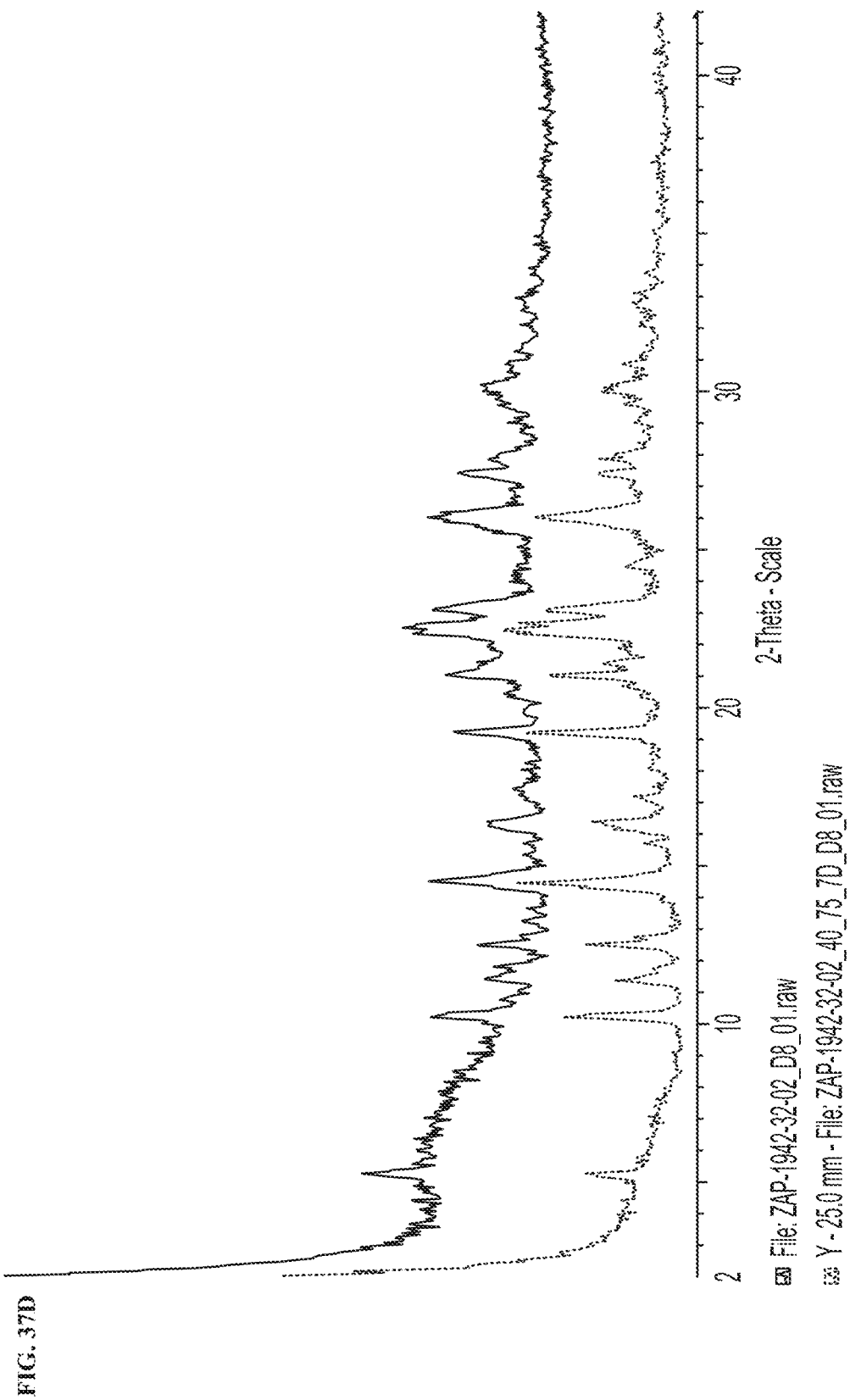

In some embodiments, the solid crystalline form of Compound III-2 is Form C. In some embodiments, Form C of compound III-2 has a X-Ray diffraction pattern substantially similar to that depicted in FIG. 37A. In some embodiments, Form C of compound III-2 has a differential scanning calorimetry (DSC) pattern substantially similar to that depicted in FIG. 37C. In some embodiments, Form C of compound III-2 has a thermogravimetric analysis pattern substantially similar to that depicted in FIG. 37C. In some embodiments, Form C of Compound III-2 can be characterized by substantial similarity to two or more of these figures simultaneously.

In some embodiments, the solid crystalline form of Compound III-2 is Form D. In some embodiments, Form D of compound III-2 has a X-Ray diffraction pattern substantially similar to that depicted in FIG. 38A. In some embodiments, Form D of Compound III-2 may be characterized by a powder X-ray diffraction pattern with at least two characteristic peaks, in degrees 2θ, each selected from the group consisting of the peaks listed in Table 33. In some embodiments, Form D of Compound III-2 may be characterized by a powder X-ray diffraction pattern with at least three characteristic peaks, in degrees 2θ, each selected from the group consisting of the peaks listed in Table 33. In some embodiments, Form D of Compound III-2 may be characterized by a powder X-ray diffraction pattern with at least four characteristic peaks, in degrees 2θ, each selected from the group consisting of the peaks listed in Table 33. In some embodiments, Form D of Compound III-2 may be characterized by a powder X-ray diffraction pattern with at least five characteristic peaks, in degrees 2θ, each selected from the group consisting of the peaks listed in Table 33. In some embodiments, Form D of Compound III-2 may be characterized by a powder X-ray diffraction pattern with at least six characteristic peaks, in degrees 2θ, each selected from the group consisting of the peaks listed in Table 33.

In some embodiments, Form D of compound III-2 has a differential scanning calorimetry (DSC) pattern substantially similar to that depicted in FIG. 38C. In some embodiments, Form D of compound III-2 has a thermogravimetric analysis pattern substantially similar to that depicted in FIG. 38C. In some embodiments, Form D of Compound III-2 can be characterized by substantial similarity to two or more of these figures simultaneously.

In another embodiment, a compound of Formula (III) is compound III-3 wherein, compound III-3 is a hydrobromide salt. In some embodiments, compound III-3 is a monohydrobromide salt. In some embodiments, compound III-3 is a bis-hydrobromide salt. In some embodiments, compound III-3 is a tris-hydrobromide salt.

In some embodiments, Compound III-3 is an amorphous solid. In some embodiments, compound III-3 is a crystalline solid. In some embodiments, Compound III-3 is a mixture of amorphous solid form and crystalline solid form.

In some embodiments, the present invention provides a form of compound III-3 substantially free of impurities. As used herein, the term "substantially free of impurities" means that the compound contains no significant amount of extraneous matter. Such extraneous matter may include different forms of compound III-3, residual solvents, or any other impurities that may result from the preparation of, and/or isolation of, compound III-3. In certain embodiments, at least about 95% by weight of compound III-3 is present. In certain embodiments, at least about 99% by weight of compound III-3 is present.

In certain embodiments, compound III-3 is a crystalline solid. In other embodiments, compound III-3 is a crystalline solid substantially free of amorphous compound III-3. As used herein, the term "substantially free of amorphous compound III-3" means that the compound contains no significant amount of amorphous compound III-3. In certain embodiments, at least about 95% by weight of crystalline compound III-3 is present. In still other embodiments of the invention, at least about 99% by weight of crystalline compound III-3 is present.

In some embodiments, the solid crystalline form of Compound III-3 is Form A. In some embodiments, Form A of compound III-3 has a X-Ray diffraction pattern substantially similar that depicted in FIG. 39A. In some embodiments, Form A of Compound III-3 may be characterized by a powder X-ray diffraction pattern with at least two characteristic peaks, in degrees 2θ, each selected from the group consisting of the peaks listed in Table 34. In some embodiments, Form A of Compound III-3 may be characterized by a powder X-ray diffraction pattern with at least three characteristic peaks, in degrees 2θ, each selected from the group consisting of the peaks listed in Table 34. In some embodiments, Form A of Compound III-3 may be characterized by a powder X-ray diffraction pattern with at least four characteristic peaks, in degrees 2θ, each selected from the group consisting of the peaks listed in Table 34. In some embodiments, Form A of Compound III-3 may be characterized by a powder X-ray diffraction pattern with at least five characteristic peaks, in degrees 2θ, each selected from the group consisting of the peaks listed in Table 34. In some embodiments, Form A of Compound III-3 may be characterized by a powder X-ray diffraction pattern with at least six characteristic peaks, in degrees 2θ, each selected from the group consisting of the peaks listed in Table 34.

In some embodiments, Form A of compound III-3 has a differential scanning calorimetry (DSC) pattern substantially similar to that depicted in FIG. 39C. In some embodiments, Form A of compound III-3 has a thermogravimetric analysis pattern substantially similar to that depicted in FIG. 39C. In some embodiments, Form A of Compound III-3 can be characterized by substantial similarity to two or more of these figures simultaneously.

In another embodiment, a compound of Formula (III) is compound III-4 wherein, compound III-4 is a sulfuric acid salt (or sulfate).

In some embodiments, Compound III-4 is an amorphous solid. In some embodiments, compound III-4 is a crystalline solid. In some embodiments, Compound III-4 is a mixture of amorphous solid form and crystalline solid form.

In some embodiments, the present invention provides a form of compound III-4 substantially free of impurities. As used herein, the term "substantially free of impurities" means that the compound contains no significant amount of extraneous matter. Such extraneous matter may include different forms of compound III-4, residual solvents, or any other impurities that may result from the preparation of, and/or isolation of, compound III-4. In certain embodiments, at least about 95% by weight of compound III-4 is present. In certain embodiments, at least about 99% by weight of compound III-4 is present.

In certain embodiments, compound III-4 is a crystalline solid. In other embodiments, compound III-4 is a crystalline solid substantially free of amorphous compound III-4. As used herein, the term "substantially free of amorphous compound III-4" means that the compound contains no significant amount of amorphous compound III-4. In certain embodiments, at least about 95% by weight of crystalline compound III-4 is present. In still other embodiments of the invention, at least about 99% by weight of crystalline compound III-4 is present.

It has been found that compound III-4 can exist in a variety of solid forms. Exemplary such forms include polymorphs such as those described herein.

In some embodiments, the solid crystalline form of Compound III-4 is Form A. In some embodiments, Form A of compound III-4 has a X-Ray diffraction pattern substantially similar to that depicted in FIG. 40A. In some embodiments, Form A of Compound III-4 may be characterized by a powder X-ray diffraction pattern with at least two characteristic peaks, in degrees 2θ, each selected from the group consisting of the peaks listed in Table 35. In some embodiments, Form A of Compound III-4 may be characterized by a powder X-ray diffraction pattern with at least three characteristic peaks, in degrees 2θ, each selected from the group consisting of the peaks listed in Table 35. In some embodiments, Form A of Compound III-4 may be characterized by a powder X-ray diffraction pattern with at least four characteristic peaks, in degrees 2θ, each selected from the group consisting of the peaks listed in Table 35. In some embodiments, Form A of Compound III-4 may be characterized by a powder X-ray diffraction pattern with at least five characteristic peaks, in degrees 2θ, each selected from the group consisting of the peaks listed in Table 35. In some embodiments, Form A of Compound III-4 may be characterized by a powder X-ray diffraction pattern with at least six characteristic peaks, in degrees 2θ, each selected from the group consisting of the peaks listed in Table 35.

In some embodiments, Form A of compound III-4 has a differential scanning calorimetry (DSC) pattern substantially similar to that depicted in FIG. 40C. In some embodiments, Form A of compound III-4 has a thermogravimetric analysis pattern substantially similar to that depicted in FIG. 40C. In some embodiments, Form A of Compound III-4 can be characterized by substantial similarity to two or more of these figures simultaneously.

In some embodiments, the solid crystalline form of Compound III-4 is Form B. In some embodiments, Form B of compound III-4 has a X-Ray diffraction pattern substantially similar to that depicted in FIG. 41A. In some embodiments, Form B of compound III-4 has a differential scanning calorimetry (DSC) pattern substantially similar to that depicted in FIG. 41C. In some embodiments, Form B of compound III-4 has a thermogravimetric analysis pattern substantially similar to that depicted in FIG. 41C. In some embodiments, Form B of Compound III-4 can be characterized by substantial similarity to two or more of these figures simultaneously.

In another embodiment, a compound of Formula (III) is compound III-5 wherein, compound III-5 is a methane sulfonic acid salt.

In some embodiments, compound III-5 is an amorphous solid. In some embodiments, compound III-5 is a crystalline solid. In some embodiments, Compound III-5 is a mixture of amorphous solid form and crystalline solid form.

In some embodiments, the present invention provides a form of compound III-5 substantially free of impurities. As used herein, the term "substantially free of impurities" means that the compound contains no significant amount of extraneous matter. Such extraneous matter may include different forms of compound III-5, residual solvents, or any other impurities that may result from the preparation of, and/or isolation of, compound III-5. In certain embodiments, at least about 95% by weight of compound III-5 is present. In certain embodiments, at least about 99% by weight of compound III-5 is present.

In other embodiments, compound III-5 is a crystalline solid substantially free of amorphous compound III-5. As used herein, the term "substantially free of amorphous compound III-5" means that the compound contains no significant amount of amorphous compound III-5. In certain embodiments, at least about 95% by weight of crystalline compound III-5 is present. In certain embodiments, at least about 99% by weight of crystalline compound III-5 is present.

In some embodiments, the solid crystalline form of Compound III-5 is Form A. In some embodiments, Form A of compound III-5 has a X-Ray diffraction pattern substantially similar to that depicted in FIG. 42A. In some embodiments, Form A of Compound III-5 may be characterized by a powder X-ray diffraction pattern with at least two characteristic peaks, in degrees 2θ, each selected from the group consisting of the peaks listed in Table 36. In some embodiments, Form A of Compound III-5 may be characterized by a powder X-ray diffraction pattern with at least three characteristic peaks, in degrees 2θ, each selected from the group consisting of the peaks listed in Table 36. In some embodiments, Form A of Compound III-5 may be characterized by a powder X-ray diffraction pattern with at least four characteristic peaks, in degrees 2θ, each selected from the group consisting of the peaks listed in Table 36. In some embodiments, Form A of Compound III-5 may be characterized by a powder X-ray diffraction pattern with at least five characteristic peaks, in degrees 2θ, each selected from the group consisting of the peaks listed in Table 36. In some embodiments, Form A of Compound III-5 may be characterized by a powder X-ray diffraction pattern with at least six characteristic peaks, in degrees 2θ, each selected from the group consisting of the peaks listed in Table 36.

In some embodiments, Form A of compound III-5 has a differential scanning calorimetry (DSC) pattern substantially similar to that depicted in FIG. 42C. In some embodiments, Form A of compound III-5 has a thermogravimetric analysis pattern substantially similar to that depicted in FIG. 42C. In some embodiments, Form A of Compound III-5 can be characterized by substantial similarity to two or more of these figures simultaneously.

In another embodiment, a compound of Formula (III) is compound III-6 wherein, compound III-6 is a tartaric acid (or tartrate) salt.

In some embodiments, compound III-6 is an amorphous solid. In some embodiments, compound III-6 is a crystalline solid. In some embodiments, Compound III-6 is a mixture of amorphous solid form and crystalline solid form.

In some embodiments, the present invention provides a form of compound III-6 substantially free of impurities. As used herein, the term "substantially free of impurities" means that the compound contains no significant amount of extraneous matter. Such extraneous matter may include different forms of compound III-6, residual solvents, or any other impurities that may result from the preparation of, and/or isolation of, compound III-6. In certain embodiments, at least about 95% by weight of compound III-6 is present. In certain embodiments, at least about 99% by weight of compound III-6 is present.

In other embodiments, compound III-6 is a crystalline solid substantially free of amorphous compound III-6. As used herein, the term "substantially free of amorphous compound III-6" means that the compound contains no significant amount of amorphous compound III-6. In certain embodiments, at least about 95% by weight of crystalline compound III-6 is present. In certain embodiments, at least about 99% by weight of crystalline compound III-6 is present.

In some embodiments, the solid crystalline form of Compound III-6 is Form A. In some embodiments, Form A of compound III-6 has a X-Ray diffraction pattern substantially similar to that depicted in FIG. 43A. In some embodiments, Form A of compound III-6 has a differential scanning calorimetry (DSC) pattern substantially similar to that depicted in FIG. 43C. In some embodiments, Form A of compound III-6 has a thermogravimetric analysis pattern substantially similar to that depicted in FIG. 43C. In some embodiments, Form A of Compound III-6 can be characterized by substantial similarity to two or more of these figures simultaneously.

Compound of Formula (IV)

In one embodiment, provided herein is a compound of Formula (IV)

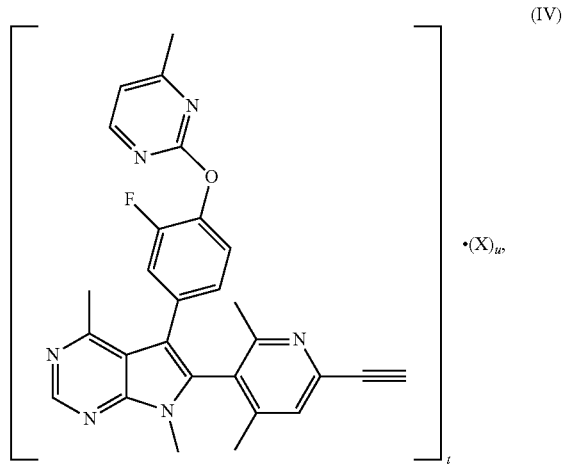

or a solvate thereof;

wherein,
t is 1, 2, 3, 4, 5, 6, 7, 8, or 9;
u is 0, 0.5, 1, 1.5, 2, 2.5, or 3; and
X is hydrochloric acid, p-toluene sulfonic acid, methane sulfonic acid, or benzene sulfonic acid.

It will be appreciated by one of ordinary skill in the art that the acid moiety indicated as "X" and 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine are ionically bonded to form a compound of Formula (IV). It will also be appreciated that when u is 0, X is absent, indicating that the compound of Formula (IV) exists as a "free base," i.e., "free form." It will further be appreciated that compounds of Formula (IV) can exist as specific rotamers or as a mixture of rotamers.

It is contemplated that a compound of Formula (IV) can exist in a variety of physical forms. For example, a compound of Formula (IV) can be in solution, suspension, or in solid form. In certain embodiments, a compound of Formula (IV) is in solid form. When a compound of Formula (IV) is in solid form, said compound may be amorphous, crystalline, or a mixture thereof. Exemplary solid forms are described in more detail below.

In some embodiments, a compound of Formula (IV), may be in a hydrate form. In some embodiments, a compound of Formula (IV), may be in a hemi-hydrate form.

In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9.

In some embodiments, u is 0. In some embodiments, u is 1. In some embodiments, u is 2. In some embodiments, u is 3. In some embodiments, u is 0.5. In some embodiments, u is 1.5. In some embodiments, u is 2.5.

In some embodiments, X is hydrochloric acid. In some embodiments, X is p-toluene sulfonic acid. In some embodiments, X is methane sulfonic acid. In some embodiments, X is benzene sulfonic acid.

In some embodiments, the present invention provides a form of a compound of Formula (IV) substantially free of impurities. As used herein, the term "substantially free of impurities" means that the compound contains no significant amount of extraneous matter. Such extraneous matter may include different forms of a compound of Formula (IV), residual solvents, or any other impurities that may result from the preparation of, and/or isolation of, a compound of Formula (IV).

In some embodiments, a compound of Formula (IV), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 weight percent where the percentages are based on the total weight of the composition. In some embodiments, a compound of Formula (IV), or a solvate thereof, or a crystalline form thereof, contains no more than about 0.40, no more than about 0.35, no more than about 0.3, no more than about 0.25, no more than about 0.2, no more than about 0.15, no more than about 0.10, or no more than about 0.05 weight percent of any single impurity wherein the percentages are based on the total weight of the composition.

In some embodiments, a compound of Formula (IV), or a solvate thereof, or a crystalline form thereof, is present in an amount of at least about 95, 95.5, 96, 96.5, 97, 97.5, 98.0, 98.5, 99, 99.1, 99.2, 99.3, 99.4, 99.5, 99.6, 99.7, 99.8, 99.9 area percent by HPLC relative to the total area of the HPLC chromatogram. In some embodiments, a compound of Formula (IV), or a solvate thereof, or a crystalline form thereof, contains no more than about 0.4, no more than about 0.35, no more than about 0.3, no more than about 0.25, no more than about 0.2, no more than about 0.15, no more than about 0.10, or no more than about 0.05 area percent HPLC of any single impurity relative to the total area of the HPLC chromatogram. In some embodiments, a HPLC method is the HPLC method as described in Example 1.

The structure depicted for compound of Formula (IV) is also meant to include all tautomeric forms. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

In some embodiments, a compound of Formula (IV) is compound IV-1 wherein, compound IV-1 is a free base (or "free form"). In some embodiments, compound IV-1 is an amorphous solid. In some embodiments, compound IV-1 is a crystalline solid. In some embodiments, Compound IV-1 is a mixture of amorphous solid form and crystalline solid form.

In some embodiments, the present invention provides a form of compound IV-1 substantially free of impurities. As used herein, the term "substantially free of impurities" means that the compound contains no significant amount of extraneous matter. Such extraneous matter may include different forms of compound IV-1, residual solvents, or any other impurities that may result from the preparation of, and/or isolation of, compound IV-1. In certain embodiments, at least about 95% by weight of compound IV-1 is present. In certain embodiments, at least about 99% by weight of compound IV-1 is present.

In other embodiments, compound IV-1 is a crystalline solid substantially free of amorphous compound IV-1. As used herein, the term "substantially free of amorphous compound IV-1" means that the compound contains no significant amount of amorphous compound IV-1. In certain embodiments, at least about 95% by weight of crystalline compound IV-1 is present. In certain embodiments, at least about 99% by weight of crystalline compound IV-1 is present.

In some embodiments, the solid crystalline form of Compound IV-1 is Form A. In some embodiments, Form A of compound IV-1 has a X-Ray diffraction pattern substantially similar to that depicted in FIG. 44A. In some embodiments, Form A of Compound IV-1 may be characterized by a powder X-ray diffraction pattern with at least two characteristic peaks, in degrees 2θ, each selected from the group consisting of the peaks listed in Table 39. In some embodiments, Form A of Compound IV-1 may be characterized by a powder X-ray diffraction pattern with at least three characteristic peaks, in degrees 2θ, each selected from the group consisting of the peaks listed in Table 39. In some embodiments, Form A of Compound IV-1 may be characterized by a powder X-ray diffraction pattern with at least four characteristic peaks, in degrees 2θ, each selected from the group consisting of the peaks listed in Table 39. In some embodiments, Form A of Compound IV-1 may be characterized by a powder X-ray diffraction pattern with at least five characteristic peaks, in degrees 2θ, each selected from the group consisting of the peaks listed in Table 39. In some embodiments, Form A of Compound IV-1 may be characterized by a powder X-ray diffraction pattern with at least six characteristic peaks, in degrees 2θ, each selected from the group consisting of the peaks listed in Table 39.

In some embodiments, Form A of compound IV-1 has a differential scanning calorimetry (DSC) pattern substantially similar to that depicted in FIG. 44C. In some embodiments, Form A of compound IV-1 has a thermogravimetric analysis pattern substantially similar to that depicted in FIG. 44C. In some embodiments, Form A of Compound IV-1 can be characterized by substantial similarity to two or more of these figures simultaneously.

In another embodiment, a compound of Formula (IV) is compound IV-2 wherein, compound IV-2 is a hydrochloride salt. In some embodiments, compound IV-2 is a mono-hydrochloride salt. In some embodiments, compound IV-2 is a bis-hydrochloride salt. In some embodiments, compound IV-2 is a tris-hydrochloride salt. In some embodiments, compound IV-2 is an amorphous solid. In some embodiments, compound IV-2 is a crystalline solid. In some embodiments, Compound IV-2 is a mixture of amorphous solid form and crystalline solid form.

In some embodiments, the present invention provides a form of compound IV-2 substantially free of impurities. As used herein, the term "substantially free of impurities" means that the compound contains no significant amount of extraneous matter. Such extraneous matter may include different forms of compound IV-2, residual solvents, or any other impurities that may result from the preparation of, and/or isolation of, compound IV-2. In certain embodiments, at least about 95% by weight of compound IV-2 is present. In certain embodiments, at least about 99% by weight of compound IV-2 is present.

In other embodiments, compound IV-2 is a crystalline solid substantially free of amorphous compound IV-2. As used herein, the term "substantially free of amorphous compound IV-2" means that the compound contains no significant amount of amorphous compound IV-2. In certain embodiments, at least about 95% by weight of crystalline compound IV-2 is present. In certain embodiments, at least about 99% by weight of crystalline compound IV-2 is present.

In some embodiments, the solid crystalline form of Compound IV-2 is Form A. In some embodiments, Form A of compound IV-2 has a X-Ray diffraction pattern substantially similar to that depicted in FIG. 45A. In some embodiments, Form A of Compound IV-2 may be characterized by a powder X-ray diffraction pattern with at least two characteristic peaks, in degrees 2θ, each selected from the group consisting of the peaks listed in Table 44. In some embodiments, Form A of Compound IV-2 may be characterized by a powder X-ray diffraction pattern with at least three characteristic peaks, in degrees 2θ, each selected from the group consisting of the peaks listed in Table 44. In some embodiments, Form A of Compound IV-2 may be characterized by a powder X-ray diffraction pattern with at least four characteristic peaks, in degrees 2θ, each selected from the group consisting of the peaks listed in Table 44. In some embodiments, Form A of Compound IV-2 may be characterized by a powder X-ray diffraction pattern with at least five characteristic peaks, in degrees 2θ, each selected from the group consisting of the peaks listed in Table 44. In some embodiments, Form A of Compound IV-2 may be characterized by a powder X-ray diffraction pattern with at least six characteristic peaks, in degrees 2θ, each selected from the group consisting of the peaks listed in Table 44.

In some embodiments, Form A of compound IV-2 has a differential scanning calorimetry (DSC) pattern substantially similar to that depicted in FIG. 45C. In some embodiments, Form A of compound IV-2 has a thermogravimetric analysis pattern substantially similar to that depicted in FIG. 45C. In some embodiments, Form A of Compound IV-2 can be characterized by substantial similarity to two or more of these figures simultaneously.

In another embodiment, a compound of Formula (IV) is compound IV-3 wherein, compound IV-3 is a p-toluene sulfonic acid salt. In some embodiments, compound IV-3 is an amorphous solid. In some embodiments, compound IV-3 is a crystalline solid. In some embodiments, Compound IV-3 is a mixture of amorphous solid form and crystalline solid form.

In some embodiments, the present invention provides a form of compound IV-3 substantially free of impurities. As used herein, the term "substantially free of impurities" means that the compound contains no significant amount of extraneous matter. Such extraneous matter may include different forms of compound IV-3, residual solvents, or any other impurities that may result from the preparation of, and/or isolation of, compound IV-3. In certain embodiments, at least about 95% by weight of compound IV-3 is present. In certain embodiments, at least about 99% by weight of compound IV-3 is present.

In other embodiments, compound IV-3 is a crystalline solid substantially free of amorphous compound IV-3. As used herein, the term "substantially free of amorphous compound IV-3" means that the compound contains no significant amount of amorphous compound IV-3. In certain embodiments, at least about 95% by weight of crystalline compound IV-3 is present. In certain embodiments, at least about 99% by weight of crystalline compound IV-3 is present.

It has been found that compound IV-3 can exist in a variety of solid forms. Exemplary such forms include polymorphs such as those described herein.

In some embodiments, the solid crystalline form of Compound IV-3 is Form A. In some embodiments, Form A of compound IV-3 has a X-Ray diffraction pattern substantially similar to that depicted in FIG. 46A. In some embodiments, Form A of Compound IV-3 may be characterized by a powder X-ray diffraction pattern with at least two characteristic peaks, in degrees 2θ, each selected from the group consisting of the peaks listed in Table 45. In some embodiments, Form A of Compound IV-3 may be characterized by a powder X-ray diffraction pattern with at least three characteristic peaks, in degrees 2θ, each selected from the group consisting of the peaks listed in Table 45. In some embodiments, Form A of Compound IV-3 may be characterized by a powder X-ray diffraction pattern with at least four characteristic peaks, in degrees 2θ, each selected from the group consisting of the peaks listed in Table 45. In some embodiments, Form A of Compound IV-3 may be characterized by a powder X-ray diffraction pattern with at least five characteristic peaks, in degrees 2θ, each selected from the group consisting of the peaks listed in Table 45. In some embodiments, Form A of Compound IV-3 may be characterized by a powder X-ray diffraction pattern with at least six characteristic peaks, in degrees 2θ, each selected from the group consisting of the peaks listed in Table 45.

In some embodiments, Form A of compound IV-3 has a differential scanning calorimetry (DSC) pattern substantially similar to that depicted in FIG. 46C. In some embodiments, Form A of compound IV-3 has a thermogravimetric analysis pattern substantially similar to that depicted in FIG. 46C. In some embodiments, Form A of Compound IV-3 can be characterized by substantial similarity to two or more of these figures simultaneously.

In some embodiments, the solid crystalline form of Compound IV-3 is Form B. In some embodiments, Form B of compound IV-3 has a X-Ray diffraction pattern substantially similar to that depicted in FIG. 47A. In some embodiments, Form B of Compound IV-3 may be characterized by a powder X-ray diffraction pattern with at least two characteristic peaks, in degrees 2θ, each selected from the group consisting of the peaks listed in Table 46. In some embodiments, Form B of Compound IV-3 may be characterized by a powder X-ray diffraction pattern with at least three characteristic peaks, in degrees 2θ, each selected from the group consisting of the peaks listed in Table 46. In some embodiments, Form B of Compound IV-3 may be characterized by a powder X-ray diffraction pattern with at least four characteristic peaks, in degrees 2θ, each selected from the group consisting of the peaks listed in Table 46. In some embodiments, Form B of Compound IV-3 may be characterized by a powder X-ray diffraction pattern with at least five characteristic peaks, in degrees 2θ, each selected from the group consisting of the peaks listed in Table 46. In some embodiments, Form B of Compound IV-3 may be characterized by a powder X-ray diffraction pattern with at least six characteristic peaks, in degrees 2θ, each selected from the group consisting of the peaks listed in Table 46.

In some embodiments, Form B of compound IV-3 has a differential scanning calorimetry (DSC) pattern substantially similar to that depicted in FIG. 47C. In some embodiments, Form B of compound IV-3 has a thermogravimetric analysis pattern substantially similar to that depicted in FIG. 47C. In some embodiments, Form B of Compound IV-3 can be characterized by substantial similarity to two or more of these figures simultaneously.

In another embodiment, a compound of Formula (IV) is compound IV-4 wherein, compound IV-4 is a methane sulfonic acid salt. In some embodiments, compound IV-4 is an amorphous solid. In some embodiments, compound IV-4 is a crystalline solid. In some embodiments, Compound IV-4 is a mixture of amorphous solid form and crystalline solid form.

In some embodiments, the present invention provides a form of compound IV-4 substantially free of impurities. As used herein, the term "substantially free of impurities" means that the compound contains no significant amount of extraneous matter. Such extraneous matter may include different forms of compound IV-4, residual solvents, or any other impurities that may result from the preparation of, and/or isolation of, compound IV-4. In certain embodiments, at least about 95% by weight of compound IV-4 is present. In certain embodiments, at least about 99% by weight of compound IV-4 is present.

In other embodiments, compound IV-4 is a crystalline solid substantially free of amorphous compound IV-4. As used herein, the term "substantially free of amorphous compound IV-4" means that the compound contains no significant amount of amorphous compound IV-4. In certain embodiments, at least about 95% by weight of crystalline compound IV-4 is present. In certain embodiments, at least about 99% by weight of crystalline compound IV-4 is present.

In some embodiments, the solid crystalline form of Compound IV-4 is Form A. In some embodiments, Form A of compound IV-4 has a X-Ray diffraction pattern substantially similar to that depicted in FIG. 48A. In some embodiments, Form A of Compound IV-4 may be characterized by a powder X-ray diffraction pattern with at least two characteristic peaks, in degrees 2θ, each selected from the group consisting of the peaks listed in Table 47. In some embodiments, Form A of Compound IV-4 may be characterized by a powder X-ray diffraction pattern with at least three characteristic peaks, in degrees 2θ, each selected from the group consisting of the peaks listed in Table 47. In some embodiments, Form A of Compound IV-4 may be characterized by a powder X-ray diffraction pattern with at least four characteristic peaks, in degrees 2θ, each selected from the group consisting of the peaks listed in Table 47. In some embodiments, Form A of Compound IV-4 may be characterized by a powder X-ray diffraction pattern with at least five characteristic peaks, in degrees 2θ, each selected from the group consisting of the peaks listed in Table 47. In some embodiments, Form A of Compound IV-4 may be characterized by a powder X-ray diffraction pattern with at least six characteristic peaks, in degrees 2θ, each selected from the group consisting of the peaks listed in Table 47.

In some embodiments, Form A of compound IV-4 has a differential scanning calorimetry (DSC) pattern substantially similar to that depicted in FIG. 48C. In some embodiments, Form A of compound IV-4 has a thermogravimetric analysis pattern substantially similar to that depicted in FIG. 48C. In some embodiments, Form A of Compound IV-4 can be characterized by substantial similarity to two or more of these figures simultaneously.

In another embodiment, a compound of Formula (IV) is compound IV-5 wherein, compound IV-5 is a benzene sulfonic acid salt. In some embodiments, compound IV-5 is an amorphous solid. In some embodiments, compound IV-5 is a crystalline solid. In some embodiments, Compound IV-5 is a mixture of amorphous solid form and crystalline solid form.

In some embodiments, the present invention provides a form of compound IV-5 substantially free of impurities. As used herein, the term "substantially free of impurities" means that the compound contains no significant amount of extraneous matter. Such extraneous matter may include different forms of compound IV-5, residual solvents, or any other impurities that may result from the preparation of, and/or isolation of, compound IV-5. In certain embodiments, at least about 95% by weight of compound IV-5 is present. In certain embodiments, at least about 99% by weight of compound IV-5 is present.

In other embodiments, compound IV-5 is a crystalline solid substantially free of amorphous compound IV-5. As used herein, the term "substantially free of amorphous compound IV-5" means that the compound contains no significant amount of amorphous compound IV-5. In certain embodiments, at least about 95% by weight of crystalline compound IV-5 is present. In certain embodiments, at least about 99% by weight of crystalline compound IV-5 is present.

In some embodiments, the solid crystalline form of Compound IV-5 is Form A. In some embodiments, Form A of compound IV-5 has a X-Ray diffraction pattern substantially similar to that depicted in FIG. 49A. In some embodiments, Form A of Compound IV-5 may be characterized by a powder X-ray diffraction pattern with at least two characteristic peaks, in degrees 2θ, each selected from the group consisting of the peaks listed in Table 48. In some embodiments, Form A of Compound IV-5 may be characterized by a powder X-ray diffraction pattern with at least three characteristic peaks, in degrees 2θ, each selected from the group consisting of the peaks listed in Table 48. In some embodiments, Form A of Compound IV-5 may be characterized by a powder X-ray diffraction pattern with at least four characteristic peaks, in degrees 2θ, each selected from the group consisting of the peaks listed in Table 48. In some embodiments, Form A of Compound IV-5 may be characterized by a powder X-ray diffraction pattern with at least five characteristic peaks, in degrees 2θ, each selected from the group consisting of the peaks listed in Table 48. In some embodiments, Form A of Compound IV-5 may be characterized by a powder X-ray diffraction pattern with at least six characteristic peaks, in degrees 2θ, each selected from the group consisting of the peaks listed in Table 48.

In some embodiments, Form A of compound IV-5 has a differential scanning calorimetry (DSC) pattern substantially similar to that depicted in FIG. 49C. In some embodiments, Form A of compound IV-5 has a thermogravimetric analysis pattern substantially similar to that depicted in FIG. 49C. In some embodiments, Form A of Compound IV-5 can be characterized by substantial similarity to two or more of these figures simultaneously.

Methods

In some embodiments, provided herein is a method for treating a patient with Intrahepatic Cholangiocarcinoma (ICC) and/or other advanced solid tumors using a compound, or a solvate thereof, or a solid form thereof, or a pharmaceutical composition thereof, as described herein. In some embodiments, a patient has an advanced, unresectable, solid tumor with an FGFR2 alteration. In some embodiments, a patient has a measurable or evaluable disease by RECIST v1.1.

In some embodiments, provided herein is a method for treating a patient with Intrahepatic Cholangiocarcinoma (ICC) and/or other advanced solid tumors using compound I-1, or a solvate thereof, or a solid form thereof, or a pharmaceutical composition thereof, as described herein. In some embodiments, compound I-1, or a solvate thereof, or a solid form thereof, or a pharmaceutical composition thereof, as described herein, is orally administered twice daily. In some embodiments, compound I-1, or a solvate thereof, or a solid form thereof, or a pharmaceutical composition thereof, as described herein, is orally administered twice daily, at 50 mg/dose.

In some embodiments, a patient is 18 years or older. In some embodiments, a patient has a disease that is refractory to standard therapy. In some embodiments, a patient has a disease that has not adequately responded to standard therapy. In some embodiments, a patient has a disease for which standard or curative therapy does not exist. In some embodiments, a patient is intolerant to or have declined standard therapy.

In some embodiments, a patient has Eastern Cooperative Oncology Group (ECOG) performance status (PS) of 0-Disease and FGFR2 status. In some embodiments, a patient has documented FGFR2 alteration in blood and/or tumor per local assessment as defined by one or more of the following:

FGFR2-fusions include genomic translocations expected to create an oncogenic FGFR2-fusion protein detected by DNA or RNA sequencing or break apart FISH;
FGFR2-amplifications include amplified FGFR2 locus with copy number ≥8 [eg. FGFR2 fold-amplification ≥4 per next generation sequencing (NGS) or FGFR2 probe:reference ratio ≥4 per fluorescence in situ hybridization (FISH)] in tumor tissue;
FGFR2 mutations include one or more of the following primary oncogenic FGFR2 mutations or acquired FGFR2 resistance mutations: H167_N173del, S252X, P253X, Y375X, C382X, M537X, N549X, V564X, E565X, L617X, K641X, K659X, and R664X (numbering based on mesenchymal isoform IIIc; X represents any amino acid change).

In some embodiments, a patient has a histologically or cytologically confirmed diagnosis of unresectable ICC or other advanced, unresectable solid tumor. In some embodiments, a patient has documented FGFR2 genomic alteration (fusion, amplification or mutation) in blood and/or tumor tissue per local assessment. In some embodiments, a patient has a potential oncogenic FGFR2 alterations (eg. FGFR2 protein or mRNA overexpression).

In some embodiments, a patient has a confirmed diagnosis of unresectable ICC with FGFR2 fusion (per local assessment of blood and/or tumor) and has received prior treatment with a pan-FGFR inhibitor (eg. pemigatinib, erdafitinib, infigratinib, TAS-120).

In some embodiments, a patient has a confirmed diagnosis of unresectable ICC with FGFR2 fusion (per local assessment of blood and/or tumor) and has NOT received prior treatment with a pan-FGFR inhibitor (eg. pemigatinib, erdafitinib, infigratinib, TAS-120).

In some embodiments, a patient has an advanced, unresectable solid tumor with FGFR2 fusion (per local assessment of blood and/or tumor) other than ICC.

In some embodiments, a patient has an advanced, unresectable solid tumor with FGFR2 amplification (per local assessment of blood and/or tumor).

In some embodiments, a patient has an advanced, unresectable solid tumor with an oncogenic FGFR2 mutation (per local assessment of blood and/or tumor).

In some embodiments, a patient is not a patent, whose cancer has a known primary driver alteration other than FGFR2 that is amenable to approved targeted therapy eg. EGFR, ALK, ROS, RET, PI3K, HER2, BRAF.

In some embodiments, a patient does not have history or ongoing, clinically significant corneal or retinal disorder.

In some embodiments, a patient does not have any of the following within 14 days prior to the first dose of Compound I-1:

a. Platelet count <75×10$^9$/L;
b. Absolute neutrophil count (ANC)<1×10$^9$/L;
c. Hemoglobin <8 g/dL (red blood cell transfusion and erythropoietin may be used to reach 8 g/dL, but must have been administered at least 2 weeks prior to the first dose of Compound I-1);
d. Aspartate aminotransferase (AST) or alanine aminotransferase (ALT) >3× the upper limit of normal (ULN) if no hepatic metastases are present; >5×ULN if hepatic metastases are present;
e. Total bilirubin >1.5×ULN, >3×ULN with direct bilirubin >1.5×ULN in presence of Gilbert's disease;
f. Estimated (Cockroft-Gault formula) or measured creatinine clearance <50 mL/min.

In some embodiments, a patient does not have known active human immunodeficiency virus (HIV) or active hepatitis B virus (HBV) and/or hepatitis C virus (HCV).

In some embodiments, a patient does not have QTcF >480 msec. In some embodiments, a patient does not have history of prolonged QT syndrome or Torsades de pointes. In some embodiments, a patient does not have a familial history of prolonged QT syndrome.

In some embodiments, a patient does not have clinically significant, uncontrolled cardiovascular disease including congestive heart failure Grade III or IV according to the New York Heart Association (NYHA) classification; myocardial infarction or unstable angina within the previous six months, uncontrolled hypertension (Grade 3 or higher), or clinically significant, uncontrolled arrythmia, including bradyarrythmias that may cause QT prolongation (eg. Type II second degree heart block or third-degree heart block).

In some embodiments, a patient does not have central nervous system (CNS) metastases or primary CNS tumor that is associated with progressive neurologic symptoms or requires increasing doses of corticosteroids to control the CNS disease. In some embodiments, a patient is a patient, who requires corticosteroids for management of CNS disease, and the dose has been stable for the 2 weeks preceding Cycle 1 Day 1 (C1D1). In some embodiments, a patient has stable or asymptomatic CNS metastases or primary CNS.

In some embodiments, a patient has not received systemic antineoplastic therapy or radiotherapy within 14 days or 5 half-lives prior to the first dose of Compound I-1.

In some embodiments, a patient has not received local, hepatic therapy (eg. TACE or Y90) within 4 weeks prior to C1D1. In some embodiments, a patient has not received neutrophil growth factor support within 14 days of the first dose of Compound I-1. In some embodiments, a patient is not a patient, who requires treatment with a prohibited medication or herbal remedy that cannot be discontinued at least 2 weeks before the start of Compound I-1 administration.

In some embodiments, a patient has not had a major surgical procedure within 14 days of the first dose of Compound I-1 (procedures such as central venous catheter placement, tumor needle biopsy, and feeding tube placement are not considered major surgical procedures).

In some embodiments, a patient does not have a history of another primary malignancy that has been diagnosed or required therapy within the past year, wherein the primary malignancies is not completely resected basal cell and squamous cell skin cancer, curatively treated localized prostate cancer, curatively treated localized thyroid cancer, or completely resected carcinoma in situ of any site.

In some embodiments, a method provided herein comprises monitoring serum phosphorus levels and/or calcium levels before and/or after administering a compound (e.g., Compound I-1), or a solvate thereof, or a solid form thereof, or a pharmaceutical composition thereof. In some embodiments, a method provided herein does not significantly increase serum phosphorus levels and/or calcium levels. In some embodiments, a method provided herein comprises an increase of serum phosphorus levels and/or calcium levels of no more than about 2%, no more than about 5%, no more than about 10%, no more than about 15%, no more than about 20%, no more than about 25%, or no more than about 30% after administration of a compound (e.g., Compound I-1), or a solvate thereof, or a solid form thereof, or a pharmaceutical composition thereof, compared to before the administration.

In some embodiments, a method provided herein comprises limiting a patient's direct exposure to sunlight to avoid potential phototoxicity. In some embodiments, a method provided herein comprises applying sunscreen on a patient. In some embodiments, a method provided herein comprises advising a patient to use sunscreen and/or to wear sunglasses.

In some embodiments, disclosed herein are methods of inhibiting of FGFR2 activity and are therefore useful for treating one or more disorders associated with activity of FGFR2 or mutants thereof. Thus, in certain embodiments, the present invention provides a method of treating an FGFR2-mediated disorder in a subject comprising administering a therapeutically effective amount of a solid form disclosed herein, or a pharmaceutically acceptable salt thereof, or a disclosed pharmaceutical composition to the subject. In some embodiments, the subject is a human.

As used herein, the term "FGFR2-mediated" disorders, diseases, and/or conditions means any disease or other deleterious condition in which FGFR2 or a mutant thereof is known to play a role. Accordingly, another embodiment of the present invention relates to treating or lessening the severity of one or more diseases in which FGFR2, or a mutant thereof, is known to play a role. Such FGFR2-mediated disorders include but are not limited to proliferative disorders (e.g. cancer) and craniosynostotic syndromes.

In some embodiments, the present invention provides a method for treating one or more disorders, wherein the disorders are selected from proliferative disorders and craniosynostotic syndromes, said method comprising administering to a patient in need thereof, a therapeutically effective amount of a compound of the present invention, or a pharmaceutically acceptable salt thereof, or a pharmaceutically acceptable composition of either of the foregoing. In some embodiments, the present invention provides a method for treating one or more disorders, wherein the disorders are selected from proliferative disorders and craniosynostotic syndromes, said method comprising administering to a patient in need thereof, a therapeutically effective amount of a compound of the present invention, or a pharmaceutically acceptable composition thereof.

In some embodiments, the disorder is associated with FGFR2 signaling. FGFR2 and other receptor tyrosine kinases (RTKs) are known to have multiple upstream and downstream signaling pathways (see Turner and Grose, Nat. Rev. Cancer (2010)10, 116), and inhibition of FGFR2 can be used to treat disorders associated with aberrant signaling within those pathways. In some embodiments, the disorder is associated with FGF signaling, JAK-STAT signaling, PI3K-Akt signaling, PLC-gamma signaling, or MAPK signaling.

In some embodiments, the method of treatment comprises the steps of: i) identifying a subject in need of such treatment; (ii) providing a disclosed compound, or a pharmaceutically acceptable salt thereof; and (iii) administering said provided compound in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a disclosed compound, or a pharmaceutically acceptable salt thereof; and (iii) administering said composition in a therapeutically effective amount to treat, suppress and/or prevent the disease state or condition in a subject in need of such treatment.

Another aspect of the invention provides a compound according to the definitions herein, or a pharmaceutically acceptable salt thereof, or a pharmaceutical composition of either of the foregoing, for use in the treatment of a disorder described herein. Another aspect of the invention provides the use of a compound according to the definitions herein, or a pharmaceutically acceptable salt thereof, or a pharmaceutical composition of either of the foregoing, for the treatment of a disorder described herein. Similarly, the invention provides the use of a compound according to the definitions herein, or a pharmaceutically acceptable salt thereof, for the preparation of a medicament for the treatment of a disorder described herein.

In some embodiments, the disorder is a proliferative disorder. In some embodiments, the proliferative disorder is cancer. In some embodiments, the proliferative disorder is leukemia, breast cancer, lung cancer, colorectal cancer, or a combination thereof. In some embodiments, the proliferative disorder is leukemia. In some embodiments, the proliferative disorder is breast cancer. In some embodiments, the proliferative disorder is lung cancer. In some embodiments, the proliferative disorder is colorectal cancer.

In some embodiments, the proliferative disorder is intrahepatic cholangiocarcinoma, hepatocellular carcinoma, breast cancer, prostate cancer, lung squamous cell carcinoma, thyroid cancer, gastric cancer, ovarian cancer, rectal cancer, endometrial carcinoma, non-small cell lung cancer, or urothelial cancer. In some embodiments, the proliferative disorder is intrahepatic cholangiocarcinoma, hepatocellular carcinoma, breast cancer, prostate cancer, lung squamous cell carcinoma, thyroid cancer, gastric cancer, or ovarian cancer. In some embodiments, the proliferative disorder is gastric cancer, breast cancer, triple negative breast cancer, or rectal cancer. In some embodiments, the proliferative disorder is endometrial carcinoma, non-small cell lung cancer, lung squamous cell carcinoma, gastric cancer, breast cancer, or urothelial cancer.

In some embodiments, the proliferative disorder is associated with one or more activating mutations in FGFR2. In some embodiments, the activating mutation in FGFR2 is a mutation to one or more of the intracellular kinase domain and the extracellular domain. In some embodiments, the activating mutation in FGFR2 is a mutation to the intracellular kinase domain. In some embodiments, the activating mutation in FGFR2 is a mutation to the extracellular domain. In some embodiments the activating mutation in FGFR2 is selected from N549K, K659N/M, S252W, P253R, and combinations thereof. In some embodiments the activating mutation in FGFR2 is N549K or K659N/M. In some embodiments the activating mutation in FGFR2 is N549K. In some embodiments the activating mutation in FGFR2 is K659N/M. In some embodiments the activating mutation in FGFR2 is S252W or P253R. In some embodiments the activating mutation in FGFR2 is S252W. In some embodiments the activating mutation in FGFR2 is P253R.

In some embodiments the proliferative disorder is associated with one or more resistance mutations in FGFR2. In some embodiments the resistance mutation in FGFR2 is selected from V564F, E565A, N549K/H/T, and L617V, and combinations thereof. In some embodiments the resistance mutation in FGFR2 is V564F. In some embodiments the resistance mutation in FGFR2 is E565A. In some embodiments the resistance mutation in FGFR2 is N549K/H/T. In some embodiments the resistance mutation in FGFR2 is L617V.

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including Noonan syndrome (NS), LEOPARD syndrome (Noonan syndrome with multiple lentigines), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2018/057884, WO 2015/107495, WO 2018/172984, and WO 2018/136265; and references cited therein; each of which is hereby incorporated by reference in its entirety. For example, SHP099, RLY1971, RMC-4550, RMC4630, JAB3068, JAB3312, or TN0155.

In some embodiments, compounds or compositions of the disclosure can be used in combination with a compound of the formula:

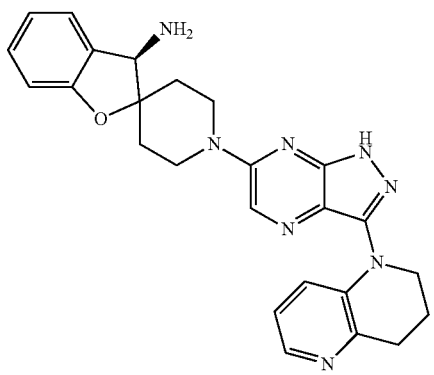

or pharmaceutically acceptable salts thereof.

For example, the compounds disclosed herein (or pharmaceutical compositions containing them) can be used in the treatment of one or more of the diseases mentioned herein, alone or in combination with another therapeutic agent. For example, a compound of Formula (I) can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[(1S,4R)-6-[[4-(Cyclobutylamino)-5-(tjifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2, 4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547. FLT3 inhibitors: sunitinib malate; midostaurin; tanutinib; sorafenib, lestaurtinib, quizartinib and crenolanib. KRAS inhibitors: MRTX849, AMG510. MEK Inhibitors—trametinib, combimetinib, binimetinib, selumetinib. VEGF receptor inhibitors: bevacizumab, axitinib, Aflibercept, (N-methyl-2-[[3-[(E)-2-pyridin-2-ylethenyl]-1H-indazol-6-yl]sulfanyl]benzamide, brivanib alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: Gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: Filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mo choline, 2-Methyl-2-[4-[3-methyl-2-oxo-8-(quinolin-3-yl)-2,3-dihydroimidazo[4,5-c]quinolin-1-yl]phenyl]propiocyano, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CS1 antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.S70, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: bacillus calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Anti-mitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK inhibitors: Alvocidib, palbociclib, ribociclib, trilaciclib, abemaciclib. TRK inhibitors: entrectinib, larotrectinib. RET inhibitors: BLU-667, LOXO-292. Gonadotropin-releasing hormone (GnRH) receptor agonists: Leuprolide or leuprolide acetate. Taxane anti-neoplastic agents: Cabazitaxel (1-hydroxy, 10-dimethoxy-9-oxo-5,20-epoxytax-11-ene-2a,4,13a-triyl-4-acetate-2-benzoate-13-[(2R,3S)-3-{[(tert-butoxy)carbonyl]amino}-2-hydroxy-3-phenylpropanoate), larotaxel ((2α,5β,7β,10β,13α)-4,10-diacetoxy-1-hydroxy-13-{[(2R,3S)-2-hydroxy-3-({[(2-methyl-2-propanyl)oxy]carbonyl}amino)-3-phenylpropanoyl]oxy}-9-oxo-5,20-epoxy-7,19-cyclotax-11-en-2-yl benzoate). 5HTla receptor agonists: Xaliproden (also known as SR57746, 1-[2-(2-naphthyl)ethyl]-4-[3-(trifluoromethyl)phenyl]-1,2,3,6-tetrahydropyridine.

HPC vaccines: Cervarix® sold by GlaxoSmithKline, Gardasil® sold by Merck;

Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine.

Plant Alkaloids: Paclitaxel protein-bound; vinblastine, vincristine, vinorelbine, paclitaxel.

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Claras®, Decutan®, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxy acetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®);

Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, Erwinia L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

Compounds described herein can function, in certain embodiments, as allosteric inhibitors and block the activation of FGFR2 by targeting the auto-inhibited conformation of FGFR2.

The compounds described herein can be linked to one end of a variable chain, while the other end of the variable chain can be bound to the E3 ligase. Recruitment of FGFR2 to the ligase will thus result in the destruction of the FGFR2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetylase inhibitor.

In some embodiments, disclosed compounds can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

A disclosed compound can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, the present disclosure provides for the use of pharmaceutical compositions and/or medicaments comprised of a compound disclosed herein, or a pharmaceutically acceptable salt thereof, in a method of treating a disease state, and/or condition caused by or related to FGFR2 kinase. For example, provided herein are methods of treating subjects in need thereof (e.g., subjects suffering from cancer (e.g., leukemia, breast, lung and/or colorectal cancer) an effective amount of a disclosed compound, and optionally an effective amount of an additional compound (e.g., therapeutic agent) such as disclosed herein.

In some embodiments, a method of treatment comprises the steps of: i) identifying a subject in need of such treatment; (ii) providing a compound disclosed herein, or a pharmaceutically acceptable salt thereof; and (iii) administering said compound in a therapeutically effective amount to treat, suppress and/or prevent the disease state or condition in a subject in need of such treatment.

In some embodiments, a method of treatment comprises the steps of: i) identifying a subject in need of such treatment; (ii) providing a composition comprising a compound disclosed herein, or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the method of treatment, prevention and/or suppression of a condition related to FGFR2 comprises the steps of: i) identifying a subject in need of such treatment; (ii) providing a compound disclosed herein or a pharmaceutically acceptable salt thereof; or a composition comprising a compound disclosed herein, or a pharmaceutically acceptable salt thereof, and a pharmaceutically acceptable carrier; and (iii) administering said compound or composition in a therapeutically effective amount to treat, prevent and/or suppress the disease state or condition related to FGFR2 in a subject in need of such treatment.

In accordance with the methods of the present disclosure, the compounds of the disclosure are administered to the subject in a therapeutically effective amount, e.g., to reduce or ameliorate symptoms related to FGFR2 kinase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years, or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Compositions

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, topical, buccal, ocular, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral, subcutaneous or intravenous administration.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, pharmaceutically acceptable compositions can contain a disclosed compound and/or a pharmaceutically acceptable salt thereof at a concentration ranging from about 0.01 to about 2.0 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the compounds of the disclosure are formulated into pharmaceutical compositions for administration to subjects in a biologically compatible form suitable for administration in vivo. According to another aspect, the present disclosure provides a pharmaceutical composition comprising a disclosed compound in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, the disclosed compound and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. For example, crystalline forms provided herein may be milled to obtain a particular particle size, and in at least some embodiments, such crystalline forms may remain substantially stable upon milling.

For example, provided herein is a composition suitable for subcutaneous administration, comprising a suspension of the disclosed crystalline form. Subcutaneous administration can be advantageous over intravenous administration, which typically requires a doctor visit, and can be more painful and invasive. A typical dose of the crystalline compound, when administered to a patient, may be about 1 mg to about 8 mg of compound. In an embodiment, disclosed herein is a pharmaceutically acceptable composition formed from a disclosed crystalline form, e.g. by mixing a crystalline form with an excipient and/or a solvent.

In an embodiment, provided herein is a composition comprising a disclosed crystalline form suitable for subcutaneous administration at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.001 mg/kg to about 4 mg/kg, from about 0.1 mg/kg to about 10 mg/kg, from about 1 mg/kg to about 25 mg/kg, of subject body weight, administered daily, one or more times a day, every other day, every third or fourth day, every week, every two weeks, every three weeks, or every four weeks. In certain embodiments, the desired dosage may be delivered using multiple administrations (e.g., two, three, four, five, six, seven, eight, nine, or ten administrations). In certain embodiments, administration may occur once, twice, or thrice weekly.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. lower dose sufficient to weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

Composition

In certain embodiments, provided herein is a pharmaceutical composition comprising a crystalline form of compound I-1, or a solvate thereof, as described herein. In certain embodiments, a pharmaceutical composition provided herein comprises one or more pharmaceutically acceptable excipient, as described herein. In some embodiments, provided herein is an immediate-release capsule comprising a crystalline form (e.g., Form A) of compound I-1, or a solvate thereof. In some embodiments, an immediate-release capsule comprises about 10 mg of a crystalline form (e.g., Form A) of compound I-1, or a solvate thereof. In some embodiments, an immediate-release capsule comprises about 50 mg of a crystalline form (e.g., Form A) of compound I-1, or a solvate thereof. In some embodiments, an immediate-release capsule comprises about 100 mg of a crystalline form (e.g., Form A) of compound I-1, or a solvate thereof. In some embodiments, an immediate-release capsule comprises a powder blend intermediate, which can be produced by directly blending a crystalline form (e.g., Form A) of compound I-1, or a solvate thereof, with one or more pharmaceutically acceptable excipients.

Kits

In one embodiment, a kit for treating or mitigating a contemplated disease of disorder is provided. For example, a disclosed kit comprises a disclosed crystalline compound, e.g. a crystalline form of a compound of Formula (I), disposed in an e.g. first container. In some embodiments, a kit may further include a pharmaceutically acceptable excipient, disposed in e.g a second container. Such contemplated kits may include written instructions describing preparation of a pharmaceutical composition suitable for administration to a patient from the crystalline form. For example, the written instructions may describe preparing a pharmaceutically acceptable form for patient administration by e.g. mixing an excipient and a crystalline compound disclosed herein. Disclosed kits may further comprise written instructions describing how to administer the resulting composition to the patient.

Processes

In some embodiments, a process for preparing a disclosed, crystalline form of a compound of Formula (I), e.g., Compound I-1, is contemplated herein, comprising: a) preparing a solution of Compound I-1 in a solvent comprising at least one of EtOH, ACN, MEK, EtOAc, IPAc, IPA, THF, MtBE, Toluene, 1,4 dioxane and water; b) heating the solution to completely dissolve the Compound I-1; c) adjusting the temperature so that solid precipitates out of the solution; and d) isolating the crystalline form of Compound I-1.

In some embodiments, the solvent is EtOH. In some embodiments, the solvent comprises ACN. In some embodiments, the solvent comprises EtOAc. In some embodiments, the solvent comprises IPAc. In some embodiments, the solvent comprises IPA. In some embodiments, the solvent comprises THF. In some embodiments, the solvent comprises MtBE. In some embodiments, the solvent comprises Toluene. In some embodiments, the solvent comprises 1,4 dioxane. In some embodiments, the solvent comprises EtOH and water (9 v/1 v). In some embodiments, heating the solution comprises heating the solution to about 50° C. In some embodiments, adjusting the temperature comprises cooling the solution to about 5° C.

Further disclosed herein is a process for preparing a compound of Formula I-1, the process comprising the step of acidifying a compound of Formula I-2 with an HCl solution, thereby forming the compound of Formula I-1:

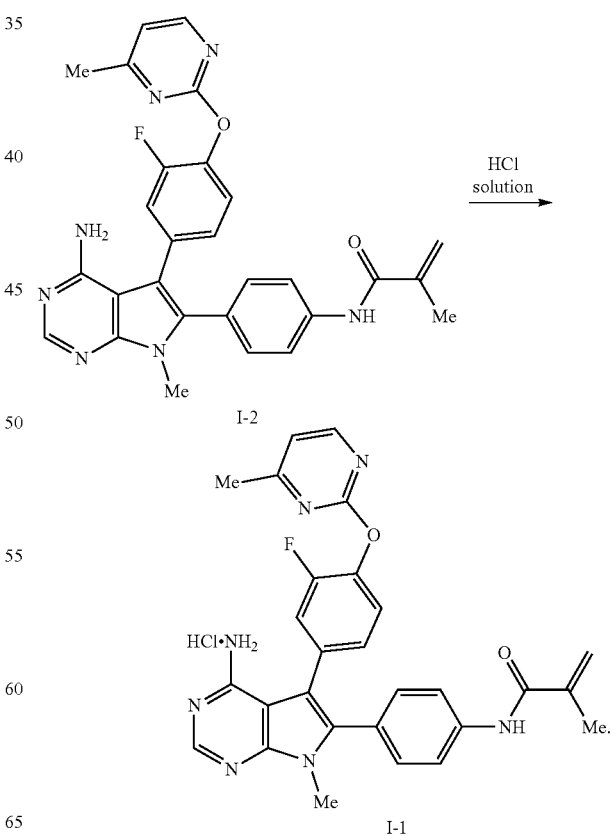

In other embodiments, a disclosed process further comprises the step of coupling a methacrylic anhydride with compound of Formula 3, thereby forming the compound of Formula I-2:

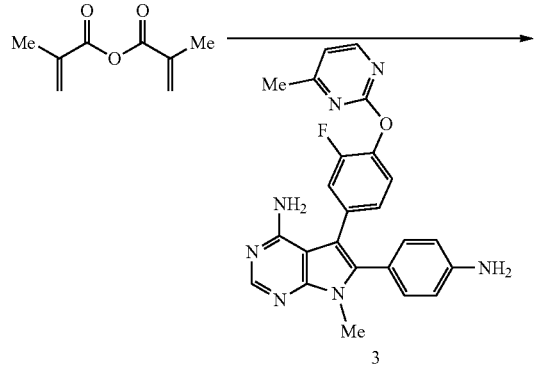

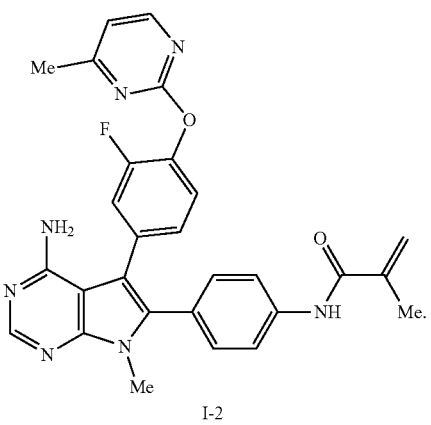

In other embodiments, a disclosed process further comprises the step of coupling a compound of Formula 1 with compound of Formula 2, thereby forming the compound of Formula 3:

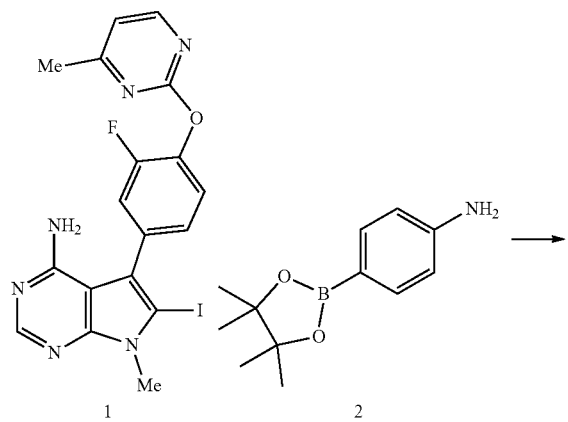

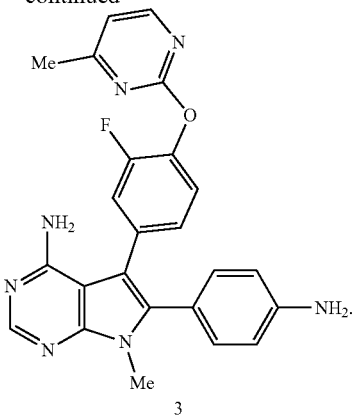

Deuterated Analogues

It will be appreciated by one of skill in the art, that deuterated analogues of compounds of Formula (I), Formula (II), Formula (III), or Formula (IV) may be made with deuterated starting materials using the synthetic processes described herein. As used herein, "deuterated analogues" of a formula means compounds having a structure of said formula except for the structure has at least one replacement of a hydrogen with a deuterium.

In one aspect, the synthetic processes and methods delineated herein contemplate the use of deuterated compounds for use in producing deuterated analogues of compounds of Formula (I). In some embodiments, the present disclosure contemplates deuterated anologues of Formula (I). For example, synthesis of deuterated analogues of Formula (I) are contemplated but not limited to the following compounds:

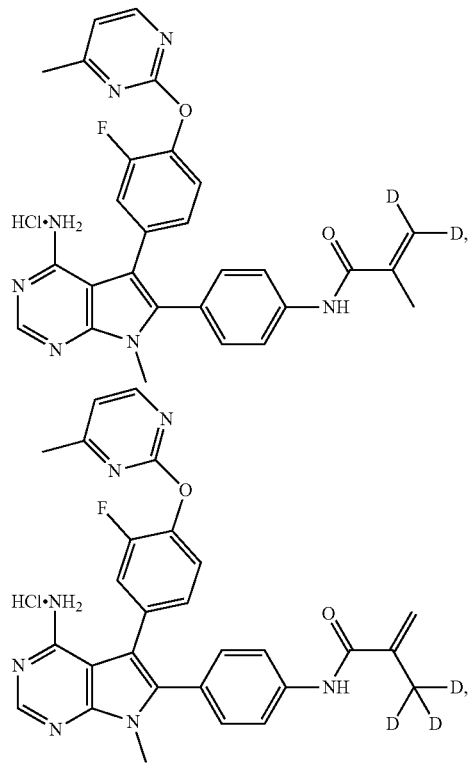

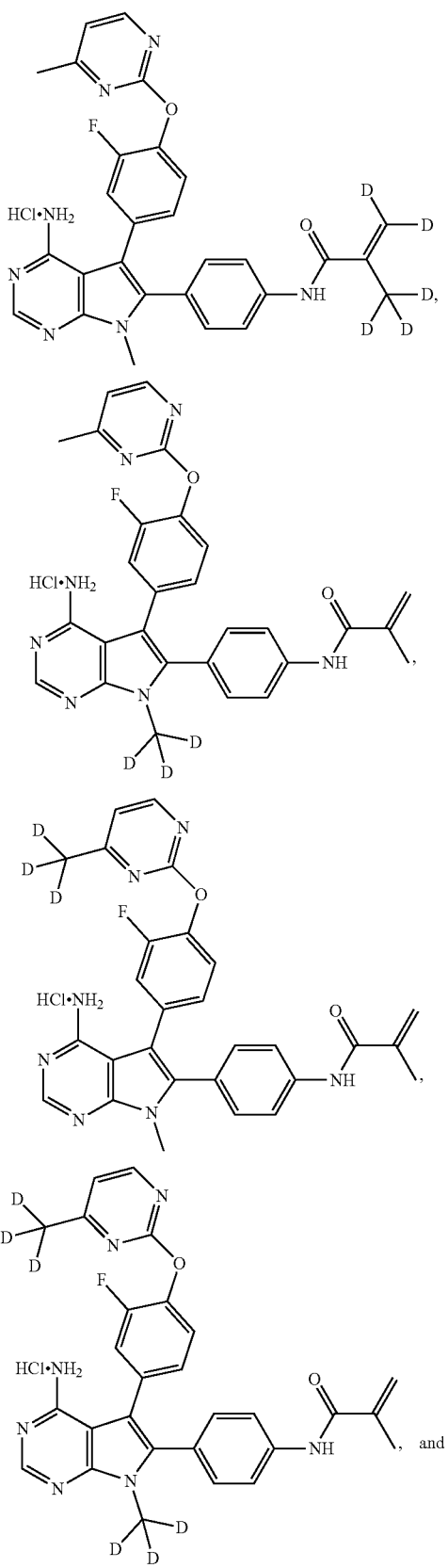

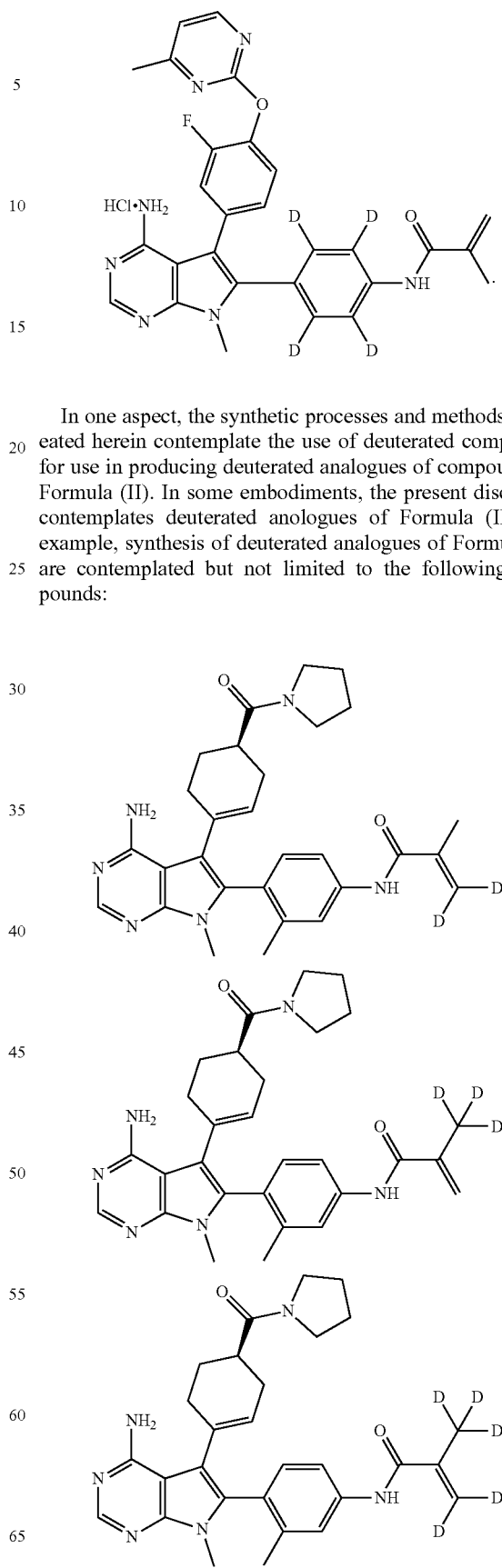

In one aspect, the synthetic processes and methods delineated herein contemplate the use of deuterated compounds for use in producing deuterated analogues of compounds of Formula (II). In some embodiments, the present disclosure contemplates deuterated anologues of Formula (II). For example, synthesis of deuterated analogues of Formula (II) are contemplated but not limited to the following compounds:

-continued

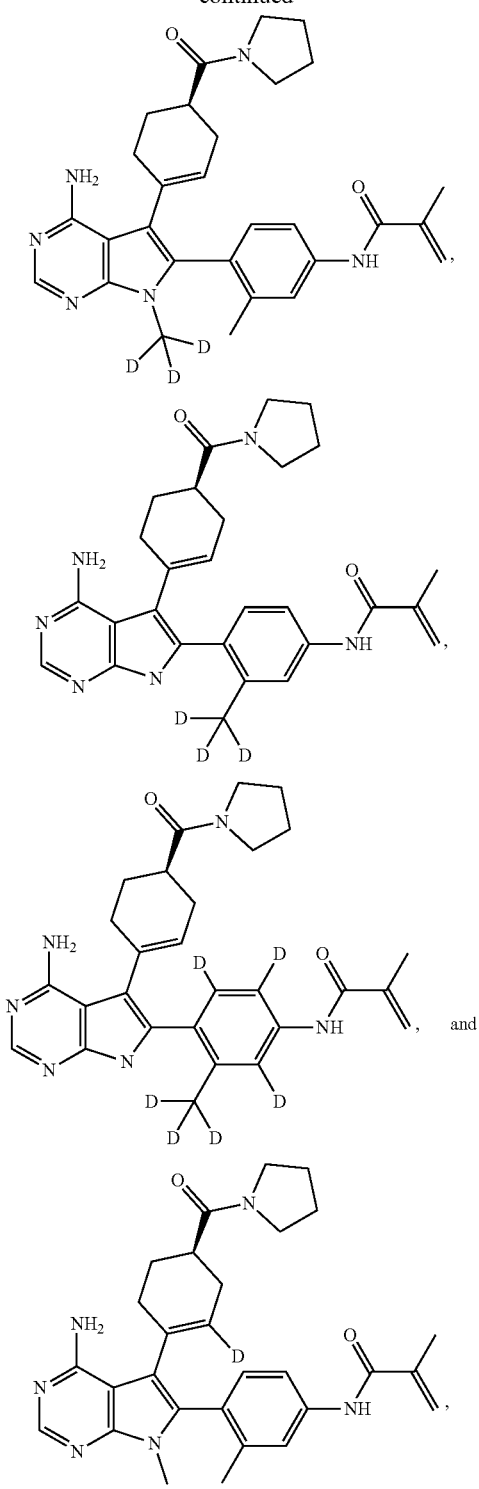

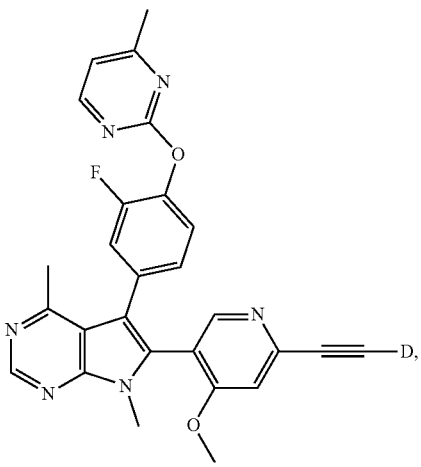

In one aspect, the synthetic processes and methods delineated herein contemplate the use of deuterated compounds for use in producing deuterated analogues of compounds of Formula (III). In some embodiments, the present disclosure contemplates deuterated anologues of Formula (III). For example, synthesis of deuterated analogues of Formula (III) are contemplated but not limited to the following compounds:

81
-continued

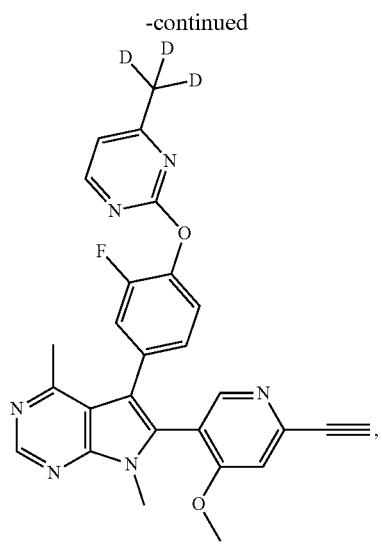

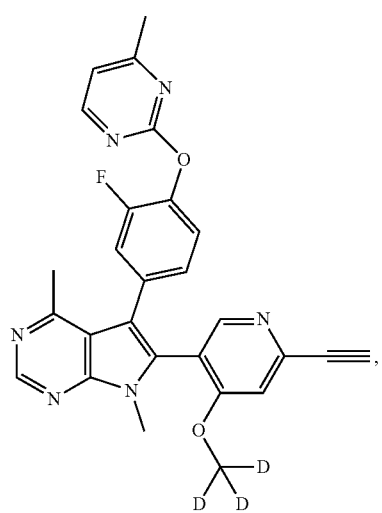

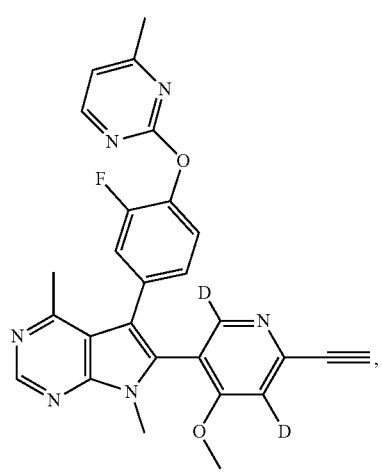

82
-continued

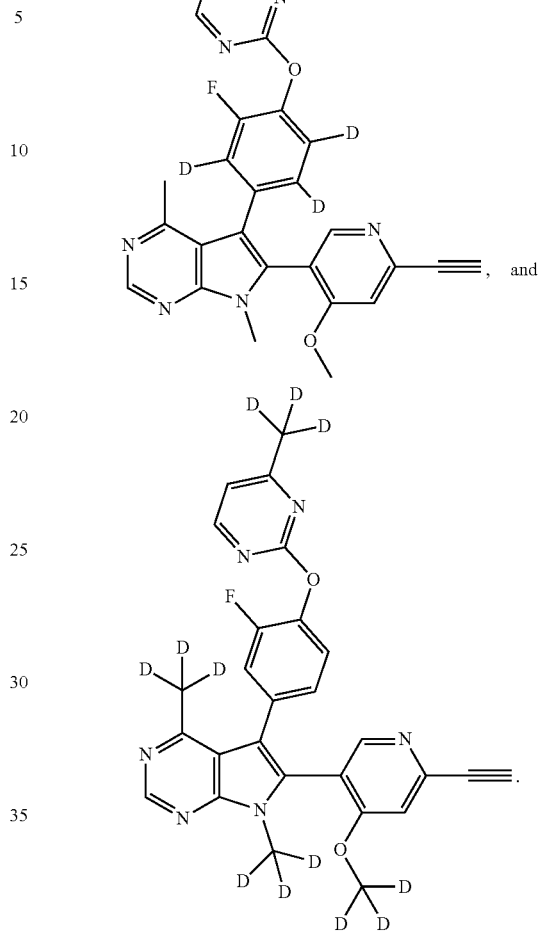

In one aspect, the synthetic processes and methods delineated herein contemplate the use of deuterated compounds for use in producing deuterated analogues of compounds of Formula (IV). In some embodiments, the present disclosure contemplates deuterated analogues of Formula (IV). For example, synthesis of deuterated analogues of Formula (IV) are contemplated but not limited to the following compounds:

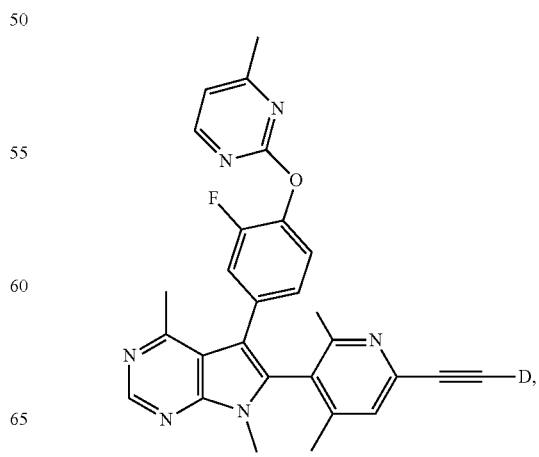

-continued
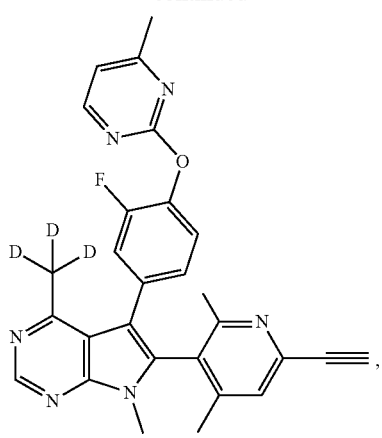
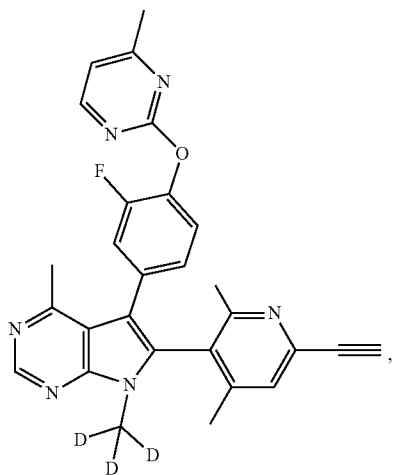
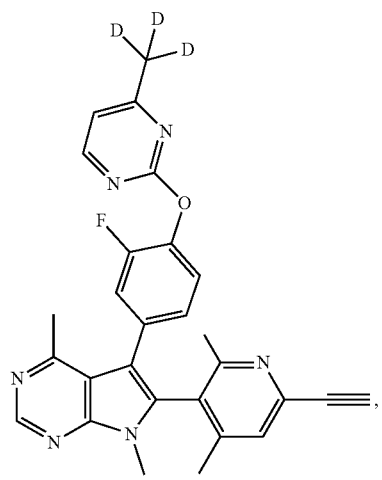
-continued
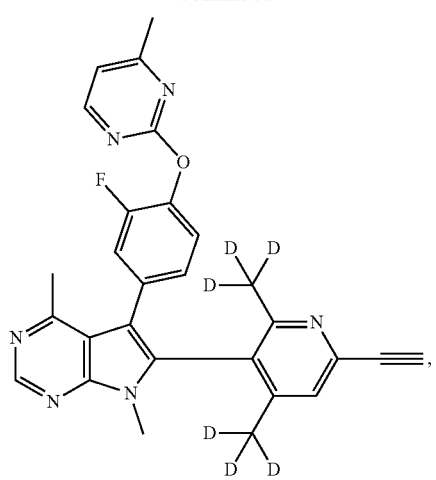
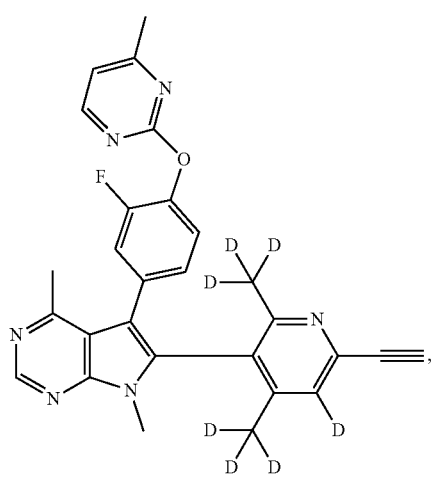
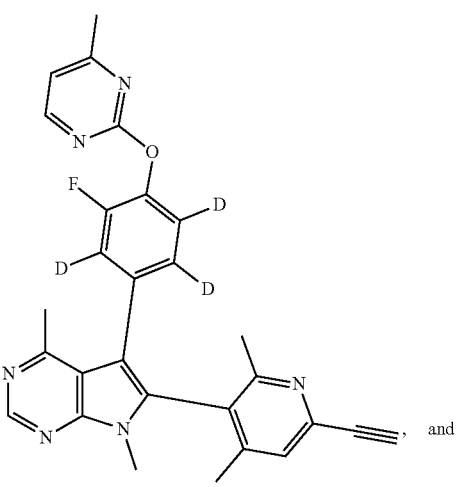
and -continued

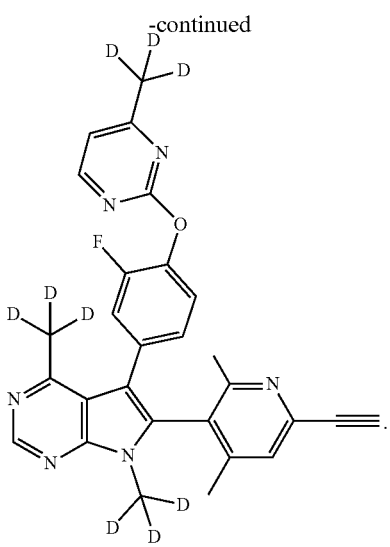

EXAMPLES

The compounds described herein can be prepared in a number of ways based on the teachings contained herein and synthetic procedures known in the art. The following non-limiting examples illustrate the disclosures herein.

X-ray Powder Diffraction (XRPD): Unless otherwise specified, X-Ray Powder Diffraction patterns were collected on a Bruker D2 Phaser Gen 2 using Cu Kα radiation (30 kV, 10 mA), θ-θ goniometer, divergence slit (0.2 mm) and an SSD160 (1D Mode) Detector with a 4.799° opening. The software used for data collection was Diffrac.Commander version 6.5.0.1 and the data was presented using Diffra.Eva version 4.2.1.11. XRPD diffractograms were acquired under ambient conditions via reflection on a flat silica zero background plate with rotation at 15 revolutions per minute. The data collection range was 3.0-40.0° 2θ with a step size of 0.02025° and a collection time of 0.25 seconds per step.

Differential Scanning calorimetry (DSC): DSC data was collected on a TA Instruments Q2000 DSC. A predefined amount of the sample, 2.0 to 10.0 mg, was placed in an aluminum pan and heated at 10° C./minute from 40 C to 300 C, or varied as experimentation dictated. A purge of dry nitrogen at 100 ml/minute was maintained over the sample. The instrument control and data acquisition are acquired using Q Advantage software release version 5.5.23. The data was processed and presented using the TA Universal Analysis 2000 software version 4.5A build 4.5.0.5.

Thermal Gravimetric Analysis (TGA): TGA data was collected on a TA Instruments Q5000 TGA. A predefined amount of the sample, 2.0 to 10.0 mg, was placed in an aluminum pan and heated at 10° C./minute from 40° C. to 300° C., or varied as experimentation dictated. A purge of dry nitrogen at 25 ml/minute was maintained over the sample. The instrument control and data acquisition are acquired using Q Advantage software release version 5.5.23. The data was processed and presented using the TA Universal Analysis 2000 software version 4.5A build 4.5.0.5.

Dynamic Vapour Sorption (DVS): Dynamic Vapour Sorption (DVS) was carried out using the TA Instruments QS000 SA. A predefined amount of the sample, 2.0 to 10.0 mg, was placed in a platinum pan. The sample was allowed to equilibrate at 50° C. at 0% relative humidity (RH) for a period of 60 minutes. The sample was then equilibrated at 25° C. before ramping the humidity from 0 to 95% RH at 5% increments every hour. A similar ramp profile was used for desorption cycle. XRPD analysis was also performed on post DVS sample.

| Hygroscopicity Classification | Water Sorption Criterion* |
|---|---|
| Deliquescent | Sufficient water is absorbed to form a liquid |
| Very Hygroscopic | W % ≥ 15% |
| Hygroscopic | W % ≥ 2% |
| Slightly Hygroscopic | W % ≥ 0.2% |
| Non-hygroscopic | W % < 0.2% |

*At 25 = 1° C. and 80 ± 2% RH (European Pharmacopoeia 6.0)

Ion Chromatography (IC): Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analyzed. Analyses were performed in duplicate and an average of the values is given unless otherwise stated. Method for cation chromatography:

| Parameter | Value |
|---|---|
| Type of method | Cation exchange |
| Column | Metrosep C 4-250 (4.0 × 250 mm) |
| Column Temperature (° C.) | Ambient |
| Injection (μl) | Various |
| Detection | Conductivity detector |
| Flow Rate (ml/min) | 0.9 |
| Eluent | 1.7 mM nitric acid 0.7 mM dipicolinic acid in a 5% acetone aqueous solution. |

Method for anion chromatography:

| Parameter | Value |
|---|---|
| Type of method | Anion exchange |
| Column | Metrosep A Supp 5-150 (4.0 × 250 mm) |
| Column Temperature (° C.) | Ambient |
| Injection (μl) | Various |
| Detection | Conductivity detector |
| Flow Rate (ml/min) | 0.7 |
| Eluent | 3.2 mM sodium carbonate 1.0 mM sodium hydrogen carbonate in a 5% acetone aqueous solution. |

Example 1—Synthesis of N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide hydrochloride (Compound I-1)

Step 1. Preparation of Compound 3

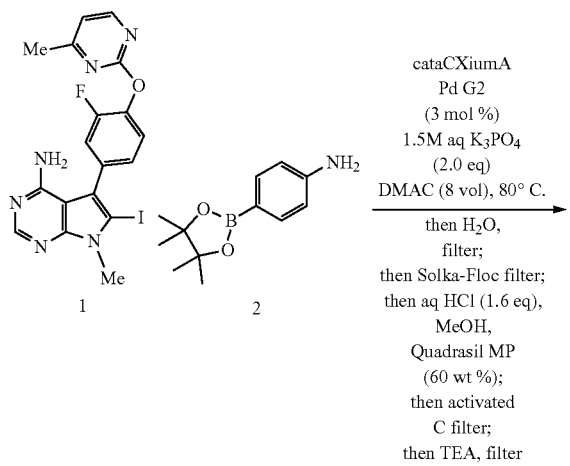

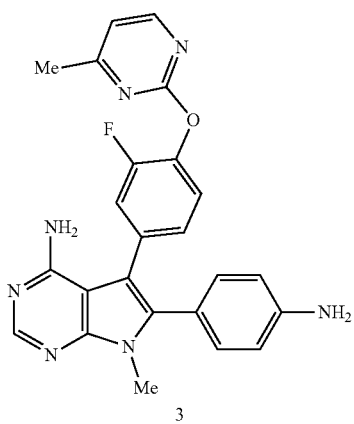

A 400 L glass-lined vessel was inerted with nitrogen and rinsed with purified water prior to starting the reaction. The 400 L vessel was charged with purified water (31.4 kg, 2.5 vol) and potassium phosphate tribasic anhydrous (11.1 kg, 2 eq). The mixture was agitated and cooled to 15.4° C. The aqueous K₃PO₄ was discharged into a clean plastic drum. The 400 L vessel was charged with compound 1 (12.5 kg, 1 eq) and compound 2 (9.6 kg, 1.2 eq), then flushed with nitrogen. Dimethylacetamide (DMAc, 94.8 kg, 8 vol) was added, followed by the aqueous K₃PO₄. Addition of aqueous K₃PO₄ was moderately exothermic. The addition rate was adjusted to keep the reaction temperature under 60° C. ($t_{max}$ 31.1° C.). The reaction mixture was heterogeneous at this point. The vessel content was degassed by nitrogen pressure cycles from 1 barg to 0 barg (3 times). Then, the vessel was charged with cataCXium A Pd G2 (chloro[(di(1-adamantyl)-N-butylphosphine)-2-(2-aminobiphenyl)]palladium(II), 0.53 kg, 3 mol %) as a suspension in DMAc (0.93+0.95 kg). The catalyst formed a thick suspension in DMAc. The vessel contents were heated at 80° C. for 2 hr. The reaction color changed from pale brown to dark brown as it progressed. The reaction mixture was cooled to 19.9° C. The vessel was charged with purified water (150.2 kg, 12 vol) over 2 hr, while keeping the contents below 25° C. (tr 15.9-20.3° C.). The reaction mixture was aged at 15.4° C. for 16 hr.

The mixture was filtered on a large Oyster filter (ø820 mm), and the cake was washed with 1:1 DMAc-water (11.6+12.5 kg, 1+1 vol), then with pure water (50.2 kg, 4 vol), to give a water-wet cake of crude material. The crude filter cake was transferred into the 400 L vessel. The vessel was then charged with MeOH (88.8 kg, 9 vol) and the contents was cooled to below 20° C. (tr 16.5° C.). Aq. HCl (4.16 kg, 1.6 eq) was added with a dosing pump over 12 min, while keeping the vessel contents below 20° C. (tr 13.9-16.8° C.). Vsolution=135 L. The large Oyster filter was charged with Solka-Floc 100 NF (6.0 kg, to form a bed ca. 5 cm thick). The contents of the 400 L vessel were then filtered through the Solka-Floc, and the waste cake was washed with MeOH (10.4 kg, 1 vol). The filtration took ca. 1.5 hr. The filtered solution of compound 4·HCl in MeOH was recharged into the 400 L vessel. A small Oyster filter (0416 mm) was charged with Quadrasil MP (7.0 kg, 60 wt % wrt theoretical compound 4), and the 400 L vessel contents were recirculated through this scavenger for 4 hr.

The solution was pumped from the small Oyster filter back into the 400 L vessel, and the scavenger cake was washed with MeOH (10.2 kg, 1 vol) into the same vessel. A 110 L CUNO unit was assembled with a 12" carbon cartridge (R53SP). The contents of the 400 L vessel were recirculated through the carbon cartridge of the CUNO unit for 1 hr. The contents of the CUNO unit were pumped into the 400 L vessel. The unit was then washed with MeOH (10.2 kg, 1 vol). The 400 L vessel was charged with a solution of triethylamine (4.26 kg, 1.6 eq) in MeOH (9.8 kg, 1 vol) over 2 hr, while keeping the contents temperature below 20° C. (tr 13.0-13.8° C.), to precipitate compound 3 as a free base. The resulting slurry was aged at 15.2° C. for 18 hr. The slurry was filtered through an Oyster filter and the filter cake was rinsed with MeOH (20.2 kg, 2 vol). The product cake was dried at 50° C. in vacuum for 16 hr. Compound 3 was obtained (11.59 kg, yield: 83.0%).

Step 2. Preparation of Compound I-1 Mixture

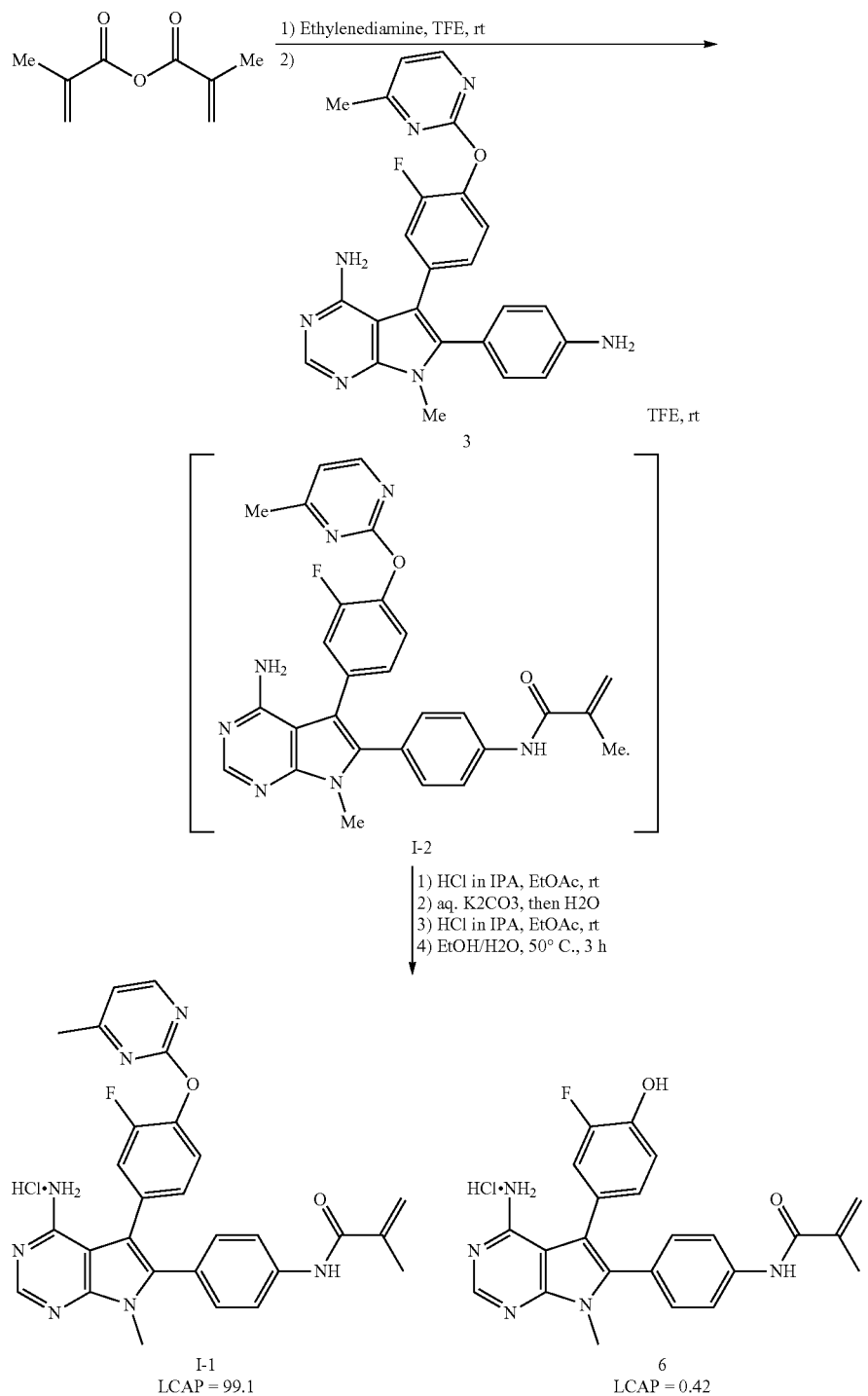

A 400 L glass-lined reactor was placed under full vacuum for 3 hours prior to starting the batch in order to remove traces of residual cleaning solvents. All processing was conducted under a nitrogen atmosphere. The reactor was charged with 2,2,2-trifluoroethanol (TFE) (52.8 kg, 4 vol) and methacrylic anhydride (7.1 kg, 94 wt %, 43.0 mol, 2.0 equiv) and the contents were cooled to 10° C. A solution of ethylenediamine (0.26 kg, 4.3 mol, 0.2 equiv) in TFE (2.8 kg, 0.2 vol) was added while keeping the temperature below 30° C. and the contents were aged at 20° C. for 1 hour. A pre-mixed solution of compound 3 (9.5 kg, 21.5 mol, 1.0 equiv) in TFE (79.2 kg, 6 vol) was added and the contents were aged at 20° C. for 16 hr. The clear solution of compound 4 was discharged from the reactor to a clean, plastic-lined drum.

All reaction mixtures, solvents, and liquid reagent from this point onward were charged to the vessel via a 1.0 micron filter to clarify the batch. The reaction mixture was recharged into the 400 L vessel and the solution concentrated under partial vacuum at <45° C. to a volume of 19 L. The resulting solution was diluted with EtOAc (171 kg, 20 vol) and the batch was cooled to 20° C. While keeping the vessel content below 25° C., 6N HCl in isopropanol (3.2 kg, 21.5 mol, 1.0 equiv) was added over 1 hour. The suspension was then aged at 20° C. for 17.5 hours.

While keeping the vessel content below 25° C., 6N HCl in isopropanol (3.2 kg, 21.5 mol, 1.0 equiv) was added over 1 hour. The suspension was then aged at 20° C. for 17.5 hours. The mixture was filtered through a large Oyster filter, and the cake washed with EtOAc (17.1 kg (2 vols)×2). The filtration was very fast (<10 min). A sample was removed from the wet cake to check the form of the solid by XRPD. The polymorph "Form D" was obtained.

The wet cake was recharged into the 400 L vessel and EtOAc (213.8 kg, 25 vols) was added. A 0.5 M solution of $K_2CO_3$ (49.7 kg, 23.77 mol, 1.1 equiv) was added over 30 mins. By the end of the addition the suspension had turned into clear, biphasic mixture. The contents were aged for 1 hour. A precipitate of the freebase forms within minutes of the end of aq. $K_2CO_3$ addition. A sample was removed from the bottom aqueous layer to check the pH using pH paper. The pH was 9. The mixture was filtered through a large Oyster filter, and the cake washed with EtOAc/$H_2O$ 1:1 (2 vols). The filtration was fast (<15 min). The biphasic aq $K_2CO_3$/EtOAc solution was recharged into the 400 L vessel and the bottom aqueous layer removed. The organic layer was washed with $H_2O$ (47.5 kg, 5 vols) and the bottom aqueous layer removed. The wet cake was charged in the 400 L vessel in EtOAc. While keeping the vessel content below 25° C., 6N HCl in isopropanol (3.6 kg, 23.7 mol, 1.1 equiv) was added over 1 hour. The suspension was then aged at 20° C. for 17.5 hours. The mixture was filtered through a large Oyster filter, and the cake washed with EtOAc (17.1 kg (2 vols)×2). The filtration was very fast (<10 min). A sample was removed from the wet cake to check the form of the solid by XRPD. The polymorph "Form J" was obtained.

The wet cake was recharged into the 400 L vessel and water (4.8 kg, 0.5 vols) and ethanol (EtOH) (33.8 kg, 4.5 vols) were added. The suspension was warmed up from 20 to 50° C. over 150 mins, kept at 50° C. for 180 mins and cooled down from 50 to 20° C. over 150 mins. The suspension was aged at 20° C. for 10 hours. The suspension was again warmed up from 20 to 50° C. over 150 mins, kept at 50° C. for 180 mins and cooled down from 50 to 20° C. over 150 mins. The suspension was aged at 20° C. for 10 hours. A sample was removed to check the form of the solid by XRPD. Polymorph "Form A" was obtained. The mixture was filtered through a medium Oyster filter, and the cake was washed with EtOH/$H_2O$ 9:1 (2 vols). The product was dried in vacuo at 60° C. under a nitrogen sweep for 18.5 hours, to afford 9.00 kg of Compound I-1 (77% yield) and compound 6. Compound I-1: MS [M+1]=510.20. $^1$H NMR (400 MHz, DMSO-d6) δ 9.92 (s, 1H), 8.47 (d, J=5.0 Hz, 1H), 8.21 (s, 1H), 7.78-7.66 (m, 2H), 7.33 (m, J=8.6, 2.3 Hz, 3H), 7.21-7.16 (m, 2H), 7.12 (s, OH), 5.80 (s, 1H), 5.54 (d, J=1.7 Hz, 1H), 3.59 (s, 3H), 2.42 (s, 3H), 1.95 (d, J=1.2 Hz, 3H).

A HPLC method on Column: HALO ES-CN, 4.6×150 mm 2.7 um; at Flow rate: 1.0 mL/min; column temp: 40 C; with Mobile Phase A: 0.1% TFA in water; Mobile Phase B: 0.1% TFA in acetonitrile; and the following gradient:

| Time (minutes) | % A | % B |
|---|---|---|
| 0 | 90 | 10 |
| 4 | 70 | 30 |
| 17.5 | 50 | 50 |
| 18 | 30 | 70 |
| 20 | 90 | 10 |
| 25 | 90 | 10 | revealed a liquid chromatography area percentage (LCAP) of 99.1 for Compound I-1 and a LCAP of 0.42 for compound 6 (RRT=0.84).

Example 2—Purification of Compound I-1

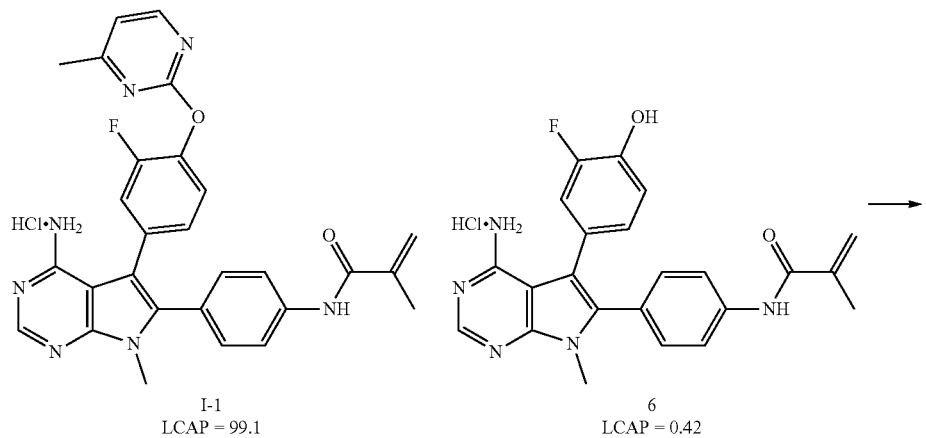

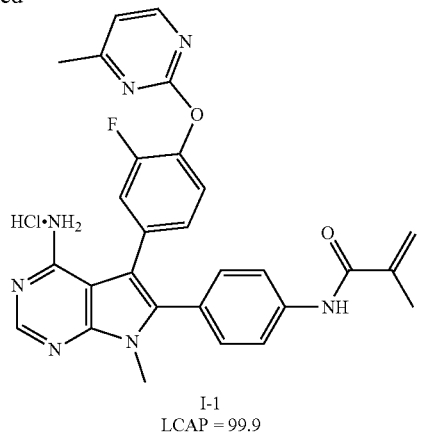

I-1
LCAP = 99.9

All processing was conducted under a nitrogen atmosphere. The vessel was rinsed with methanol (MeOH) (12.6 kg), which was discarded to waste. All solvents and liquid reagent from this point onward were charged to the vessel via a 1.0 micron filter to clarify the batch. The reactor was charged with the crude mixture, containing Compound I-1 (3.8 kg, 7.0 mol, 1.0 eq) and impurity compound 6 from Step 2 of Example 1, and methanol (42.1 kg, 14 vol), and the contents were cooled to 18° C. A solution of NaOH (46-51% in $H_2O$, 1.1 kg, 8.4 mol, 1.2 eq) in MeOH (3.0 kg, 1.0 vol) was added over 5 minutes. During the addition of NaOH the solvent was absorbed by the solid forming a gel which turned again to a suspension after 3-4 mins.

The contents were aged at 20° C. for 3 hrs. A sample was removed to check the LCAP of impurity compound 6 in the solid by HPLC. The LCAP of compound 6 in the solid was 0.02. The suspension was filtered through a small Oyster filter, and the cake was washed with MeOH (4 vols). The wet cake was recharged in the vessel and ethyl acetate (34.3 kg, 10 vols) was added. While keeping the vessel content below 25° C., 6N HCl in isopropanol (1.0 kg, 7.0 mol, 1.0 eq) was added over 30 mins. The suspension was then aged at 20° C. for 4 hrs. A sample was removed to check the LCAP of impurity compound 6 in the solid by HPLC. The LCAP of compound 6 in the solid was 0.02. The suspension was filtered through a small Oyster filter, and the cake washed with EtOAc (6.9 kg (2 vols) and then with ethanol (EtOH) (12.0 kg (4 vols)×2). A sample was removed from the wet cake to check the form of the solid by XRPD. A mixture of polymorphs Form A and 4 was obtained.

The wet cake was recharged into the vessel and water (1.9 kg, 0.5 vols) and ethanol (13.5 kg, 4.5 vol) were added. The suspension was warmed up from 20 to 50° C. over 150 mins, kept at 50° C. for 180 mins and cooled down from 50 to 20° C. over 150 mins. The suspension was aged at 20° C. for 10 hrs. A sample was removed to check the form of the solid by XRPD. Polymorph "Form A" was obtained. A sample was removed to check the LCAP of impurity compound 6 in the solid by HPLC (Column: HALO ES-CN, 4.6×150 mm 2.7 um; Flow rate: 1.0 mL/min; column temp: 40 C; run time: 25 min; Mobile Phase A: 0.1% TFA in water; Mobile Phase B: 0.1% TFA in acetonitrile; RT1: 7.8 min (compound 6); RT2: 9.1 min (compound I-1)). The LCAP of compound 6 in the solid was 0.02. The mixture was filtered through a small Oyster filter, and the cake was washed with EtOH/$H_2O$ 9:1 (2 vols). The filtration was very fast (<10 min). The product was dried in vacuo at 60° C. under a nitrogen sweep for 18.5 hours, to afford 2.8 kg of Compound I-1 (74% yield, LCAP=99.9)

Conclusion: The goal was to develop a process to reduce the level of the impurity RRT 0.84 from 0.42 LCAP, as shown in Example 1, to less than 0.15 LCAP. Using this optimized process, the impurity RRT 0.84 was reduced to 0.02 LCAP against a target of less than 0.15 LCAP, and the overall purity was increased from 99.1 LCAP to 99.9 LCAP.

Example 3—Synthesis of (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide (Compound II-1)

methacryloyl chloride

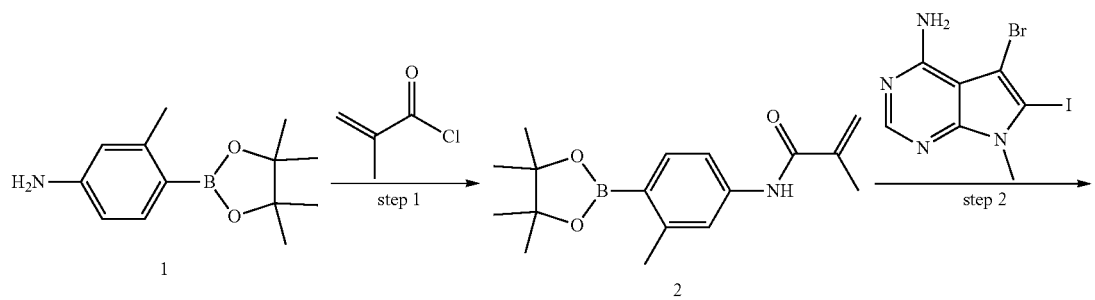

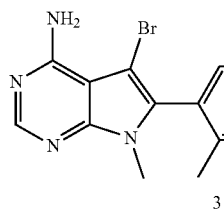

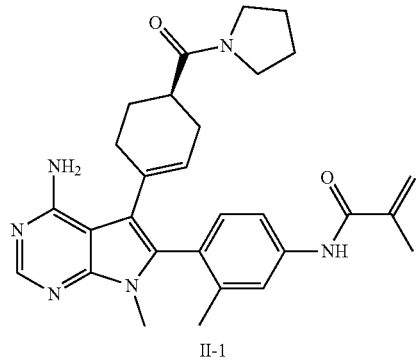

Step 1. Preparation of N-(3-methyl-4-(4,4,5,5-tetramethyl-1,3,2-dioxaborolan-2-yl)phenyl)methacrylamide

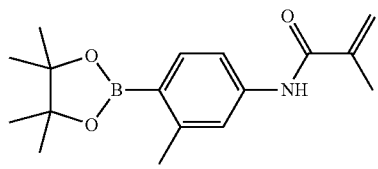 [SMILES: C=C(C)C(=O)Nc1ccc(B2OC(C)(C)C(C)(C)O2)c(C)c1]

A round bottomed flask was charged with 3-methyl-4-(4,4,5,5-tetramethyl-1,3,2-dioxaborolan-2-yl)aniline (10 g, 42.8 mmol), methacryloyl chloride (3.87 g, 42.8 mmol), pyridine (10.1 g, 128 mmol), dichloromethane (150 mL) and a stirbar. The solution was stirred for 1 h at 0° C. The reaction mixture was quenched with water, extracted with DCM. The organic phase was dried over $Na_2SO_4$, filtered, and evaporated in vacuo. The resulting crude material was purified by silica gel chromatography. Concentration in vacuo resulted in N-(3-methyl-4-(4,4,5,5-tetramethyl-1,3,2-dioxaborolan-2-yl)phenyl)methacrylamide (12 g, 98%) as a yellow oil.

Step 2: Preparation of N-(4-(4-amino-5-bromo-7-methyl-7H-pyrrolo[2,3-d]pyrimidin-6-yl)-3-methylphenyl)methacrylamide

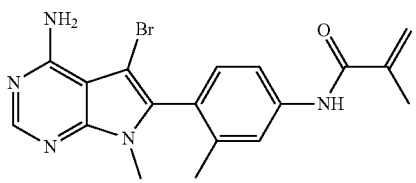 [SMILES: C=C(C)C(=O)Nc1ccc(-c2c(Br)c3c(N)ncnc3n2C)c(C)c1]

A round bottomed flask was charged with N-(3-methyl-4-(4,4,5,5-tetramethyl-1,3,2-dioxaborolan-2-yl)phenyl)methacrylamide (1 g, 3.48 mmol), 5-bromo-6-iodo-7-methyl-7H-pyrrolo[2,3-d]pyrimidin-4-amine (1.22 g, 3.48 mmol), Pd(dppf)Cl$_2$ (254 mg, 348 μmol), K$_3$PO$_4$ (2.20 g, 10.4 mmol), DMF/H$_2$O (16:1) (15 mL) and a stirbar. The solution was stirred for 2 h at 50° C. The reaction mixture was quenched with water, extracted with DCM. The organic phase was washed with brine three times, dried over $Na_2SO_4$, filtered, and evaporated in vacuo. The resulting crude material was purified by silica gel chromatography. Concentration in vacuo resulted in N-(4-(4-amino-5-bromo-7-methyl-7H-pyrrolo[2,3-d]pyrimidin-6-yl)-3-methylphenyl)methacrylamide (440 mg, 33%) as a solid.

Step 3: (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide

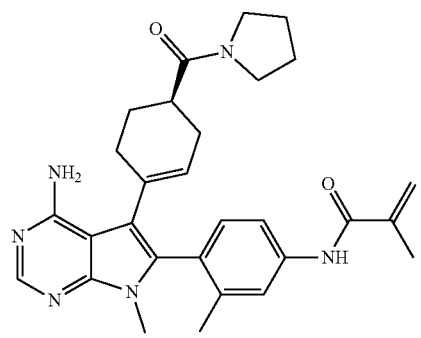 [SMILES: C=C(C)C(=O)Nc1ccc(-c2c(C3=CC[C@H](C(=O)N4CCCC4)CC3)c3c(N)ncnc3n2C)c(C)c1]

A resealable reaction vial was charged with N-(4-(4-amino-5-bromo-7-methyl-7H-pyrrolo[2,3-d]pyrimidin-6-yl)-3-methylphenyl)methacrylamide (200 mg, 517 μmol), 1-[(1R)-4-(4,4,5,5-tetramethyl-1,3,2-dioxaborolan-2-yl)cyclohex-3-ene-1-carbonyl]pyrrolidine (156 mg, 517 μmol), Pd(pddf)Cl₂ (37.8 mg, 517 μmol), Na₂CO₃ (164 mg, 1.55 mmol), DMF (10 mL) and a stirbar before being evacuated and purged with nitrogen three times. The mixture was stirred for 2 h at 90'C. The reaction mixture was quenched with water, extracted with DCM. The organic phase was washed with brine three times, dried over Na₂SO₄, filtered, and evaporated in vacuo. The resulting crude material was purified by prep-HPLC (Column: YMC-Actus Triart C18, 30*250.5 um; Mobile Phase A: Water (10 MMOL/L NH₄HCO₃), Mobile Phase B: ACN; Flow rate: 50 mL/min; Gradient: 40 B to 62 B in 8 min; 220 nm. Lyophilization yielded (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide (40 mg, 16%) as a solid. MS [M+1]=499.35. 1H NMR (400 MHz, DMSO-d6) δ 9.87 (s, 1H), 8.10 (s, 1H), 7.71 (t, J=2.7 Hz, 1H), 7.62 (ddd, J=8.0, 5.6, 2.2 Hz, 1H), 7.18 (dd, J=8.3, 6.6 Hz, 1H), 6.48 (d, J=17.0 Hz, 2H), 5.91-5.79 (m, 1H), 5.66 (ddt, J=14.5, 4.1, 2.2 Hz, 1H), 5.54 (t, J=1.5 Hz, 1H), 3.56-3.39 (m, 2H), 3.34 (s, 3H), 3.27 (q, J=6.9 Hz, 2H), 2.73 (p, J=6.3 Hz, 1H), 2.21 (q, J=15.7, 12.1 Hz, 2H), 2.06 (s, 3H), 2.01-1.80 (m, 7H), 1.80-1.70 (m, 2H), 1.56 (q, J=7.9, 7.0 Hz, 2H).

Example 4—Synthesis of 6-(6-ethynyl-4-methoxy-pyridin-3-yl)-5-(3-fluoro-4-((4-methylpyrimidin-2-yl)oxy)phenyl)-4,7-dimethyl-7H-pyrrolo[2,3-d]pyrimidine (Compound III-1)

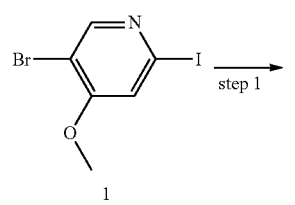

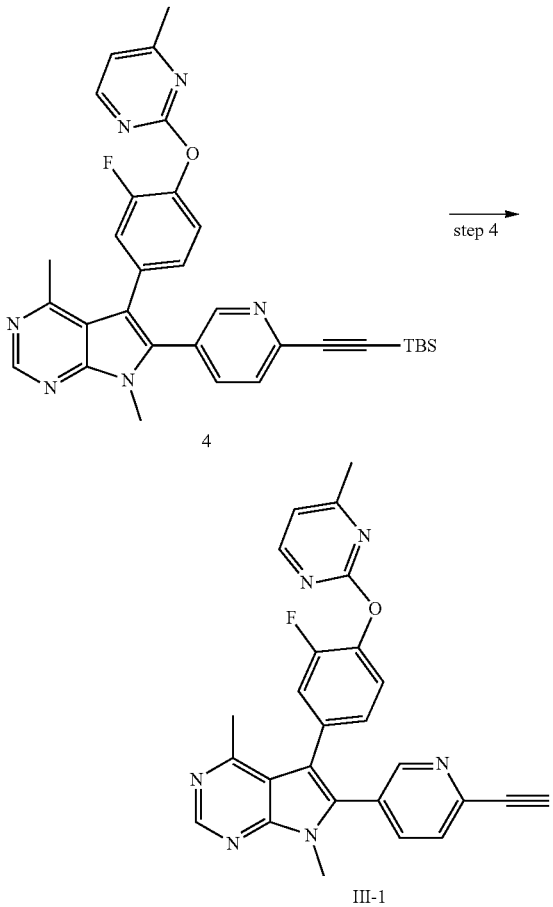

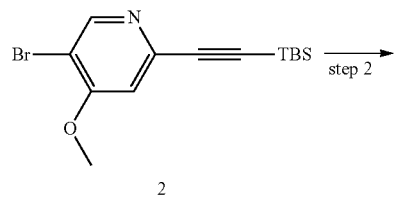

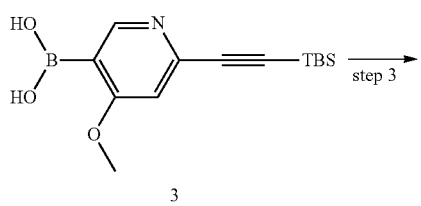

Step 1. Preparation of 5-bromo-2-((tert-butyldimethylsilyl)ethynyl)-4-methoxypyridine

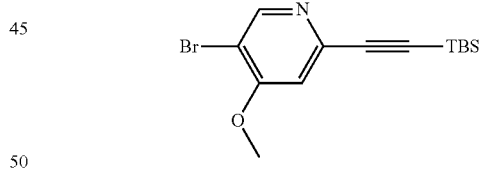

A resealable reaction vial was charged with 5-bromo-2-iodo-4-methoxypyridine (600 mg, 2.00 mmol), CuI (152 mg, 800 μmol), Et₃N (606 mg, 6.00 mmol), Pd(PPh₃)₂Cl₂ (280 mg, 400 μmol), DMF (15 mL), and a stir bar before being evacuated and purged with nitrogen three times, tert-butyl(ethynyl)dimethylsilane (280 mg, 2.00 mmol) was added, and the mixture was stirred at 50° C. for 2 h. The reaction mixture was diluted with water (20 mL), and the aqueous phase was extracted with ethyl acetate (20 mL) three times. The combined organic layers were washed with brine, dried over sodium sulfate, filtered, and concentrated in vacuo. The resulting crude material was purified by silica gel chromatography (PE:EA=8:1). Concentration in vacuo resulted 5-bromo-2-((tert-butyldimethylsilyl)ethynyl)-4-methoxypyridine (500 mg, 80%) as a solid.

Step 2. Preparation of (6-((tert-butyldimethylsilyl)ethynyl)-4-methoxypyridin-3-yl)boronic Acid

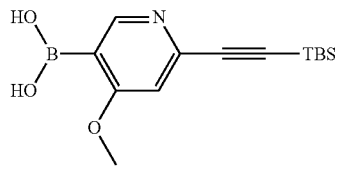

A resealable reaction vial was charged with 5-bromo-2-((tert-butyldimethylsilyl)ethynyl)-4-methoxypyridine (480 mg, 1.54 mmol), 4,4,5,5-tetramethyl-2-(4,4,5,5-tetramethyl-1,3,2-dioxaborolan-2-yl)-1,3,2-dioxaborolane (467 mg, 1.84 mmol), AcOK (452 mg, 4.62 mmol), Pd(dppf)Cl₂ (112 mg, 154 μmol), dioxane (10 mL) was added, and a stir bar before being evacuated and purged with nitrogen three times, and the mixture was stirred at 80° C. for 2 h. The reaction mixture was diluted with water (15 mL), and the aqueous phase was extracted with EA (15 mL) three times. The combined organic layers were washed with brine, dried over sodium sulfate, filtered, and concentrated in vacuo. The resulting crude material was purified by HPLC (acetonitrile/water 0%~60%, 30 min). Lyophilization yielded (6-((tert-butyldimethylsilyl)ethynyl)-4-methoxypyridin-3-yl)boronic acid (400 mg, 94%) as a solid.

Step 3. Preparation of 6-(6-((tert-butyldimethylsilyl)ethynyl)-4-methoxypyridin-3-yl)-5-(3-fluoro-4-((4-methylpyrimidin-2-yl)oxy)phenyl)-4,7-dimethyl-7H-pyrrolo[2,3-d]pyrimidine

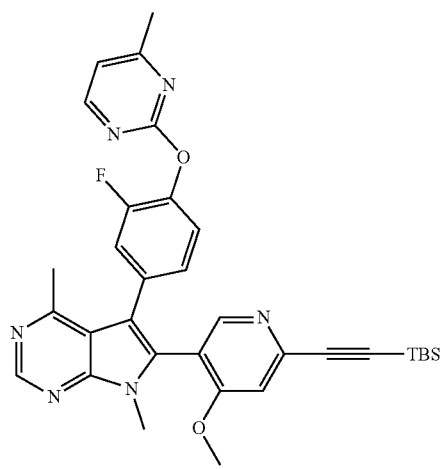

A resealable reaction vial was charged with 5-(3-fluoro-4-((4-methylpyrimidin-2-yl)oxy)phenyl)-6-iodo-4,7-dimethyl-7H-pyrrolo[2,3-d]pyrimidine (520 mg, 1.13 mmol), (6-((tert-butyldimethylsilyl)ethynyl)-4-methoxypyridin-3-yl)boronic acid (380 mg, 1.37 mmol), Na₂CO₃ (358 mg, 3.38 mmol), Pd(dppf)Cl₂ (82.6 mg, 113 μmol), DMF/H2O=16/1 (15 mL) was added and a stir bar before being evacuated and purged with nitrogen three times, and the mixture was stirred at 90° C. for 1 h. The reaction mixture was diluted with water (15 mL), and the aqueous phase was extracted with DCM (15 mL) three times. The combined organic layers were washed with brine, dried over sodium sulfate, filtered, and concentrated in vacuo. The resulting crude material was purified by HPLC (DCM/MeOH=15/1). Lyophilization yielded 6-(6-((tert-butyldimethylsilyl)ethynyl)-4-methoxypyridin-3-yl)-5-(3-fluoro-4-((4-methylpyrimidin-2-yl)oxy)phenyl)-4,7-dimethyl-7H-pyrrolo[2,3-d]pyrimidine (200 mg, 34%) as a solid.

Step 4. Preparation of 6-(6-ethynyl-4-methoxypyridin-3-yl)-5-(3-fluoro-4-((4-methylpyrimidin-2-yl)oxy)phenyl)-4,7-dimethyl-7H-pyrrolo[2,3-d]pyrimidine

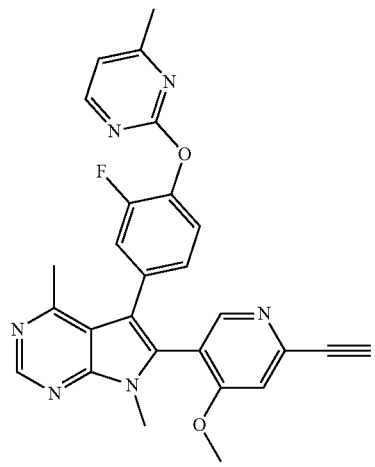 [SMILES: C#Cc1cc(OC)c(-c2c(-c3ccc(Oc4nccc(C)n4)c(F)c3)c3c(C)ncnc3n2C)cn1]

A round bottomed flask was charged with 6-(6-((tert-butyldimethylsilyl)ethynyl)-4-methoxypyridin-3-yl)-5-(3-fluoro-4-((4-methylpyrimidin-2-yl)oxy)phenyl)-4,7-dimethyl-7H-pyrrolo[2,3-d]pyrimidine (180 mg, 303 μmol), TBAF (638 μg, 638 μmol) and a stir bar. Tetrahydrofuran (5 mL) was added, and the solution was stirred at 25° C. for 1 h. The reaction mixture was diluted with water (10 mL), and the aqueous phase was extracted with dichloromethane (10 mL) three times. The combined organic layers were washed with brine ten times, dried over sodium sulfate, filtered, and concentrated in vacuo. The resulting crude material was purified by HPLC (Column: SunFire Prep C18 OBD Column, 19×150 mm 5um 10 nm; Mobile Phase A: Water (0.05% FA), Mobile Phase B: ACN (0.1% DEA)—HPLC—; Flow rate: 25 mL/min; Gradient: 15 B to 38 B in 8 min; 220 nm). Lyophilization yielded 6-(6-ethynyl-4-methoxypyridin-3-yl)-5-(3-fluoro-4-((4-methylpyrimidin-2-yl)oxy)phenyl)-4,7-dimethyl-7H-pyrrolo[2,3-d]pyrimidine (31.1 mg, 21%) as a brown amorphous solid. MS [M+1]=481.15. 1H NMR (400 MHz, DMSO-d6) δ 8.77 (s, 1H), 8.49 (d, J=5.0 Hz, 1H), 8.29 (s, 1H), 7.42 (s, 1H), 7.36-7.27 (m, 2H), 7.19 (d, J=5.0 Hz, 1H), 7.14-7.07 (m, 1H), 4.48 (s, 1H), 3.87 (s, 3H), 3.61 (s, 3H), 2.41 (s, 6H).

Example 5—Synthesis of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (Compound IV-1)

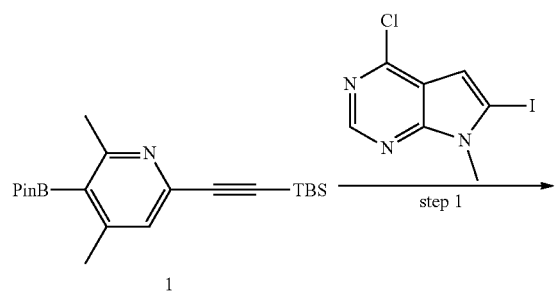

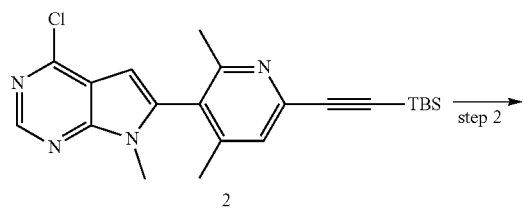

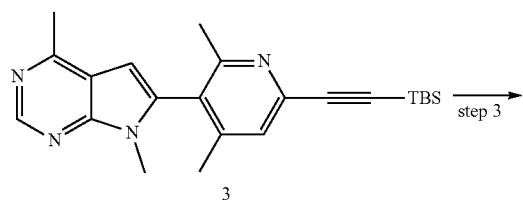

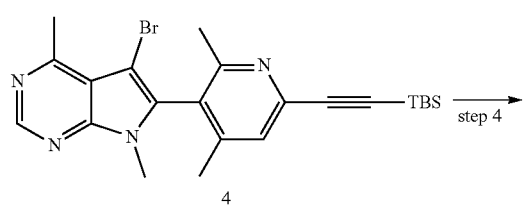

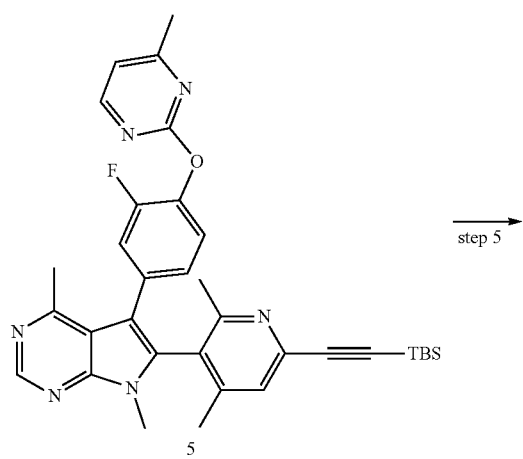

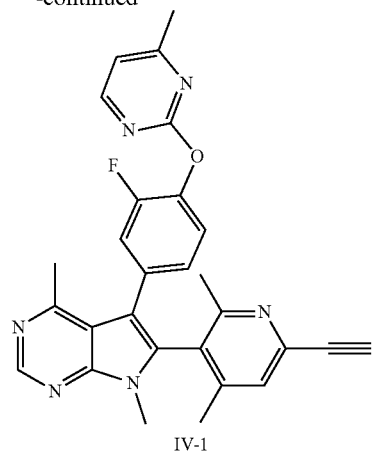

Step 1. Preparation of 6-(6-((tert-butyldimethylsilyl)ethynyl)-2,4-dimethylpyridin-3-yl)-4-chloro-7-methyl-7H-pyrrolo[2,3-d]pyrimidine

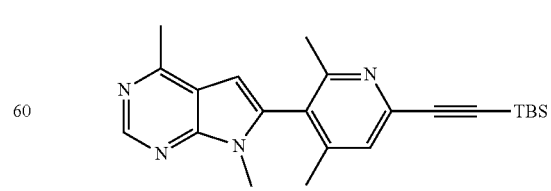

A resealable reaction vial was charged with 4-chloro-6-iodo-7-methyl-7H-pyrrolo[2,3-d]pyrimidine (1.2 g, 4.1 mmol), N 6-((tert-butyldimethylsilyl)ethynyl)-2,4-dimethyl-3-(4,4,5,5-tetramethyl-1,3,2-dioxaborolan-2-yl)pyridine (1.82 g, 4.91 mmol), PAd2nBu Pd-G2 (0.27 g, 0.41 mmol), PAd2nBu (0.29 g, 0.82 mmol), $K_3PO_4$ (2.61 g, 12.3 mmol), dioxane (30 mL), H2O (3 mL) and a stir bar before being evacuated and purged with nitrogen three times. The mixture was stirred for 15 h at 70° C. The reaction mixture was concentrated in vacuo. The resulting crude material was purified silica gel chromatography (eluting with MeOH/DCM=1/100~1/20). Concentration in vacuo resulted in 6-(6-((tert-butyldimethylsilyl)ethynyl)-2,4-dimethylpyridin-3-yl)-4-chloro-7-methyl-7H-pyrrolo[2,3-d]pyrimidine (0.7 g, 42%) as solid.

Step 2. Preparation of 6-(6-((tert-butyldimethylsilyl)ethynyl)-2,4-dimethylpyridin-3-yl)-4,7-dimethyl-7H-pyrrolo[2,3-d]pyrimidine A resealable reaction vial was charged with 6-(6-((tert-butyldimethylsilyl)ethynyl)-2,4-dimethylpyridin-3-yl)-4-chloro-7-methyl-7H-pyrrolo[2,3-d]pyrimidine (0.7 g, 1.7 mmol), Pd(PPh$_3$)$_4$ (0.2 g, 0.17 mmol), THF (20 mL) and a stir bar before being evacuated and purged with nitrogen three times. Zn(CH3)2 (1M, 2.04 mL, 2.04 mmol). The mixture was stirred for 2 h at 70° C. The reaction mixture was quenched with water, extracted with DCM, dried over Na$_2$SO$_4$, concentrated in vacuo. The resulting crude material was purified by silica gel chromatography (eluting with MeOH/DCM=1/100~1/30). Concentration in vacuo resulted in 6-(6-((tert-butyldimethylsilyl)ethynyl)-2,4-dimethylpyridin-3-yl)-4,7-dimethyl-7H-pyrrolo[2,3-d]pyrimidine (0.4 g, 60%) as solid.

Step 3. Preparation of 5-bromo-6-(6-((tert-butyldimethylsilyl)ethynyl)-2,4-dimethylpyridin-3-yl)-4,7-dimethyl-7H-pyrrolo[2,3-d]pyrimidine

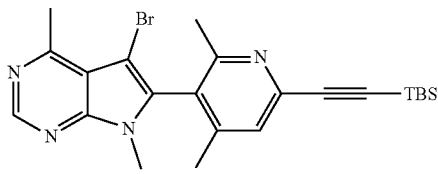

A round bottomed flask was charged with 6-(6-((tert-butyldimethylsilyl)ethynyl)-2,4-dimethylpyridin-3-yl)-4,7-dimethyl-7H-pyrrolo[2,3-d]pyrimidine (0.4 g, 1 mmol), DMF (10 mL) and a stir bar. NBS (0.18 g, 1 mmol) was added. The mixture was stirred for 1 h. The reaction was quenched with saturated NaHSO$_3$ aqueous solution, extracted with DCM (50 mL*3), the organic phase was combined and washed with brine for two times, dried with Na$_2$SO$_4$, evaporated in vacuo, the residue was dissolved with ACN (25 mL), and filtered, the filter cake was washed with ACN, dried under reduced pressure to afford 5-bromo-6-(6-((tert-butyldimethylsilyl)ethynyl)-2,4-dimethylpyridin-3-yl)-4,7-dimethyl-7H-pyrrolo[2,3-d]pyrimidine (440 mg, 94%) as solid.

Step 4. Preparation of 6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine

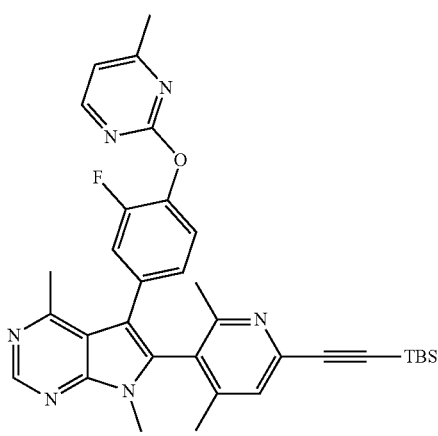

A round bottomed flask was charged with 5-bromo-6-(6-((tert-butyldimethylsilyl)ethynyl)-2,4-dimethylpyridin-3-yl)-4,7-dimethyl-7H-pyrrolo[2,3-d]pyrimidine (440 mg, 0.94 mmol), 2-(2-fluoro-4-((4,4,5,5-tetramethyl-1,3,2-dioxaborolan-2-yl)phenoxy)-4-methylpyrimidine (371.5 mg, 1.1 mmol), Pd(PPh$_3$)$_4$ (104 mg, 0.09 mmol), K$_3$PO$_4$ (598 mg, 2.82 mmol), DME/H2O (10:1, 10 mL) and a stir bar before being evacuated and purged with nitrogen three times. The mixture was stirred for 2 h at 90° C. After cooling, the mixture was diluted with water, extracted with DCM, dried over Na$_2$SO$_4$, evaporated in vacuo, the residue was purified by silica gel chromatography (eluting with MeOH/DCM=1/100~1/10) to afford 6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (300 mg, 54%) as a solid.

Step 5: Preparation of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine

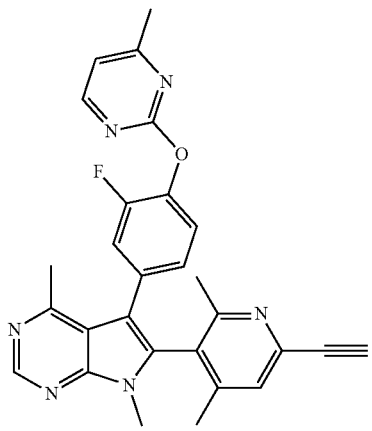 [SMILES: C#Cc1cc(C)c(-c2c(-c3ccc(Oc4nccc(C)n4)c(F)c3)c3c(C)ncnc3n2C)c(C)n1]

A round bottomed flask was charged with 6-(6-((tert-butyldimethylsilyl)ethynyl)-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (300 mg, 0.51 mmol), THF (10 mL) and a stir bar. TBAF (0.61 mL, 0.61 mmol) was added dropwise. The mixture was stirred for 0.5 h at r.t. The mixture was diluted with water, extracted with DCM, washed with brine, dried over Na$_2$SO$_4$, evaporated in vacuo, the residue was purified by prep-HPLC to afford 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (100 mg, 41%) as a solid. MS [M+1]=479.35. $^1$H NMR (400 MHz, DMSO-d6) δ 8.78 (s, 1H), 8.48 (d, J=5.0 Hz, 1H), 7.45 (s, 1H), 7.34-7.25 (m, 2H), 7.18 (d, J=5.0 Hz, 1H), 7.07 (d, J=8.9 Hz, 1H), 4.39 (s, 1H), 3.51 (s, 3H), 2.44 (s, 3H), 2.40 (s, 3H), 2.19 (s, 3H), 2.05 (s, 3H).

100 mg of the target was sent to chiral separation (Column: CHIRALPAK IF, 2*25 cm, 5um; Mobile Phase A: Hex (0.5% 2M NH$_3$-MeOH), Mobile Phase B: EtOH:DCM=1:1—HPLC; Flow rate: 20 mL/min; Gradient: 2θ B to 2θ B in 15.5 min; 220/254 nm; RT1:10.826; RT2:12.649; Injection Volume: 0.8 ml; Number Of Runs: 5). Lyophilization afforded separated rotamers of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine represented by a first peak (43.4 mg) and later peak (40.2 mg).

Example 6—Polymorph Screen of N-(4-(4-amino-5-(3-fluoro-44(4-methylpyrimidin-2-yl)oxy)phenyl)-7-methyl-7H-pyrrolo[2,3-d]pyrimidin-6-yl)phenyl) methacrylamide Hydrochloride (Compound I-1)

Figure 12:
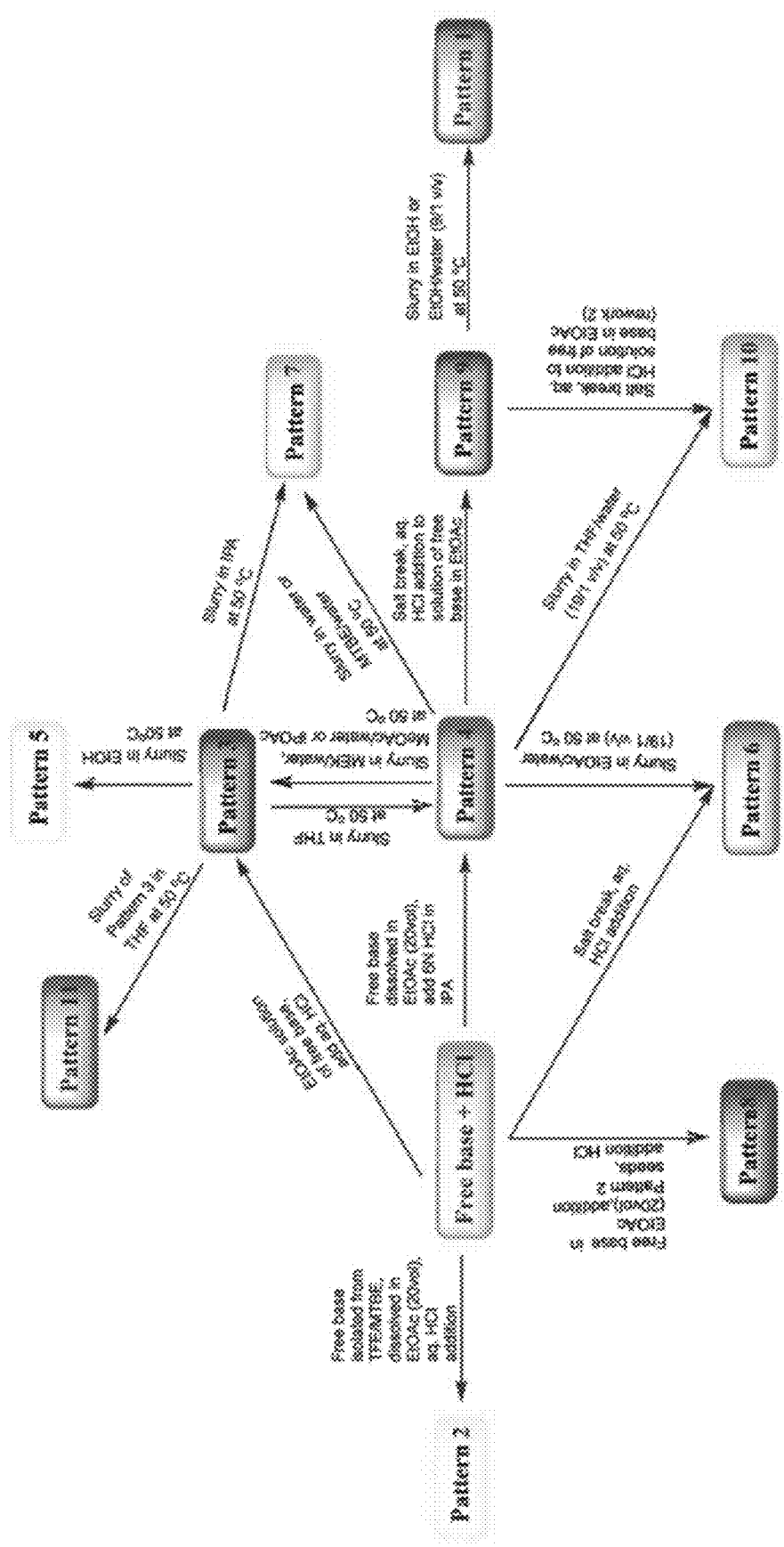
FIG. 12 depicts procedures for producing Patterns 1-11 corresponding to Forms A-K of Compound I-1. Pattern 1 corresponds to Form A. Pattern 2 corresponds to Form B. Pattern 3 corresponds to Form C. Pattern 4 corresponds to Form D. Pattern 5 corresponds to Form E. Pattern 6 corresponds to Form F. Pattern 7 corresponds to Form G. Pattern 8 corresponds to Form H. Pattern 9 corresponds to Form I. Pattern 10 corresponds to Form J. Pattern 11 corresponds to Form K.

Polymorph screening of the Compound I-1 (also referred to as N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide hydrochloride) was performed in 24 different solvents by a temperature cycling method. If no suspended solids were observed when the system was cooled to 25° C., then the solution was evaporated. Details of operation procedures were listed as below:

Conversion of Compound I-1 (Form D) was studied under anhydrous and aqueous conditions at 50° C. Table 1 summarizes the results of Form D conversion investigated in these studies. Compound I-1 (ca. 100 mg, Form D) and appropriate solvent (10 vol) were charged into separate 1.5 ml clear glass vials, heated at 0.5° C./min (over 1 hour) to 50° C., stirred at 50° C. for 16 hours and cooled at −0.5° C./min (over 1 hour). After this time, products were isolated by centrifuging at 10,000 RPM for 10 minutes, dried under reduced pressure at 40° C. and analysed by XRPD, HPLC and 1H NMR. If a new XRPD pattern was identified, the dry solids with new XRPD patterns were also characterized by PLM, DSC and TGA. Further polymorph screening was conducted as shown in the map of the identified forms (FIG. 12).

A summary of the solvents examined can be found in Table 1:

TABLE 1

| # | Solvents | XRPD Results |
|---|---|---|
| 1 | Ethanol | Form A |
| 2 | Butanol | Form A |
| 3 | 2-Propanol | Form A |
| 4 | Acetonitrile | Form A |
| 5 | Acetone | Form A |
| 6 | Dichloromethane | Form A |
| 7 | Methyl ethyl ketone | Form A |
| 8 | Methyl-tert-butyl ether | Form A |
| 9 | Tetrahydrofuran | Form D |
| 10 | Methyl acetate | Form D |
| 11 | Isopropyl acetate | Form D |
| 12 | Ethyl acetate | Form D |
| 13 | EtOH/Water (19/1 v/v) | Form A |
| 14 | Butanol/Water (19/1 v/v) | Form A |
| 15 | 2-Propanol/Water (19/1 v/v) | Form A |
| 16 | Acetonitrile/Water (19/1 v/v) | Form A |
| 17 | Acetone/Water (19/1 v/v) | Form A |
| 18 | Methyl ethyl ketone/Water (19/1 v/v) | Form C |
| 19 | Methyl-tert-butyl ether (19/1 v/v) | Form G |
| 20 | Tetrahydrofuran/Water (19/1 v/v) | Form J |
| 21 | Methyl acetate/Water (19/1 v/v) | From C |
| 22 | Isopropyl acetate/Water (19/1 v/v) | Form C |
| 23 | Ethyl acetate/Water (19/1 v/v) | Form F |
| 24 | Water | From G |

Form A

After polymorph screening experiments described above, obtained solids all showed XRPD patterns, including Form A. Form A was also obtained by heating Form G to 230° C.

Figure 1C:
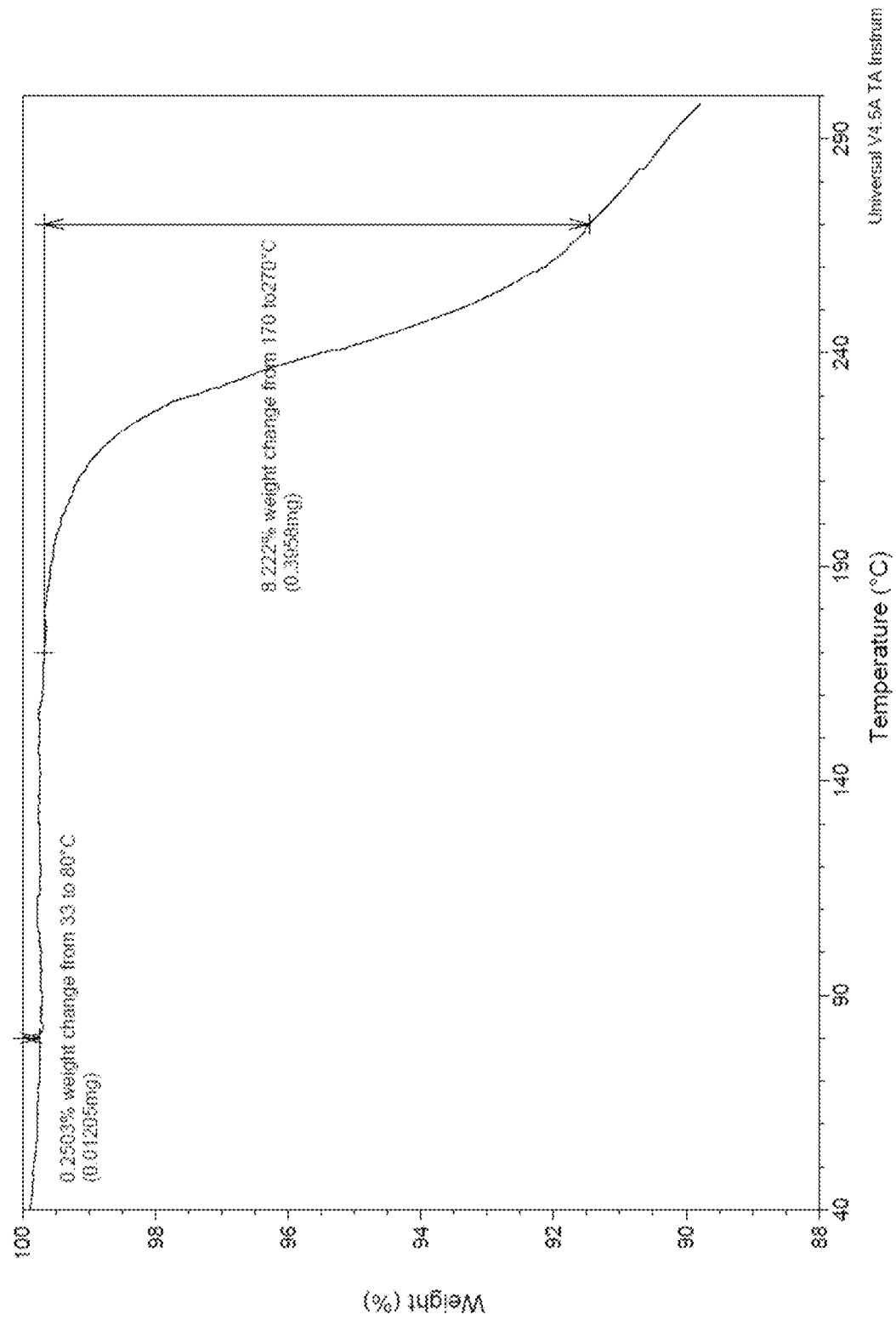
FIG. 1C depicts the characterization of Form A of Compound I-1 by thermogravimetric analysis (TGA).
Figure 1D:
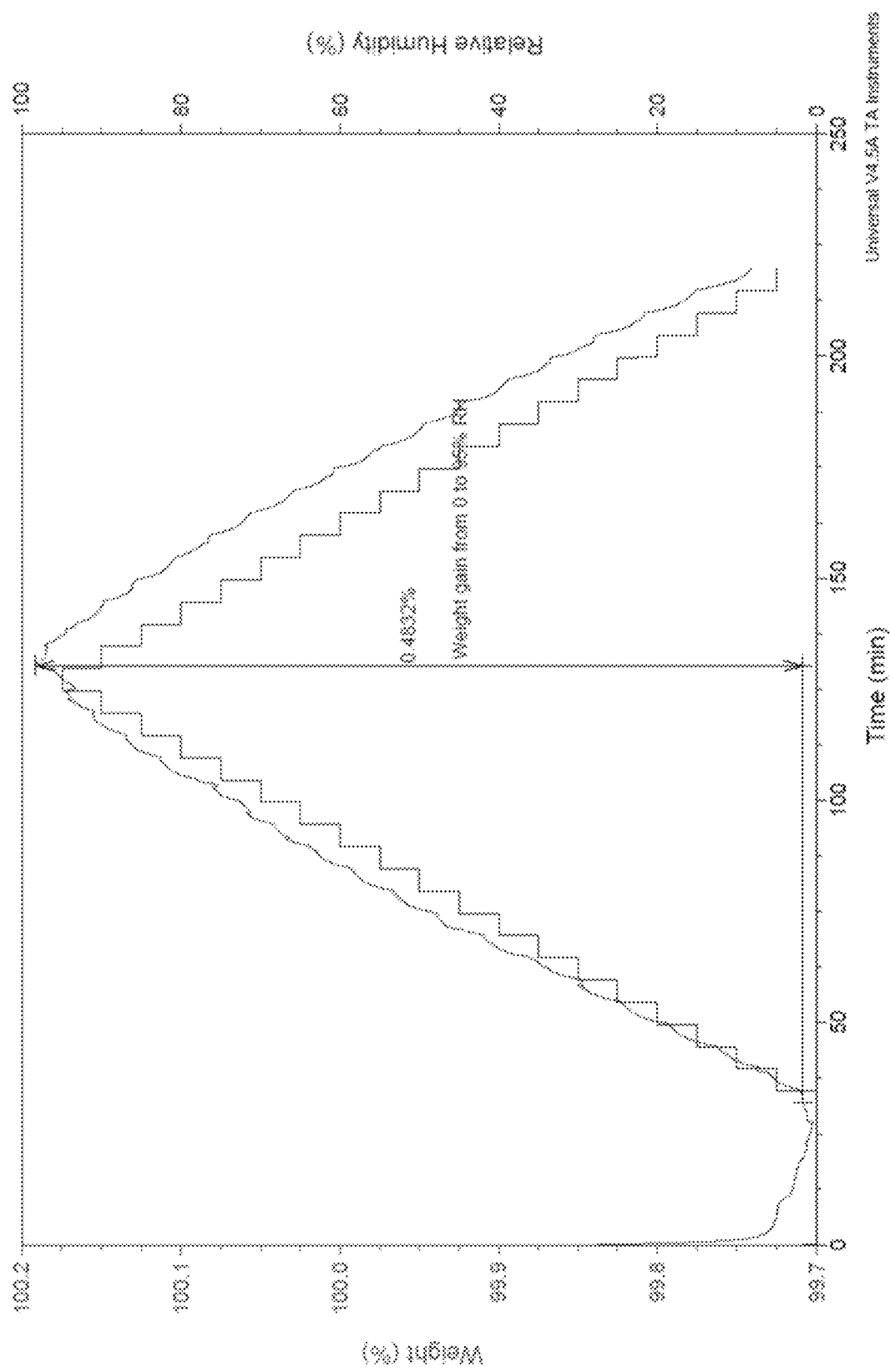
FIG. 1D depicts the characterization of Form A of Compound I-1 by dynamic vapor sorption (DVS).

Form A of Compound I-1 was then characterized by DSC, TGA and DVS. DSC scan of Form A in FIG. 1B showed a single endothermic peak at the onset of 277.67° C. (enthalpy: 140.7 J/g). TGA scan (FIG. 1C) showed a weight loss of 0.2503% from 33° C. to 80° C. and a weight loss of 0.222% from 170° C. to 270° C. Dynamic vapor sorption (DVS) data for Form A of Compound I-1 is shown in FIG. 1D.

The XRPD of Form A of Compound I-1 is shown in FIG. 1A. Table 2.1 below sets out the X-Ray diffraction peaks observed for Form A of Compound I-1, wherein each value is in degrees 2θ:

TABLE 2.1

| Angle (2θ)° [1] | Rel. Intensity % |
|---|---|
| 7.5 | 2.9 |
| 9.2 | 12.3 |
| 10.4 | 27.2 |
| 11.1 | 23.9 |
| 11.8 | 9.3 |
| 12.3 | 100.0 |
| 12.7 | 30.3 |
| 13.2 | 11.0 |
| 14.0 | 19.4 |
| 14.2 | 9.2 |
| 14.4 | 10.2 |
| 15.2 | 21.5 |
| 15.6 | 38.0 |
| 17.5 | 3.2 |
| 18.2 | 5.6 |
| 18.5 | 17.4 |
| 18.8 | 7.9 |
| 19.2 | 9.2 |
| 19.5 | 16.3 |
| 20.6 | 7.2 |
| 21.7 | 2.6 |
| 22.9 | 11.6 |
| 24.0 | 43.4 |
| 24.8 | 12.0 |
| 25.5 | 4.3 |
| 26.9 | 5.2 |
| 28.1 | 17.5 |
| 29.5 | 3.6 |

[1] In this and all subsequent tables, the position 2θ is within ±0.2.

Form B

After polymorph screening experiments described above, obtained solids all showed XRPD patterns, including Form B. Form B was also obtained by the addition of aq. HCl to the solution of the free base in 2-propanol. Additionally, Form B was obtained by heating Form I to about 220° C., Form F to about 220° C., and Form J to about 220° C.

Figure 2D:
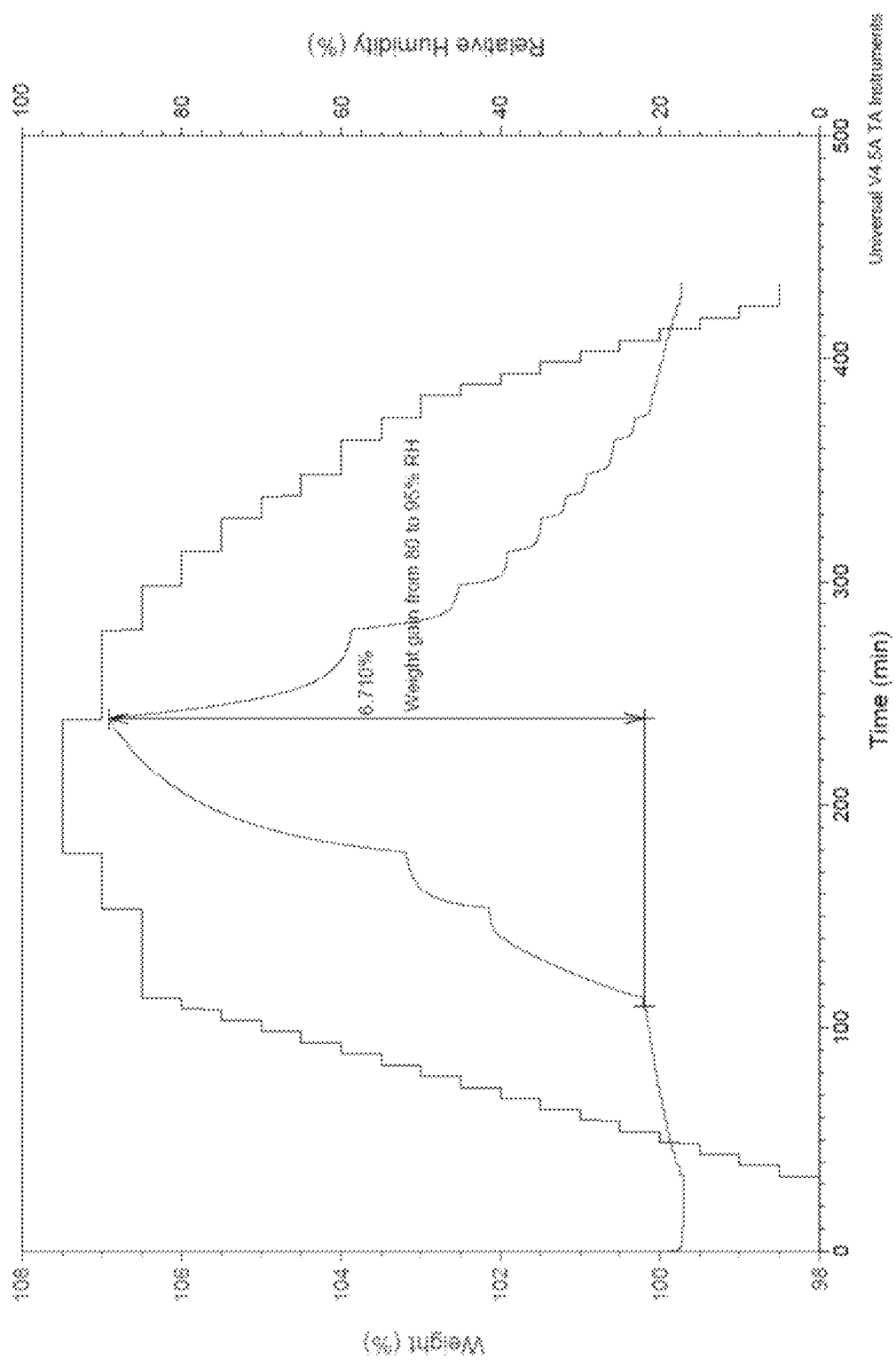
FIG. 2D depicts the characterization of Form B of Compound I-1 by dynamic vapor sorption (DVS).

Form B of Compound I-1 was then characterized by DSC, TGA and DVS. A DSC scan of Form B in FIG. 2B showed an endothermic peak at the onset of about 217° C. (enthalpy: 3.86 J/g). TGA scan (FIG. 2C) showed a weight loss of 7.15% from about 160° C. to about 250° C. In summary, Form B is a pure crystalline form of Compound I-1. Dynamic vapor sorption (DVS) data for Form B of Compound I-1 is shown in FIG. 2D.

The XRPD of Form B of Compound I-1 is shown in FIG. 2A. Table 2.2 below sets out the X-Ray diffraction peaks observed for Form B of Compound I-1, wherein each value is in degrees 2θ:

TABLE 2.2

| Angle (2θ)° [1] | Relative Intensity % |
|---|---|
| 8.0 | 100.0 |
| 10.5 | 7.3 |
| 11.3 | 5.7 |
| 12.1 | 8.2 |

TABLE 2.2-continued

| Angle (2θ)° [1] | Relative Intensity % |
|---|---|
| 12.6 | 11.0 |
| 13.3 | 10.2 |
| 13.7 | 2.6 |
| 14.2 | 9.2 |
| 14.5 | 42.4 |
| 16.0 | 12.3 |
| 17.3 | 19.1 |
| 17.7 | 11.7 |
| 18.0 | 4.6 |
| 18.6 | 3.6 |
| 18.9 | 1.8 |
| 20.0 | 5.0 |
| 20.6 | 21.3 |
| 21.2 | 2.7 |
| 22.8 | 2.9 |
| 23.4 | 45.2 |
| 23.8 | 6.6 |
| 24.2 | 1.5 |
| 25.4 | 5.2 |
| 26.8 | 6.6 |
| 27.6 | 1.7 |
| 28.3 | 2.7 |
| 29.4 | 0.9 |
| 31.5 | 1.3 |
| 32.1 | 2.2 |
| 32.5 | 2.6 |
| 34.3 | 1.2 |
| 38.4 | 1.2 |

[1] In this and all subsequent tables, the position 2θ is within ±0.2.

Form C

After polymorph screening experiments described above, obtained solids all showed XRPD patterns, including Form C. Form C was also obtained by the addition of aq. HCl to the solution of the free base in ethyl acetate. Additionally, Form C was obtained from a slurry of Form D in methyl ethyl ketone/water (19/1 v/v), methyl acetate/water (19/1 v/v), or isopropyl acetate/water (19/1 v/v).

Figure 3D:
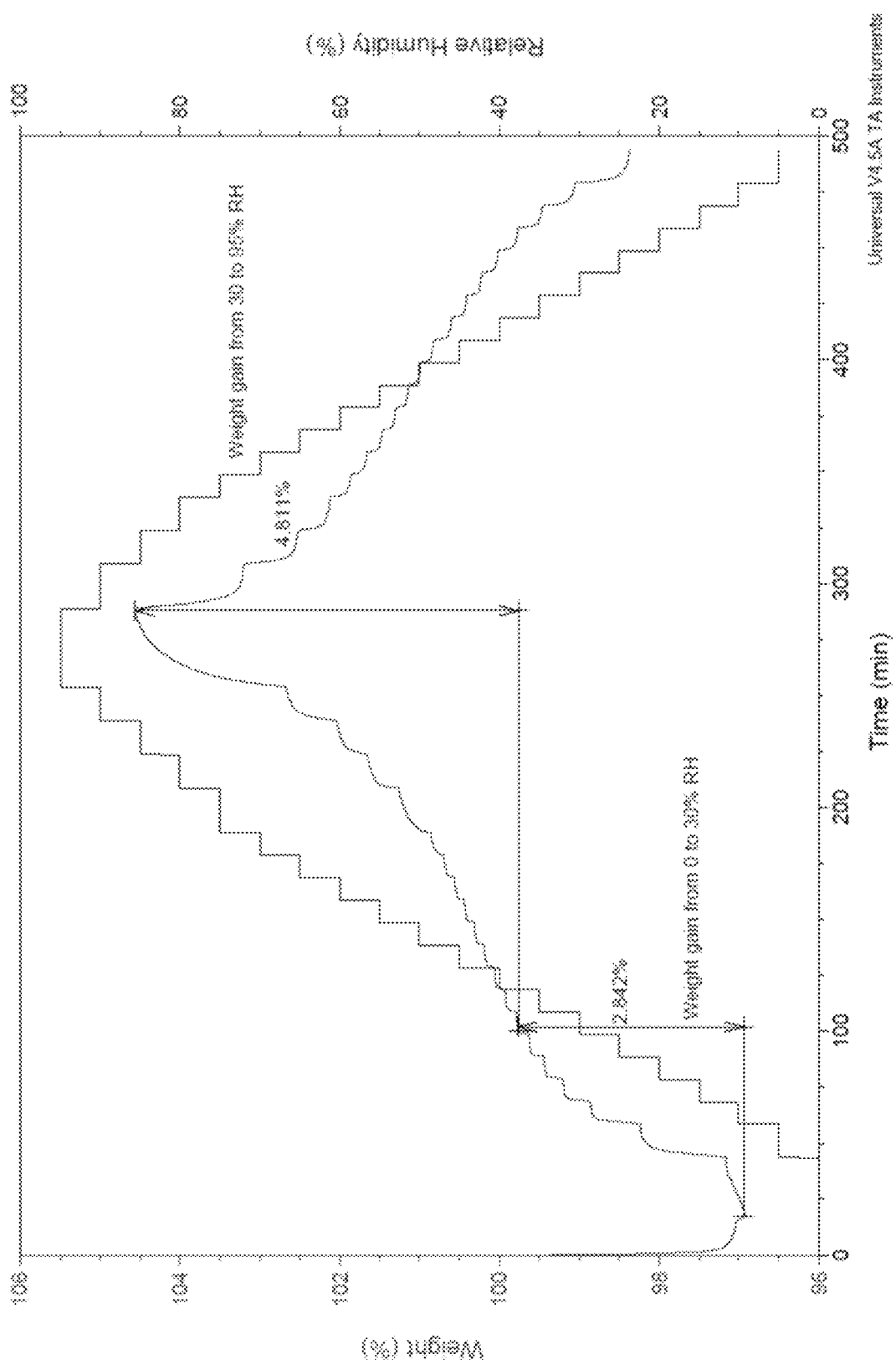
FIG. 3D depicts the characterization of Form C of Compound I-1 by dynamic vapor sorption (DVS).

Form C of Compound I-1 was then characterized by DSC, TGA and DVS. DSC scan of Form C in FIG. 3B showed an endothermic peak at the onset of about 190° C. (enthalpy: 44.6 J/g). The TGA analysis of Form C of Compound I-1 is shown in FIG. 3B. Dynamic vapor sorption (DVS) data for Form C of Compound I-1 is shown in FIG. 3D.

The XRPD of Form C of Compound I-1 is shown in FIG. 3A. Table 2.3 below sets out the X-Ray diffraction peaks observed for Form C of Compound I-1, wherein each value is in degrees 2θ:

TABLE 2.3

| Angle (2θ)° [1] | Relative Intensity % |
|---|---|
| 6.1 | 20.5 |
| 7.2 | 100.0 |
| 8.9 | 78.6 |
| 9.5 | 24.9 |
| 9.9 | 5.6 |
| 11.3 | 3.8 |
| 12.9 | 58.0 |
| 13.4 | 34.8 |
| 13.8 | 32.8 |
| 14.3 | 8.5 |
| 14.9 | 46.0 |
| 15.8 | 4.6 |
| 16.2 | 35.9 |
| 17.4 | 15.3 |
| 19.1 | 34.8 |
| 20.2 | 6.6 |
| 21.1 | 20.2 |
| 21.8 | 26.3 |
| 22.1 | 8.3 |

TABLE 2.3-continued

| Angle (2θ)° [1] | Relative Intensity % |
|---|---|
| 23.0 | 64.8 |
| 23.5 | 11.0 |
| 25.4 | 5.3 |
| 27.0 | 19.7 |
| 27.8 | 6.9 |
| 28.9 | 10.5 |
| 30.8 | 5.2 |
| 32.1 | 4.8 |
| 34.3 | 2.6 |
| 37.0 | 2.6 |
| 37.2 | 3.5 |
| 38.7 | 2.8 |

[1] In this and all subsequent tables, the position 2θ is within ±0.2.

Form D

After polymorph screening experiments described above, obtained solids all showed XRPD patterns, including Form D. Form D was also obtained by the addition of 6N HCl in 2-propanol to the free base in ethyl acetate (20 vol).

Figure 4D:
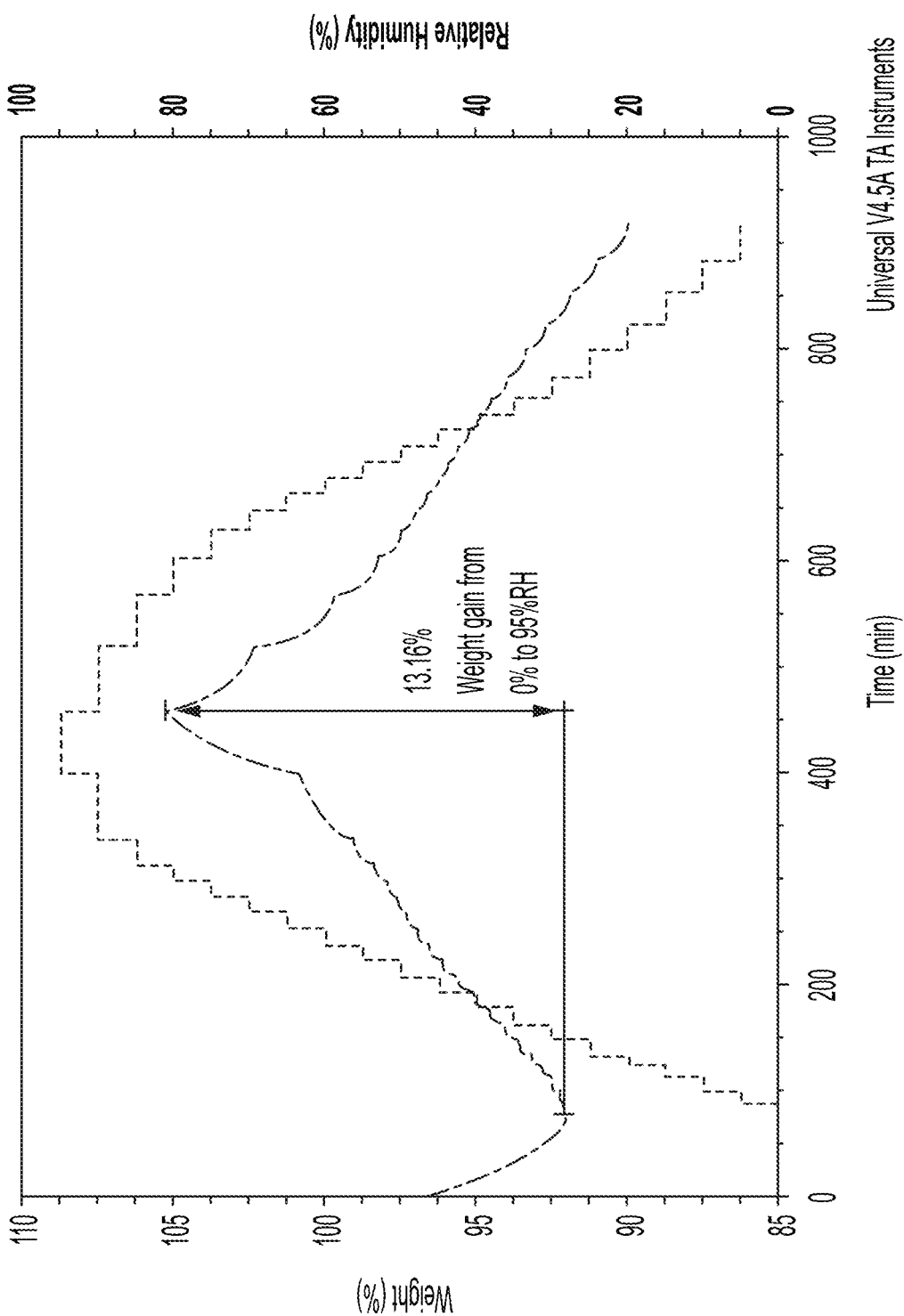
FIG. 4D depicts the characterization of Form D of Compound I-1 by dynamic vapor sorption (DVS).
Figure 4E:
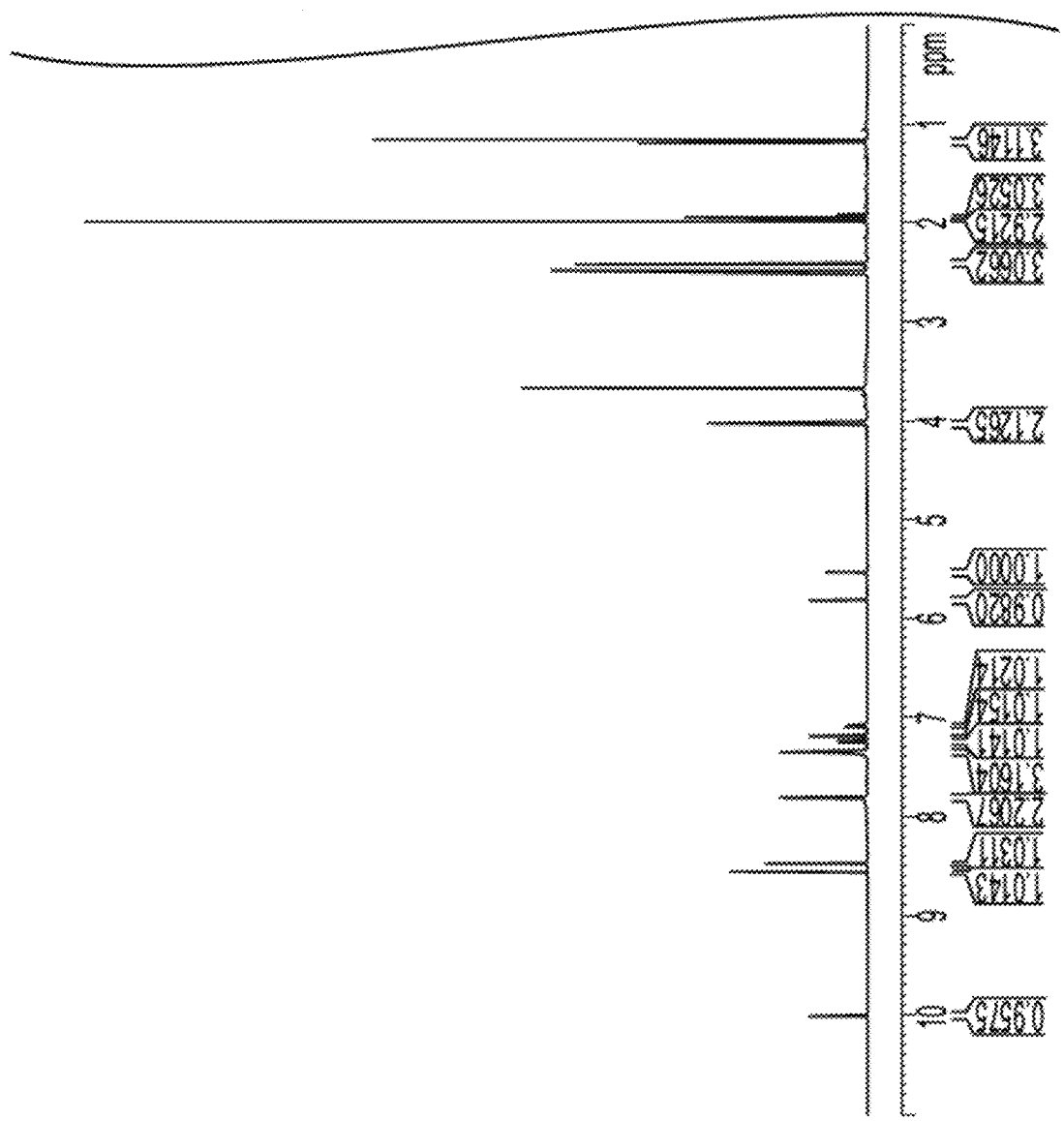
FIG. 4E depicts the characterization of Form D of Compound I-1 by $^1$H nuclear magnetic resonance ($^1$HNMR) in D6-DMSO at 400 MHz.
Figure 4E:
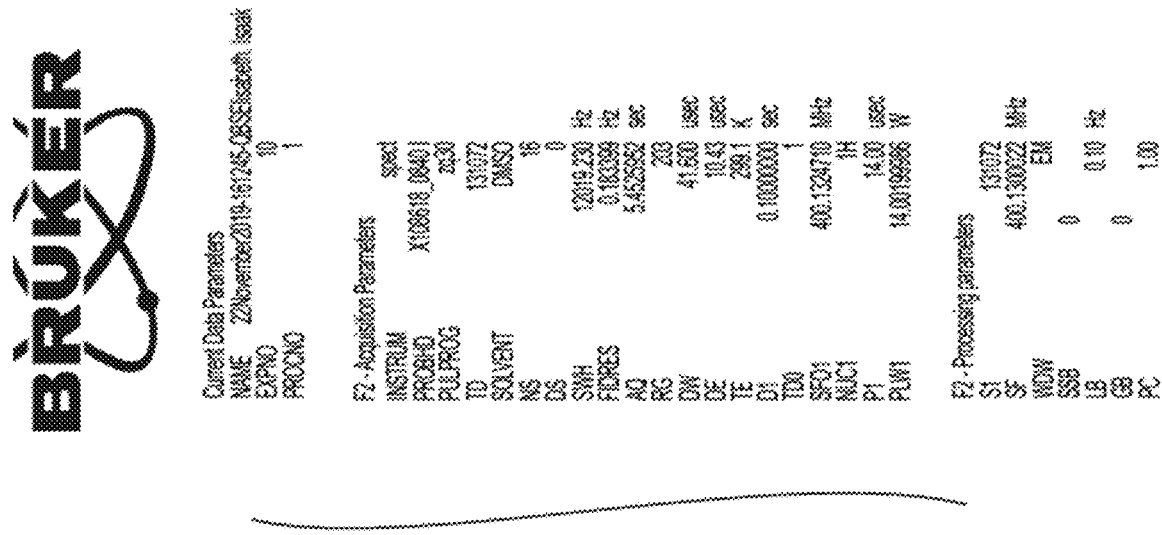

Form D of Compound I-1 was then characterized by DSC, TGA, DVS, and $^1$HNMR. DSC scan of Form D in FIG. 4B showed an endothermic peak at the onset of 156° C. (enthalpy: 53.3 J/g). TGA scan (FIG. 4C) showed a weight loss of 12.4% from 40° C. to 130° C. Dynamic vapor sorption data for Form D of Compound I-1 is shown in FIG. 4D.

The XRPD of Form D of Compound I-1 is shown in FIG. 4A. Table 2.4 below sets out the X-Ray diffraction peaks observed for Form D of Compound I-1, wherein each value is in degrees 2θ:

TABLR 2.4

| Angle (2θ)° [1] | Relative Intensity % |
|---|---|
| 6.6 | 51.5 |
| 7.9 | 62.6 |
| 10.4 | 100.0 |
| 10.8 | 5.4 |
| 11.1 | 6.2 |
| 12.8 | 58.6 |
| 13.2 | 36.9 |
| 13.8 | 38.3 |
| 14.1 | 17.7 |
| 15.3 | 13.5 |
| 15.8 | 26.0 |
| 16.7 | 19.1 |
| 17.0 | 18.0 |
| 18.9 | 11.9 |
| 19.0 | 13.8 |
| 19.6 | 13.6 |
| 20.3 | 30.0 |
| 20.8 | 16.9 |
| 21.0 | 43.3 |
| 21.6 | 11.3 |
| 22.3 | 7.0 |
| 22.6 | 11.6 |
| 23.2 | 4.3 |
| 23.8 | 23.9 |
| 24.3 | 7.9 |
| 24.8 | 5.5 |
| 25.1 | 8.4 |
| 25.5 | 28.2 |
| 26.0 | 4.4 |
| 26.7 | 4.6 |
| 27.4 | 13.3 |
| 28.0 | 4.6 |
| 28.4 | 5.8 |
| 28.9 | 2.5 |

TABLE 2.4-continued

| Angle (2θ)° [1] | Relative Intensity % |
|---|---|
| 30.2 | 3.1 |
| 31.6 | 2.1 |
| 34.0 | 4.7 |
| 36.1 | 2.2 |

[1] In this and all subsequent tables, the position 2θ is within ±0.2.

Form E

After polymorph screening experiments described above, obtained solids all showed XRPD patterns, including Form E. Form E was also obtained by slurrying Form C in ethanol (25 vol) for 16 hrs at 50° C. Additionally, Form E was obtained by heating Form D to 220° C.

Form E of Compound I-1 was then characterized by DSC. The DSC scan of Form E of Compound I-1 is shown in FIG. 5B. Dynamic vapor sorption data for Form E of Compound I-1 is shown in FIG. 5D.

The XRPD of Form E of Compound I-1 is shown in FIG. 5A. Table 2.5 below sets out the X-Ray diffraction peaks observed for Form E of Compound I-1, wherein each value is in degrees 2θ:

TABLE 2.5

| Angle (2θ)° [1] | Relative Intensity % |
|---|---|
| 4.6 | 15.7 |
| 5.6 | 67.9 |
| 8.1 | 20.8 |
| 8.8 | 28.5 |
| 10.9 | 91.7 |
| 12.3 | 9.0 |
| 12.8 | 96.8 |
| 13.5 | 27.5 |
| 14.6 | 36.5 |
| 14.9 | 70.6 |
| 16.5 | 51.6 |
| 16.9 | 60.5 |
| 18.4 | 12.2 |
| 19.2 | 23.9 |
| 20.8 | 18.5 |
| 22.0 | 21.0 |
| 23.1 | 20.6 |
| 23.7 | 100.0 |
| 25.8 | 26.4 |
| 26.4 | 22.5 |
| 28.7 | 17.2 |
| 29.4 | 9.2 |

[1] In this and all subsequent tables, the position 2θ is within ±0.2.

Form F

After polymorph screening experiments described above, obtained solids all showed XRPD patterns, including Form F. Form F was also obtained by the addition of HCl to the free base in ethyl acetate that was seeded with Form B. Additionally, Form F was obtained by slurrying Form D in ethyl acetate/water (19/1 v/v) at 50° C. Form F was also obtained by heating Form I to 120° C.

Figure 6D:
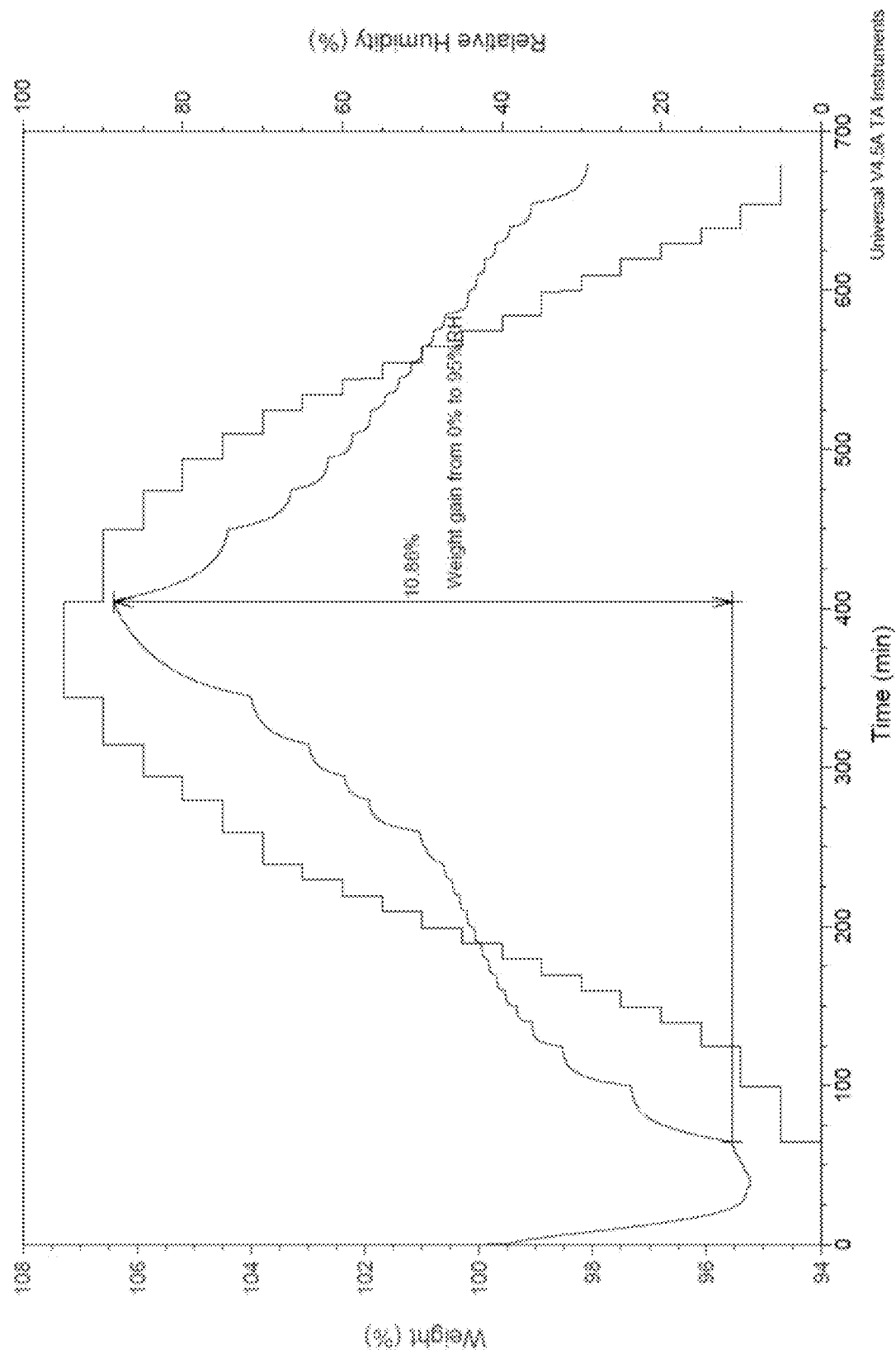
FIG. 6D depicts the characterization of Form F of Compound I-1 by dynamic vapor sorption (DVS).

Form F of Compound I-1 was then characterized by DSC, TGA and DVS. DSC scan of Form F in FIG. 6B showed an endothermic peak at the onset of 162° C. (enthalpy: 15.5 J/g). TGA scan (FIG. 6B) showed a weight loss of 4.7% from 43° C. to 95° C., 1.2° C. from 125° C. to 160° C., and 4.4% from 220° C. to 260° C. The Dynamic vapor sorption data for Form F of Compound I-1 is shown in FIG. 6D.

XRPD of Form F of Compound I-1 is shown in FIG. 6A. Table 2.6 below sets out the X-Ray diffraction peaks observed for Form F of Compound I-1, wherein each value is in degrees 2θ:

TABLE 2.6

| Angle (2θ)° [1] | Relative Intensity % |
|---|---|
| 6.1 | 4.3 |
| 7.4 | 100.0 |
| 8.4 | 3.5 |
| 9.3 | 11.4 |
| 9.7 | 11.5 |
| 12.0 | 21.1 |
| 13.0 | 23.8 |
| 13.8 | 21.4 |
| 14.1 | 13.9 |
| 14.8 | 19.1 |
| 15.1 | 38.6 |
| 15.6 | 17.3 |
| 16.8 | 5.5 |
| 17.6 | 9.5 |
| 18.7 | 4.0 |
| 19.4 | 11.0 |
| 19.7 | 34.9 |
| 20.0 | 14.6 |
| 21.2 | 38.9 |
| 21.9 | 28.2 |
| 22.9 | 4.3 |
| 24.1 | 6.0 |
| 25.2 | 4.3 |
| 26.1 | 6.7 |
| 27.7 | 5.4 |
| 31.8 | 5.2 |

[1] In this and all subsequent tables, the position 2θ is within ±0.2.

Form G

After polymorph screening experiments described above, obtained solids all showed XRPD patterns, including Form G. Form G was also obtained by slurrying Form D in water at 50° C. Additionally, Form G was obtained from a Form C slurry in 2-propanol at 50° C.

Figure 7D:
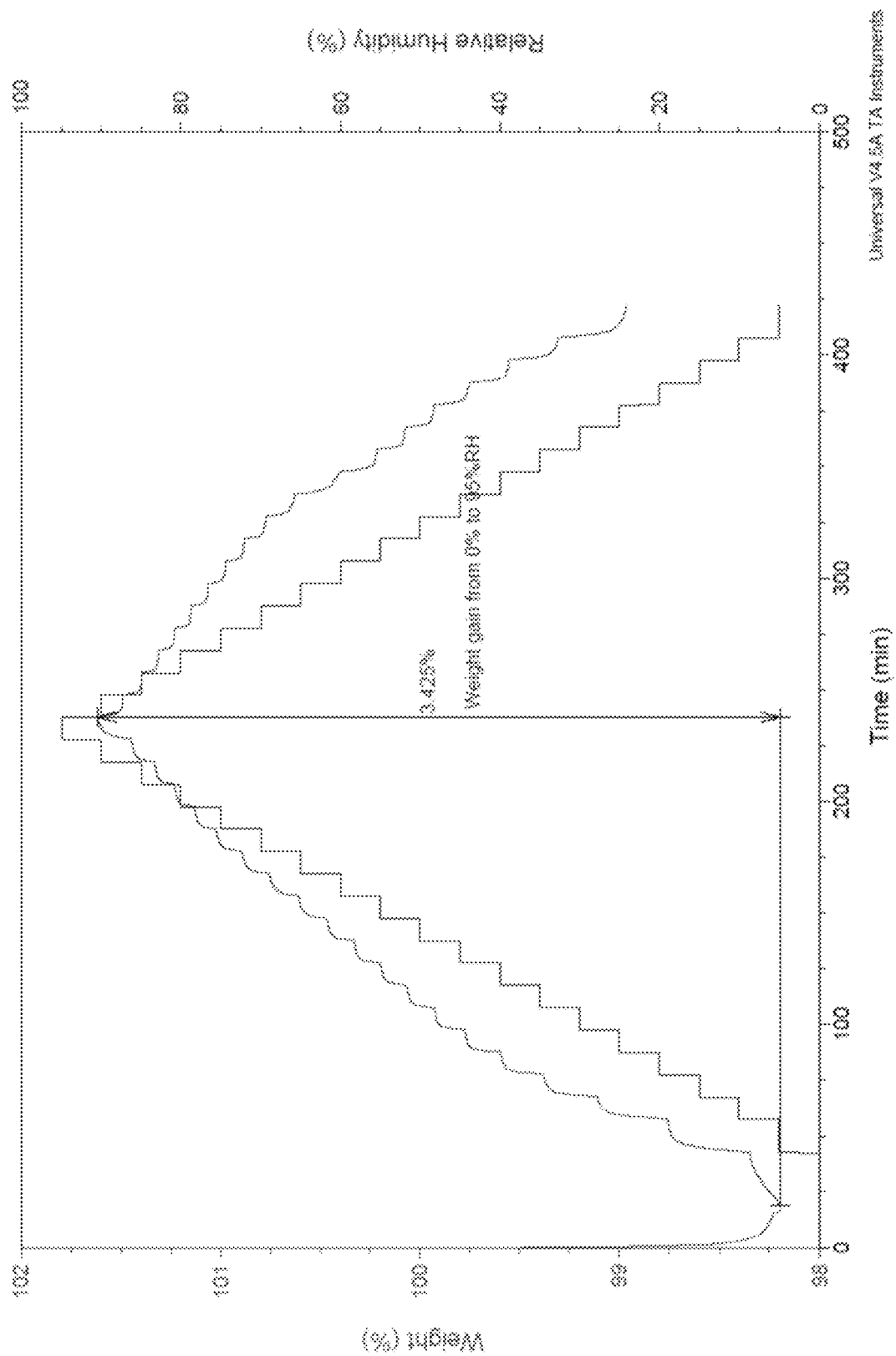
FIG. 7D depicts the characterization of Form G of Compound I-1 by dynamic vapor sorption (DVS).

Form G of Compound I-1 was then characterized by DSC, TGA and DVS. DSC scan of Form G in FIG. 7B showed an endothermic peak at the onset of about 145° C. (enthalpy: 66.9 J/g). TGA scan (FIG. 7C) showed a weight loss of 4.2% from 40° C. to 140° C. Dynamic vapor sorption data for Form G of Compound I-1 is shown in FIG. 7D.

The XRPD of Form G of Compound I-1 is shown in FIG. 7A. Table 2.7 below sets out the X-Ray diffraction peaks observed for Form G of Compound I-1, wherein each value is in degrees 2θ:

TABLE 2.7

| Angle (2θ)° [1] | Relative Intensity % |
|---|---|
| 7.5 | 100.0 |
| 10.7 | 11.8 |
| 11.0 | 7.7 |
| 12.3 | 2.0 |
| 13.0 | 3.8 |
| 13.7 | 25.8 |
| 14.6 | 8.4 |
| 14.9 | 10.4 |
| 15.7 | 9.1 |
| 16.2 | 13.4 |
| 17.4 | 1.2 |
| 19.1 | 2.7 |
| 19.3 | 3.9 |
| 20.0 | 16.8 |
| 21.5 | 17.5 |
| 22.1 | 1.9 |
| 23.7 | 2.9 |
| 23.9 | 2.2 |
| 24.5 | 1.3 |
| 25.4 | 1.7 |
| 26.3 | 3.0 |
| 27.5 | 1.7 |
| 29.4 | 2.0 |

TABLE 2.7-continued

| Angle (2θ)° [1] | Relative Intensity % |
|---|---|
| 31.7 | 2.4 |
| 37.8 | 1.8 |

[1] In this and all subsequent tables, the position 2θ is within ±0.2.

Form H

After polymorph screening experiments described above, obtained solids all showed XRPD patterns, including Form H. Form H was also obtained from the free base in ethyl acetate (2θ vol) that was seeded with Form B, followed by addition of HCl.

Figure 8D:
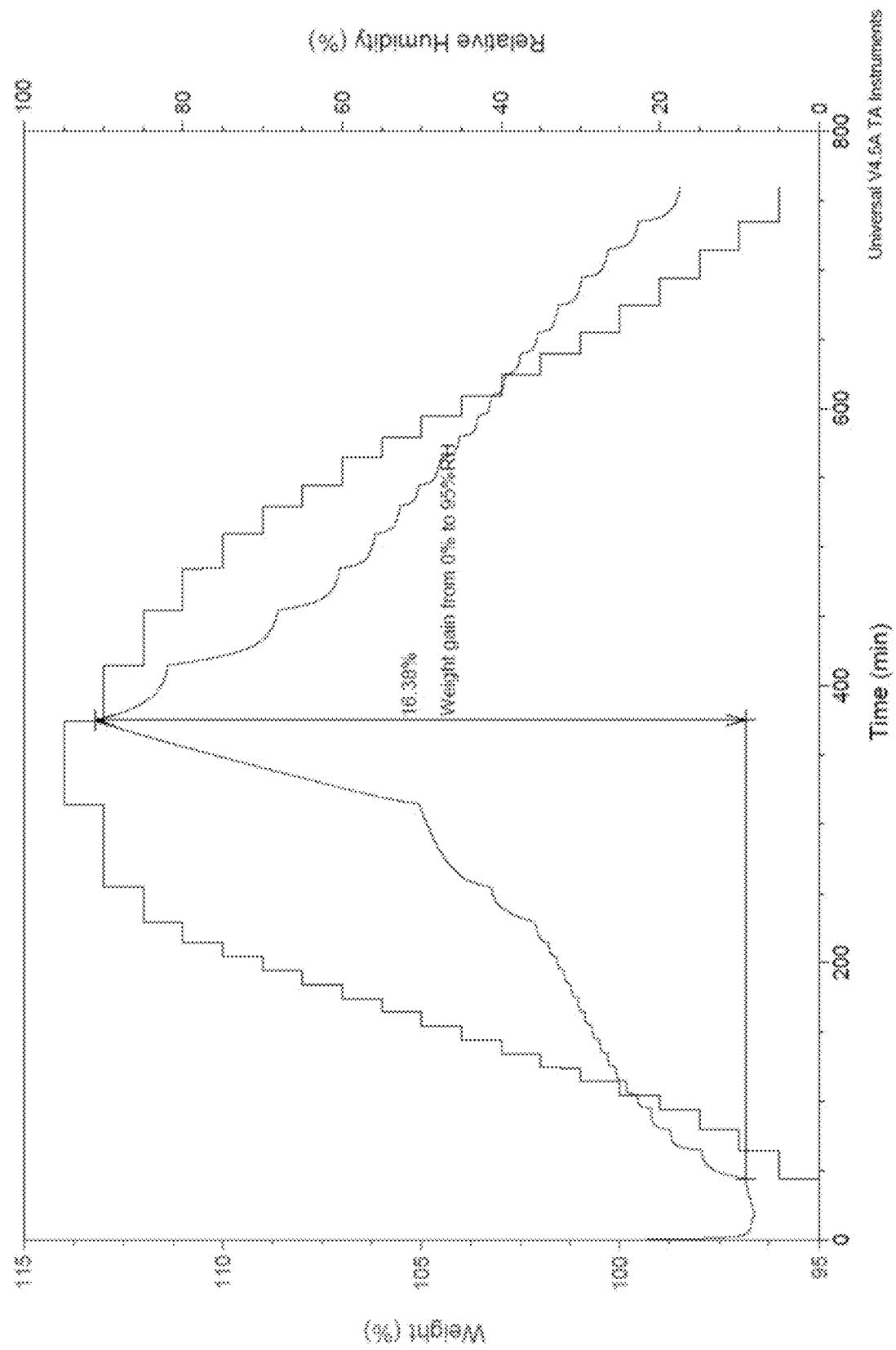
FIG. 8D depicts the characterization of Form H of Compound I-1 by dynamic vapor sorption (DVS).

Form H of Compound I-1 was then characterized by DSC, TGA and DVS. DSC scan of Form H in FIG. 8B showed an endothermic peak at the onset of about 186° C. (enthalpy: 39.1 J/g). TGA scan (FIG. 8B) showed a weight loss of 5.4% from 40° C. to 80° C. and 3.7% from 190° C. to 260° C. Dynamic vapor sorption data for Form H of Compound I-1 is shown in FIG. 8D.

The XRPD of Form H of Compound I-1 is shown in FIG. 8A. Table 2.8 below sets out the X-Ray diffraction peaks observed for Form H of Compound I-1, wherein each value is in degrees 2θ:

TABLE 2.8

| Angle (2θ)° [1] | Relative Intensity % |
|---|---|
| 3.4 | 2.7 |
| 6.1 | 100.0 |
| 7.1 | 4.7 |
| 8.9 | 4.6 |
| 9.9 | 19.4 |
| 10.3 | 10.7 |
| 11.3 | 9.6 |
| 12.1 | 4.9 |
| 13.2 | 9.6 |
| 13.7 | 6.3 |
| 14.4 | 5.9 |
| 14.9 | 14.9 |
| 15.8 | 11.0 |
| 17.0 | 3.1 |
| 17.9 | 3.8 |
| 18.2 | 7.6 |
| 19.2 | 5.3 |
| 20.8 | 2.4 |
| 21.1 | 2.0 |
| 21.8 | 12.1 |
| 22.2 | 21.6 |
| 22.7 | 4.3 |
| 28.4 | 4.3 |

[1] In this and all subsequent tables, the position 2θ is within ±0.2.

Form I

After polymorph screening experiments described above, obtained solids all showed XRPD patterns, including Form I. Form I was also obtained by a salt break of Form D, followed by salt formation with HCl in ethyl acetate.

Form I of Compound I-1 was then characterized by DSC, TGA, DVS, and $^1$HNMR. DSC scan of Form I in FIG. 9B showed an endothermic peak at the onset of 155.7° C. (enthalpy: 33.4 J/g). TGA scan (FIG. 9B) showed a weight loss of 12.1% from 40° C. to 140° C. In summary, Form I is a pure crystalline form of Compound I-1. Dynamic vapor sorption data for Form I of Compound I-1 is shown in FIG. 9D.

Figure 9A:
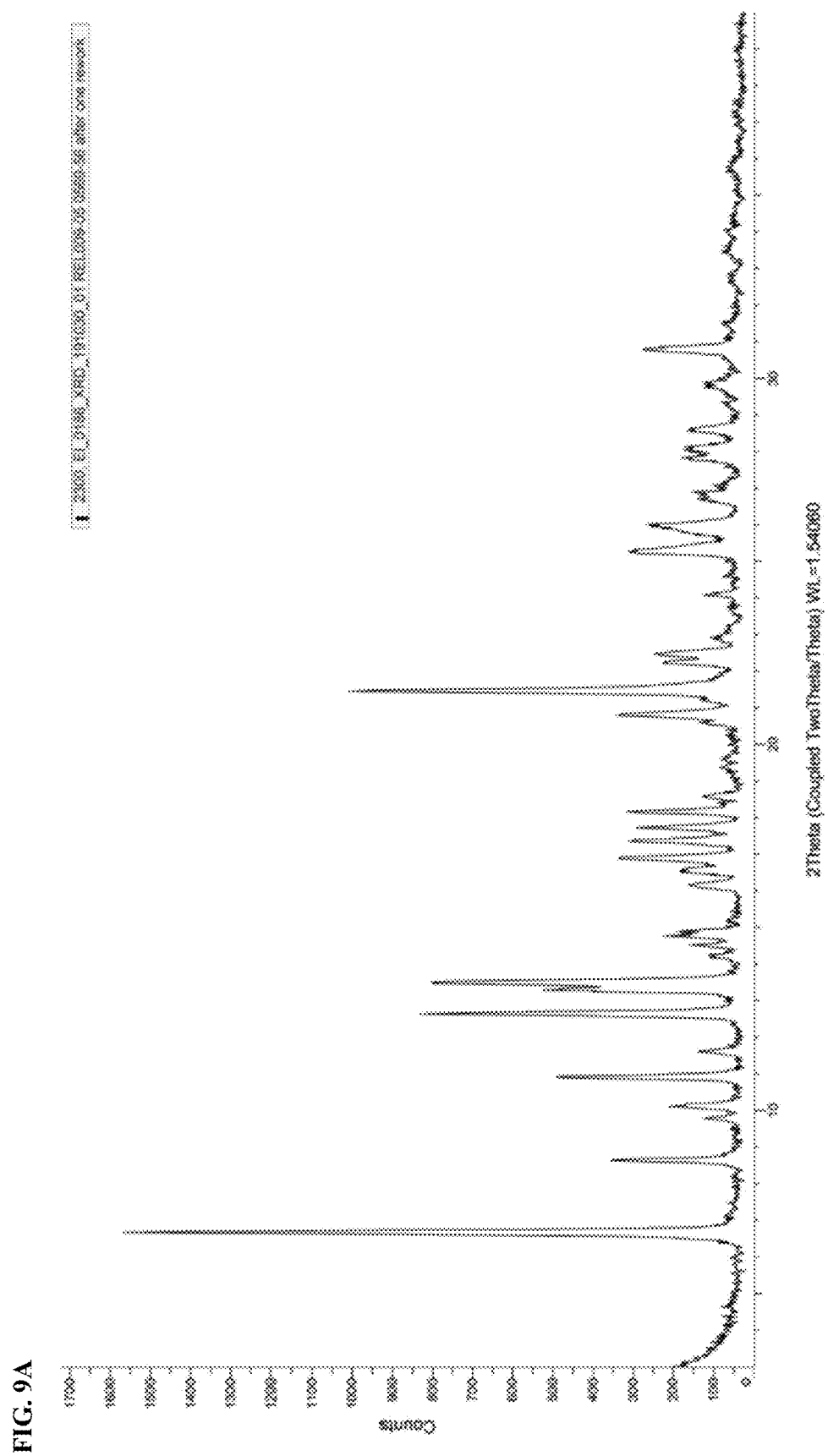
FIG. 9A depicts an X-ray diffraction pattern of Form I of Compound I-1.
Figure 9B:
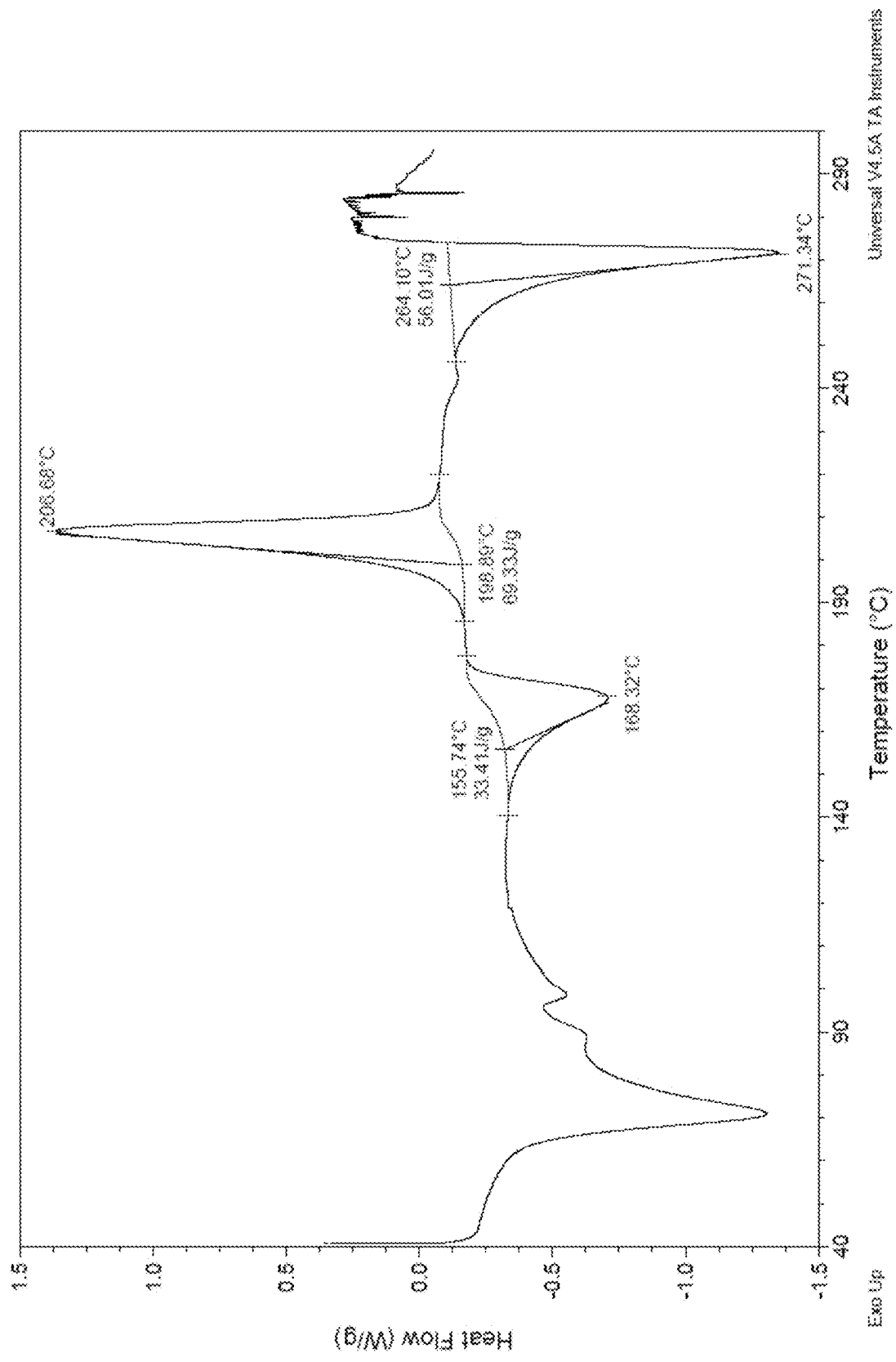
FIG. 9B depicts the characterization of Form I of Compound I-1 by differential scanning calorimetry (DSC).
Figure 9C:
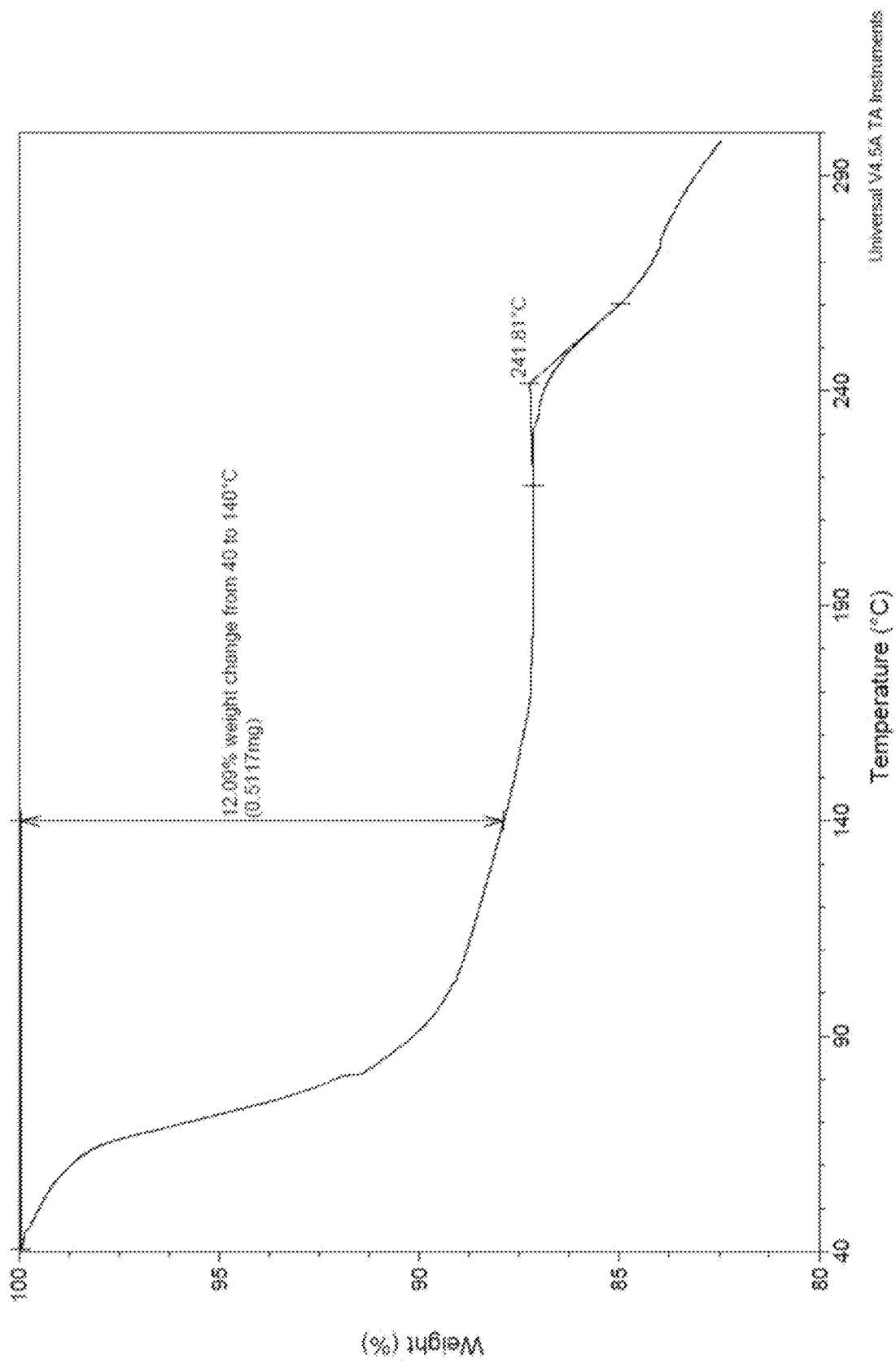
FIG. 9C depicts the characterization of Form I of Compound I-1 by thermogravimetric analysis (TGA).
Figure 9D:
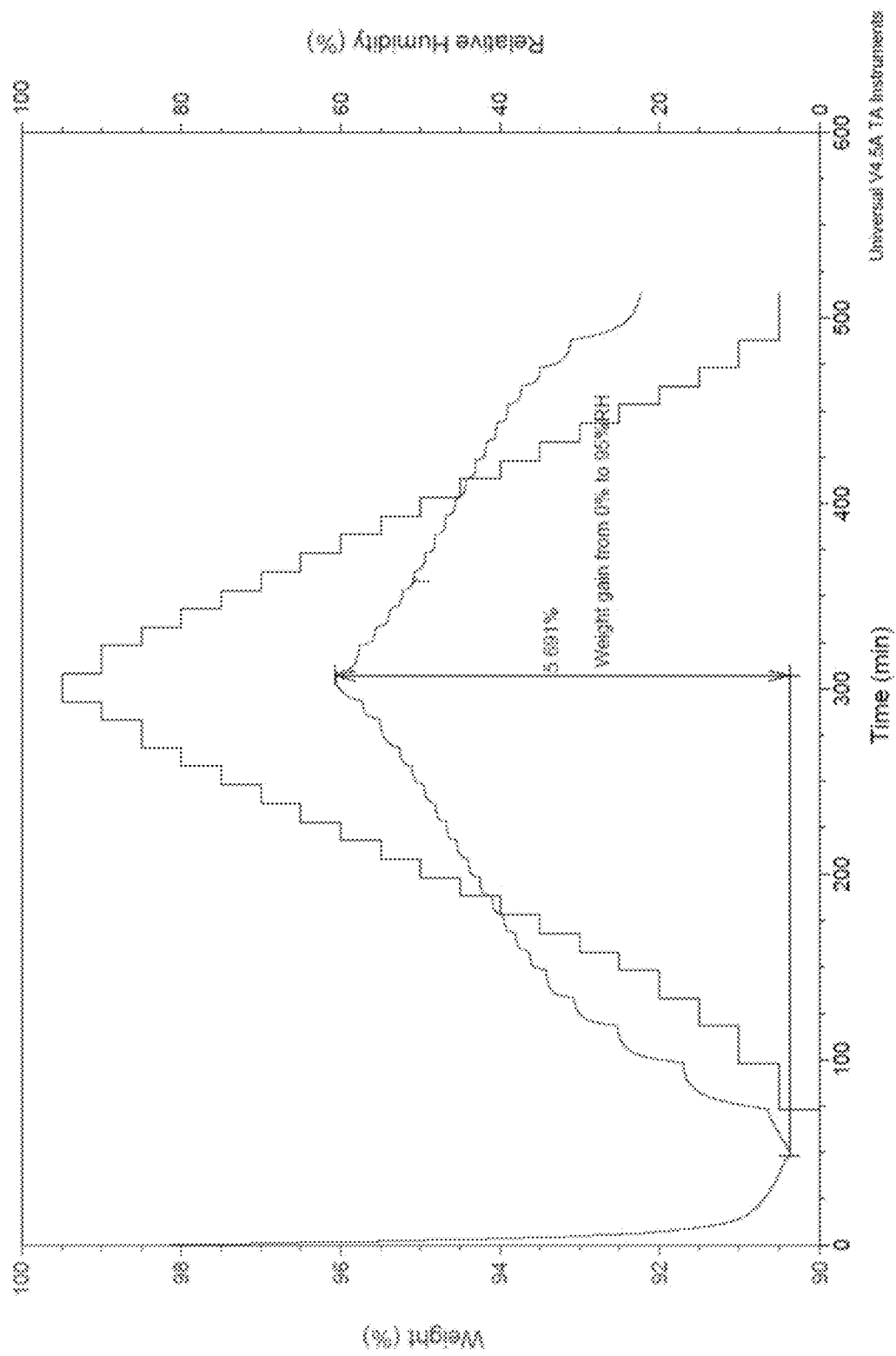
FIG. 9D depicts the characterization of Form I of Compound I-1 by dynamic vapor sorption (DVS).
Figure 9E:
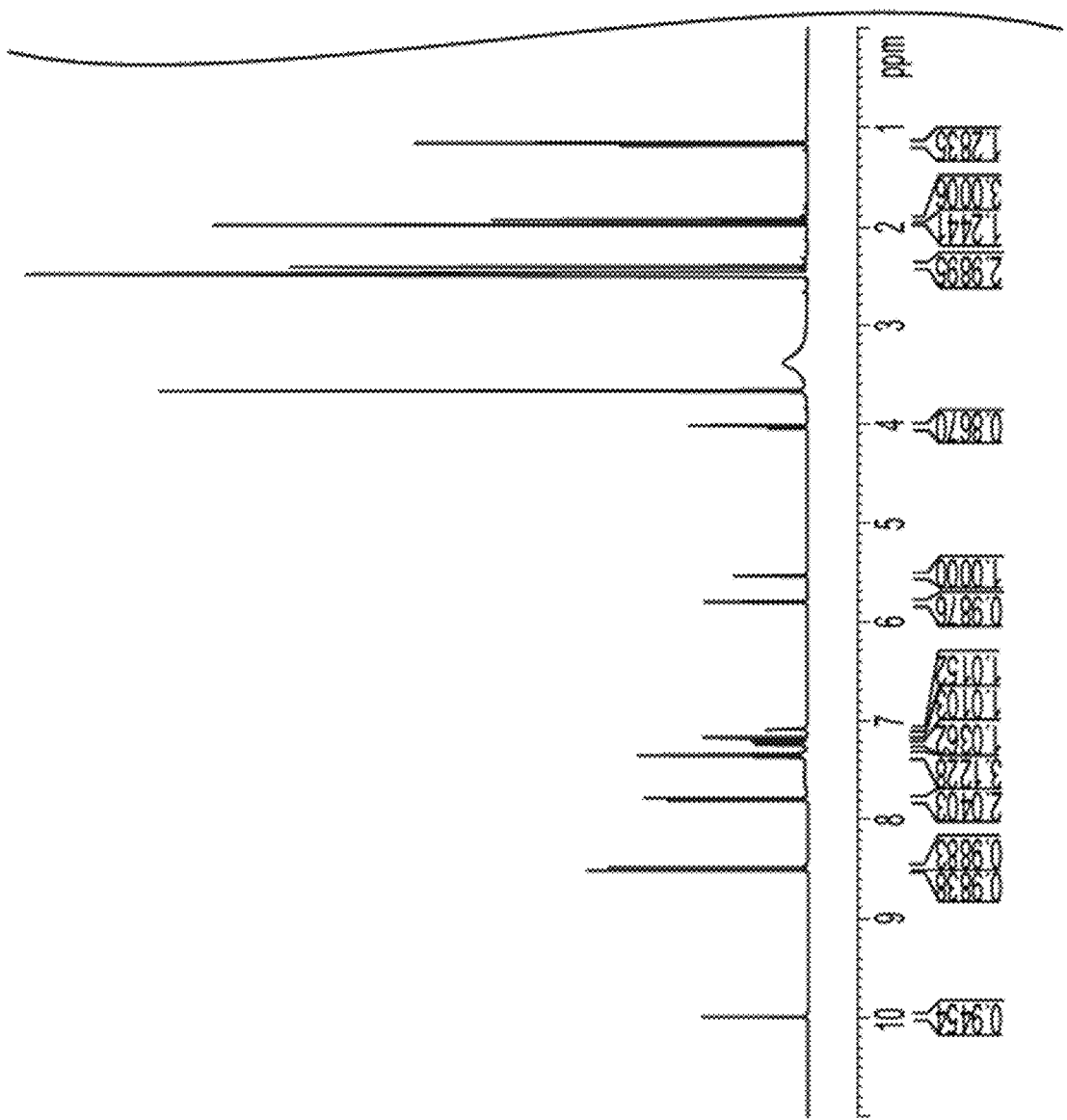
FIG. 9E depicts the characterization of Form I of Compound I-1 by $^1$H nuclear magnetic resonance ($^1$HNMR) in D6-DMSO at 400 MHz.
Figure 9E:
Figure 9E:
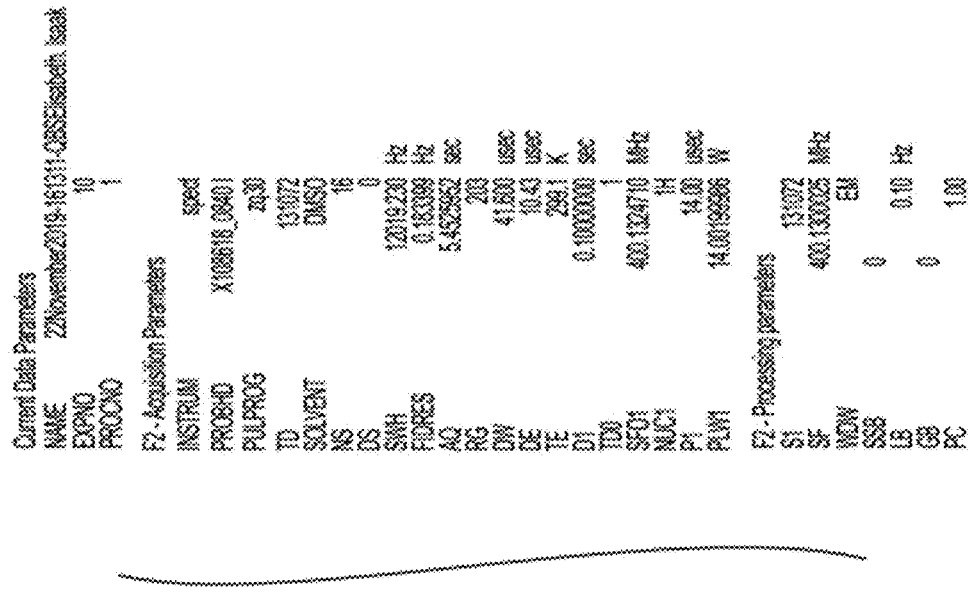

The XRPD of Form I of Compound I-1 is shown in FIG. 9A. Table 2.9 below sets out the X-Ray diffraction peaks observed for Form I of Compound I-1, wherein each value is in degrees 2θ:

TABLE 2.9

| Angle (2θ)° [1] | Relative Intensity % |
|---|---|
| 6.7 | 100.0 |
| 8.6 | 20.9 |
| 9.8 | 5.4 |
| 10.1 | 10.1 |
| 10.9 | 29.6 |
| 11.6 | 6.5 |
| 12.6 | 51.5 |
| 13.5 | 49.6 |
| 14.2 | 4.0 |
| 14.5 | 7.0 |
| 14.8 | 8.6 |
| 16.2 | 7.8 |
| 16.6 | 8.8 |
| 16.9 | 19.1 |
| 17.4 | 16.9 |
| 17.7 | 15.5 |
| 18.2 | 17.0 |
| 18.6 | 5.2 |
| 19.6 | 2.4 |
| 20.8 | 18.8 |
| 21.5 | 61.3 |
| 22.2 | 11.1 |
| 22.5 | 12.7 |
| 22.9 | 2.8 |
| 23.1 | 1.8 |
| 24.1 | 5.0 |
| 25.3 | 17.2 |
| 26.0 | 13.0 |
| 26.8 | 5.0 |
| 27.1 | 3.8 |
| 27.8 | 7.8 |
| 28.1 | 8.0 |
| 28.6 | 6.9 |
| 29.3 | 1.7 |
| 29.8 | 3.4 |
| 30.8 | 15.0 |
| 31.5 | 2.3 |
| 32.7 | 1.9 |
| 34.0 | 2.0 |
| 35.8 | 2.4 |

[1] In this and all subsequent tables, the position 2θ is within ±0.2.

Form J

After polymorph screening experiments described above, obtained solids all showed XRPD patterns, including Form J. Form J was also obtained by a salt break of Form I, followed by salt formation with HCl in ethyl acetate.

Figure 10D:
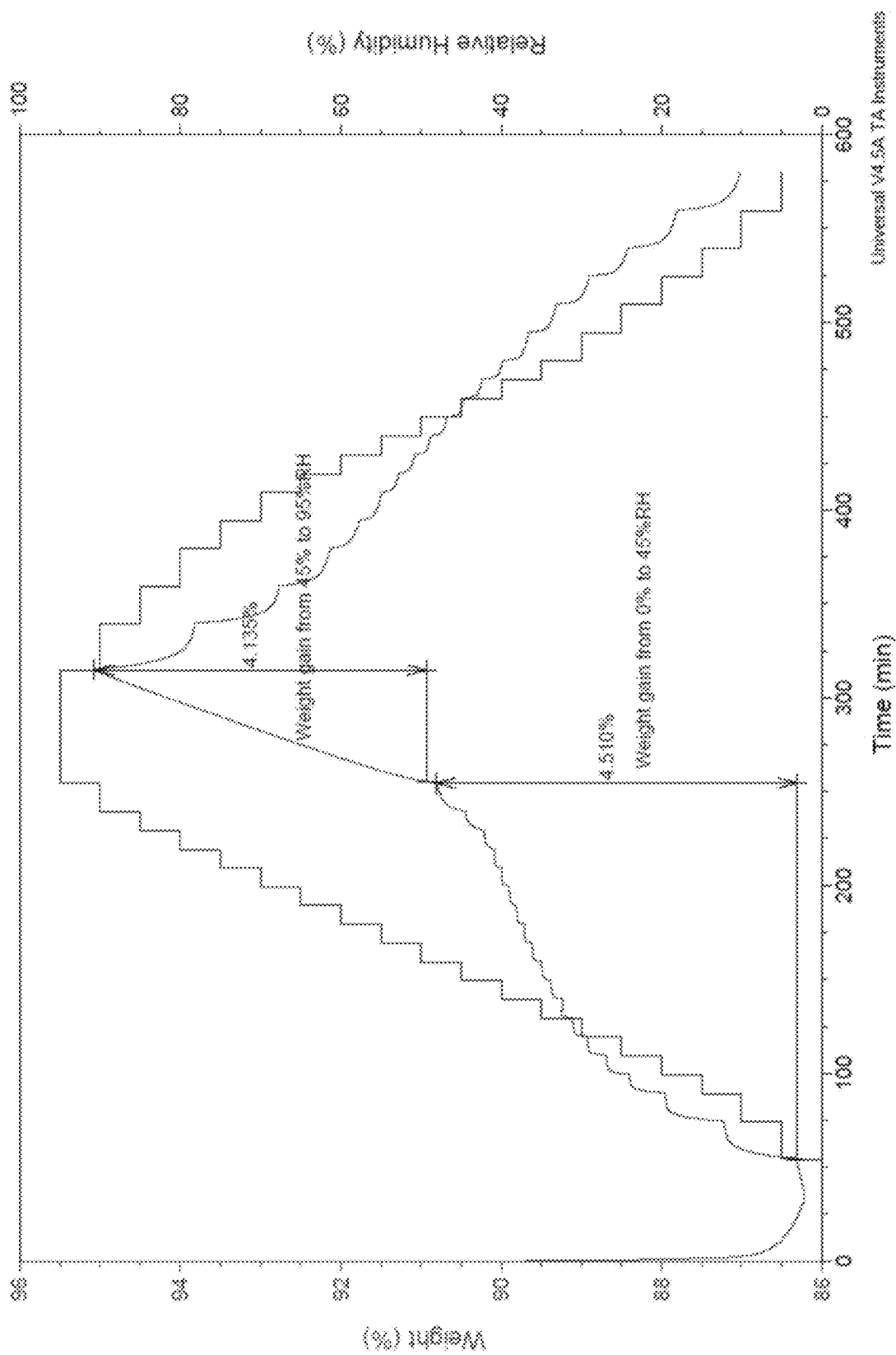
FIG. 10D depicts the characterization of Form J of Compound I-1 by dynamic vapor sorption (DVS).

Form J of Compound I-1 was then characterized by DSC, TGA and DVS. DSC scan of Form J in FIG. 10B showed an endothermic peak at the onset of 193.8° C. (enthalpy: 20.6 J/g). TGA scan (FIG. 10B) showed a weight loss of 9.1% from 40° C. to 100° C. In summary, Form J is a pure crystalline form of Compound I-1. Dynamic vapor sorption data for Form J of Compound I-1 is shown in FIG. 10D.

The XRPD of Form J of Compound I-1 is shown in FIG. 10A. Table 2.10 below sets out the X-Ray diffraction peaks observed for Form J of Compound I-1, wherein each value is in degrees 2θ:

TABLE 2.10

| Angle (2θ)° [1] | Relative Intensity % |
|---|---|
| 6.1 | 100.0 |
| 7.8 | 15.9 |
| 8.5 | 2.7 |
| 9.1 | 2.5 |
| 9.7 | 7.3 |
| 10.0 | 7.9 |
| 10.3 | 7.5 |
| 11.4 | 3.4 |
| 12.2 | 11.7 |

TABLE 2.10-continued

| Angle (2θ)° [1] | Relative Intensity % |
|---|---|
| 12.4 | 23.0 |
| 13.2 | 1.9 |
| 13.8 | 2.4 |
| 14.3 | 5.7 |
| 15.1 | 7.8 |
| 15.6 | 7.7 |
| 15.8 | 6.8 |
| 16.2 | 4.9 |
| 16.9 | 1.8 |
| 18.2 | 2.8 |
| 19.2 | 3.6 |
| 21.2 | 16.6 |
| 22.2 | 9.4 |
| 22.7 | 3.4 |
| 23.6 | 9.6 |
| 24.9 | 6.9 |
| 29.2 | 3.6 |
| 30.1 | 3.6 |

[1] In this and all subsequent tables, the position 2θ is within ±0.2.

Form K

After polymorph screening experiments described above, obtained solids all showed XRPD patterns, including Form K. Form K was also obtained by slurrying Form C in THF (25 vol) at 50° C. for 16 hrs.

Figure 11D:
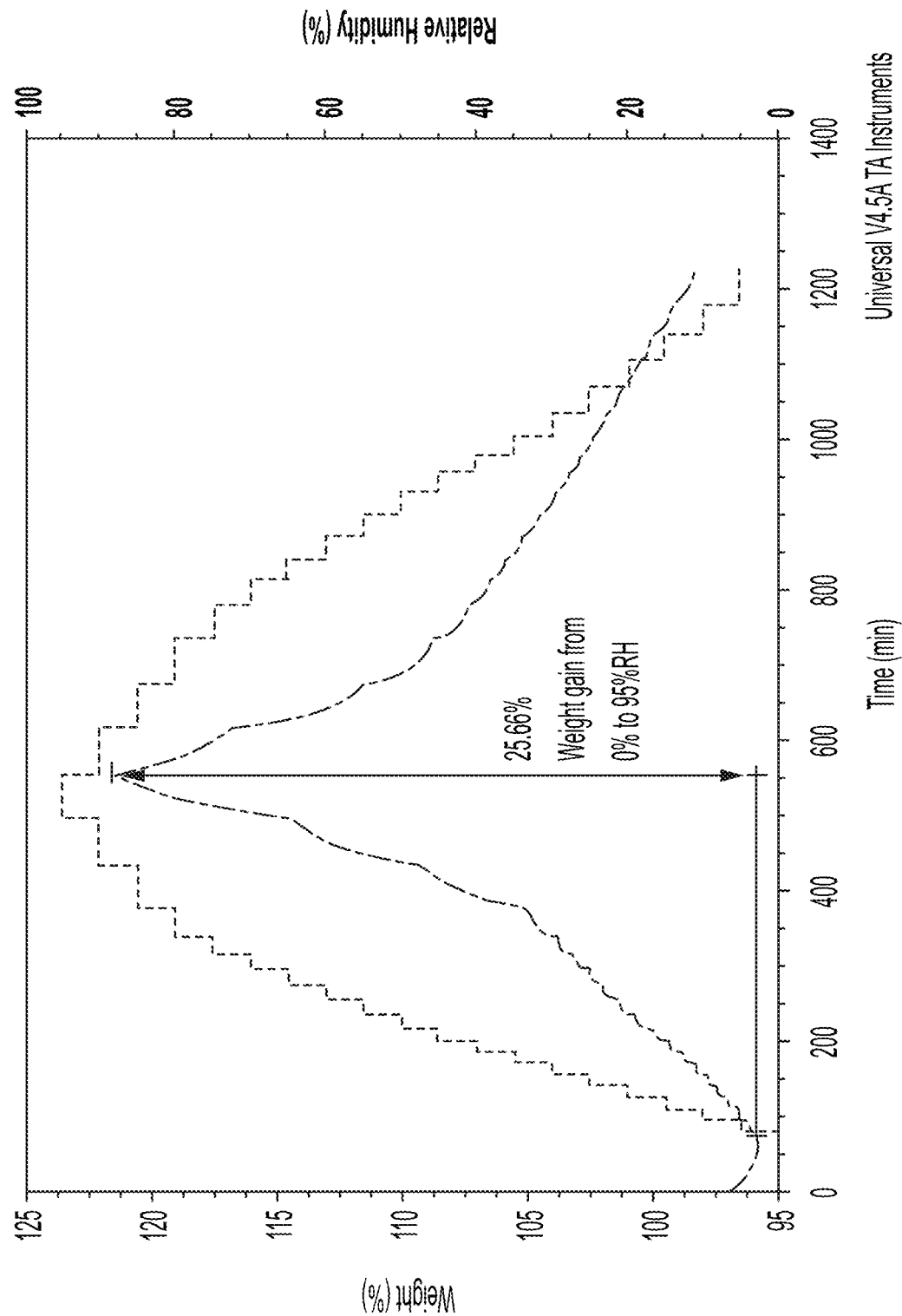
FIG. 11D depicts the characterization of Form K of Compound I-1 by dynamic vapor sorption (DVS).

Form K of Compound I-1 was then characterized by DSC, TGA and DVS. DSC scan of Form K in FIG. 11B showed an endothermic peak at the onset of about 147° C. (enthalpy: 10.7 J/g). TGA scan (FIG. 11B) showed a weight loss of 5.4% from 170° C. to 230° C. In summary, Form K is a pure crystalline form of Compound I-1. Dynamic vapor sorption data for Form K of Compound I-1 is shown in FIG. 11D.

The XRPD of Form K of Compound I-1 is shown in FIG. 11A. Table 2.11 below sets out the X-Ray diffraction peaks observed for Form K of Compound I-1, wherein each value is in degrees 2θ:

TABLE 2.11

| Angle (2θ)° [1] | Relative Intensity % |
|---|---|
| 5.7 | 30.0 |
| 6.6 | 100.0 |
| 8.0 | 28.9 |
| 8.9 | 8.4 |
| 10.4 | 77.9 |
| 10.9 | 21.5 |
| 12.9 | 46.6 |
| 13.7 | 38.8 |
| 15.4 | 17.2 |
| 16.6 | 21.6 |
| 17.0 | 35.7 |
| 17.2 | 18.2 |
| 20.9 | 23.2 |
| 21.0 | 25.0 |
| 23.7 | 36.4 |
| 28.8 | 8.4 |

[1] In this and all subsequent tables, the position 2θ is within ±0.2.

Example 7—Competitive Suspension Equilibrium Studies of N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide Hydrochloride (Compound I-1)

Competitive suspension equilibrium studies were performed. Equivalent quantities of different polymorphs and appropriate solvent (25 vol) were charged into separate 1.5 ml clear glass vials and stirred at 25° C. and 50° C. The form conversion was monitored by XRPD analysis.

Competitive suspension equilibration experiments investigating the stability of the forms in different organic solvents demonstrated that Form A was obtained from the majority of the conditions investigated (Table 3.1). The fastest transformation rate occurred in solvents with the highest solubility. The conversion of the mixture of different forms to Form A was observed in methanol (solubility 18.7 mg/ml) after 24 hours at both temperatures 25° C. and 50° C. and in ethanol (solubility 2.3 mg/ml) between 24 hours and 4 days. Conversion of mixtures of crystalline forms to Form A was observed in various solvents (Table 3.1), however the fastest conversion to Form A was observed in methanol and ethanol at both temperatures.

TABLE 3.1

| # | Solvent | Temp° C. | Input Forms | Output | Time of conversion |
|---|---|---|---|---|---|
| 1 | Methanol | 25° C. | Form A/Form B/Form C/Form D/Form F, 1/1/1/1/1 w/w/w/w/w | Form A | 24 h |
| 2 | Methanol | 50° C. | Form A/Form B/Form C/Form D/Form F, 1/1/1/1/1 w/w/w/w/w | Form A | 24 h |
| 3 | Methanol | 50° C. | Form B | Form A | 24 h |
| 4 | Ethanol | 50° C. | Form A/Form B, 1/1 w/w | Form A | 24 h |
| 5 | Ethanol | 50° C. | Form A/Form B/Form C/Form D/Form F, 1/1/1/1/1 w/w/w/w/w | Form A | 4 days |
| 6 | Ethanol | 25° C. | Form A/Form B/Form C/Form D/Form F, 1/1/1/1/1 w/w/w/w/w | Form A | 4 days |
| 7 | Ethanol | 50° C. | Form B | Form A | 4 days |
| 8 | Acetonitrile | 50° C. | Form A/Form B, 1/1 w/w | Form A | 48 h |
| 9 | 2-Propanol | 50° C. | Form A/Form B, 1/1 w/w | Form A | 5 days |
| 10 | 2-Propanol | 50° C. | Form A/Form B/Form C/Form D/Form F, 1/1/1/1/1 w/w/w/w/w | Form A | 7 days |
| 11 | Ethyl Acetate | 50° C. | Form A/Form B/Form C/Form D/Form F, Form G 1/1/1/1/1/1 w/w/w/w/w/w | Form A | 7 days |
| 12 | Ethyl Acetate | 50° C. | Form A/Form B, 1/1 w/w | Form A | 8 days |
| 13 | 2-Propanol | 25° C. | Form A/Form B, 1/1 w/w | Form A | 7 days |
| 14 | 2-Propanol | 25° C. | Form A/Form B/Form C/Form D/Form F, 1/1/1/1/1 w/w/w/w/w | Form A | 7 days |
| 15 | 2-Propanol | 25° C. | Form B | Form B | 7 days |
| 16 | 2-Propanol | 50° C. | Form B | Form B | 7 days |

Further investigations were conducted to establish the stability of polymorphs when Form D and Form I are matured when Form A seed is absent.

A mixture of the two forms (1/1 w/w) were charged into 1.5 ml clear glass vials and stirred at 50° C. for 16 hours. After this time, products were isolated by centrifuging at 10000 rpm for 10 minutes, dried under reduced pressure at 40° C. and analysed by)(RFD, HPLC and 1H NMR. Competitive slurry conversion experiments containing equivalent portions of Form D and Form I in ethanol/water (19/1 v/v, 10 vol) resulted in the production of Form A after 24 hours at 20° C. and 50° C. (Table 3.2). The conversion of the mixture of Form D and Form I to Form A was observed in ethanol after 7 days at 50° C. Form E was generated from slurrying the mixture Form D and Form I in ethanol at 20° C.

TABLE 3.2

| # | Solvent | Temp° C. | Input Forms | Output | Time of conversion |
|---|---|---|---|---|---|
| 1 | Ethanol/water (19/1 v/v) | 20° C. | Form D/ Form I, 1/1 w/w | Form A | 24 h |
| 2 | Ethanol/water (19/1 v/v) | 50° C. | Form D/ Form I, 1/1 w/w | Form A | 24 h |
| 3 | Ethanol | 50° C. | Form D/ Form I, 1/1 w/w | Form A | 7 days |
| 4 | Ethanol | 20° C. | Form D/ Form I, 1/1 w/w | Form E | 16 days |

Example 8—Preparation of salt forms of N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide The free base of Compound I-1 (compound I-2, 30 mg) was suspended in IPA (20 Vol., 600 µl at 50° C.). The solutions/suspensions were then treated with 1 mol eq. of the acids shown in table 4. The suspensions were then cooled down to 5° C. at 0.1° C./min and were held at this temperature for 16 hrs. Stirring (500 rpm) was maintained throughout. Any gums that formed were maturated between 25 and 50° C. (4 hours at each temperature for 24 hrs). The suspensions were isolated by filtration under suction and air dried then analysed by XRPD. Any new patterns identified by XRPD were analysed further by NMR, TGA, DSC and stability at 40 C/75% RH for 1 week.

Several samples were analyzed for solubility in Fasted State Simulated Intestinal Fluid (FaSSIF) and final pH in solution.

Results of the salt screen are summarised in Table 4.1. Several new patterns were found by XRPD.

TABLE 4.1

| # | Acid | Solubility in FaSSIF (mg/mL) | Final pH | XRPD |
|---|---|---|---|---|
| 1 | Hydrobromic acid | 0.0045 | 5.5 | HBr - Form A (FIG. 14A) |
| 2 | Hydrochloric acid | 0.0051 | 4.06 | HCl - Form A (FIG. 1E) |
| 3 | Sulfuric acid | 0.0012 | 5.86 | Sulfate - Form B (FIG. 15A) |
| 4 | p-Toluene sulfonic acid | nt | nt | p-Tosylate - Form A (FIG. 16A) |
| 5 | Methane Sulfonic acid | 0.0065 | 4.82 | Mesylate - Form A (FIG. 17A) |
| 6 | Benzene sulfonic acid | nt | nt | Besylate - Form A (FIG. 18A) |
| 7 | Oxalic acid | nt | nt | Partially crystalline - *free form - Form A |

TABLE 4.1-continued

| # | Acid | Solubility in FaSSIF (mg/mL) | Final pH | XRPD |
|---|---|---|---|---|
| 8 | L-Aspartic acid | nt | nt | *Free form - Form A (FIG. 13A) |
| 9 | Maleic acid | nt | nt | Maleate - Form A (FIG. 19A) |
| 10 | Phosphoric acid | nt | nt | *Free form - Form A |
| 11 | Ethane sulfonic acid | nt | nt | *Free form - Form A |
| 12 | Ketoglutaric acid | nt | nt | *Free form - Form A |
| 13 | Malonic acid | acid | nt | *Free form - Form A |
| 14 | L-Tartaric acid | nt | nt | *Free form - Form A |
| 15 | Fumaric acid | nt | nt | *Free form - Form A |
| 16 | Citric acid | nt | nt | *Free form - Form A |

"*" indicates that the free form of Compound I-1 was obtained, and a salt was not formed.
"nt" indicates that the value was not tested.

Polymorphism of the free form of Compound I-1 (compound I-2), the HBr salt (compound I-3), and the sulfate salt (compound I-4) was further investigated. Each was weighed (15 mg) into HPLC vials, and the solvent shown in Table 4.2 was added (50 Vol., 750 µl) and stirred at 50 C for 30 mins. Suspensions were slurried at 50 C for 24 hrs, and any clear solutions were cooled to 5 C at 0.1 C/min and held overnight. Solids were isolated by filtration under gravity and air dried, the solids were then tested by XRPD.

Results of the polymorph screen for the free form, HBr salt, and sulfate salt are summarized in Table 4.2. Several new patterns were found by XRPD.

TABLE 4.2

| Starting Material | Solvent | XRPD |
|---|---|---|
| Free Form compound 1-2 (Free form Form B) | EtOAc | Free Form Form B |
| | IPAc | Free Form Form B |
| | IPA | Free Form Form A |
| | MEK | Free Form Form B |
| | Acetone | Free Form Form B |
| | EtOH | Free Form Form C |
| | THF | Free Form Form D |
| | MeOH | Free Form Form E |
| | ACN | Free Form Form B |
| | TBME | Free Form Form B |
| | Acetone:water (9:1) | Free Form Form B |
| | IPA:water (9:1) | Free Form Form B |
| HBr salt Compound 1-3 (HBr Form A) | EtOAc | HBr Form A |
| | IPAc | HBr Form A |
| | IPA | HBr Form A |
| | MEK | HBr Form A |
| | Acetone | HBr Form A |
| | EtOH | HBr Form A |
| | THF | HBr Form A |
| | MeOH | HBr Form A |
| | ACN | HBr Form A |
| | TBME | HBr Form A |
| | Acetone:water (9:1) | HBr Form A |
| Sulfate salt Compound 1-4 (Sulfate Form B) | EtOAc | Sulfate Form B |
| | IPAc | Sulfate Form B |
| | IPA | Sulfate Form B |
| | MEK | Sulfate Form B |
| | Acetone | Sulfate Form B |
| | EtOH | Sulfate Form A |
| | THF | Sulfate Form B |

TABLE 4.2-continued

| Starting Material | Solvent | XRPD |
|---|---|---|
| | ACN | Sulfate Form B |
| | TBME | Sulfate Form B |
| | Acetone:water (9:1) | Sulfate Form C |
| | IPA:water (9:1) | Sulfate Form C |

Figure 13A:
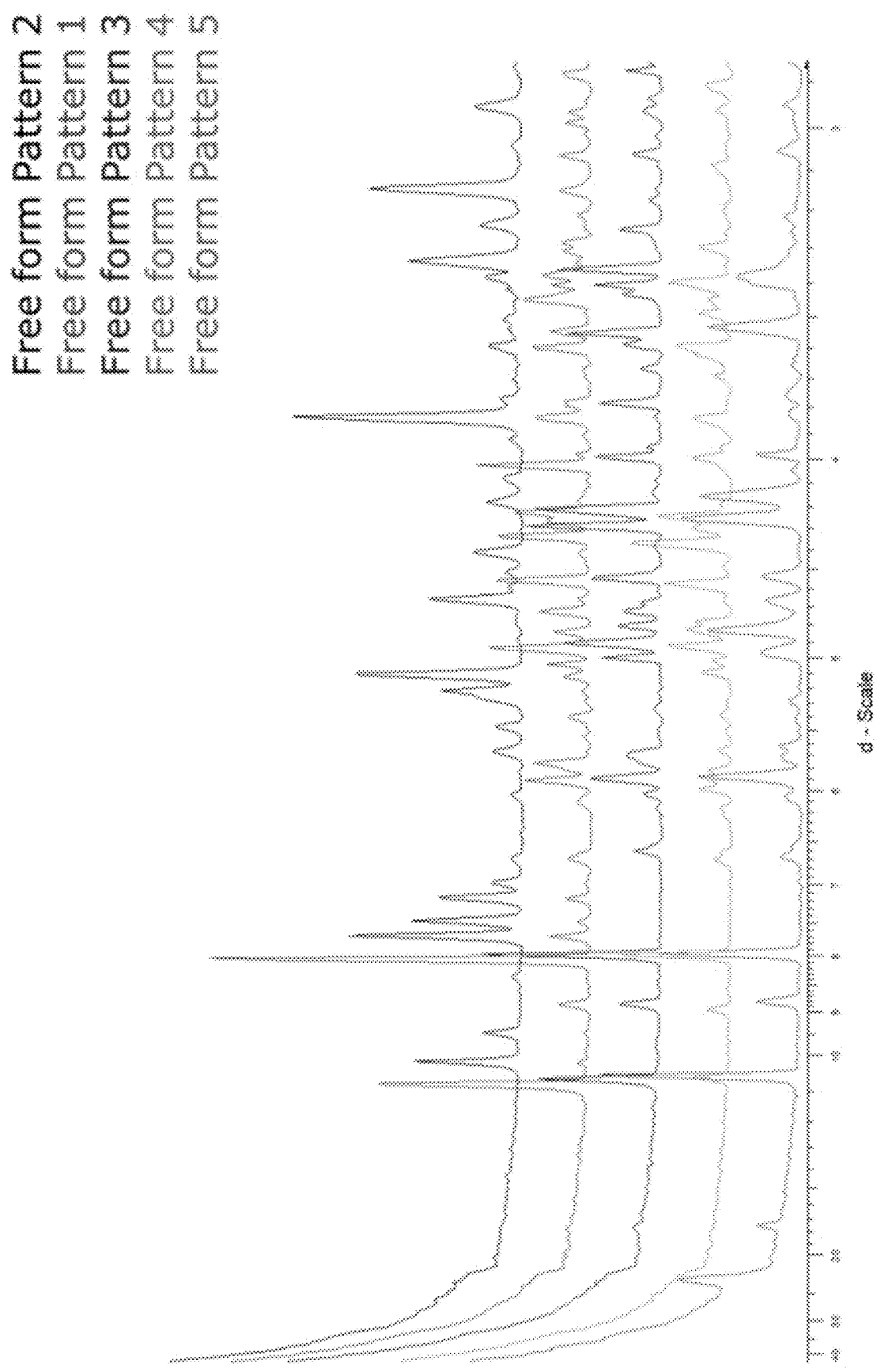
FIG. 13A depicts X-ray diffraction Patterns 1 to 5 (Forms A-E) of Compound I-2 (free form).
Figure 13B:
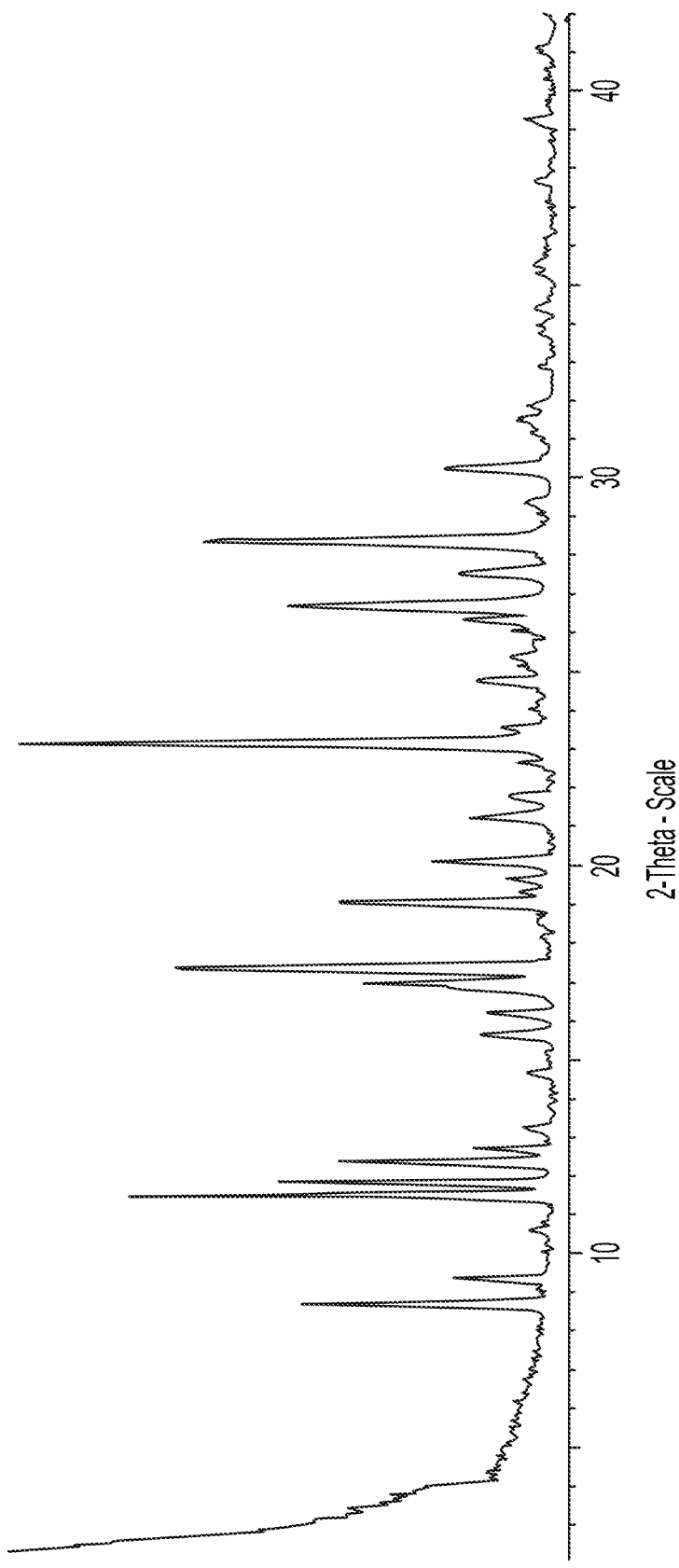
FIG. 13B depicts an X-ray diffraction pattern of Form B of Compound I-2 (free form).
Figure 13C:
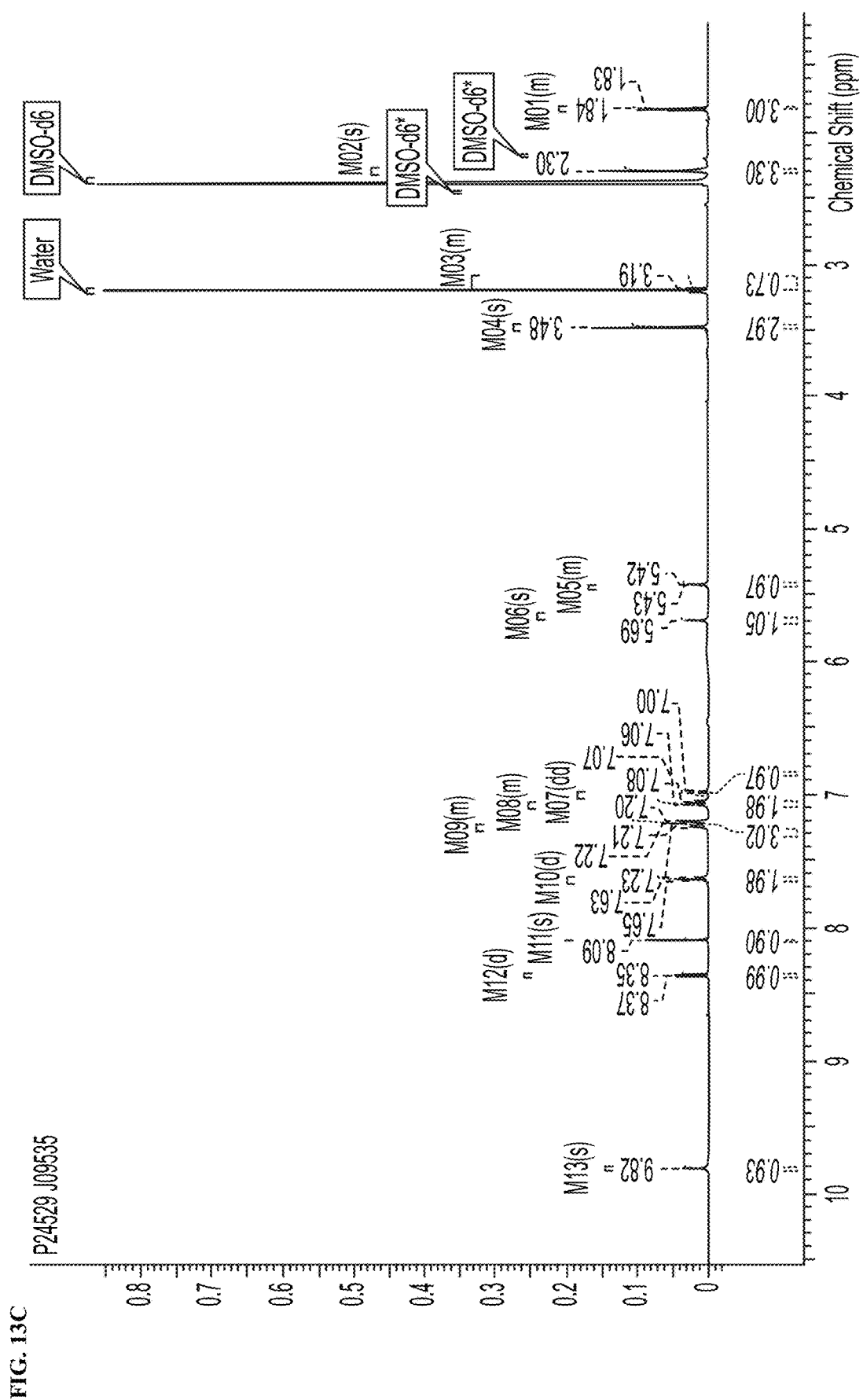
FIG. 13C depicts the characterization of Form B of Compound I-2 by $^1$H nuclear magnetic resonance ($^1$H NMR) in D6-DMSO at 400 MHz.
Figure 13D:
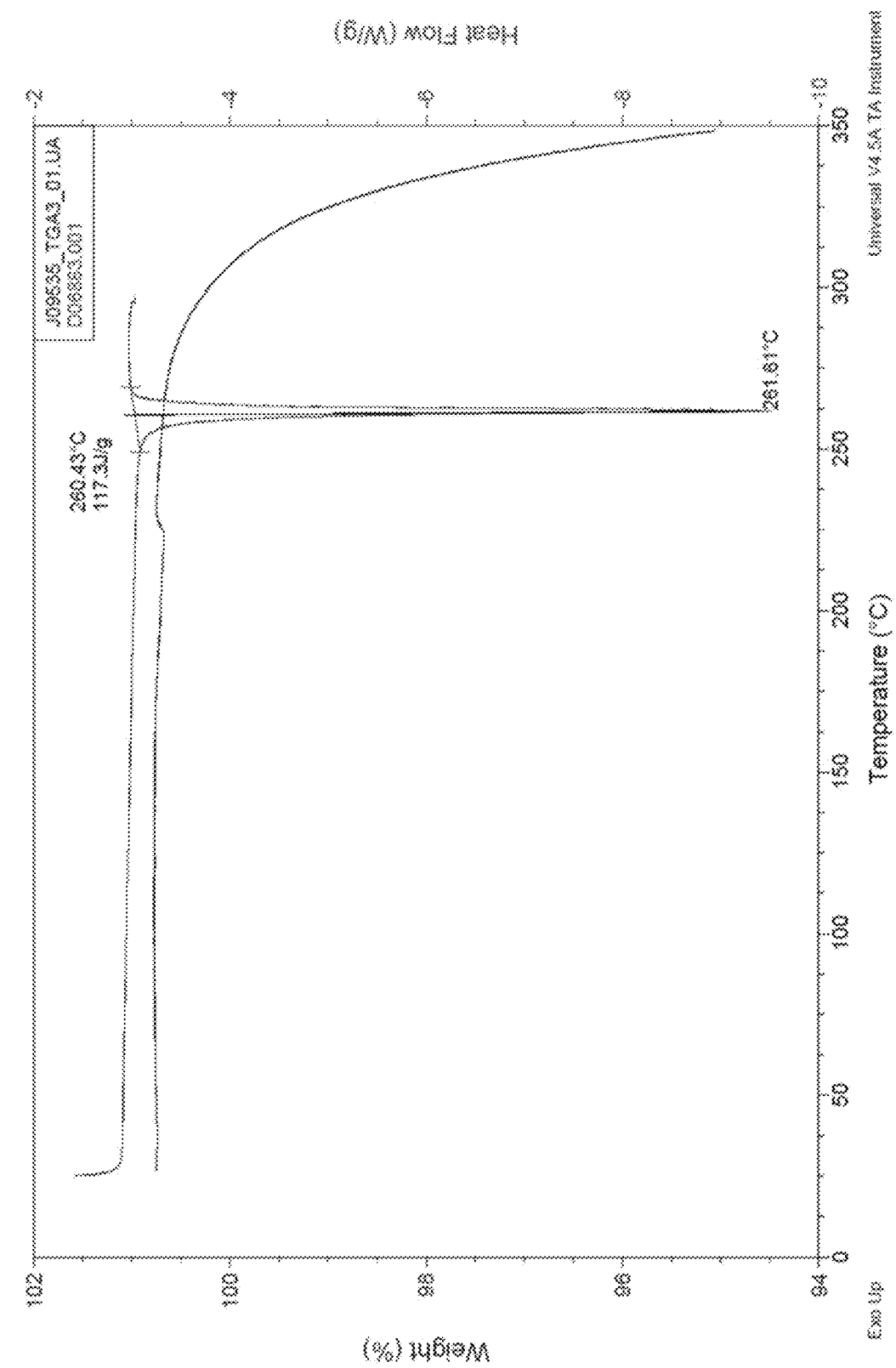
FIG. 13D depicts the characterization of Form B of Compound I-2 thermogravimetric analysis (below) and differential scanning calorimetry (above).
Figure 13E:
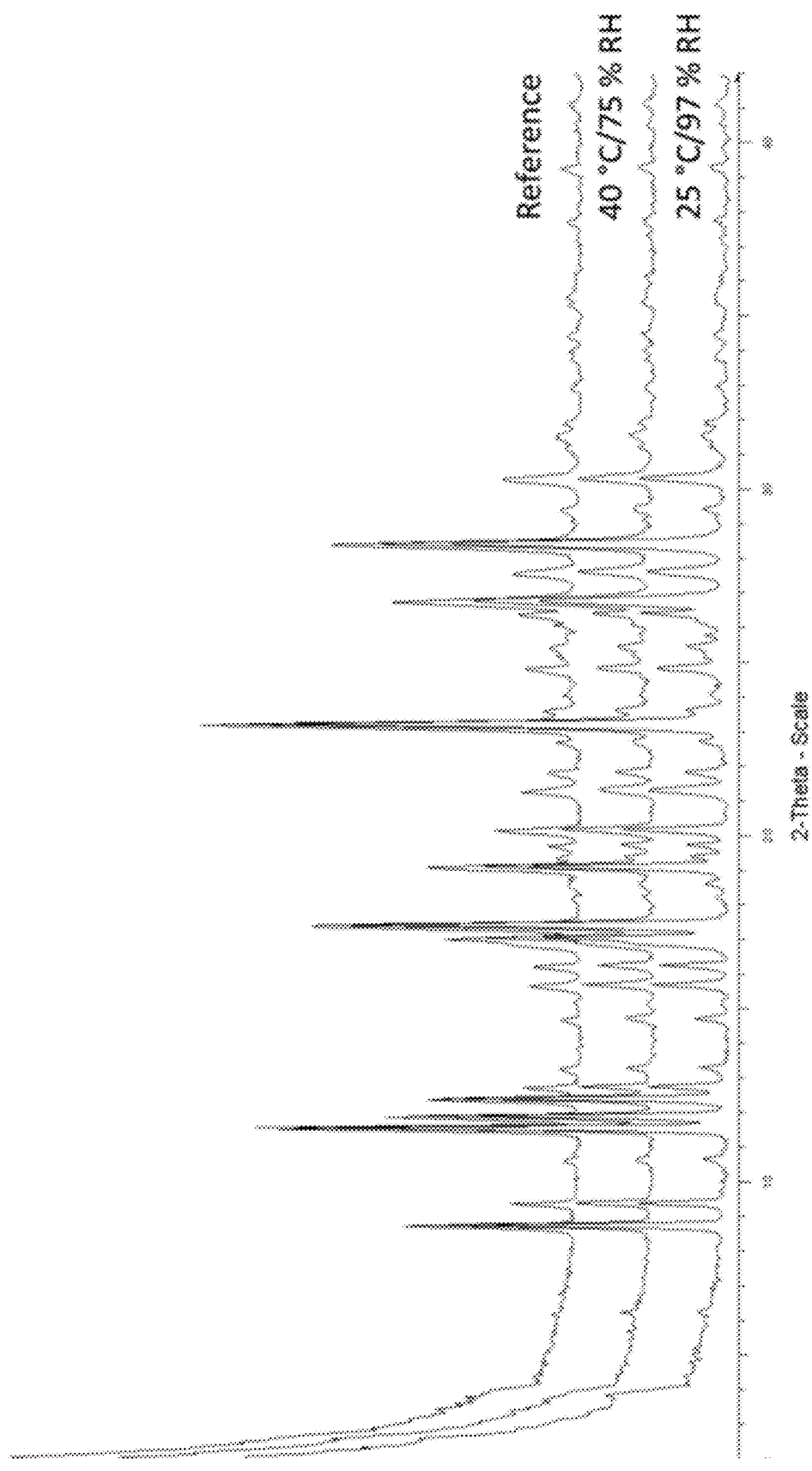
FIG. 13E depicts an X-ray diffraction pattern of Form B of Compound I-2 before and after static storage at 40 C, 75% relative humidity, and 25 C, 97% relative humidity.

The XRPDs of Patterns 1-5 for the free form (compound I-2) is shown in FIG. 13A.

The XRPD of Form A for the HBr salt (compound I-3) is shown in FIG. 14A.

The XRPD of Form B for the sulfate salt (compound I-4) is shown in FIG. 15A.

Example 9—Cocrystal screening studies on of N-(4-(4-amino-5-(3-fluoro-4-((4-methylpyrimidin-2-yl)oxy)phenyl)-7-methyl-7H-pyrrolo[2,3-d]pyrimidin-6-yl)phenyl)methacrylamide Hydrochloride (Compound I-1)

Cocrystal screening was performed using two methods: solvent drop grinding and maturation of slurries.

For the solvent drop grinding method (or liquid-assisted grinding), the free form of Compound I-1 (compound I-2) was weighed into 18 HPLC vials (30 mg/vial), and the co-formers were then weighed into separate HPLC vials (neat, 1 mol eq. added as solid or liquid). The HPLC vials were then poured into the sample vials containing the co-formers. Two stainless steel ball bearings and 5 μl of ethanol were then added to the HPLC vials and the samples were ground for 2 h at 650 rpm using a Fritsch Pulverisette milling system. The solids collected after grinding were then analyzed by XRPD, and any new XRPD patterns were isolated and analyzed.

For the maturation of slurries method, samples that remained as physical mixtures and did not form a new XRPD pattern post liquid assisted grinding, were suspended in ethanol and were subjected to heat-cool cycles between 25 and 50° C. (4 hours at each temperature cycling) for 24 hours. Suspensions collected from this experiment were filtered and analyzed by XRPD analysis.

From the screening procedures involving liquid assisted grinding and maturation, 5 unique cocrystal XRPD patterns were observed as shown in Table 5.

TABLE 5

Figure 20:
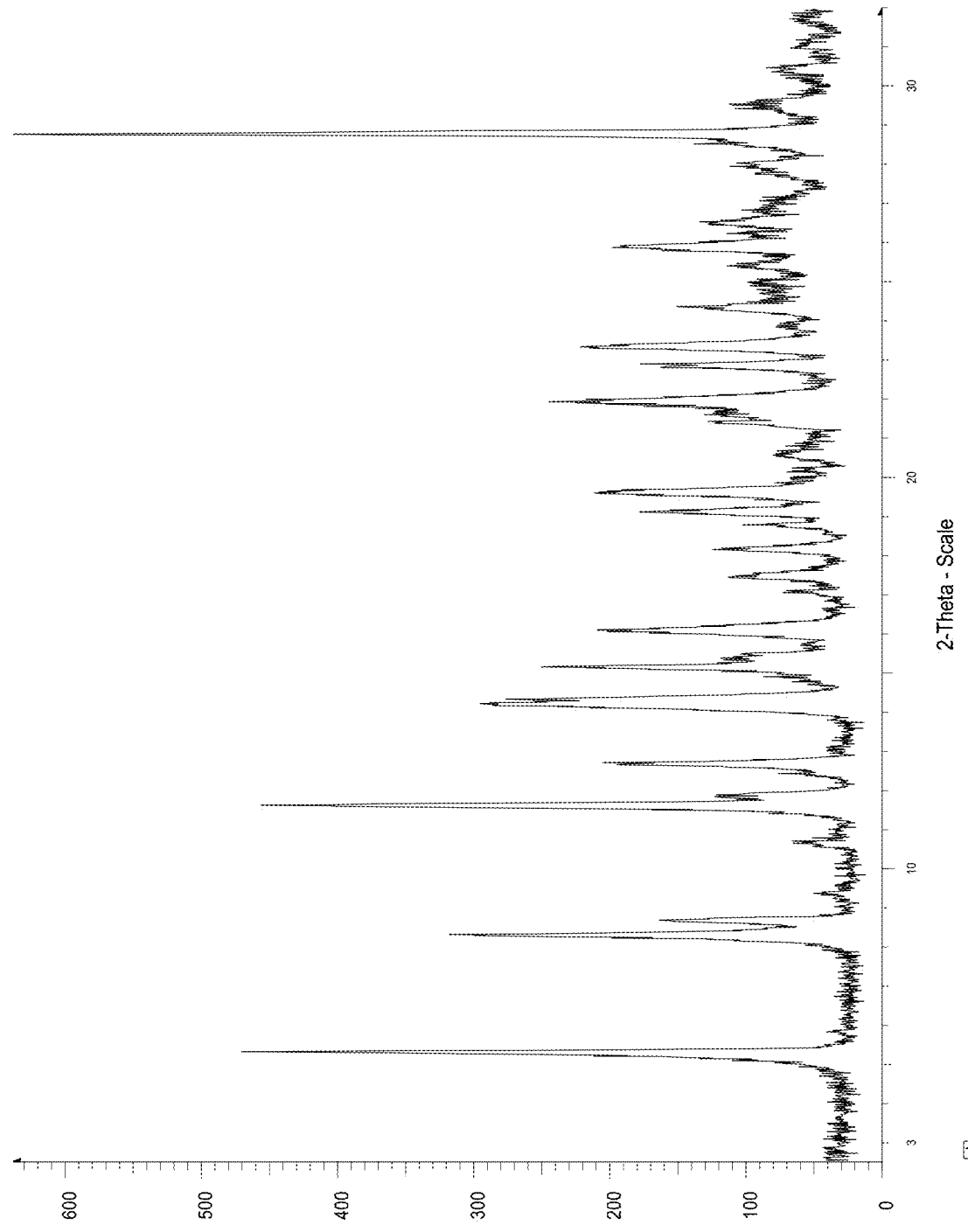
FIG. 20 depicts an X-ray diffraction pattern of Form A of a fumaric acid cocrystal of Compound I-2.
Figure 21:
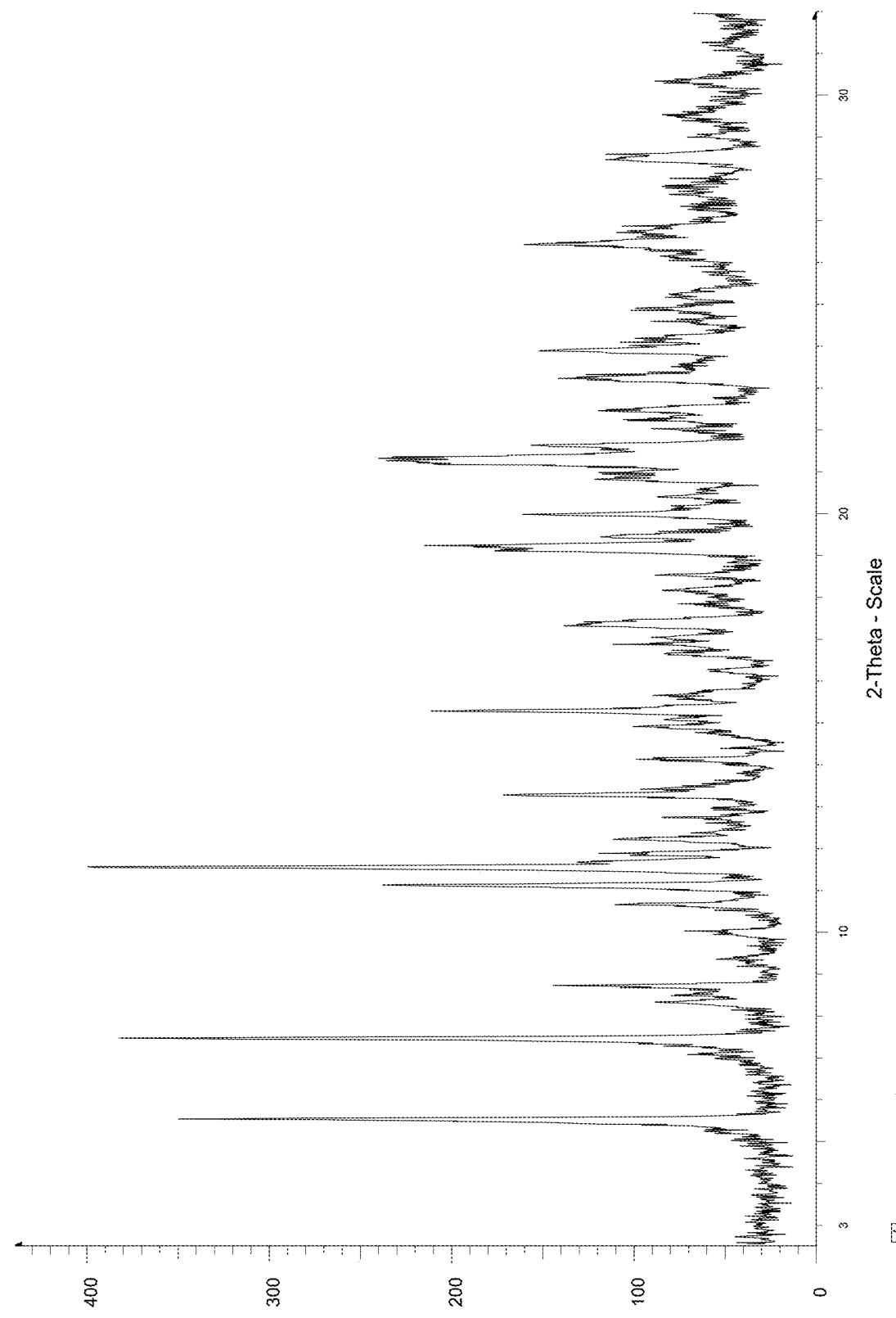
FIG. 21 depicts an X-ray diffraction pattern of Form A of a malonic acid cocrystal of Compound I-2.
Figure 22:
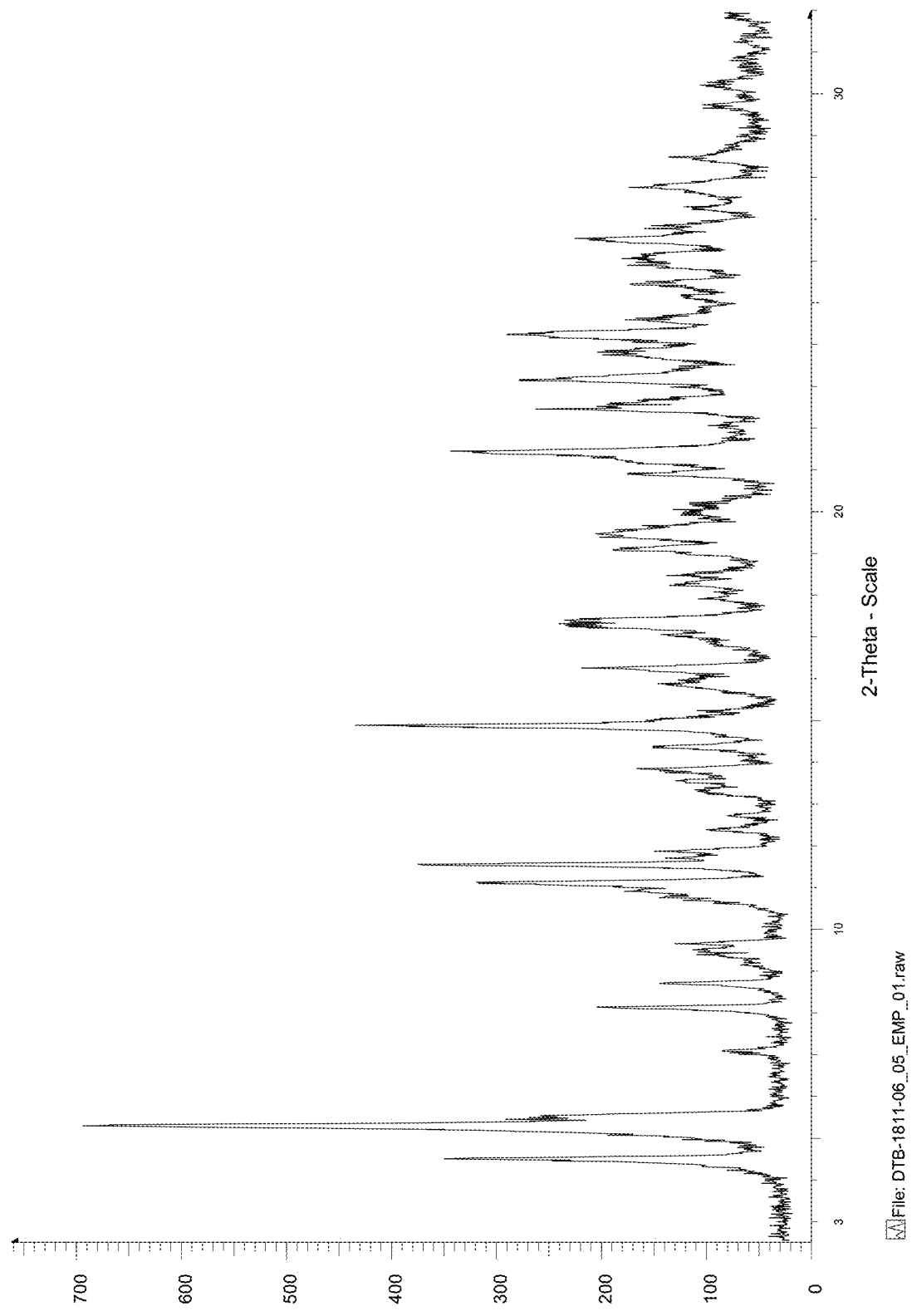
FIG. 22 depicts an X-ray diffraction pattern of Form A of a benzoic acid cocrystal of Compound I-2.
Figure 23:
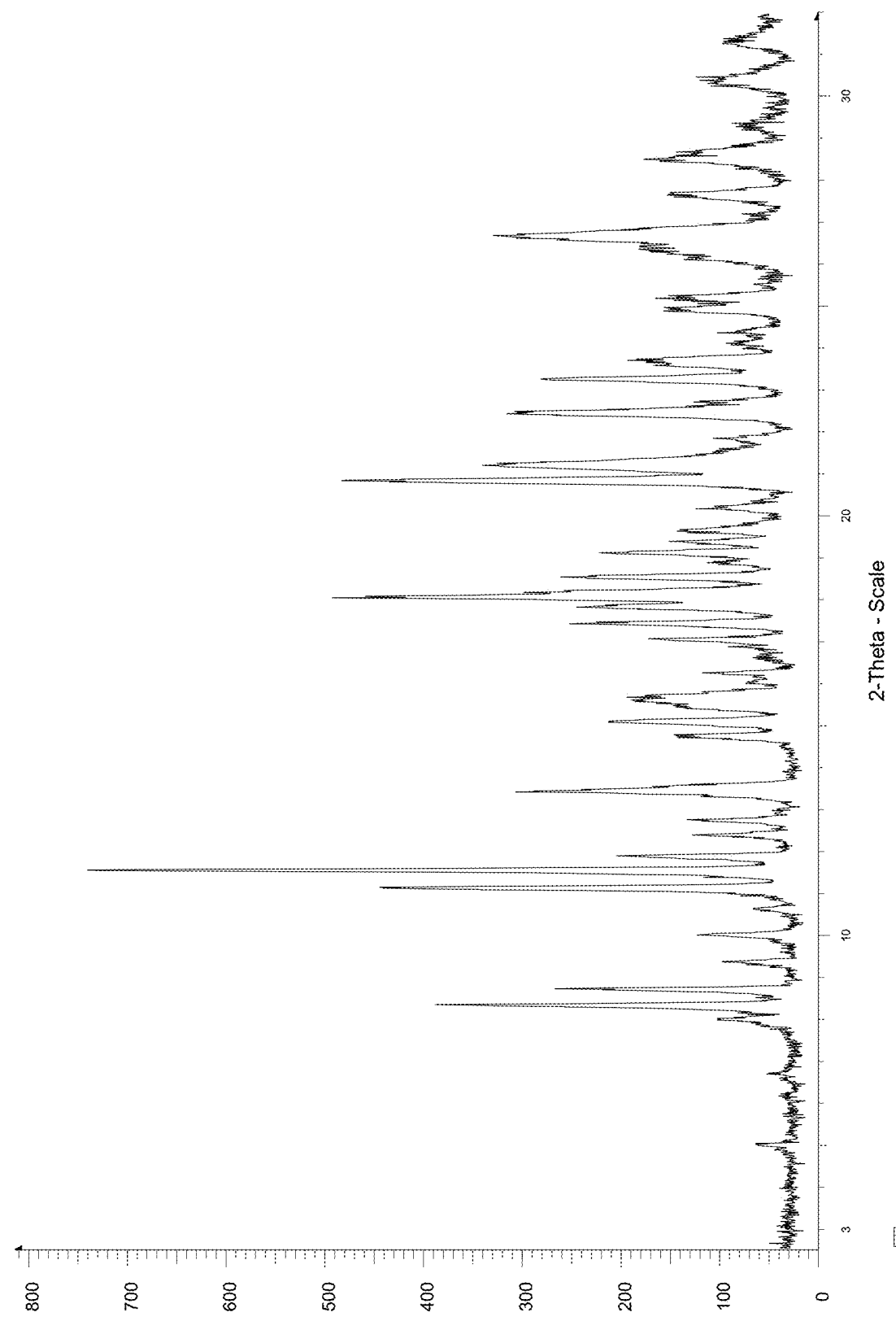
FIG. 23 depicts an X-ray diffraction pattern of Form A of a benzamide cocrystal of Compound I-2.

| Co-former | XRPD post grinding | XRPD post slurries |
|---|---|---|
| Fumaric acid | fumaric cocrystal Form A (FIG. 20) | — |
| Malonic acid | malonic cocrystal Form A (FIG. 21) | — |
| L-Lactic Acid | — | — |
| Succinic acid | — | — |
| Benzoic acid | benzoic cocrystal Form A (FIG. 22) | — |
| Adipic acid | — | adipic cocrystal Form A |
| Sorbic acid | — | — |
| Caffeic acid | — | — |
| Nicotinic acid | — | — |
| Orotic acid | — | — |
| Salicylamide | — | — |
| Nicotinamide | — | — |
| Benzamide | benzamide cocrystal Form A (FIG. 23) | — |
| Propyl gallate | — | — |
| Methylparaben | — | — |
| Urea | — | — |
| Glycerol | — | — |
| Theobromine | — | — |

"-" indicates that a cocrystal was not formed.

Example 10—Polymorph Screen of (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide (Compound II-1)

Compound II-1 (40 mg) was treated with an aliquot of solvent (200 μl for 5 vol, 400 μl for 10 vol, 800 μl for 20 vol) and left to stir at 25° C. for 15 minutes. After 15 minutes, suspensions were treated with another aliquot of solvent and left to stir for the same duration again. Any solutions were removed from stirring and further solvent additions. This procedure was repeated up to 40 vol.

At 40 vol, any remaining suspensions were heated to 40° C. at a rate of 10° C./min. Samples that remained as suspensions at 40° C. were moved to the maturation chamber (RT/50° C.) for 4 days. All solutions from solvent additions were heated to 50° C. before cooling to 5° C. at a rate of 0.1° C./min, then held at 5° C. overnight.

After cooling, any solutions and thin suspensions were left uncapped to evaporate. After maturation, suspensions were filtered, and solids dried under suction; solutions were left uncapped to evaporate.

TABLE 6

| Solvent | Treatment | Observation after treatment | Further treatment | Observation after treatment | XRPD |
|---|---|---|---|---|---|
| n-Heptane | Maturation | Suspension | — | — | Form A |
| Ethyl acetate | Maturation | Suspension | — | — | Form A |
| Isopropyl acetate | Maturation | Suspension | — | — | Form A |
| 2-Propanol | Cooling | Solution | Evaporation | White solid | Form A |
| MEK | Maturation | Suspension | — | — | Form A |
| Acetone | Maturation | Suspension | — | — | Form A |
| Ethanol | Cooling | Solution | Evaporation | White solid | Form A |
| TBME | Maturation | Suspension | — | — | Form A |
| Methanol | Cooling | Solution | Evaporation | White solid | Form B |
| THF | Cooling | Suspension | — | — | Form A |
| 10% Water/MeCN | Cooling | Solution | Evaporation | White solid | Poorly crystalline |
| Water | Maturation | Suspension | — | — | Amorphous |
| 10% Water/IPA | Cooling | Solution | Evaporation | White solid | Form A |

Amorphous Compound II-1 was found to have reasonable solubility in polar solvents. Compound 1 was most soluble in THF (20 vol at 25° C.), ethanol (20 vol at 25° C.) and 10% $H_2O$/IPA (10 vol at 25° C.). A precipitate formed after dissolving Compound 1 in THF. Based on the solubility measurements ethanol was selected for the salt screening.

After further treatment by maturation of suspensions or evaporation of solutions solids were formed for all experiments. 10 of the 13 experiments produced the same crystalline form, Form A.

A single other crystalline form was also produced from this screen. The other form, Form B, was produced after evaporating Compound II-1 dissolved in methanol. 10% $H_2O$/MeCN and $H_2O$ produced amorphous and poorly crystalline patterns respectively.

TABLE 7

| XRPD | Form A | Form B |
|---|---|---|
| $^1$H NMR | Resonances consistent with structure. THF present at 0.1 molar equivalents | Resonances consistent with structure. No additional solvent peaks |
| TGA | *Mass loss of 2.7% between RT and 130° C. Mass loss of 0.8% between 210 and 250° C. corresponding to melt. Compound begins to decompose around 300° C. | Mass loss between 25 and 75° C. of 5% corresponding to 1.5 molar equivalents of water. Compound decomposition begins at 325° C. |
| DSC | Single large endotherm (89 J/g) with onset at 232.3° C. | Broad endotherm (43 J/g) with onset at 66.2° C. Endotherm (16 J/g) with onset 148.8° C. Small endotherm (1 J/g) with onset 233.7° C. |
| Storage at 40° C./75% RH for 7 days | Unchanged | Unchanged |

Crystalline Form A shows a straightforward thermal profile. DSC of crystalline Form A shows only a single thermal event at 232° C. which is postulated to be the melt of Form A. TGA suggests that Form A is slightly hygroscopic as a small mass loss of 2.7% was observed between RT and 130° C. which would correspond to the loss of ~0.6 equivalents of water. As Form A formed in solvents immiscible with water it is unlikely to be a hydrate.

$^1$H NMR of the analyzed Form A sample showed close to 0.1 molar equivalents of THF which indicates that the form is anhydrous. Form A showed no change by XRPD after being stored for one week at 40° C./75% RH.

Form B shows no solvent peaks by $^1$H NMR, but a ~5% weight loss by TGA between 25 and 75° C. with a corresponding endotherm by DSC with an onset at 66° C. In combination analysis suggests that Pattern 2 is likely to be a hydrate of Compound II-1. The 5% weight loss in TGA corresponds to the loss of 1.5 molar equivalents of water which suggests that Compound 1 Pattern 2 is hygroscopic. The DSC of Form B shows two additional events, an endotherm with onset 149° C. and a small endotherm which begins at 234° C. The endotherm at 234° C. corresponds to the single endotherm observed for Form A which potentially indicates that Form B thermally converts to Form A after being desolvated.

TABLE 8

XRPD Peak list of Compound II-1 Form A

| Angle (2-Theta °) [1] | Intensity (%) | Angle (2-Theta °) [1] | Intensity (%) |
|---|---|---|---|
| 9.8 | 44.3 | 22.8 | 39.6 |
| 10.9 | 33.1 | 23.3 | 29.6 |
| 12.6 | 43.4 | 24.4 | 31.3 |
| 13.1 | 44.8 | 24.8 | 17.1 |
| 13.6 | 16.8 | 25.4 | 28.4 |
| 14.9 | 49.4 | 26.3 | 21.3 |
| 16.9 | 46.7 | 26.9 | 16.3 |
| 17.2 | 27.4 | 27.5 | 14.4 |
| 18.7 | 100 | 28.2 | 10.4 |
| 19.6 | 30.7 | 28.8 | 21.1 |
| 20.4 | 27.6 | 29.1 | 11.8 |
| 21.4 | 38.7 | 29.6 | 11.8 |
| 22.0 | 18.2 | 30.7 | 10.2 |

[1] In this and all subsequent tables, the position 2θ is within ±0.2.

TABLE 9

XRPD peak list of Compound II-I Form B

| Angle (2-Theta °) [1] | Intensity (%) | Angle (2-Theta °) [1] | Intensity (%) |
|---|---|---|---|
| 7.7 | 39.4 | 21.6 | 16.6 |
| 10.5 | 100 | 22.0 | 27.1 |
| 11.0 | 11.4 | 22.2 | 22.6 |
| 11.3 | 17.6 | 22.6 | 11.1 |
| 11.8 | 9.4 | 23.2 | 7.6 |
| 12.1 | 8.3 | 23.7 | 13.6 |
| 12.7 | 11.1 | 23.9 | 14.2 |
| 13.3 | 10.8 | 24.4 | 28.7 |
| 14.7 | 16.7 | 24.9 | 8.4 |
| 15.2 | 59.1 | 25.4 | 8.9 |
| 15.9 | 39.1 | 26.0 | 20.2 |
| 16.8 | 19.4 | 26.8 | 11.5 |
| 17.4 | 86 | 27.2 | 7.4 |
| 18.3 | 20.9 | 27.5 | 12 |
| 18.6 | 43.7 | 27.8 | 16.8 |
| 18.8 | 21.3 | 28.6 | 9.4 |
| 19.5 | 42.6 | 29.5 | 5.1 |
| 20.0 | 33.1 | 30.1 | 8.3 |
| 20.2 | 19.2 | 30.4 | 10.5 |
| 20.7 | 49.7 | — | — |

[1] In this and all subsequent tables, the position 2θ is within ±0.2.

Example 11—Preparation of salt forms of (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide (Compound II-1)

Compound II-1 (520 mg) was dissolved in ethanol (10.4 ml, 2θ vol) by stirring at RT for 15 minutes to produce a yellow solution. The API solution was dispensed into vials 800 μl (~40 mg) in each and heated to 50° C.

Acid solution (1.1 eq, 88 μl for 1 M, 176 μl for 0.5 M) was added to the API solutions. The samples were cooled to 5° C. at a rate of 0.1° C./min and held at 5° C. for 1 day. After cooling, any remaining solutions were left uncapped to evaporate at RT. Solids from suspensions were filtered and dried under suction and analysed by XRPD on a metal well plate.

After initial XRPD analysis, solids from either suspensions, evaporation, or gums found to be amorphous by XRPD were suspended in TBME (500 μl) and placed into maturation (RT/50° C.) for 6 days. After maturation in TBME, the suspensions were aliquoted onto a glass slide and after airdrying solids were analysed by XRPD.

After XRPD analysis, samples found to be amorphous or consistent with the free form were uncapped and once dry the samples were treated with heptane (500 μl) and returned to maturation for 4 days. After maturation in heptane, the suspensions were aliquoted onto a glass slide and after airdrying solids were analysed by XRPD.

After XRPD analysis, samples found to be amorphous or consistent with the free base form were uncapped and once dry the samples were treated with ethyl acetate (500 μl) and returned to maturation for 2 days. After maturation in ethyl acetate, the suspensions were aliquoted onto a flat silicon XRPD sample holders and after airdrying solids were analysed by XRPD.

Upon cooling of the acid-API solutions of Compound 1, samples with sulfonic acids formed suspensions but all others remained as solutions. Solids produced were white powders when dried.

Analysis of the solids from suspensions showed that crystalline salts were obtained from p-toluene sulfonic acid, and benzene sulfonic acid.

TABLE 10

Initial salt screen

| Counter-ion | Observation on acid addition | Observation after cooling | XRPD after cooling |
|---|---|---|---|
| Hydrobromic acid - HBr | Solution | Clear solution | — |
| Hydrochloric acid - HCl | Solution | Clear solution | — |
| Sulfuric acid - SO4 | Solution | Clear solution | — |
| p-Toluene sulfonic acid - pTSA | Solution | Suspension | Toluene sulfonate Form A |
| Methane sulfonic acid - MSA | Solution | Clear solution | — |
| Benzene sulfonic acid - BSA | Solution | Suspension | Benzene sulfonate Form A |
| Maleic acid - MEA | Solution | Clear solution | — |
| Phosphoric acid - PHOA | Solution | Clear solution | — |
| Malonic acid - MLNA | Solution | Clear solution | — |
| L-Tartaric acid - TAR | Solution | Clear solution | — |
| Fumaric acid - FUA | Solution | Clear solution | — |
| Citric acid - CA | Solution | Clear solution | — |

Key: — = not conducted

TABLE 1

Secondary salt screen

| Counter-ion | XRPD after evaporation | XRPD after TBME maturation | XRPD after heptane maturation | XRPD after EtOAc maturation |
|---|---|---|---|---|
| Hydrobromic acid - HBr | Amorphous | Amorphous | HBr FormA | — |
| Hydrochloric acid - HCl | Amorphous | Amorphous | Amorphous | HCl Form A |
| Sulfuric acid - SO4 | Amorphous | Amorphous | Amorphous | Amorphous |
| Methane sulfonic acid - MSA | Amorphous | Methane sulfonate Form A | — | — |
| Maleic acid - MEA | Amorphous | Amorphous | Amorphous | Amorphous |
| Phosphoric acid - PHOA | Amorphous | Amorphous | Amorphous | Amorphous |
| Maionic acid - MLNA | Amorphous | Amorphous | Amorphous | Amorphous |
| L-Tartaric acid - TAR | Amorphous | Amorphous | Amorphous | Amorphous |
| Fumaric acid - FUA | Amorphous | Fumarate Form A | — | — |
| Citric acid - CA | Amorphous | Amorphous | Amorphous | Amorphous |

Key: — = not conducted

Samples which remained as clear solutions after cooling were left to evaporate but all resulted in amorphous solids as characterised by XRPD. These amorphous solids were treated with TBME and subjected to maturation followed by evaporation and characterisation by XRPD. This resulted in an additional two crystalline salts forming: a methane sulfonate salt and a fumarate salt. These two salts were characterised further.

The remaining amorphous materials were matured in heptane, which produced another crystalline salt. The crystalline material produced was characterised further by ion chromatography and found to be a bromide salt.

A final round of maturation on amorphous solids was performed in EtOAc, which after evaporation, produced a single new crystalline form. Characterisation by ion chromatography and XRPD showed it to be a chloride salt. No further crystalline salts were obtained from the screen.

The bromide salt is a mono salt with ~1.0 eq bromide present by IC. 1H NMR of the salt showed that all compound protons were still present, but shifted due to salt formation; several trace solvents were found, corresponding to the solvents the sample had been matured in. It is unlikely that the bromide salt is a solvate as each of the solvents were only found in trace quantities. A single large weight loss of 5.3% was observed by TGA, which potentially suggests that bromide Form A could be a hydrate. DSC corroborates this with a broad endotherm with an onset of 33° C. before the melt at 225° C. After storage in accelerating conditions for one-week (40° C./75% RH) bromide Form A was observed to convert to an amorphous form, showing a loss of crystallinity.

The chloride salt is a mono salt with ~0.9 eq chloride present by IC. The lower than expected stoichiometry indicates that the sample possibly contains amorphous free form, as no peaks of crystalline free base forms were seen in the XRPD diffractogram of the chloride salt. 1H NMR of the chloride salt showed that trace ethyl acetate was present and that the compound peaks had shifted due to salt formation. The TGA of chloride Form A showed a mass loss of 5%, equivalent to 0.2 equivalents of ethyl acetate, more than observed by NMR. This discrepancy suggests that either the sample dried between the TGA and NMR measurements, or the chloride salt is hygroscopic and part of the TGA mass loss is the loss of water. A broad endotherm with an onset of 54° C. (8 J/g) and peak maximum of 76.2° C. was also observed by DSC before the perceived melt at ~220° C. Storage of the chloride salt for one week in accelerating conditions (40° C./75% RH) showed no change to the Form A XRPD pattern.

The tosylate salt of Compound II-1 is a mono salt, as measured by 1H NMR which showed ~1 molar equivalent of p-toluene sulfonate ion. The NMR showed no trace of solvate, which was corroborated by TGA which showed no mass loss between RT and 100° C. before decomposition at 270° C. suggesting that the tosylate salt is anhydrous. DSC of the tosylate salt showed a doublet endotherm at 243° C. Storage of the tosylate salt for one week in accelerating conditions (40° C./75% RH) showed no change to the Form A XRPD pattern.

The mesylate salt of Compound II-1 is a mono salt with ~1 eq of methane sulfonate present by 1H NMR. The mesylate showed two weight losses by TGA, a 12% weight loss corresponding to the loss of ~0.8 eq of TBME, more than found by TGA (0.5 eq) which would suggest that the salt is hygroscopic. The second TGA weight loss begins at 260° C. and corresponds to the decomposition of Compound II-1. The DSC of the mesylate salt shows multiple endotherms, only one of which is at a similar temperature to a TGA mass loss. Storage of the mesylate salt for one week in accelerating conditions (40° C./75% RH) showed no change to the Form A XRPD pattern.

The besylate salt is a mono salt with ~1 eq benzene sulfonate present by 1H NMR. The besylate salt showed only a single weight loss due to the decomposition of the compound. The DSC also showed only one thermal event corresponding to the melt of Compound II-1 at 237° C. The salt showed also showed trace ethanol by 1H NMR, but it can be assumed to be anhydrous. Storage of the besylate salt for one week in accelerating conditions (40° C./75% RH) showed no change to the Form A XRPD pattern.

The fumarate salt of Compound II-1 is a mono salt with ~1 eq fumarate present by 1H NMR. 1H NMR also showed 0.4 eq of TBME present. TGA shows two thermal events, a mass loss of 1.9% corresponding to the loss of 0.1 eq of TBME followed by a 17.2% mass loss between 130 and 260° C. which could be due to the loss of fumarate. DSC showed a corresponding thermal event at 150° C. followed by a small endotherm at 187° C. suggesting that fumarate salt 1 thermally decomposes. Storage of the fumarate salt for one week in accelerating conditions (40° C./75% RH) showed no change to the Form A XRPD pattern.

Further Polymorph Screening of Tosylate Salts

Compound II-1 (40 mg) was treated with solvent (400 μl, 10 vol) and heated to 50° C. p-Toluene sulfonic acid solution (1.1 eq, 88 μl for 1 M) were added to the API suspensions and the samples were cooled to 5° C. at a rate of 0.2° C./min. Suspensions were isolated and dried under suction.

Solution samples were left uncapped to evaporate at RT and analysed by XRPD when dry. Suspensions at 5° C. were aliquoted onto a metal well plate, then left to dry in air before analysis by XRPD. Suspension samples which were found to be new forms by XRPD were matured between 25 and 50° C. for 3 days. Evaporated samples were not further treated.

Samples started out as a mixture of suspensions and solutions before addition of the acids. After cooling, most samples had produced suspensions for analysis. The results of the reactive crystallisation, polymorphism assessment on Compound II-1 pTSA are shown in Table 10.

The tosylate salt showed two new polymorphs, which have been assigned pTSA Form B and pTSA Form C. Both new polymorphs have only been observed as a mixture with pTSA Form A.

TABLE 2

Results of Polymorphism assessment on Compound II pTSA salts

| Solvent | Observation on solvent addition | Observation on pTSA addition | Observation after cooling to 5° C. | Treatment | XRPD after treatment |
|---|---|---|---|---|---|
| n-Heptane | Suspension | Suspension | Gum | Maturation | pTSA Form A + pTSA Form B |
| Ethyl acetate | Suspension | Suspension | Suspension | Maturation | pTSA Form A + pTSA Form C |
| Isopropyl acetate | Suspension | Suspension | Suspension | Maturation | pTSA Form A |
| 2-propanol | Clear solution | Suspension | Suspension | — | — |
| MEK | Suspension | Clear solution | Suspension | Maturation | pTSA Form A + pTSA Form C |
| Acetone | Suspension | Clear solution | Suspension | — | — |
| Ethanol | Clear solution | Clear solution | Suspension | — | — |
| TBME | Suspension | Suspension | Suspension | Maturation | pTSA Form A |
| Methanol | Suspension | Suspension | Suspension | — | — |
| THF | Clear solution | Clear solution | Suspension | Maturation | pTSA Form A |
| 10% water/MeCN | Clear solution | Clear solution | Clear solution | Evaporation | Amorphous |
| water | Gel | Suspension | Gel | Maturation | pTSA Form A |
| 10% water/IPA | Clear solution | Clear solution | Clear solution | Evaporation | pTSA Form A + pTSA Form B |

Key: — = not conducted

Neither pTSA Form B or pTSA Form C were observed as pure phases. TGA and $^1$H NMR of Pattern 2 and Pattern 3 suggest that both might be anhydrous. Storage of both polymorphs showed conversion to pTSA Form A. See Table 11.

TABLE 3

Characterisation of Compound II pTSA salt polymorphs

| | pTSA Form A | pTSA Form B | pTSA Form C |
|---|---|---|---|
| XRPD from screening | pTSA Form A | pTSA Form B | pTSA Form C |
| High resolution XRPD | pTSA Form A | pTSA Form B + pTSA Form A | pTSA Form A + pTSA Form C |
| ¹H NMR | Consistent with structure. Toluene sulfonic acid ~1 eq | Consistent with structure. Toluene sulfonic acid ~0.9 eq THF ~0.1 eq Trace heptane ~0.01 eq | Consistent with structure. Toluene sulfonic acid ~1 eq |
| TGA | No weight loss between 25-100° C. Decomposition begins at 270° C. | No mass loss between RT and 250° C. | No mass loss between RT and 270° C. Decomposition begins at 270° C. |
| DSC | Doublet endotherm (68 J/g) with an onset at 243.3° C. | Insufficient material | Insufficient material |
| Storage at 40° C./75% RH for 7 days | XRPD unchanged | Converted to pTSA Form A | Converted to pTSA Form A |

TABLE 14

XRPD peak list of Compound II HCl Form A

| Angle (2θ°)¹ | Intensity (%) | Angle (2θ°)¹ | Intensity (%) |
|---|---|---|---|
| 6.6 | 100 | 18.9 | 35.8 |
| 9.4 | 35 | 19.5 | 68.6 |
| 11.1 | 30 | 20.2 | 29.4 |
| 11.9 | 44.3 | 21.2 | 83.2 |
| 12.6 | 48.2 | 22.5 | 27.7 |
| 13.2 | 23.8 | 23.8 | 30.2 |
| 13.7 | 22.6 | 24.6 | 26.7 |
| 15.6 | 27.1 | 25.5 | 57.5 |
| 16.2 | 54.2 | 26.2 | 25.2 |
| 16.7 | 28.8 | 27.7 | 43.1 |
| 16.9 | 28.8 | 28.5 | 49.7 |
| 17.5 | 50.8 | 29.6 | 28.3 |
| 18.3 | 31.1 | 29.8 | 26.7 |

¹ In this and all subsequent tables, the position 2θ is within ±0.2.

TABLE 4

XRPD Peak list of Compound II p-toluene sulfonate salt Form A

| Angle (2-Theta °)¹ | Intensity (%) | Angle (2-Theta °)¹ | Intensity (%) |
|---|---|---|---|
| 5.7 | 100 | 19.6 | 10.4 |
| 9.8 | 14 | 20.2 | 16.1 |
| 10.3 | 14.4 | 20.7 | 7.1 |
| 11.0 | 7.2 | 22.0 | 21 |
| 11.4 | 22.8 | 22.3 | 6.1 |
| 12.4 | 11.6 | 23.3 | 13.5 |
| 13.2 | 4.8 | 23.6 | 14.9 |
| 13.6 | 7.2 | 24.5 | 14.4 |
| 13.9 | 13.7 | 25.4 | 8.1 |
| 15.1 | 22.7 | 25.9 | 11.7 |
| 15.4 | 14.8 | 26.4 | 12.1 |
| 15.9 | 6.9 | 26.7 | 6.7 |
| 16.4 | 3.9 | 27.5 | 7.9 |
| 16.9 | 34.9 | 27.9 | 9.9 |
| 17.3 | 38.9 | 28.2 | 11.9 |
| 17.7 | 14.7 | 28.8 | 4.6 |
| 18.6 | 13.6 | 29.6 | 6.2 |
| 19.0 | 30.9 | 30.1 | 4.9 |

¹ In this and all subsequent tables, the position 2θ is within ±0.2.

TABLE 15

XRPD peak list of Compound II HBr Form A

| Angle (2-Theta °)¹ | Intensity (%) | Angle (2-Theta °)¹ | Intensity (%) |
|---|---|---|---|
| 6.6 | 80.7 | 21.2 | 66.4 |
| 11.8 | 29.8 | 21.6 | 39.5 |
| 12.6 | 38.9 | 22.3 | 39.8 |
| 13.2 | 23.2 | 23.5 | 43 |
| 13.7 | 32.3 | 23.9 | 49.7 |
| 14.5 | 24.5 | 24.3 | 51.4 |
| 15.3 | 35.7 | 24.9 | 40.6 |
| 16.1 | 75.2 | 25.4 | 77.1 |
| 16.7 | 47.8 | 26.5 | 40.6 |
| 17.3 | 68.2 | 27.3 | 55.7 |
| 18.1 | 44.4 | 27.6 | 46.2 |
| 18.4 | 40.9 | 28.3 | 43 |
| 18.7 | 51.4 | 28.5 | 47.5 |
| 19.5 | 100 | 29.3 | 44.6 |
| 20.0 | 45.4 | 29.8 | 41.1 |

¹ In this and all subsequent tables, the position 2θ is within ±0.2.

TABLE 17

XRFD peak list of Compound II methane sulfonate saly Form A

| Angle (2-Theta °)¹ | Intensity (%) | Angle (2-Theta °)¹ | Intensity (%) |
|---|---|---|---|
| 5.3 | 100 | 20.8 | 30.3 |
| 9.8 | 28.3 | 21.4 | 41.2 |
| 10.7 | 28.3 | 22.0 | 32 |
| 11.3 | 19.8 | 22.7 | 30.6 |
| 12.2 | 21.7 | 23.0 | 41.5 |
| 13.5 | 26.8 | 23.5 | 21.9 |
| 14.1 | 17.6 | 24.3 | 28.9 |
| 14.5 | 18.1 | 25.4 | 25.5 |
| 15.1 | 20.9 | 26.6 | 23.3 |
| 15.6 | 31 | 26.9 | 22.7 |
| 16.0 | 17 | 27.8 | 16.3 |
| 16.4 | 22.5 | 28.3 | 19 |
| 17.6 | 72.3 | 28.8 | 15.2 |
| 18.2 | 61.1 | 29.3 | 13.7 |
| 18.8 | 46 | 29.7 | 13.4 |
| 19.7 | 37.6 | — | — |

¹ In this and all subsequent tables, the position 2θ is within ±0.2.

TABLE 18

XRPD peak list of Compound II benzene sulfonate salt Form A

| Angle (2-Theta °) [1] | Intensity (%) | Angle (2-Theta °) [1] | Intensity (%) |
|---|---|---|---|
| 6.1 | 100 | 19.4 | 20.6 |
| 9.5 | 37.8 | 19.9 | 17 |
| 10.3 | 12.1 | 20.5 | 13.8 |
| 11.2 | 12 | 20.9 | 76.1 |
| 11.6 | 8.1 | 21.5 | 7.9 |
| 12.1 | 34.9 | 23.0 | 10.5 |
| 13.4 | 26.7 | 23.4 | 38.7 |
| 14.5 | 77.6 | 24.5 | 22.3 |
| 15.3 | 15.9 | 25.6 | 34.7 |
| 16.2 | 56 | 26.3 | 31.1 |
| 16.7 | 13.5 | 27.0 | 13.7 |
| 17.2 | 10.8 | 27.8 | 12.7 |
| 18.1 | 26 | 28.7 | 12.6 |
| 18.5 | 17.7 | 29.1 | 20 |
| 18.9 | 32.1 | — | — |

[1] In this and all subsequent tables, the position 2θ is within ±0.2.

TABLE 19

XRPD peak list for Compound II Fumarate salt Form A

| Angle (2-Theta °) [1] | Intensity (%) | Angle (2-Theta °) [1] | Intensity (%) |
|---|---|---|---|
| 5.9 | 42.8 | 20.2 | 10.1 |
| 7.45 | 64.8 | 21.0 | 55.5 |
| 7.9 | 40.8 | 21.6 | 27.7 |
| 8.9 | 35.8 | 22.1 | 10.2 |
| 10.2 | 22.1 | 22.8 | 27.8 |
| 12.7 | 43.4 | 24.1 | 26.1 |
| 14.9 | 20.2 | 24.4 | 32.8 |
| 15.4 | 93 | 25.0 | 15.1 |
| 16.0 | 22.2 | 25.8 | 12.1 |
| 16.8 | 34.8 | 26.2 | 14.2 |
| 17.7 | 53.3 | 26.6 | 11.6 |
| 18.1 | 13.8 | 28.9 | 10.6 |

[1] In this and all subsequent tables, the position 2θ is within ±0.2.

Example 12—Solubility Measurements of (R)—N-(4-(4-amino-7-methyl-5-(4-(pyrrolidine-1-carbonyl)cyclohex-1-en-1-yl)-7H-pyrrolo[2,3-d]pyrimidin-6-yl)-3-methylphenyl)methacrylamide (Compound II-1)

The free base (Form A), the para-toluene sulfonic acid salt (Form A) and benzene sulfonic acid salt (Form A) were scaled up for solubility analysis. Both salts were confirmed to match the XRPD pattern found in the salt screen.
The results from the solubility measurements in simulated gastric fluid (SGF), simulated fed state conditions in the small intestines (FeSSIF), and simulated fasting state conditions in the small intestines fluid (FaSSIF) are summarised in Table 12. The salts show reduced solubility in SGF compared to the free form. Compound II-1 para-toluene sulfonic acid salt Form A shows the highest solubility in FeSSIF and FaSSIF, while the benzene sulfonic acid salt shows low solubility in all media. XRPD of residues show that the forms all remained stable in the solubility media.

TABLE 20

| Form | Media | pH at 24 hrs | Solubility (mg/ml) | Average Solubility (mg/ml) | XRPD of residue |
|---|---|---|---|---|---|
| Free Base Form A | SGF | 2.7 | 8.80 | 9.20 | — |
|  |  | 2.7 | 9.50 |  |  |
|  | FeSSIF | 5.0 | 0.59 | 0.63 | Unchanged |
|  |  | 5.0 | 0.66 |  |  |
|  | FaSSIF | 6.5 | 0.071 | 0.071 | Unchanged |
|  |  | 6.5 | 0.070 |  |  |
| p-Toluene sulfonic Acid (pTSA) Form A | SGF | 1.7 | 0.92 | 1.1 | Unchanged |
|  |  | 1.7 | 1.30 |  |  |
|  | FeSSIF | 4.9 | 0.74 | 0.71 | Unchanged |
|  |  | 4.9 | 0.68 |  |  |
|  | FaSSIF | 4.7 | 0.30 | 0.30 | Unchanged |
|  |  | 4.7 | 0.29 |  |  |
| Benzenesulfonic Acid (BSA) Form A | SGF | 1.8 | 0.51 | 0.51 | Unchanged |
|  |  | 1.7 | 0.51 |  |  |
|  | FeSSIF | 5.0 | 0.93 | 0.95 | Unchanged |
|  |  | 5.0 | 0.96 |  |  |
|  | FaSSIF | 6.0 | 0.087 | 0.087 | Unchanged |
|  |  | 6.0 | 0.086 |  |  |

Example 13—Polymorph Screen of 6-(6-ethynyl-4-methoxypyridin-3-yl)-5-(3-fluoro-4-((4-methylpyrimidin-2-yl)oxy)phenyl)-4,7-dimethyl-7H-pyrrolo[2,3-d]pyrimidine (Compound III-1)

Compound III-1 (40 mg) was treated with an aliquot of solvent (200 μl for 5 vol, 400 μl for 10 vol, 800 μl for 2θ vol) and left to stir at 25° C. for 5 mins. After 5 mins, resulting suspensions were treated with additional aliquot of solvent and left to stir again. Any clear solutions were removed from stirring and further solvent additions. This procedure was repeated up to a total of 40 vol (1.6 ml).

At 40 vol, any remaining suspensions were heated to 50° C. Samples that remained suspensions at 50° C. were moved to maturation (RT/50° C.) for 4 days. All solutions from solvent additions were heated to 50° C. before cooling to 5° C. at 0.1° C./min overnight.

After cooling, any solutions and thin suspensions were left uncapped to evaporate. After maturation, suspensions were filtered and solids dried under suction. All solids were analysed by XRPD using a metal well plate.

The results from the solubility and polymorphism assessment of Compound III-1 are summarized in the Table below. Compound III-1 was found to have low solubility in the 13 solvents tested. Clear solutions were only obtained in THF (40 vol at 25° C.), methanol, acetone and 10% water/MeCN (all 40 vol at 50° C.). Based on the solubility, THF was selected for the salt screening as Compound III-1 showed the greatest solubility within it and most of the acid solutions are prepared in THF.

After further treatment of suspensions and solutions, solids resulted from all experiments. Of the 13 experiments conducted, 11 resulted in Form A, with most of these samples showing greater crystallinity than the input material.

Two new crystalline forms were also produced during this screen, although neither sample was phase pure and both still displayed peaks of Form A in the XRPD diffractograms. Form B was produced from IPA and Form C was produced from water. These samples were characterised further along with a sample of Form C from THF.

TABLE 21

Results of solubility and polymorphism assessment of Compound III-1

| Solvent | Treatment | Observation after treatment | Further Treatment | Observation after further treatment | XRPD |
|---|---|---|---|---|---|
| n-Heptane | Maturation | Suspension | | | Form A |
| Ethyl acetate | Maturation | Suspension | | | Form A |
| Isopropyl acetate | Maturation | Suspension | | | Form A |
| 2-Propanol | Maturation | Suspension | | | Form B + Form A peaks |
| MEK | Maturation | Suspension | | | Form A |
| Acetone | Cooling | Very thin suspension | Evaporation | Brown solid | Form A |
| Ethanol | Maturation | Suspension | | | Form A |
| TBME | Maturation | Suspension | | | Form A |
| Methanol | Cooling | Very thin suspension | Evaporation | Brown solid | Form A |
| THF | Cooling | Clear solution | Evaporation | Brown solid | Form A |
| 10% Water/ MeCN | Cooling | Clear solution | Evaporation | Brown solid | Form A |
| Water | Maturation | Suspension | | | Form C + Form A peaks |
| 10% Water/ IPA | Maturation | Suspension | | | Form A |

TABLE 22

Characterisation of Compound III-1 polymorphs

| XRPD | Form A | Form B with peaks of Form A | From C with peaks of Form A |
|---|---|---|---|
| $^1$H NMR | Trace THF and BHT | ~0.7 eq IPA | No solvents present |
| TGA | 2.1 wt % loss 35-175° C. 0.9 wt % loss 175-260° C. (total weight loss: ~0.8 eq water) | 1.9 wt % loss 25-60° C. 7.3 wt % loss 60-120° C. (total weight loss: ~0.7 eq IPA and ~0.4 eq water) | 2.7 wt % loss 40-110° C. (~0.7 eq water) |
| DSC | Sharp endotherm onset 217.7° C. (39 J/g) Large endotherm onset 223.6° C. (260 J/g) | Broad endotherm onset 27.5° C. (39 J/g) Endotherm onset 88.2° C. (59 J/g) Exotherm onset 125.1° C. (37 J/g) Sharp endotherm onset 222.1° C. (64 J/g) Large exotherm onset 225.8° C. (288 J/g) | Broad endotherm onset 96.7° C. (60 J/g) Exotherm onset 116.6° C. (35 J/g) Small endotherm onset 192.2° C. (1 J/g) Small exotherm onset 200.9° C. (3 J/g) Sharp endotherm onset 215.1° C. (21 J/g) Large endotherm onset 221.5° C. (250 J/g) |
| Storage at 40° C./75% RH for 7 days | No change in form - Form A | Change in form - From A + extra peaks | No change in form - Form C + peaks of Form A |

Crystalline Form A shows much simpler thermal analysis than the received poorly crystalline sample. The DSC of crystalline Form A shows only two events: a sharp endotherm onset 217.7° C., which is possibly the sample melt and a large exotherm onset 223.6° C. potentially degradation of the sample. The TGA still shows weight losses of 3.0 wt %, which could be due to the residual solvents seen by $^1$H NMR or indicate that the material is hygroscopic and taking up ~0.8 eq water. Form A also showed no change in form after one week at 40° C./75% RH. Form A is an anhydrous form that is potentially hygroscopic.

Form B shows ~0.7 eq IPA by $^1$H NMR and the weight losses in the TGA are larger than expected for this amount of solvent. This indicates that there is additional water (~0.4 eq) in the sample and Form B is also possibly hygroscopic. As the sample is a mixture of Form B and a small amount of Form A, the $^1$H NMR solvent content indicates that a pure phase Form B would have ~1.0 eq IPA. The DSC of Form B shows multiple events. The endotherms onset 27.5° C. and 88.2° C. are likely due to the loss of IPA and/or water and correspond to both weight losses by TGA. The exotherm onset 125.1° C. is possibly a change in form, as the sharp endotherm onset 222.1° C. is a similar temperature to the melt of Form A. Form B also showed conversion to Form A (plus additional peaks) after one week at 40°/75% RH. Form B is characterised as an IPA solvate.

Form C shows no residual solvents by $^1$H NMR and the weight loss in the TGA are is equal to ~0.7 eq. As the sample is a mixture of Form C and a small amount of Form A, the TGA weight loss indicates that a pure phase Form C would have ~1.0 eq water. The DSC of Form C shows multiple endothermic and exothermic events. The broad endotherm onset 97.6° C. is likely due to the loss of water and corresponds to the weight loss by TGA. The exotherm onset 116.6° C. is possibly a change in form after dehydration of the solid. The nature of the further small endotherm and exotherm around 190° C. is unknown, but the sharp endotherm onset 215.1° C. is likely to be the melt of the sample. Form C showed no change in form after one week at 40° C./75% RH, remaining a mixture with a small amount of Form A. Form C is characterised as a hydrated form.

TABLE 5

XRPD peak list of Compound III-1 Form A

| Angle (2-Theta °) [1] | Intensity (%) | Angle (2-Theta °) [1] | Intensity (%) |
|---|---|---|---|
| 5.0 | 97.8 | 22.2 | 66.8 |
| 10.0 | 14.9 | 22.4 | 63.7 |
| 11.1 | 21.2 | 22.9 | 40.2 |
| 11.8 | 30.8 | 23.2 | 35.1 |

TABLE 5-continued

XRPD peak list of Compound III-1 Form A

| Angle (2-Theta °)[1] | Intensity (%) | Angle (2-Theta °)[1] | Intensity (%) |
|---|---|---|---|
| 12.4 | 48.9 | 23.4 | 30.7 |
| 14.0 | 20.4 | 23.6 | 30.1 |
| 14.4 | 100.0 | 24.7 | 67.5 |
| 15.5 | 47.1 | 24.9 | 49.9 |
| 16.0 | 80.3 | 25.9 | 41.5 |
| 17.2 | 10.2 | 26.1 | 66.3 |
| 17.7 | 22.1 | 26.6 | 22.9 |
| 18.1 | 65.3 | 27.4 | 43.5 |
| 18.8 | 10.0 | 27.8 | 39.6 |
| 19.3 | 36.6 | 28.3 | 36.0 |
| 20.1 | 64.4 | 29.0 | 24.2 |
| 20.8 | 16.8 | 29.8 | 15.5 |
| 21.6 | 57.5 | 30.6 | 19.4 |

[1] In this and all subsequent tables, the position 2θ is within ±0.2.

Example 14—Preparation of salt forms of 6-(6-ethynyl-4-methoxypyridin-3-yl)-5-(3-fluoro-44(4-methylpyrimidin-2-yl)oxy)phenyl)-4,7-dimethyl-7H-pyrrolo[2,3-d]pyrimidine (Compound III-1)

Compound III-1 (520 mg) was dissolved in THF (20.8 ml, 40 vol) at RT. The API solution was dispensed into 4 ml vials (1.6 ml, ~40 mg J10433) and heated to 50° C.

Acid solutions (1.1 eq, 92 µl for 1 M, 184 µl for 0.5 M) were added to the API solutions. The samples were cooled to 5° C. at 0.1° C./min and left for 1 day. After 1 day at 5° C., any remaining clear solutions were left uncapped to evaporate at RT. Suspensions at 5° C. were filtered solids dried under suction and on a metal well plate.

After initial XRPD analysis, solids that were found to be amorphous by XRPD were suspended in TBME (500 µl) and placed into maturation (RT/50° C.) for 6 days. After solutions had evaporated to dryness, resulting gums were treated with TBME (500 µl) and placed into maturation for 2 days. After maturation in TBME, the suspensions were aliquoted onto a glass slide and after airdrying solids were analysed by XRPD.

After XRPD analysis, samples found to be amorphous or consistent with the free form were uncapped and once dry the samples were treated with heptane (500 µl) and returned to maturation for 4 days. After maturation in heptane, the suspensions were aliquoted onto a glass slide and after airdrying, solids were analysed by XRPD.

After XRPD analysis, samples found to be amorphous or consistent with the free base form were uncapped and once dry the samples were treated with ethyl acetate (500 µl) and returned to maturation for 2 days. After maturation in ethyl acetate, the suspensions were aliquoted onto a flat silicon XRPD sample holders and after airdrying, solids were analysed by XRPD.

Results from the salt screen on Compound III-1 are summarised in Table and Table. Upon addition of the acid to the solution of Compound III-1, samples with inorganic acids formed a suspension but those with organic acids remained as solutions. After cooling to 5° C., no further samples precipitated but all samples had changed color from brown to reds and purples.

Analysis of the solids from suspensions showed that crystalline salts were obtained from HBr, HCl, sulfuric and methane sulfonic acids. These samples were all characterised further. Amorphous solids were also obtained from p-toluene sulfonic, benzene sulfonic and phosphoric acids.

Clear solutions after cooling were left to evaporate but all resulted in gums. The gums and amorphous solids were all treated with TBME and subjected to maturation. This resulted in an additional crystalline salt from l-tartaric acid, but the sample was not phase pure and contained peaks of crystalline free base in the XRPD diffractogram.

The remaining samples were either amorphous solids or consistent with the crystalline free base so were matured further first in heptane and then ethyl acetate. No further crystalline salts were obtained from the screen.

TABLE 24

Initial Results of salt screen on Compound III-1

| Counter-ion | Observation on acid addition | Observation after cooling | XRPD after cooling |
|---|---|---|---|
| Hydrobromic acid - HBr | Suspension | Red suspension | HBr Form A |
| Hydrochloric acid - HCl | Suspension | Pink suspension | HCl Form A |
| Sulfuric acid - SO4 | Suspension | Red suspension | SO4 Form A |
| p-Toluene sulfonic acid - pTSA | Suspension | Purple suspension | Amorphous |
| Methane sulfonic acid - MSA | Suspension | Purple suspension | MSA Form A |
| Benzene sulfonic acid - BSA | Suspension | Purple suspension | Amorphous |
| Maleic acid - MEA | Clear solution | Clear solution | — |
| Phosphoric acid - PHOA | Suspension | Purple suspension | Amorphous |
| Malonic acid - MLNA | Clear solution | Clear solution | — |
| L-Tartaric acid - TAR | Clear solution | Clear solution | — |
| Fumaric acid - FUA | Clear solution | Clear solution | — |
| Citric acid - CA | Clear solution | Clear solution | — |

Key: — = not conducted,

TABLE 25

Secondary Results of salt screen on Compound III-1

| Counterion | Observation after maturation in TBME | XRPD after TBME maturation | Observation after maturation in heptane | XRPD after heptane maturation | Observation after maturation in EtOAc | XRPD after EtOAc maturation |
|---|---|---|---|---|---|---|
| p-Toluene sulfonic acid - pTSA | Purple suspension | Amorphous | Purple suspension | Amorphous | Purple suspension | Amorphous |
| Benzene sulfonic acid - BSA | Purple suspension | Amorphous | Purple suspension | Amorphous | Purple suspension | Amorphous |

TABLE 25-continued

| | | | | | | |
|---|---|---|---|---|---|---|
| Maleic acid - MEA | Red suspension | Amorphous | Red suspension | Amorphous | Red suspension | Amorphous |
| Phosphoric acid - PHOA | Purple suspension | Amorphous | Purple suspension | Amorphous | — | Amorphous |
| Malonic acid - MLNA | Red suspension | Poorly crystalline FB Form A | Red suspension | Amorphous | Red suspension | Amorphous |
| L-Tartaric acid - TAR | Red suspension | TAR Form A + peaks of FB Form A | — | — | — | — |
| Fumaric acid - FUA | Red suspension | FB Form A | Red suspension | FB Form A | Red suspension | FB Form A |
| Citric acid - CA | Red suspension | Poorly crystalline FB Form A | Red suspension | Poorly crystalline FB Form A | Red suspension | Amorphous |

Key: — = not conducted, FB - free base

TABLE 26

Characterisation of Compound III salts

| | HBr Form A | HCl Form A | SO4 Form A | MSA Form A | TAR Form A |
|---|---|---|---|---|---|
| XRPD | | | | | peaks of free base Form A |
| $^1$H NMR | Peak shifts due to salt formation ~0.3 eq THF | Peak shifts due to salt formation ~2.8 eq THF | Peak shifts due to salt formation ~0.2 eq THF | Peak shifts due to salt formation ~1.7 eq methane sulfonic acid ~0.9 eq THF | ~0.9 eq 1-tartaric acid Trace THF, BHT and TBME |
| IC | 0.98 eq bromide | 0.77 eq chloride | 0.95 eq sulfate | — | — |
| TGA | 1.8 wt % loss 40-140° C. 7.2 wt % loss 140-240° C. | 2.0 wt % loss 40-140° C. 5.1 wt % loss 140-200° C. | 3.0 wt % loss 40-100° C. (~0.3 eq THF) | 2.2 wt % loss 40-110° C. 8.2 wt % loss 110-180° C. | 4.8 wt % loss 25-160° C. 15.4 wt % loss 160-240° C. |
| DSC | Broad endotherm onset 30.4° C. (4 J/g) Large exotherm onset 189.4° C. (110 J/g) | Broad endotherm onset 28.4° C. (5 J/g) Large double exotherm onset 182.2° C. (89 J/g) | Broad endotherm onset 48.3° C. (82 J/g) Small exotherm onset 170.6° C. (6 J/g) Large exotherm onset 193.9° C. | Broad endotherm onset 29.6° C. (53 J/g) Large exotherm onset 142.9° C. (65 J/g) | Broad endotherm onset 43.6° C. (54 J/g) Large double exotherm onset 138.6° C. (105 J/g) |
| Storage at 40° C./75% RH for 7 days | Change in form - HBr Form B | Change in form - HCl Form B | Small changes to diffractogram seen | Loss of crystallinity - Amorphous | No change in form - TAR Form A + peaks of free base Form A |

The bromide salt is a mono salt with ~1.0 eq bromide present by IC. The bromide salt showed two weight losses by TGA. The first small weight loss is possibly due to the residual THF seen in the $^1$H NMR alone or with residual water. There is a second weight loss of 7.2 wt %, which could possibly be dissociation of the salt and loss of the counter-ion or degradation, this weight loss is also accompanied by a large exotherm in the DSC. Unlike the free form, the DSC of the salt shows no sharp endotherm indicating a melt. The bromide salt was found to change form after one week at 40° C./75% RH. The new form was designated HBr Form B but not characterized any further.

The chloride salt is a mono salt with ~0.8 eq chloride present by IC. This lower than expected stoichiometry indicates that the sample possibly contains amorphous free form, as no peaks of crystalline free base forms were seen in the XRPD diffractogram of the chloride salt. The chloride salt showed two weight losses by TGA. The first weight loss is likely due to the residual THF seen in the $^1$H NMR, as the sample appeared to be quite wet with ~2.8 eq THF present. There is a second weight loss of 5.1 wt %, which could possibly be further solvent loss, dissociation of the salt and loss of the counter-ion or degradation, this weight loss is also accompanied by a large exotherm in the DSC. The chloride salt also displayed the absence of a sharp endotherm indicating a melt. The chloride salt was found to change form after one week at 40° C./75% RH.

The sulfate salt is a mono salt with ~1.0 eq sulfate present by IC. The sulfate salt showed one weight loss by TGA of 3.0 wt %, this weight loss is equivalent to the amount of residual THF seen in the $^1$H NMR of the salt. This weight loss is also accompanied by a broad endotherm for the loss of the solvent in the DSC. The sulfate salt does not show any second larger weight loss unlike the other salts, however the beginning of large exotherm is still present in the DSC. There is also a small exotherm onset 170.6° C. but the nature of this is not known. This salt also shows no sharp endotherm indicating a melt. The sulfate salt shows small changes in the XRPD diffractogram after one week at 40° C./75% RH.

The mesylate salt is a bis salt with ~1.7 eq methane sulfonate present by $^1$H NMR. This lower stoichiometry indicates that the sample possibly contains amorphous free form, as no peaks of crystalline free base forms were seen in the XRPD diffractogram of the salt. The mesylate salt showed two weight losses by TGA. The first weight loss is likely due to the residual THF seen in the $^1$H NMR, as the sample appeared to be wet with ~0.9 eq THF present. This solvent loss is also indicated by a broad endotherm in the DSC. There is a second weight loss of 8.2 wt %, which could possibly be further solvent loss, dissociation of the salt and loss of the counter-ion or degradation, this weight loss is also accompanied by a large exotherm in the DSC. The mesylate salt also displayed the absence of a sharp endotherm indicating a melt. The mesylate salt was found to lose crystallinity after one week at 40° C./75% RH, resulting in amorphous material.

The tartrate salt is a mono salt with ~0.9 eq tartrate present by $^1$H NMR. This lower stoichiometry is not surprising considering the XRPD diffractogram of the salt displays peaks of the crystalline free base. The tartrate salt showed two weight losses by TGA. The first weight loss is likely due to the residual solvents seen in the $^1$H NMR. This weight loss is also accompanied by a broad endotherm in the DSC. There is a second weight loss of 15.4 wt %, which could possibly be dissociation of the salt and loss of the counter-ion or degradation, this weight loss is also accompanied by a large exotherm in the DSC. The tartrate salt also displayed the absence of a sharp endotherm indicating a melt. No change in form was seen after one week at 40° C./75% RH for the tartrate salt.

Further Selected Polymorph Screening

The chloride salt showed a total of four different polymorphs after analysis of the solids by XRPD. HCl Form A, the same polymorph isolated from the salt screen in THF, was only isolated from THF. HCl Form B resulted from five out of 13 experiments and a range of solvents: heptane, isopropyl acetate (with additional peaks), MEK, acetone and TBME. HCl Form B was seen previously after storage of HCl Form A at 40° C./75% RH. HCl Form C only resulted from ethyl acetate and HCl Form D was produced by only IPA. All clear solutions evaporated to amorphous solids.

The sulfate salt showed two different polymorphs after analysis of the solids by XPRD. SO4 Form A, the polymorph isolated from salt screening in THF, was produced from isopropyl acetate, TBME and THF. A new form SO4 Form B resulted from heptane, MEK and acetone. A mixture of SO4 Form A and SO4 Form B was produced from ethyl acetate.

TABLE 27

Results of polymorphism assessment on Compound III HCl salt

| Solvent | Observation on HCl addition | Observation after cooling | XRPD | XRPD after maturation |
|---|---|---|---|---|
| n-Heptane | Gum | Suspension/gum | HCl Form B | — |
| Ethyl acetate | Gum | Suspension/gum | HCl Form C | — |
| Isopropyl acetate | Gum | Suspension/gum | HCl Form B + ep | — |
| 2-Propanol | Clear solution | Suspension | HCl Form D | — |
| MEK | Gum | Suspension/gum | HCl Form B | — |
| Acetone | Gum | Suspension/gum | HCl Form B | — |
| Ethanol | Clear solution | Clear solution | Amorphous | — |
| TBME | Gum | Suspension/gum | HCl Form B | — |
| Methanol | Clear solution | Clear solution | Amorphous | — |
| THF | Gum | Suspension/gum | HCl Form A | — |
| 10 % Water/MeCN | Clear solution | Oil | — | Amorphous |
| Water | Suspension | Clear solution | Amorphous | — |
| 10 % Water/IPA | Clear solution | Clear solution | Amorphous | — |

Key: — = not conducted

TABLE 28

Results of polymorphism assessment on Compound III SO4 salt

| Solvent | Observation on H2SO4 addition | Observation after cooling | XRPD | XRPD after maturation |
|---|---|---|---|---|
| n-Heptane | Gum | Suspension/gum | SO4 Form B | — |
| Ethyl acetate | Gum | Suspension/gum | SO4 Patterns 1 and 2 + ep | — |
| Isopropyl acetate | Gum | Suspension/gum | SO4 Form A | — |
| 2-Propanol | Gum | Solid on walls | Amorphous | Poorly crystalline |
| MEK | Gum | Suspension/gum | SO4 Form B | — |
| Acetone | Gum | Suspension/gum | SO4 Form B | — |
| Ethanol | Clear solution | Solid on walls | Amorphous | Amorphous |
| TBME | Gum | Suspension/gum | SO4 Form A | — |
| Methanol | Clear solution | Clear solution | Amorphous | — |
| THF | Gum | Suspension/gum | SO4 Form A | — |
| 10% Water/MeCN | Clear solution | Oil | — | Poorly crystalline |
| Water | Clear solution | Clear solution | Amorphous | — |
| 10% Water/IPA | Clear solution | Solid on walls | Amorphous | Amorphous |

Key: — = not conducted, ep - extra peaks

TABLE 69

Characterisation of Compound III HCl salt polymorphs

| | HCl Form A | HCl Form B | HCl Form C | HCl Form D |
|---|---|---|---|---|
| XRPD from screening | HCl Form A | HCl Form B | HCl Form C | HCl Form D |
| High resolution XRPD | HCl Form A | HCl Form B | HCl Patterns 3 and 5 - mixture of forms with previously unseen form | HCl Form D |
| $^1$H NMR | Peak shifts due to salt formation ~2.8 eq THF | Peak shifts due to salt formation ~0.4 eq THF and trace acetone | Peak shifts due to salt formation Trace EtOAc | Peak shifts due to salt formation Trace IPA |
| IC | 0.77 eq chloride | 0.89 eq chloride | 0.93 eq chloride | 0.91 eq chloride |
| TGA | 2.0 wt % loss 40-140° C. 5.1 wt % loss 140-200° C. | 4.4 wt % loss 40-110° C. 1.7 wt % loss 110-150° C. 4.0 wt % loss 150-200° C. | 3.7 wt % loss 25-130° C. (~0.2 eq EtOAc) 5.3 wt % loss 130-200° C. | 7.0 wt % loss 40-200° C. |
| DSC | Broad endotherm onset 28.4° C. (5 J/g) Large double exotherm onset 182.2° C. (89 J/g) | Broad endotherm onset 33.4° C. (9 J/g) Broad endotherm containing sharper endotherm onset 120.5° C. (31 J/g) Large double endotherm onset 170.2° C. (108 J/g) | Broad endotherm onset 49.2° C. (19 J/g) Large double exotherm onset 188.7° C. (11 J/g) | Large exotherm onset 206.1° C. (115 J/g) |
| Storage at 40° C./75% RH for 7 days | Change in form - HCl Form B | Reduced crystallinity | No change in form - HCl Form C and 5 | No change in form - HCl Form D |

Based on the characterisation of HCl Form A during the salt screen and that conducted during this polymorphism assessment HCl Form A was only isolated from THF. The sample characterised from the salt screening contained a large amount of THF by $^1$H NMR, although the repeated preparation for solubility measurements which was dried under vacuum showed only trace amounts of THF. HCl Form A is unstable to 40° C./75% RH converting to HCl Form B after 7 days.

HCl Form B resulted from multiple solvents and the sample from acetone was selected for characterisation as it displayed the highest crystallinity. HCl Form B shows ~0.9 eq chloride by IC, indicating the sample may contain a small amount of amorphous free form. The $^1$H NMR shows a small amount of residual THF from the acid solution and a trace amount of acetone. The thermal analysis shows multiple events and weight losses. The first weight loss by TGA is likely due to the loss of residual solvents alone or with water, this is accompanied by a broad endotherm in the DSC (33.4° C.). The second and third weight losses could possibly be further solvent loss, dissociation of the salt and loss of the counter-ion or degradation. There is a second broad endotherm, which also contains a sharper endotherm, the nature of this is unknown (120.5° C.). Finally, there is a large double exotherm in the DSC (170.2° C.). As seen in all salt forms characterised, there is no sharp endotherm indicating a melt. HCl Form B shows a large reduction in crystallinity after storage at 40° C./75% RH for a week.

HCl Form C shows conversion after isolation, the resulting solid appears to be a mixture of HCl Form C and another form which has not been identified before. The IC results show the solid contains ~0.9 eq chloride, indicating the unknown phase likely to be another polymorph of chloride salt and therefore this sample was noted as a mixture of HCl Patterns 3 and 5. The $^1$H NMR shows a trace amount of ethyl acetate. The thermal analysis shows two weight losses by TGA. The first weight loss by TGA is likely due to the loss of residual ethyl acetate alone or with water, this is accompanied by a broad endotherm in the DSC (49.2° C.). The second weight loss could possibly be dissociation of the salt and loss of the counter-ion or degradation, this weight loss is also accompanied by a large exotherm in the DSC. (188.7° C.) As seen in all salt forms previously, there is no sharp endotherm indicating a melt. HCl Patterns 3 and 5 show no change in form, remaining a mixture of forms after storage at 40° C./75% RH for a week. HCl Form C is a metastable form.

HCl Form D shows ~0.9 eq chloride by IC, indicating the sample may contain a small amount of amorphous free form. The $^1$H NMR shows a trace amount of IPA. The thermal analysis shows multiple events and weight losses. The thermal analysis shows one large weight loss by TGA. This weight loss by TGA is likely due to the loss of residual solvent, dissociation of the salt and loss of the counter-ion or degradation, this weight loss is also accompanied by a large exotherm in the DSC (206.1° C.). As seen in all salt forms, there is no sharp endotherm indicating a melt. HCl Form D shows no change in form after storage at 40° C./75% RH for a week. HCl Form D is possibly an IPA solvate, that is stable to the loss of solvent.

TABLE 30

Characterisation of Compound III SO4 salt polymorphs

| | SO4 Form B | SO4 Form B |
|---|---|---|
| XRPD from screening | SO4 Form B | SO4 Form B |
| High resolution XRPD | SO4 Form A | SO4 Form A |
| $^1$H NMR | Peak shifts due to salt formation Trace THF | Peak shifts due to salt formation ~0.3 eq THF and trace acetone |
| IC | 1.02 eq sulfate | 1.10 eq sulfate |
| TGA | 3.0 wt % loss 40-90° C. (~1.0 eq water) | 7.0 wt % loss 40-110° C. |
| DSC | Broad endotherm onset 44.3° C. (87 J/g) Small endotherm onset 126.0° C. (1 J/g) Exotherm onset 173.7° C. (9 J/g) Exotherm onset 195.7° C. | Broad endotherm onset 44.9° C. (78 J/g) Double exotherm onset 170.6° C. (17 J/g) Exotherm onset 194.3° C. |

TABLE 30-continued

Characterisation of Compound III SO4 salt polymorphs

| Storage at 40° C./75% RH for 7 days | Small changes to diffractogram seen | Small changes to diffractogram seen |
|---|---|---|

From the characterisation of SO$_4$ Form A produced during the salt screen it was characterised as an anhydrous form.

The first sample of SO4 Form B, was found to have converted to SO4 Form A once isolated and analysed by high resolution XRPD. A further sample of SO4 Form B was isolated and dried under suction for a shorter period of time, in attempt to reduce any conversion by loss of solvent on drying. However, the second sample, also converted to SO4 Form A.

TABLE 7

XRPD peak list of Compound III HCl Form A

| Angle (2-Theta °)[1] | Intensity (%) | Angle (2-Theta °)[1] | Intensity (%) |
|---|---|---|---|
| 6.2 | 100.0 | 21.4 | 31.7 |
| 9.3 | 43.4 | 22.1 | 18.7 |
| 10.7 | 92.7 | 22.7 | 24.6 |
| 12.3 | 35.5 | 23.4 | 23.9 |
| 13.1 | 11.0 | 24.4 | 27.0 |
| 13.8 | 36.0 | 25.7 | 35.0 |
| 15.0 | 19.1 | 26.3 | 64.4 |
| 16.9 | 38.2 | 26.6 | 43.1 |
| 17.9 | 36.7 | 27.0 | 38.9 |
| 18.8 | 86.0 | 28.1 | 23.8 |
| 20.0 | 36.5 | 29.7 | 44.5 |
| 20.5 | 30.4 | 30.7 | 26.9 |
| 20.7 | 31.2 | — | — |

[1] In this and all subsequent tables, the position 2θ is within ±0.2.

TABLE 32

XRPD peak list of Compound III HCl Form B

| Angle (2-Theta °)[1] | Intensity (%) | Angle (2-Theta °)[1] | Intensity (%) |
|---|---|---|---|
| 5.2 | 100.0 | 21.4 | 43.2 |
| 9.6 | 43.4 | 21.8 | 82.4 |
| 9.9 | 75.5 | 22.3 | 47.6 |
| 10.4 | 47.0 | 22.8 | 38.2 |
| 12.3 | 19.5 | 23.5 | 55.2 |
| 12.7 | 51.3 | 24.3 | 28.7 |
| 14.0 | 76.6 | 24.6 | 48.0 |
| 14.4 | 36.1 | 25.3 | 52.9 |
| 14.9 | 36.1 | 25.7 | 40.6 |
| 15.7 | 62.3 | 26.7 | 22.5 |
| 17.7 | 55.7 | 27.5 | 53.0 |
| 18.2 | 50.5 | 27.9 | 24.2 |
| 18.9 | 28.9 | 28.3 | 33.3 |
| 19.4 | 19.8 | 28.6 | 33.3 |
| 20.3 | 20.0 | 29.2 | 41.1 |
| 20.7 | 42.5 | 29.9 | 31.5 |
| 20.9 | 36.1 | 30.3 | 30.8 |
| 21.2 | 38.8 | — | — |

[1] In this and all subsequent tables, the position 2θ is within ±0.2.

TABLE 33

XRPD peak list of Compound III HCl Form D

| Angle (2-Theta °)[1] | Intensity (%) | Angle (2-Theta °)[1] | Intensity (%) |
|---|---|---|---|
| 7.1 | 36.1 | 22.6 | 16.2 |
| 9.1 | 37.4 | 23.2 | 14.3 |
| 12.6 | 19.8 | 23.9 | 13.2 |
| 14.0 | 58.9 | 24.6 | 100.0 |
| 14.8 | 14.2 | 25.4 | 39.4 |
| 15.1 | 22.4 | 26.1 | 19.6 |
| 16.0 | 10.4 | 26.9 | 20.0 |
| 16.8 | 18.0 | 27.0 | 21.2 |
| 18.3 | 53.6 | 28.1 | 26.6 |
| 19.3 | 13.1 | 28.5 | 29.2 |
| 19.6 | 29.3 | 29.7 | 18.0 |
| 19.8 | 33.7 | 30.0 | 14.2 |
| 20.3 | 38.6 | 30.6 | 10.6 |
| 20.8 | 23.1 | 30.7 | 10.9 |
| 21.4 | 51.3 | — | — |

[1] In this and all subsequent tables, the position 2θ is within ±0.2.

TABLE 8

XRPD peak list of Compound III HBr Form A

| Angle (2-Theta °)[1] | Intensity (%) | Angle (2-Theta °)[1] | Intensity (%) |
|---|---|---|---|
| 6.3 | 49.2 | 22.3 | 32.9 |
| 6.9 | 50.3 | 23.0 | 41.3 |
| 9.7 | 37.2 | 23.4 | 37.0 |
| 10.2 | 29.8 | 23.9 | 27.3 |
| 11.1 | 28.5 | 24.1 | 30.1 |
| 11.6 | 30.5 | 24.7 | 44.3 |
| 14.0 | 23.0 | 25.3 | 38.1 |
| 14.8 | 14.9 | 26.9 | 62.9 |
| 15.5 | 31.8 | 27.9 | 42.8 |
| 16.7 | 74.9 | 28.7 | 39.1 |
| 18.4 | 33.1 | 30.6 | 35.1 |
| 20.3 | 37.1 | — | — |

[1] In this and all subsequent tables, the position 2θ is within ±0.2.

TABLE 9

XRPD peak list of Compound III SO4 salt Form A

| Angle (2-Theta °)[1] | Intensity (%) |
|---|---|
| 6.3 | 50.4 |
| 6.7 | 66.0 |
| 9.6 | 40.8 |
| 10.5 | 30.7 |
| 11.2 | 30.2 |
| 12.6 | 13.1 |
| 13.5 | 36.5 |
| 14.9 | 94.9 |
| 15.9 | 14.2 |
| 16.6 | 36.2 |
| 18.0 | 38.9 |
| 18.8 | 61.7 |
| 19.4 | 33.8 |
| 20.1 | 29.3 |
| 20.9 | 30.7 |
| 21.7 | 34.7 |
| 22.5 | 29.2 |
| 23.6 | 23.7 |
| 24.2 | 100.0 |
| 24.7 | 41.3 |
| 25.7 | 22.0 |
| 26.7 | 24.0 |
| 27.5 | 23.2 |
| 27.9 | 18.7 |

[1] In this and all subsequent tables, the position 2θ is within ±0.2.

TABLE 10

XRPD peak list of Compound III methane sulfonic acid salt Form A

| Angle (2-Theta °) [1] | Intensity (%) |
|---|---|
| 9.4 | 84.1 |
| 10.1 | 45.0 |
| 11.9 | 66.5 |
| 12.2 | 87.0 |
| 12.7 | 75.8 |
| 13.2 | 34.7 |
| 13.9 | 34.0 |
| 14.1 | 23.5 |
| 14.5 | 67.1 |
| 15.4 | 53.6 |
| 16.5 | 90.5 |
| 17.4 | 47.3 |
| 18.0 | 59.2 |
| 18.9 | 61.7 |
| 20.3 | 82.0 |
| 20.9 | 46.2 |
| 21.2 | 85.9 |
| 21.8 | 56.5 |
| 23.0 | 41.8 |
| 23.6 | 81.6 |
| 24.5 | 55.3 |
| 25.7 | 100.0 |
| 26.4 | 72.6 |
| 27.7 | 40.3 |
| 29.0 | 41.5 |
| — | — |

[1] In this and all subsequent tables, the position 2θ is within ±0.2.

Example 15—Solubility measurements of 6-(6-ethynyl-4-methoxypyridin-3-yl)-5-(3-fluoro-44(4-methylpyrimidin-2-yl)oxy)phenyl)-4,7-dimethyl-7H-pyrrolo[2,3-d]pyrimidine (Compound III-1)

Crystalline FB Form A, HCl Form A, and the sufate salt Form A were scaled up for solubility analysis. All samples were found to contain a trace amount of solvents after vacuum drying. Both salts showed ~1.0 eq counter-ion by IC.

All samples show the highest solubility in SGF, the free form showed the lowest solubility in FaSSIF whereas the salts displayed the lowest solubility in FeSSIF. Both salts show increased solubility compared to the free form in all media, apart from the chloride salt in FeSSIF which has a lower solubility than the free form. The sulfate salt appears to be slightly more soluble than the chloride salt in both FeSSIF and FaSSIF.

Both salts completely dissolved in SGF, so greater than values are reported for the solubility. This also meant there were no residual solids to analyse for these samples. Analysis of the remaining residual solids showed that the free form Form A remained unchanged in all media. Both salts converted to free form Form C (hydrated form) in FeSSIF media. The chloride salt in FaSSIF displayed a new form that was not the seen from the polymorphism screening of either the free form or chloride salt, the nature of this form is unknown and was not characterised further. The sulfate salt in FaSSIF was too poorly crystalline to assign.

TABLE 37

Solubility results of Compound III-1, HCl and sulfate salts

| Form | Media | pH at 24 hrs | Solubility (mg/ml) | Average Solubility (mg/ml) | XRPD of residual solid |
|---|---|---|---|---|---|
| Free form Form A | SGF | 2.0 | 1.10 | 1.30 | FB Form A |
| | | 2.0 | 1.40 | | FB Form A |
| | FeSSIF | 5.0 | 0.12 | 0.12 | FB Form A |
| | | 5.0 | 0.11 | | FB Form A |
| | FaSSIF | 6.4 | 0.044 | 0.047 | FB Form A |
| | | 6.4 | 0.050 | | FB Form A |
| HCl Form A | SGF | 2.2 | >10.4 | >10.5 | — |
| | | 2.2 | >10.6 | | — |
| | FeSSIF | 4.7 | 0.052 | 0.055 | FB Form C |
| | | 4.7 | 0.058 | | FB Form C |
| | FaSSIF | 2.8 | 0.75 | 0.74 | — |
| | | 2.8 | 0.73 | | — |
| SO4 Form A | SGF | 1.7 | >10.2 | >10.5 | — |
| | | 1.7 | >10.7 | | — |
| | FeSSIF | 4.4 | 0.24 | 0.23 | FB Form C |
| | | 4.4 | 0.22 | | FB Form C |
| | FaSSIF | 2.6 | 2.00 | 1.95 | Poorly crystalline |
| | | 2.7 | 1.90 | | Poorly crystalline |

Key: — = not conducted

Example 16—Polymorph Screen of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (Compound IV-1)

Compound IV-1 (40 mg) was treated with an aliquot of solvent (200 μl for 5 vol, 400 μl for 10 vol, 800 μl for 20 vol) and left to stir at 25° C. for 5 mins. After 5 mins, resulting suspensions were treated with additional aliquot of solvent and left to stir again. Any clear solutions were removed from stirring and further solvent additions. This procedure was repeated up to a total of 40 vol (1.6 ml).

At 40 vol, any remaining suspensions were heated to 50° C. Samples that remained suspensions at 50° C. were moved to maturation (RT/50° C.) for 4 days. All solutions from solvent additions were heated to 50° C. before cooling to 5° C. at 0.1° C./min overnight.

After cooling, any solutions and thin suspensions were left uncapped to evaporate. After maturation, suspensions were filtered, and solids dried under suction. All solids were analysed by XRPD using a metal well plate.

Compound IV-1 was found to be soluble in all but three of the solvents tested: heptane, TBME and water. Based on the solubility, THF was selected for the salt screening as Compound 3 showed the greatest solubility within it and most of the acid solutions are prepared in THF.

After further treatment of suspensions and solutions, solids resulted from all experiments. Form A resulted from all solvents.

TABLE 11

Results of solubility and polymorphism assessment of Compound IV-1

| Solvent | Treatment | Observation after treatment | Further Treatment | XRPD |
|---|---|---|---|---|
| n-Heptane | Maturation | Suspension | — | Form A |
| Ethyl acetate | Cooling | Clear solution | Evaporation | Form A |
| Isopropyl acetate | Cooling | Clear solution | Evaporation | Form A |
| 2-Propanol | Cooling | Clear solution | Evaporation | Form A |
| MEK | Cooling | Clear solution | Evaporation | Form A |
| Acetone | Cooling | Clear solution | Evaporation | Form A |

TABLE 11-continued

Results of solubility and polymorphism assessment of Compound IV-1

| Solvent | Treatment | Observation after treatment | Further Treatment | XRPD |
|---|---|---|---|---|
| Ethanol | Cooling | Clear solution | Evaporation | Form A |
| TBME | Maturation | Suspension | — | Form A |
| Methanol | Cooling | Clear solution | Evaporation | Form A |
| THF | Cooling | Clear solution | Evaporation | Form A |
| 10% Water/ MeCN | Cooling | Clear solution | Evaporation | Form A |
| Water | Maturation | Suspension | — | Form A |
| 10% Water/ IPA | Cooling | Clear solution | Evaporation | Form A |

Key: — = not conducted

TABLE 39

XRPD peak list of Compound IV-1 Form A

| Angle (2-Theta °) [1] | Intensity (%) |
|---|---|
| 8.8 | 15.5 |
| 10.0 | 30.1 |
| 11.4 | 7.7 |
| 11.7 | 25.6 |
| 12.7 | 21.4 |
| 14.1 | 27.5 |
| 14.4 | 90.9 |
| 15.2 | 100.0 |
| 16.5 | 16.7 |
| 16.9 | 14.7 |
| 17.6 | 6.7 |
| 18.2 | 9.5 |
| 18.7 | 8.4 |
| 20.2 | 63.9 |
| 21.0 | 12.1 |
| 21.6 | 6.4 |
| 22.0 | 30.1 |
| 22.9 | 19.2 |
| 24.0 | 7.1 |
| 24.5 | 27.4 |
| 24.8 | 31.2 |
| 25.8 | 14.2 |
| 26.1 | 9.4 |
| 26.6 | 10.5 |
| 27.0 | 19.6 |
| 27.7 | 9.2 |
| 28.4 | 25.1 |
| 29.0 | 24.3 |
| 29.5 | 8.0 |
| 29.9 | 7.5 |
| 30.7 | 18.8 |
| 23.0 | 15.1 |

[1] In this and all subsequent tables, the position 2θ is within ±0.2.

Example 17—Preparation of salt forms of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (Compound IV-1)

Compound Iv-1 (520 mg) was dissolved in THF (2.6 ml, 5 vol) at RT. The API solution was dispensed into 4 ml vials (200 μl, ~40 mg) and heated to 50° C.

Acid solutions (1.1 eq, 92 μl for 1 M, 184 μl for 0.5 M) were added to the API solutions. The samples were cooled to 5° C. at 0.1° C./min and left for 1 day. After 1 day at 5° C., any remaining clear solutions were left uncapped to evaporate at RT. Suspensions at 5° C. were filtered and solids were dried under suction and transferred to a metal well plate.

After initial XRPD analysis, solids that were found to be amorphous by XRPD were suspended in TBME (500 μl) and placed into maturation (RT/50° C.) for 6 days. After solutions had evaporated to dryness, resulting gums were treated with TBME (500 μl) and placed into maturation for 2 days. After maturation in TBME, the suspensions were aliquoted onto a glass slide and after airdrying, solids were analysed by XRPD.

After XRPD analysis, samples found to be amorphous or consistent with the free form were uncapped and once dry the samples were treated with heptane (500 μl) and returned to maturation for 4 days. After maturation in heptane, the suspensions were aliquoted onto a glass slide and air dried before being analysed by XRPD.

After XRPD analysis, samples found to be amorphous, poorly crystalline or consistent with the free base form were uncapped and once dry the samples were treated with ethyl acetate (500 μl) and returned to maturation for 2 days. After maturation in ethyl acetate, the suspensions were aliquoted onto a flat silicon XRPD sample holders and after airdrying, solids were analysed by XRPD.

Upon addition of the acid to the solution of Compound IV-1, samples with inorganic acids formed gums but those with organic acids remained as clear solutions. After cooling to 5° C., no further samples precipitated but all samples had changed colour from yellow to orange. Several of the samples that precipitated as gums on acid addition had become suspensions after cooling. However, samples from HBr, sulfuric and phosphoric acids remained as gums after cooling, these were then subjected to maturation.

Analysis of the solids from suspensions showed that crystalline salts were obtained from HCl, p-toluene sulfonic, methane sulfonic and benzene sulfonic acids. These samples were all characterised further.

Clear solutions obtained following cooling were left to evaporate but all resulted in gums. All obtained gums were treated with TBME and matured. This maturation converted the gums into suspensions, but after XRPD analysis most were still amorphous solids or consistent with the free base. The sample from sulfuric acid displayed a poorly crystalline diffractogram. However, after high resolution XRPD analysis it was decided the sample was too poorly crystalline for further characterisation and was matured with the other samples.

The remaining samples were matured further first in heptane and then ethyl acetate. No further crystalline salts were obtained from the screen. The sulfuric acid sample showed no increase in crystallinity after further maturation.

TABLE 40

Results of salt screen on Compound IV-1

| Counter-ion | Observation on acid addition | Observation after cooling | XRPD after cooling |
|---|---|---|---|
| Hydrobromic acid - HBr | Gum | Gum | — |
| Hydrochloric acid - HCl | Gum | Suspension | HCl Form A |
| Sulfuric acid - SO4 | Gum | Gum | — |
| p-Toluene sulfonic acid - pTSA | Gum | Suspension | pTSA Form A |
| Methane sulfonic acid - MSA | Gum | Suspension | MSA Form A |
| Benzene sulfonic acid - BSA | Gum | Suspension | BSA Form A |
| Maleic acid - MEA | Clear solution | Clear solution | — |
| Phosphoric acid - PHOA | Gum | Gum | — |
| Malonic acid - MLNA | Clear solution | Clear solution | — |
| L-Tartaric acid - TAR | Clear solution | Clear solution | — |
| Fumaric acid - FUA | Clear solution | Clear solution | — |
| Citric acid - CA | Clear solution | Clear solution | — |

Key: — = not conducted

TABLE 41

Results of salt screen on Compound IV-1

| Counter-ion | Treatment 1 | XRPD after TBME maturation | XRPD after heptane maturation | XRPD after EtOAc maturation |
|---|---|---|---|---|
| Hydrobromic acid - HBr | Maturation | Amorphous | Amorphous | Amorphous |
| Sulfuric acid - SO4 | Maturation | Poorly crystalline SO4 Form A | Poorly crystalline SO4 Form A | Poorly crystalline SO4 Form A |
| Maleic acid - MEA | Evaporation | Amorphous | Amorphous | Amorphous |
| Phosphoric acid - PHOA | Maturation | Amorphous | Amorphous | Amorphous |
| MaIonic acid - MLNA | Evaporation | Amorphous | Amorphous | Amorphous |
| L-Tartaric acid - TAR | Evaporation | Amorphous | Poorly crystalline FB Form A | Amorphous |
| Fumaric acid - FUA | Evaporation | Amorphous | FB Form A | Fumaric acid |
| Citric acid - CA | Evaporation | FB Form A | Amorphous | Amorphous |

TABLE 42

Characterisation of Compound IV salts

| HCl Form A | pTSA Form A | MSA Form A | BSA Form A |
|---|---|---|---|
| Peak shifts due to salt formation | Peak shifts due to salt formation | Peak shifts due to salt formation | Peak shifts due to salt formation |
| ~0.5 eq THF | ~1.0 eq p-toluene sulfonic acid ~0.4 eq THF | Degradation of API seen between 2.0-2.8 ppm and 7.0-7.5 ppm ~1.2 eq methane sulfonic acid Trace THF | ~1.0 eq benzene sulfonic acid ~0.4 eq THF |
| 0.85 eq chloride | — | — | — |
| 10.1 wt % loss 40-210° C. | 3.2 wt % loss . 40-150° C (~0.3 eq THF) | 3.2 wt % loss 40-160° C. | 5.0 wt % loss 25-200° C. |
| Broad endotherm onset 138.6° C. (64 J/g) | Large exotherm onset 223.3° C. (110 J/g) | Broad endotherm onset 29.1° C. (9 J/g) | Broad endotherm onset 32.7° C. (21 J/g) |
| Large exotherm onset 186.8° C. (170 J/g) | | Broad endotherm onset 88.8° C. (3 J/g) Small endotherm onset 139.6° C. (3 J/g) Large exotherm onset 154.2° C. (53 J/g) | Small endotherm onset 121.7° C. (2 J/g) Large exotherm onset 176.7° C. (133 J/g) |
| Reduced crystallinity - HCl Form A | Change in form - pTSA Form B | Loss of crystallinity - Amorphous | Change in form - BSA Form B |

Key: — = not conducted

The chloride salt is a mono salt with ~0.9 eq chloride present by IC. This lower than expected stoichiometry indicates that the sample possibly contains amorphous free form, as no peaks of crystalline free base were seen in the XRPD diffractogram of the HCl salt. The chloride salt shows a large weight loss by TGA of 10.1 wt % this could be due to loss of residual THF (seen by 1H NMR), dissociation of the salt and loss of the counter-ion or degradation. The weight loss is also accompanied by an endotherm and large exotherm in the DSC. Unlike the free form, the DSC of the salt shows no sharp endotherm indicating a melt. The chloride salt showed no change to form after one week at 40° C./75% RH.

The tosylate salt is a mono salt with ~1.0 eq p-toluene sulfonate present by 1H NMR. The tosylate salt showed one weight loss by TGA of 3.2 wt %, this weight loss is slightly less than the amount of residual THF seen in the 1H NMR of the salt. The tosylate salt does not show any second larger weight loss unlike the chloride salt, however a large exotherm is still present in the DSC. This salt also shows no sharp endotherm indicating a melt. The tosylate salt was found to change form after one week at 40° C./75% RH.

The mesylate salt shows degradation in the 1H NMR as indicated by changes in the spectrum between 2.0-2.8 ppm and 7.0-7.5 ppm, apart from this ~1.2 eq methane sulfonate present by 1H NMR and a trace amount of THF. The sample also shows low crystallinity when compared to the other salts. The mesylate salt showed one weight loss by TGA of 3.2 wt %, this weight loss is slightly larger than the amount of residual THF seen in the 1H NMR of the salt. The mesylate salt does not show any second larger weight loss unlike the chloride salt but does show a total of three small endotherms and large exotherm by DSC. This salt also shows no sharp endotherm indicating a melt. The mesylate salt was found to lose crystallinity after one week at 40° C./75% RH, resulting in amorphous material.

The besylate salt is a mono salt with ~1.0 eq benzene sulfonate present by 1H NMR. The besylate salt showed one weight loss by TGA of 5.0 wt %, this weight loss is slightly larger than the amount of residual THF seen in the 1H NMR of the salt. The besylate salt does not show any second larger weight loss unlike the HCl salt, however two endotherms and a large exotherm are still present in the DSC. This salt also shows no sharp endotherm indicating a melt. The besylate salt was found to change form after one week at 40° C./75% RH.

Further Selected Polymorph Screening

The tosylate salt showed two different polymorphs after analysis of the solids by XPRD. pTSA Form A, the polymorph isolated from salt screening in THF, was produced from heptane (with additional peaks), IPA, 10% water/MeCN and 10% water/IPA. pTSA Form B resulted from eight out of 13 experiments and a range of solvents: ethyl acetate, isopropyl acetate, MEK, acetone, ethanol, TBME, methanol and THF. pTSA Form B was seen previously after storage of pTSA Form A at 40° C./75% RH. The samples from evaporation of water resulted in amorphous material.

TABLE 12

Results of polymorphism assessment on Compound IV pTSA salt

| Solvent | Observation in 10 vol at 50° C. | Observation on pTSA addition | Observation after cooling | XRPD |
| --- | --- | --- | --- | --- |
| n-Heptane | Suspension | Gum | Suspension/gum | pTSA Form A + ep |
| Ethyl acetate | Suspension | Gum | Suspension/gum | pTSA Form B |
| Isopropyl acetate | Suspension | Gum | Suspension/gum | pTSA Form B |
| 2-Propanol | Suspension | Clear solution | Suspension | pTSA Form A |
| MEK | Clear solution | Clear solution | Suspension | pTSA Form B |
| Acetone | Clear solution | Clear solution | Suspension | pTSA Form B |
| Ethanol | Suspension | Clear solution | Suspension | pTSA Form B |
| TBME | Suspension | Gum | Suspension/gum | pTSA Form B |
| Methanol | Clear solution | Clear solution | Clear solution | pTSA Form B |
| THF | Clear solution | Clear solution | Suspension | pTSA Form B |
| 10% Water/MeCN | Clear solution | Clear solution | Clear solution | pTSA Form A |
| Water | Suspension | Clear solution | Clear solution | Amorphous |
| 10% Water/IPA | Clear solution | Clear solution | Suspension | pTSA Form A |

Key: — = not conducted, ep - extra peaks

TABLE 44

XRPD peak list of Compound IV HC1 Form A

| Angle (2-Theta °) [1] | Intensity (%) |
| --- | --- |
| 8.7 | 87.0 |
| 9.7 | 22.0 |
| 12.2 | 11.4 |
| 12.5 | 51.3 |
| 12.7 | 77.1 |
| 13.4 | 43.6 |
| 13.8 | 35.7 |
| 14.0 | 94.6 |
| 14.5 | 9.2 |
| 16.3 | 28.4 |
| 17.4 | 19.9 |
| 17.8 | 53.7 |
| 18.5 | 91.3 |
| 18.9 | 15.4 |
| 19.2 | 85.1 |
| 19.5 | 19.2 |
| 20.4 | 49.6 |
| 20.7 | 18.4 |
| 21.0 | 40.9 |
| 21.3 | 22.4 |
| 21.7 | 90.6 |
| 23.2 | 19.1 |
| 23.7 | 100.0 |
| 24.7 | 19.8 |
| 25.0 | 62.0 |

TABLE 44-continued

XRPD peak list of Compound IV HC1 Form A

| Angle (2-Theta °) [1] | Intensity (%) |
| --- | --- |
| 25.5 | 45.2 |
| 25.9 | 29.8 |
| 26.3 | 37.2 |
| 26.8 | 30.3 |
| 27.2 | 34.7 |
| 27.3 | 51.2 |
| 27.6 | 33.6 |
| 28.2 | 29.8 |
| 28.5 | 21.8 |
| 28.8 | 20.7 |
| 29.3 | 78.8 |
| 29.7 | 14.3 |

[1] In this and all subsequent tables, the position 2θ is within ±0.2.

TABLE 45

XRPD peak list of Compound IV pTSA Form A

| Angle (2-Theta °) [1] | Intensity (%) |
| --- | --- |
| 5.6 | 100.0 |
| 9.4 | 10.0 |
| 11.3 | 31.7 |
| 12.0 | 6.6 |
| 12.4 | 8.4 |
| 12.9 | 5.8 |
| 14.0 | 11.2 |
| 15.3 | 9.4 |
| 15.8 | 4.2 |
| 16.1 | 22.3 |
| 16.4 | 26.7 |
| 16.9 | 64.5 |
| 17.6 | 4.1 |
| 17.8 | 4.4 |
| 18.3 | 14.3 |
| 18.8 | 6.1 |
| 19.2 | 27.5 |
| 19.6 | 12.8 |
| 20.1 | 6.7 |
| 20.7 | 9.9 |
| 20.9 | 5.6 |
| 21.3 | 21.0 |
| 21.5 | 20.7 |
| 21.8 | 7.6 |
| 22.7 | 12.3 |

TABLE 45-continued

XRPD peak list of Compound IV pTSA Form A

| Angle (2-Theta °)[1] | Intensity (%) |
|---|---|
| 23.4 | 10.3 |
| 24.6 | 12.8 |
| 25.2 | 11.1 |
| 25.4 | 12.2 |
| 25.5 | 10.4 |
| 26.1 | 9.6 |
| 26.6 | 12.3 |
| 27.4 | 11.5 |
| 27.8 | 11.2 |
| 28.4 | 39.0 |
| 29.2 | 8.6 |

[1] In this and all subsequent tables, the position 2θ is within ±0.2.

TABLE 13

XRPD peak list of Compound IV pTSA Form B

| Angle (2-Theta °)[1] | Intensity (%) |
|---|---|
| 5.6 | 100.0 |
| 9.4 | 17.7 |
| 9.8 | 16.7 |
| 11.3 | 33.5 |
| 12.0 | 10.1 |
| 12.5 | 19.5 |
| 12.9 | 7.5 |
| 14.0 | 10.6 |
| 15.3 | 13.2 |
| 15.6 | 8.8 |
| 16.6 | 85.2 |
| 16.9 | 44.5 |
| 17.7 | 9.8 |
| 18.3 | 11.9 |
| 18.9 | 20.7 |
| 19.5 | 40.4 |
| 20.6 | 17.5 |
| 21.3 | 34.0 |
| 22.4 | 11.0 |
| 22.6 | 12.8 |
| 23.0 | 14.4 |
| 23.4 | 23.1 |
| 24.6 | 15.2 |
| 24.8 | 11.7 |
| 25.3 | 18.5 |
| 25.5 | 22.7 |
| 25.9 | 12.5 |
| 26.4 | 16.3 |
| 27.2 | 9.6 |
| 27.7 | 14.2 |
| 28.0 | 20.5 |
| 28.4 | 30.5 |
| 28.6 | 14.4 |
| 29.1 | 12.8 |
| 30.8 | 11.0 |

[1] In this and all subsequent tables, the position 2θ is within ±0.2.

TABLE 47

XRPD peak list of Compound IV methane sulfonic acid Form A

| Angle (2-Theta °)[1] | Intensity (%) |
|---|---|
| 3.8 | 100.0 |
| 6.1 | 27.7 |
| 7.5 | 32.1 |
| 7.8 | 42.1 |
| 9.5 | 20.4 |
| 11.3 | 29.8 |
| 13.0 | 12.1 |
| 14.4 | 22.0 |
| 15.1 | 13.8 |
| 15.5 | 14.8 |
| 16.3 | 20.9 |
| 16.7 | 16.4 |
| 17.6 | 17.1 |
| 19.4 | 42.4 |
| 20.0 | 35.0 |
| 20.6 | 30.2 |
| 23.0 | 24.6 |
| 24.1 | 50.5 |
| 24.7 | 25.9 |
| 26.2 | 18.7 |
| 28.4 | 18.8 |

[1] In this and all subsequent tables, the position 2θ is within ±0.2.

TABLE 14

XRPD peak list of Compound IV benzene sulfonic acid Form A

| Angle (2-Theta °)[1] | Intensity (%) |
|---|---|
| 6.4 | 79.3 |
| 8.9 | 55.3 |
| 10.3 | 25.2 |
| 10.6 | 23.2 |
| 12.9 | 100.0 |
| 14.1 | 24.8 |
| 14.7 | 20.6 |
| 15.5 | 53.1 |
| 16.1 | 16.8 |
| 16.8 | 18.9 |
| 18.1 | 85.4 |
| 19.5 | 24.0 |
| 21.0 | 55.0 |
| 21.4 | 49.5 |
| 23.1 | 52.6 |
| 24.4 | 70.2 |
| 26.0 | 74.5 |
| 26.5 | 36.2 |
| 27.6 | 25.1 |

[1] In this and all subsequent tables, the position 2θ is within ±0.2.

Example 18—Solubility measurements of 6-(6-ethynyl-2,4-dimethylpyridin-3-yl)-5-(3-fluoro-4-((4-methylpyrimidin-2-yl)oxy)phenyl)-4,7-dimethyl-7H-pyrrolo[2,3-d]pyrimidine (Compound IV-1)

HCl Form A was successfully scaled up for solubility analysis. The tosylate salt displayed an XRPD pattern the same as seen after storage at 40° C./75% RH for the screening sample, pTSA Form B. The tosylate salt also appeared to contain a small amount of excess p-toluene sulfonic acid.

The results from the solubility measurements are summarised in Table. All samples show the highest solubility in SGF, the free form showed its lowest solubility in FaSSIF whereas the salts displayed the lowest solubility in FeSSIF. Both salts show increased solubility compared to the free form in all media. The chloride salt appears to be more soluble than the tosylate salt in all media.

The chloride salt completely dissolved in SGF, so greater than values are reported for the solubility. This also meant there were no residual solids to analyse for these samples. Analysis of the remaining residual solids showed that the free form Form A remained unchanged in all media. The chloride salt converted to free form Form A in FeSSIF and FaSSIF media. The tosylate salt remained unchanged in SGF and FaSSIF, but in FeSSIF was too poorly crystalline to assign.

TABLE 49

Solubility results of Compound IV-1, HCl and pTSA salts

| Form | Media | pH at 24 hrs | Solubility (mg/ml) | Average Solubility (mg/ml) | XRPD of residual solid |
|---|---|---|---|---|---|
| Free form Form A | SGF | 2.3 | 4.20 | 4.30 | FB Form A |
| | | 2.3 | 4.40 | | FB Form A |
| | FeSSIF | 5.0 | 0.47 | 0.49 | FB Form A |
| | | 5.0 | 0.52 | | FB Form A |
| | FaSSIF | 6.5 | 0.061 | 0.061 | FB Form A |
| | | 6.5 | 0.061 | | FB Form A |
| HCl Form A | SGF | 2.2 | >10.7 | >10.9 | — |
| | | 2.2 | >11.0 | | — |
| | FeSSIF | 4.8 | 1.60 | 1.70 | FB Form A |
| | | 4.8 | 1.70 | | FB Form A |
| | FaSSIF | 3.1 | 1.80 | 2.1 | FB Form A |
| | | 3.1 | 2.30 | | FB Form A |
| pTSA Form B | SGF | 1.9 | 4.20 | 4.3 | pTSA Form B |
| | | 1.9 | 4.30 | | pTSA Form B |
| | FeSSIF | 4.8 | 1.10 | 1.01 | Poorly crystalline |
| | | 4.8 | 0.92 | | Poorly crystalline |
| | FaSSIF | 3.7 | 1.60 | 1.5 | pTSA Form B |
| | | 3.7 | 1.40 | | pTSA Form B |

Key: — = not conducted

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

Example 19. A First-In-Human Study of Compound I-1 in Patients with Intrahepatic Cholangiocarcinoma (ICC) and Other Advanced Solid Tumors 1. Study Objectives
Primary Objectives
  To determine the MTD and RP2D of Compound I-1
  To determine the safety and tolerability of Compound I-1
Secondary Objectives
  To evaluate FGFR2 status in blood and tumor tissue by next generation nucleic acid sequencing
  To define the PK profile of Compound I-1 and/or of its metabolites
  To assess the pharmacodynamics of Compound I-1 by monitoring blood markers (eg. CA 19-9, CEA, FGF23)
  To characterize the preliminary anti-tumor activity of Compound I-1 per RECIST 1.1
Exploratory Objectives
  To correlate FGFR2 genotype with response.
  To explore other measures of disease progression including progression free survival (PFS) and overall survival (OS)
  To identify potential new blood and tumor tissue biomarkers (eg. deoxyribonucleic acid [DNA], ribonucleic acid [RNA], and/or protein markers) of pharmacodynamic activity, antineoplastic activity, resistance and/or toxicity
  To assess changes in quality of life (QoL) for ICC and other advanced solid tumors patients (Part 2)

2. Study Design
This is a Phase 1, open-label, FIH study designed to evaluate the safety, tolerability, PK, pharmacodynamics, and preliminary antineoplastic activity of Compound I-1, a potent and highly selective FGFR2 inhibitor in patients with ICC and other advanced solid tumors. The study consists of 2 parts, a dose-escalation (Part 1) and a dose expansion (Part 2). Both Parts will enroll patients who have disease that is refractory to standard therapy, disease that has not adequately responded to standard therapy, disease for which standard or curative therapy does not exist, or must be intolerant to or have declined standard therapy.

The Part 1 dose-escalation employs the Bayesian optimal interval (BOIN) design to determine the MTD/RP2D of Compound I-1. Dose escalation will enroll in cohorts of 3-6 (1-3 for the first 3 dose levels) patients until 12 patients are treated and evaluable for dose-limiting toxicity (DLT) at one dose level, at which time the MTD or RP2D can be determined. The total number of patients to be enrolled during the dose escalation part of the study could vary depending on the toxicity profile of Compound I-1 and the number of dose levels tested prior to reaching the MTD.

Part 2 will enroll patients with advanced, unresectable, solid tumors with an FGFR2 alteration. Patients will be treated with Compound I-1 at the MTD/RP2D as determined in Part 1 and must have measurable or evaluable disease by RECIST v1.1.

3. Investigational Medicinal Product
Compound I-1 is an oral selective inhibitor of FGFR2. The drug product (DP) is formulated by blending Compound I-1 drug substance with pharmaceutical grade excipients followed by filling the blend into capsules. Clinical study material for Compound I-1 will be supplied as 10 mg, 50 mg, and 100 mg capsules filled in 30 count high-density polyethylene (HDPE) bottles. The capsules will be orally administered twice daily.

4. Number of Subjects
Approximately 125 patients will be enrolled in this study, including:
  approximately 50 patients in Part 1
  approximately 75 patients in Part 2
The total number of participants to be enrolled in the Part 1 is dependent upon the observed safety profile, which will determine the number of patients per dose cohort as well as the number of cohorts required to define MTD (Maximum tolerated dose) and RP2D (Recommended phase 2 dose).

5. Study Population
Main Inclusion Criteria:
  1. Patient is willing and able to provide written informed consent for the study prior to the performance of any study-specific procedures.
  2. Patient is ≥18 years of age.
  3. Patient must have disease that is refractory to standard therapy, disease that has not adequately responded to standard therapy, disease for which standard or curative therapy does not exist, or the patient must be intolerant to or have declined standard therapy.
  4. Patient must have measurable or evaluable disease per RECIST 1.1.
  5. Patient has Eastern Cooperative Oncology Group (ECOG) performance status (PS) of 0-Disease and FGFR2 status
  6. Patient has documented FGFR2 alteration in blood and/or tumor per local assessment as defined by:
    FGFR2-fusions include genomic translocations expected to create an oncogenic FGFR2-fusion protein detected by DNA or RNA sequencing or break apart FISH.
    FGFR2-amplifications must include amplified FGFR2 locus with copy number ≥8 [eg. FGFR2 fold-amplification ≥4 per next generation sequencing (NGS) or FGFR2 probe:reference ratio ≥4 per fluorescence in situ hybridization (FISH)] in tumor tissue. No amplification cutoff is defined for circulating tumor DNA (ctDNA).

FGFR2 mutations must include one or more of the following primary oncogenic FGFR2 mutations or acquired FGFR2 resistance mutations: H167_N173del, S252X, P253X, Y375X, C382X, M537X, N549X, V564X, E565X, L617X, K641X, K659X, and R664X (numbering based on mesenchymal isoform IIIc; X represents any amino acid change). Other potentially oncogenic and/or resistance FGFR2 mutations may be considered, but must be approved by the Sponsor prior to enrollment.

Other potential FGFR2-dependent tumor types may be considered for Part 1 (see below) Part 1:

7. Patient has a histologically or cytologically confirmed diagnosis of unresectable ICC or other advanced, unresectable solid tumor.
8. Patient has documented FGFR2 genomic alteration (fusion, amplification or mutation) in blood and/or tumor tissue per local assessment. Patients with other potential oncogenic FGFR2 alterations (eg. FGFR2 protein or mRNA overexpression) and other tumor types may be eligible for the dose escalation (Part 1) of the study after consultation with the Sponsor.
9. Patient agrees to provide archived tumor tissue (if available) or is willing to undergo pre-treatment tumor biopsy (if considered safe and medically feasible) to assess FGFR2 status. If the patient does not have available archived tumor tissue or tumor amenable to tumor biopsy, he/she may be eligible for the study upon consultation with the Sponsor.

Part 2:

10. Patient will enroll based on their tumor type and prior therapy status:
    a. Group 1: patient must have a confirmed diagnosis of unresectable ICC with FGFR2 fusion (per local assessment of blood and/or tumor) and has received prior treatment with a pan-FGFR inhibitor (eg. pemigatinib, erdafitinib, infigratinib, TAS-120).
    b. Group 1: patient must have a confirmed diagnosis of unresectable ICC with FGFR2 fusion (per local assessment of blood and/or tumor) and has NOT received prior treatment with a pan-FGFR inhibitor (eg. pemigatinib, erdafitinib, infigratinib, TAS-120).
    c. Group 1: patient has an advanced, unresectable solid tumor with FGFR2 fusion (per local assessment of blood and/or tumor) other than ICC.
    d. Group 1: patient has an advanced, unresectable solid tumor with FGFR2 amplification (per local assessment of blood and/or tumor).
    e. Group 1: patient has an advanced, unresectable solid tumor with an oncogenic FGFR2 mutation (per local assessment of blood and/or tumor).
11. Patient must submit tumor tissue (archived or newly obtained biopsy) prior to study treatment initiation for determination of FGFR2 status.

Main Exclusion Criteria:

1. Patient's cancer has a known primary driver alteration other than FGFR2 that is amenable to approved targeted therapy eg. EGFR, ALK, ROS, RET, PI3K, HER2, BRAF.
2. Patient has history or ongoing, clinically significant corneal or retinal disorder.
3. Patient has any of the following within 14 days prior to the first dose of Compound I-1:
   g. Platelet count $<75 \times 10^9$/L
   h. Absolute neutrophil count (ANC)$<1 \times 10^9$/L
   i. Hemoglobin <8 g/dL (red blood cell transfusion and erythropoietin may be used to reach 8 g/dL, but must have been administered at least 2 weeks prior to the first dose of Compound I-1)
   j. Aspartate aminotransferase (AST) or alanine aminotransferase (ALT) >3× the upper limit of normal (ULN) if no hepatic metastases are present; >5×ULN if hepatic metastases are present.
   k. Total bilirubin >1.5×ULN; >3×ULN with direct bilirubin >1.5×ULN in presence of Gilbert's disease
   l. Estimated (Cockroft-Gault formula) or measured creatinine clearance <50 mL/min
4. Patient has known active human immunodeficiency virus (HIV) or active hepatitis B virus (HBV) and/or hepatitis C virus (HCV). Testing is not required.
5. Patient has QTcF >480 msec. Patient has history of prolonged QT syndrome or Torsades de pointes. Patient has a familial history of prolonged QT syndrome.
6. Patient has clinically significant, uncontrolled cardiovascular disease including congestive heart failure Grade III or IV according to the New York Heart Association (NYHA) classification; myocardial infarction or unstable angina within the previous six months, uncontrolled hypertension (Grade 3 or higher), or clinically significant, uncontrolled arrythmia, including bradyarrythmias that may cause QT prolongation (eg. Type II second degree heart block or third-degree heart block).
7. Patient has central nervous system (CNS) metastases or primary CNS tumor that is associated with progressive neurologic symptoms or requires increasing doses of corticosteroids to control the CNS disease. If patient requires corticosteroids for management of CNS disease, the dose must have been stable for the 2 weeks preceding Cycle 1 Day 1 (C1D1). Patients with stable or asymptomatic CNS metastases or primary CNS can be eligible after consultation with the Sponsor.
8. Patient received systemic antineoplastic therapy or radiotherapy within 14 days or 5 half-lives prior to the first dose of Compound I-1. Compound I-1 may be started within 5 days of 5 half-lives of prior therapy if considered by the Investigator to be safe and within the best interest of the patient—this must be approved by the Sponsor prior to dosing.
9. Patient received local, hepatic therapy (eg. TACE or Y90) within 4 weeks prior to C1D1.
10. Patient received neutrophil growth factor support within 14 days of the first dose of Compound I-1.
11. Patient requires treatment with a prohibited medication or herbal remedy that cannot be discontinued at least 2 weeks before the start of Compound I-1 administration.
12. Patient has had a major surgical procedure within 14 days of the first dose of Compound I-1 (procedures such as central venous catheter placement, tumor needle biopsy, and feeding tube placement are not considered major surgical procedures). Study centers should discuss other minor surgeries with the Sponsor.
13. Patient has a history of another primary malignancy that has been diagnosed or required therapy within the past year. The following prior malignancies are not exclusionary: completely resected basal cell and squamous cell skin cancer, curatively treated localized prostate cancer, curatively treated localized thyroid cancer, and completely resected carcinoma in situ of any site.

14. Patient is unwilling or unable to comply with scheduled visits, drug administration plan, laboratory tests, or other study procedures and study restrictions.
15. Women who are unwilling, if not postmenopausal or surgically sterile, to abstain from sexual intercourse or employ highly effective contraception during the Compound I-1 administration period and for at least 30 days after the last dose of Compound I-1. Men who are unwilling, if not surgically sterile, to abstain from sexual intercourse or employ highly effective contraception during the Compound I-1 administration period and for at least 90 days after the last dose of Compound I-1.
16. Pregnant females, as documented by a serum beta human chorionic gonadotropin (β-hCG) pregnancy test consistent with pregnancy, obtained within 7 days prior to the first dose of Compound I-1. Females with β hCG values that are within the range for pregnancy but are not pregnant (false-positives) may be enrolled with written consent of the Sponsor, after pregnancy has been ruled out. Females of nonchildbearing potential (postmenopausal for more than 1 year; bilateral tubal ligation; bilateral oophorectomy; hysterectomy) do not require a serum β-hCG test.
17. If female, patient is breastfeeding.
18. Patient has prior or ongoing clinically significant illness, medical condition, surgical history, physical finding, or laboratory abnormality that, in the Investigator's opinion, could affect the safety of the patient; alter the absorption, distribution, metabolism, or excretion of the Compound I-1; or impair the assessment of study results.

6. Criteria for Evaluation
Primary
  MTD and RP2D
  Overall safety profile of Compound I-1 as assessed by the type, frequency, severity, timing and relationship to Compound I-1 of any adverse events (AEs), serious AEs (SAEs), changes in vital signs, electrocardiograms (ECGs) and safety laboratory tests. All AEs and SAEs will be collected and graded according to CTCAE, Version 5.0
Secondary
  FGFR2 genotype in blood and tumor tissue
  PK parameters of Compound I-1 including, but not limited to Maximum Concentration (Cmax), Time to Maximum Concentration (Tmax), Area Under the Concentration-Time Curve (AUC), terminal half-life (T½), clearance (CL), and other relevant parameters
  Pharmacodynamic parameters: including, but not limited to blood markers (eg. CA 19-9, CEA, FGF23)
  Overall response rate (ORR), Duration of Response (DOR), and Disease Control Rate (DCR) per RECIST 1.1
Exploratory
  FGFR2 genotype vs. response
  Levels of other exploratory biomarkers and potential relationships with clinical activity
  Other measures of disease progression including Median, 6- and 9-month PFS; Median, 6- and 12-month OS
  Changes in patient reported outcomes as assessed by the European Organization for Research and Treatment of Cancer Core QoL Questionnaire (EORTC QLQ-C30) in patients with ICC and other advanced solid tumors 7. Statistical Methods
For the dose escalation Part 1 of the study a BOIN design will be applied. The MTD will be determined based on Cycle 1 DLT using isotonic regression across all dose levels. The sample size for Part 1 will depend on the actual dose levels and the number of DLT observed.

For the dose expansion Part 2, the sample size is estimated to be a total of 75 patients from 5 groups (n=15 for each group) based on FGFR2 status. No formal sample size considerations will be applied. With a sample size of 15 patients per group, the half width of the 95% confidence interval (CI) for ORR would be maximum 25%. As an example, if 7/15 responses would be observed, this would correspond to ORR of 47% and 95% CI (25%, 70%).

Descriptive statistics will be provided for selected demographic, safety, PK, pharmacodynamic, imaging and biomarker data as appropriate. Descriptive statistics on continuous data will include means, medians, standard deviations, and ranges, while categorical data will be summarized using frequency counts and percentages including 95% CIs. Efficacy analyses include ORR, DOR, DCR, PFS and OS by RECIST v1.1.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed:
1. A crystalline solid form of a compound of Formula I-1:

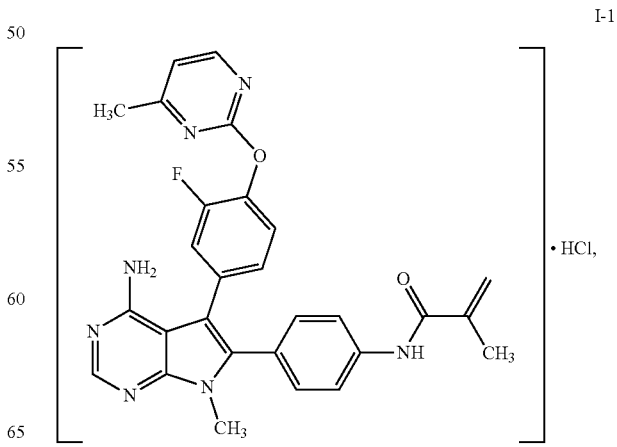

wherein the crystalline solid form is characterized by a powder X-ray diffraction pattern with at least two characteristic peaks, in degrees 2θ, each selected from the group consisting of:

| Angle (2θ)° |
| --- |
| 7.5 |
| 9.2 |
| 10.4 |
| 11.1 |
| 11.8 |
| 12.3 |
| 12.7 |
| 13.2 |
| 14.0 |
| 14.2 |
| 14.4 |
| 15.2 |
| 15.6 |
| 17.5 |
| 18.2 |
| 18.5 |
| 18.8 |
| 19.2 |
| 19.5 |
| 20.6 |
| 21.7 |
| 22.9 |
| 24.0 |
| 24.8 |
| 25.5 |
| 26.9 |
| 28.1 and |
| 29.5, | wherein each peak is ±0.2°.

2. A pharmaceutical composition comprising the crystalline solid form of claim 1 and a pharmaceutically acceptable carrier.

3. A kit comprising the crystalline solid form of claim 1.

4. The crystalline solid form of claim 1, wherein the crystalline solid form is substantially free of amorphous compound of Formula I-1.

5. The crystalline solid form of claim 1, wherein the crystalline solid form is substantially free of impurities.

6. The crystalline solid form of claim 1, further characterized by a powder X-ray diffraction pattern with at least two characteristic peaks, in degrees 2θ, each selected from the group consisting of 12.3, 24.0 and 15.6, wherein each peak is +0.2°.

7. The crystalline solid form of claim 1, further characterized by a powder X-ray diffraction pattern with at least two characteristic peaks, in degrees 2θ, each selected from the group consisting of 12.3, 24.0, 15.6, 12.7, 10.4, 11.1 and 15.2, wherein each peak is ±0.2°.

8. The crystalline solid form of claim 1, further characterized by a powder X-ray diffraction pattern with at least three characteristic peaks, in degrees 2θ, each selected from the group consisting of 12.3, 24.0, 15.6, 12.7, 10.4, 11.1 and 15.2, wherein each peak is ±0.2°.

9. The crystalline solid form of claim 1, further characterized by a powder X-ray diffraction pattern with at least four characteristic peaks, in degrees 2θ, each selected from the group consisting of 12.3, 24.0, 15.6, 12.7, 10.4, 11.1 and 15.2, wherein each peak is ±0.2°.

10. The crystalline solid form of claim 1, further characterized by a powder X-ray diffraction pattern with at least five characteristic peaks, in degrees 2θ, each selected from the group consisting of 12.3, 24.0, 15.6, 12.7, 10.4, 11.1 and 15.2, wherein each peak is ±0.2°.

11. The crystalline solid form of claim 1, further characterized by a powder X-ray diffraction pattern with at least six characteristic peaks, in degrees 2θ, each selected from the group consisting of 12.3, 24.0, 15.6, 12.7, 10.4, 11.1 and 15.2, wherein each peak is ±0.2°.

12. The crystalline solid form of claim 1, further characterized by an X-Ray diffraction pattern as depicted in FIG. 1A.

13. The crystalline solid form of claim 1, further characterized by a powder X-ray diffraction pattern with at least three characteristic peaks, in degrees 2θ, each selected from the group consisting of:

| Angle (2θ)° |
| --- |
| 7.5 |
| 9.2 |
| 10.4 |
| 11.1 |
| 11.8 |
| 12.3 |
| 12.7 |
| 13.2 |
| 14.0 |
| 14.2 |
| 14.4 |
| 15.2 |
| 15.6 |
| 17.5 |
| 18.2 |
| 18.5 |
| 18.8 |
| 19.2 |
| 19.5 |
| 20.6 |
| 21.7 |
| 22.9 |
| 24.0 |
| 24.8 |
| 25.5 |
| 26.9 |
| 28.1 and |
| 29.5, | wherein each peak is ±0.2°.

14. The crystalline solid form of claim 1, further characterized by a powder X-ray diffraction pattern with at least four characteristic peaks, in degrees 2θ, each selected from the group consisting of:

| Angle (2θ)° |
| --- |
| 7.5 |
| 9.2 |
| 10.4 |
| 11.1 |
| 11.8 |
| 12.3 |
| 12.7 |
| 13.2 |
| 14.0 |
| 14.2 |
| 14.4 |
| 15.2 |
| 15.6 |
| 17.5 |
| 18.2 |
| 18.5 |
| 18.8 |
| 19.2 |
| 19.5 |
| 20.6 |
| 21.7 |
| 22.9 |

-continued

| Angle (2θ)° |
| --- |
| 24.0 |
| 24.8 |
| 25.5 |
| 26.9 |
| 28.1 and |
| 29.5, | wherein each peak is ±0.2°.

15. The crystalline solid form of claim 1, further characterized by a powder X-ray diffraction pattern with at least five characteristic peaks, in degrees 2θ, each selected from the group consisting of:

| Angle (2θ)° |
| --- |
| 7.5 |
| 9.2 |
| 10.4 |
| 11.1 |
| 11.8 |
| 12.3 |
| 12.7 |
| 13.2 |
| 14.0 |
| 14.2 |
| 14.4 |
| 15.2 |
| 15.6 |
| 17.5 |
| 18.2 |
| 18.5 |
| 18.8 |
| 19.2 |
| 19.5 |
| 20.6 |
| 21.7 |
| 22.9 |
| 24.0 |
| 24.8 |
| 25.5 |
| 26.9 |
| 28.1 and |
| 29.5, | wherein each peak is ±0.2°.

16. The crystalline solid form of claim 1, further characterized by a powder X-ray diffraction pattern with at least six characteristic peaks, in degrees 2θ, each selected from the group consisting of:

| Angle (2θ)° |
| --- |
| 7.5 |
| 9.2 |
| 10.4 |
| 11.1 |
| 11.8 |
| 12.3 |
| 12.7 |
| 13.2 |
| 14.0 |
| 14.2 |
| 14.4 |
| 15.2 |
| 15.6 |
| 17.5 |
| 18.2 |
| 18.5 |
| 18.8 |
| 19.2 |
| 19.5 |
| 20.6 |
| 21.7 |
| 22.9 |
| 24.0 |
| 24.8 |
| 25.5 |
| 26.9 |
| 28.1 and |
| 29.5, | wherein each peak is ±0.2°.

17. The crystalline solid form of claim 1, further characterized by a differential scanning calorimetry (DSC) pattern as depicted in FIG. 1B.

18. The crystalline solid form of claim 1, further characterized by a thermogravimetric analysis (TGA) pattern as depicted in FIG. 1C.

19. A crystalline solid form of a compound of Formula I-1, wherein the crystalline solid form is Form A.

* * * * *